US007442506B2

(12) United States Patent
Dhallan

(10) Patent No.: US 7,442,506 B2
(45) Date of Patent: Oct. 28, 2008

(54) METHODS FOR DETECTION OF GENETIC DISORDERS

(75) Inventor: Ravinder S. Dhallan, Bethesda, MD (US)

(73) Assignee: Ravgen, Inc., Columbia, MD (US)

( * ) Notice: Subject to any disclaimer, the term of this patent is extended or adjusted under 35 U.S.C. 154(b) by 19 days.

(21) Appl. No.: 11/212,386

(22) Filed: Aug. 26, 2005

(65) Prior Publication Data

US 2006/0160105 A1 Jul. 20, 2006

Related U.S. Application Data

(63) Continuation of application No. PCT/US03/27308, filed on Aug. 29, 2003, which is a continuation-in-part of application No. PCT/US03/06198, filed on Feb. 28, 2003, application No. 11/212,386, filed on Aug. 26, 2005, which is a continuation-in-part of application No. 10/661,165, filed on Sep. 11, 2003, now Pat. No. 7,332,277, which is a continuation-in-part of application No. PCT/US03/06198.

(60) Provisional application No. 60/378,354, filed on May 8, 2002.

(51) Int. Cl.
*C12Q 1/68* (2006.01)
*C07H 19/00* (2006.01)
*C07H 21/00* (2006.01)

(52) U.S. Cl. ........................................ 435/6; 536/22.1

(58) Field of Classification Search .................... 435/6; 536/22.1

See application file for complete search history.

(56) References Cited

U.S. PATENT DOCUMENTS

| | | | |
|---|---|---|---|
| 4,521,509 | A | 6/1985 | Benkovic et al. |
| 4,683,195 | A | 7/1987 | Mullis et al. |
| 4,683,202 | A | 7/1987 | Mullis |
| 4,800,159 | A | 1/1989 | Mullis et al. |
| 4,889,818 | A | 12/1989 | Gelfand et al. |
| 4,965,188 | A | 10/1990 | Mullis et al. |
| 4,994,372 | A | 2/1991 | Tabor et al. |
| 5,023,171 | A | 6/1991 | Ho et al. |
| 5,066,584 | A | 11/1991 | Gyllensten et al. |
| 5,075,216 | A | 12/1991 | Innis et al. |
| 5,079,352 | A | 1/1992 | Gelfand et al. |
| 5,091,310 | A | 2/1992 | Innis |
| 5,098,839 | A | 3/1992 | Polisson |
| 5,104,792 | A | 4/1992 | Silver et al. |
| 5,153,117 | A | 10/1992 | Simons |
| 5,326,857 | A | 7/1994 | Yamamoto et al. |
| 5,426,026 | A | 6/1995 | Jordan |
| 5,432,054 | A | 7/1995 | Saunders et al. |
| 5,501,963 | A | 3/1996 | Burckhardt et al. |
| 5,538,848 | A | 7/1996 | Livak et al. |
| 5,538,871 | A | 7/1996 | Nuovo et al. |
| 5,545,552 | A | 8/1996 | Mathur |
| 5,565,339 | A | 10/1996 | Bloch et al. |
| 5,576,176 | A | 11/1996 | Adams et al. |
| 5,582,989 | A | 12/1996 | Caskey et al. |
| 5,618,664 | A | 4/1997 | Kiessling |
| 5,631,147 | A | 5/1997 | Lohman et al. |
| 5,635,348 | A | 6/1997 | Leong |
| 5,639,611 | A | 6/1997 | Wallace et al. |
| 5,641,628 | A | 6/1997 | Bianchi |
| 5,648,222 | A | 7/1997 | Tse et al. |
| 5,693,469 | A | 12/1997 | Hogan |
| 5,723,591 | A | 3/1998 | Livak et al. |
| 5,744,301 | A | 4/1998 | Birkenbach et al. |
| 5,759,772 | A | 6/1998 | Kirkpatrick et al. |
| 5,817,797 | A | 10/1998 | Mitchell et al. |
| 5,831,065 | A | 11/1998 | Brenner et al. |
| 5,858,671 | A | 1/1999 | Jones |
| 5,882,857 | A | 3/1999 | Western et al. |
| 5,965,363 | A | 10/1999 | Monforte et al. |
| 5,985,260 | A | 11/1999 | Shanbrom |
| 5,998,141 | A | 12/1999 | Acton |
| 6,004,744 | A | 12/1999 | Goelet et al. |
| 6,013,431 | A | 1/2000 | Soderlund et al. |

(Continued)

FOREIGN PATENT DOCUMENTS

| | | | |
|---|---|---|---|
| EP | 0994963 A1 | | 4/2000 |
| EP | 0994963 B1 | | 4/2000 |
| GB | 2299166 A | | 9/1996 |
| GB | 2299166 B | | 9/1996 |
| WO | WO-91-08304 A1 | | 6/1991 |
| WO | WO-95/06137 A1 | | 3/1995 |

(Continued)

OTHER PUBLICATIONS

Lo et al., Increased Fetal DNA concentrations in the plasma of pregnant women carrying fetuses with Trisomy 21. Clinical Chemistry 45 (10): 1747-1751(1999).*

Ahlquist, D. A. et al. (2000). "Colorectal Cancer Screening by Detection of Altered Human DNA in Stool: Feasibility of a Multitarget Assay Panel," *Gastroenterology* 119:1219-1227.

(Continued)

*Primary Examiner*—Ethan Whisenant
(74) *Attorney, Agent, or Firm*—Michael Cronin; Whyte Hirschboeck Dudek, S.C.

(57) ABSTRACT

The invention provides a method useful for detection of genetic disorders. The method comprises determining the sequence of alleles of a locus of interest, and quantitating a ratio for the alleles at the locus of interest, wherein the ratio indicates the presence or absence of a chromosomal abnormality. The present invention also provides a non-invasive method for the detection of chromosomal abnormalities in a fetus. The invention is especially useful as a non-invasive method for determining the sequence of fetal DNA. The invention further provides methods of isolation of free DNA from a sample.

14 Claims, 33 Drawing Sheets

U.S. PATENT DOCUMENTS

| | | | |
|---|---|---|---|
| 6,017,699 | A | 1/2000 | Jordan |
| 6,033,861 | A | 3/2000 | Schafer et al. |
| 6,043,031 | A | 3/2000 | Koster et al. |
| 6,090,553 | A | 7/2000 | Matson |
| 6,100,029 | A | 8/2000 | Lapidus et al. |
| 6,110,709 | A | 8/2000 | Ausubel et al. |
| 6,117,679 | A | 9/2000 | Stemmer |
| 6,124,120 | A | 9/2000 | Lizardi |
| 6,132,970 | A | 10/2000 | Stemmer |
| 6,140,054 | A | 10/2000 | Wittwer et al. |
| 6,153,410 | A | 11/2000 | Arnold et al. |
| 6,156,504 | A | 12/2000 | Gocke et al. |
| 6,156,886 | A | 12/2000 | Sone |
| 6,165,793 | A | 12/2000 | Stemmer |
| 6,174,681 | B1 | 1/2001 | Halling et al. |
| 6,177,263 | B1 | 1/2001 | Arnold et al. |
| 6,180,372 | B1 | 1/2001 | Franzen et al. |
| 6,180,406 | B1 | 1/2001 | Stemmer |
| 6,183,958 | B1 | 2/2001 | Stanton, Jr. |
| 6,197,563 | B1 | 3/2001 | Erlich et al. |
| 6,203,989 | B1 | 3/2001 | Goldberg et al. |
| 6,214,558 | B1 | 4/2001 | Shuber et al. |
| 6,221,600 | B1 | 4/2001 | MacLeod et al. |
| 6,225,061 | B1 | 5/2001 | Becker et al. |
| 6,251,639 | B1 | 6/2001 | Kurn |
| 6,258,540 | B1 | 7/2001 | Lo et al. |
| 6,268,146 | B1 | 7/2001 | Shultz et al. |
| 6,269,957 | B1 | 8/2001 | Bowers et al. |
| 6,277,638 | B1 | 8/2001 | Stemmer |
| 6,280,949 | B1 | 8/2001 | Lizardi |
| 6,287,861 | B1 | 9/2001 | Stemmer et al. |
| 6,291,242 | B1 | 9/2001 | Stemmer |
| 6,297,053 | B1 | 10/2001 | Stemmer |
| 6,323,009 | B1 | 11/2001 | Lasken et al. |
| 6,323,030 | B1 | 11/2001 | Stemmer |
| 6,344,356 | B1 | 2/2002 | Stemmer |
| 6,357,601 | B1 | 3/2002 | Bowers et al. |
| 6,365,375 | B1 | 4/2002 | Dietmaier et al. |
| 6,372,497 | B1 | 4/2002 | Stemmer |
| 6,379,896 | B1 | 4/2002 | Stanton, Jr. |
| 6,387,621 | B1 | 5/2002 | Wittwer |
| 6,395,547 | B1 | 5/2002 | Stemmer |
| 6,413,774 | B1 | 7/2002 | Stemmer et al. |
| 6,440,706 | B1 | 8/2002 | Vogelstein et al. |
| 6,444,468 | B1 | 9/2002 | Stemmer et al. |
| 6,475,736 | B1 | 11/2002 | Stanton, Jr. |
| 6,506,561 | B1 | 1/2003 | Cheval et al. |
| 6,506,602 | B1 | 1/2003 | Stemmer |
| 6,518,065 | B1 | 2/2003 | Stemmer |
| 6,537,746 | B2 | 3/2003 | Arnold et al. |
| 6,573,098 | B1 | 6/2003 | Stemmer |
| 6,573,300 | B2 | 6/2003 | Chang et al. |
| 6,582,906 | B1 | 6/2003 | Cao et al. |
| 6,602,986 | B1 | 8/2003 | Stemmer et al. |
| 6,613,517 | B2 | 9/2003 | Michelotti |
| 6,617,137 | B2 | 9/2003 | Dean et al. |
| 6,638,722 | B2 | 10/2003 | Ji et al. |
| 6,642,034 | B2 | 11/2003 | Lizardi |
| 6,673,541 | B1 | 1/2004 | Klein et al. |
| 6,673,551 | B2 | 1/2004 | Stanton, Jr. |
| 6,703,228 | B1 | 3/2004 | Landers et al. |
| 6,730,517 | B1 | 5/2004 | Koster et al. |
| 6,780,593 | B1 | 8/2004 | Galibert et al. |
| 6,977,162 | B2 | 12/2005 | Dhallan |
| 6,995,841 | B2 | 2/2006 | Scott et al. |
| 7,208,274 | B2 | 4/2007 | Dhallan |
| 7,332,277 | B2 | 2/2008 | Dhallan |
| 2001/0051341 | A1 | 12/2001 | Lo et al. |
| 2002/0045176 | A1 | 4/2002 | Lo et al. |
| 2002/0119478 | A1 | 8/2002 | Umansky et al. |
| 2003/0044388 | A1 | 3/2003 | Dennis et al. |
| 2003/0044791 | A1 | 3/2003 | Flemington |
| 2003/0054386 | A1 | 3/2003 | Antonarakis et al. |
| 2003/0082576 | A1 | 5/2003 | Jones et al. |
| 2003/0099964 | A1 | 5/2003 | Patil et al. |
| 2003/0180746 | A1 | 9/2003 | Kmiec et al. |
| 2003/0186239 | A1 | 10/2003 | Dhallan |
| 2003/0232348 | A1 | 12/2003 | Jones et al. |
| 2003/0235834 | A1 | 12/2003 | Dunlop et al. |
| 2004/0106102 | A1 | 6/2004 | Dhallan |
| 2004/0137470 | A1 | 7/2004 | Dhallan |
| 2004/0185495 | A1 | 9/2004 | Schueler et al. |
| 2005/0037388 | A1 | 2/2005 | Antonarakis et al. |
| 2005/0095621 | A1 | 5/2005 | Sidranksy |
| 2005/0260656 | A1 | 11/2005 | Dhallan |
| 2006/0121452 | A1 | 6/2006 | Dhallan |
| 2007/0122835 | A1 | 5/2007 | Dhallan |
| 2007/0178478 | A1 | 8/2007 | Dhallan et al. |
| 2007/0196842 | A1 | 8/2007 | Dhallan |

FOREIGN PATENT DOCUMENTS

| | | | |
|---|---|---|---|
| WO | WO-98/12355 | A1 | 3/1998 |
| WO | WO-98/39474 | A1 | 9/1998 |
| WO | WO-99/54498 | A1 | 10/1999 |
| WO | WO-01/42504 | A2 | 6/2001 |
| WO | WO-01/42504 | A3 | 6/2001 |
| WO | WO-02/04672 | A2 | 1/2002 |
| WO | WO-02/04672 | A3 | 1/2002 |
| WO | WO-02/055985 | A2 | 7/2002 |
| WO | WO-02/055985 | A3 | 7/2002 |
| WO | WO-02/083839 | A2 | 10/2002 |
| WO | WO-02/083839 | A3 | 10/2002 |
| WO | WO-03/001181 | A2 | 1/2003 |
| WO | WO-03/001181 | A3 | 1/2003 |
| WO | WO-03/074723 | A2 | 9/2003 |
| WO | WO-03/074723 | A3 | 9/2003 |
| WO | WO-03/074740 | A1 | 9/2003 |
| WO | WO-03/106642 | A2 | 12/2003 |
| WO | WO-03/106642 | A3 | 12/2003 |
| WO | WO-2004/058987 | A2 | 7/2004 |
| WO | WO-2004/058987 | A3 | 7/2004 |
| WO | WO-2004/078994 | A2 | 9/2004 |
| WO | WO-2004/078994 | A3 | 9/2004 |
| WO | WO-2004/079011 | A1 | 9/2004 |
| WO | WO-2007/075836 | A2 | 7/2007 |

OTHER PUBLICATIONS

Amicucci, P. et al. (2000). "Prenatal Diagnosis of Myotonic Dystrophy Using Fetal DNA Obtained from Maternal Plasma," *Clinical Chemistry* 46(2):301-302.

Angert, R.M. et al. (Jan. 2003). "Fetal Cell-Free Plasma DNA Concentrations in Maternal Blood Are Stable 24 Hours after Collection: Analysis of First- and Third-Trimester Samples," *Clinical Chemistry* 49(1):195-198.

Anker, P. et al. (Apr. 1997). "K-ras Mutations are Found in DNA Extracted from the Plasma of Patients with Colorectal Cancer," *Gastroenterology* 112(4):1114-1120.

Anker, P. et al. eds. (Apr. 2000). "Circulating Nucleic Acids in Plasma or Serum," Table of Contents from the First International Symposium on Circulating Nucleic Acids in Plasma/Serum: Implication in Cancer Diagnosis, Prognosis, or Follow-up and in Prenatal Diagnosis, Apr. 18-20, 1999 in Menthon Saint-Bernard, France, located at <http.//www.unige.ch/LABPV/symposium/cnaps/cnaps_book.html> last visited on Mar. 27, 2001, four pages.

Anonymous, (Dec. 16, 1996). "Birth Defects: Maternal Blood Gets Put to the Test," Physician's Weekly Clinical Updates located at: <http://www.physweekly.com/archive/96/12_16_19/cu4.html> last visited on Mar. 27, 2001, one page.

Anonymous. (Dec. 17, 1998). "Strategies for the Rapid Prenatal Detection of Down's Syndrome," CMGS located at <http://www.ich.ucl/ac/uk/cmgs/downs98.html> last visited on Mar. 27, 2001, four pages.

Anonymous. (2001). "Molecular Indexing (MI) Home Page," Helix Research Institute located at <http://www.hri.co.jp/MI> last visited Apr. 16, 2001, four pages.
Anonymous. (Feb. 5, 2001). "Methods of Ultrasensitive Bioanalysis: DNA Sequencing and Indexing" Union Bay Ultrasensitive Bioanalysis Team located at <http://faculty.washington.edu/dovichi/research/application/DNA/DNASequencing.html> last visited Apr. 16, 2001, four pages.
Applied Biosystems. (Date Unknown). "AmplitTaq DNA Polymerase," located at <http://www.appliedbiosystems.com> last visited on Jan. 7, 2007, two pages.
Barnett, E.V. (Jun. 1968). "Detection of Nuclear Antigens (DNA) in Normal and Pathologic Human Fluids by Quantitative Complement Fixation," *Arthritis and Rheumatism* 11(3):407-417.
Bauer, M. et al. (Jan. 2002). "Detection of Maternal Deoxyribonucleic Acid in Umbilical Cord Plasma by Using Fluorescent Polymerase Chain Reaction Amplification of Short Tandem Repeat Sequences," *Am. J. Obstet. Gynecol.* 186:117-120.
Beer, A.E. et al. (Sep. 7, 1994). "The Biological Basis of Passage of Fetal Cellular Material into the Maternal Circulation," *Annals New York Academy of Sciences* 731:21-35.
Bennett, P.R. et al. (Aug. 26, 1993). "Prenatal Determination of Fetal RhD Type by DNA Amplification," *The New England Journal of Medicine* 329(9):607-610.
Bianchi, D.W. (1998). "Current Knowledge About Fetal Blood Cells in the Maternal Circulation," *J. Perinat. Med.* 26:175-185.
Bianchi, D.W. (1998). "Fetal DNA in Maternal Plasma: The Plot Thickens and the Placental Barrier Thins," *Am. J. Hum. Genet.* 62:763-764.
Bianchi, D.W. (2000). "A Guest Editorial: State of Fetal Cells in Maternal Blood: Diagnosis or Dilemma," *Obstetrical and Gynecological Survey* 55(11):665-667.
Bianchi, D.W. (Dec. 1995). "Prenatal Diagnosis by Analysis of Fetal Cells in Maternal Blood," *The Journal of Pediatrics* 127(6):847-856.
Bianchi, D.W. (May 2002). "Prenatal Exclusion of Recessively Inherited Disorders: Should Maternal Plasma Analysis Precede Invasive Techniques?" *Clinical Chemistry* 48(5):689-670.
Bianchi, D.W. (Sep. 2000). "Fetal Cells in the Mother: From Genetic Diagnosis to Diseases Associated with Fetal Cell Microchimerism," *European Journal of Obstetrics & Gynecology and Reproductive Biology*92:103-108.
Bianchi, D.W. et al. (1990). "Isolation of Fetal DNA From Nucleated Erythrocytes in Maternal Blood," *Proc. Natl. Acad. Sci USA* 87: 3279-3283.
Bianchi, D.W. et al. (1997). "PCR Quantitation of Fetal Cells in Maternal Blood in Normal and Aneuploid Pregnancies," *Am. J. Hum. Genet.* 61:822-829.
Bianchi, D.W. et al. (2001). "Longitudinal Fetal DNA Quantitation Studies in Maternal Cells and Plasma over a 24 Hour Period," Program Nr: 2377 located at <http://www.faseb.org/genetics/ashg00/f2377.html> last visited on Mar. 27, 2001, one page.
Bianchi, D.W. et al. (Jul. 2002). "Fetal Gender and Aneuploidy Detection Using Fetal Cells in Maternal Blood: Analysis of NIFTY I Data," *Prenatal Diagnosis* 22:609-615.
Bianchi, D.W. et al. (May 12-13, 2001). "Thoughts on the Origin of Fetal DNA in the Pregnant Woman," Abstract 3.4 In Chapter 3 "Clinical Applications of Fetal DNA in Maternal Plasma," In Abstracts, 12th Fetal Cell Workshop, *Fetal Diagn. Ther:* 16:450.
Bianchi, D.W. et al. (1996). "Male Fetal Progenitor Cells Persist in Maternal Blood for as Long as 27 Years Postpartum," *Proc. Natl. Acad. Sci. USA* 93:705-708.
Bianchard, A.P. and L. Hood (1996). "Sequence to Array: Probing the Genome's Secrets," *Nature Biotechnology* 149:1649.
Bradley, A.F. et al. (1996). "Recent Developments in Automatic DNA Sequencing," *Pure & Applied Chemistry* 68(10):1907-1912.
Brambati, B. (Sep. 7, 1994). "Prenatal Diagnosis by Isolating and Analyzing Fetal Nucleated Red Cells: Dream or Reality?" *Annals New York Academy of Sciences* 731:248-252.
Brenner, S. et al. (2000). "Gene Expression Analysis by Massively Parallel Signature Sequencing (MPSS) on Microbead Arrays," *Nature Biotechnology* 18:630-634.
Broude, N. et al. (2001). "High-Level Multiplex DNA Amplification," *Antisense & Nucleic Acid Drug Development* 11:327-332.
Brown, E. L. et al. (1979). "Chemical Synthesis and Cloning of a Tyrosine tRNA Gene," *Methods in Enzymology* 68:109-151.
Bruch, J. F. et al. (1991). "Trophoblast-Like Cells Sorted From Peripheral Maternal Blood Using Flow Cytometry: A Multiparametric Study Involving Transmission Electron Microsopy and Fetal DNA Amplification," *Prenatal Diagnosis* 11:787-798.
Byrne, B.M. et al. (Jul. 1, 2003). "Fetal DNA Quantitation in Peripheral Blood Is Not Useful as a Marker of Disease Severity in Women with Preeclampsia," *Hypertens Pregnancy* 22(2):157-164.
Cairns, P. et al. (Sep. 2001). "Molecular Detection of Prostate Cancer in Urine by GSTP1 Hypermethylation," *Clin. Can. Res.* 7:2727-2730.
Camaschella, C. et al. (Jun. 1, 1990). "Prenatal Diagnosis of Fetal Hemoglobin Lepore-Boston Disease on Maternal Peripheral Blood," *Blood* 75(11):2102-2106.
Center for Medical Genetics. (1998-2003). "Human Insertion/Deletion Polymorphisms," at <http://research.marshfieldclinicorg/genetics/>. last visited on Apr. 14, 2003, three pages.
Chen, J. et al. (2000). "A Microsphere-Based Assay for Multiplexed Single Nucleotide Polymorphism Analysis Using Single Base Chain Extension," *Genome Research* 10:549-557.
Chen, X.Q. et al. (Sep. 1996). "Microsatellite Alterations in Plasma DNA of Small Cell Lung Cancer Patients," *Nature Medicine* 2(9):1033-1035.
Cheung, V.G. et al. (Dec. 1996). "Whole Genome Amplification Using a Degenerate Oligonucleotide Primer Allows Hundreds of Genotypes to be Performed on Less Than One Nanogram of Genomic DNA," *PNAS* 93:14676-14679.
Chicurel, M. (Aug. 9, 2001). "Faster, Better, Cheaper Genotyping," *Nature* 412:580-582.
Cohen, J. (Oct. 2002). "Fetal Fortunes," *Technology Review* 54-61.
Collins, F. S. and Mansoura, M.K. (2001). "The Human Genome Project: Revealing the Shared Inheritance of All Humankind," presented at *7th Biennial Symposium on Minorities, the Medically Underserved* and *Cancer* 91(1):221-225.
Cooper, D. N. and Krawczak, M. eds. (1993). "Human Gene Mutation," *In Duchenne Muscular Dystrophy, Alzheimer's Disease, Cystic Fibrosis, and Huntington's Disease.* BIOS Scientific Publishers Limited. (Table of Contents only).
Cox, R.A. et al. (Feb. 1977). "DNA Concentrations in Serum and Plasma," *Clinical Chemistry* 23(2): 297.
Cunningham, J. et al. (Oct. 1999). "Non-Invasive RNA-Based Determination of Fetal Rhesus D Type: A Prospective Study Based on 96 Pregnancies," *British J. of Ob-Gyn* 106:1023-1028.
Cutler, D. J. et al. (2001). "High-Throughput Variation Detection and Genotyping Using Microarrays," *Genome Research* 11:1913-1925.
Davis, G.L. et al. (Jan.-Feb., 1973). "Detection of Circulating DNA by Counterimmuno-electrophoresis (CIE)," *Arthritis and Rheumatism* 16(1):52-58.
Dean, F. B. et al. (2001). "Rapid Amplification of Plasmid and Phage DNA Using Phi29 DNA Polymerase and Multiple-Printed Rolling Circle Amplification," *Genomic Research* 11:1095-99.
Dean, F.B. et al. (Apr. 16, 2002). "Comprehensive Human Genome Amplification Using Multiple Displacement Amplification," *PNAS* 99(8):5261-5266.
DeFrancesco, L. (1998). "The Next New Wave in Genome Analysis: Invader™ Assays Developed by Third Wave Technologies, Inc.," *The Scientist* 12(21):16.
Dhallan, R. et al. (Mar. 3, 2004). "Methods to Increase the Percentage of Free Fetal DNA Recovered From the Maternal Circulation," *JAMA* 291(9):1114-1119.
Ding, C. et al. (Jul. 20, 2004). "MS Analysis of Single-Nucleotide Differences in Circulating Nucleic Acids: Application to Noninvasive Prenatal Diagnosis," *PNAS* 101(29):10762-10767.
Douglas, G.W. et al. (Nov. 1959). "Trophoblast in the Circulating Blood During Pregnancy," *American Journal of Obstetrics and Gynecology* 78(5):960-973.
Drábek, J. (2001). "A Commented Dictionary of Techniques for Genotyping," *Electrophoresis* 22:1024-1045.
Durant, J. et al. (Jun. 26, 1999). "Drug-Resistance Genotyping in HIV-1 Therapy: The VIRADAPT Randomised Controlled Trial," *The Lancet* 353:2195-2199.

Durant, J. et al. (Sep. 25, 1999). "Drug-Resistant Genotyping in HIV-1 Therapy," *The Lancet* 354:1120-1122.
Egholm, M. et al. (1992). "Peptide Nucleic Acids (PNA). Oligonucleotide Analogues with an Achiral Peptide Backbone," *J. Am. Chem. Soc.* 114(5):1895-1897.
El-Naggar, A.K. et al. (2001). "Genetic Heterogeneity in Saliva from Patients with ORal Squamous Carcinomas: Implications in Molecular Diagnosis and Screening," *J. Mol. Diag.* 3(4):164-170.
Emmaunuel, S.L. et al. (1993). "Amplification of Specific Gene Products from Human Serum," *GATA* 10(6):144-146.
Erich, H. A. ed. (1989). PCR Technology: Principals and Applications of DNA Amplification, Stockton Press. pp. ix-x. (Table of Contents only).
Fan, S. et al. (Aug. 12, 1998). "Down-Regulation of BRCA1 and BRCA2 in Human Ovarian Cancer Cells Exposed to Adriamycin and Ultraviolet Radiation," *International Journal of Cancer* 77(4):600-609.
Farnia, A. et al. (1998). "Fetal Cells in Maternal Blood as a Second Non-Invasive Step for Fetal Down Syndrome Screening," *Prenat. Diagn.* 18:983-986.
Field, J.K. et al. (Jun. 1, 1999). "Genetic Alterations in Bronchial Lavage as a Potential Marker for Individuals with a High Risk of Developing Lung Cancer," *Cancer Research* 59:2690-2695.
Foreman, K. E. et al. (Jun. 1997). "In Situ Polymerase Chain Reaction-Based Localization Studies Support Role of Human Herpesvirus-8 as the Cause of Two AIDS-related Neoplasms: Kaposi's Sarcoma and Body Cavity Lymphoma." *J. Clinical Inves*, 99(12):2971-2978.
Fortina, P. et al. (2001). "DOP-PCR Amplification of Whole Genomic DNA and Microchip-Based Capillary Electrophoresis," *Methods Mol Biol.* 163:211-219.
Fournié, G.J. et al. (1993). "Plasma DNA as Cell Death Marker in Elderly Patients," *Gerontology* 39:215-221.
Fowke, K.R. et al. (1995). "Genetic Analysis of Human DNA Recovered From Minute Amounts of Serum or Plasma," *Journal of Immunological Methods* 180:45-51.
Gadkar, V. et al. (Jan. 1, 2005). "Application of Phi29 DNA Polymerase Mediated Whole Genome Amplification on Single Spores of Arbuscular Mycorrhizal (AM) Fungi," *FEMS Microbiology Letters* 242(1):65-71.
Gänshirt-Ahlert, D. et al. (May 1992). "Magnetic Cell Sorting and the Transferrin Receptor as Potential Means of Prenatal Diagnosis from Materanl Blood," *Am. J. Obstet. Geynecol.* 166:1350-1355.
Gerhold, D. et al. (1999). "DNA Chips: Promising Toys have Become Powerful Tools," *TIBS* 24:168-173.
Green, A. et al. (1990). "Direct Single Stranded Sequencing from Agarose of Polymerase Chain Reaction Products," *Nucleic Acids Res.* 18(20):6163-6164.
Grösch, S. et al. (2001). "A Rapid Screening Method for a Single Nucleotide Polymorphism (SNP) in the Human MOR Gene," *Br. J. Clin Pharmacol* 52:711-714.
Gusev, Y. et al. (Jul. 2001). "Technical Advance: Rolling Circle Amplification—A New Approach to Increase Sensitivity for Immunohistochemistry and Flow Cytometry," *American Journal of Pathology* 159 (1):63-69.
Hahn, S. et al. (May 12-13, 2001). "An Examination of Fetal Cells, Free Fetal DNA and Fetal Cell Culture: The Basel Experience," Abstract 3.2 In Chapter 3 "Clinical Applications of Fetal DNA in Maternal Plasma," In Abstracts, 12th Fetal Cell Workshop, *Fetal Diagn. Ther.* 16:449.
Hahn, S. et al. (Sep. 2002). "Prenatal Diagnosis Using Fetal Cells and Cell-Free Fetal DNA in Maternal Blood: What is Currently Feasible?" *Clinical Obstetrics and Gynecology* 45(3):649-656.
Harrington, J.J. et al. (1994). "Functional Domains within FEN-1 RAD2 Define a Family of Structure-specific Endonucleases: Implications for Nucleotide Excision Repair," *Gene and Development* 8:1344-1355.
Hedenfalk, I. et al. (Feb. 22, 2001). "Gene-Expression Profiles in Hereditary Breast Cancer," *New Engl. Jnl. Med.* 344(8):539-548.
Heinemann, J.A. et al. (Apr. 2000). "New Hypotheses on the Material Nature of Horizontally Mobile Genes," *Annals New York Academy of Sciences* 906:169-186..
Herzenberg, L.A. et al. (1979). "Fetal Cells in the Blood of Pregnant Women: Detection and Enrichment by Fluorescence-Activated Cell Sorting," *Proc. Natl. Acad. Sci. USA* 76(3):1453-1455.
Hielm, S. et al. (Feb. 1998). "Genomic Analysis of *Clostridium Botulinum* Group II by Pulsed-Field Gel Electrophoresis," *Applied and Environmental Microbiology* 64(2):703-708.
Hogervorst, F.B.L. et al. (1995)l "Rapid Detection of BRCA1 Mutations by the Protein Truncation Test," *Nature Genetics* 10:208-212.
Holzgreve, W. et al. (2000). "Fetal Cells in Cervical Mucus and Maternal Blood," *Bailliere's Clinical Obstetrics and Gynaecology* 14(4):709-722.
Holzgreve, W. et al. (Jun. 2001). "Prenatal Diagnosis Using Fetal Cells and Free Fetal DNA in Maternal Blood," *Clinical Perinatology* 28(2):353-365.
Hosono, S. et al. (Apr. 14, 2003). "Unbiased Whole-Genome Amplification Directly From Clinical Samples," *Genome Research* 13(5)954-964.
Hsu, T. M. et al. (2001). "Genotyping Single-Nucleotide Polymorphisms by the Invader Assay with Dual-Color Fluorescence Polarization Detection," *Clinical Chemistry* 47(8):1373-1377.
Huber, M. et al. (2001). "Detection of Single Base Alterations in Genomic DNA by Solid Phase Polymerase Chain Reaction on Oligonucleotide Microarrays," *Analytical Biochemistry* 299:24-30.
Hughes, G.R. et al. (Mar.-Apr. 1971). "The Release of DNA into Serum and Synovial Fluid," *Arthritis and Rheumatology* 14(2):259-266.
Human Gene Mutation Database (HGMD). (Date Unknown). Located at <http:archive.uwcm.ac.uk/uwcm/mg/hgmd0.html> last visited on Sep. 20, 2004. 3 pages total.
Imamura, A. et al. (1996). "Short Communication: Prenatal Diagnosis of Adrenoleukodystrophy by Means of Mutation Analysis," *PreNatal Diagnosis* 16:259-261.
Innis, M. A. ed., (1990). PCR Protocols: A Guide to Methods and Applications. Academic Press, Inc. pp. v-x. (Table of Contents only).
International Search Report mailed on Jul. 17, 2003, for PCT Patent Application No. PCT/US03/06376 filed on Feb. 28, 2003, four pages.
International Search Report mailed on Jul. 20, 2004 for PCT patent application No. PCT/US03/27308 filed Aug. 29, 2003, eight pages.
International Search Report mailed on Jun. 14, 2005 for PCT patent application No. PCT/US04/06337 filed Mar. 1, 2004, five pages.
International Search Report mailed on Sep. 02, 2003, for PCT patent application No. PCT/US03/06198 filed Feb. 28, 2003, nine pages.
International Search Report mailed on Jun. 14, 2005 for PCT patent application No. PCT/US04/06337 filed Mar. 1, 2004, five pages.
James, P. et al. (1994). "Protein Identification in DNA Databases by Peptide Mass Fingerprinting," *Protein Science* 3:1347-1350.
Kamm, R.C. et al. (1972). "Nucleic Acid Concentrations in Normal Human Plasma," *Clinical Chemistry* 18(6):519-522.
Kamm, R.C. et al. (1975). "Plasma Deoxyribonucleic Acid Concentrations of Women in Labor and Umbilical Cords," *American Journal of Obstetrics and Gynecology* 121(1):29-31.
Kandpal, R.P. et al. (1990). "Selective Enrichment of a Large Size Genomic DNA Fragment by Affinity Capture: An Approach for Genome Mapping," *Nucleic Acids Res.* 18(7):1789-1795.
Kaneoka, H. et al. (1991). "Solid-Phase Direct DNA Sequencing of Allele-Specific Polymerase Chain Reaction-Amplified HLA-DR Genes," *Biotechniques* 10(1):30,32 and 34 only.
Kang, A. et al. (1999). "Fetal Cells in Maternal Blood: Their Role in Non-Invasive Prenatal Diagnosis and in the Etiology of Certain Diseases," ("Fetale Zellen im mütterlichen Blut—ihre Bedeutung für eine nicht-invasive pränatale Diagnostik und bei der Ä tiologie bestimmter Erkrankugen.") *Schweiz Med. Wochenschr* 129:1470-1743. English Translation and original language article.
Kawasaki, E.S. (1990). "Sample Preparation From Blood, Cells and Other Fluids," Chapter 18 In *PCR Protocol: A Guide to Methods and Applications.* Innis, M.A. et al., eds., Academic Press, Inc., pp. 146-152.
Kinzler, K.W. et al. (Aug. 9, 1991). "Identification of FAP Locus Genes from Chromosome 5q21," *Science* 253:661-665.
Kosel, S. et al. (May 8, 2001). "Inter-Laboratory Comparison of DNA Preservation in Archival Paraffin-Embedded Human Brain Tissue from Participating Centres on Four Continents," *Neurogenetics* 3(3):164-170.

Kuo, P-L. (1999). "Fetal Cell Isolation From Maternal Blood—Clinical and Biological Implications," *Adv. Obstet. Perinatol.* 10(1):15-24.
Kusaka, T. et al. (Oct. 2000). "Analysis of K-ras Codon 12 Mutations and P53 Overexpression in Colorectal Nodule-Aggregating Tumors," *Journal of Gastroenterology and Hepatology* 15(10):1151-1157.
Kwak, J.Y.H. et al. (Sep. 7, 1994). "Biological Basis of Fetoplacental Antigenic Determinants in the Induction of the Antiphospholipid Antibody Syndrome and Recurrent Pregnancy Loss," *Annals New York Academy of Sciences* 731:242-245.
Kwok, P-Y. (2001). "Methods for Genotyping Single Nucleotide Polymorphisms," *Annual Review of Genomics and Human. Genetics* 2:235-258.
Lagona, F. et al. (1998). "Multiple Testing in Fetal Gender Determination from Maternal Blood by Polymerase Chain Reaction," *Human Genetics* 102:687-690.
Lagona, F. et al. (Apr. 2000). "Fetal DNA Analysis from Maternal Plasma and Nucleated Blood Cells," *Annals New York Academy of Sciences* 906:156-160.
Lander, E.S. et al. (2001). "Initial Sequencing and Analysis of the Human Genome," *Nature* 409:860-921.
Lee, M.-S. et al. (1989). "Detection of Two Alternative bcr/abl mRNA Junctions and Minimal Residual Disease in Philadelphia Chromosome Positive Chronic Myelogenous Leukemia by Polymerase Chain Reaction," *Blood* 73(8):2165-2170.
Lee, T. et al. (Nov. 2002). "Down Syndrome and Cell-Free Fetal DNA in Archived Maternal Serum," *Am. J. Obstet. Gynecol.* 187:1217-1221.
Leon, S.A. et al. (1977). "Free DNA in the Serum of Reheumatoid Arthritis Patients," *Journal of Rheumatology* 4(2):139-143.
Leon, S.A. et al. (Mar. 1977). "Free DNA in the Serum of Cancer Patients and the Effect of Therapy," *Cancer Research* 37:646-650.
Li, J. et al. (1999). "Single Nucleotide Polymorphism Determination using Primer Extension and Time-of-Flight Mass Spectrometry," *Electrophoresis* 20:1258-1265.
Liloglou, T. et al. (2001). "Cancer-Secific Genomic Instability in Bronchial Lavage: A Molecular Tool for Lung Cancer Detection," *Cancer Research* 61:1624-1628.
Lindblad-Toh, K. et al. (2000). "Loss of-Heterozygoisty Analysis of Small-Cell Lung Carcinomas Using Single-Nucleotide Polymorphism Arrays," *Nature Biotechnology* 18:1001-1005.
Livak, K.J. et al. (1995). "Oligonucleotides With Fluorescent Dyes at Opposite Ends Provide a Quenched Probe System Useful for Detecting PCR Product and Nucleic Acid Hybridization," *PCR Methods and Applications* 4:357-362.
Lo, Y.M. D. et al. (Sep. 7, 1994). "Strategies for the Detection of Autosomal Fetal DNA Sequence from Maternal Peripheral Blood," *Annals New York Academy of Sciences* 731:204-213.
Lo, Y.M.D. (Apr. 2000). "Fetal DNA in Maternal Plasma," *Annals of New York Academy of Sciences* 906:141-147.
Lo, Y.M.D. (Dec. 1994) "Non-Invasive Prenatal Diagnosis Using Fetal Cells in Maternal Blood," *Journal of Clinical Pathology* 47(12):1060-1065.
Lo, Y.M.D. (1999). "Fetal RhD Genotyping From Maternal Plasma," *Annals of Medicine* 31(5):308-312.
Lo, Y.M.D. (1999). "Rapid Clearance of Fetal DNA from Maternal Plasma," *Am. J. Hum. Genet.* 64:218-224.
Lo, Y.M.D. (Dec., 2000). "Fetal DNA in Maternal Plasma: Biology and Diagnostic Applications," *Clinical Chemistry* 46(12):1903-1906.
Lo, Y.M.D. (Jan. 2003). "Fetal DNA in Maternal Plasma/Serum: The First 5 Years," *Pediatric Research* 53(1):16-17.
Lo, Y.M.D. (Jun. 2001). "Fetal DNA in Maternal Plasma: Application to Non-Invasive Blood Group Genotyping of the Fetus," *Transfus. Clin. Biol.* 8(3):306-310.
Lo, Y.M.D. (May 12-13, 2001). "Fetal DNA in Maternal Plasma," Abstract 3.1 In Chapter 3 "Clinical Applications of Fetal DNA in Maternal Plasma," In Abstracts, 12th Fetal Cell Workshop, *Fetal Diagn. Ther.* 16:448-449.
Lo, Y.M.D. (Sep. 7, 1994). "An Improved PCR-Based System for Prenatal Sex Determination from Maternal Peripheral Blood," *Annals New York Academy of Sciences* 731:214-216.
Lo, Y.M.D. (Sep. 7, 1994). "Prenatal Determination of Fetal Rhesus D Status by DNA Amplification of Peripheral Blood of Rhesus-Negative Mothers," *Annals New York Academy of Sciences* 731:229-236.
Lo, Y.M.D. et al. (1994). "Detection of Fetal RhD Sequence From Peripheral Blood of Sensitized RhD-Negative Women," *British Journal of Hematology* 87:658-660.
Lo, Y.M.D. et al. (1998). "Quantitative Anaylysis of Fetal DNA in Maternal Plasma and Serum: Implications for Noninvasive Prenatal Diagnosis," *Am. J. Hum. Genet.* 62:768-775.
Lo, Y.M.D. et al. (1999). "Increased Fetal DNA Concentrations in the Plasma of Pregnant Women Carrying Fetuses with Trisomy 21," *Clinical Chemistry* 45(10):1747-1751.
Lo, Y.M.D. et al. (Aug. 16, 1997). "Presence of Fetal DNA in Maternal Plasma and Serum," *The Lancet* 350:485-487.
Lo, Y.M.D. et al. (Dec. 1, 1996). "Two-Way Cell Traffic Between Mother and Fetus: Biologic and Clinical Implications," *Blood* 88(11):4390-4395.
Lo. Y.M.D. et al. (Dec. 9, 1989). "Prenatal Sex Determination by DNA Amplification From Maternal Peripheral Blood," *The Lancet* 2:1363-1365.
Lo, Y.M.D. et al. (Jun. 16, 1990). "Detection of Single-Copy Fetal DNA Sequence From Maternal Blood," *The Lancet* 335:1463-1464.
Lockhart, D. J. and Winzeler, E.A. (2000). "Genomics, Gene Expression and DNA Arrays," *Nature* 405:827-836.
Longo, M.C. et al. (1990). "Use of Uracil DNA Glycosylase to Control Carry-Over Contamination in Polymerase Chain Reactions," *Gene* 125-128.
Maiwald, M. et al. (May 1995). "Evaluation of the Detection of Borrelia Burgdorferi DNA in Urine Samples by Polymerase Reaction," *Infection* 23(3):173-179.
Mao, L. et al. (Feb. 2, 1996). "Molecular Detection of Primary Bladder Cancer by Microsatellite Analysis," *Science* 271:659-662.
Martin, M. et al. (Feb. 1992). "A Method for Using Serum or Plasma as a Source of DNA for HLA Typing," *Human Immunology* 33(2):108-113.
Maxam, A. M. and Gilbert, W. (1977). "A New Method for Sequencing DNA," *Proc. Natl. Acad. Sci.* 74(2):560-564.
McPherson, M. J. et al. eds., (1991). PCR: A Practical Approach, IRL Press at Oxford University Press. six pages. (Table of Contents).
Miller, D. ed. (Aug. 16, 1996). "Notes on Fifth Fetal Cell Workshop," Amsterdam, May 3, 1996, published and located at <http://iubio.bio.indiana.edu> last visited on Mar. 27, 2001, four pages.
Mueller, U.W. et al. (Jul. 28, 1990). "Isolation of Fetal Trophoblast Cells From Peripheral Blood of Pregnant Women," *The Lancet* 336:197-200.
Mulcahy, H.E. et al. (Sep. 7, 1996). "Cancer and Mutant DNA in Blood Plasma," *The Lancet* 348(9028):628.
Muller, F. et al. (Mar. 2000). "Parental Origin of the Extra Chromosome in Prenatally Diagnosed Fetal Trisomy 21," *Hum. Genet.* 106:340-344.
Munoz, N. et al. (2003). "Epidemiologic Classification of Human Papillomavirus Types Associated with Cervical Cancer," *New England Jnl. Med.* 348:518-527.
Narang, S. A. et al. (1979). "Improved Phosphotriester Method for the Synthesis of Gene Fragments," *Methods in Enzymology* 68:90-98.
Nawroz, H. et al. (Sep. 1996). "Microsatellite Alterations in Serum DNA of Head and Neck Cancer Patients," *Nature Medicine* 2(9):1035-1037.
Newman, L. (Nov.-Dec. 2002). "Ductal Lavage for Breast Cancer Risk Assessment," *Cancer Control* 9(6):473-479.
Nielsen, P.E. et al. (1991). "Sequence-Selective Recognition of DNA by Strand Displacement with a Thymine-Substituited Polyamide," *Science* 254:1497-1500.
Oliphant, A. et al. (Jun. 2002). "BeadArray™ Technology: Enabling An Accurate, Cost-Effective Approach to High-Throughput Genotyping," *Biotechniques* 32(Suppl):S56-S61.
Orban, T. et al. (2000). "Sequence Alterations Can Mask Eash Other's Presence during Screening with SSCP or Heterodulplex Analysis: BRCA Genes as Examples," *Bio Techniques* 29(1):94-98.

Orchid Biosciences Profiling Genetic Uniqueness. (2003). located at <www.orchidbio.com/products/lsg/products/snpstream.asp.> Last visited on Jan. 19, 2004, one page.

Pertl, B. et al. (Jan. 6, 2000). "Detection of Male and Female Fetal DNA in Maternal Plasma by Multiplex Fluorescent Polymerase Chain Reaction Amplification of Short Tandem Repeats," *Hum. Genet.* 106:45-49.

Pertl, B. et al. (Mar. 27, 2001). "Detection of Male and Female Fetal DNA in Maternal Plasma by Multiplex Fluorescent Polymerase Chain Reaction Amplification of Short Tandem Repeats,"located at <http://link.springer.de/link/service/journals/00439/contents/99/00166/s00439900166ch002.html> last visited on Mar. 27, 2001, one page.

Pertl. B. et al. (Mar. 27, 2001). "Detection of Male and Female Fetal DNA in Maternal Plasma by Multiplex Fluorescent Polymerase Chain Reaction Amplification of Short Tandem Repeats (STRs)," Program Nr: 410 located at <http://www.faseb.org.genetics/ashg99/f410.html> last visited Mar. 27, 2001, one page.

Pertl. B. et al. (May 14, 1994). "Rapid Molecular Method for Prenatal Detection of Down's Syndrome," *The Lancet* 343:1197-1198.

Pertl. B. et al. (Oct. 1999). "First Trimester Prenatal Diagnosis: Fetal Cells in the Maternal Circulation," *Seminars in Perinatology* 23(5):393-402.

Pertl. B. et al. (Sep. 2001). "Fetal DNA in Maternal Plasma: Emerging Clinical Applications," *Obstetrics and Gynecology* 98(3):483:490.

Pierce Catalog and Handbook, Life Science & Analytical Research Products. located at <www.pierenet.com/products.> Last visited on Jan. 22, 2004, two pages.

Poch, M. T. et al. (1997). "Sth1321, A Novel Class-IIS Restriction Endonuclease of Streptococcus Thermophilus ST132," *Gene* 195:201-206.

Poon, L.L.M. (2000). "Presence of Fetal RNA in Maternal Plasma," *Clin. Chem.* 46(11):1832-1834.

Poon, L.L.M. et al. (Nov. 2001). "Circulating Fetal DNA in Maternal Plasma," *Clinica Chimmica Acta* 313:151-155.

Poon, L.L.M. et al. (Nov. 25, 2000). "Prenatal Detection of Fetal Down's Syndrome from Maternal Plasma," *The Lancet* 356:1819-1820.

Premier Biosoft Interanational (2004). "Software to Accelerate Molecular Biology Research," located at <http://premierbiosoft.com/netprimer/netprtlaunch.html> Last visited on Jan. 19, 2004, one page.

Promega, Inc. (Dec. 1999). "Wizard® DNA Clean-Up System," *Promega Corp. Technical Bulletin* TB141:1-4.

Ramster, B. (Jul. 2, 2001). "IVF Screening for Down's Syndrome Flawed, Say Experts," BioMedNet located at <http://news.bmn,com/news/story?=010703&story> last visited Jul. 3, 2001, one page.

Raptis, L. et al. (Dec. 1980). "Quantitation and Characterization of Plasma DNA in Normals and Patients with Systemic Lupis Erythematosus," *Journal of Clinical Investigation* 66:1391-1399.

Riordan, J. R. et al. (1989). "Identification of the Cystic Fibrosis Gene: Cloning and Characterization of Complementary DNA," *Science*245(4922):1066-1073.

Roest, P.A.M. et al. (1993). "Protein Truncation Test (PTT) for Rapid Detection of Translation-Terminating Mutations," *Human Molecular Genetics* 2(10):1719-1721.

Rommens, J.M. et al. (1989). "Identification of the Cystic Fibrosis Gene: Chromosome Walking and Jumping," *Science* 245:1059-1065.

Ryan, B. M. et al. (2003). "A Prospective Study of Circulationg Mutant KRAS2 in the Serum of Patients with Colorectal Neoplasia: Strong Prognostic Indicator in Postoperative Follow Up," *Gut.* 52:101-108.

Saiki et al. (1988). "Diagnosis of Sickle Cell Anemia and Beta-Thalassemia with Enzymatically Amplified DNA and Non-Raadioactive Allele-Specific Oligonucleotide Probes," *New England Journal of Medicine* 319(9):537-541.

Saito, H. et al. (Sep. 30, 2000). "Prenatal DNA Diagnosis of a Single-Gene Disorder from Maternal Plasma," *The Lancet* 356:1170.

Sambrook, J. and Russell, D. W. eds. (2001). *Molecular Cloning Laboratory Manual.* Third Edition, Cold Spring Harbor Laboratory Press. vol. 2, pp. v-xx. (Table of Contents only).

Samura, O. et al. (Jul. 2000). "Female Fetal Cells in Maternal Blood: Use of DNA Polymorphisms to Prove Origin," *Hum. Genet.* 107:28-32.

Samura, O. et al. (Sep. 2001). "Diagnosis of Trisomy 21 in Fetal Nucleated Erythrocytes from Maternal Blood by Use of Short Tandem Repeat Sequences," *Clinical Chemistry* 47(9):1622-1626.

Sanger, F. et al. (1977). "DNA Sequencing with Chain-Terminating Inhibitors," *PNAS USA* 74(12):5463-5467.

Shah, J. S. et al. (1995). "Q-Beta Replicase-Amplified Assay for Detection of Mycobacterium Tuberculosis Directly from Clinical Specimens," *Journal of Clinical Microbiology* 33(6):1435-1441.

Shapero, M. H. et al. (2001). "SNP Genotyping by Multiplexed Solid-Phase Amplification and Fluorescent Minisequencing," *Genome Research* 11:1926-1934.

Shapiro, B. et al. (1983). "Determination of Circulating DNA Levels in Patients with Benign or Malignant Gastrointestinal Disease," *Cancer* 51:2116-2120.

Shi, M.M. (2001). "Enabling Large-Scale Pharmacogenetic Studies by High-Throughput Mutation Detection and Genotyping Technologies," *Clinical Chemistry* 47(2):164-172.

Sibson, D. R. et al. (2001). "Molecular Indexing of Human Genomic DNA," *Nucleic Acids Research* 29(19):1-10.

Sidransky, D. (Apr. 2000). "Circulating DNA: What We Know and What We Need to Learn," In Circulating Nucleic Acids in Plasma or Serum, *Annals New York Academy of Sciences* 906:1-4.

Simpson, J.L. et al. (1994). "Isolating Fetal Cells in Maternal Circulation for Prenatal Diagnosis," *Prenatal Diagnosis* 14:1229-1242.

Simpson, J.L. et al. (Mar. 3, 2004). "Cell-Free Fetal DNA in Maternal Blood," *JAMA* 291(9):1135-1137.

Simpson, J.L. et al. (Sep. 7, 1994). "Fetal Cells in Maternal Blood. Overview and Historical Perspetive," *Annals New York Academy of Sciences* 731:1-8.

Siva, S.C. et al. (Feb. 3, 2003). "Evaluation of the Clinical Usefulness of Isolation of Fetal DNA from the Maternal Circulation," *Australian and New Zealand Journal of Obstetrics and Gynecology* 43(1):10-15.

Small, K. M. et al. (Oct. 2002). "Synergistic Polymorphisms of β1-and a2c-Adrenergic Receptors and The Risk of Congestive Heart Failure," *New Eng. Jnl Med.* 347(15):1135-1142.

Smid, M. et al. (1999). "Evaluation of Different Approaches for Fetal DNA Analysis from Maternal Plasma and Nucleated Blood Cells," *Clinical Chemistry* 45(8):1570-1572.

Smid, M. et al. (2001). "Quantitative Analysis of Fetal DNA in Maternal Plasma in Pregnancies Affected by Insulin-Dependent Diabetes mellitus (IDDM)," Abstract 3.3 In Chapter 3 "Clinical Applications of Fetal DNA in Maternal Plasma," In Abstracts, 12th Fetal Cell Workshop, *Fetal Diagn. Ther.* 16:449-450.

Smirnov, D.A. et al. (May 2004). "Method for Manufacturing Whole-Genome Microarrays by Rolling Circle Amplification," *Genes, Chromosomes, & Cancer* 40(1):72-77.

SNP Entry Report for HC21S00007. (Date Unknown). located at <http://csnp.unige.ch/cgi-bin/csnp_fetch?entry=HC21S00007> last visited on Sep. 27, 2004, one page.

SNP Entry Report for HC21S00027. (Date Unknown). located at <http://csnp.unige.ch/cgi-bin/csnp_fetch?html &entry=HC21S00027> last visited on Sep. 27, 2004, one page.

SNP Entry Report for HC21S00131. (Date Unknown). located at <http://csnp.unige.ch/cgi-bin/csnp_fetch?db+csnp&format=html &entry=HC21S00131> last visited on Sep. 27, 2004, one page.

SNP Entry Report for HC21S00340. (Date Unknown). located at <http://csnp.unige.ch/cgi-bin/csnp_fetch?entry=HC21S00340> last visited on Sep. 27, 2004, 2 pages.

SNP Report for TSC 0034767. (Mar. 2000). http://snp.cshl.org/snpsearch.shtml. Last visted on Aug. 12, 2003, 2 pages.

SNP Report for TSC 0087315. (Aug. 2000). http://snp.cshl.org/snpsearch.shtml. Last visited on Apr. 14, 2003, 2 pages.

SNP Report for TSC 0095512. (Aug. 2000). http://snp.cshl.org/snpsearch.shtml. Last visited on Apr. 14, 2003, 2 pages.

SNP Report for TSC 0115603. (Apr. 2000). http://snp.cshl.org/snpsearch.shtml. Last visited on Aug. 12, 2003, 2 pages.

SNP Report for TSC 0195492. (Aug. 2000). http://snp.cshl.org/snpsearch.shtml. Last visited on Aug. 12, 2003, 2 pages.

SNP Report for TSC 0197279. (Aug. 2000). http://snp.cshl.org/snpsearch.shtml. Last visited on Aug. 12, 2003, 2 pages.
SNP Report for TSC 0198557. (Aug. 2000). http://snp.cshl.org/snpsearch.shtml. Last visited on Aug. 12, 2003, 2 pages.
SNP Report for TSC 0200347. (Aug. 2000). http://snp.cshl.org/snpsearch.shtml. Last visited on Sep. 10, 2003, 2 pages.
SNP Report for TSC 0214366. (Oct. 2000). (http://snp.cshl.org/snpsearch.shtml. Last visited on Dec. 30, 2003, 2 pages.
SNP Report for TSC 0264580. (Aug. 2000). http://snp.cshl.org/snpsearch.shtml. Last visited on Apr. 14, 2 pages.
SNP Report for TSC 0309610. (Aug. 2000). http://snp.cshl.org/snpsearch.shtml. Last visited on Sep. 10, 2003, 2 pages.
SNP Report for TSC 0413944. (Aug. 2000). http://snp.cshl.org/snpsearch.shtml. Last visited on Apr. 14, 2003, 2 pages.
SNP Report for TSC 0597888. (Oct. 2000). http://snp.cshl.org/snpsearch.shtml. Last visited on Aug. 12, 2003, 2 pages.
SNP Report for TSC 0607185. (Oct. 2000). http://snp.cshl.org/snpsearch.shtml. Last visited on Sep. 11, 2003, 2 pages.
SNP Report for TSC 0813773. (Oct. 2000). http://snp.cshl.org/snpsearch.shtml. Last visited on Aug. 12, 2003, 2 pages.
SNP Report for TSC 0837969. (Dec. 2000). http://snp.cshl.org/snpsearch.shtml. Last visited on Aug. 12, 2003, 2 pages.
SNP Report for TSC 1130902. (May 2001). http://snp.cshl.org/snpsearch.shtml. Last visited on Aug. 12, 2003, 2 pages.
Spafford, M.F. et al. (Mar. 2001). "Detection of Head and Neck Squamous Cell Carcinoma Among Exfoliated Oral Mucosal Cells by Microsatellite Analysis," *Clinical Cancer Research* 7:607-612.
Steele, C.D. et al. (Dec. 1996). "Prenatal Diagnosis Using Fetal Cells Isolated From Maternal Peripheral Blood: A Review," *Clinical Obstetrics and Gynecology* 39(4):801-813.
Stratagene Corporation. (1988). "Gene Characterization Kits," *The Stratagene Catalog,* p. 39.
Strickland, S. et al. (Oct. 30, 1992). "Invasion of the Trophoblasts," *Cell* 71:355-357.
Stroun, M. et al. (Apr. 2000). "The Origin and Mechanism of Circulating DNA," *Annals New York Academy of Sciences* 906:161-168.
Stults, J. R. et al. (2001). "Application of the 5' Fluorogenic Exonudease Assay (TaqMan) for Quantitative Ribosomel DNA and rNA Anaylsis in Sediments," *Applies and Enivormental Microbiology* 67(6):2781-2789.
Subramanian, G. et al. (2001) "Implications of the Human Genome for Understanding Human Biology and Medicine," *JAMA* 286(18):2296-2307.
Supplementary European Search Report mailed on Jan. 10, 2007 for EP Application No. 03 74 9291.5, five pages.
Supplementary European Search Report mailed on Jan. 22, 2007 for EP Application No. 04 71 6171.6, five pages.
Supplementary European Search Report mailed on Jul. 12, 2006 for EP Application No. 03 71 3793.2, three pages.
Supplementary European Search Report mailed on Jul. 4, 2006 for EP Application No. 03 74 3737.3, three pages.
Syvänen, A-C. (1999). "From Gels to Chips: "Minisequencing"Primer Extension for Analysis of Point Mutations and Single Nucleotide Polymorphisms," *Human Mutation* 13:1-10.
Szybalski, W. et al. (1991). "Class-IIS Restriction Enzymes—A Review," *Gene* 100:13-16.
Tan, E.M. et al. (1966). "Deoxyribonucleic Acid (DNA) and Antibodies to DNA in the Serum of Patients with Systemic Lupis Erythematosus," *Journal of Clinical Investigation* 45(11):1732-1740.
Tang, N.L.S. et al. (1999). "Detection of Fetal-Derived Paternally Inherited X-Chromosome Polymorphisms in Maternal Plasma," *Clinical Chemistry* 45(11):2033-2035.
Taton, T.A. et al. (2000). "Scanometric DNA Array Detection with Nanoparticle Probes," *Science* 289:1757-1760.
Telenius, H. et al. (1992). "Degenerate Oligonucleotide-Primed PCR: General Amplification of Target DNA by a Single Degenerate Primer," *Genomics* 13:718-725.
Thomas, M.R. et al. (Sep. 7, 1994). "The Time of Appearance, and Quantitation, of Fetal DNA in the Maternal Circulation," *Annals New York Academy of Sciences* 731:217-225.
Tockman, M. (Jan. -Feb. 2000). "Advances in Sputum Analysis for Screening and Early Detection of Lung Cancer," *Cancer Control* 7(1):19-24.
Traverso, G. et al. (Jan. 31, 2002). "Detection of APC Mutations in Fecal DNA from Patients With Colorectal Tumors," *New England Journal of Medicine* 346(5):311-320.
Tsao, J. et al. (Sep. 1994). "Further Evidence That One of the Earliest Alterations in Colorectal Carcinogenesis Involves APC," *Am. J. Pathol.* 145(3): 531-534.
Tsongalis, G. J. et al. (2001). "READIT: A Novel Technology Used in the Interrogation of Nucleic Acid Sequences for Single-Nucleotide Polymorphisms," *Experimental and Molecular Pathology* 71:222-225.
Ugozzoli, L. et al. (1992). "Detection of Specific Alleles by Using Allele-Specific Primer Extension Followed by Capture on Solid Support," *GATA* 9(4):107-112.
Uitto, J. et al. (Aug. 2003). "Probing the Fetal Genome: Progress in Non-Invasive Prenatal Diagnosis," *Trends in Molecular Medicine* 9(8):239-243.
Unrau, P. et al. (Aug. 5, 1994) "Non-Cloning Amplification of Specific DNA Fragments from Whole Genomic DNA Digests Using DNA 'Indexers'," *Gene* 145(1):163-169.
Utting, M. et al. (Jan. 2002). "Micorsatellite Analysis of Free Tumor DNA in Urine, Serum, and Plasma of Patients: A Minimally Invasive Method for the Detection of Bladder Cancer," *Clinical Cancer Res.* 8:35-40.
van der Luijt, R. et al. (1994). "Rapid Detection of Translation-Terminating Mutations at the Ademomatous Polyposis Coli (APC) Gene by Direct Protein Truncation Test," *Genomics* 20:1-4.
van Rhijin, Bas, W. G. et al. (2003). "Combined Microsatellite and FGFR3 Mutation analysis Enables a Highly Sensitive Detection of Urothelial Cell Carcinoma in Voided Urine," *Clincial Cancer Res.* 9:257-263.
van Wijk, I.J. et al. (2000). "Detection of Apoptotic Fetal Cells in Plasma of Pregnant Women," *Clinical Chemistry* 46(5):729-731.
Velculescu, V.E. et al. (Oct. 2000). "Analysing Uncharted Transcriptomes with SAGE," *TIG* 16(10):423-425.
Venter, J.C. et al. (2001). "The Sequence of the Human Genome," *Science* 291:1304-1351. (Erratum attached, 1 page Jun. 2001.
Verma, L. et al. (Jul. 4, 1998). "Rapid and Simple Prenatal DNA Diagnosis of Down's Syndrome," *The Lancet* 352:9-11.
Walknowska, J. et al. (1969). "Practical and Theoretical Implications of Fetal/Maternal Lymphocyte Transfer," *The Lancet* 1:1119-1122.
Wallace, R.W. (1997). "DNA on a Chip: Serving Up the Genome for Diagnostics and Research," *Molecular Medicine Today* 3:384-389.
Wang, D. G. et al. (1998). "Large-Scale Identification, Mapping, and Genotyping of Single-Nucleotide Polymorphisms in the Human Genome," *Science* 280:1077-1082.
Wang, G. et al. (May 21, 2004). "Balanced-PCR Amplification Allows Unbiased Identification of Genomic Copy Changes in Minute Cell and Tissue Samples," *Nucleic Acids Research* 32(9): e76, 10 pages.
Wataganara, T. et al. (Jan. 2003). "Maternal Serum Cell-Free Fetal DNA Levels are Increased in Cases of Trisomy 13 but not Trisomy 18," *Hum. Genet.* 112(1):204-208.
Waterston, R.H. and McPherson, J.D. (2001). "A Map of Human Genome Sequence Variation Containing 1.42 Million Single Nucleotide Polymorphisms," *Nature* 409:928-933.
Wells, D. et al. (1999). "Detailed Chromosomal and Molecular Genetic Analysis of Single Cells by Whole Genome Amplification and Comparative Genomic Hybridisation," *Nucelic Acids Res.* 27(4):1214-1218.
Welsh K. and Bunce, M. (1999). "Molecular Typing for the MHC with PCR-SSP," *Reviews in Immunogenetics* 1:157-176.
Westin, L. et al. (2000). "Anchored Multiplex Amplification on a Microelectronic Chip Array," *Nature Biotechnology* 18:199-204.
Wilson, K. S. et al. (Oct. 2002). "Differential Gene Expression Patterns in HER2/neu-Positive and -Negative Breast Cancer Cell Lines and Tissues," *Am. J. Pathol.* 161 (4):1171-1185.
Written Opinion mailed on Jun. 14, 2005 for PCT patent application No. PCT/US04/06337 filed Mar. 1, 2004, six pages.
Written Opinion mailed on Mar. 10, 2005 for PCT patent application No. PCT/US03/06376 filed Feb. 28, 2003, three pages.

Written Opinion mailed on May 23, 2005 for PCT patent application No. PCT/US03/06198 filed Feb. 28, 2003, eight pages.
Xie, D. et al. (Mar. 1, 2000). "Population-Based, Case-Control Study of HER2 Genetic Polymorphism and Breast Cancer Risk," *J. Natl. Cancer Institute* 92(5):412-417.
Yamamoto et al. (Mar. 1, 1994). "Anti-ssDNA and dsDNA Antibodies in Preeclampsia," *Asia Oceania J. Obstet Gynaecol.* 20(1):93-99.
Zhang, L. et al. (Jul. 1992). "Whole Genome Amplification From a Single Cell: Implications for Genetic Analysis," *Proc. Nat. Acad. Sci.* 89:5847-5851.
Zhen, D.K. et al. (1998). "Poly-Fish: A Technique of Repeated Hybridizations That Improves Cytogenetic Analysis of Fetal Cells in Maternal Blood," *Prenat. Diagn.* 18:1181-1185.
Zheng, S. et al. (Jun. 2001). "Whole Genome Amplification Increases the Efficiency and Validity of Buccal Cell Genotyping in Pediatric Populations," *Cancer Epidemiology, Biomarkers, & Prevention* 10:697-700.
Zhong, X.Y. et al. (2000). "Fetal DNA in Maternal Plasma is Elevated in Pregnancies with Aneuploid Fetuses," *Prenatal Diagnosis* 20:795-798.
Zhou, G-H. et al. (2001). "Quantitative Detection of Single Nucleotide Polymorphisms for a Pooled Sample by a Bioluminometric Assay Coupled with Modified Primer Extension Reactions (BAMPER)," *Nucleic Acids Research* 29(19):1-11.
Dhallan, R. et al. (Feb. 10, 2007, e-pub. Feb. 2, 2007). "A Non-Invasive Test for Prenatal Diagnosis Based on Fetal DNA Present in Maternal Blood: A Preliminary Study," The Lancet 369(9560):474-481.
Final Office Action mailed on Oct. 12, 2006, for U.S. Appl. No. 10/661,165, filed Sep. 11, 2003, 6 pages.
International Search Report mailed on Oct. 25, 2007 for PCT Patent Application No. PCT/US2006/048686 filed Dec. 19, 2006, 8 pages.
Li, Y. et al. (Nov. 2004). "Improved Prenatal Detection of a Fetal Point Mutation for Achondroplasia by the Use of Size-Fractionated Circulatory DNA in Maternal Plasma-Case Report,"24(11):896-898.
Li, Y. et al. (Feb. 16, 2005). "Detection of Paternally Inherited Fetal Point Mutations for β-Thalassemia Using Size-Fractionated Cell-Free DNA in Maternal Plasma," *Journal of the American Medical Association* 293(7):843-849 (erratum Apr. 13, 2005, 293(14):1728).
Moreton, J.A. et al. (1999). "Use of Virkon as a Disinfectant for Clinical Samples Carrying a High Risk of Infection in Inductively Coupled Plasma Mass Spectrometry," *Journal of Analytical Atomic Spectrometry* 14:893-894.
National Kidney and Urologic Diseases Information Clearinghouse. (Dec. 2005). "Urinary Tract Infections in Adults," NIH Publication No. 06-2097, located at <http://kidney.niddk.nih.gov/kudiseases/pubs/utiadult>, last visited on Apr. 26, 2007, eight pages.
Non-Final Office Action mailed on Mar. 17, 2006, for U.S. Appl. No. 10,661,165, filed Sep. 11, 2003, 18 pages.
Non-Final Office Action mailed on Jan. 30, 2007, for U.S. Appl. No. 10/661,165, filed Sep. 11, 2003, 73 pages.
Non-Final Office Action mailed on Jun. 15, 2007, for U.S. Appl. No. 11/212,812, filed Aug. 26, 2005, 18 pages.
Notice of Allowability mailed on Sep. 26, 2007, for US Appl. No. 10/661,165, filed Sep. 11, 2003, 3 pages.
Reaney, P. (Feb. 1, 2007). "New Down's Test Eliminates Miscarriage Risk," located at <http://www.reuters.com/articlePrint?articleId=USL0159969820070202>, two pages.
The Internet Pathology Laboratory. (Date Unknown). "Human Immunodeficiency Virus (HIV)," located at <http://library.med.utah.edu/WebPath/TUTORIAL/AIDS/HIV.html>, last visited on Apr. 11, 2007, seven pages.
Tong, Y. et al. (Jan. 2006). "Diagnostic Developments Involving Cell-free (Circulating) Nucleic Acids," *Clinica Chimica Acta* 363(1-2):187-196.
Written Opinion mailed on Oct. 25, 2007 for PCT Patent Application No. PCT/US2006/048686 filed Dec. 19, 2006, 7 pages.
Barrett, Michael T. et al, "Genotypic analysis of multiple loci in somatic cells by whole genome amplification", Nucleic Acids Research, (1995) 23(17): 3488-3492.
Blin, Nikolaus, and Stafford, Darrel W., "A General Method for isolation of high molecular weight DNA from eukaryotes," Nucleic Acids Research (1976) 3(9) 2303-2308.
Jung, Janet M et al, "Extraction Strategy for obtaining DNA from bloodstains for PCR amplification and typing of the HLA-DQa gene," Int J Leg Med (1991) 104: 145-148.
Pastinen, Tomi et al, "Minisequencing: A specific tool for DNA analysis and diagnostics on oligonucleotide arrays," Genome Reasearch (1997) 7: 606-614.
Final Office Action mailed on Mar. 14, 2008 for U.S. Appl. No. 11/212,812, filed on Aug. 26, 2005, 6 pages.
Non-Final Office Action mailed on Mar. 11, 2008 for U.S. Appl. No. 11/313,993, filed on Dec. 20, 2005, 16 pages.
Non-Final Office Action mailed Mar. 14, 2008 for U.S. Appl. No. 11/648,778, filed on Dec. 28, 2006, 12 pages.

* cited by examiner

Lane M 1 2 3 4

Annealing Temp. 1st Cycle (TM1) 37°C
Annealing Temp. 2nd Cycle (TM2) 57°C
Annealing Temp. 3rd Cycle (TM3) 64°C 1 2 3 4

40°C
60°C
67°C 1 2 3 4

46°C
65°C
72°C

```
5´              EcoRI
•— ATAACCGTATGCGAATTCTATAATTTTCCTGATAAAGGCTG. . .(59 nt). . CAATTTGCACTARTGAAGTTTACCTAGTCCCCAGATTTAAG 3´
    TATTGGCATACGCTTAAGATATTAAAAGGACTATTTCCGAC. . .(59 nt). . GTTAAACGTGATrACTTCAAATGGATCAGGGGACTAAATTC 5´
3´                                                                                        BsmFI
```

*FIG. 5A*

```
5´              EcoRI
— ATAACCGTATGCGAATTCTATAATTTTCCTGATAAAGGCTG. . .(59 nt). . CAATTTGCACTARTGAAGTTTACCTAGCCGTCAGATTTAAG 3´
   TATTGGCATACGCTTAAGATATTAAAAGGACTATTTCCGAC. . .(59 nt). . GTTAAACGTGATrACTTCAAATGGATCGGCAGACTAAATTC 5´
3´                                                                                        BceAI
```

*FIG. 5B*

```
5´              EcoRI
•— AAGTTTAGATCAGAATTCGTGAAAGCAGAAGTTGTCTGATAATC. . .(82 nt). .CCAAGGSCTTTACTCGATGAGTCCCTTATCGTGAT 3´
3´ TTCAAATCTAGTCTTAAGCACTTTCGTCTTCAACAGACTATTAG. . .(82 nt). .GGTTCCsGAAATGAGCTACTCAGGGAATAGCACTA 5´
                                                                                        BsmFI
```

*FIG. 5C*

```
5´              EcoRI
•— AAGTTTAGATCAGAATTCGTGAAAGCAGAAGTTGTCTGATAATC. . .(82 nt). .CCAAGGSCTTTACTCGATGAGCCGTTTATCGTGAT 3´
3´ TTCAAATCTAGTCTTAAGCACTTTCGTCTTCAACAGACTATTAG. . .(82 nt). .GGTTCCsGAAATGAGCTACTCGGCAAATAGCACTA 5´
                                                                                       BceAI
```

*FIG. 5D*

```
5'             EcoRI                                                           3'
•— ATAACCGTATGCGAATTCTATAATTTTCCTGATAAAGGCTG. . .(59 nt). . CAATTTGCACTA
3' TATTGGCATACGCTTAAGATATTAAAAGGACTATTTCCGAC. . .(59 nt). . GTTAAACGTGATrACT 5'

                                                            5'                              3'
                                                              RTGAAGTTTACCTAGTCCCCAGATTTAAG
                                                            3' TCAAATGGATCAGGGGACTAAATTC 5'
                                                                         BsmFI
```

FIG. 6A

```
5'             EcoRI                                                           3'
•— ATAACCGTATGCGAATTCTATAATTTTCCTGATAAAGGCTG. . .(59 nt). . CAATTTGCACTA
3' TATTGGCATACGCTTAAGATATTAAAAGGACTATTTCCGAC. . .(59 nt). . GTTAAACGTGATrA 5'

                                                            5'                              3'
                                                              RTGAAGTTTACCTAGCCGTCAGATTTAAG
                                                            3' CTTCAAATGGATCGGCAGACTAAATTC 5'
                                                                         BceAI
```

FIG. 6B

```
5´           EcoRI                                              3´
•— AAGTTTAGATCAGAATTCGTGAAAGCAGAAGTTGTCTGATAATC. . .(82 nt). .CCAAGG
   TTCAAATCTAGTCTTAAGCACTTTCGTCTTCAACAGACTATTAG. . .(82 nt). .GGTTCCsGAA  5´
3´

                                                      5´                              3´
                                                        SCTTTACTCGATGAGTCCCTTATCGTGAT
                                                            ATGAGCTACTCAGGGAATAGCACTA 5´
                                                       3´             BsmFI
```

FIG. 6C

```
5´           EcoRI                                              3´
•— AAGTTTAGATCAGAATTCGTGAAAGCAGAAGTTGTCTGATAATC. . .(82 nt). .CCAAGG
   TTCAAATCTAGTCTTAAGCACTTTCGTCTTCAACAGACTATTAG. . .(82 nt). .GGTTCCsG  5´
3´

                                                      5´                              3´
                                                        SCTTTACTCGATGAGCCGTTTATCGTGAT
                                                      3´ AAATGAGCTACTCGGCAAATAGCACTA 5´
                                                                      BceAI
```

FIG. 6D

```
5'               EcoRI                                                        *    3'
 •-ATAACCGTATGCGAATTCTATAATTTTCCTGATAAAGGCTG. . .(59 nt). . CAATTTGCACTAR-dd
   TATTGGCATACGCTTAAGATATTAAAAGGACTATTTCCGAC. . .(59 nt). . GTTAAACGTGATrACT
3'                                                                                 5'
```

FIG. 7A

```
5'               EcoRI                                                        *    3'
 •-ATAACCGTATGCGAATTCTATAATTTTCCTGATAAAGGCTG. . .(59 nt). . CAATTTGCACTAR-dd
   TATTGGCATACGCTTAAGATATTAAAAGGACTATTTCCGAC. . .(59 nt). . GTTAAACGTGATrA
3'                                                                              5'
```

FIG. 7B

5´ EcoRI * 3´
•— ATAACCGTATGCGAATTCTATAATTTTCCTGATAAAGGCTG. . .(59 nt). . CAATTTGCACTAR-dd
3´ TATTGGCATACGCTTAAGATATTAAAAGGACTATTTCCGAC. . .(59 nt). . GTTAAACGTGATrACT 5´

+

5´ EcoRI * 3´
•— ATAACCGTATGCGAATTCTATAATTTTCCTGATAAAGGCTG. . .(59 nt). . CAATTTGCACTART-dd
3´ TATTGGCATACGCTTAAGATATTAAAAGGACTATTTCCGAC. . .(59 nt). . GTTAAACGTGATrACT 5´

+

5´ EcoRI * 3´
•— ATAACCGTATGCGAATTCTATAATTTTCCTGATAAAGGCTG. . .(59 nt). . CAATTTGCACTARTG-dd
3´ TATTGGCATACGCTTAAGATATTAAAAGGACTATTTCCGAC. . .(59 nt). . GTTAAACGTGATrACT 5´

+

5´ EcoRI * 3´
•— ATAACCGTATGCGAATTCTATAATTTTCCTGATAAAGGCTG. . .(59 nt). . CAATTTGCACTARTGA-dd
3´ TATTGGCATACGCTTAAGATATTAAAAGGACTATTTCCGAC. . .(59 nt). . GTTAAACGTGATrACT 5´

*FIG. 7E*

```
5'→ ATAACCGTATGCG              3'       5'- AATTCTATAATTTCCTGATAAAGGCTG...(59 nt)...CAATTTGCACTAR*-dd 3'
3'  TATTGGCATACGCTTAA          5'       3'- GATATTAAAAGGACTATTTCCGAC...(59 nt)...GTTAAACGTGATrACT  5'
```

```
5'→ ATAACCGTATGCG              3'       5'- AATTCTATAATTTCCTGATAAAGGCTG...(59 nt)...CAATTTGCACTAR*-dd 3'
3'  TATTGGCATACGCTTAA          5'       3'- GATATTAAAAGGACTATTTCCGAC...(59 nt)...GTTAAACGTGATrA    5'
```

| Nucleotides | G A T C | G A T C | G A T C | G A T C | G A T C |
|---|---|---|---|---|---|
| SNP | HC21S00027 | TSC0095512 | TSC0095512 | TSC0264580 | HC21S00027 |
| Restriction Enzyme Site on Second Primer | BceA I | BceA I | BsmF I | BsmF I | BsmF I |
| 5' Overhang | 3' A T r A 5' | 3' G C s G 5' | 3' G C s GAA 5' | 3' T A r CCC 5' 3' A T A r CC 5' | 3' A T r ACT 5' 3' T A T r AC 5' |
| R | G/A | G/C | G/C | A/C | G/A |
| S | | | | | |

| Chromosome | 21 | | 21 | | 13 | | 13 | | 13 | |
|---|---|---|---|---|---|---|---|---|---|---|
| SNP | TSC0115603 | | TSC0309610 | | ss813773 | | TSC0198557 | | TSC0200347 | |
| Nucleotide | T | A | T | C | A | C | T | C | T | C |
| Nucleotide Ratio | 36:63 | | 66:33 | | 46:54 | | 49:51 | | 50:49 | |

FIG. 19
A. TSC0470003
IA M1 M2 M3
B. TSC1261039
IA M1 M2 M3
C. TSC0310507
IA M1 M2 M3
D. TSC1335008
IA M1 M2 M3
Allele 2
Allele 1

METHODS FOR DETECTION OF GENETIC DISORDERS

CROSS-REFERENCE TO RELATED APPLICATIONS

This application is a continuation of International Application No. PCT/US03/27308, filed Aug. 29, 2003, which is a continuation-in-part of International Application No. PCT/US03/06198, filed Feb. 28, 2003, which claims the priority benefit of U.S. Provisional Application Ser. No. 60/378,354, filed May 8, 2002, the contents of each of which are hereby incorporated by reference herein in their entirety. This application is also a continuation-in-part of U.S. patent application Ser. No. 10/661,165, filed Sep. 11, 2003 now U.S. Pat. No. 7,332,277, which is a continuation-in-part of International Application No. PCT/US03/06198, filed Feb.28, 2003, which claims the priority benefit of U.S. Provisional Application Ser. No. 60/378,354, filed May 8, 2002. The contents of each of the following applications are also hereby incorporated by reference in their entirety herein: U.S. patent application Ser. No. 10/093,618, filed Mar. 11, 2002; and U.S. Provisional Application Ser. No. 60/360,232, filed Mar. 1, 2002.

BACKGROUND OF THE INVENTION

1. Field of the Invention

The present invention is directed to a method for the detection of genetic disorders including chromosomal abnormalities and mutations. The present invention provides a rapid, non-invasive method for determining the sequence of DNA from a fetus. The method is especially useful for detection of chromosomal abnormalities in a fetus including translocations, transversions, monosomies, trisomies, and other aneuplodies, deletions, additions, amplifications, translocations and rearrangements.

2. Background Art

Chromosomal abnormalities are responsible for a significant portion of genetic defects in liveborn humans. The nucleus of a human cell contains forty-six (46) chromosomes, which contain the genetic instructions, and determine the operations of the cell. Half of the forty-six chromosomes originate from each parent. Except for the sex chromosomes, which are quite different from each other in normal males, the chromosomes from the mother and the chromosomes from the father make a matched set. The pairs were combined when the egg was fertilized by the sperm. Occasionally, an error occurs in either the formation or combination of chromosomes, and the fertilized egg is formed with too many or too few chromosomes, or with chromosomes that are mixed in some way. Because each chromosome contains many genes, chromosomal abnormalities are likely to cause serious birth defects, affecting many body systems and often including developmental disability (e.g., mental retardation).

Cells mistakenly can rejoin broken ends of chromosomes, both spontaneously and after exposure to chemical compounds, carcinogens, and irradiation. When rejoining occurs within a chromosome, a chromosome segment between the two breakpoints becomes inverted and is classified as an inversion. With inversions, there is no loss of genetic material; however, inversions can cause disruption of a critical gene, or create a fusion gene that induces a disease related condition.

In a reciprocal translocation, two non-homologous chromosomes break and exchange fragments. In this scenario, two abnormal chromosomes result: each consists of a part derived from the other chromosome and lacks a part of itself. If the translocation is of a balanced type, the individual will display no abnormal phenotypes. However, during germ-cell formation in the translocation-bearing individuals, the proper distribution of chromosomes in the egg or sperm occasionally fails, resulting in miscarriage, malformation, or mental retardation of the offspring.

In a Robertsonian translocation, the centromeres of two acrocentric (a chromosome with a non-centrally located centromere) chromosomes fuse to generate one large metacentric chromosome. The karyotype of an individual with a centric fusion has one less than the normal diploid number of chromosomes.

Errors that generate too many or too few chromosomes can also lead to disease phenotypes. For example, a missing copy of chromosome X (monosomy X) results in Turner's. Syndrome, while an additional copy of chromosome 21 results in Down's Syndrome. Other diseases such as Edward's Syndrome, and Patau Syndrome are caused by an additional copy of chromosome 18, and chromosome 13, respectively.

One of the most common chromosome abnormalities is known as Down syndrome. The estimated incidence of Down's syndrome is between 1 in 1,000 to 1 in 1,100 live births. Each year approximately 3,000 to 5,000 children are born in the U.S. with this chromosomal disorder. The vast majority of children with Down syndrome (approximately 95 percent) have an extra chromosome 21. Most often, the extra chromosome originates from the mother. However, in about 3-4 percent of people with Down syndrome, a translocation between chromosome 21 and either 14 or 22 is responsible for the genetic abnormality. Finally, another chromosome problem, called mosaicism, is noted in about 1 percent of individuals with Down's syndrome. In this case, some cells have 47 chromosomes and others have 46 chromosomes. Mosiacism is thought to be the result of an error in cell division soon after conception.

Chromosomal abnormalities are congential, and therefore, prenatal diagnosis can be used to determine the health and condition of an unborn fetus. Without knowledge gained by prenatal diagnosis, there could be an untoward outcome for the fetus or the mother or both. Congenital anomalies account for 20 to 25% of perinatal deaths. Specifically, prenatal diagnosis is helpful for managing the remaining term of the pregnancy, planning for possible complications with the birth process, preparing for problems that can occur in the newborn infant, and finding conditions that may affect future pregnancies.

There are a variety of non-invasive and invasive techniques available for prenatal diagnosis including ultrasonography, amniocentesis, chorionic villus sampling (CVS), fetal blood cells in maternal blood, maternal serum alpha-fetoprotein, maternal serum beta-HCG, and maternal serum estriol. However, the techniques that are non-invasive are less specific, and the techniques with high specificity and high sensitivity are highly invasive. Furthermore, most techniques can be applied only during specific time periods during pregnancy for greatest utility.

Ultrasonography

This is a harmless, non-invasive procedure. High frequency sound waves are used to generate visible images from the pattern of the echoes made by different tissues and organs, including the fetus in the amniotic cavity. The developing embryo can be visualized at about 6 weeks of gestation. The major internal organs and extremities can be assessed to determine if any are abnormal at about 16 to 20 weeks gestation.

An ultrasound examination can be useful to determine the size and position of the fetus, the amount of amniotic fluid, and the appearance of fetal anatomy; however, there are limitations to this procedure. Subtle abnormalities, such as Down syndrome, where the morphologic abnormalities are often not marked, but only subtle, may not be detected at all.

Amniocentesis

This is a highly invasive procedure in which a needle is passed through the mother's lower abdomen into the amniotic cavity inside the uterus. This procedure can be performed at about 14 weeks gestation. For prenatal diagnosis, most amniocenteses are performed between 14 and 20 weeks gestation. However, an ultrasound examination is performed, prior to amniocentesis, to determine gestational age, position of the fetus and placenta, and determine if enough amniotic fluid is present. Within the amniotic fluid are fetal cells (mostly derived from fetal skin) which can be grown in culture for chromosomal, biochemical, and molecular biologic analyses.

Large chromosomal abnormalities, such as extra or missing chromosomes or chromosome fragments, can be detected by karyotyping, which involves the identification and analysis of all 46 chromosomes from a cell and arranges them in their matched pairs, based on subtle differences in size and structure. In this systematic display, abnormalities in chromosome number and structure are apparent. This procedure typically takes 7-10 days for completion.

While amniocentesis can be used to provide direct genetic information, risks are associated with the procedure including fetal loss and maternal Rh sensitization. The increased risk for fetal mortality following amniocentesis is about 0.5% above what would normally be expected. Rh negative mothers can be treated with RhoGam.

Chorionic Villus Sampling (CVS)

In this procedure, a catheter is passed via the vagina through the cervix and into the uterus to the developing placenta with ultrasound guidance. The introduction of the catheter allows cells from the placental chorionic villi to be obtained and analyzed by a variety of techniques, including chromosome analysis to determine the karyotype of the fetus. The cells can also be cultured for biochemical or molecular biologic analysis. Typically, CVS is performed between 9.5 and 12.5 weeks gestation.

CVS has the disadvantage of being an invasive procedure, and it has a low but significant rate of morbidity for the fetus; this loss rate is about 0.5 to 1% higher than for women undergoing amniocentesis. Rarely, CVS can be associated with limb defects in the fetus. Also, the possibility of maternal Rh sensitization is present. Furthermore, there is also the possibility that maternal blood cells in the developing placenta will be sampled instead of fetal cells and confound chromosome analysis.

Maternal Serum Alpha-Fetoprotein (MSAFP)

The developing fetus has two major blood proteins—albumin and alpha-fetoprotein (AFP). The mother typically has only albumin in her blood, and thus, the MSAFP test can be utilized to determine the levels of AFP from the fetus. Ordinarily, only a small amount of AFP gains access to the amniotic fluid and crosses the placenta to mother's blood. However, if the fetus has a neural tube defect, then more AFP escapes into the amniotic fluid. Neural tube defects include anencephaly (failure of closure at the cranial end of the neural tube) and spina bifida (failure of closure at the caudal end of the neural tube). The incidence of such defects is about 1 to 2 births per 1000 in the United States. Also, if there are defects in the fetal abdominal wall, the AFP from the fetus will end up in maternal blood in higher amounts.

The amount of MSAFP increases with gestational age, and thus for the MSAFP test to provide accurate results, the gestational age must be known with certainty. Also, the race of the mother and presence of gestational diabetes can influence the level of MSAFP that is to be considered normal. The MSAFP is typically reported as multiples of the mean (MoM). The greater the MoM, the more likely a defect is present. The MSAFP test has the greatest sensitivity between 16 and 18 weeks gestation, but can be used between 15 and 22 weeks gestation. The MSAFP tends to be lower when Down's Syndrome or other chromosomal abnormalities is present.

While the MSAFP test is non-invasive, the MSAFP is not 100% specific. MSAFP can be elevated for a variety of reasons that are not related to fetal neural tube or abdominal wall defects. The most common cause for an elevated MSAFP is a wrong estimation of the gestational age of the fetus. Therefore, results from an MSAFP test are never considered definitive and conclusive.

Maternal Serum Beta-HCG

Beginning at about a week following conception and implantation of the developing embryo into the uterus, the trophoblast will produce detectable beta-HCG (the beta subunit of human chorionic gonadotropin), which can be used to diagnose pregnancy. The beta-HCG also can be quantified in maternal serum, and this can be useful early in pregnancy when threatened abortion or ectopic pregnancy is suspected, because the amount of beta-HCG will be lower than normal.

In the middle to late second trimester, the beta-HCG can be used in conjunction with the MSAFP to screen for chromosomal abnormalities, in particular for Down syndrome. An elevated beta-HCG coupled with a decreased MSAFP suggests Down syndrome. High levels of HCG suggest trophoblastic disease (molar pregnancy). The absence of a fetus on ultrasonography along with an elevated HCG suggests a hydatidiform mole.

Maternal Serum Estriol

The amount of estriol in maternal serum is dependent upon a viable fetus, a properly functioning placenta, and maternal well-being. Dehydroepiandrosterone (DHEA) is made by the fetal adrenal glands, and is metabolized in the placenta to estriol. The estriol enters the maternal circulation and is excreted by the maternal kidney in urine or by the maternal liver in the bile. Normal levels of estriol, measured in the third trimester, will give an indication of general well-being of the fetus. If the estriol level drops, then the fetus is threatened and an immediate delivery may be necessary. Estriol tends to be lower when Down syndrome is present and when there is adrenal hypoplasia with anencephaly.

The Triple Screen Test

The triple screen test comprises analysis of maternal serum alpha-feto-protein (MSAFP), human chorionic gonadotrophin (hCG), and unconjugated estriol (uE3). The blood test is usually performed 16-18 weeks after the last menstrual period. While the triple screen test is non-invasive, abnormal test results are not indicative of a birth defect. Rather, the test only indicates an increased risk and suggests that further testing is needed. For example, 100 out of 1,000 women will have an abnormal result from the triple screen test. However, only 2-3 of the 100 women will have a fetus with a birth defect. This high incidence of false positives causes tremendous stress and unnecessary anxiety to the expectant mother.

Fetal Cells Isolated From Maternal Blood

The presence of fetal nucleated cells in maternal blood makes it possible to use these cells for noninvasive prenatal diagnosis (Walknowska, et al., Lancet 1:1119-1122, 1969; Lo et al., Lancet 2:1363-65, 1989; Lo et al., Blood 88:4390-95, 1996). The fetal cells can be sorted and analyzed by a variety of techniques to look for particular DNA sequences (Bianchi et al., Am. J. Hum. Genet. 61:822-29, (1997); Bianchi et al., PNAS 93:705-08, (1996)). Fluorescence in-situ hybridization (FISH) is one technique that can be applied to identify particular chromosomes of the fetal cells recovered from maternal blood and diagnose aneuploid conditions such as trisomies and monosomy X. Also, it has been reported that the number of fetal cells in maternal blood increases in aneuploid pregnancies.

The method of FISH uses DNA probes labeled with colored fluorescent tags that allow detection of specific chromosomes or genes under a microscope. Using FISH, subtle genetic abnormalities that cannot be detected by standard karyotyping are readily identifiable. This procedure typically takes 24-48 hours to complete. Additionally, using a panel of multi-colored DNA FISH probes, abnormal chromosome copy numbers can be seen.

While improvements have been made for the isolation and enrichment of fetal cells, it is still difficult to get many fetal blood cells. There may not be enough to reliably determine anomalies of the fetal karyotype or assay for other abnormalities. Furthermore, most techniques are time consuming, require high-inputs of labor, and are difficult to implement for a high throughput fashion.

Fetal DNA From Maternal Blood

Fetal DNA has been detected and quantitated in maternal plasma and serum (Lo et al., Lancet 350:485-487 (1997); Lo et al., Am. J. hum. Genet. 62:768-775 (1998)). Multiple fetal cell types occur in the maternal circulation, including fetal granulocytes, lymphocytes, nucleated red blood cells, and trophoblast cells (PertI, and Bianchi, Obstetrics and Gynecology 98: 483-490 (2001)). Fetal DNA can be detected in the serum at the seventh week of gestation, and increases with the term of the pregnancy. The fetal DNA present in the maternal serum and plasma is comparable to the concentration of DNA obtained from fetal cell isolation protocols.

Circulating fetal DNA has been used to determine the sex of the fetus (Lo et al., Am. J. hum. Genet. 62:768-775 (1998)). Also, fetal rhesus D genotype has been detected using fetal DNA. However, the diagnostic and clinical applications of circulating fetal DNA is limited to genes that are present in the fetus but not in the mother (Pertl and Bianchi, Obstetrics and Gynecology 98: 483-490 (2001)). Thus, a need still exists for a non-invasive method that can determine the sequence of fetal DNA and provide definitive diagnosis of chromosomal abnormalities in a fetus.

BRIEF SUMMARY OF THE INVENTION

The invention is directed to a method for detection of genetic disorders including mutations and chromosomal abnormalities. In a preferred embodiment, the present invention is used to detect mutations, and chromosomal abnormalities including but not limited to translocation, transversion, monosomy, trisomy, and other aneuploidies, deletion, addition, amplification, fragment, translocation, and rearrangement. Numerous abnormalities can be detected simultaneously. The present invention also provides a non-invasive method to determine the sequence of fetal DNA from a sample of a pregnant female. The present invention can be used to detect any alternation in gene sequence as compared to the wild type sequence including but not limited to point mutation, reading frame shift, transition, transversion, addition, insertion, deletion, addition-deletion, frame-shift, missense, reverse mutation, and microsatellite alteration. The present invention also provides a method for isolating free nucleic acid from a sample containing nucleic acid.

In one embodiment, the present invention is directed to a method for detecting chromosomal abnormalities said method comprising: (a) determining the sequence of alleles of a locus of interest on template DNA, and (b) quantitating a ratio for the alleles at a heterozygous locus of interest that was identified from the locus of interest of (a), wherein said ratio indicates the presence or absence of a chromosomal abnormality.

In another embodiment, the present invention provides a non-invasive method for determining the sequence of a locus of interest on fetal DNA, said method comprising: (a) obtaining a sample from a pregnant female; (b) adding a cell lysis inhibitor, a cell membrane stabilizer, or a cross-linker to the sample of (a); (c) obtaining template DNA from the sample of (b), wherein said template DNA comprises fetal DNA and maternal DNA; and (d) determining the sequence of a locus of interest on template DNA.

In another embodiment, the template DNA is obtained from a sample including but not limited to a cell, tissue, blood, serum, plasma, saliva, urine, tears, vaginal secretion, sweat, umbilical cord blood, chorionic villi, amniotic fluid, embryonic tissue, embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, lymph fluid, cerebrospinal fluid, mucosa secretion, peritoneal fluid, ascitic fluid, fecal matter, or body exudate.

In one embodiment, the template DNA is obtained from a sample from a pregnant female. In a preferred embodiment, the template DNA is obtained from a pregnant human female. 100351 In another embodiment, the template DNA is obtained from an embryo. In a preferred embodiment, the template DNA is obtained from a single cell from an embryo.

In another embodiment, a cell lysis inhibitor is added to the sample including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. In a preferred embodiment, formalin is present in the sample at a percentage including but not limited to 0.0001-0.03%, 0.03-0.05%, 0.05-0.08%, 0.08-0.1%, 0.1-0.3%, 0.3-0.5%, 0.5-0.7%, 0.7-0.9%, 0.9-1.2%, 1.2-1.5%, 1.5-2%, 2-3%, 3-5%, and greater than 5%.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

In another embodiment, an agent that prevents DNA destruction is added to the sample including but not limited to DNase inhibitors, zinc chloride, ethylenediaminetetraacetic acid, guanidine-HCl, guanidine isothiocyanate, N-lauroylsarcosine, and Na-dodecylsulphate.

In a preferred embodiment, template DNA is obtained from the plasma of the blood from a pregnant female. In another embodiment, the template DNA is obtained from the serum of the blood from a pregnant female.

In another embodiment, template DNA comprises fetal DNA and maternal DNA.

In another embodiment, the locus of interest on the template DNA is selected from a maternal homozygous locus of interest. In another embodiment, the locus of interest on the template DNA is selected from a maternal heterozygous locus of interest.

In another embodiment, the locus of interest on the template DNA is selected from a paternal homozygous locus of interest. In another embodiment, the locus of interest on the template DNA is selected from a paternal heterozygous locus of interest.

In one embodiment, the sequence of alleles of multiple loci of interest on a single chromosome is determined. In a preferred embodiment, the sequence of alleles of multiple loci of interest on multiple chromosomes is determined.

In another embodiment, determining the sequence of alleles of a locus of interest comprises a method including but not limited to allele specific PCR, gel electrophoresis, ELISA, mass spectrometry, hybridization, primer extension, fluorescence polarization, fluorescence detection, fluorescence resonance energy transfer (FRET), sequencing, DNA microarray, SNP-IT, GeneChips, HuSNP, BeadArray, TaqMan assay, Invader assay, MassExtend, MassCleave™ (hMC) method, southern blot, slot blot, dot blot, and MALDI-TOF mass spectrometry.

In a preferred embodiment, determining the sequence of alleles of a locus of interest comprises (a) amplifying the locus of interest using a first and second primers, wherein the second primer contains a recognition site for a restriction enzyme that generates a 5' overhang containing the locus of interest; (b) digesting the amplified DNA with the restriction enzyme that recognizes the recognition site on the second primer; (c) incorporating a nucleotide into the digested DNA of (b) by using the 5' overhang containing the locus of interest as a template; and (d) determining the sequence of the locus of interest by determining the sequence of the DNA of (c).

In one embodiment, the amplification can comprise polymerase chain reaction (PCR). In a further embodiment, the annealing temperature for cycle 1 of PCR can be about the melting temperature of the annealing length of the second primer. In another embodiment, the annealing temperature for cycle 2 of PCR can be about the melting temperature of the 3' region, which anneals to the template DNA, of the first primer. In another embodiment, the annealing temperature for the remaining cycles can be about the melting temperature of the entire sequence of the second primer.

In another embodiment, the recognition site on the second primer is for a restriction enzyme that cuts at a distance from its binding site and generates a 5' overhang, which contains the locus of interest. In a preferred embodiment, the recognition site on the second primer is for a Type IIS restriction enzyme. The Type IIS restriction enzyme includes but is not limited to Alw I, Alw26 I, Bbs I, Bbv I, BceA I, Bmr I, Bsa I, Bst71I, BsmA I, BsmB I, BsmF I, BspM I, Ear I, Fau I, Fok I, Hga I, Pie I, Sap I, SSfaN I, and Sthi32 I, and more preferably BceA I and BsmF I.

In one embodiment, the 3' end of the second primer is adjacent to the locus of interest.

In another embodiment, the annealing length of the second primer is selected from the group consisting of 35-30, 30-25, 25-20, 20-15, 15, 14, 13, 12, 11, 10, 9, 8, 7, 6, 5, 4, and less than 4 bases.

In another embodiment, amplifying the loci of interest comprises using first and second primers that contain a portion of a restriction enzyme recognition site, wherein said recognition site contains at least one variable nucleotide, and after amplification the full restriction enzyme recognition site is generated, and the 3' region of said primers can contain mismatches with the template DNA, and digestion with said restriction enzyme generates a 5' overhang containing the locus of interest.

In a preferred embodiment, the recognition site for restriction enzymes including but not limited to BsaJ I (5' C↓CNNGG 3'), BssK I (5'↓CCNGG 3'), Dde I (5'C↓TNAG 3'), EcoN I (5'CCTNN↓NNNAGG 3') (SEQ ID NO: 7), Fnu4H I (5'GC↓NGC 3'), Hinf I (5'G↓ANTC 3'), PflF I(5'GACN↓NNGTC 3'), Sau96 I (5' G↓GNCC 3'), ScrF I (5' CC↓NGG 3'), Tthl 11 I (5' GACN↓NNGTC 3'), and more preferably Fnu4H I and EcoN I, is generated after amplification.

In another embodiment, the 5' region of the first and/or second primer contains a recognition site for a restriction enzyme. In a preferred embodiment, the restriction enzyme recognition site is different from the restriction enzyme recognition site that generates a 5' overhang containing the locus of interest.

In a further embodiment, the method of the invention further comprises digesting the DNA with a restriction enzyme that recognizes the recognition site at the 5' region of the first and/or second primer.

The first and/or second primer can contain a tag at the 5' terminus. Preferably, the first primer contains a tag at the 5' terminus. The tag can be used to separate the amplified DNA from the template DNA. The tag can be used to separate the amplified DNA containing the labeled nucleotide from the amplified DNA that does not contain the labeled nucleotide. The tag can be any chemical moiety including but not limited to radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof. Preferably, the tag is biotin. The biotin tag is used to separate amplified DNA from the template DNA using a streptavidin matrix. The streptavidin matrix is coated on wells of a microtiter plate.

The incorporation of a nucleotide in the method of the invention is by a DNA polymerase including but not limited to *E. coli* DNA polymerase, Klenow fragment of *E. coli* DNA polymerase I, T7 DNA polymerase, T4 DNA polymerase, T5 DNA polymerase, Klenow class polymerases, Taq polymerase, Pfu DNA polymerase, Vent polymerase, bacteriophage 29, REDTaq™ Genomic DNA polymerase, or sequenase. The incorporation of a nucleotide can further comprise using a mixture of labeled and unlabeled nucleotides. One nucleotide, two nucleotides, three nucleotides, four nucleotides, five nucleotides, or more than five nucleotides can be incorporated. A combination of labeled and unlabeled nucleotides can be incorporated. The labeled nucleotide is selected from the group consisting of a dideoxynucleotide triphosphate (also referred to as "dideoxy") and deoxynucleotide triphosphate (also referred to as "deoxy"). The unlabeled nucleotide is selected from the group consisting of a dideoxynucleotide triphosphate and deoxynucleotide triphosphate. The labeled nucleotide is labeled with a molecule including but not limited to radioactive molecule, fluorescent molecule, antibody, antibody fragment, hapten, carbohydrate, biotin, and derivative of biotin, phosphorescent moiety, luminescent moiety, electrochemiluminescent moiety, chromatic moiety, and moiety, having a detectable electron spin resonance, electrical capacitance, dielectric constant or electrical conductivity. Preferably, the labeled nucleotide is labeled with a fluorescent molecule. The incorporation of a fluorescent labeled nucleotide further comprises using a mixture of fluorescent and unlabeled nucleotides.

In one embodiment, the determination of the sequence of the locus of interest comprises detecting the incorporated nucleotide. In one embodiment, the detection is by a method selected from the group consisting of gel electrophoresis, capillary electrophoresis, microchannel electrophoresis, polyacrylamide gel electrophoresis, fluorescence detection, fluorescence polarization, DNA sequencing, Sanger dideoxy sequencing, ELISA, mass spectrometry, time of flight mass spectrometry, quadrupole mass spectrometry, magnetic sector mass spectrometry, electric sector mass spectrometry, fluorometry, infrared spectrometry, ultraviolet spectrometry, palentiostatic amperometry, DNA hybridization, DNA microarray, GeneChip arrays, HuSNP arrays, BeadArrays, MassExtend, SNP-IT, TaqMan assay, Invader assay, MassCleave, southern blot, slot blot, and dot blot.

In one embodiment, the sequence of alleles of one to tens to hundreds to thousands of loci of interest on a single chromosome on template DNA is determined. In a preferred embodiment, the sequence of alleles of one to tens to hundreds to thousands of loci of interest on multiple chromosomes is determined.

In a preferred embodiment, the locus of interest is suspected of containing a single nucleotide polymorphism or mutation. The method can be used for determining sequences of multiple loci of interest concurrently. The template DNA can comprise multiple loci from a single chromosome. The template DNA can comprise multiple loci from different chromosomes. The loci of interest on template DNA can be amplified in one reaction. Alternatively, each of the loci of interest on template DNA can be amplified in a separate reaction. The amplified DNA can be pooled together prior to digestion of the amplified DNA. Each of the labeled DNA containing a locus of interest can be separated prior to determining the sequence of the locus of interest. In one embodiment, at least one of the loci of interest is suspected of containing a single nucleotide polymorphism or a mutation.

In another embodiment, the ratio of alleles at a heterozygous locus of interest on a chromosome is compared to the ratio of alleles at a heterozygous locus of interest on a different chromosome. There is no limitation as to the chromosomes that can be compared. The ratio for the alleles at a heterozygous locus of interest on any chromosome can be compared to the ratio for the alleles at a heterozygous locus of interest on any other chromosome. In a preferred embodiment, the ratio of alleles at multiple heterozygous loci of interest on a chromosome are summed and compared to the ratio of alleles at multiple heterozygous loci of interest on a different chromosome.

In another embodiment, the ratio of alleles at a heterozygous locus of interest on a chromosome is compared to the ratio of alleles at a heterozygous locus of interest on two, three, four or more than four chromosomes. In another embodiment, the ratio of alleles at multiple loci of interest on a chromosome is compared to the ratio of alleles at multiple loci of interest on two, three, four, or more than four chromosomes.

In another embodiment, the ratio of the alleles at a locus of interest on a chromosome is compared to the ratio of the alleles at a locus of interest on a different chromosome, wherein a difference in the ratios indicates the presence or absence of a chromosomal abnormality. In another embodiment, the ratio of the alleles at multiple loci of interest on a chromosome is compared to the ratio of the alleles at multiple loci of interest on a different chromosome, wherein a difference in the ratios indicates the presence or absence of a chromosomal abnormality.

In another embodiment, the sequence of one to tens to hundreds to thousands of loci of interest on the template DNA obtained from a sample of a pregnant female is determined. In one embodiment, the loci of interest are on one chromosome. In another embodiment, the loci of interest are on multiple chromosomes.

In another embodiment, the present invention provides a method for isolating nucleic acid said method comprising (a) obtaining a sample containing nucleic acid; (b) adding a cell lysis inhibitor, cell membrane stabilizer, or cross-linker to the sample of (a); and (c) isolating nucleic acid. In a preferred embodiment, the method is used for isolating free nucleic acid. In a most preferred embodiment, the method is used for isolating free fetal nucleic acid.

In another embodiment, the presnt invention provides a method for isolating free fetal nucleic acid said method comprising (a) obtaining a sample containing nucleic acid; (b) adding a cell lysis inhibitor, cell membrane stabilizer, or cross-linker to the sample of (a); (c) isolating the plasma from the blood sample, wherein the plasma is isolated by centrifuging the blood sample; and (d) removing the supernatant, which contains the plasma, using procedures to minimize disruption of the "buffy-coat."

In another embodiment, the sample containing the nucleic acid is obtained from any nucleic acid containg source including but not limited to a cell, tissue, blood, serum, plasma, saliva, urine, tears, breast fluid, breast milk, vaginal secretion, sweat, umbilical cord blood, chorionic villi, amniotic fluid, embryonic tissue, embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, lymph fluid, cerebrospinal fluid, mucosa secretion, peritoneal fluid, ascitic fluid, fecal matter, or body exudate.

In one embodiment, the sample containing the nucleic acid is obtained from a pregnant female. In a preferred embodiment, the sample is obtained from a pregnant human female. In a preferred embodiment, the sample is blood obtained from a pregnant female.

In another embodiment, a cell lysis inhibitor, a cell membrane stabilizer or a cross-linker is added to the sample including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII.

An agent that stabilizes cell membranes may be added to the sample including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

In another embodiment, an agent that prevents DNA destruction is added to the sample including but not limited to DNase inhibitors, zinc chloride, ethylenediaminetetraacetic acid, guanidine-HCl, guanidine isothiocyanate, N-lauroylsarcosine, and Na-dodecylsulphate.

In a preferred embodiment, the nucleic acid is isolated from plasma obtained from blood of a pregnant female. In another embodiment, the nucleic acid is isolated from plasma, which is generated using procedures designed to minimize the amount of maternal cell lysis. In another embodiment, the nucleic acid is isolated from plasma by centrifuging blood from a pregnant female, and allowing the centrifuge to stop without applying a brake.

In a preferred embodiment, free nucleic acid is isolated from plasma obtained from blood from a pregnant female. In another embodiment, the free nucleic acid is isolated from plasma, which is generated by centrifuging blood obtained from a pregnant female, and allowing the centrifuge to stop without applying a brake (the centrifuge comes to a stop by natural deceleration). In another embodiment, the blood from a pregnant female is centrifuged at a speed including but not limited to 0-50 rpm, 50-100 rpm, 100-200 rpm, 200-300 rpm, 300-400 rpm, 400-500 rpm, 500-600 rpm, 600-700 rpm, 700-800 rpm, 800-900 rpm, 900-1000 rpm, 1000-2000 rpm, 2000-3000 rpm, 3000-4000 rpm, 4000-5000 rpm, 5000-6000 rpm, 6000-7000 rpm, 7000-8000 rpm, and greater than 8000 rpm. In a preferred embodiment, the blood from the pregnant female is centrifuged at a speed less than 4000 rpm. In another embodiment, the acceleration power of the centrifuge is not used.

The first primer is shown modified with biotin at the 5' end to aid in purification. The sequence of the 3' end of the primers is such that the primers anneal at a desired distance upstream and downstream of the locus of interest. The second primer anneals close to the locus of interest; the annealing site, which is depicted as region "c," is designed such that the 3' end of the second primer anneals one base away from the locus of interest. The second primer can anneal any distance from the locus of interest provided that digestion with the restriction enzyme, which recognizes the region "d" on this primer, generates a 5' overhang that contains the locus of interest. The first primer annealing site, which is depicted as region "b," is about 20 bases.

Figure 1A:
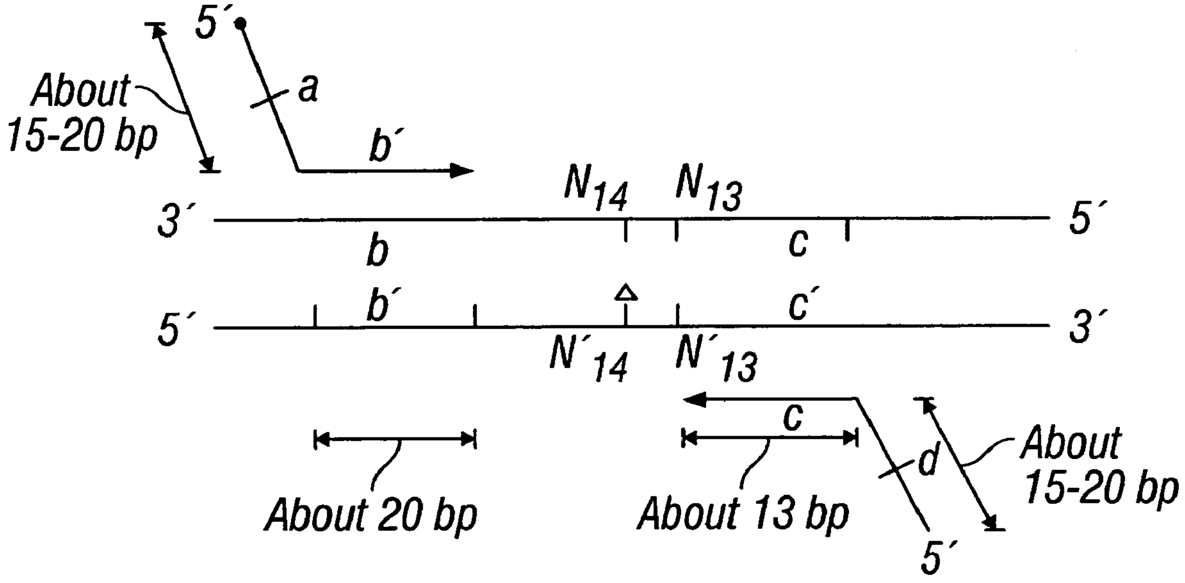
FIG. 1A. A Schematic diagram depicting a double stranded DNA molecule. A pair of primers, depicted as bent arrows, flank the locus of interest, depicted as a triangle symbol at base N14. The locus of interest can be a single nucleotide polymorphism, point mutation, insertion, deletion, translocation, etc. Each primer contains a restriction enzyme recognition site about 10 by from the 5' terminus depicted as region "a" in the first primer and as region "d" in the second primer. Restriction recognition site "a" can be for any type of restriction enzyme but recognition site "d" is for a restriction enzyme, which cuts "n" nucleotides away from its recognition site and leaves a 5' overhang and a recessed 3' end. Examples of such enzymes include but are not limited to BceAI and BsmF I. The 5' overhang serves as a template for incorporation of a nucleotide into the 3' recessed end.
Figure 1B:
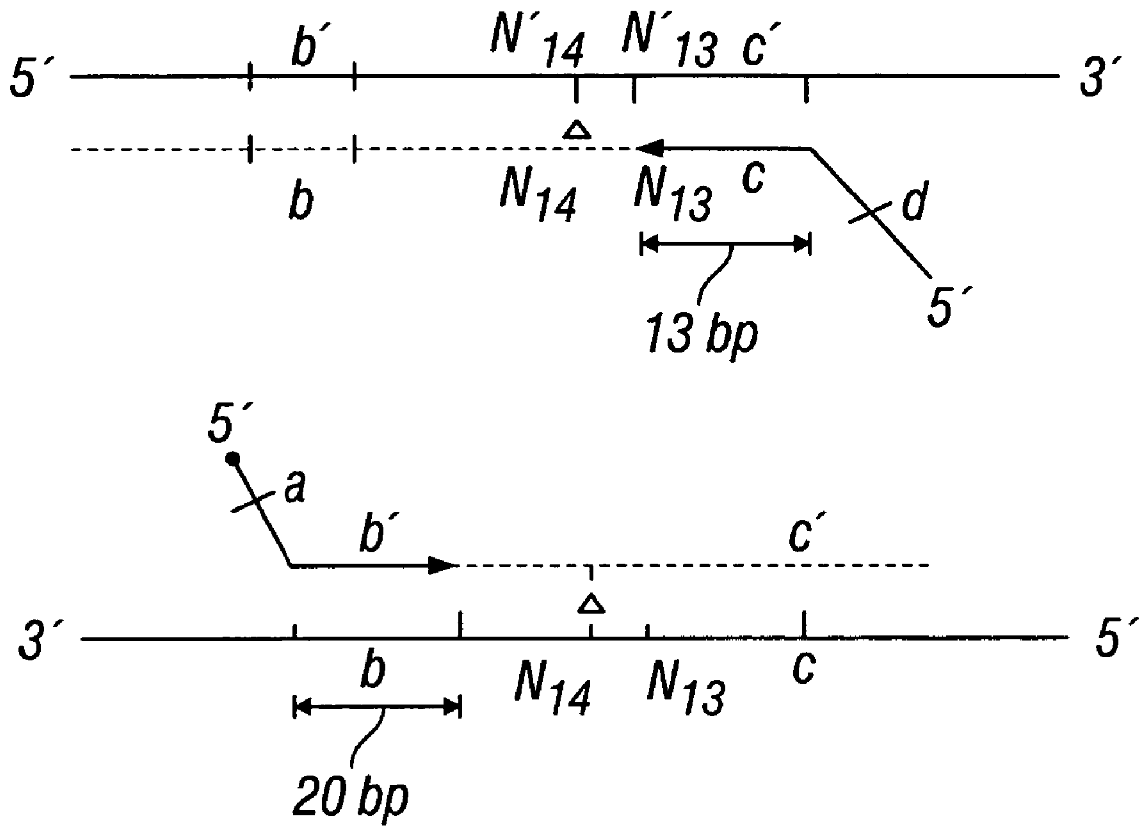

FIG. 1B. A schematic diagram depicting the annealing and extension steps of the first cycle of amplification by PCR. The first cycle of amplification is performed at about the melting temperature of the 3' region, which anneals to the template DNA, of the second primer, depicted as region "c," and is 13 base pairs in this example. At this temperature, both the first and second primers anneal to their respective complementary strands and begin extension, depicted by dotted lines. In this first cycle, the second primer extends and copies the region b where the first primer can anneal in the next cycle.

Figure 1C:
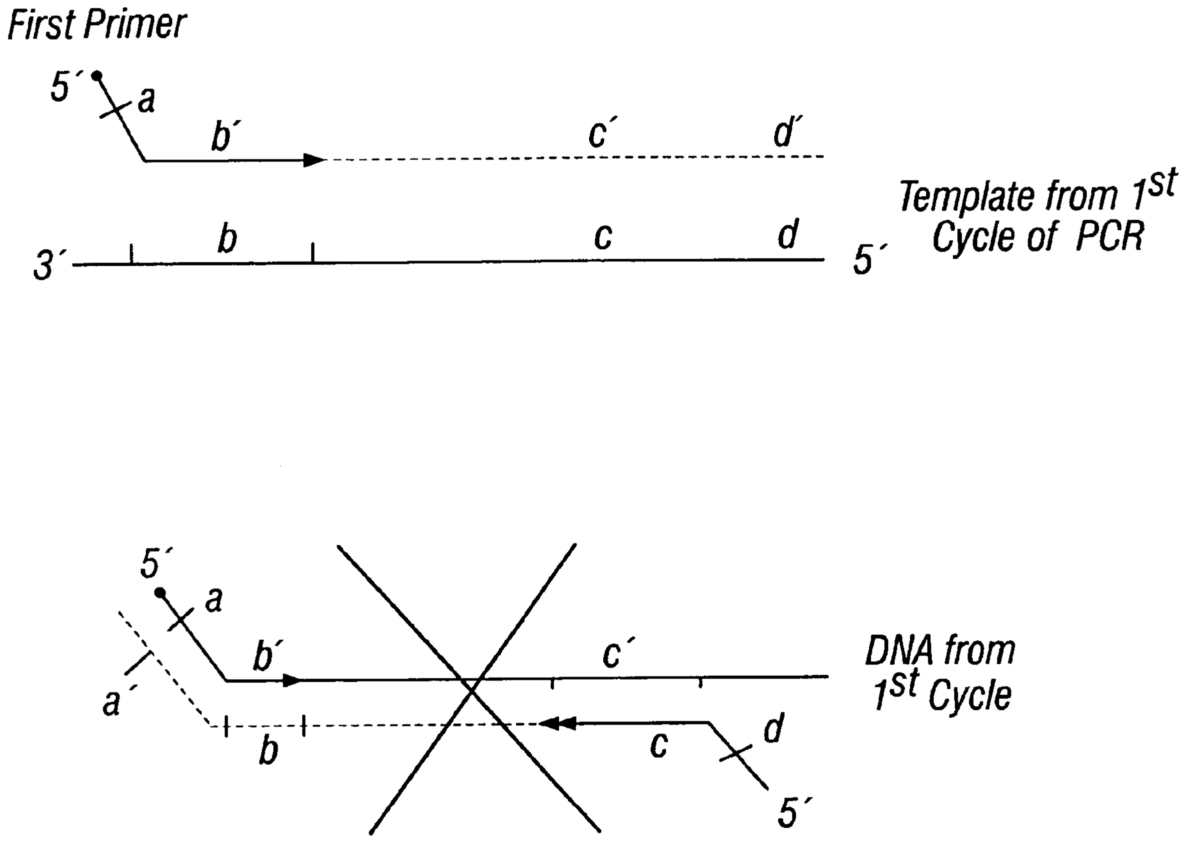

FIG. 1C. A schematic diagram depicting the annealing and extension steps following denaturation in the second cycle of amplification of PCR. The second cycle of amplification is performed at a higher annealing temperature (TM2), which is about the melting temperature of the 20 by of the 3' region of the first primer that anneals to the template DNA, depicted as region "b." Therefore at TM2, the first primer, which contains region b' which is complementary to region b, can bind to the DNA that was copied in the first cycle of the reaction. However, at TM2 the second primer cannot anneal to the original template DNA or to DNA that was copied in the first cycle of the reaction because the annealing temperature is too high. The second primer can anneal to 13 bases in the original template DNA but TM2 is calculated at about the melting temperature of 20 bases.

Figure 1D:
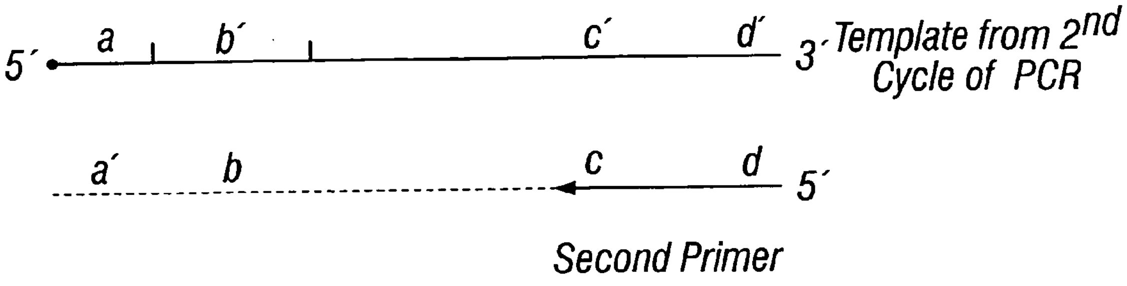

FIG. 1D. A schematic diagram depicting the annealing and extension reactions after denaturation during the third cycle of amplification. In this cycle, the annealing temperature, TM3, is about the melting temperature of the entire second primer, including regions "c" and "d." The length of regions "c"+"d" is about 27-33 by long, and thus TM3 is significantly higher than TM1 and TM2. At this higher TM the second primer, which contain regions c' and d', anneals to the copied DNA generated in cycle 2.

Figure 1E:
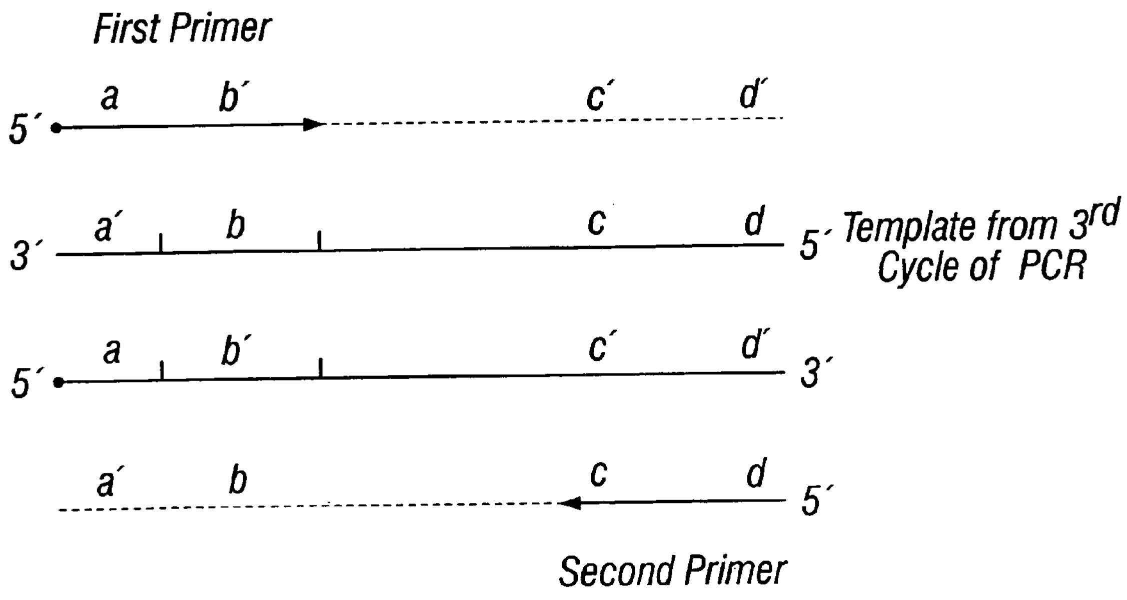

FIG. 1E. A schematic diagram depicting the annealing and extension reactions for the remaining cycles of amplification. The annealing temperature for the remaining cycles is TM3, which is about the melting temperature of the entire second primer. At TM3, the second primer binds to templates that contain regions c' and d' and the first primer binds to templates that contain regions a' and b. By raising the annealing temperature successively in each cycle for the first three cycles, from TM1, TM2, and TM3, nonspecific amplification is significantly reduced.

Figure 1F:
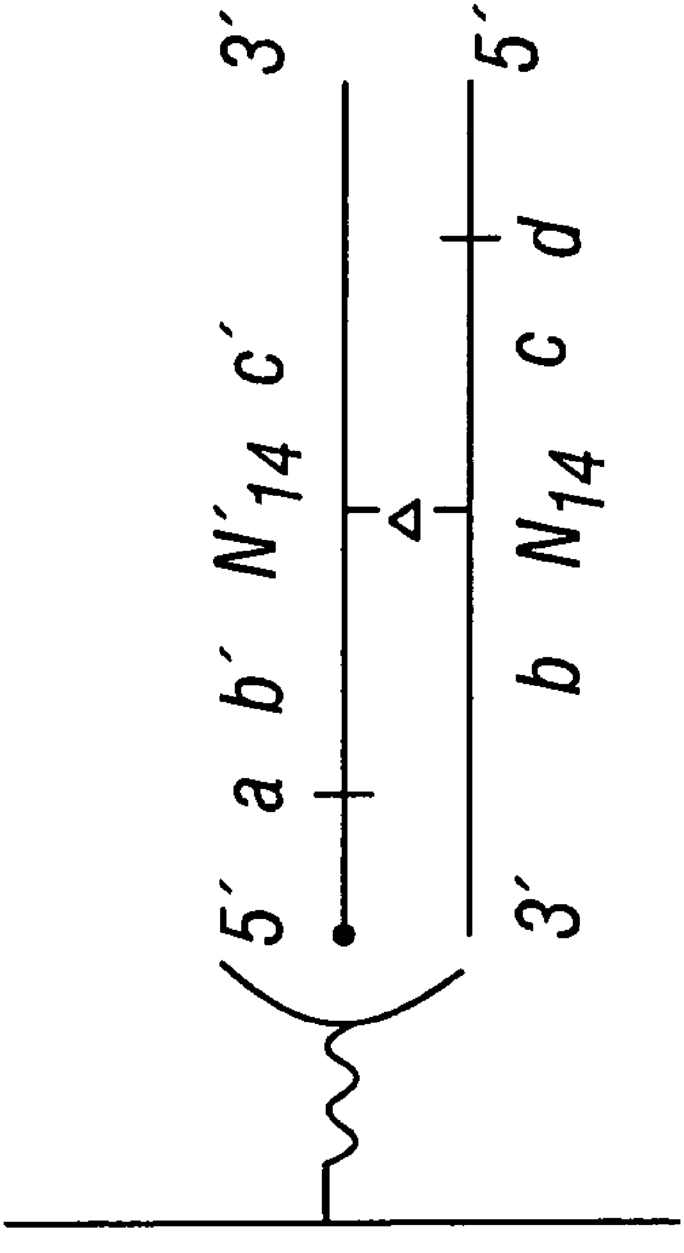

FIG. 1F. A schematic diagram depicting the amplified locus of interest bound to a solid matrix.

Figure 1G:
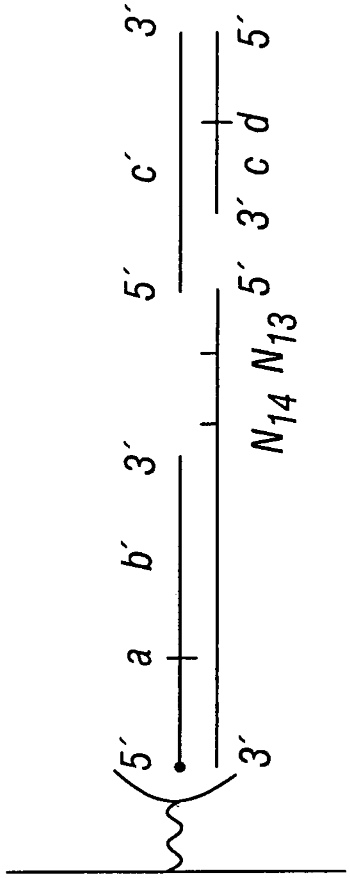

FIG. 1G. A schematic diagram depicting the bound, amplified DNA after digestion with restriction enzyme "d." The "downstream" end is released into the supernatant, and can be removed by washing with any suitable buffer. The upstream end containing the locus of interest remains bound to the solid matrix.

Figure 1H:
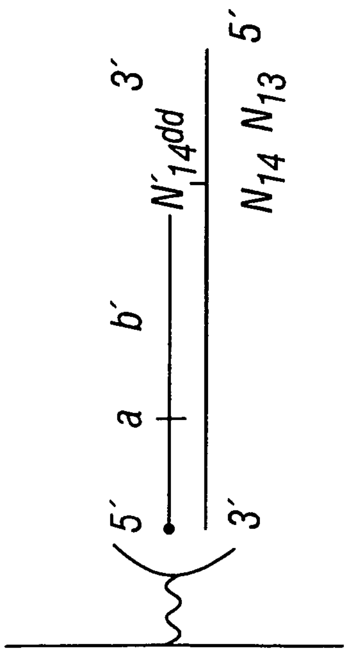

FIG. 1H. A schematic diagram depicting the bound amplified DNA, after "filling in" with a labeled ddNTP. A DNA polymerase is used to "fill in" the base (N'14) that is complementary to the locus of interest (N14). In this example, only ddNTPs are present in this reaction, such that only the locus of interest or SNP of interest is filled in.

Figure 1I:
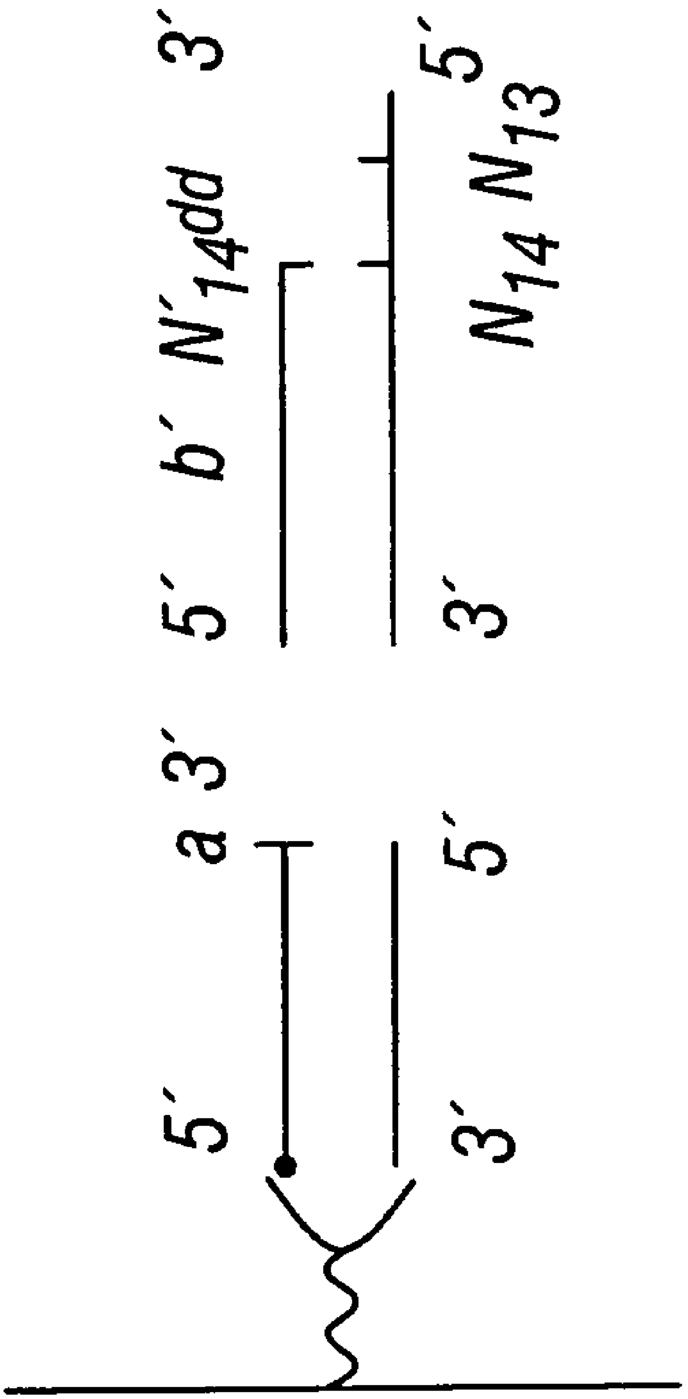

FIG. 1I. A schematic diagram depicting the labeled, bound DNA after digestion with restriction enzyme "a." The labeled DNA is released into the supernatant, which can be collected to identify the base that was incorporated.

Figure 2:
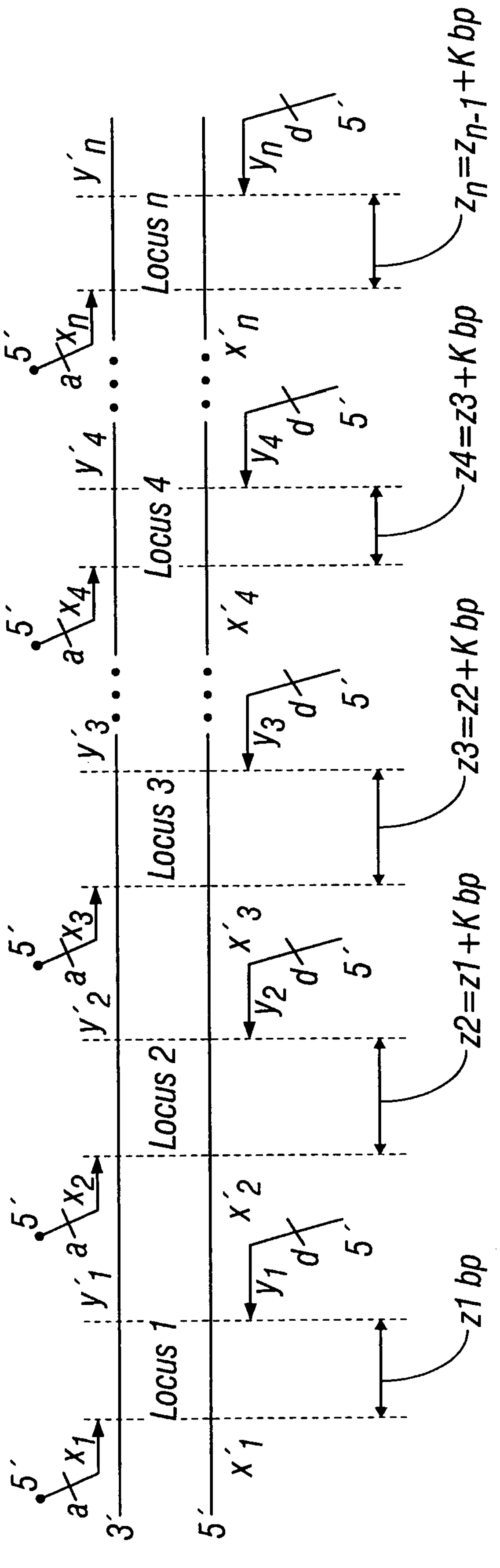

FIG. 2. A schematic diagram depicting double stranded DNA templates with n number of loci of interest and n number of primer pairs, $x_1$, $y_1$ to $x_n$, $y_n$, specifically annealed such that a primer flanks each locus of interest. The first primers are biotinylated at the 5' end, depicted by ·, and contain a restriction enzyme recognition site, "a", which can be any type of restriction enzyme. The second primers contain a restriction enzyme recognition site, "d," where "d" is a recognition site for a restriction enzyme that cuts "n" nucleotides away from its recognition site, and generates a 5' overhang containing the locus of interest and a recessed 3' end. The second primers anneal adjacent to the respective loci of interest. The exact position of the restriction enzyme site "d" in the second primers is designed such that digesting the PCR product of each locus of interest with restriction enzyme "d" generates a 5' overhang containing the locus of interest and a 3' recessed end. The annealing sites of the first primers are about 20 bases long and are selected such that each successive first primer is further away from its respective second primer. For example, if at locus 1 the 3' ends of the first and second primers are Z base pairs apart, then at locus 2, the 3' ends of the first and second primers are Z+K base pairs apart, where K=1, 2, 3 or more than three bases. Primers for locus N are $Z_{N-1}$+K base pairs apart. The purpose of making each successive first primer further apart from their respective second primers is such that the "filled in" restriction fragments (generated after amplification, purification, digestion and labeling as described in FIGS. 1B-1I) differ in size and can be resolved, for example by electrophoresis, to allow detection of each individual locus of interest.

FIG. 3. PCR amplification of SNPs using multiple annealing temperatures. A sample containing genomic DNA templates from thirty-six human volunteers was analyzed for the following four SNPs: SNP HC21S00340 (lane 1), identification number as assigned in the Human Chromosome 21 cSNP Database, located on chromosome 21; SNP TSC 0095512 (lane 2), located on chromosome 1, SNP TSC 0214366 (lane 3), located on chromosome 1; and SNP TSC 0087315 (lane 4), located on chromosome 1. Each SNP was amplified by PCR using three different annealing temperature protocols, herein referred to as the low stringency annealing temperature; medium stringency annealing temperature; and high stringency annealing temperature. Regardless of the annealing temperature protocol, each SNP was amplified for 40 cycles of PCR. The denaturation step for each PCR reaction was performed for 30 seconds at 95° C.

Figure 3A:
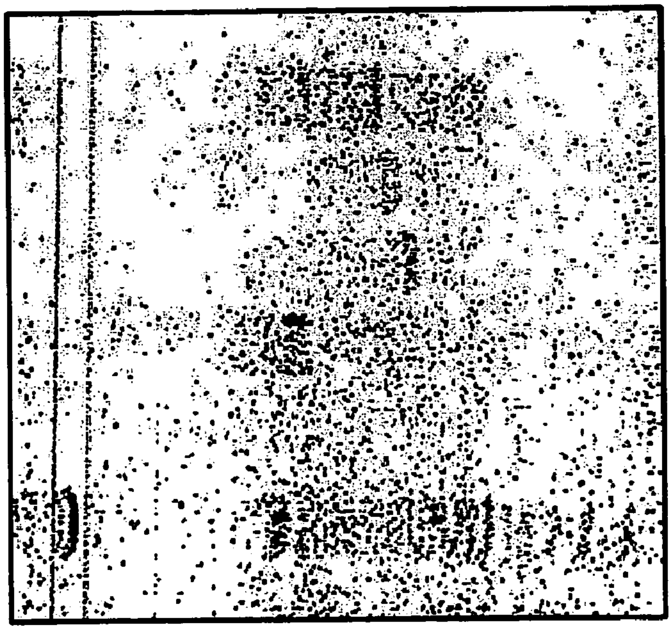

FIG. 3A. Photograph of a gel demonstrating PCR amplification of the 4 different SNPs using the low stringency annealing temperature protocol.

Figure 3B:
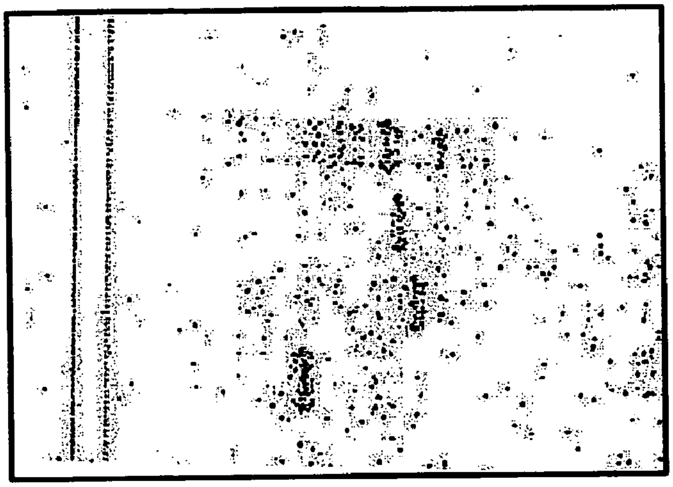

FIG. 3B. Photograph of a gel demonstrating PCR amplification of the 4 different SNPs using medium stringency annealing temperature protocol.

Figure 3C:
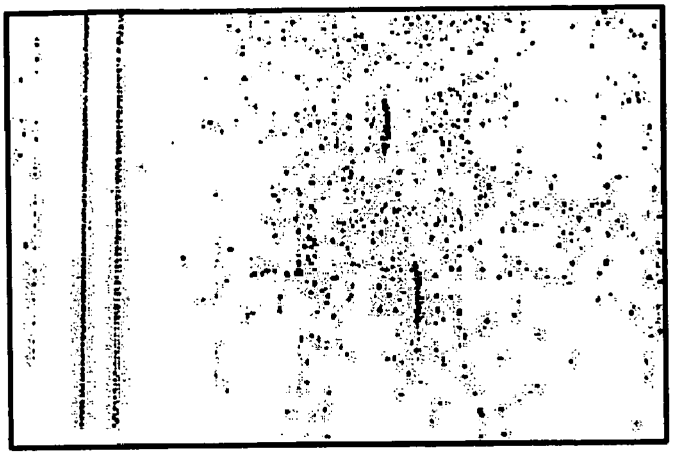

FIG. 3C. Photograph of a gel demonstrating PCR amplification of the 4 different SNPs using the high stringency annealing temperature protocol.

Figure 4A:
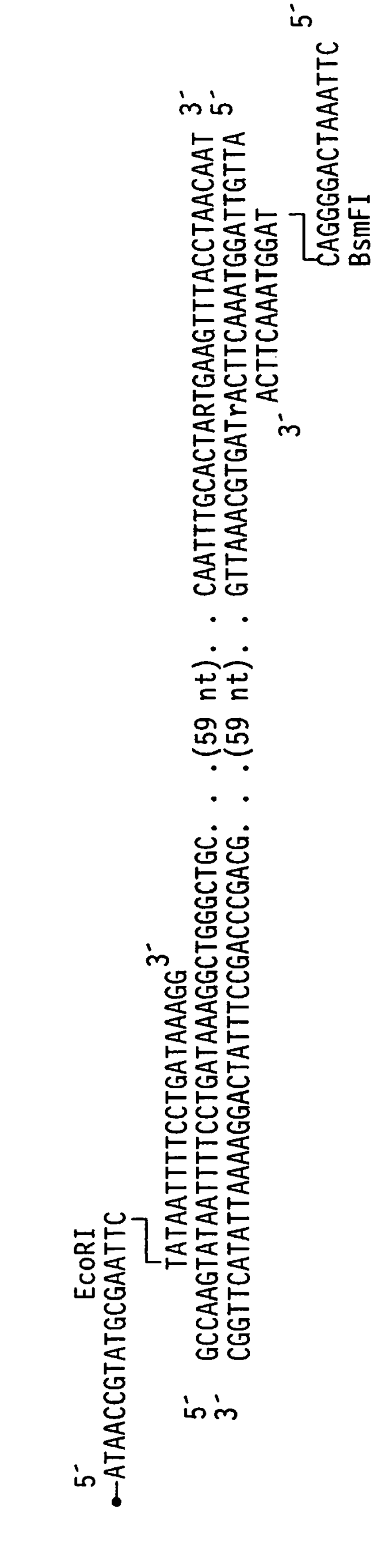

FIG. 4A. (From top to bottom: SEQ ID NOS: 17, 667, 668, 18.) A depiction of the DNA sequence of SNP HC21S00027, as assigned by the Human Chromosome 21 cSNP database, located on chromosome 21. A first primer and a second primer are indicated above and below, respectively, the sequence of HC21 S00027. The first primer is biotinylated and contains the restriction enzyme recognition site for EcoRI. The second primer contains the restriction enzyme recognition site for BsmF I and contains 13 bases that anneal to the DNA sequence. The SNP is indicated by R (A/G) and r (T/C) (complementary to R).

Figure 4B:
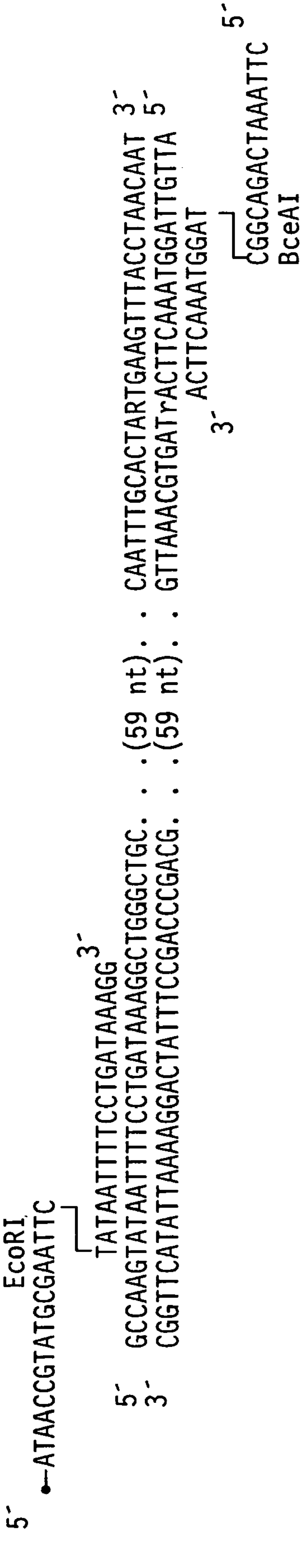

FIG. 4B. (From top to bottom: SEQ ID NOS: 17, 667, 668, 19.) A depiction of the DNA sequence of SNP HC21S00027, as assigned by the Human Chromosome 21 cSNP database, located on chromosome 21. A first primer and a second primer are indicated above and below, respectively, the sequence of HC21S00027. The first primer is biotinylated and contains the restriction enzyme recognition site for EcoRI. The second primer contains the restriction enzyme recognition site for BceA I and has 13 bases that anneal to the DNA sequence. The SNP is indicated by R (A/G) and r (T/C) (complementary to R).

Figure 4C:
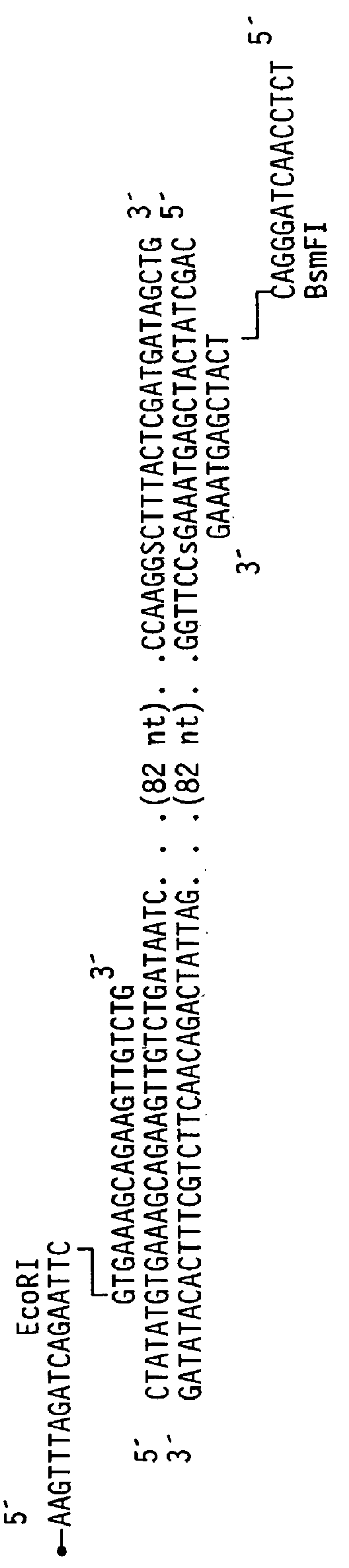

FIG. 4C. (From top to bottom: SEQ ID NOS: 11, 669, 670, 20.) A depiction of the DNA sequence of SNP TSC0095512 from chromosome 1. The first primer and the second primer are indicated above and below, respectively, the sequence of TSC0095512. The first primer is biotinylated and contains the restriction enzyme recognition site for EcoRI. The second primer contains the restriction enzyme recognition site for BsmF I and has 13 bases that anneal to the DNA sequence. The SNP is indicated by S (G/C) and s (C/G) (complementary to S).

Figure 4D:
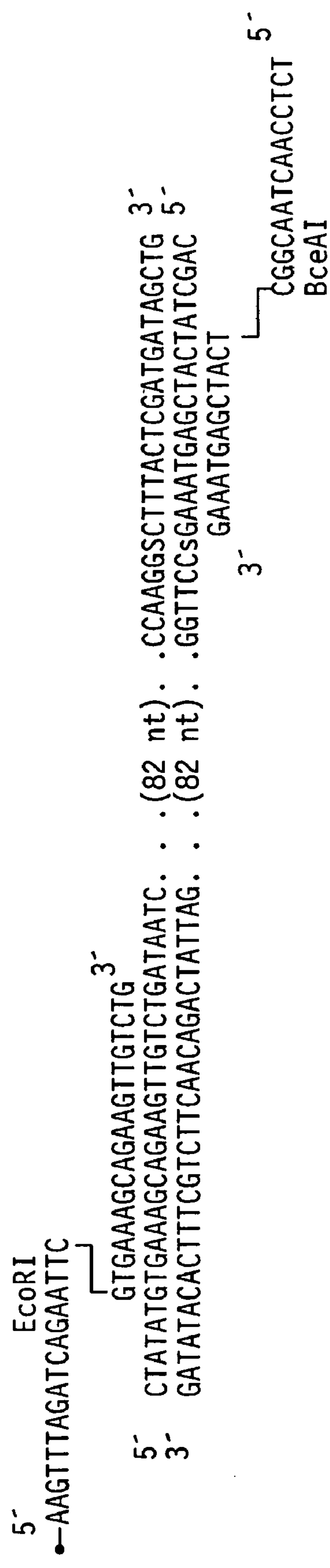

FIG. 4D. (From top to bottom: SEQ ID NOS: 11, 669, 670, 12.) A depiction of the DNA sequence of SNP TSC0095512 from chromosome 1. The first primer and the second primer are indicated above and below, respectively, the sequence of TSC0095512. The first primer is biotinylated and contains the restriction enzyme recognition site for EcoRI. The second primer contains the restriction enzyme recognition site for BceA I and has 13 bases that anneal to the DNA sequence. The SNP is indicated by S (G/C) and s (C/G) (complementary to S).

FIGS. 5A-5D. (FIG. 5A: SEQ ID NOS: 671 (top) and 672 (bottom); FIG. 5B: SEQ ID NOS: 673 (top) and 674 (bottom); FIG. 5C: SEQ ID NOS: 675 (top) and 676 (bottom); FIG. 5D: SEQ ID NOS: 677 (top) and 678 (bottom)). A schematic diagram depicting the nucleotide sequences of SNP HC21 IS00027 (FIGS. 5A and 5B) and SNP TSC0095512 (FIGS. 5C and 5D) after amplification with the primers described in FIGS. 4A-4D. Restriction sites in the primer sequence are indicated in bold.

FIGS. 6A-6D. A schematic diagram depicting the nucleotide sequences of each amplified SNP after digestion with the appropriate Type IIS restriction enzyme. FIGS. 6A (SEQ ID NOS: 679 (upper left), 680 (upper right), 681 (lower left) and 682 (lower right)) and 6B (SEQ ID NOS: 679 (upper left), 683 (upper right), 684 (lower left) and 685 (lower right)) depict fragments of SNP HC21S00027 digested with the Type IIS restriction enzymes BsmF I and BceA I, respectively. FIGS. 6C (SEQ ID NOS: 686 (upper left), 687 (upper right), 688 (lower left) and 689 (lower right)) and 6D (SEQ ID NOS: 686 (upper left), 690 (upper right), 691 (lower left) and 692 (lower right)) depict fragments of SNP TSC0095512 digested with the Type IIS restriction enzymes BsmF I and BceA I, respectively.

Figure 7C:
Figure 7D:
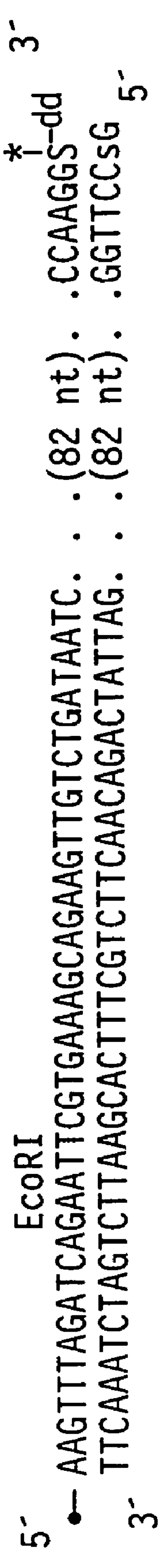

FIGS. 7A-7D. A schematic diagram depicting the incorporation of a fluorescently labeled nucleotide using the 5' overhang of the digested SNP site as a template to "fill in" the 3' recessed end. FIGS. 7A (SEQ ID NOS: 693 (top) and 694 (bottom)) and 7B (SEQ ID NOS: 693 (top) and 695 (bottom)) depict the digested SNP HC21S00027 locus with an incorporated labeled ddNTP (*$Rw^{-dd}$=fluorescent dideoxy nucleotide). FIGS. 7C (SEQ ID NOS: 696 (top) and 697 (bottom)) and 7D (SEQ ID NOS: 696 (top) and 698 (bottom)) depict the digested SNP TSC0095512 locus with an incorporated labeled ddNTP (*$S^{-dd}$=fluorescent dideoxy nucleotide). The use of ddNTPs ensures that the 3' recessed end is extended by one nucleotide, which is complementary to the nucleotide of interest or SNP site present in the 5' overhang.

FIG. 7E. (From top to bottom: SEQ ID NOS: 693, 694, 699, 694, 700, 694, 701, 694.) A schematic diagram depicting the incorporation of dNTPs and a ddNTP into the 5' overhang containing the SNP site. SNP HC21S00007 was digested with BsmF I, which generates a four base 5' overhang. The use of a mixture of dNTPs and ddNTPs allows the 3' recessed end to be extended one nucleotide (a ddNTP is incorporated first); two nucleotides (a dNTP is incorporated followed by a ddNTP); three nucleotides (two dNTPs are incorporated, followed by a ddNTP); or four nucleotides (three dNTPs are incorporated, followed by a ddNTP). All four products can be separated by size, and the incorporated nucleotide detected (*$R^{-dd}$=fluorescent dideoxy nucleotide). Detection of the first nucleotide, which corresponds to the SNP or locus site, and the next three nucleotides provides an additional level of quality assurance. The SNP is indicated by R (A/G) and r (T/C) (complementary to R).

Figure 8A:
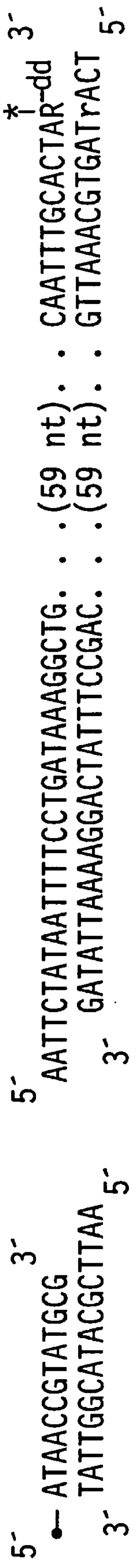
Figure 8B:
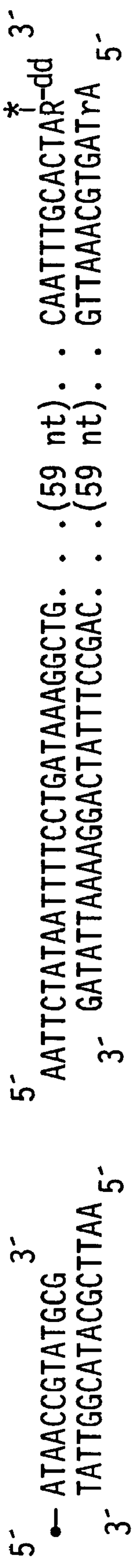
Figure 8C:
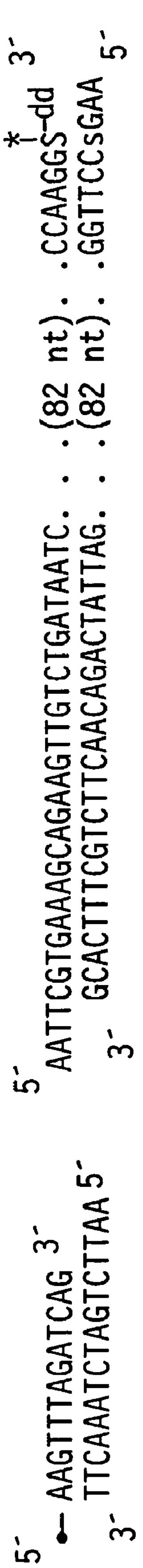
Figure 8D:
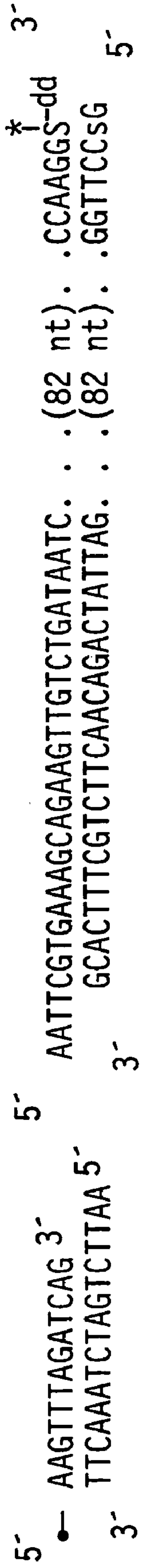

FIGS. 8A-8D. Release of the "filled in" SNP from the solid support matrix, i.e. streptavidin coated well. SNP HC21S00027 is shown in FIGS. 8A (SEQ ID NOS: 702 (upper left), 703 (upper right), 704 (lower left) and 705 (lower right)) and 8B (SEQ ID NOS: 702 (upper left), 703 (upper right), 704 (lower left) and 706 (lower right)), while SNP TSC0095512 is shown in FIGS. 8C (SEQ ID NOS: 707 (upper left), 708 (upper right), 709 (lower left) and 710 (lower right)) and 8D (SEQ ID NOS: 707 (upper left), 708 (upper right), 709 (lower left) and 711 (lower right)). The "filled in" SNP is free in solution, and can be detected.

Figures 9A, 9B, 9C, 9D:
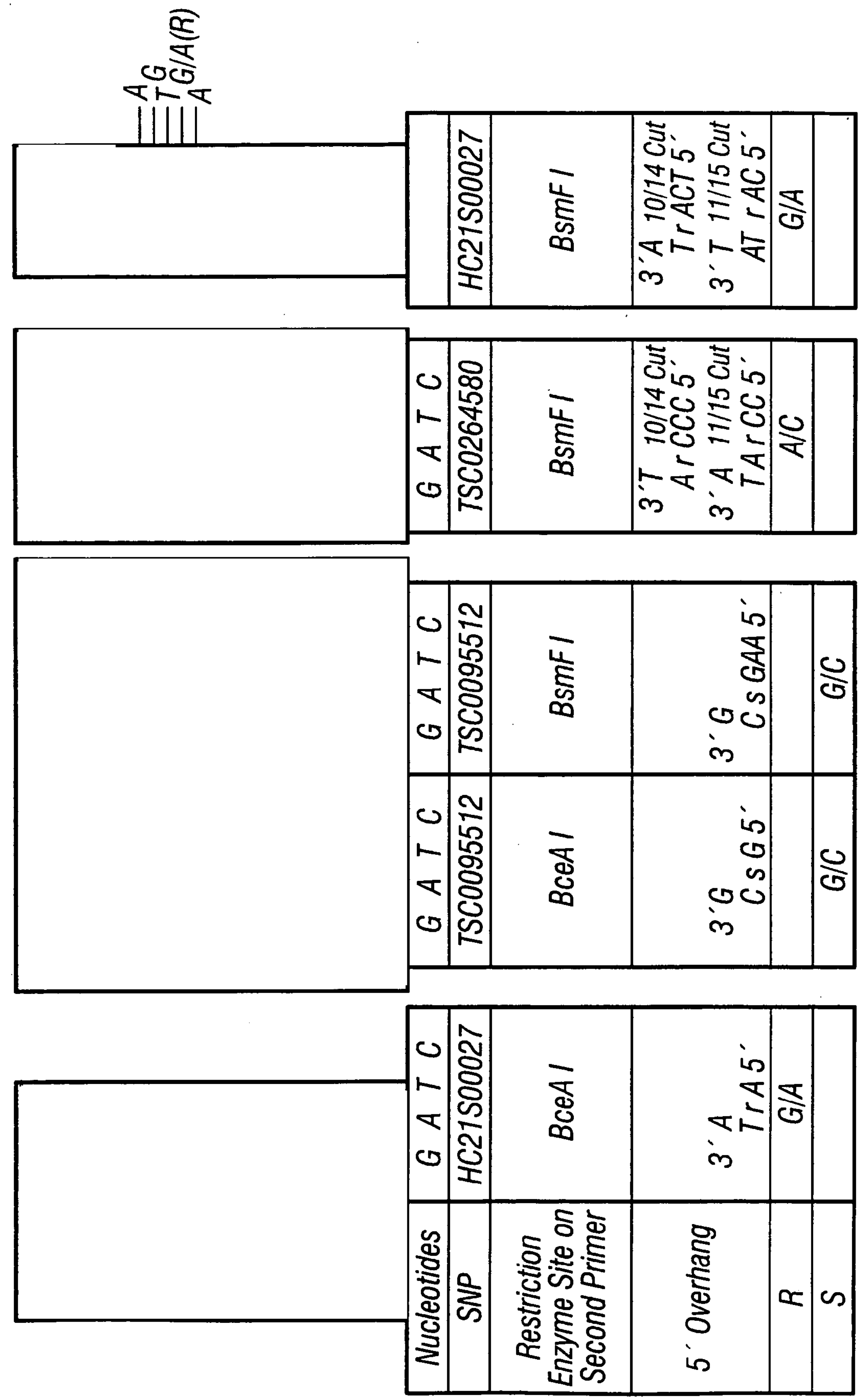

FIG. 9A. Sequence analysis of SNP HC21S00027 digested with BceAI. Four "fill in" reactions are shown; each reaction contained one fluorescently labeled nucleotide, ddGTP, ddATP, ddTTP, or ddCTP, and unlabeled ddNTPs. The 5' overhang generated by digestion with BceA I and the expected nucleotides at this SNP site are indicated.

FIG. 9B. Sequence analysis of SNP TSC0095512. SNP TSC0095512 was amplified with a second primer that contained the recognition site for BceA I, and in a separate reaction, with a second primer that contained the recognition site for BsmF I. Four fill in reactions are shown for each PCR product; each reaction contained one fluorescently labeled nucleotide, ddGTP, ddATP, ddTTP, or ddCTP, and unlabeled ddNTPs. The 5' overhang generated by digestion with BceA I and with BsmF I and the expected nucleotides are indicated.

FIG. 9C. Sequence analysis of SNP TSC0264580 after amplification with a second primer that contained the recognition site for BsmF I. Four fill in reactions are shown; each reaction contained one fluorescently labeled nucleotide, which was ddGTP, ddATP, ddTTP, or ddCTP and unlabeled ddNTPs. Two different 5' overhangs are depicted: one represents the DNA molecules that were cut 11 nucleotides away on the sense strand and 15 nucleotides away on the antisense strand and the other represents the DNA molecules that were cut 10 nucleotides away on the sense strand and 14 nucleotides away on the antisense strand. The expected nucleotides also are indicated.

FIG. 9D. Sequence analysis of SNP HC21S00027 amplified with a second primer that contained the recognition site for BsmF I. A mixture of labeled ddNTPs and unlabeled dNTPs was used to fill in the 5' overhang generated by digestion with BsmF I. Two different 5' overhangs are depicted: one represents the DNA molecules that were cut 11 nucleotides away on the sense strand and 15 nucleotides away on the antisense strand and the other represents the DNA molecules that were cut 10 nucleotides away on the sense strand and 14 nucleotides away on the antisense strand. The nucleotide upstream from the SNP, the nucleotide at the SNP site (the sample contained DNA templates from 36 individuals; both nucleotides would be expected to be represented in the sample), and the three nucleotides downstream of the SNP are indicated.

Figure 10:
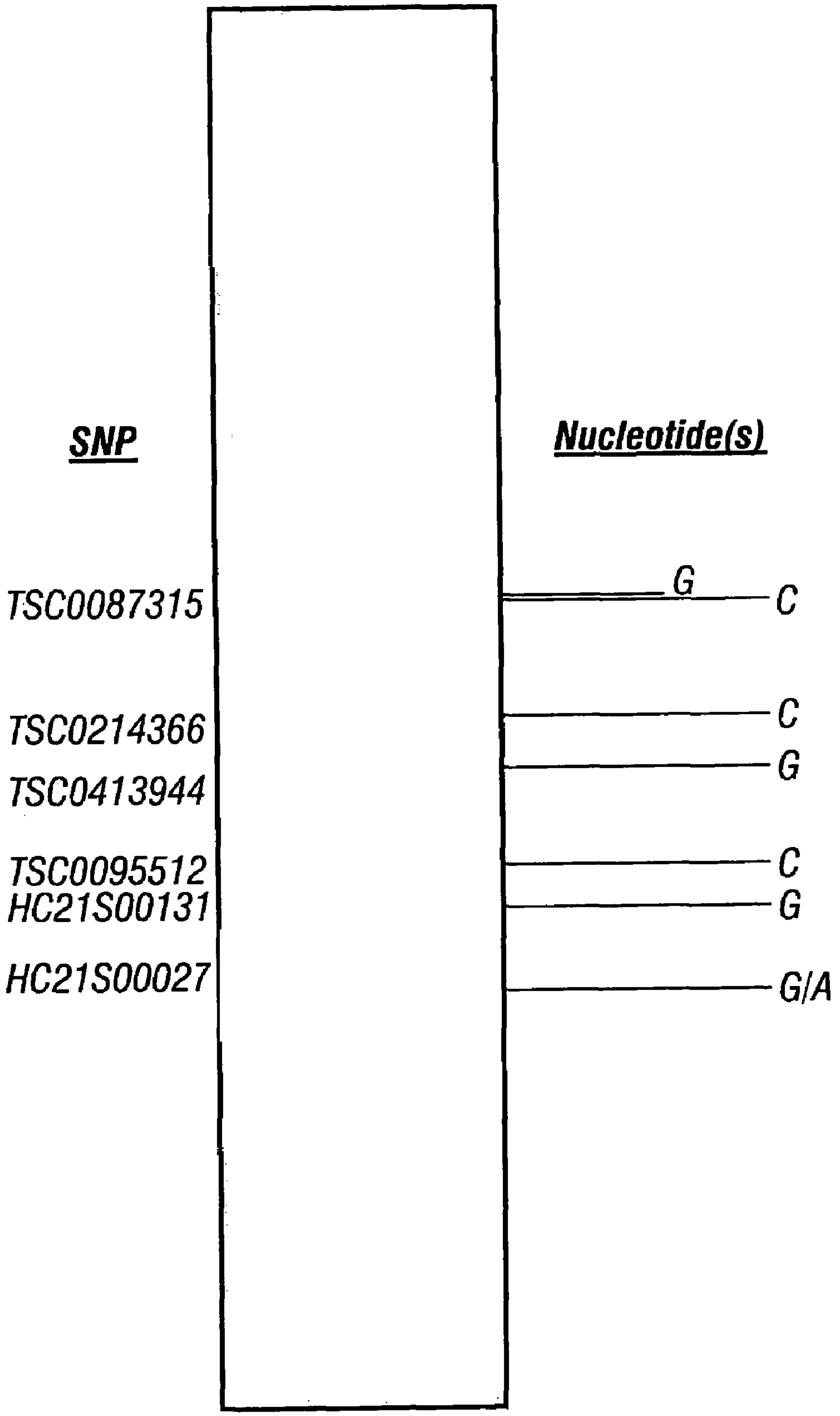

FIG. 10. Sequence analysis of multiple SNPs. SNPs HC21S00131, and HC21S00027, which are located on chromosome 21, and SNPs TSC0087315, SNP TSC0214366, SNP TSC0413944, and SNP TSC0095512, which are on chromosome 1, were amplified in separate PCR reactions with second primers that contained a recognition site for BsmF I. The primers were designed so that each amplified locus of interest was of a different size. After amplification, the reactions were pooled into a single sample, and all subsequent steps of the method performed (as described for FIGS. 1F-1I) on that sample. Each SNP and the nucleotide found at each SNP are indicated.

FIG. 11. Quantification of the percentage of fetal DNA in maternal blood. Blood was obtained from a pregnant human female with informed consent. DNA was isolated and serial dilutions were made to determine the percentage of fetal DNA present in the sample. The SRY gene, which is located on chromosome Y, was used to detect fetal DNA. The cystic fibrosis gene, which is located on chromosome 7, was used to detect both maternal and fetal DNA.

Figure 11A:
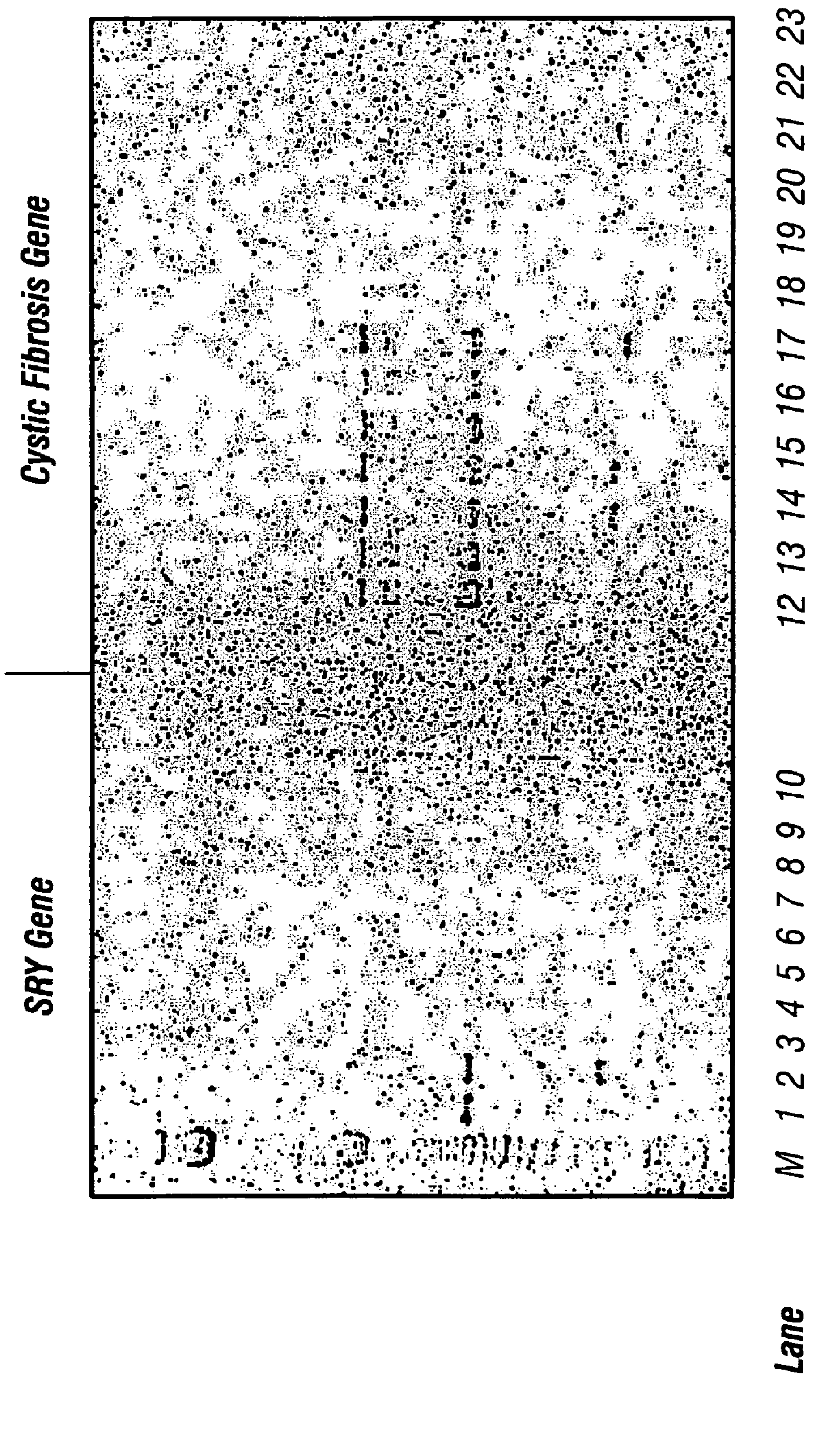

FIG. 11A. Amplification of the SRY gene and the cystic fibrosis gene using a DNA template isolated from a blood sample that was treated with EDTA.

Figure 11B:
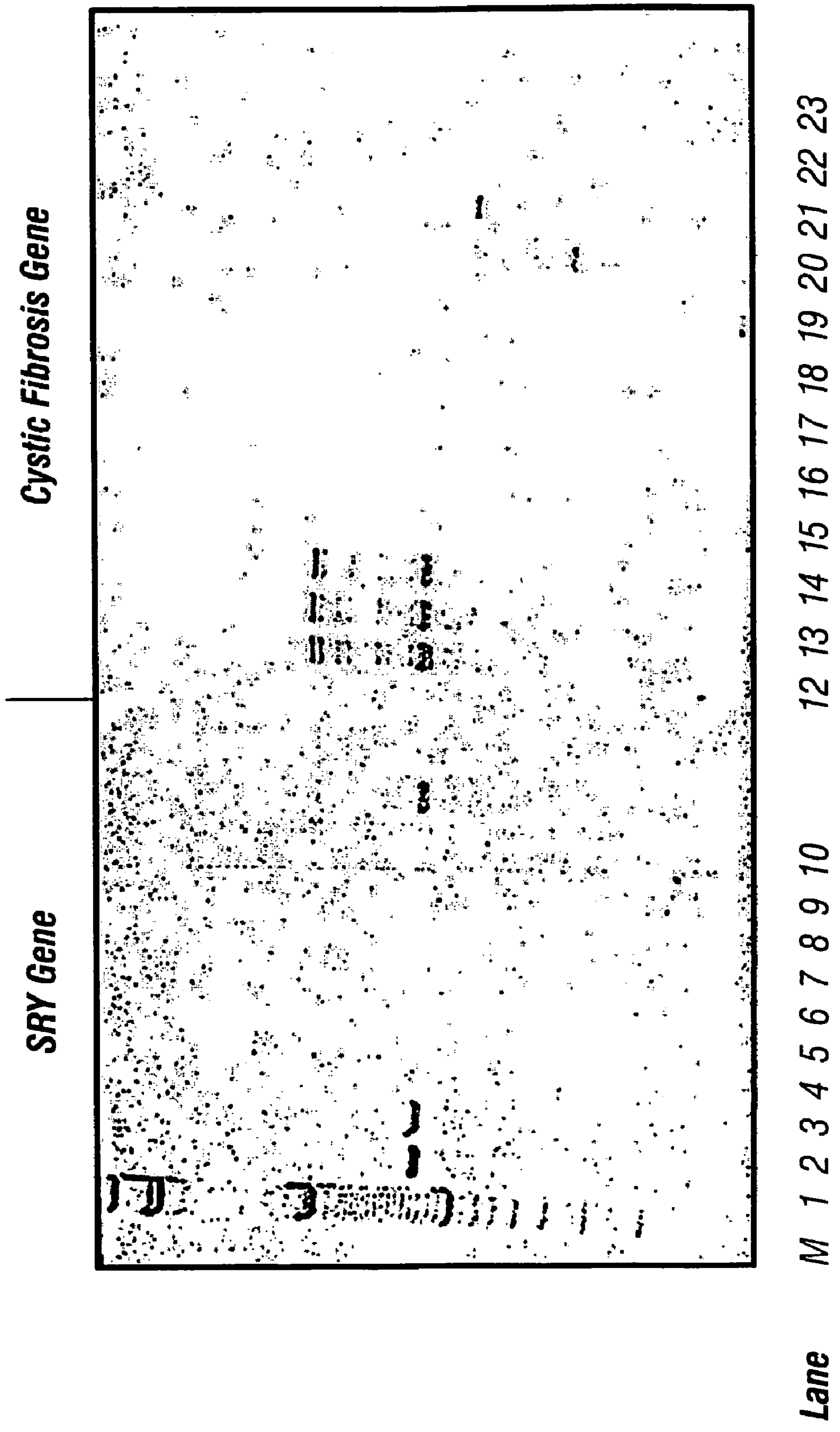

FIG. 11B. Amplification of the SRY gene and the cystic fibrosis gene using a DNA template that was isolated from a blood sample that was treated with formalin and EDTA.

Figure 12:
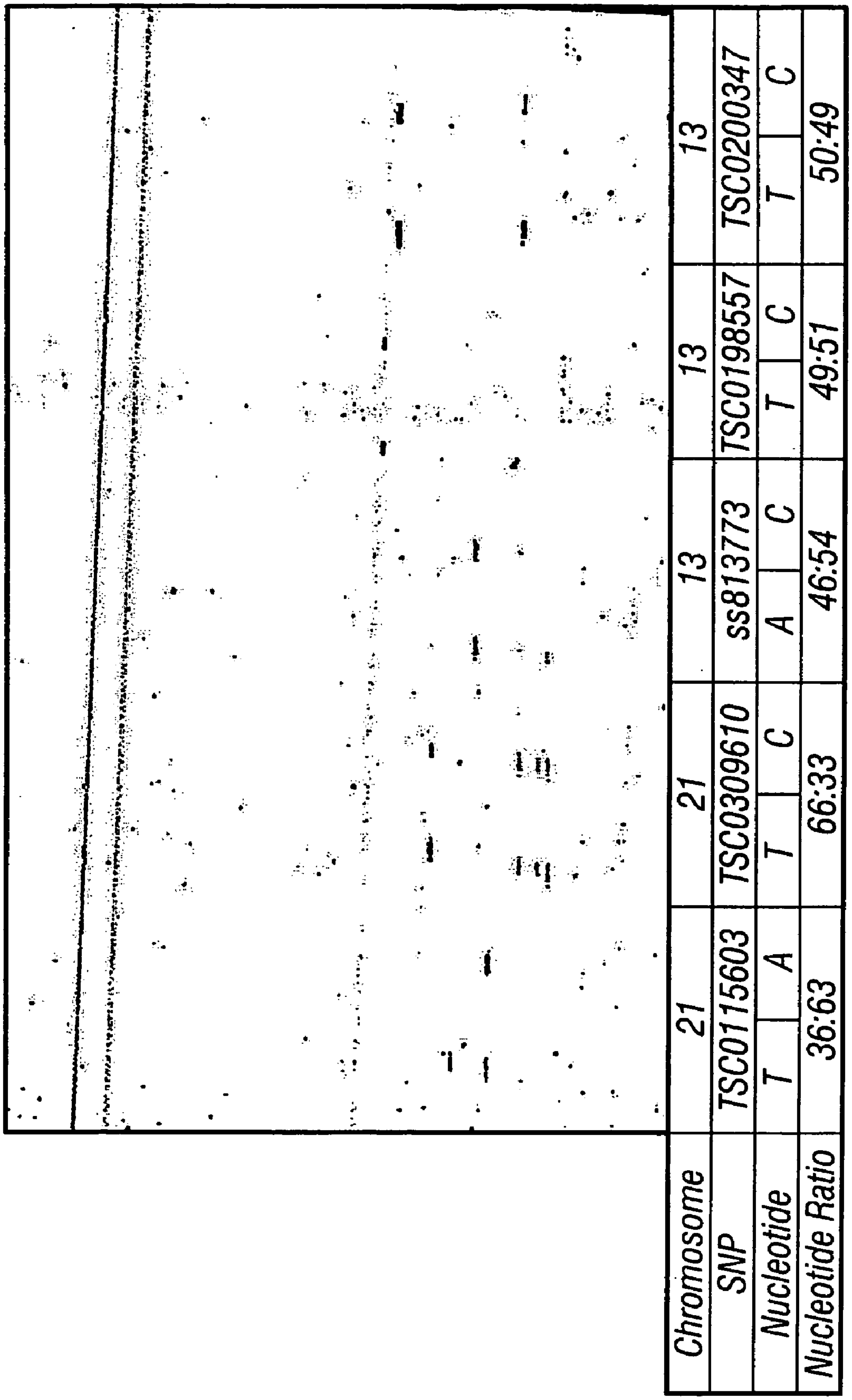

FIG. 12. Genetic analysis of an individual previously genotyped with Trisomy 21 (Down's Syndrome). Blood was collected, with informed consent, from an individual who had previously been genotyped with trisomy 21. DNA was isolated and two SNPs on chromosome 21 and two SNPs on chromosome 13 were genotyped. As shown in the photograph of the gel, the SNPs at chromosome 21 show disproportionate ratios of the two nucleotides. Visual inspection of the gel demonstrates that one nucleotide of the two nucleotides at the SNP sites analyzed for chromosome 21 is of greater intensity, suggesting it is not present in a 50:50 ratio. However, visual inspection of the gel suggests that the nucleotides at the heterozygous SNP sites analyzed on chromosome 13 are present in the expected 50:50 ratio.

Figure 13:
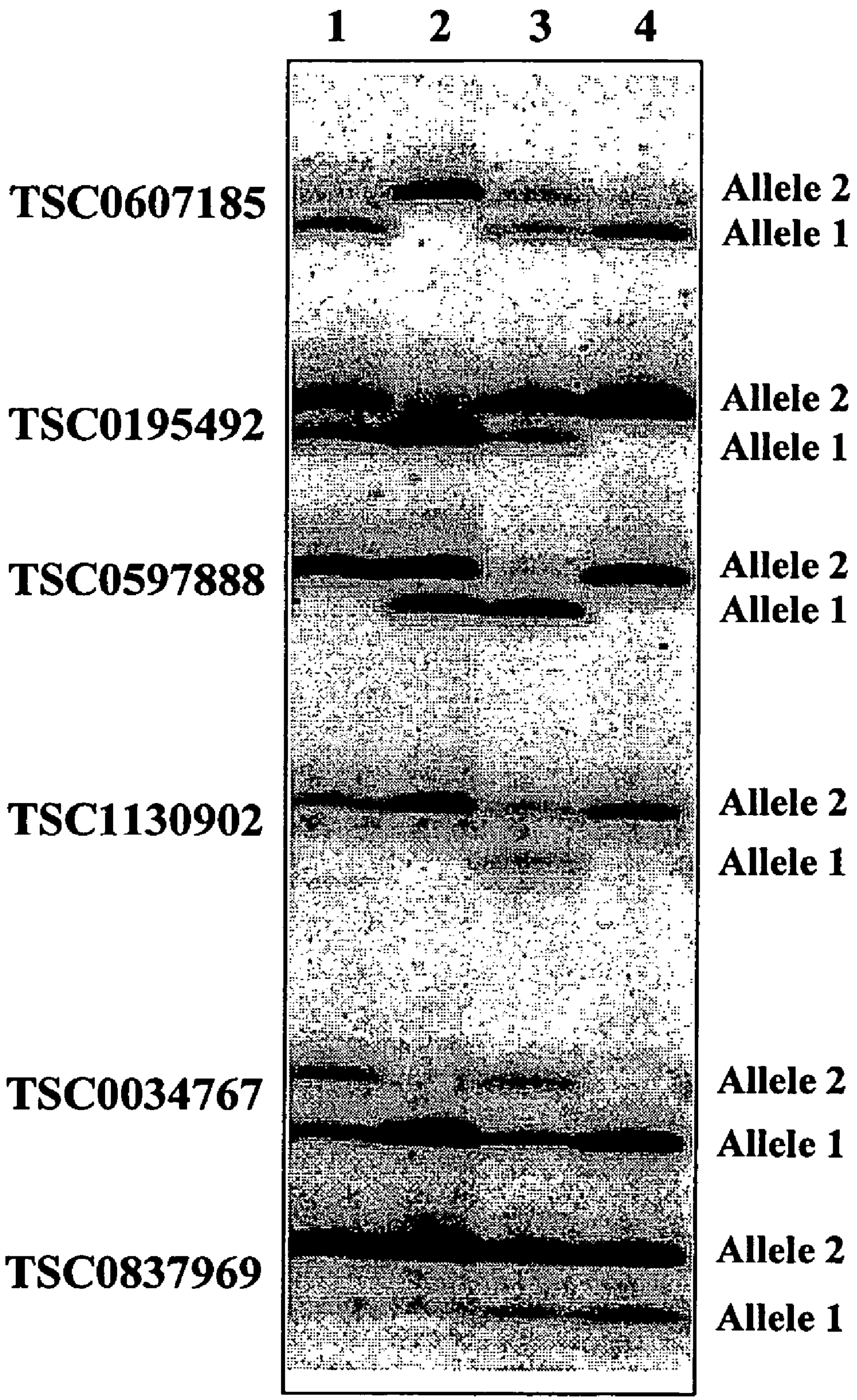

FIG. 13. Sequence determination of both alleles of SNPs TSC0837969, TSC0034767, TSC1130902, TSC0597888, TSC0195492, TSC0607185 using one fluorescently labeled nucleotide. Labeled ddGTP was used in the presence of unlabeled dATP, dCTP, dTTP to fill-in the overhang generated by digestion with BsmF I. The nucleotide preceding the variable site on the strand that was filled-in was not guanine, and the nucleotide after the variable site on the strand that was filled in was not guanine. The nucleotide two bases after the variable site on the strand that was filled-in was guanine. Alleles that contain guanine at variable site are filled in with labeled ddGTP. Alleles that do not contain guanine are filled in with unlabeled dATP, dCTP, or dTTP, and the polymerase continues to incorporate nucleotides until labeled ddGTP is filled in at position 3 complementary to the overhang.

Figure 14:
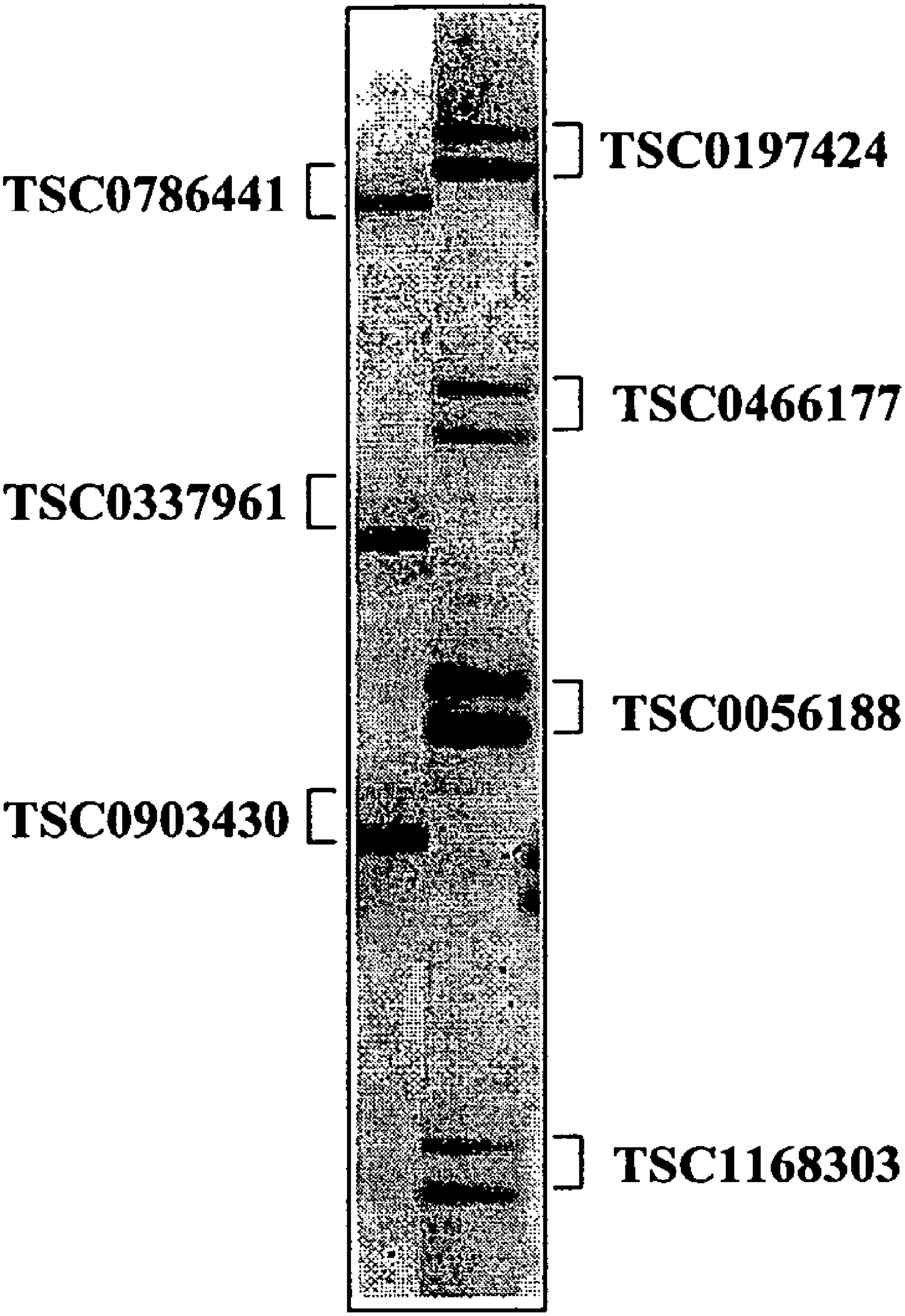

FIG. 14. Identification of SNPs with alleles that are variable within the population. The sequences of both alleles of seven SNPs located on chromosome 13 were determined using a template DNA comprised of DNA obtained from two hundred and forty five individuals. Labeled ddGTP was used in the presence of unlabeled dATP, dCTP, dTTP to fill-in the overhang generated by digestion with BsmF I. The nucleotide preceding the variable site on the strand that was filled-in was not guanine, and the nucleotide after the variable site on the strand that was filled in was not guanine. The nucleotide two bases after the variable site on the strand that was filled-in was guanine. Alleles that contain guanine at variable site are filled in with labeled ddGTP. Alleles that do not contain guanine are filled in with unlabeled dATP, dCTP, or dTTP, and the polymerase continues to incorporate nucleotides until labeled ddGTP is filled in at position 3 complementary to the overhang.

Figure 15:
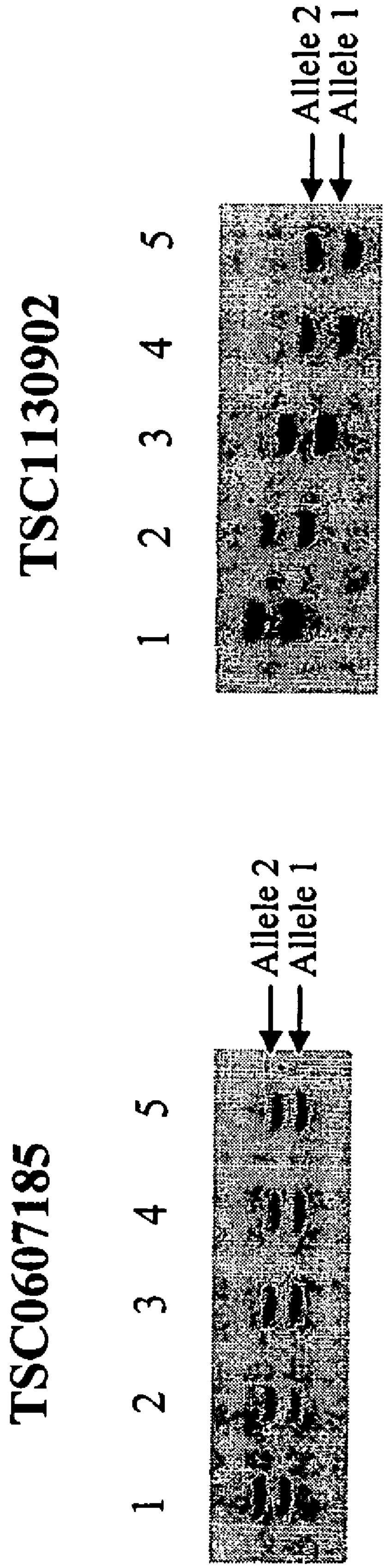

FIG. 15. Determination of the ratio for one allele to the other allele at heterozygous SNPs. The observed nucleotides for SNP TSC0607185 are cytosine (referred to as allele 1) and thymidine (referred to as allele 2) on the sense strand. The ratio of allele 2 to allele I was calculated using template DNA isolated from five individuals. The ratio of allele 2 to allele 1 (allele 2/ allele 1) was consistently 1:1.

The observed nucleotides for SNP TSC1130902 are guanine (referred to as allele 1) and adenine (referred to as allele 2) on the sense strand. The ratio of allele 2 to allele 1 was calculated using template DNA isolated from five individuals. The ratio of allele 2 to allele 1 (allele 2 allelel) was consistently 75:25.

Figure 16:
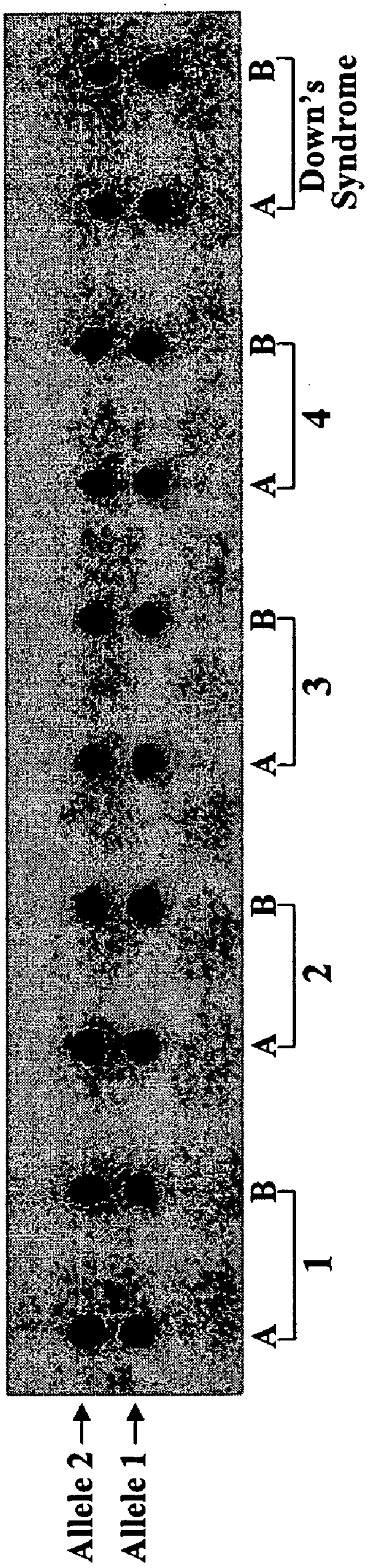

FIG. 16. The percentage of allele 2 to allele 1 at SNP TSC0108992 remains linear when calculated on template DNA containing an extra copy of chromosome 21. SNP TSC0108992 was amplified using template DNA from four individuals, and two separate fill-in reactions (labeled as A and B) were performed for each PCR reaction (labeled 1 through 4). The calculated percentage of allele 2 to allele 1 on template DNA from normal individuals was 0.47. The deviation from the theoretically predicted percentage of 0.50 remained linear on template DNA isolated from an individual with Down's syndrome.

FIG. 17A. Analysis of a SNP located on chromosome 21 from template DNA isolated from an individual with a normal genetic karyotype. SNP TSC0108992 was amplified using the methods described herein, and after digestion with the type IIS restriction enzyme BsmF I, the 5' overhang was filled in using labeled ddTTP, and unlabeled dATP, dCTP, and dGTP. Three separate PCR reactions were performed, and each PCR reaction was split into two samples. The percentage of allele 2 at the SNP site (allele 2/(allele 2+allele 1)) was calculated, which resulted in mean of 0.50.

FIG. 17B. Analysis of a SNP located on chromosome 21 from template DNA isolated from an individual with a trisomy 21 genetic karyotype. SNP TSC0108992 was amplified using the methods described herein, and after digestion with the type IIS restriction enzyme BsmF I, the 5' overhang was filled in using labeled ddTTP, and unlabeled dATP, dCTP, and dGTP. Three separate PCR reactions were performed, and each PCR reaction was split into two samples. The percentage of allele 2 at the SNP site (allele 2/(allele 2+allele 1)) was calculated, which resulted in mean of 0.30.

FIG. 17C. Analysis of a SNP located on chromosome 21 from a mixture comprised of template DNA from an individual with Trisomy 21, and template DNA from an individual with a normal genetic karyotype in a ratio of 3:1 (Trisomy 21: Normal). SNP TSC0108992 was amplified from the mixture of template DNA using the methods described herein, and after digestion with the type IIS restriction enzyme BsmF I, the 5' overhang was filled in using labeled ddTTP, and unlabeled dATP, dCTP, and dGTP. Three separate PCR reactions were performed, and each PCR reaction was split into two samples. The percentage of allele 2 at the SNP site (allele 2/(allele 2+allele 1)) was calculated, which resulted in mean of 0.319.

FIG. 17D. Analysis of a SNP located on chromosome 21 from a mixture comprised of template DNA from an individual with Trisomy 21, and template DNA from an individual with a normal genetic karyotype in a ratio of 1:1 (Trisomy 21: Normal). SNP TSC0108992 was amplified from the mixture of template DNA using the methods described herein, and after digestion with the type IIS restriction enzyme BsmF I, the 5' overhang was filled in using labeled ddTTP, and unlabeled dATP, dCTP, and dGTP. Three separate PCR reactions were performed, and each PCR reaction was split into two samples. The percentage of allele 2 at the SNP site (allele 2/(allele 2+allele 1)) was calculated, which resulted in mean of 0.352.

FIG. 17E. Analysis of a SNP located on chromosome 21 from a mixture comprised of template DNA from an individual with Trisomy 21, and template DNA from an individual with a normal genetic karyotype in a ratio of 1:2.3 (Trisomy 21: Normal). SNP TSC0108992 was amplified from the mixture of template DNA using the methods described herein, and after digestion with the type IIS restriction enzyme BsmF I, the 5' overhang was filled in using labeled ddTTP, and unlabeled dATP, dCTP, and dGTP. Three separate PCR reactions were performed, and each PCR reaction was split into two samples. The percentage of allele 2 at the SNP site (allele 2/(allele 2+allele 1)) was calculated, which resulted in mean of 0.382.

FIG. 17F. Analysis of a SNP located on chromosome 21 from a mixture comprised of template DNA from an individual with Trisomy 21, and template DNA from an individual with a normal genetic karyotype in a ratio of 1:4 (Trisomy 21: Normal). SNP TSC0108992 was amplified from the mixture of template DNA using the methods described herein, and after digestion with the type IIS restriction enzyme BsmF I, the 5' overhang was filled in using labeled ddTTP, and unlabeled dATP, dCTP, and dGTP. Three separate PCR reactions were performed, and each PCR reaction was split into two samples. The percentage of allele 2 at the SNP site (allele 2/(allele 2+allele 1)) was calculated, which resulted in mean of 0.397.

Figure 18A:
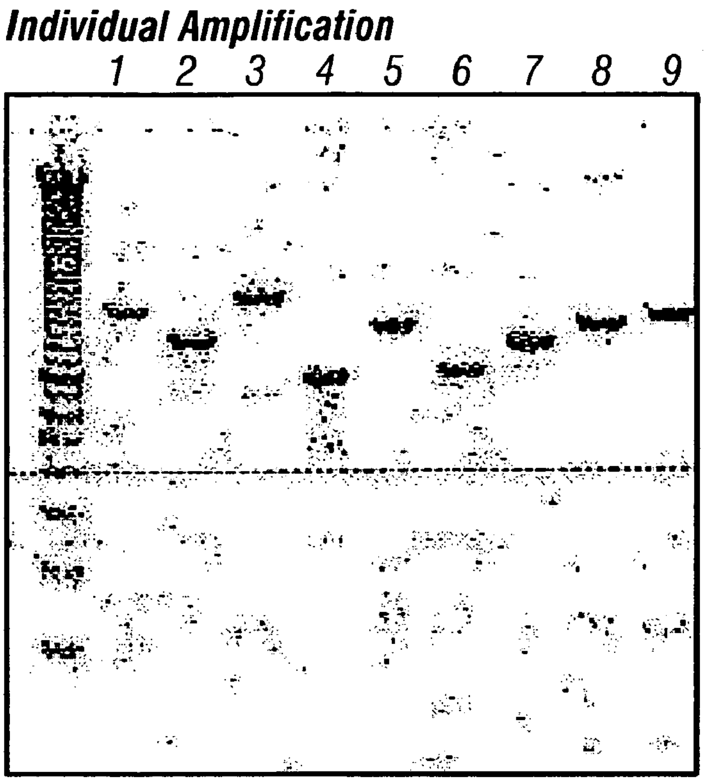

FIG. 18A. Agarose gel analysis of nine (9) SNPs amplified from template DNA. Each of the nine SNPs were amplified from genomic DNA using the methods described herein. Lane 1 corresponds to SNP TSC0397235, lane 2 corresponds to TSC0470003, lane 3 corresponds to TSC1649726, lane 4 corresponds to TSC1261039, lane 5 corresponds to TSC0310507, lane 6 corresponds to TSC1650432, lane 7 corresponds to TSC1335008, lane 8 corresponds to TSC0128307, and lane 9 corresponds to TSC0259757.

Figure 18B:
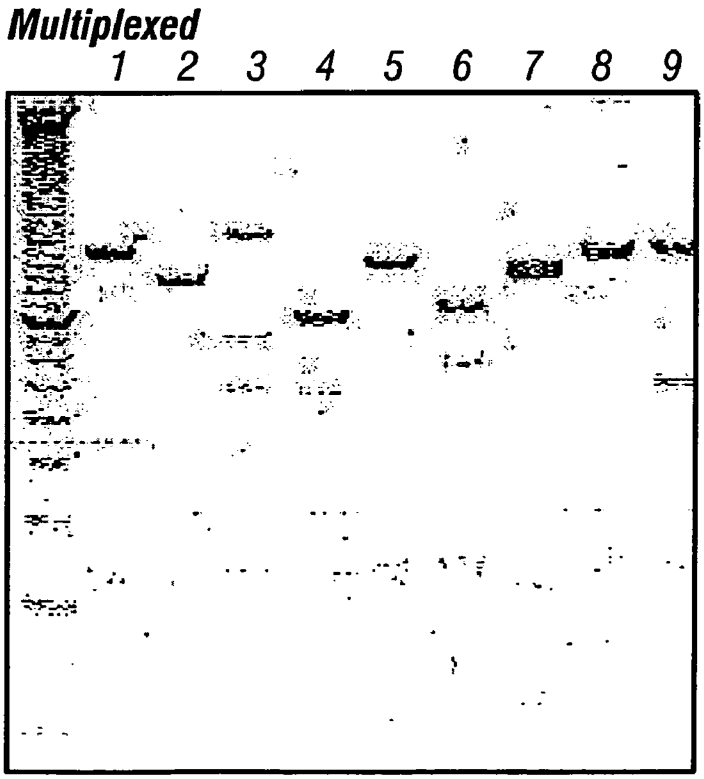

FIG. 18B. The original template DNA was amplified using 12 base primers that annealed to various regions on chromosome 13. One hundred different primer sets were used to amplify regions throughout chromosome 13. For each of the nine SNPs, a primer that annealed approximately 130 bases from the locus of interest and 130 bases downstream of the locus of interest were used. This amplification reaction, which contained a total of 100 different primer sets, was used to amplify the regions containing the loci of interest. The resulting PCR product was used in a subsequent PCR reaction, wherein each of the nine SNPs were individually amplified using a first primer and a second primer, wherein the second primer contained the binding site for the type IIs restriction enzyme BsmF I. SNPs were loaded in the same order as FIG. 18A.

FIG. 19A. Quantification of the percentage of allele 2 to allele 1 for SNP TSC047003 on original template DNA (IA) and multiplexed template DNA (M1-M3), wherein the DNA was first amplified using 12 base primers that annealed 150 bases upstream and downstream of the loci of interest. Then, three separate PCR reactions were performed on the multiplexed template DNA, using a first and second primer.

FIG. 19B. Quantification of the percentage of allele 2 to allele 1 for SNP TSC1261039 on original template DNA (IA) and multiplexed template DNA (M1-M3), wherein the DNA was first amplified using 12 base primers that annealed 150 bases upstream and downstream of the loci of interest. Then, three separate PCR reactions were performed on the multiplexed template DNA, using a first and second primer.

FIG. 19C. Quantification of the percentage of allele 2 to allele 1 for SNP TSC310507 on original template DNA (IA) and multiplexed template DNA (M1-M3), wherein the DNA was first amplified using 12 base primers that annealed 150 bases upstream and downstream of the loci of interest. Then, three separate PCR reactions were performed on the multiplexed template DNA, using a first and second primer.

FIG. 19D. Quantification of the percentage of allele 2 to allele 1 for SNP TSC1335008 on original template DNA (IA) and multiplexed template DNA (M1-M3), wherein the DNA was first amplified using 12 base primers that annealed 150 bases upstream and downstream of the loci of interest. Then, three separate PCR reactions were performed on the multiplexed template DNA, using a first and second primer.

Figure 20:
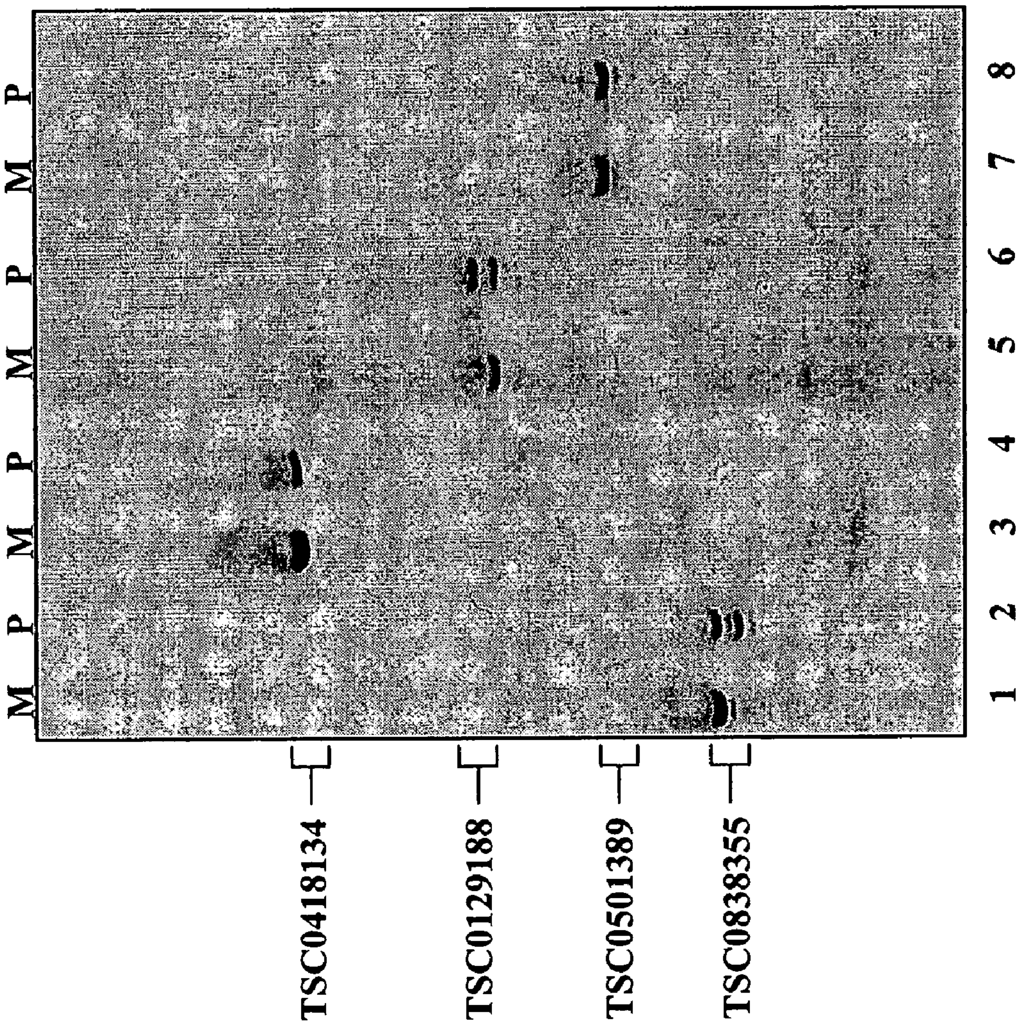

FIG. 20. Detection of fetal DNA from plasma DNA isolated from a pregnant female. Four SNPs wherein the maternal DNA was homozygous were analyzed on the plasma DNA. The maternal DNA was homozygous for adenine at TSC0838335 (lane 1), while the plasma DNA displayed a heterozygous pattern (lane 2). The guanine allele represented the fetal DNA, which was clearly distinguished from the maternal signal. Both the maternal DNA and the plasma DNA were homozygous for adenine at TSC0418134 (lanes 3 and 4). The maternal DNA was homozygous for guanine at TSC0129188 (lane 5), while the plasma DNA displayed a heterozygous pattern (lane 6). The adenine allele represented the fetal DNA. Both the maternal DNA and the plasma DNA were homozygous for adenine at TSC0501389 (lanes 7 and 8).

DETAILED DESCRIPTION OF THE INVENTION

The present invention provides a method for detecting genetic disorders, including but not limited to mutations, insertions, deletions, and chromosomal abnormalities, and is especially useful for the detection of genetic disorders of a fetus. The method is especially useful for detection of a translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy, tetraploidy, and sex chromosome abnormalities including but not limited to XO, XXY, XYY, and XXX. The method also provides a non-invasive technique for determining the sequence of fetal DNA and identifying mutations within the fetal DNA.

The invention is directed to a method for detecting chromosomal abnormalities, the method comprising: (a) determining the sequence of alleles of a locus of interest on a template DNA; and (b) quantitating a ratio for the alleles at a heterozygous locus of interest that was identified from the locus of interest of (a), wherein said ratio indicates the presence or absence of a chromosomal abnormality.

In another embodiment, the present invention provides a non-invasive method for determining the sequence of a locus of interest on fetal DNA, said method comprising: (a) obtaining a sample from a pregnant female; (b) adding a cell lysis inhibitor, cell membrane stabilizer or cross-linker to the sample of (a); (c) obtaining template DNA from the sample of (b), wherein said template DNA comprises fetal DNA and maternal DNA; and (d) determining the sequence of a locus of interest on template DNA.

In another emobodiment, th present invention is directed to a method for isolating DNA, said method comprising (a) obtaining a sample containing nucleic acid; (b) adding a cell lysis inhibitor, cell membrane stabilizer or cross-linker to sample of (a); and (c) isolating the DNA.

In another emobodiment, th present invention is directed to a method for isolating free DNA, said method comprising (a) obtaining a sample containing nucleic acid; (b) adding a cell lysis inhibitor, cell membrane stabilizer or cross-linker to sample of (a); and (c) isolating the DNA.

In another embodiment, the present invention is directed to a method for isolating free DNA from a sample containing nucleic acid to which a cell lysis inhibitor, cell membrane stabilizer or cross-linker has been added, said method corm-prising isolating the DNA.

In another emobodiment, the present invention is directed to a method for isolating free fetal DNA, said method comprising (a) obtaining a sample containing nucleic acid; (b) adding a cell lysis inhibitor, cell membrane stabilizer or cross-linker to sample of (a); and (c) isolating the DNA. In another embodiment, the DNA is isolated using any technique suitable in the art including but not limited to cesium chloride gradients, gradients, sucrose gradients, glucose gradients, centrifugation protocols, boiling, Qiagen purification systems, QIA DNA blood purification kit, HiSpeed Plasmid Maxi Kit, QIAfilter plasmid kit, Promega DNA purification systems, MangeSil Paramagnetic Particle based systems, Wizard SV technology, Wizard Genomic DNA purification kit, Amersham purification systems, GFX Genomic Blood DNA purification kit, Invitrogen Life Technologies Purification Systems, CONCERT purification system, Mo Bio Laboratories purification systems, UltraClean BloodSpin Kits, and UlraClean Blood DNA Kit.

In another emobodiment, the present invention is directed to a method for isolating free fetal DNA from a sample containing nucleic acid to which a cell lysis inhibitor, cell membrane stabilizer or cross-linker has been added, said method comprising isolating the DNA. In a preferred embodiment, the free fetal DNA is isolated from plasma or serum obtained from the blood of a pregnant female.

In another embodiment, the DNA is isolated using techniques and/or protocols that substantially reduce the amount of maternal DNA in the sample including but not limited to centrifuging the samples, with the braking power for the centrifuge set to zero (the brake on the centrifuge is not used), transferring the supernatant to a new tube with minimal or no disturbance of the “buffy-coat,” and transferring only a portion of the supernatant to a new tube. In a preferred embodiment, both acceleration power and braking power for the centrifuge are set to zero.

In another embodiment, the DNA is isolated using techniques and/or protocols that substantially reduce the amount of maternal DNA in the sample including but not limited to centrifuging the samples, with the acceleration power for the centrifuge set to zero, transferring the supernatant to a new tube with minimal or no disturbance of the "buffy-coat," and transferring only a portion of the supernatant to a new tube.

In another embodiment, the "buffy-coat" is removed from the tube prior to removal of the supernatant using any applicable method including but not limited to using a syringe or needle to withdraw the "buffy-coat."

In another embodiment, the braking power for the centrifuge is set at a percentage including but not limited to 1-5%, 5-10%, 10-20%, 20-30%, 30-40%, 40-50%, 50-60%, 60-70%, 70-80%, 80-90%, 90-95%, 95-99% of maximum braking power.

In another embodiment, the acceleration power for the centrifuge is set at a percentage including but not limited to 1-5%, 5-10%, 10-20%, 20-30%, 30-40%, 40-50%, 50-60%, 60-70%, 70-80%, 80-90%, 90-95%, 95-99% of maximum acceleration power.

In another embodiment, the present invention is directed to a composition comprising free fetal DNA and free maternal DNA, wherein the composition comprises a relationship of free fetal DNA to free maternal DNA including but not limited to at least about 15% free fetal DNA, at least about 20% free fetal DNA, at least about 30% free fetal DNA, at least about 40% free fetal DNA, at least about 50% free fetal DNA, at least about 60% free fetal DNA, at least about 70% free fetal DNA, at least about 80% free fetal DNA, at least about 90% free fetal DNA, at least about 91% free fetal DNA, at least about 92% free fetal DNA, at least about 93% free fetal DNA, at least about 94% free fetal DNA, at least about 95% free fetal DNA, at least about 96% free fetal DNA, at least about 97% free fetal DNA, at least about 98% free fetal DNA, at least about 99% free fetal DNA, and at least about 99.5% free fetal DNA.

In another embodiment, the present invention is directed to a method of using a composition comprising free fetal DNA and free maternal DNA for prenatal diagnostics, wherein the composition comprises a relationship of free fetal DNA to free maternal DNA including but not limited to at least about 15% free fetal DNA, at least about 20% free fetal DNA, at least about 30% free fetal DNA, at least about 40% free fetal DNA, at least about 50% free fetal DNA, at least about 60% free fetal DNA, at least about 70% free fetal DNA, at least about 80% free fetal DNA, at least about 90% free fetal DNA, at least about 91% free fetal DNA, at least about 92% free fetal DNA, at least about 93% free fetal DNA, at least about 94% free fetal DNA, at least about 95% free fetal DNA, at least about 96% free fetal DNA, at least about 97% free fetal DNA, at least about 98% free fetal DNA, at least about 99% free fetal DNA, and at least about 99.5% free fetal DNA.

In another embodiment, the present invention is directed to a composition comprising free fetal DNA and free maternal DNA, wherein the composition comprises a relationship of free fetal DNA to free maternal DNA including but not limited to about 13-15% free fetal DNA, about 15-16% free fetal DNA, about 16-17% free fetal DNA, about 17-18% free fetal DNA, about 18-19% free fetal DNA, about 19-20% free fetal DNA, about 20-21% free fetal DNA, about 21-22% free fetal DNA, about 22-23% free fetal DNA, about 23-24% free fetal DNA, about 24-25% free fetal DNA, about 25-35% free fetal DNA, about 35-45% free fetal DNA, about 45-55% free fetal DNA, about 55-65% free fetal DNA, about 65-75% free fetal DNA, about 75-85% free fetal DNA, about 85-90% free fetal DNA, about 90-91% free fetal DNA, about 91-92% free fetal DNA, about 92-93% free fetal DNA, about 93-94% free fetal DNA, about 94-95% free fetal DNA, about 95-96% free fetal DNA, about 96-97% free fetal DNA, about 97-98% free fetal DNA, about 98-99% free fetal DNA, and about 99-99.7% free fetal DNA.

In another embodiment, the present invention is directed to a-method of using a composition comprising free fetal DNA and free maternal DNA for prenatal diagnostics, wherein the composition comprises a relationship of free fetal DNA to free maternal DNA including but not limited to about 13-15% free fetal DNA, about 15-16% free fetal DNA, about 16-17% free fetal DNA, about 17-18% free fetal DNA, about 18-19% free fetal DNA, about 19-20% free fetal DNA, about 20-21% free fetal DNA, about 21-22% free fetal DNA, about 22-23% free fetal DNA, about 23-24% free fetal DNA, about 24-25% free fetal DNA, about 25-35% free fetal DNA, about 35-45% free fetal DNA, about 45-55% free fetal DNA, about 55-65% free fetal DNA, about 65-75% free fetal DNA, about 75-85% free fetal DNA, about 85-90% free fetal DNA, about 90-91% free fetal DNA, about 91-92% free fetal DNA, about 92-93% free fetal DNA, about 93-94% free fetal DNA, about 94-95% free fetal DNA, about 95-96% free fetal DNA, about 96-97% free fetal DNA, about 97-98% free fetal DNA, about 98-99% free fetal DNA, or about 99-99.7% free fetal DNA.

In another embodiment, the present invention is directed to a composition comprising free fetal DNA and free maternal DNA, wherein the composition comprises a relationship of free fetal DNA to free maternal DNA including but not limited a maximum of 13%-15% free fetal DNA, a maximum of 15-18% free fetal DNA, a maximum of 18-20% free fetal DNA, a maximum of 20-40% free fetal DNA, a maximum of 40-50% free fetal DNA, a maximum of 50-60% free fetal DNA, a maximum of 60-70% free fetal DNA, a maximum of 70-80% free fetal DNA, a maximum of 80-90% free fetal DNA, a maxium of 90-92% free fetal DNA, a maxium of 92-94% free fetal DNA, a maximum of 94-95% free fetal DNA, a maxium of 95-96% free fetal DNA, a maxium of 96-97% free fetal DNA, a maxium of 97-98% free fetal DNA, a maximum of 98-99% free fetal DNA, a maximun of 99-99.5% free fetal DNA, and a maximum of 99.5-99.9% free fetal DNA.

In another embodiment, the present invention is directed to a method of using a composition comprising free fetal DNA and free maternal DNA for prenatal diagnostics, wherein the composition comprises a relationship of free fetal DNA to free maternal DNA including but not limited a maximum of 13%-15% free fetal DNA, a maximum of 15-18% free fetal DNA, a maximum of 18-20% free fetal DNA, a maximum of 20-40% free fetal DNA, a maximum of 40-50% free fetal DNA, a maximum of 50-60% free fetal DNA, a maximum of 60-70% free fetal DNA, a maximum of 70-80% free fetal DNA, a maximum of 80-90% free fetal DNA, a maximum of 90-92% free fetal DNA, a maximum of 92-94% free fetal DNA, a maximum of 94-95% free fetal DNA, a maximum of 95-96% free fetal DNA, a maximum of 96-97% free fetal DNA, a maximum of 97-98% free fetal DNA, a maximum of 98-99% free fetal DNA, a maximum of 99-99.5% free fetal DNA, and a maximum of 99.5-99.9% free fetal DNA.

DNA Template

By a "locus of interest" is intended a selected region of nucleic acid that is within a larger region of nucleic acid. A locus of interest can include but is not limited to 1-100, 1-50, 1-20, or 1 -10 nucleotides, preferably 1-6, 1-5, 1-4, 1-3, 1-2, or 1 nucleotide(s).

As used herein, an "allele" is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

For example, bacteria typically have one large strand of DNA. The term allele with respect to bacterial DNA refers to the form of a gene found in one cell as compared to the form of the same gene in a different bacterial cell of the same species.

Alleles can have the identical sequence or can vary by a single nucleotide or more than one nucleotide. With regard to organisms that have two copies of each chromosome, if both chromosomes have the same allele, the condition is referred to as homozygous. If the alleles at the two chromosomes are different, the condition is referred to as heterozygous. For example, if the locus of interest is SNP X on chromosome 1, and the maternal chromosome contains an adenine at SNP X (A allele) and the paternal chromosome contains a guanine at SNP X (G allele), the individual is heterozygous at SNP X.

As used herein, sequence means the identity of one nucleotide or more than one contiguous nucleotides in a polynucleotide. In the case of a single nucleotide, e.g., a SNP, "sequence" and "identity" are used interchangeably herein.

The term "chromosomal abnormality" refers to a deviation between the structure of the subject chromosome and a normal homologous chromosome. The term "normal" refers to the predominate karyotype or banding pattern found in healthy individuals of a particular species. A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. A chromosomal abnormality can be correlated with presence of a pathological condition or with a predisposition to develop a pathological condition. As defined herein, a single nucleotide polymorphism ("SNP") is not a chromosomal abnormality.

As used herein, incorporation of a nucleotide by a polymerase is referred to as an elongation reaction or a fill-in reaction interchangeably.

As used herein with respect to individuals, "mutant alleles" refers to variant alleles that are associated with a disease state.

The term "template" refers to any nucleic acid molecule that can be used for amplification in the invention. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The template DNA can be obtained from any source including but not limited to humans, non-humans, mammals, reptiles, cattle, cats, dogs, goats, swine, pigs, monkeys, apes, gorillas, bulls, cows, bears, horses, sheep, poultry, mice, rats, fish, dolphins, whales, and sharks.

The template DNA can be from any appropriate sample including but not limited to, nucleic acid-containing samples of tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), umbilical cord blood, chorionic villi, amniotic fluid, an embryo, a two-celled embryo, a four-celled embryo, an eight-celled embryo, a 16-celled embryo, a 32- celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

In one embodiment, the template DNA can be obtained from a sample of a pregnant female.

In another embodiment, the template DNA can be obtained from an embryo. In a preferred embodiment, the template DNA can be obtained from a single-cell of an embryo.

In one embodiment, the template DNA is fetal DNA. Fetal DNA can be obtained from sources including but not limited to maternal blood, maternal serum, maternal plasma, fetal cells, umbilical cord blood, chorionic villi, amniotic fluid, urine, saliva, cells or tissues.

In another embodiment, a cell lysis inhibitor is added to the sample including but not limited to formaldehyde, formaldehyde derivatives, formalin, glutaraldehyde, glutaraldehyde derivatives, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. In another embodiment, two, three, four, five or more than five cell lysis inhibitors can be added to the sample. In a preferred embodiment, formalin is present in the sample at a percentage including but not limited to 0.0001-0.03%, 0.03-0.05%, 0.05-0.08%, 0.08-0.1%, 0.1-0.3%, 0.3-0.5%, 0.5-0.7%, 0.7-0.9%, 0.9-1.2%, 1.2-1.5%, 1.5-2%, 2-3%, 3-5%, and greater than 5%. In another embodiment, any combination of cross-linker, cell membrane stabilizer, or cell lysis inhibitor can be added to the sample including but not limited to a cross-linker and a cell membrane stabilizer, a cross-linker and a cell lysis inhibitor, and a cell membrane stabilizer and a cell lysis inhibitor. More than one cross-linker can be used with more than one cell membrane stabilizer. More than one cross-linker can be used with more than one cell lysis inhibitor. More than one cell membrane stabilizer can be used with more than cell lysis inhibitor.

In another embodiment, the cell lysis inhibitor is added to the sample such that lysis is less than about 10% of the cells. In a preferred embodiment, the cell lysis inhibitor is added to the sample such that lysis is less than about 5% of the cells. In a most preferred embodiment, the cell lysis inhibitor is added to the sample such that lysis is less than about 1% of the cells.

In another embodiment, a cell membrane stabilizer is added to the sample such that lysis is less than about 10% of the cells. In a preferred embodiment, the cell membrane stabilizer is added to the sample such that lysis is less than about 5% of the cells. In a most preferred embodiment, the cell membrane stabilizer is added to the sample such that lysis is less than about 1% of the cells.

In another embodiment, a cross-linker is added to the sample such that lysis is less than about 10% of the cells. In a preferred embodiment, the cross-linker is added to the sample such that lysis is less than about 5% of the cells. In a most preferred embodiment, the cross-linker is added to the sample such that lysis is less than about 1% of the cells.

In another embodiment, the cell lysis inhibitor, cross-linker or cell membrane stabilizer is added to the sample in an applicable time period including but not limited to 1-10 seconds, 10-30 seconds, 30-60 seconds, 1-5 minutes, 5-10 minutes, 10-20 minutes, 20-30 minutes, 30-40 minutes, 40-50 minutes, 60-90 minutes, 90-180 minutes or greater than 180 minutes after collection of the sample. In another embodiment, the cell lysis inhibitor, cross-linker, or cell membrane stabilizer is present in the apparatus to which the sample is collected including but not limited to a glass tube, a plastic tube, a circular container, an eppendorf tube, an IV bag, or any other appropriate collection device. In another embodiment, after the addition of the cell lysis inhibitor, cell membrane stabilizer, or cross-linker, the sample is left at about room temperature for the period of time to allow the reagent to function, including but not limited to 1-5, 5-10, 10-20, 20-40, 40-60, 60-90, 90-120, 120-150, 150-180, 180-240, 240-300 or greater than 300 minutes.

In another embodiment, the template DNA contains both maternal DNA and fetal DNA. In a preferred embodiment, template DNA is obtained from blood of a pregnant female. Blood is collected using any standard technique for blood-drawing including but not limited to venipuncture. For example, blood can be drawn from a vein from the inside of the elbow or the back of the hand. Blood samples can be collected from a pregnant female at any time during fetal gestation. For example, blood samples can be collected from human females at 1-4, 4-8, 8-12, 12-16, 16-20, 20-24, 24-28, 28-32, 32-36, 36-40, or 40-44 weeks of fetal gestation, and preferably between 8-28 weeks of fetal gestation.

The blood sample is centrifuged to separate the plasma from the maternal cells. The plasma and maternal cell fractions are transferred to separate tubes and re-centrifuged. The plasma fraction contains cell-free fetal DNA and maternal DNA. Any standard DNA isolation technique can be used to isolate the fetal DNA and the maternal DNA including but not limited to QIAamp DNA Blood Midi Kit supplied by QIAGEN (Catalog number 51183).

In a preferred embodiment, blood can be collected into an apparatus containing a magnesium chelator including but not limited to EDTA, and is stored at 4° C. Optionally, a calcium chelator, including but not limited to EGTA, can be added.

In another embodiment, a cell lysis inhibitor is added to the maternal blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfydryl addition or disulfide reduction, carbohydrate reactive crosslinkers, carboxyl reactive crosslinkers, photoreactive crosslinkers, cleavable crosslinkers, AEDP, APG, BASED, BM(PEO)$_3$, BM(PEO)$_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS, or compounds listed in Table XXIII.

In another embodiment, an agent that stabilizes cell membranes may be added to the maternal blood samples to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

In another embodiment, the template DNA is obtained from the plasma or serum of the blood of the pregnant female. The percentage of fetal DNA in maternal plasma is between 0.39-11.9% (Pertl, and Bianchi, *Obstetrics and Gynecology* 98: 483-490 (2001)). The majority of the DNA in the plasma sample is maternal, which makes using the DNA for genotyping the fetus difficult. However, methods that increase the percentage of fetal DNA in the maternal plasma allow the sequence of the fetal DNA to be determined, and allow for the detection of genetic disorders including mutations, insertions, deletions, and chromosomal abnormalities. The addition of cell lysis inhibitors, cell membrane stabilizers or cross-linkers to the maternal blood sample can increase the relative percentage of fetal DNA. While lysis of both maternal and fetal cells is inhibited, the vast majority of cells are maternal, and thus by reducing the lysis of maternal cells, there is a relative increase in the percentage of free fetal DNA. See Example 4.

In another embodiment, any blood drawing technique, method, protocol, or equipment that reduce the amount of cell lysis can be used, including but not limited to a large boar needle, a shorter length needle, a needle coating that increases laminar flow, e.g., teflon, a modification of the bevel of the needle to increase laminar flow, or techniques that reduce the rate of blood flow. The fetal cells likely are destroyed in the maternal blood by the mother's immune system. However, it is likely that a large portion of the maternal cell lysis occurs as a result of the blood draw or processing of the blood sample. Thus, methods that prevent or reduce cell lysis-will reduce the amount of maternal DNA in the sample, and increase the relative percentage of free fetal DNA.

In another embodiment, an agent that preserves or stabilizes the structural integrity of cells can be used to reduce the amount of cell lysis.

In another embodiment, any protocol that reduces the amount of free maternal DNA in the maternal blood can be used prior to obtaining the sample. In another embodiment, prior to obtaining the sample, the pregnant female rests without physical activity for a period of time including but not limited to 0-5, 5-10, 10-15, 15-20, 20-25, 25-30, 30-35, 35-40, 40-45, 45-50, 50-55, 55-60, 60-120, 120-180, 180-240, 240-300, 300-360, 360-420, 420-480, 480-540, 540-600, 600-660, 660-720, 720-780, 780-840, 840-900, 900-1200, 1200-1500, 1500-1800, 1800-2100, 2100-2400, 2400-2700, 2700-3000, 3000-3300, 3300-3600, 3600-3900, 3900-4200, 4200-4500, and greater than 4500 minutes. In another embodiment, the sample is obtained from the pregnant female after her body has reached a relaxed state. The period of rest prior to obtaining the sample may reduce the amount of maternal nucleic acid in the sample. In another embodiment, the sample is obtained from the pregnant female in the a.m., including but not limited to 4-5 am, 5-6 am, 6-7 am, 7-8 am, 8-9 am, 9-10 am, 10-11 am, and 11-12 am.

In another embodiment, the sample is obtained from the pregnant female after she has slept for a period of time including but not limited to 0-1, 1-2, 2-3, 3-4, 4-5, 5-6, 6-7, 7-8, 8-9, 9-10, 10-11, 11-12, or greater than 12 hours.

In another embodiment, prior to obtaining the sample, the pregnant female exercises for a period of time followed by a period of rest. In another embodiment, the period of exercise includes but is not limited to 0-15, 15-30, 30-45, 45-60, 60-120, 120-240, or greater than 240 minutes.

In another embodiment, agents that prevent the destruction of DNA, including but not limited to a DNase inhibitor, zinc chloride, ethylenediaminetetraacetic acid, guanidine-HCl, guanidine isothiocyanate, N-lauroylsarcosine, and Na-dodecylsulphate, can be added to the blood sample.

In another embodiment, fetal DNA is obtained from a fetal cell, wherein said fetal cell can be isolated from sources including but not limited to maternal blood, umbilical cord blood, chorionic villi, amniotic fluid, embryonic tissues and mucous obtained from the cervix or vagina of the mother.

In a preferred embodiment, fetal cells are isolated from maternal peripheral blood. An antibody specific for fetal cells can be used to purify the fetal cells from the maternal serum (Mueller et al., Lancet 336: 197-200 (1990); Ganshirt-Ahlert et al., *Am. J. Obstet. GynecoL* 166: 1350-1355 (1992)). Flow cytometry techniques can also be used to enrich fetal cells (Herzenberg et al., *PNAS* 76: 1453-1455 (1979); Bianchi et al., *PNAS* 87: 3279-3283 (1990); Bruch et al., *Prenatal Diagnosis* 11: 787-798 (1991)). U.S. Pat. No. 5,432,054 also describes a technique for separation of fetal nucleated red blood cells, using a tube having a wide top and a narrow, capillary bottom made of polyethylene. Centrifugation using a variable speed program results in a stacking of red blood cells in the capillary based on the density of the molecules. The density fraction containing low density red blood cells, including fetal red blood cells, is recovered and then differentially hemolyzed to preferentially destroy maternal red blood cells. A density gradient in a hypertonic medium is used to separate red blood cells, now enriched in the fetal red blood cells from lymphocytes and ruptured maternal cells. The use of a hypertonic solution shrinks the red blood cells, which increases their density, and facilitate purification from the more dense lymphocytes. After the fetal cells have been isolated, fetal DNA can be purified using standard techniques in the art.

The nucleic acid that is to be analyzed can be any nucleic acid, e.g., genomic, plasmid, cosmid, yeast artificial chromosomes, artificial or man-made DNA, including unique DNA sequences, and also DNA that has been reverse transcribed from an RNA sample, such as cDNA. The sequence of RNA can be determined according to the invention if it is capable of being made into a double stranded DNA form to be used as template DNA.

The terms "primer" and "oligonucleotide primer" are interchangeable when used to discuss an oligonucleotide that anneals to a template and can be used to prime the synthesis of a copy of that template.

"Amplified" DNA is DNA that has been "copied" once or multiple times, e.g. by polymerase chain reaction. When a large amount of DNA is available to assay, such that a sufficient number of copies of the locus of interest are already present in the sample to be assayed, it may not be necessary to "amplify" the DNA of the locus of interest into an even larger number of replicate copies. Rather, simply "copying" the template DNA once using a set of appropriate primers, which may contain hairpin structures that allow the restriction enzyme recognition sites to be double stranded, can suffice.

"Copy" as in "copied DNA" refers to DNA that has been copied once, or DNA that has been amplified into more than one copy.

In one embodiment, the nucleic acid is amplified directly in the original sample containing the source of nucleic acid. It is not essential that the nucleic acid be extracted, purified or isolated; it only needs to be provided in a form that is capable of being amplified. Hybridization of the nucleic acid template with primer, prior to amplification, is not required. For example, amplification can be performed in a cell or sample lysate using standard protocols well, known in the art. DNA that is on a solid support, in a fixed biological preparation, or otherwise in a composition that contains non-DNA substances and that can be amplified without first being extracted from the solid support or fixed preparation or non-DNA substances in the composition can be used directly, without further purification, as long as the DNA can anneal with appropriate primers, and be copied, especially amplified, and the copied or amplified products can be recovered and utilized as described herein.

In a preferred embodiment, the nucleic acid is extracted, purified or isolated from non-nucleic acid materials that are in the original sample using methods known in the art prior to amplification.

In another embodiment, the nucleic acid is extracted, purified or isolated from the original sample containing the source of nucleic acid and prior to amplification, the nucleic acid is fragmented using any number of methods well known in the art including but not limited to enzymatic digestion, manual shearing, or sonication. For example, the DNA can be digested with one or more restriction enzymes that have a recognition site, and especially an eight base or six base pair recognition site, which is not present in the loci of interest. Typically, DNA can be fragmented to any desired length, including 50, 100, 250, 500, 1,000, 5,000, 10,000, 50,000 and 100,000 base pairs long. In another embodiment, the DNA is fragmented to an average length of about 1000 to 2000 base pairs. However, it is not necessary that the DNA be fragmented.

Fragments of DNA that contain the loci of interest can be purified from the fragmented DNA before amplification. Such fragments can be purified by using primers that will be used in the amplification (see "Primer Design" section below) as hooks to retrieve the loci of interest, based on the ability of such primers to anneal to the loci of interest. In a preferred embodiment, tag-modified primers are used, such as e.g. biotinylated primers.

By purifying the DNA fragments containing the loci of interest, the specificity of the amplification reaction can be improved. This will minimize amplification of nonspecific regions of the template DNA. Purification of the DNA fragments can also allow multiplex PCR (Polymerase Chain Reaction) or amplification of multiple loci of interest with improved specificity.

The loci of interest that are to be sequenced can be selected based upon sequence alone. In humans, over 1.42 million single nucleotide polymorphisms (SNPs) have been described (*Nature* 409:928-933 (2001); The SNP Consortium LTD). On the average, there is one SNP every 1.9 kb of human genome. However, the distance between loci of interest need not be considered when selecting the loci of interest to be sequenced according to the invention. If more than one locus of interest on genomic DNA is being analyzed, the selected loci of interest can be on the same chromosome or on different chromosomes.

In a preferred embodiment, the selected loci of interest can be clustered to a particular region on a chromosome. Multiple loci of interest can be located within a region of DNA such that even with any breakage or fragmentation of the DNA, the multiple loci of interest remain linked. For example, if the DNA is obtained and by natural forces is broken into fragments of 5 Kb, multiple loci of interest can be selected within the 5 Kb regions. This allows each fragment, as measured by the loci of interest within that fragment, to serve as an experimental unit, and will reduce any possible experimental noise of comparing loci of interest on multiple chromosomes.

The loci of interest on a chromosome can be any distance from each other including but not limited to 10-50, 50-100, 100-150, 150-200, 200-250, 250-500, 500-750, 750-1000, 1000-1500, 1500-2000, 2000-2500, 2500-3000, 3000-3500, 3500-4000, 4000-4500, 4500-5000, 5000-10,000 and greater than 10,000 base pairs.

In a preferred embodiment, the length of sequence that is amplified is preferably different for each locus of interest so that the loci of interest can be separated by size.

In fact, it is an advantage of the invention that primers that copy an entire gene sequence need not be utilized. Rather, the copied locus of interest is preferably only a small part of the total gene or a small part of a non-coding region of DNA. There is no advantage to sequencing the entire gene as this can increase cost and delay results. Sequencing only the desired bases or loci of interest maximizes the overall efficiency of the method because it allows for the sequence of the maximum number of loci of interest to be determined in the fastest amount of time and with minimal cost.

Because a large number of sequences can be analyzed together, the method of the invention is especially amenable to the large-scale screening of a number of loci of interest.

Any number of loci of interest can be analyzed and processed, especially at the same time, using the method of the invention. The sample(s) can be analyzed to determine the sequence at one locus of interest or at multiple loci of interest at the same time. The loci of interest can be present on a single chromosome or on multiple chromosomes.

Alternatively, 2, 3, 4, 5, 6, 7, 8, 9, 10-20, 20-25, 25-30, 30-35, 35-40, 40-45, 45-50, 50-100, 100-250, 250-500, 500-1,000, 1,000-2,000, 2,000-3,000, 3,000-5,000, 5,000-10,000, 10,000-50,000 or more than 50,000 loci of interest can be analyzed at the same time when a global genetic screening is desired. Such a global genetic screening might be desired when using the method of the invention to provide a genetic fingerprint to identify an individual or for SNP genotyping.

The locus of interest to be copied can be within a coding sequence or outside of a coding sequence. Preferably, one or more loci of interest that are to be copied are within a gene. In a preferred embodiment, the template DNA that is copied is a locus or loci of interest that is within a genomic coding sequence, either intron or exon. In a highly preferred embodiment, exon DNA sequences are copied. The loci of interest can be sites where mutations are known to cause disease or predispose to a disease state. The loci of interest can be sites of single nucleotide polymorphisms. Alternatively, the loci of interest that are to be copied can be outside of the coding sequence, for example, in a transcriptional regulatory region, and especially a promoter, enhancer, or repressor sequence.

Method for Determining the Sequence of a Locus of Interest

Any method that provides information on the sequence of a nucleic acid can be used including but not limited to allele specific PCR, PCR, gel electrophoresis, ELISA, mass spectrometry, MALDI-TOF mass spectrometry hybridization, primer extension, fluorescence detection, fluorescence resonance energy transfer (FRET), fluorescence polarization, DNA sequencing, Sanger dideoxy sequencing, DNA sequencing gels, capillary electrophoresis on an automated DNA sequencing machine, microchannel electrophoresis, microarray, southern blot, slot blot, dot blot, single primer linear nucleic acid amplification, as described in U.S. Pat. No. 6,251,639, SNP-IT, GeneChips, HuSNP, BeadArray, TaqMan assay, Invader assay, MassExtend, or MassCleave™ (hMC) method.

The preferred method of determining the sequence has previously been described in U.S. application Ser. No. 10/093,618, filed on Mar. 11, 2002, hereby incorporated by reference in its entirety.

I. Primer Design

Published sequences, including consensus sequences, can be used to design or select primers for use in amplification of template DNA. The selection of sequences to be used for the construction of primers that flank a locus of interest can be made by examination of the sequence of the loci of interest, or immediately thereto. The recently published sequence of the human genome provides a source of useful consensus sequence information from which to design primers to flank a desired human gene locus of interest.

By "flanking" a locus of interest is meant that the sequences of the primers are such that at least a portion of the 3' region of one primer is complementary to the antisense strand of the template DNA and upstream from the locus of interest site (forward primer), and at least a portion of the 3' region of the other primer is complementary to the sense strand of the template DNA and downstream of the locus of interest (reverse primer). A "primer pair" is intended a pair of forward and reverse primers. Both primers of a primer pair anneal in a manner that allows extension of the primers, such that the extension results in amplifying the template DNA in the region of the locus of interest.

Primers can be prepared by a variety of methods including but not limited to cloning of appropriate sequences and direct chemical synthesis using methods well known in the art (Narang et al., *Methods Enzymol.* 68:90 (1979); Brown et al., *Methods Enzymol.* 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. In a preferred embodiment, one of the primers of the prime pair is longer than the other primer. In a preferred embodiment, the 3' annealing lengths of the primers, within a primer pair, differ. Also, the annealing position of each primer pair can be designed such that the sequence and length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Net Primer (free web based program at http://premierbiosoft.com/netprimer/netprlaunch/netprlaunch.html; internet address as of Apr. 17, 2002).

In another embodiment, the annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers is incorporated into the products from each loci of interest, thus the TM can be recalculated based on both the sequences of the 5' half and the 3' half of each primer.

For example, in FIG. 1B, the first cycle of amplification is performed at about the melting temperature of the 3' region, which anneals to the template DNA, of the second primer (region "c"), which is 13 bases. After the first cycle, the annealing temperature can be raised to TM2, which is about the melting temperature of the 3' region, which anneals to the template DNA, of the first primer, which is depicted as region "b." The second primer cannot bind to the original template DNA because it only anneals to 13 bases in the original DNA template, and TM2 is about the melting temperature of approximately 20 bases, which is the 3' annealing region of the first primer (FIG. 1C). However, the first primer can bind to the DNA that was copied in the first cycle of the reaction. In the third cycle, the annealing temperature is raised to TM3, which is about the melting temperature of the entire sequence of the second primer, which is depicted as regions "c" and "d." The DNA template produced from the second cycle of PCR contains both regions c' and d', and therefore, the second primer can anneal and extend at TM3 (FIG. 1D). The remaining cycles are performed at TM3. The entire sequence of the first primer (a+b') can anneal to the template from the third cycle of PCR, and extend (FIG. 1E). Increasing the annealing temperature will decrease non-specific binding and increase the specificity of the reaction, which is especially useful if amplifying a locus of interest from human genomic DNA, which is about $3\times10^9$ base pairs long.

As used herein, the term "about" with regard to annealing temperatures is used to encompass temperatures within 10 degrees celcius of the stated temperatures.

In one embodiment, one primer pair is used for each locus of interest. However, multiple primer pairs can be used for each locus of interest.

In one embodiment, primers are designed such that one or both primers of the primer pair contain sequence in the 5' region for one or more restriction endonucleases (restriction enzyme).

As used herein, with regard to the position at which restriction enzymes digest DNA, the "sense" strand is the strand reading 5' to 3' in the direction in which the restriction enzyme cuts. For example, BsmF I recognizes the following sequences:

```
5' GGGAC(N)10 3'        (SEQ ID NO: 1)
5' (N)14GTCCC 3'        (SEQ ID NO: 2)
3' CCCTG(N)14 5'        (SEQ ID NO: 2)
3' (N)10CAGGG 5'        (SEQ ID NO: 1)
```

The sense strand is the strand containing the "GGGAC" sequence as it reads 5' to 3' in the direction that the restriction enzyme cuts.

As used herein, with regard to the position at which restriction enzymes digest DNA, the "antisense" strand is the strand reading 3' to 5' in the direction in which the restriction enzyme cuts.

In another embodiment, one of the primers in a primer pair is designed such that it contains a restriction enzyme recognition site for a restriction enzyme that cuts "n" nucleotides away from the recognition site, and produces a recessed 3' end and a 5' overhang that contains the locus of interest (herein referred to as a "second primer"). "N" is a distance from the recognition site to the site of the cut by the restriction enzyme. In other words, the second primer of a primer pair contains a recognition site for a restriction enzyme that does not cut DNA at the recognition site but cuts "n" nucleotides away from the recognition site. For example, if the recognition sequence is for the restriction enzyme BceA I, the enzyme will cut ten (10) nucleotides from the recognition site on the sense strand, and twelve (12) nucleotides away from the recognition site on the antisense strand.

The 3' region and preferably, the 3' half, of the primers is designed to anneal to a sequence that flanks the loci of interest (FIG. 1A). The second primer can anneal any distance from the locus of interest provided that digestion with the restriction enzyme that recognizes the restriction enzyme recognition site on this primer generates a 5' overhang that contains the locus of interest. The 5' overhangs can be of any size, including but not limited to 1, 2, 3, 4, 5, 6, 7, 8, and more than 8 bases.

In a preferred embodiment, the 3' end of the primer that anneals closer to the locus of interest (second primer) can anneal 1, 2, 3, 4, 5, 6, 7, 8, 9, 10, 11, 12, 13, 14, or more than 14 bases from the locus of interest or at the locus of interest.

In a preferred embodiment, the second primer is designed to anneal closer to the locus of interest than the other primer of a primer pair (the other primer is herein referred to as a "first primer"). The second primer can be a forward or reverse primer and the first primer can be a reverse or forward primer, respectively. Whether the first or second primer should be the forward or reverse primer can be determined by which design will provide better sequencing results.

For example, the primer that anneals closer to the locus of interest can contain a recognition site for the restriction enzyme BsmF I, which cuts ten (10) nucleotides from the recognition site on the sense strand, and fourteen (14) nucleotides from the recognition site on the antisense strand. In this case, the primer can be designed so that the restriction enzyme recognition site is 13 bases, 12 bases, 10 bases or 11 bases from the locus of interest. If the recognition site is 13 bases from the locus of interest, digestion with BsmF I will generate a 5' overhang (RXXX), wherein the locus of interest (R) is the first nucleotide in the overhang (reading 3' to 5'), and X is any nucleotide. If the recognition site is 12 bases from the locus of interest, digestion with BsmF I will generate a 5' overhang (XRXX), wherein the locus of interest (R) is the second nucleotide in the overhang (reading 3' to 5'). If the recognition site is 11 bases from the locus of interest, digestion with BsmF I will generate a 5' overhang (XXRX), wherein the locus of interest (R) is the third nucleotide in the overhang (reading 3' to 5'). The distance between the restriction enzyme recognition site and the locus of interest should be designed so that digestion with the restriction enzyme generates a 5' overhang, which contains the locus of interest. The effective distance between the recognition site and the locus of interest will vary depending on the choice of restriction enzyme.

In another embodiment, the primer that anneals closer to the locus of interest site, relative to the other primer, can be designed so that the restriction enzyme that generates the 5' overhang, which contains the locus of interest, will see the same sequence at the cut site, independent of the nucleotide at the locus of interest site. For example, if the primer that anneals closer to the locus of interest is designed so that the recognition site for the restriction enzyme BsmF I (5' GGGAC 3') is thirteen bases from the locus of interest, the restriction enzyme will cut the antisense strand one base from the locus of interest. The nucleotide at the locus of interest is adjacent to the cut site, and may vary from DNA molecule to DNA molecule. If it is desired that the nucleotides adjacent to the cut site be identical, the primer can be designed so that the restriction enzyme recognition site for BsmF I is twelve bases away from the locus of interest site. Digestion with BsmF I will generate a 5' overhang, wherein the locus of interest site is in the second position of the overhang (reading 3' to 5') and is no longer adjacent to the cut site. Designing the primer so that the restriction enzyme recognition site is twelve (12) bases from the locus of interest site allows the nucleotides adjacent to the cut site to be the same, independent of the nucleotide at the locus of interest. Also, primers that have been designed so that the restriction enzyme recognition site, BsmF I, is eleven (11) or ten (10) bases from the locus of interest site will allow the nucleotides adjacent to the cut site to be the same, independent of the nucleotide at the locus of interest. Similar strategies of primer design can be employed with other restriction enzymes so that the nucleotides adjacent to the cut site will be the same, independent of the nucleotide at the loci of interest.

The 3' end of the first primer (either the forward or the reverse) can be designed to anneal at a chosen distance from the locus of interest. Preferably, for example, this distance is between 1-10, 10-25, 25-50, 50-75, 75-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000 and greater than 1000 bases away from the locus of interest. The annealing sites of the first primers are chosen such that each successive upstream primer is further and further away from its respective downstream primer.

For example, if at locus of interest 1 the 3' ends of the first and second primers are Z bases apart, then at locus of interest 2, the 3' ends of the upstream and downstream primers are Z+K bases apart, where K=1, 2, 3, 4, 5-10, 10-20, 20-30, 30-40, 40-50, 50-60, 60-70, 70-80, 80-90, 90-100, 100-200, 200-300, 300-400, 400-500, 500-600, 600-700, 700-800, 800-900, 900-1000, or greater than 1000 bases (FIG. 2). The purpose of making the first primers further and further apart from their respective second primers is so that the PCR products of all the loci of interest differ in size and can be separated, e.g., on a sequencing gel. This allows for multiplexing by pooling the PCR products in later steps.

In one embodiment, the 5' region of the first or second primer can have a recognition site for any type of restriction enzyme. In a preferred embodiment, the 5' region of the first and/or second primer has at least one restriction enzyme recognition site that is different from the restriction enzyme recognition site that is used to generate the 5' overhang, which contains the locus of interest.

In one embodiment, the 5' region of the first primer can have a recognition site for any type of restriction enzyme. In a preferred embodiment, the first primer has at least one restriction enzyme recognition site that is different from the restriction enzyme recognition site in the second primer. In another preferred embodiment, the first primer anneals further away from the locus of interest than the second primer.

In a preferred embodiment, the second primer contains a restriction enzyme recognition sequence for a Type IIS restriction enzyme including but not limited to BceA I and BsmF I, which produce a two base 5' overhang and a four base 5' overhang, respectively. Restriction enzymes that are Type IIS are preferred because they recognize asymmetric base sequences (not palindromic like the orthodox Type II enzymes). Type IIS restriction enzymes cleave DNA at a specified position that is outside of the recognition site, typically up to 20 base pairs outside of the recognition site. These properties make Type IIS restriction enzymes, and the recognition sites thereof, especially useful in the method of the invention. Preferably, the Type IIS restriction enzymes used in this method leave a 5' overhang and a recessed 3'.

A wide variety of Type IIS restriction enzymes are known and such enzymes have been isolated from bacteria, phage, archeabacteria and viruses of eukaryotic algae and are commercially available (Promega, Madison Wis.; New England Biolabs, Beverly, Mass.; Szybalski W. et al., Gene 100: 13-26, 1991). Examples of Type IIS restriction enzymes that would be useful in the method of the invention include, but are not limited to enzymes such as those listed in Table I.

| Enzyme-Source | Recognition/Cleavage Site | Supplier |
|---|---|---|
| Alw I - *Acinetobacter lwoffii* | GGATC(4/5) | NE Biolabs |
| Alw26 I - *Acinetobacter lwoffi* | GTCTC(1/5) | Promega |
| Bbs I - *Bacillus laterosporus* | GAAGAC(2/6) | NE Biolabs |
| Bbv I - *Bacillus brevis* | GCAGC(8/12) | NE Biolabs |
| BceA I - *Bacillus cereus* 1315 | IACGGC(12/14) | NE Biolabs |
| Bmr I - *Bacillus megaterium* | CTGGG(5/4) | NE Biolabs |
| Bsa I - *Bacillus stearothermophilus* 6-55 | GGTCTC(1/5) | NE Biolabs |
| Bst71 I - *Bacillus stearothermophilus* 71 | GCAGC(8/12) | Promega |
| BsmA I - *Bacillus stearothermophilus* A664 | GTCTC(1/5) | NE Biolabs |
| BsmB I - *Bacillus stearothermophilus* B61 | CGTCTC(1/5) | NE Biolabs |
| BsmF I - *Bacillus stearothermophilus* F | GGGAC(10/14) | NE Biolabs |
| BspM I - *Bacillus* species M | ACCTGC(4/8) | NE Biolabs |
| Ear I - *Enterobacter aerogenes* | CTCTTC(1/4) | NE Biolabs |
| Fau I - *Flavobacterium aquatile* | CCCGC(4/6) | NE Biolabs |
| Fok I - *Flavobacterium okeonokoites* | GGATG(9/13) | NE Biolabs |
| Hga I - *Haemophilus gallinarum* | GACGC(5/10) | NE Biolabs |
| Ple I - *Pseudomonas lemoignei* | GAGTC(4/5) | NE Biolabs |
| Sap I - *Saccharopolyspora* species | GCTCTTC(1/4) | NE Biolabs |
| SfaN I - *Streptococcus faecalis* ND547 | GCATC(5/9) | NE Biolabs |
| Sth132 I - *Streptococcus thermophilus* ST132 | CCCG(4/8) | No commercial supplier (Gene 195: 201-206 (1997)) |

In one embodiment, a primer pair has sequence at the 5' region of each of the primers that provides a restriction enzyme recognition site that is unique for one restriction enzyme.

In another embodiment, a primer pair has sequence at the 5' region of each of the primers that provide a restriction site that is recognized by more than one restriction enzyme, and especially for more than one Type IIS restriction enzyme. For example, certain consensus sequences can be recognized by more than one enzyme. For example, BsgI, Eco571 and BpmI all recognize the consensus (G/C)TGnAG and cleave 16 by away on the antisense strand and 14 by away on the sense strand. A primer that provides such a consensus sequence would result in a product that has a site that can be recognized by any of the restriction enzymes BsgI, Eco571 and BpmI.

Other restriction enzymes that cut DNA at a distance from the recognition site, and produce a recessed 3' end and a 5' overhang include Type III restriction enzymes.

For example, the restriction enzyme EcoP15I recognizes the sequence 5' CAGCAG 3' and cleaves 25 bases downstream on the sense strand and 27 bases on the antisense strand. It will be further appreciated by a person of ordinary skill in the art that new restriction enzymes are continually being discovered and can readily be adopted for use in the subject invention.

In another embodiment, the second primer can contain a portion of the recognition sequence for a restriction enzyme, wherein the full recognition site for the restriction enzyme is generated upon amplification of the template DNA such that digestion with the restriction enzyme generates a 5' overhang containing the locus of interest. For example, the recognition site for BsmF I is 5' GGGAC$N_{10}$↓3'. The 3' region, which anneals to the template DNA, of the second primer can end with the nucleotides "GGG," which do not have to be complementary with the template DNA. If the 3' annealing region is about 10-20 bases, even if the last three bases do not anneal, the primer will extend and, generate a BsmF I site.

```
Second primer:
5' GGAAATTCCATGATGCGTGGG→            (SEQ ID NO: 3)

Template DNA
3' CCTTTAAGGTACTACGCAN1N2N3TG 5'     (SEQ ID NO: 27)

5' GGAAATTCCATGATGCCTN1.N2.N3.AC 3'  (SEQ ID NO: 4)
```

The second primer can be designed to anneal to the template DNA, wherein the next two bases of the template DNA are thymidine and guanine, such that an adenosine and cytosine are incorporated into the primer forming a recognition site for BsmF I, 5' GGGAC$N_{10}$↓3' (SEQ ID NO: 1). The second primer can be designed to anneal in such a manner that digestion with BsmF I generates a 5' overhang containing the locus of interest.

In another embodiment, the second primer can contain an entire or full recognition site for a restriction enzyme or a portion of a recognition site, which generates a full recognition site upon primer-dependent replication of the template DNA such that digestion with a restriction enzyme that cuts at the recognition site and generates a 5' overhang that contains the locus of interest. For example, the restriction enzyme BsaJ I binds the following recognition site: 5' C↓C$N_1N_2$GG 3'. The second primer can be designed such that the 3' region, which anneals to the template DNA of the primer ends with "CC", the SNP of interest is represented by "$N_1$", and the template sequence downstream of the SNP is "$N_2$GG."

```
Second primer:
5' GGAAATTCCATGATGCGTACC→            (SEQ ID NO: 5)

Template DNA
3' CCTTTAAGGTACTACGCATGGN1N2CC 5'    (SEQ ID NO: 28)

5' GGAAATTCCATGATGCCTACCN1.N2.GG 3'  (SEQ ID NO: 6)
```

After digestion with BsaJ I, a 5' overhang of the following sequence would be generated:

```
5' C        3'
3' GGN1N2CC 5'
```

If the nucleotide guanine is not reported at the locus of interest, the 3' recessed end can be filled in with unlabeled cytosine, which is complementary to the first nucleotide in the overhang. After removing the excess cytosine, labeled ddNTPs can be used to fill in the next nucleotide, $N_1$, which represents the locus of interest. Other restriction enzymes can be used including but not limited to BssK I (5'↓CCNGG 3'), Dde I (5' C↓TNAG 3'), EcoN I (5' CCTNN↓NNNAGG 3') (SEQ ID NO: 7), Fnu4H I (5' GC↓NGC 3'), Hinf I(5' G↓ANTC 3') PflF I(5' GACN↓NNGTC 3'), Sau96 I(5' G↓GNCC 3'), ScrF I(5' CC↓NGG 3'), and Tthl 11 I(5' GACNINNGTC 3').

It is not necessary that the 3' region, which anneals to the template DNA, of the second primer be 100% complementary to the template DNA. For example, the last 1, 2, or 3 nucleotides of the 3' end of the second primer can be mismatches with the template DNA. The region of the primer that anneals to the template DNA will target the primer, and allow the primer to extend. Even if the last two nucleotides are not complementary to the template DNA, the primer will extend and generate a restriction enzyme recognition site. For example, the last two nucleotides in the second primer are "CC." The second primer anneals to the template DNA, and allows extension even if "CC" is not complementary to the nucleotides Na, and Nb, on the template DNA.

```
Second primer:
                                          (SEQ ID NO: 5)
5' GGAAATTCCATGATGCGTACC→

Template DNA
                                         (SEQ ID NO: 29)
3' CCTTTAAGGTACTACGCATNa.Nb.N1.N2.CC 5'

                                          (SEQ ID NO: 8)
5' GGAAATTCCATGATGCCTANaNbN1N2GG 3'
```

After digestion with BsaJ I, a 5' overhang of the following sequence would be generated:

```
5' C        3'
3' GGN1N2CC 5'
```

If the nucleotide guanine is not reported at the locus of interest, the 5' overhang can be filled in with unlabeled cytosine. The excess cytosine can be rinsed away, and filled in with labeled ddNTPs. The first nucleotide incorporated ($N_1$') corresponds to the locus of interest. If guanine is reported at the locus of interest, the loci of interest can be filled in with unlabeled cytosine and a nucleotide downstream of the locus of interest can be detected. For example, assume $N_2$ is adenine. If the locus of interest is guanine, unlabeled cytosine can be used in the fill in reaction. After removing the cytosine, a fill in reaction with labeled thymidine can be used. The labeled thymidine will be incorporated only if the locus of interest was a guanine. Thus, the sequence of the locus of interest can be determined by detecting a nucleotide downstream of the locus of interest.

In another embodiment, the first and second primers contain a portion of a recognition sequence for a restriction enzyme, wherein the full recognition site for the restriction enzyme is generated upon amplification of the template DNA such that digestion with the restriction enzyme generates a 5' overhang containing the locus of interest. The recognition site for any restriction enzyme that contains one or more than one variable nucleotide can be generated including but not limited to the restriction enzymes BssK I (5'↓CCNGG 3'), Dde I (5'C↓TNAG 3'), Econ I (5' CCTNN↓NNNAGG 3') (SEQ ID NO. 7), Fnu4H I (5'GC↓NGC 3'), Hinf I (5'G↓ANTC 3'), PflF I(5' GACN↓NNGTC 3'), Sau96 I(5'G↓GNCC 3'), ScrF I (5'CC↓NGG 3'), and Tthl 11 I (5' GACN↓NNGTC 3').

In a preferred embodiment, the 3' regions of the first and second primers contain the partial sequence for a restriction enzyme, wherein the partial sequence contains 1, 2, 3, 4 or more than 4 mismatches with the template DNA; these mismatches create the restriction enzyme recognition site. The number of mismatches that can be tolerated at the 3' end depends on the length of the primer. For example, if the locus of interest is represented by $N_1$, a first primer can be designed to be complementary to the template DNA, depicted below as region "a." The 3' region of the first primer ends with "CC," which is not complementary to the template DNA. The second primer is designed to be complementary to the template DNA, which is depicted below as region "b'". The 3' region of the second primer ends with "CC," which is not complementary to the template DNA.

First primer 5' ___a___CC→
Template DNA 3' ___a'___AA$N_1$,$N_2$,TT ___b'___5'
5' ___a___TT$N_1N_2$AA ___b___3'
←CC ___b'___5' Second primer After one round of amplification the following products would be generated:

5' ___a___CC$N_1N_2$AA ___b___3' and

5' ___b___CC$N_2$,$N_1$,AA ___a'___3'.

In cycle two, the primers can anneal to the templates that were generated from the first cycle of PCR:

5' ___a___CC$N_1N_2$AA ___b___3'
←CC ___b'___5'
←CC ___a___5'
5' ___b'___CC$N_2N_1$AA ___a'___3'

After cycle two of PCR, the following products would be generated:

5' a CC$N_1N_2$GG ___b___3'
3' a' GG$N_1N_2$CC ___b'___5'

The restriction enzyme recognition site for BsaJ I is generated, and after digestion with BsaJ I, a 5' overhang containing the locus of interest is created. The locus of interest can be detected as described in detail below.

In another embodiment, a primer pair has sequence at the 5' region of each of the primers that provides two or more restriction sites that are recognized by two or more restriction enzymes.

In a most preferred embodiment, a primer pair has different restriction enzyme recognition sites at the 5' regions, especially 5' ends, such that a different restriction enzyme is required to cleave away any undesired sequences. For example, the first primer for locus of interest "A" can contain sequence recognized by a restriction enzyme, "X," which can be any type of restriction enzyme, and the second primer for locus of interest "A," which anneals closer to the locus of interest, can contain sequence for a restriction enzyme, "Y," which is a Type IIS restriction enzyme that cuts "n" nucleotides away and leaves a 5'overhang and a recessed 3' end. The 5' overhang contains the locus of interest. After binding the amplified DNA to streptavidin coated wells, one can digest with enzyme "Y," rinse, then fill in with labeled nucleotides and rinse, and then digest with restriction enzyme "X," which will release the DNA fragment containing the locus of interest from the solid matrix. The locus of interest can be analyzed by detecting the labeled nucleotide that was "filled in" at the locus of interest, e.g. SNP site.

In another embodiment, the second primers for the different loci of interest that are being amplified according to the invention contain recognition sequence in the 5' regions for the same restriction enzyme and likewise all the first primers also contain the same restriction enzyme recognition site, which is a different enzyme from the enzyme that recognizes the second primers.

In another embodiment, the second primers for the multiple loci of interest that are being amplified according to the invention contain restriction enzyme recognition sequences in the 5' regions for different restriction enzymes.

In another embodiment, the first primers for the multiple loci of interest that are being amplified according to the invention contain restriction enzyme recognition sequences in the 5' regions for different restriction enzymes. Multiple restriction enzyme sequences provide an opportunity to influence the order in which pooled loci of interest are released from the solid support. For example, if 50 loci of interest are amplified, the first primers can have a tag at the extreme 5' end to aid in purification and a restriction enzyme recognition site, and the second primers can contain a recognition site for a type IIS restriction enzyme. For example, several of the first primers can have a restriction enzyme recognition site for EcoR I, other first primers can have a recognition site for Pst I, and still other first primers can have a recognition site for BamH I. After amplification, the loci of interest can be bound to a solid support with the aid of the tag on the first primers. By performing the restriction digests one restriction enzyme at a time, one can serially release the amplified loci of interest. If the first digest is performed with EcoR I, the loci of interest amplified with the first primers containing the recognition site for EcoR I will be released, and collected while the other loci of interest remain bound to the solid support. The amplified loci of interest can be selectively released from the solid support by digesting with one restriction enzyme at a time. The use of different restriction enzyme recognition sites in the first primers allows a larger number of loci of interest to be amplified in a single reaction tube.

In a preferred embodiment, any region 5' of the restriction enzyme digestion site of each primer can be modified with a functional group that provides for fragment manipulation, processing, identification, and/or purification. Examples of such functional groups, or tags, include but are not limited to biotin, derivatives of biotin, carbohydrates, haptens, dyes, radioactive molecules, antibodies, and fragments of antibodies, peptides, and immunogenic molecules.

In another embodiment, the template DNA can be replicated once, without being amplified beyond a single round of replication. This is useful when there is a large amount of the DNA available for analysis such that a large number of copies of the loci of interest are already present in the sample, and further copies are not needed. In this embodiment, the primers are preferably designed to contain a "hairpin" structure in the 5' region, such that the sequence doubles back and anneals to a sequence internal to itself in a complementary manner. When the template DNA is replicated only once, the DNA sequence comprising the recognition site would be single-stranded if not for the "hairpin" structure. However, in the presence of the hairpin structure, that region is effectively double stranded, thus providing a double stranded substrate for activity by restriction enzymes.

To the extent that the reaction conditions are compatible, all the primer pairs to analyze a locus or loci of interest of DNA can be mixed together for use in the method of the invention. In a preferred embodiment, all primer pairs are mixed with the template DNA in a single reaction vessel. Such a reaction vessel can be, for example, a reaction tube, or a well of a microtiter plate.

Alternatively, to avoid competition for nucleotides and to minimize primer dimers and difficulties with annealing temperatures for primers, each locus of interest or small groups of loci of interest can be amplified in separate reaction tubes or wells, and the products later pooled if desired. For example, the separate reactions can be pooled into a single reaction vessel before digestion with the restriction enzyme that generates a 5' overhang, which contains the locus of interest or SNP site, and a 3' recessed end. Preferably, the primers of each primer pair are provided in equimolar amounts. Also, especially preferably, each of the different primer pairs is provided in equimolar amounts relative to the other pairs that are being used.

In another embodiment, combinations of primer pairs that allow efficient amplification of their respective loci of interest can be used (see e.g. FIG. 2). Such combinations can be determined prior to use in the method of the invention. Multi-well plates and PCR machines can be used to select primer pairs that work efficiently with one another. For example, gradient PCR machines, such as the Eppendorf Mastercycler® gradient PCR machine, can be used to select the optimal annealing temperature for each primer pair. Primer pairs that have similar properties can be used together in a single reaction tube.

In another embodiment, a multi-sample container including but not limited to a 96-well or more plate can be used to amplify a single locus of interest with the same primer pairs from multiple template DNA samples with optimal PCR conditions for that locus of interest. Alternatively, a separate multi-sample container can be used for amplification of each locus of interest and the products for each template DNA sample later pooled. For example, gene A from 96 different DNA samples can be amplified in microtiter plate 1, gene B from 96 different DNA samples can be amplified in microtiter plate 2, etc., and then the amplification products can be pooled.

The result of amplifying multiple loci of interest is a preparation that contains representative PCR products having the sequence of each locus of interest. For example, if DNA from only one individual is used as the template DNA and if hundreds of disease-related loci of interest were amplified from the template DNA, the amplified DNA would be a mixture of small, PCR products from each of the loci of interest. Such a preparation could be further analyzed at that time to determine the sequence at each locus of interest or at only some loci of interest. Additionally, the preparation could be stored in a manner that preserves the DNA and can be analyzed at a later time. Information contained in the amplified DNA can be revealed by any suitable method including but not limited to fluorescence detection, sequencing, gel electrophoresis, and mass spectrometry (see "Detection of Incorporated Nucleotide" section below).

II. Amplification of Loci of Interest

The template DNA can be amplified using any suitable method known in the art including but not limited to PCR (polymerase chain reaction), 3SR (self-sustained sequence reaction), LCR (ligase chain reaction), RACE-PCR (rapid amplification of cDNA ends), PLCR (a combination of polymerase chain reaction and ligase chain reaction), Q-beta phage amplification (Shah et al., *J. Medical Micro.* 33: 1435-41 (1995)), SDA (strand displacement amplification), SOE-PCR (splice overlap extension PCR), and the like. These methods can be used to design variations of the releasable primer mediated cyclic amplification reaction explicitly described in this application. In the most preferred embodiment, the template DNA is amplified using PCR (PCR: A Practical Approach, M. J. McPherson, et al., IRL Press (1991); PCR Protocols: A Guide to Methods and Applications, Innis, et al., Academic Press (1990); and PCR Technology: Principals and Applications of DNA Amplification, H. A. Erlich, Stockton Press (1989)). PCR is also described in numerous U.S. patents, including U.S. Pat. Nos. 4,683,195; 4,683,202; 4,800,159; 4,965,188; 4,889,818; 5,075,216; 5,079,352; 5,104,792, 5,023,171; 5,091,310; and 5,066,584.

The components of a typical PCR reaction include but are not limited to a template DNA, primers, a reaction buffer (dependent on choice of polymerase), dNTPs (dATP, dTTP, dGTP, and dCTP) and a DNA polymerase. Suitable PCR primers can be designed and prepared as discussed above (see "Primer Design" section above). Briefly, the reaction is heated to 95° C. for 2 min. to separate the strands of the template DNA, the reaction is cooled to an appropriate temperature (determined by calculating the annealing temperature of designed primers) to allow primers to anneal to the template DNA, and heated to 72° C. for two minutes to allow extension.

In a preferred embodiment, the annealing temperature is increased in each of the first three cycles of amplification to reduce non-specific amplification. See also Example 1, below. The TM1 of the first cycle of PCR is about the melting temperature of the 3' region of the second primer that anneals to the template DNA. The annealing temperature can be raised in cycles 2-10, preferably in cycle 2, to TM2, which is about the melting temperature of the 3' region, which anneals to the template DNA, of the first primer. If the annealing temperature is raised in cycle 2, the annealing temperature remains about the same until the next increase in annealing temperature. Finally, in any cycle subsequent to the cycle in which the annealing temperature was increased to TM2, preferably cycle 3, the annealing temperature is raised to TM3, which is about the melting temperature of the entire second primer. After the third cycle, the annealing temperature for the remaining cycles can be at about TM3 or can be further increased. In this example, the annealing temperature is increased in cycles 2 and 3. However, the annealing temperature can be increased from a low annealing temperature in cycle 1 to a high annealing temperature in cycle 2 without any further increases in temperature or the annealing temperature can progressively change from a low annealing temperature to a high annealing temperature in any number of incremental steps. For example, the annealing temperature can be changed in cycles 2, 3, 4, 5, 6, etc.

After annealing, the temperature in each cycle is increased to an "extension" temperature to allow the primers to "extend" and then following extension the temperature in each cycle is increased to the denaturization temperature. For PCR products less than 500 base pairs in size, one can eliminate the extension step in each cycle and just have denaturization and annealing steps. A typical PCR reaction consists of 25-45 cycles of denaturation, annealing and extension as described above. However, as previously noted, one cycle of amplification (one copy) can be sufficient for practicing the invention.

In another embodiment, multiple sets of primers wherein a primer set comprises a forward primer and a reverser primer, can be used to amplify the template DNA for 1-5, 5-10, 10-15, 15-20 or more than 20 cycles, and then the amplified product is further amplified in a reaction with a single primer set or a subset of the multiple primer sets. In a preferred embodiment, a low concentration of each primer set is used to minimize primer-dimer formation. A low concentration of starting DNA can be amplified using multiple primer sets. Any number of primer sets can be used in the first amplification reaction including but not limiting to 1-10, 10-20, 20-30, 30-40, 40-50, 50-60, 60-70, 70-80, 80-90, 90-100, 100-150, 150-200, 200-250, 250-300, 300-350, 350-400, 400-450, 450-500, 500-1000, and greater than 1000. In another embodiment, the amplified product is amplified in a second reaction with a single primer set. In another embodiment, the amplified product is further amplified with a subset of the multiple primer pairs including but not limited to 2-10, 10-20, 20-30, 30-40, 40-50, 50-60, 60-70, 70-80, 80-90, 90-100, 100-150, 150-200, 200-250, and more than 250.

The multiple primer sets will amplify the loci of interest, such that a minimal amount of template DNA is not.limiting for the number of loci that can be detected. For example, if template DNA is isolated from a single cell or the template DNA is obtained from a pregnant female, which comprises both maternal template DNA and fetal template DNA, low concentrations of each primer set can be used in a first amplification reaction to amplify the loci of interest. The low concentration of primers reduces the formation of primer-dimer and increases the probability that the primers will anneal to the template DNA and allow the polymerase to extend. The optimal number of cycles performed with the multiple primer sets is determined by the concentration of the primers. Following the first amplification reaction, additional primers can be added to further amplify the loci of interest. Additional amounts of each primer set can be added and further amplified in a single reaction. Alternatively, the amplified product can be further amplified using a single primer set in each reaction or a subset of the multiple primers sets. For example, if 150 primer sets were used in the first amplification reaction, subsets of 10 primer sets can be used to further amplify the product from the first reaction.

Any DNA polymerase that catalyzes primer extension can be used including but not limited to *E. coli* DNA polymerase, Klenow fragment of *E. coli* DNA polymerase 1, T7 DNA polymerase, T4 DNA polymerase, Taq polymerase, Pfu DNA polymerase, Vent DNA polymerase, bacteriophage 29, REDTaq™ Genomic DNA polymerase, or sequenase. Preferably, a thermostable DNA polymerase is used. A "hot start" PCR can also be performed wherein the reaction is heated to 95° C. for two minutes prior to addition of the polymerase or the polymerase can be kept inactive until the first heating step in cycle 1. "Hot start" PCR can be used to minimize nonspecific amplification. Any number of PCR cycles can be used to amplify the DNA, including but not limited to 2, 5, 10, 15, 20, 25, 30, 35, 40, or 45 cycles. In a most preferred embodiment, the number of PCR cycles performed is such that equimolar amounts of each loci of interest are produced.

III. Purification of Amplified DNA

Purification of the amplified DNA is not necessary for practicing the invention. However, in one embodiment, if purification is preferred, the 5' end of the primer (first or second primer) can be modified with a tag that facilitates purification of the PCR products. In a preferred embodiment, the first primer is modified with a tag that facilitates purification of the PCR products. The modification is preferably the same for all primers, although different modifications can be used if it is desired to separate the PCR products into different groups.

The tag can be any chemical moiety including but not limited to a radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof.

As one example, the 5' ends of the primers can be biotinylated (Kandpal et al., *Nucleic Acids Res.* 18:1789-1795 (1990); Kaneoka et al., *Biotechniques* 10:30-34 (1991); Green et al., *Nucleic Acids Res.* 18:6163-6164 (1990)). The biotin provides an affinity tag that can be used to purify the copied DNA from the genomic DNA or any other DNA molecules that are not of interest. Biotinylated molecules can be purified using a streptavidin coated matrix as shown in FIG. 1F, including but not limited to Streptawell, transparent, High-Bind plates from Roche Molecular Biochemicals (catalog number 1 645 692, as listed in Roche Molecular Biochemicals, 2001 Biochemicals Catalog).

The PCR product of each locus of interest is placed into separate wells of a Streptavidin coated plate. Alternatively, the PCR products of the loci of interest can be pooled and placed into a streptavidin coated matrix, including but not limited to the Streptawell, transparent, High-Bind plates from Roche Molecular Biochemicals (catalog number 1 645 692, as listed in Roche Molecular Biochemicals, 2001 Biochemicals Catalog).

The amplified DNA can also be separated from the template DNA using non-affinity methods known in the art, for example, by polyacrylamide gel electrophoresis using standard protocols.

IV. Digestion of Amplified DNA

The amplified DNA can be digested with a restriction enzyme that recognizes a sequence that had been provided on the first or second primer using standard protocols known within the art (FIGS. 6A-6D). Restriction enzyme digestions are performed using standard protocols well known within the art. The enzyme used depends on the restriction recognition site generated with the first or second primer. See "Primer Design" section, above, for details on restriction recognition sites generated on primers.

Type IIS restriction enzymes are extremely useful in that they cut approximately 10-20 base pairs outside of the recognition site. Preferably, the Type IIS restriction enzymes used are those that generate a 5' overhang and a recessed 3' end, including but not limited to BceA I and BsmF I (see e.g. Table 1). In a most preferred embodiment, the second primer (either forward or reverse) contains a restriction enzyme recognition sequence for BsmF I or BceA I. The Type IIS restriction enzyme BsmF I recognizes the nucleic acid sequence GGGAC, and cuts 14 nucleotides from the recognition site on the antisense strand and 10 nucleotides from the recognition site on the sense strand. Digestion with BsmF I generates a 5' overhang of four (4) bases.

For example, if the second primer is designed so that after amplification the restriction enzyme recognition site is 13 bases from the locus of interest, then after digestion, the locus of interest is the first base in the 5' overhang (reading 3' to 5'), and the recessed 3' end is one base from the locus of interest. The 3' recessed end can be filled in with a nucteotide that is complementary to the locus of interest. One base of the overhang can be filled in using dideoxynucleotides. However, 1, 2, 3, or 4 bases of the overhang can be filled in using deoxynucleotides or a mixture of dideoxynucleotides and deoxynucleotides.

The restriction enzyme BsmF I cuts DNA ten (10) nucleotides from the recognition site on the sense strand and fourteen (14) nucleotides from the recognition site on the antisense strand. However, in a sequence dependent manner, the restriction enzyme BsmF I also cuts eleven (11) nucleotides from the recognition site on the sense strand and fifteen (15) nucleotides from the recognition site on the antisense strand. Thus, two populations of DNA molecules exist after digestion: DNA molecules cut at 10/14 and DNA molecules cut at 11/15. If the recognition site for BsmF I is 13 bases from the locus of interest in the amplified product, then DNA molecules cut at the 11/15 position will generate a 5' overhang that contains the locus of interest in the second position of the overhang (reading 3' to 5'). The 3' recessed end of the DNA molecules can be filled in with labeled nucleotides. For example, if labeled dideoxynucleotides are used, the 3' recessed end of the molecules cut at 11/15 would be filled in with one base, which corresponds to the base upstream from the locus of interest, and the 3' recessed end of molecules cut at 10/14 would be filled in with one base, which corresponds to the locus of interest. The DNA molecules that have been cut at the 10/14 position and the DNA molecules that have been cut at the 11/15 position can be separated by size, and the incorporated nucleotides detected. This allows detection of both the nucleotide before the locus of interest, detection of the locus of interest, and potentially the three bases after the locus of interest.

Alternatively, if the base upstream from the locus of interest and the locus of interest are different nucleotides, then the 3' recessed end of the molecules cut at 11/15 can be filled in with deoxynucleotide that is complementary to the upstream base. The remaining deoxynucieotide is washed away, and the locus of interest site can be filled in with either labeled deoxynucleotides, unlabeled deoxynucleotides, labeled dideoxynucleotides, or unlabeled dideoxynucleotides. After the fill in reaction, the nucleotide can be detected by any suitable method. Thus, after the first fill in reaction with dNTP, the 3' recessed end of the molecules cut at 10/14 and 11/15 is upstream from the locus of interest. The 3' recessed end can now be filled in one base, which corresponds to the locus of interest, two bases, three bases or four bases.

The restriction enzyme BceA I recognizes the nucleic acid sequence ACGGC and cuts 12 (twelve) nucleotides from the recognition site on the sense strand and 14 (fourteen) nucleotides from the recognition site on the antisense strand. If the distance from the recognition site for BceA I on the second primer is designed to be thirteen (13) bases from the locus of interest (see FIGS. 4A-4D), digestion with BceA I will generate a 5' overhang of two bases, which contains the locus of interest, and a recessed 3' end that is upstream from the locus of interest. The locus of interest is the first nucleotide in the 5' overhang (reading 3' to 5').

Alternative cutting is also seen with the restriction enzyme BceA I, although at a much lower frequency than is seen with BsmF I. The restriction enzyme BceA I can cut thirteen (13) nucleotides from the recognition site on the sense strand and fifteen (15) nucleotides from the recognition site on the antisense strand. Thus, two populations of DNA molecules exist: DNA molecules cut at 12/14 and DNA molecules cut at 13/15. If the restriction enzyme recognition site is 13 bases from the locus of interest in the amplified product, DNA molecules cut at the 13/15 position yield a 5' overhang, which contains the locus of interest in the second position of the overhang (reading 3' to 5'). Labeled dideoxynucleotides can be used to fill in the 3' recessed end of the DNA molecules. The DNA molecules cut at 13/15 will have the base upstream from the locus of interest filled in, and the DNA molecules cut at 12/14 will have the locus of interest site filled in. The DNA molecules cut at 13/15 and those cut at 12/14 can be separated by size, and the incorporated nucleotide detected. Thus, the alternative cutting can be used to obtain additional sequence information.

Alternatively, if the two bases in the 5' overhang are different, the 3' recessed end of the DNA molecules, which were cut at 13/15, can be filled in with the deoxynucleotide complementary to the first base in the overhang, and excess deoxynucleotide washed away. After filling in, the 3' recessed end of the DNA molecules that were cut at 12/14 and the DNA molecules that were cut at 13/15 are upstream from the locus of interest. The 3' recessed ends can be filled with either labeled dideoxynucleotides, unlabeled dideoxynucleotides, labeled deoxynucleotides, or unlabeled deoxynucleotides.

If the primers provide different restriction sites for certain of the loci of interest that were copied, all the necessary restriction enzymes can be added together to digest the copied DNA simultaneously. Alternatively, the different restriction digests can be made in sequence, for example, using one restriction enzyme at a time, so that only the product that is specific for that restriction enzyme is digested.

Optimal restriction enzyme digestion conditions, including but not limited to the concentration of enzyme, temperature, buffer conditions, and the time of digestion can be optimized for each restriction enzyme. For example, the alternative cutting seen with the type IIS restriction enzyme BsmF I can be reduced, if desired, by performing the restriction enzyme digestion at lower temperatures including but not limited to 25-16°, 16-12° C., 12-8° C., 8-4° C., or 4-0° C.

V. Incorporation of Labeled Nucleotides

Digestion with the restriction enzyme that recognizes the sequence on the second primer generates a recessed 3' end and a 5' overhang, which contains the locus of interest (FIG. 1G). The recessed 3' end can be filled in using the 5' overhang as a template in the presence of unlabeled or labeled nucleotides or a combination of both unlabeled and labeled nucleotides. The nucleotides can be labeled with any type of chemical group or moiety that allows for detection including but not limited to radioactive molecules, fluorescent molecules, antibodies, antibody fragments, haptens, carbohydrates, biotin, derivatives of biotin, phosphorescent moieties, luminescent moieties, electrochemiluminescent moieties, chromatic moieties, and moieties having a detectable electron spin resonance, electrical capacitance, dielectric constant or electrical conductivity. The nucleotides can be labeled with one or more than one type of chemical group or moiety. Each nucleotide can be labeled with the same chemical group or moiety.

Alternatively, each different nucleotide can be labeled with a different chemical group or moiety. The labeled nucleotides can be dNTPs, ddNTPs, or a mixture of both dNTPs and ddNTPs. The unlabeled nucleotides can be dNTPs, ddNTPs or a mixture of both dNTPs and ddNTPs.

Any combination of nucleotides can be used to incorporate nucleotides including but not limited to unlabeled deoxynucleotides, labeled deoxynucleotides, unlabeled dideoxynucleotides, labeled dideoxynucleotides, a mixture of labeled and unlabeled deoxynucleotides, a mixture of labeled and unlabeled dideoxynucleotides, a mixture of labeled deoxynucleotides and labeled dideoxynucleotides, a mixture of labeled deoxynucleotides and unlabeled dideoxynucleotides, a mixture of unlabeled deoxynucleotides and unlabeled dideoxynucleotides, a mixture of unlabeled deoxynucleotides and labeled dideoxynucleotides, dideoxynucleotide analogues, deoxynucleotide analogues, a mixture of dideoxynucleotide analogues and deoxynucleotide analogues, phosphorylated nucleoside analogues, 2'-deoxynucleotide-5'-triphosphate, and modified 2'-deoxynucleotide-5'-triphosphate.

For example, as shown in FIG. 1H, in the presence of a polymerase, the 3' recessed end can be filled in with fluorescent ddNTP using the 5' overhang as a template. The incorporated ddNTP can be detected using any suitable method including but not limited to fluorescence detection.

All four nucleotides can be labeled with different fluorescent groups, which will allow one reaction to be performed in the presence of all four labeled nucleotides. Alternatively, four separate "fill in" reactions can be performed for each locus of interest; each of the four reactions will contain a different labeled nucleotide (e.g. ddATP*, ddTTP*, ddGTP*, or ddCTP*, where * indicates a labeled nucleotide). Each nucleotide can be labeled with different chemical groups or the same chemical groups. The labeled nucleotides can be dideoxynucleotides or deoxynucleotides.

In another embodiment, nucleotides can be labeled with fluorescent dyes including but not limited to fluorescein, pyrene, 7-methoxycoumarin, Cascade Blue.TM., Alexa Flur 350, Alexa Flur 430, Alexa Flur 488, Alexa Flur 532, Alexa Flur 546, Alexa Flur 568, Alexa Flur 594, Alexa Flur 633, Alexa Flur 647, Alexa Flur 660, Alexa Flur 680, AMCA-X, dialkylaminocoumarin, Pacific Blue, Marina Blue, BODIPY 493/503, BODIPY Fl-X, DTAF, Oregon Green 500, Dansyl-X, 6-FAM, Oregon Green 488, Oregon Green 514, Rhodamine Green-X, Rhodol Green, Calcein, Eosin, ethidium bromide, NBD, TET, 2', 4', 5', 7' tetrabromosulfonefluorescien, BODIPY-R6G, BODIPY-Fl BR2, BODIPY 530/550, HEX, BODIPY 558/568, BODIPY-TMR-X., PyMPO, BODFPY 564/570, TAMRA, BODIPY 576/589, Cy3, Rhodamine Red-x, BODIPY 581/591, carboxyXrhodamine, Texas Red-X, BODIPY-TR-X., Cy5, SpectrumAqua, SpectrumGreen #1, SpectrumGreen #2, SpectrumOrange, SpectrumRed, or naphthofluorescein.

In another embodiment, the "fill in" reaction can be performned with fluorescently labeled dNTPs, wherein the nucleotides are labeled with different fluorescent groups. The incorporated nucleotides can be detected by any suitable method including but not limited to Fluorescence Resonance Energy Transfer (FRET).

In another embodiment, a mixture of both labeled ddNTPs and unlabeled dNTPs can be used for filling in the recessed 3' end of the SNP or locus of interest. Preferably, the 5' overhang consists of more than one base, including but not limited to 2, 3, 4, 5, 6 or more than 6 bases. For example, if the 5' overhang consists of the sequence "XGAA," wherein X is the locus of interest, e.g. SNP, then filling in with a mixture of labeled ddNTPs and unlabeled dNTPs will produce several different DNA fragments. If a labeled ddNTP is incorporated at position "X," the reaction will terminate and a single labeled base will be incorporated. If however, an unlabeled dNTP is incorporated, the polymerase continues to incorporate other bases until a labeled ddNTP is incorporated. If the first two nucleotides incorporated are dNTPs, and the third is a ddNTP, the 3' recessed end will be extend by three bases. This DNA fragment can be separated from the other DNA fragments that were extended by 1, 2, or 4 bases by size. A mixture of labeled ddNTPs and unlabeled dNTPs will allow all bases of the overhang to be filled in, and provides additional sequence information about the locus of interest, e.g. SNP (see FIGS. 7E and 9D).

After incorporation of the labeled nucleotide, the amplified DNA can be digested with a restriction enzyme that recognizes the sequence provided by the first primer. For example, in FIG. 1I, the amplified DNA is digested with a restriction enzyme that binds to region "a," which releases the DNA fragment containing the incorporated nucleotide from the streptavidin matrix.

Alternatively, one primer of each primer pair for each locus of interest can be attached to a solid support matrix including but not limited to a well of a microtiter plate. For example, streptavidin-coated microtiter plates can be used for the amplification reaction with a primer pair, wherein one primer is biotinylated. First, biotinylated primers are bound to the streptavidin-coated microtiter plates. Then, the plates are used as the reaction vessel for PCR amplification of the loci of interest. After the amplification reaction is complete, the excess primers, salts, and template DNA can be removed by washing. The amplified DNA remains attached to the microtiter plate. The amplified DNA can be digested with a restriction enzyme that recognizes a sequence on the second primer and generates a 5' overhang, which contains the locus of interest. The digested fragments can be removed by washing. After digestion, the SNP site or locus of interest is exposed in the 5' overhang. The recessed 3' end is filled in with a labeled nucleotide, including but not limited to, fluorescent ddNTP in the presence of a polymerase. The labeled DNA can be released into the supernatant in the microtiter plate by digesting with a restriction enzyme that recognizes a sequence in the 5' region of the first primer.

In another embodiment, one nucleotide can be used to determine the sequence of multiple alleles of a gene. A nucleotide that terminates the elongation reaction can be used to determine the sequence of multiple alleles of a gene. At one allele, the terminating nucleotide is complementary to the locus of interest in the 5' overhang of said allele. The nucleotide is incorporated and terminates the reaction. At a different allele, the terminating nucleotide is not complementary to the locus of interest, which allows a non-terminating nucleotide to be incorporated at the locus of interest of the different allele. However, the terminating nucleotide is complementary to a nucleotide downstream from the locus of interest in the 5' overhang of said different allele. The sequence of the alleles can be determined by analyzing the patterns of incorporation of the terminating nucleotide. The terminating nucleotide can be labeled or unlabeled.

In a another embodiment, the terminating nucleotide is a nucleotide that terminates or hinders the elongation reaction including but not limited to a dideoxynucleotide, a dideoxynucleotide derivative, a dideoxynucleotide analog, a dideoxynucleotide homolog, a dideoxynucleotide with a sulfur chemical group, a deoxynucleotide, a deoxynucleotide derivative, a deoxynucleotide homolog, a deoxynucleotide analog, a deoxynucleotide with a sulfur chemical group, arabinoside triphosphate, a arabinoside triphosphate analog, a arabinoside triphosphate homolog, or an arabinoside derivative.

In another embodiment, a terminating nucleotide labeled with one signal generating moiety tag, including but not limited to a fluorescent dye, can be used to determine the sequence of the alleles of a locus of interest. The use of a single nucleotide labeled with one signal generating moiety tag eliminates any difficulties that can arise when using different fluorescent moieties. In addition, using one nucleotide labeled with one signal generating moiety tag to determine the sequence of alleles of a locus of interest reduces the number of reactions, and eliminates pipetting errors.

For example, if the second primer contains the restriction enzyme recognition site for BsmFI, digestion will generate a 5' overhang of 4 bases. The second primer can be designed such that the locus of interest is located in the first position of the overhang. A representative overhang is depicted below, where R represents the locus of interest:

```
5' CAC
3' GTG                    R     T     G     G
Overhang position         1     2     3     4
```

One nucleotide with one signal generating moiety tag can be used to determine whether the variable site is homozygous or heterozygous. For example, if the variable site is adenine (A) or guanine (G), then either adenine or guanine can be used to determine the sequence of the alleles of the locus of interest, provided that there is an adenine or guanine in the overhang at position 2, 3, or 4.

For example, if the nucleotide in position 2 of the overhang is thymidine, which is complementary to adenine, then labeled ddATP, unlabeled dCTP, dGTP, and dTTP can be used to determine the sequence of the alleles of the locus of interest. The ddATP can be labeled with any signal generating moiety including but not limited to a fluorescent dye. If the template DNA is homozygous for adenine, then labeled ddATP* will be incorporated at position 1 complementary to the overhang at the alleles, and no nucleotide incorporation will be seen at position 2, 3 or 4 complementary to the overhang.

```
Allele 1             5' CCC    A*
                     3' GGG    T    T    G    G
Overhang position              1    2    3    4

Allele 2 5' CCC      A*
                     3' GGG    T    T    G    G
Overhang position              1    2    3    4
```

One signal will be seen corresponding to incorporation of labeled ddATP at position 1 complementary to the overhang, which indicates that the individual is homozygous for adenine at this position. This method of labeling eliminates any difficulties that may arise from using different dyes that have different quantum coefficients.

Homozygous Guanine

If the template DNA is homozygous for guanine, then no ddATP will be incorporated at position 1 complementary to the overhang, but ddATP will be incorporated at the first available position, which in this case is position 2 complementary to the overhang. For example, if the second position in the overhang corresponds to a thymidine, then:

```
Allele 1             5' CCC    G    A*
                     3' GGG    C    T    G    G
Overhang position              1    2    3    4

Allele 2             5' CCC    G    A*
                     3' GGG    C    T    G    G
Overhang position              1    2    3    4
```

One signal will be seen corresponding to incorporation of ddATP at position 2 complementary to the overhang, which indicates that the individual is homozygous for guanine. The molecules that are filled in at position 2 complementary to the overhang will have a different molecular weight than the molecules filled in at position 1 complementary to the overhang.

<u>Heterozygous condition:</u>

```
Allele 1             5' CCC A*
                     3' GGG T       T    G    G
Overhang position           1       2    3    4

Allele 2             5' CCC G       A*
                     3' GGG C       T    G    G
Overhang position           1       2    3    4
```

Two signals will be seen; the first signal corresponds to the ddATP filled in at position one complementary to the overhang and the second signal corresponds to the ddATP filled in at position 2 complementary to the overhang. The two signals can be separated based on molecular weight; allele 1 and allele 2 will be separated by a single base pair, which allows easy detection and quantitation of the signals. Molecules filled in at position one can be distinguished from molecules filled in at position two using any method that discriminates based on molecular weight including but not limited to gel electrophoresis, capillary gel electrophoresis, DNA sequencing, and mass spectrometry. It is not necessary that the nucleotide be labeled with a chemical moiety; the DNA molecules corresponding to the different alleles can be separated based on molecular weight.

If position 2 of the overhang is not complementary to adenine, it is possible that positions 3 or 4 may be complementary to adenine. For example, position 3 of the overhang may be complementary to the nucleotide adenine, in which case labeled ddATP may be used to determine the sequence of both alleles.

<u>Homozygous for adenine:</u>

```
Allele 1             5' CCC    A*
                     3' GGG    T    G    T    G
Overhang position              1    2    3    4

Allele 2             5' CCC    A*
                     3' GGG    T    G    T    G
Overhang position              1    2    3    4
```

<u>Homozygous for guanine:</u>

```
Allele 1             5' CCC    G    C    A*
                     3' GGG    C    G    T    G
Overhang position              1    2    3    4

Allele 2             5' CCC    G    C    A*
                     3' GGG    C    G    T    G
Overhang position              1    2    3    4
```

<u>Heterozygous:</u>

-continued

| | | | | | |
|---|---|---|---|---|---|
| Allele 1 | 5' CCC | **A*** | | | |
| | 3' GGG | T | G | T | G |
| Overhang position | | 1 | 2 | 3 | 4 |
| Allele 2 | 5' CCC | **G** | C | **A*** | |
| | 3' GGG | C | G | T | G |
| Overhang position | | 1 | 2 | 3 | 4 |

Two signals will be seen; the first signal corresponds to the ddATP filled in at position 1 complementary to the overhang and the second signal corresponds to the ddATP filled in at position 3 complementary to the overhang. The two signals can be separated based on molecular weight; allele 1 and allele 2 will be separated by two bases, which can be detected using any method that discriminates based on molecular weight.

Alternatively, if positions 2 and 3 are not complementary to adenine (i.e positions 2 and 3 of the overhang correspond to guanine, cytosine, or adenine) but position 4 is complementary to adenine, labeled ddATP can be used to determine the sequence of both alleles.

Homozygous for adenine:

| | | | | | |
|---|---|---|---|---|---|
| Allele 1 | 5' CCC | **A*** | | | |
| | 3' GGG | T | G | G | T |
| Overhang position | | 1 | 2 | 3 | 4 |
| Allele 2 | 5' CCC | **A*** | | | |
| | 3' GGG | T | G | G | T |
| Overhang position | | 1 | 2 | 3 | 4 |

One signal will be seen that corresponds to the molecular weight of molecules filled in with ddATP at position one complementary to the overhang, which indicates that the individual is homozygous for adenine at the variable site.

Homozygous for guanine:

| | | | | | |
|---|---|---|---|---|---|
| Allele 1 | 5' CCC | **G** | C | C | **A*** |
| | 3' GGG | C | G | G | T |
| Overhang position | | 1 | 2 | 3 | 4 |
| Allele 2 | 5' CCC | **G** | C | C | **A*** |
| | 3' GGG | C | G | G | T |
| Overhang position | | 1 | 2 | 3 | 4 |

One signal will be seen that corresponds to the molecular weight of molecules filled in at position 4 complementary to the overhang, which indicates that the individual is homozygous for guanine.

Heterozygous:

| | | | | | |
|---|---|---|---|---|---|
| Allele 1 | 5' CCC | **A*** | | | |
| | 3' GGG | **T** | G | G | T |
| Overhang position | | 1 | 2 | 3 | 4 |
| Allele 2 | 5' CCC | **G** | C | C | **A*** |
| | 3' GGG | **C** | G | G | T |
| Overhang position | | 1 | 2 | 3 | 4 |

Two signals will be seen; the first signal corresponds to the ddATP filled in at position one complementary to the overhang and the second signal corresponds to the ddATP filled in at position 4 complementary to the overhang. The two signals can be separated based on molecular weight; allele 1 and allele 2 will be separated by three bases, which allows detection and quantitation of the signals. The molecules filled in at position 1 and those filled in at position 4 can be distinguished based on molecular weight, As discussed above, if the variable site contains either adenine or guanine, either labeled adenine or labeled guanine can be used to determine the sequence of both alleles. If positions 2, 3, or 4 of the overhang are not complementary to adenine but one of the positions is complementary to a guanine, then labeled ddGTP can be used to determine whether the template DNA is homozygous or heterozygous for adenine or guanine. For example, if position 3 in the overhang corresponds to a cytosine then the following signals will be expected if the template DNA is homozygous for guanine, homozygous for adenine, or heterozygous:

Homozygous for guanine:

| | | | | | |
|---|---|---|---|---|---|
| Allele 1 | 5' CCC | **G*** | | | |
| | 3' GGG | C | T | C | T |
| Overhang position | | 1 | 2 | 3 | 4 |
| Allele 2 | 5' CCC | **G*** | | | |
| | 3' GGG | C | T | C | T |
| Overhang position | | 1 | 2 | 3 | 4 |

One signal will be seen that corresponds to the molecular weight of molecules filled in with ddGTP at position one complementary to the overhang, which indicates that the individual is homozygous for guanine.

Homozygous for adenine:

| | | | | | |
|---|---|---|---|---|---|
| Allele 1 | 5' CCC | **A** | A | **G*** | |
| | 3' GGG | T | T | C | T |
| Overhang position | | 1 | 2 | 3 | 4 |
| Allele 2 | 5' CCC | **A** | A | **G*** | |
| | 3' GGG | T | T | C | T |
| Overhang position | | 1 | 2 | 3 | 4 |

One signal will be seen that corresponds to the molecular weight of molecules filled in at position 3 complementary to the overhang, which indicates that the individual is homozygous for adenine at the variable site.

Heterozygous:

| | | | | | |
|---|---|---|---|---|---|
| Allele 1 | 5' CCC | **G*** | | | |
| | 3' GGG | C | T | C | T |
| Overhang position | | 1 | 2 | 3 | 4 |
| Allele 2 | 5' CCC | **A** | A | **G*** | |
| | 3' GGG | T | T | C | T |
| Overhang position | | 1 | 2 | 3 | 4 |

Two signals will be seen; the first signal corresponds to the ddGTP filled in at position one complementary to the overhang and the second signal corresponds to the ddGTP filled in at position 3 complementary to the overhang. The two signals can be separated based on molecular weight; allele 1 and allele 2 will be separated by two bases, which allows easy detection and quantitation of the signals.

In another embodiment, the nucleotide labeled with a single chemical moiety, which is used to determine the sequence of alleles of interest, can be analyzed by a variety of methods including but not limited to fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend, or MassCleave™ (hMC) method.

Some type IIS restriction enzymes also display alternative cutting as discussed above. For example, BsmFI will cut at 10/14 and 11/15 from the recognition site. However, the cutting patterns are not mutually exclusive; if the 11/15 cutting pattern is seen at a particular sequence, 10/14 cutting is also seen. If the restriction enzyme BsmF I cuts at 10/14 from the recognition site, the 5' overhang will be $X_1X_2X_3X_4$. If BsmF I cuts 11/15 from the recognition site, the 5' overhang will be $X_0X_1X_2X_3$. If position $X_0$ of the overhang is complementary to the labeled nucleotide, the labeled nucleotide will be incorporated at position $X_0$ and provides an additional level of quality assurance. It provides additional sequence information.

For example, if the variable site is adenine or guanine, and position 3 in the overhang is complementary to adenine, labeled ddATP can be used to determine the genotype at the variable site. If position 0 of the 11/15 overhang contains the nucleotide complementary to adenine, ddATP will be filled in and an additional signal will be seen.

Heterozygous:

| | | | | | |
|---|---|---|---|---|---|
| 10/14 Allele 1 | 5' CCA | **A*** | | | |
| | 3' GGT | T | G | T | G |
| Overhang position | | 1 | 2 | 3 | 4 |
| 10/14 Allele 2 | 5' CCA | **G** | C | **A*** | |
| | 3' GGT | C | G | T | G |
| Overhang position | | 1 | 2 | 3 | 4 |
| 11/15 Allele 1 | 5' CC | **A*** | | | |
| | 3' GG | T | T | G | T |
| Overhang position | | 0 | 1 | 2 | 3 |
| 11/15 Allele 2 | 5' CC | **A*** | | | |
| | 3' GG | T | C | G | T |
| Overhang position | | 0 | 1 | 2 | 3 |

Three signals are seen; one corresponding to the ddATP incorporated at position 0 complementary to the overhang, one corresponding to the ddATP incorporated at position 1 complementary to the overhang, and one corresponding to the ddATP incorporated at position 3 complementary to the overhang. The molecules filled in at position 0, 1, and 3 complementary to the overhang differ in molecular weight and can be separated using any technique that discriminates based on molecular weight including but not limited to gel electrophoresis, and mass spectrometry.

For quantitating the ratio of one allele to another allele or when determining the relative amount of a mutant DNA sequence in the presence of wild type DNA sequence, an accurate and highly sensitive method of detection must be used. The alternate cutting displayed by type IIS restriction enzymes may increase the difficulty of determining ratios of one allele to another allele because the restriction enzyme may not display the alternate cutting (11/15) pattern on the two alleles equally. For example, allele 1 may be cut at 10/14 80% of the time, and 11/15 20% of the time. However, because the two alleles may differ in sequence, allele 2 may be cut at 10/14 90% of the time, and 11/15 20% of the time.

For purposes of quantitation, the alternate cutting problem can be eliminated when the nucleotide at position 0 of the overhang is not complementary to the labeled nucleotide. For example, if the variable site corresponds to adenine or guanine, and position 3 of the overhang is complementary to adenine (i.e, a thymidine is located at position 3 of the overhang), labeled ddATP can be used to determine the genotype of the variable site. If position 0 of the overhang generated by the 11/15 cutting properties is not complementary to adenine, (i.e, position 0 of the overhang corresponds to guanine, cytosine, or adenine) no additional signal will be seen from the fragments that were cut 11/15 from the recognition site. Position 0 complementary to the overhang can be filled in with unlabeled nucleotide, eliminating any complexity seen from the alternate cutting pattern of restriction enzymes. This method provides a highly accurate method for quantitating the ratio of a variable site including but not limited to a mutation, or a single nucleotide polymorphism.

For instance, if SNP X can be adenine or guanine, this method of labeling allows quantitation of the alleles that correspond to adenine and the alleles that correspond to guanine, without determining if the restriction enzyme displays any differences between the alleles with regard to alternate cutting patterns.

Heterozygous:

| | | | | | |
|---|---|---|---|---|---|
| 10/14 Allele 1 | 5' CCG | **A*** | | | |
| | 3' GGC | T | G | T | G |
| Overhang position | | 1 | 2 | 3 | 4 |
| 10/14 Allele 2 | 5' CCG | **G** | C | **A*** | |
| | 3' GGC | C | G | T | G |
| Overhang position | | 1 | 2 | 3 | 4 |

The overhang generated by the alternate cutting properties of BsmF I is depicted below:

| | | | | | |
|---|---|---|---|---|---|
| 11/15 Allele 1 | 5' CC | | | | |
| | 3' GG | C | T | G | T |
| Overhang position | | 0 | 1 | 2 | 3 |
| 11/15 Allele 2 | 5' CC | | | | |
| | 3' GG | C | C | G | T |
| Overhang position | | 0 | 1 | 2 | 3 |

After filling in with labeled ddATP and unlabeled dGTP, dCTP, dTTP, the following molecules would be generated:

| | | | | | |
|---|---|---|---|---|---|
| 11/15 Allele 1 | 5' CC | G | **A*** | | |
| | 3' GG | C | T | G | T |
| Overhang position | | 0 | 1 | 2 | 3 |
| 11/15 Allele 2 | 5' CC | G | **G** | C | **A*** |
| | 3' GG | C | C | G | T |
| Overhang position | | 0 | 1 | 2 | 3 |

Two signals are seen; one corresponding to the molecules filled in with ddATP at position one complementary to the overhang and one corresponding to the molecules filled in with ddATP at position 3 complementary to the overhang. Position 0 of the 11/15 overhang is filled in with unlabeled nucleotide, which eliminates any difficulty in quantitating a ratio for the nucleotide at the variable site on allele 1 and the nucleotide at the variable site on allele 2.

Any nucleotide can be used including adenine, adenine derivatives, adenine homologues, guanine, guanine derivatives, guanine homologues, cytosine, cytosine derivatives, cytosine homologues, thymidine, thymidine derivatives, or thymidine homologues, or any combinations of adenine, adenine derivatives, adenine homologues, guanine, guanine derivatives, guanine homologues, cytosine, cytosine derivatives, cytosine homologues, thymidine, thymidine derivatives, or thymidine homologues.

The nucleotide can be labeled with any chemical group or moiety, including but not limited to radioactive molecules, fluorescent molecules, antibodies, antibody fragments, haptens, carbohydrates, biotin, derivatives of biotin, phosphorescent moieties, luminescent moieties, electrochemiluminescent moieties, chromatic moieties, and moieties having a detectable electron spin resonance, electrical capacitance, dielectric constant or electrical conductivity. The nucleotide can be labeled with one or more than one type of chemical group or moiety.

In another embodiment, labeled and unlabeled nucleotides can be used. Any combination of deoxynucleotides and dideoxynucleotides can be used including but not limited to labeled dideoxynucleotides and labeled deoxynucleotides; labeled dideoxynucleotides and unlabeled deoxynucleotides; unlabeled dideoxynucleotides and unlabeled deoxynucleotides; and unlabeled dideoxynucleotides and labeled deoxynucleotides.

In another embodiment, nucleotides labeled with a chemical moiety can be used in the PCR reaction. Unlabeled nucleotides then are used to fill-in the 5' overhangs generated after digestion with the restriction enzyme. An unlabeled terminating nucleotide can be used to in the presence of unlabeled nucleotides to determine the sequence of the alleles of a locus of interest.

For example, if labeled dTTP was used in the PCR reaction, the following 5' overhang would be generated after digestion with BsmF I:

```
10/14 Allele 1        5' CT*G   A
                      3' GA C   T     G     T     G
Overhang position               1     2     3     4

10/14 Allele 2        5' CT*G   G     C     A
                      3' GA C   C     G     T     G
Overhang position               1     2     3     4
```

Unlabeled ddATP, unlabeled dCTP, unlabeled dGTP, and unlabeled dTTP can be used to fill-in the 5' overhang. Two signals will be generated; one signal corresponds to the DNA molecules filled in with unlabeled ddATP at position 1 complementary to the overhang and the second signal corresponds to DNA molecules filled in with unlabeled ddATP at position 3 complementary to the overhang. The DNA molecules can be separated based on molecular weight and can be detected by the fluorescence of the dTTP, which was incorporated during the PCR reaction.

The labeled DNA loci of interest sites can be analyzed by a variety of methods including but not limited to fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend, or MassCleave™ (hMC) method.

This method of labeling is extremely sensitive and allows the detection of alleles of a locus of interest that are in various ratios including but not limited to 1: 1, 1:2, 1:3, 1:4, 1:5, 1:6-1:10, 1:11-1:20, 1:21 -1:30, 1:31-1:40, 1:41-1:50, 1:51-1:60, 1:61-1:70, 1:71-1:80, 1:81-1:90, 1:91:1:100, 1:101-1:200, 1:250, 1:251-1:300, 1:301-1:400, 1:401-1:500, 1:501-1:600, 1:601-1:700, 1:701-1:800, 1:801-1:900, 1:901-1:1000, 1:1001-1:2000, 1:2001-1:3000, 1:3001-1:4000, 1:4001-1:5000, 1:5001-1:6000, 1:6001-1:7000, 1:7001-1:8000, 1:8001-1:9000, 1:9001-1:10,000; 1:10,001-1:20,000, 1:20,001:1:30,000, 1:30,001-1:40,000, 1:40,001-1:50,000, and greater than 1:50,000.

For example, this method of labeling allows one nucleotide labeled with one signal generating moiety to be used to determine the sequence of alleles at a SNP locus, or detect a mutant allele amongst a population of normal alleles, or detect an allele encoding antibiotic resistance from a bacterial cell amongst alleles from antibiotic sensitive bacteria, or detect an allele from a drug resistant virus amongst alleles from drug-sensitive virus, or detect an allele from a non-pathogenic bacterial strain amongst alleles from a pathogenic bacterial strain.

As shown above, a single nucleotide can be used to determine the sequence of the alleles at a particular locus of interest. This method is especially useful for determining if an individual is homozygous or heterozygous for a particular mutation or to determine the sequence of the alleles at a particular SNP site. This method of labeling eliminates any errors caused by the quantum coefficients of various dyes. It also allows the reaction to proceed in a single reaction vessel including but not limited to a well of a microtiter plate, or a single eppendorf tube.

This method of labeling is especially useful for the detection of multiple genetic signals in the same sample. For example, this method is useful for the detection of fetal DNA in the blood, serum, or plasma of a pregnant female, which contains both maternal DNA and fetal DNA. The maternal DNA and fetal DNA may be present in the blood, serum or plasma at ratios such as 97:3; however, the above-described method can be used to detect the fetal DNA. This method of labeling can be used to detect two, three, four or more than four different genetic signals in the sample population This method of labeling is especially useful for the detection of a mutant allele that is among a large population of wild type alleles. Furthermore, this method of labeling allows the detection of a single mutant cell in a large population of wild type cells. For example, this method of labeling can be used to detect a single cancerous cell among a large population of normal cells. Typically, cancerous cells have mutations in the DNA sequence. The mutant DNA sequence can be identified even if there is a large background of wild type DNA sequence. This method of labeling can be used to screen, detect, or diagnosis any type of cancer including but not limited to colon, renal, breast, bladder, liver, kidney, brain, lung, prostate, and cancers of the blood including leukemia.

This labeling method can also be used to detect pathogenic organisms, including but not limited to bacteria, fungi, viruses, protozoa, and mycobacteria. It can also be used to discriminate between pathogenic strains of microorganism and non-pathogenic strains of microorganisms including but not limited to bacteria, fungi, viruses, protozoa, and mycobacteria.

For example, there are several strains of *Escherichia coli* (*E. coli*), and most are non-pathogenic. However, several strains, such as *E. coli* 0157 are pathogenic. There are genetic differences between non-pathogenic *E. coli* strains and pathogenic *E. coli*. The above described method of labeling can be used to detect pathogenic microorganisms in a large population of non-pathogenic organisms, which are sometimes associated with the normal flora of an individual.

VI. Analysis of the Locus of Interest

The loci of interest can be analyzed by a variety of methods including but not limited to fluorescence detection, DNA sequencing gel, capillary electrophoresis on an automated DNA sequencing machine, (e.g. the ABI Prism 3100 Genetic Analyzer or the ABI Prism 3700 Genetic Analyzer), miicro-channel electrophoresis, and other methods of sequencing, Sanger dideoxy sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blot, Slot Blot, Dot Blot, and DNA microarray, wherein DNA fragments would be useful as both “probes” and “targets,” ELISA, fluorimetry, fluorescence polarization, Fluorescence Resonance Energy Transfer (FRET), SNP-IT, GeneChips, HuSNP, BeadArray, TaqMan assay, Invader assay, MassExtend, or MassCleave™ (hMC) method.

The loci of interest can be analyzed using gel electrophoresis followed by fluorescence detection of the incorporated nucleotide. Another method to analyze or read the loci of interest is to use a fluorescent plate reader or fluorimeter directly on the 96-well streptavidin coated plates. The plate can be placed onto a fluorescent plate reader or scanner such as the Pharmacia 9200 Typhoon to read each locus of interest.

Alternatively, the PCR products of the loci of interest can be pooled and after “filling in” (FIG. 10), the products can be separated by size, using any method appropriate for the same, and then analyzed using a variety of techniques including but not limited to fluorescence detection, DNA sequencing gel, capillary electrophoresis on an automated DNA sequencing machine, microchannel electrophoresis, other methods of sequencing, Sanger dideoxy sequencing, DNA hybridization techniques including Southern Blot, Slot Blot, Dot Blot, and DNA microarray, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry. For example, polyacrylamide gel electrophoresis can be used to separate DNA by size and the gel can be scanned to determine the color of fluorescence in each band (using e.g., ABI 377 DNA sequencing machine or a Pharmacia Typhoon 9200).

In another embodiment, the sequence of the locus of interest can be determined by detecting the incorporation of a nucleotide that is 3' to the locus of interest, wherein said nucleotide is a different nucleotide from the possible nucleotides at the locus of interest. This embodiment is especially useful for the sequencing and detection of SNPs. The efficiency and rate at which DNA polymerases incorporate nucleotides varies for each nucleotide.

According to the data from the Human Genome Project, 99% of all SNPs are binary. The sequence of the human genome can be used to determine a nucleotide that is 3' to the SNP of interest. When a nucleotide that is 3' to the SNP site differs from the possible nucleotides at the SNP site, a nucleotide that is one or more than one base 3' to the SNP can be used to determine the sequence of the SNP site.

For example, suppose the sequence of SNP X on chromosome 13 is to be determined. The sequence of the human genome indicates that SNP X can either be adenosine or guanine and that a nucleotide 3' to the locus of interest is a thymidine. A primer that contains a restriction enzyme recognition site for BsmF I, which is designed to be 13 bases from the locus of interest after amplification, is used to amplify a DNA fragment containing SNP X. Digestion with the restriction enzyme BsmF I generates a 5' overhang that contains the locus of interest, which can either be adenosine or guanine. The digestion products can be split into two “fill in” reactions: one contains dTTP, and the other reaction contains dCTP. If the locus of interest is homozygous for guanine, only the DNA molecules that were mixed with dCTP will be filled in. If the locus of interest is homozygous for adenosine, only the DNA molecules that were mixed with dTTP will be filled in. If the locus of interest is heterozygous, the DNA molecules that were mixed with dCTP will be filled in as well as the DNA molecules that were mixed with dTTP. After washing to remove the excess dNTP, the samples are filled in with labeled ddATP, which is complimentary to the nucleotide (thymidine) that is 3' to the locus of interest. The DNA molecules that were filled in by the previous reaction will be filled in with labeled ddATP. If the individual is homozygous for adenosine, the DNA molecules that were mixed with dTTP subsequently will be filled in with the labeled ddATP. However, the DNA molecules that were mixed with dCTP, would not have incorporated that nucleotide, and therefore, could not incorporate the ddATP. Detection of labeled ddATP only in the molecules that were mixed with dTTP indicates that the nucleotide at SNP X on chromosome 13 is adenosine.

In another embodiment, large scale screening for the presence or absence of single nucleotide polymorphisms or mutations can be performed. One to tens to hundreds to thousands of loci of interest on a single chromosome or on multiple chromosomes can be amplified with primers as described above in the “Primer Design” section. The primers can be designed so that each amplified loci of interest is of a different size (FIG. 2). The multiple loci of interest can be of a DNA sample from one individual representing multiple loci of interest on a single chromosome, multiple chromosomes, multiple genes, a single gene, or any combination thereof.

When human data is being analyzed, the known sequence can be a specific sequence that has been determined from one individual (including e.g. the individual whose DNA is currently being analyzed), or it can be a consensus sequence such as that published as part of the human genome.

Ratio of Alleles at Heterozygous Locus of Interest

In one embodiment, the ratio of alleles at a heterozygous locus of interest can be calculated. The intensity of a nucleotide at the loci of interest can be quantified using any number of computer programs including but not limited to GeneScan and ImageQuant. For example, for a heterozygous SNP, there are two nucleotides, and each should be present in a 1:1 ratio. In a preferred embodiment, the ratio of multiple heterozygous SNPs can be calculated.

In one embodiment, the ratio for a variable nucleotide at alleles at a heterozygous locus of interest can be calculated. The intensity of each variable nucleotide present at the loci of interest can be quantified using any number of computer programs including but not limited to GeneScan and ImageQuant. For example, for a heterozygous SNP, there will be two nucleotides present, and each may be present in a 1:1 ratio. In a preferred embodiment, the ratio of multiple heterozygous SNPs can be calculated.

In another embodiment, the ratio of alleles at a heterozygous locus of interest on a chromosome is summed and compared to the ratio of alleles at a heterozygous locus of interest on a different chromosome. In a preferred embodiment, the ratio of alleles at multiple heterozygous loci of interest on a chromosome is summed and compared to the ratio of alleles at multiple heterozygous loci of interest on a different chromosome. The ratio obtained from SNP 1, SNP 2, SNP 3, SNP 4, etc on chromosome 1 can be summed. This ratio can then be compared to the ratio obtained from SNP A, SNP B, SNP C, SNP D, etc.

For example, 100 SNPs can be analyzed on chromosome 1. Of these 100 SNPs, assume 50 are heterozygous. The ratio of the alleles at heterozygous SNPs on chromosome 1 can be summed, and should give a ratio of approximately 50:50. Likewise, of 100 SNPs analyzed on chromosome 21, assume 50 are heterozygous. The ratio of alleles at heterozygous SNPs on chromosome 21 is summed. With a normal number of chromosomes, the ratio should be approximately 50:50, and thus there should be no difference between the ratio obtained from chromosome 1 and 21. However, if there is an additional copy of chromosome 21, an additional allele will be provided, and the ratio should be approximately 66:33. Thus, the ratio for nucleotides at heterozygous SNPs can be used to detect the presence or absence of chromosomal abnormalities. Any chromosomal abnormality can be detected including aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. The method is especially useful for the detection of trisomy 13, trisomy 18, trisomy 21, XXY, and XYY.

The present invention provides a method to quantitate a ratio for the alleles at a heterozygous locus of interest. The loci of interest include but are not limited to single nucleotide polymorphisms, mutations. There is no need to amplify the entire sequence of a gene or to quantitate the amount of a particular gene product. The present invention does not rely on quantitative PCR.

Detection of Fetal Chromosomal Abnormalities

As discussed above in the section entitled "DNA template," the template DNA can be obtained from a sample of a pregnant female, wherein the template DNA comprises maternal template DNA and fetal template DNA. In one embodiment, the template DNA is obtained from the blood of a pregnant female. In a preferred embodiment, the template DNA is obtained from the plasma or serum from the blood of a pregnant female.

In one embodiment, the template DNA from the sample from the pregnant female comprises both maternal template DNA and fetal template DNA. In another embodiment, maternal template DNA is obtained from any nucleic acid containing source including but not limited to cell, tissue, blood, serum, plasma, saliva, urine, tears, vaginal secretion, lymph fluid, cerebrospinal fluid, mucosa secretion, peritoneal fluid, ascitic fluid, fecal matter, or body exudates, and sequenced to identify homozygous or heterozygous loci of interest, which are the loci of interest analyzed on the template DNA obtained from the sample from the pregnant female.

In a preferred embodiment, the sequence of the alleles of multiple loci of interest on maternal template DNA is determined to identify homozygous loci of interest. In another embodiment, the sequence of the alleles of multiple loci of interest on maternal template DNA is determined to identify heterozygous loci of interest. The sequence of the alleles of multiple loci of interest on maternal template DNA can be determined in a single reaction or in multiple reactions.

For example, if 100 maternal loci of interest on chromosome 21 and 100 maternal loci of interest on chromosome 1 are analyzed, one would predict approximately 50 loci of interest on each chromosome to be homozygous and 50 to be heterozygous. The 50 homozygous loci of interest, or the 50 heterozygous loci of interest or the 50 homozygous and 50 heterozygous loci of interest, or any combination of the homozygous and heterozygous loci of interest on each chromosome can be analyzed using the template DNA from the sample from the pregnant female.

The locus of interest on the template DNA from the sample of the pregnant female is analyzed using the amplification, isolation, digestion, fill in, and detection methods described above. The same primers used to analyze the locus of interest on the maternal template DNA are used to screen the template DNA from the sample from the pregnant female. Any number of loci of interest can be analyzed on the template DNA from the sample from the pregnant female. For example, 1, 1-5, 5-10, 10-20, 20-30, 30-40, 40-50, 50-60, 60-70, 70-80, 80-90, 90-100, 100-150, 150-200, 200-250, 250-300, 300-500, 500-1000, 1000-2000, 2000-3000, 3000-4000 or more than 4000 homozygous maternal loci of interest can be analyzed in the template DNA from the sample from the pregnant female. In a preferred embodiment, multiple loci of interest on multiple chromosomes are analyzed.

From the population of homozygous maternal loci of interest, there will be both heterozygous and homozygous loci of interest from the template DNA from the sample from the pregnant female; the heterozygous loci of interest can be further analyzed. At heterozygous loci of interest, the ratio of alleles can be used to determine the number of chromosomes that are present.

The percentage of fetal DNA present in the sample from the pregnant female can be calculated by determining the ratio of alleles at a heterozygous locus of interest on a chromosome that is not typically associated with a chromosomal abnormality. In a preferred embodiment, the ratio of alleles at multiple heterozygous loci of interest on a chromosome can be used to determine the percentage of fetal DNA. For example, chromosome 1, which is the largest chromosome in the human genome, can be used to determine the percentage of fetal DNA.

For example, suppose SNP X is homozygous at the maternal template DNA (A/A). At SNP X, the template DNA from the sample from the pregnant female, which can contain both fetal DNA and maternal DNA, is heterozygous (A/G). The nucleotide guanine represents the fetal DNA because at SNP X the mother is homozygous, and thus the guanine is attributed to the fetal DNA. The guanine at SNP X can be used to calculate the percentage of fetal DNA in the sample.

Alternatively, multiple loci of interest on two or more chromosomes can be examined to determine the percentage of fetal DNA. For example, multiple loci of interest can be examined on chromosomes 13, and 18 to determine the percentage of fetal DNA because organisms with chromosomal abnormalities at chromosome 13 and 18 are not viable.

Alternatively, for a male fetus, a marker on the Y chromosome can be used to determine the amount of fetal DNA present in the sample. A panel of serial dilutions can be made using the template DNA isolated from the sample from the pregnant female, and quantitative PCR analysis performed. Two PCR reactions can be performed: one PCR reaction to amplify a marker on the Y chromosome, for example SRY, and the other reaction to amplify a region on any of the autosomal chromosomes. The amount of fetal DNA can be calculated using the following formula:

Percent Fetal DNA: (last dilution Y chromosome detected/last dilution autosomal chromosome detected)*2*100.

If at SNP A, the mother is homozygous A/A, and the fetus is heterozygous A/G, then the ratio of A:G can be used to detect chromosomal abnormalities. If the fetal DNA is fifty percent (50%) of the DNA in the maternal blood, then at SNP A where the maternal nucleotide is an adenine and the other nucleotide is a guanine, one would expect the ratio of adenine (two adenines from the maternal template DNA and one from the fetal template DNA) to guanine (from the fetal template DNA) to be 25:75 or 0.33. However, if the fetus has a trisomy of this particular chromosome, and the additional chromosome is contributed by the mother, and thus an additional adenine nucleotide is present, then one would expect the ratio of 0.25 (50 (G)/(2*50 maternal A+2*50 fetal A). Thus, there is a difference of 8% between the ratio obtained from a chromosome present in two copies, and a chromosome present in a trisomy condition. On the other hand, if the additional chromosome is contributed by the father, and thus, an additional guanine is present, then one would expect the ratio of 0.66 (2*50 for G fetal allele/(2*50 maternal A allele+50 for fetal A allele).

However, if the fetal DNA is 40% of the DNA in the maternal blood, the expected ratio without a trisomy is 0.25 (40 for fetal G allele/2*60 for maternal A allele+1 *60 for fetal A allele). If the fetus has a trisomy, and the additional chromosome is provided by the mother, the expected ratio would be 0.20 (40 for fetal G allele/(2*60 for maternal A allele+2*40 for fetal A allele). A 5% difference between the ratios obtained from a chromosome present in two copies and a chromosome present in the Trisomy condition is detected.

In another embodiment, multiple loci of interest on multiple chromosomes can be examined. The ratios for the alleles at each heterozygous locus of interest on a chromosome can be summed and compared to the ratios for the alleles at each locus of interest on a different chromosome. The chromosomes that are compared can be of human origin, and include but are not limited to chromosomes 1, 2, 3, 4, 5, 6, 7, 8, 9, 10, 11, 12, 13, 14, 15, 16, 17, 18, 19, 20,21, 22,X, and Y. The ratio obtained from multiple chromosomes can be compared to the ratio obtained for a single chromosome or from multiple chromosomes.

In one embodiment, one of the chromosomes used in the comparison can be chromosome 13, 15, 16; 18, 21, 22, X or Y. In a preferred embodiment, the ratios on chromosomes 13, 18, and 21 are compared.

For example, assuming 40% fetal DNA in the sample from the pregnant female, the ratio of the alleles at a heterozygous locus of interest on chromosome 1 will be 0.25 (40 for fetal G allele/(2*60 for maternal A allele+40 for fetal A allele). Likewise, the ratio of alleles at a heterozygous locus of interest on chromosome 21 will be present in a ratio of 0.25. However, in a fetus with trisomy 21 where the additional chromosome is contributed by the mother, the nucleotides at a heterozygous locus of interest on chromosome 21 will be present in a ratio of 0.20 (40 for fetal G allele/(60*2 for maternal A allele+40*2 for fetal A allele). By contrast, the ratio for chromosome 1 will remain at 0.25, and thus the 5% difference in ratios will signify an additional chromosome. One to tens to hundreds to thousands of loci of interest can be analyzed.

In another embodiment, the loci of interest on the template DNA from the sample from the pregnant female can be genotyped without prior identification of the homozygous maternal loci of interest. It is not necessary to genotype the maternal template DNA prior to analysis of the template DNA containing both maternal and fetal template DNA.

The ratio of the alleles at the loci of interest can be used to determine the presence or absence of a chromosomal abnormality. The template DNA from the sample from the pregnant female contains both maternal template DNA and fetal template DNA. There are 3 possibilities at each SNP for either the maternal template DNA or the fetal template DNA: heterozygous, homozygous for allele 1, or homozygous for allele 2. The possible nucleotide ratios for a SNP that is either an adenine or a guanine are shown in Table II. The ratios presented in Table II are calculated with the fetal DNA at 50% of the DNA in the sample from the pregnant female.

TABLE II

Ratios for nucleotides for a heterozygous SNP.

| | Fetal SNP | | |
|---|---|---|---|
| Maternal SNP | A/A | G/G | A/G |
| A/A | 100% A | N/A | 75% A, 25% G |
| G/G | N/A | 100% G | 25% A, 75% G |
| A/G | 75% A, 25% G | 25% A, 75% G | 50% A, 50% G |

There are three nucleotide ratios: 100% of a single nucleotide, 50:50, or 75:25. These ratios will vary depending on the amount of fetal DNA present in sample from the pregnant female. However, the percentage of fetal DNA should be constant regardless of the chromosome analyzed. Therefore, if chromosomes are present in two copies, the above calculated ratios will be seen.

On the other hand, these percentages will vary when an additional chromosome is present. For example, assume that SNP X can be adenine or guanine, and that the percentage of fetal DNA in the sample from the pregnant female is 50%. Analysis of the loci of interest on chromosome 1 will provide the ratios discussed above: 100:0, 50:50, and 75:25. The possible ratios for a SNP that is A/G with an additional chromosome are provided in Table III.

TABLE III

Nucleotides ratios at a SNP when an additional copy of a chromosome is present

| Maternal | Fetal SNP | | | |
|---|---|---|---|---|
| SNPX | A/A/A | G/G/G | A/G/G | A/A/G |
| A/A | 100% A | N/A | 60% A, 40% G | 80% A, 20% G |
| G/G | N/A | 100% G | 20% A, 80% G | 40% A, 60% G |
| A/G | 80% A, 20% G | 20% A, 80% G | 40% A, 60% G | 60% A, 40% G |

The possible ratios for the alleles at a heterozygous SNP with an additional copy of a chromosome are: 0: 100, 40:60, and 20:80. Two of these ratios, 40:60, and 20:80 differ from the ratios of alleles at heterozygous SNPs obtained with two copies of a chromosome. As discussed above, the ratios for the nucleotides at a heterozygous SNP depend on the amount of fetal DNA present in the sample. However, the ratios, whatever they are, will remain constant across chromosomes unless there is a chromosomal abnormality.

The ratio of alleles at heterozygous loci of interest on a chromosome can be compared to the ratio for alleles at heterozygous loci of interest on a different chromosome. For example, the ratio for multiple loci of interest on chromosome 1 (the ratio at SNP 1, SNP 2, SNP 3, SNP 4, etc.) can be compared to the ratio for multiple loci of interest on chromosome 21 (the ratio at SNP A, SNP B, SNP C, SNP D, etc.). Any chromosome can be compared to any other chromosome. There is no limit to the number of chromosomes that can be compared.

Referring back to the data in Tables II and III, the ratios for nucleotides at a heterozygous SNP on chromosome 1, which was present in two copies, were 25:75, and 50:50. On the other, the ratio for nucleotides at a heterozygous SNP on chromosome 21, which was present in three copies, were 40:60, and 20:80. The difference between these two ratios indicates a chromosomal abnormality. The ratios can be pre-calculated for the full range of varying degrees of fetal DNA present in the maternal serum. Tables II and III demonstrate that both maternal homozygous and heterozygous loci of interest can be used to detect the presence of a fetal chromosomal abnormality.

The above example illustrates how the ratios for nucleotides at heterozygous SNPs can be used to detect the presence of an additional chromosome. The same type of analysis can be used to detect chromosomal rearrangements, translocations, mini-chromosomes, duplications of regions of chromosomes, monosomies, deletions of regions of chromosomes, and fragments of chromosomes. The method does not require genotyping of the mother or the father, however, it may be done to reduce the number of SNPs that need to be analyzed with the plasma sample.

The present invention does not quantitate the amount of a fetal gene product, nor is the utility of the present invention limited to the analysis of genes found on the Y chromosome. The present invention does not merely rely on the detection of a paternally inherited nucleic acid, rather, the present invention provides a method that allows the ratio of maternal to fetal alleles at loci of interest, including SNPs, to be calculated.

In another embodiment, a single allele at a locus of interest can be used to determine the presence or absence of a chromosomal abnormality and detect a genetic disorder in the fetus. In a preferred embodiment, the maternal allele at a locus of interest is used to determine the presence or absence of a chromosomal abnormality in the fetus. The biological mother can be genotyped to identify a homozygous locus of interest. Likewise, the biological father can be genotyped to identify a homozygous locus of interest. The locus of interest wherein the maternal template DNA is homozygous for one allele and the paternal template DNA is homozygous for the other allele is analyzed using the template DNA obtained from the plasma of the mother, which contains both maternal and fetal template DNA. Any number of loci of interest can be analyzed including but not limited to 1, 1-5, 5-10, 10-20, 20-30, 30-40, 40-50, 50-60, 60-70, 70-80, 80-90, 90-100, 100-150, 150-200, 200-250, 250-300, 300-500, 500-1000, 1000-2000, 2000-3000, 3000-4000, 4000-8000, 8000-16000, 16000-32000 or greater than 32000 loci of interest.

In a preferred embodiment, the signal from the maternal genome and the fetal allele, which was inherited from the mother, at the locus of interest is quantitated. For example, if the 5' overhang, which is generated after digestion with the type IIS enzyme, is filled in with a nucleotide that is fluorescently labeled, the intensity of the incorporated dye can be quantitated Maternal Template DNA - - Homozygous for Adenine

| | | | | | |
|---|---|---|---|---|---|
| Allele 1 | 5' CCG | **A*** | | | |
| | 3' GGC | T | G | T | G |
| Overhang position | | 1 | 2 | 3 | 4 |
| Allele 2 | 5' CCG | **A*** | | | |
| | 3' GGC | T | G | T | G |
| Overhang position | | 1 | 2 | 3 | 4 |

-continued

Paternal Template DNA - - Homozygous for Cytosine

| | | | | | |
|---|---|---|---|---|---|
| Allele 1 | 5' CCG | **C*** | | | |
| | 3' GGC | G | G | T | G |
| Overhang position | | 1 | 2 | 3 | 4 |
| Allele 2 | 5' CCG | **C*** | | | |
| | 3' GGC | T | G | T | G |
| Overhang position | | 1 | 2 | 3 | 4 |

Template DNA in the plasma - - both maternal template DNA and fetal template DNA Maternal Template DNA - - Homozygous for Adenine

| | | | | | |
|---|---|---|---|---|---|
| Allele 1 | 5' CCG | **A*** | | | |
| | 3' GGC | T | G | T | G |
| Overhang position | | 1 | 2 | 3 | 4 |
| Allele 2 | 5' CCG | **A*** | | | |
| | 3' GGC | T | G | T | G |
| Overhang position | | 1 | 2 | 3 | 4 |

Fetal Template DNA - - Heterozygous

| | | | | | |
|---|---|---|---|---|---|
| Allele 1 | 5' CCG | **A*** | | | |
| | 3' GGC | T | G | T | G |
| Overhang position | | 1 | 2 | 3 | 4 |
| Allele 2 | 5' CCG | dd**C** | | | |
| | 3' GGC | T | G | T | G |
| Overhang position | | 1 | 2 | 3 | 4 |

The template DNA obtained from the plasma of the pregnant female is filled in with labeled ddATP, and unlabeled ddCTP (depicted as ddC above), ddGTP, and ddTTP. The plasma DNA contains two maternal adenine alleles, and one fetal adenine allele. By filling in with labeled ddATP and unlabeled ddCTP, only the maternal allele and the fetal allele inherited from the mother are detected. The paternal allele is not detected in this manner. The fill-in reactions can be performed as described in the Examples below.

A single locus of interest can be analyzed or multiple loci of interest. The intensity of the maternal allele at multiple loci of interest can be quantitated. An average can be calculated for a chromosome and compared to the average obtained for a different chromosome. For example, the average intensity of the maternal allele and the fetal allele inherited from the mother at chromosome 1 can be compared to the average intensity of the maternal allele and the fetal allele inherited from the mother at chromosomes 13, 18, or 21. In a preferred embodiment, chromosomes 13, 15, 18, 21, 22, X and Y, when applicable, are compared.

The signal from a locus of interest may be stronger than another locus of interest. However, there is no reason why the signal from the locus of interest on one chromosome would be stronger than the signal from the locus of interest on another chromosome. While the signal from various loci of interest may be variable, the variation should be seen across the genome. The average signal of the loci of interest should be the same when any chromosomes are compared.

The conditions of the PCR reaction can be optimized so that an equivalent amount of PCR product is produced. For example, the concentration of the primers, the concentration of nucleotides, and the number of cycles for each loci of interest can be optimized. In addition, the fill-in reactions can be done under conditions such that any increase in a specific allele can be detected. The fill-in reaction conditions can be optimized to detect any increase in the allele of interest including but not limited to the concentration of reagents, the time of the fill-in reaction, and the temperature of the reaction.

With a normal genetic karyotype, the signal at each locus of interest comprise signal from the maternal genome, and signal from the fetal allele, which was inherited from the mother. The percent of fetal DNA in the sample remains constant, regardless of the chromosome that is analyzed. For example, if at SNP X, the maternal genome is A/A, and the paternal genome is G/G, then the fetal genome will be A/G, and the fetal adenine allele will comprise a specified percentage of the signal from the adenine allele. If the percentage of fetal DNA is 20% in the maternal plasma, then the fetal adenine allele will contribute 20% of the signal for the adenine allele. The contribution of the fetal allele, which was inherited from the mother, will be constant for any locus of interest that is analyzed.

When there is a chromosomal abnormality, the signal from the maternal genome and the fetal allele, which was inherited from the mother, at the loci of interest will differ from the signal observed for other chromosomes. For example, with a Trisomy, the signal at the locus of interest will comprise the maternal genome and two fetal alleles, which were inherited from the mother. The signal from the loci of interest for the chromosome that is present in three copies will have the contribution of an additional fetal allele, which will alter the signal of the alleles at these loci of interest.

In another embodiment, a ratio can be calculated using a single allele and a standard DNA of known quantity. In a preferred embodiment, a ratio is calculated using the alleles of the maternal genome, and the fetal allele, which was inherited from the mother, and a standard DNA. The biological mother can be genotyped to identify a homozygous locus of interest. Likewise, the biological father can be genotyped to identify a homozygous locus of interest. The locus of interest wherein the maternal template DNA is homozygous for one allele and the paternal template DNA is homozygous for the other allele is analyzed using the template DNA obtained from the plasma of the mother, which contains both maternal and fetal template DNA.

In a preferred embodiment, the signal from the maternal genome and the fetal allele, which was inherited from the mother, at the locus of interest is quantitated. For example, if the 5' overhang, which is generated after digestion with the type IIS enzyme, is filled in with a nucleotide that is fluorescently labeled, the intensity of the incorporated dye can be quantitated.

```
Template DNA in the plasma - - both maternal
template DNA and fetal template DNA
Maternal Template DNA - - Homozygous for Adenine

Allele 1              5' CCG    A*
                      3' GGC    T     G     T     G
Overhang position               1     2     3     4

Allele 2              5' CCG    A*
                      3' GGC    T     G     T     G
Overhang position               1     2     3     4

Fetal Template DNA - - Heterozygous

Allele 1              5' CCG    A*
                      3' GGC    T     G     T     G
Overhang position               1     2     3     4

Allele 2              5' CCG    ddC
                      3' GGC    T     G     T     G
Overhang position               1     2     3     4
```

The template DNA obtained from the plasma of the pregnant female is filled in with labeled ddATP, and unlabeled ddCTP (depicted as ddC above), ddGTP, and ddTTP. The plasma DNA contains two maternal adenine alleles, and one fetal adenine allele. By filling in with labeled ddATP and unlabeled ddCTP, only the maternal allele and the fetal allele inherited from the mother are detected.

A single locus of interest or multiple loci of interest can be analyzed. For each locus of interest, a DNA molecule is designed to migrate at about the same position as the locus of interest. In a preferred embodiment, the DNA molecule is of known quantity. A ratio is calculated using the alleles of the maternal genome and the fetal allele, which was inherited from the mother, and the DNA molecule designed to migrate at about the same position as the locus of interest. For example, if the locus of interest is designed to migrate at 30 base pairs, the DNA molecule can be designed to migrate at about 30 base pairs including but not limited to 20-25, 25-30, 30-35, 35-45, and greater than 45. The alleles of the maternal genome and the fetal allele, which was inherited from the mother, and the standard DNA molecule can be analyzed in the same reaction or can be analyzed in a separate reaction. The alleles of the maternal genome and the fetal allele, which was inherited from the mother, and the standard DNA molecule can be analyzed in the same lane of a gel or can be analyzed in separate lanes of a gel. The use of standard DNA molecules of known quantity, which are designed to migrate at the same position as the loci of interest, will correct for various factors including but not limited to the intensity of the bands relative to the location on the gel.

The ratio of multiple loci of interest on a chromosome can be quantitated, and an average calculated. The average can be compared to the average obtained for another chromosome. The ratio is used to indicate the presence or. absence of a chromosomal abnormality. Analysis of the alleles of the maternal genome and the fetal allele also allows detection of single gene or multi-gene genetic disorders.

Any chromosome of any organism can be analyzed using the methods of the invention. For example, in humans, chromosome 1, 2, 3, 4, 5, 6, 7, 8, 9, 10, 11, 12, 13, 14, 15, 16, 17, 18, 19, 20, 21, 22, X or Y can be analyzed using the methods of the invention. The ratio for the alleles at a heterozygous locus of interest on any chromosome can be compared to the ratio for the alleles at a heterozygous locus of interest on any other chromosome.

Thus, the present invention provides a non-invasive technique, which is independent of fetal cell isolation, for rapid, accurate and definitive detection of chromosome abnormalities in a fetus. The present invention also provides a non-invasive method for determining the sequence of DNA from a fetus. The present invention can be used to detect any alternation in gene sequence as compared to the wild type sequence including but not limited to point mutation, reading frame shift, transition, transversion, addition, insertion, deletion, addition-deletion, frame-shift, missense, reverse mutation, and microsatellite alteration.

Detection of Fetal Chromosomal Abnormalities Using Short Tandem Repeats

Short tandem repeats (STRs) are short sequences of DNA, normally of 2-5 base pairs in length, which are repeated numerous times in a head-tail manner. Tandemly repeated DNA sequences are widespread throughout the human genome, and show sufficient variability among the individuals in a population. Minisatellites have core repeats with 9-80 base pairs.

In another embodiment, short tandem repeats can be used to detect fetal chromosomal abnormalities. Template DNA can be obtained from a nucleic acid containing sample including but not limited to cell, tissue, blood, serum, plasma, saliva, urine, tears, vaginal secretion, lymph fluid, cerebrospinal fluid, mucosa secretion, peritoneal fluid, ascitic fluid, fecal matter, or body exudates. In another embodiment, a cell lysis inhibitor is added to the nucleic acid containing sample. In a preferred embodiment, the template DNA is obtained from the blood of a pregnant female. In another embodiment, the template DNA is obtained from the plasma or serum from the blood of a pregnant female.

The template DNA obtained from the bibod of the pregnant female will contain both fetal DNA and maternal DNA. The fetal DNA comprises STRs from the mother and the father. The variation in the STRs between the mother and father can be used to detect chromosomal abnormalities.

Primers can be designed to amplify short tandem repeats. Any method of amplification can be used including but not limited to polymerase chain reaction, self-sustained sequence reaction, ligase chain reaction, rapid amplification of cDNA ends, polymerase chain reaction and ligase chain reaction, Q-beta phage amplification, strand displacement amplification, and splice overlap extension polymerase chain reaction. In a preferred embodiment, PCR is used.

Any number of short tandem repeats can be analyzed including but not limited to 1-5, 5-10, 10-50, 50-100, 100-200, 200-300, 300-400, 400-500, 500-1000, and greater than 1000. The short tandem repeats can be analyzed in a single PCR reaction or in multiple PCR reactions. In a preferred embodiment, STRs from multiple chromosomes are analyzed.

After amplification, the PCR products can be analyzed by any number of methods including but not restricted to gel electrophoresis, and mass spectrometry. The template DNA from the pregnant female comprises STRs of maternal and paternal origin. The STRs of paternal origin represent the fetal DNA. The paternal and maternal STRs may be identical in length or the maternal and the paternal STRs may differ.

Heterozygous STRs are those of which the maternal and paternal differ in length. The amount of each PCR product can be quantitated for each heterozygous STR. With a normal number of chromosomes, the amount of each PCR product should be approximately equal. However, with an extra chromosome, one of the STR PCR products will be present at a greater amount.

For example, multiple STRs on chromosome 1 can be analyzed on the template DNA obtained from the blood of the pregnant female. Each STR, whether of maternal or paternal origin, should be present at approximately the same amount. Likewise, with two chromosome 21s, each STR should be present at approximately the same amount. However, with a trisomy 21, one of the STR PCR products, when the maternal and paternal differ in length (a heterozygous STR) should be present at a higher amount. The ratio for each heterozygous STR on one chromosome can be compared to the ratio for each heterozygous STR on a different chromosome, wherein a difference indicates the presence or absence of a chromosomal abnormality.

Kits

The methods of the invention are most conveniently practiced by providing the reagents used in the methods in the form of kits. A kit preferably contains one or more of the following components: written instructions for the use of the kit, appropriate buffers, salts, DNA extraction detergents, primers, nucleotides, labeled nucleotides, 5' end modification materials, and if desired, water of the appropriate purity, confined in separate containers or packages, such components allowing the user of the kit to extract the appropriate nucleic acid sample, and analyze the same according to the methods of the invention. The primers that are provided with the kit will vary, depending upon the purpose of the kit and the DNA that is desired to be tested using the kit.

A kit can also be designed to detect a desired or variety of single nucleotide polymorphisms, especially those associated with an undesired condition or disease. For example, one kit can comprise, among other components, a set or sets of primers to amplify one or more loci of interest associated with Huntington's disease. Another kit can comprise, among other components, a set or sets of primers for genes associated with a predisposition to develop type I or type II diabetes. Still, another kit can comprise, among other components, a set or sets of primers for genes associated with a predisposition to develop heart disease. Details of utilities for such kits are provided in the "Utilities" section below.

Utilities

The methods of the invention can be used whenever it is desired to know the genotype of an individual. The method of the invention is especially useful for the detection of genetic disorders. The method of the invention is especially useful as a non-invasive technique for the detection of genetic disorders in a fetus. In a preferred embodiment, the method of the invention provides a method for identification of single nucleotide polymorphisms.

In a preferred embodiment, the method is useful for detecting chromosomal abnormalities including but not limited to trisomies, monosomies, duplications, deletions, additions, chromosomal rearrangements, translocations, and other aneuploidies. The method is especially useful for the detection of chromosomal abnormalities in a fetus.

In a preferred embodiment, the method of the invention provides a method for identification of the presence of a disease in a fetus, especially a genetic disease that arises as a result of the presence of a genomic sequence, or other biological condition that it is desired to identify in an individual for which it is desired to know the same. The identification of such sequence in the fetus based on the presence of such genomic sequence can be used, for example, to determine if the fetus is a carrier or to assess if the fetus is predisposed to developing a certain genetic trait, condition or disease. The method of the invention is especially useful in prenatal genetic testing of parents and child.

Examples of diseases that can be diagnosed by this invention are listed in Table IV.

TABLE IV

| |
|---|
| Achondroplasia |
| Adrenoleukodystrophy, X-Linked |
| Agammaglobulinemia, X-Linked |
| Alagille Syndrome |
| Alpha-Thalassemia X-Linked Mental Retardation Syndrome |
| Alzheimer Disease |
| Alzheimer Disease, Early-Onset Familial |
| Amyotrophic Lateral Sclerosis Overview |
| Androgen Insensitivity Syndrome |
| Angelman Syndrome |
| Ataxia Overview, Hereditary |
| Ataxia-Telangiectasia |
| Becker Muscular Dystrophy also The Dystrophinopathies) |
| Beckwith-Wiedemann Syndrome |
| Beta-Thalassemia |
| Biotinidase Deficiency |
| Branchiootorenal Syndrome |
| BRCA1 and BRCA2 Hereditary Breast/Ovarian Cancer |
| Breast Cancer |
| CADASIL |
| Canavan Disease |
| Cancer |
| Charcot-Marie-Tooth Hereditary Neuropathy |

TABLE IV-continued

| |
|---|
| Charcot-Marie-Tooth Neuropathy Type 1 |
| Charcot-Marie-Tooth Neuropathy Type 2 |
| Charcot-Marie-Tooth Neuropathy Type 4 |
| Charcot-Marie-Tooth Neuropathy Type X |
| Cockayne Syndrome |
| Colon Cancer |
| Contractural Arachnodactyly, Congenital |
| Craniosynostosis Syndromes (FGFR-Related) |
| Cystic Fibrosis |
| Cystinosis |
| Deafness and Hereditary Hearing Loss |
| DRPLA (Dentatorubral-Pallidoluysian Atrophy) |
| DiGeorge Syndrome (also 22q11 Deletion Syndrome) |
| Dilated Cardiomyopathy, X-Linked |
| Down Syndrome (Trisomy 21) |
| Duchenne Muscular Dystrophy (also The Dystrophinopathies) |
| Dystonia, Early-Onset Primary (DYT1) |
| Dystrophinopathies, The |
| Ehlers-Danlos Syndrome, Kyphoscoliotic Form |
| Ehlers-Danlos Syndrome, Vascular Type |
| Epidermolysis Bullosa Simplex |
| Exostoses, Hereditary Multiple |
| Facioscapulohumeral Muscular Dystrophy |
| Factor V Leiden Thrombophilia |
| Familial Adenomatous Polyposis (FAP) |
| Familial Mediterranean Fever |
| Fragile X Syndrome |
| Friedreich Ataxia |
| Frontotemporal Dementia with Parkinsonism-17 |
| Galactosemia |
| Gaucher Disease |
| Hemochromatosis, Hereditary |
| Hemophilia A |
| Hemophilia B |
| Hemorrhagic Telangiectasia, Hereditary |
| Hearing Loss and Deafness, Nonsyndromic, DFNA (Connexin 26) |
| Hearing Loss and Deafness, Nonsyndromic, DFNB 1 (Connexin 26) |
| Hereditary Spastic Paraplegia |
| Hermansky-Pudlak Syndrome |
| Hexosaminidase A Deficiency (also Tay-Sachs) |
| Huntington Disease |
| Hypochondroplasia |
| Ichthyosis, Congenital, Autosomal Recessive |
| Incontinentia Pigmenti |
| Kennedy Disease (also Spinal and Bulbar Muscular Atrophy) |
| Krabbe Disease |
| Leber Hereditary Optic Neuropathy |
| Lesch-Nyhan Syndrome Leukemias |
| Li-Fraumeni Syndrome |
| Limb-Girdle Muscular Dystrophy |
| Lipoprotein Lipase Deficiency, Familial |
| Lissencephaly |
| Marfan Syndrome |
| MELAS (Mitochondrial Encephalomyopathy, Lactic Acidosis, and Stroke-Like Episodes) |
| Monosomies |
| Multiple Endocrine Neoplasia Type 2 |
| Multiple Exostoses, Hereditary Muscular Dystrophy, Congenital |
| Myotonic Dystrophy |
| Nephrogenic Diabetes Insipidus |
| Neurofibromatosis 1 |
| Neurofibromatosis 2 |
| Neuropathy with Liability to Pressure Palsies, Hereditary |
| Niemann-Pick Disease Type C |
| Nijmegen Breakage Syndrome Norrie Disease |
| Oculocutaneous Albinism Type 1 |
| Oculopharyngeal Muscular Dystrophy |
| Ovarian Cancer |
| Pallister-Hall Syndrome |
| Parkin Type of Juvenile Parkinson Disease |
| Pelizaeus-Merzbacher Disease |
| Pendred Syndrome |
| Peutz-Jeghers Syndrome Phenylalanine Hydroxylase Deficiency |
| Prader-Willi Syndrome |
| PROP 1-Related Combined Pituitary Hormone Deficiency (CPHD) |
| Prostate Cancer |
| Retinitis Pigmentosa |
| Retinoblastoma |
| Rothmund-Thomson Syndrome |

TABLE IV-continued

| |
|---|
| Smith-Lemli-Opitz Syndrome |
| Spastic Paraplegia, Hereditary |
| Spinal and Bulbar Muscular Atrophy (also Kennedy Disease) |
| Spinal Muscular Atrophy |
| Spinocerebellar Ataxia Type 1 |
| Spinocerebellar Ataxia Type 2 |
| Spinocerebellar Ataxia Type 3 |
| Spinocerebellar Ataxia Type 6 |
| Spinocerebellar Ataxia Type 7 |
| Stickler Syndrome (Hereditary Arthroophthalmopathy) |
| Tay-Sachs (also GM2 Gangliosidoses) |
| Trisomies |
| Tuberous Sclerosis Complex |
| Usher Syndrome Type I |
| Usher Syndrome Type II |
| Velocardiofacial Syndrome (also 22q11 Deletion Syndrome) |
| Von Hippel-Lindau Syndrome |
| Williams Syndrome |
| Wilson Disease |
| X-Linked Adrenoleukodystrophy |
| X-Linked Agammaglobulinemia |
| X-Linked Dilated Cardiomyopathy (also The Dystrophinopathies) |
| X-Linked Hypotonic Facies Mental Retardation Syndrome |

The method of the invention is useful for screening an individual at multiple loci of interest, such as tens, hundreds, or even thousands of loci of interest associated with a genetic trait or genetic disease by sequencing the loci of interest that are associated with the trait or disease state, especially those most frequently associated with such trait or condition. The invention is useful for analyzing a particular set of diseases including but not limited to heart disease, cancer, endocrine disorders, immune disorders, neurological disorders, musculoskeletal disorders, ophthalmologic disorders, genetic abnormalities, trisomies, monosomies, transversions, translocations, skin disorders, and familial diseases.

The method of the invention can also be used to confirm or identify the relationship of a DNA of unknown sequence to a DNA of known origin or sequence, for example, for use in, maternity or paternity testing, and the like.

Having now generally described the invention, the same will become better understood by reference to certain specific examples which are included herein for purposes of illustration only and are not intended to be limiting unless other wise specified.

EXAMPLES

The following examples are illustrative only and are not intended to limit the scope of the invention as defined by the claims.

Example 1

DNA sequences were amplified by PCR, wherein the annealing step in cycle 1 was performed at a specified temperature, and then increased in cycle 2, and further increased in cycle 3 for the purpose of reducing non-specific amplification. The TM1 of cycle 1 of PCR was determined by calculating the melting temperature of the 3' region, which anneals to the template DNA, of the second primer. For example, in FIG. 1B, the TM1 can be about the melting temperature of region "c." The annealing temperature was raised in cycle 2, to TM2, which was about the melting temperature of the 3' region, which anneals to the template DNA, of the first primer. For example, in FIG. 1C, the annealing temperature (TM2) corresponds to the melting temperature of region "b." In cycle 3, the annealing temperature was raised to TM3, which was about the melting temperature of the entire sequence of the second primer. For example, in FIG. 1D, the annealing temperature (TM3) corresponds to the melting temperature of region "c" +region "d". The remaining cycles of amplification were performed at TM3.

Preparation of Template DNA

The template DNA was prepared from a 5 ml sample of blood obtained by venipuncture from a human volunteer with informed consent. Blood was collected from 36 volunteers. Template DNA was isolated from each blood sample using QIAamp DNA Blood Midi Kit supplied by QIAGEN (Catalog number 51183). Following isolation, the template DNA from each of the 36 volunteers was pooled for further analysis.

Primer Design

The following four single nucleotide polymorphisms were analyzed: SNP HC21S00340, identification number as assigned by Human Chromosome 21 cSNP Database, (FIG. 3, lane 1) located on chromosome 21; SNP TSC 0095512 (FIG. 3, lane 2) located on chromosome 1, SNP TSC 0214366 (FIG. 3, lane 3) located on chromosome 1; and SNP TSC 0087315 (FIG. 3, lane 4) located on chromosome 1. The SNP Consortium Ltd database can be accessed at http://snp.cshl.org/, website address effective as of Feb. 14, 2002.

SNP HC21S00340 was amplified using the following primers:

```
First primer:
                                    (SEQ ID NO: 9)
5'TAGAATAGCACTGAATTCAGGAATACAATCATTGTCAC 3'

Second primer:
                                   (SEQ ID NO: 10)
5'ATCACGATAAACGGCCAAACTCAGGTTA3'
```

SNP TSC0095512 was amplified using the following primers:

```
First primer:
                                   (SEQ ID NO: 11)
5'AAGTTTAGATCAGAATTCGTGAAAGCAGAAGTTGTCTG 3'

Second primer:
                                   (SEQ ID NO: 12)
5'TCTCCAACTAACGGCTCATCGAGTAAAG 3'
```

SNP TSC0214366 was amplified using the following primers:

```
First primer:
                                   (SEQ ID NO: 13)
5'ATGACTAGCTATGAATTCGTTCAAGGTAGAAAATGGAA 3'

Second primer:
                                   (SEQ ID NO: 14)
5'GAGAATTAGAACGGCCCAAATCCCACTC3'
```

SNP TSC 0087315 was amplified using the following primers:

```
First primer:
                                   (SEQ ID NO: 15)
5'TTACAATGCATGAATTCATCTTGGTCTCTCAAAGTGC 3'

Second primer:
                                   (SEQ ID NO: 16)
5'TGGACCATAAACGGCCAAAAACTGTAAG 3'.
```

All primers were designed such that the 3' region was complementary to either the upstream or downstream sequence flanking each locus of interest and the 5' region contained a restriction enzyme recognition site. The first primer contained a biotin tag at the 5' end and a recognition site for the restriction enzyme EcoRI. The second primer contained the recognition site for the restriction enzyme BceA I.

PCR Reaction

All four loci of interest were amplified from the template genomic DNA using PCR (U.S. Pat. Nos. 4,683,195 and 4,683,202). The components of the PCR reaction were as follows: 40 ng of template DNA, 5 μM first primer, 5 μM second primer, 1 × HotStarTaq Master Mix as obtained from Qiagen (Catalog No. 203443). The HotStarTaq Master Mix contained DNA polymerase, PCR buffer, 200 μM of each dNTP, and 1.5 mM $MgCl_2$.

Amplification of each template DNA that contained the SNP of interest was performed using three different series of annealing temperatures, herein referred to as low stringency annealing temperature, medium stringency annealing temperature, and high stringency annealing temperature. Regardless of the annealing temperature protocol, each PCR reaction consisted of 40 cycles of amplification. PCR reactions were performed using the HotStarTaq Master Mix Kit supplied by QIAGEN. As instructed by the manufacturer, the reactions were incubated at 95° C. for 15 min. prior to the first cycle of PCR. The denaturation step after each extension step was performed at 95° C. for 30 sec. The annealing reaction was performed at a temperature that permitted efficient extension without any increase in temperature.

The low stringency annealing reaction comprised three different annealing temperatures in each of the first three cycles. The annealing temperature for the first cycle was 37° C. for 30 sec.; the annealing temperature for the second cycle was 57° C. for 30 sec.; the annealing temperature for the third cycle was 64° C. for 30 sec. Annealing was performed at 64° C. for subsequent cycles until completion.

As shown in the photograph of the gel (FIG. 3A), multiple bands were observed after amplification of SNP TSC 0087315 (lane 4). Amplification of SNP HC21S00340 (lane 1), SNP TSC0095512 (lane 2), and SNP TSC0214366 (lane 3) generated a single band of high intensity and one band of faint intensity, which was of higher molecular weight. When the low annealing temperature conditions were used, the correct size product was generated and this was the predominant product in each reaction.

The medium stringency annealing reaction comprised three different annealing temperatures in each of the first three cycles. The annealing temperature for the first cycle was 40° C. for 30 seconds; the annealing temperature for the second cycle was 60° C. for 30 seconds; and the annealing temperature for the third cycle was 67° C. for 30 seconds. Annealing was performed at 67° C. for subsequent cycles until completion. Similar to what was observed under low stringency annealing conditions, amplification of SNP TSC0087315 (FIG. 3B, lane 4) generated multiple bands under conditions of medium stringency. Amplification of the other three SNPs (lanes 1-3) produced a single band. These results demonstrate that variable annealing temperatures can be used to cleanly amplify loci of interest from genomic DNA with a primer that has an annealing length of 13 bases.

The high stringency annealing reaction was comprised of three different annealing temperatures in each of the first three cycles. The annealing temperature of the first cycle was 46° C. for 30 seconds; the annealing temperature of the second cycle was 65° C. for 30 seconds; and the annealing temperature for the third cycle was 72° C. for 30 seconds. Annealing was performed at 72° C. for subsequent cycles until completion. As shown in the photograph of the gel (FIG. 3C), amplification of SNP TSC0087315 (lane 4) using the high stringency annealing temperatures generated a single band of the correct molecular weight. By raising the annealing temperatures for each of the first three cycles, non-specific amplification was eliminated. Amplification of SNP TSC0095512 (lane 2) generated a single band. SNPs HC21S00340 (lane 1), and TSC0214366 (lane 3) failed to amplify at the high stringency annealing temperatures, however, at the medium stringency annealing temperatures, these SNPs amplified as a single band. These results demonstrate that variable annealing temperatures can be used to reduce non-specific PCR products, as demonstrated for SNP TSC0087315 (FIG. 3, lane 4).

Example 2

SNPs on chromosomes 1 (TSC0095512), 13 (TSC0264580), and 21 (HC21S00027) were analyzed. SNP TSC0095512 was analyzed using two different sets of primers, and SNP HC21S00027 was analyzed using two types of reactions for the incorporation of nucleotides.

Preparation of Template DNA

The template DNA was prepared from a 5 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit. Following isolation, template DNA from thirty-six human volunteers were pooled together and cut with the restriction enzyme EcoRI. The restriction enzyme digestion was performed as per manufacturer's instructions.

Primer Design

SNP HC21S00027 was amplified by PCR using the following primer set:

```
First primer:
                                    (SEQ ID NO: 17)
5' ATAACCGTATGCGAATTCTATAATTTTCCTGATAAAGG 3'

Second primer:
                                    (SEQ ID NO: 18)
5' CTTAAATCAGGGGACTAGGTAAACTTCA 3'.
```

The first primer contained a biotin tag at the extreme 5' end, and the nucleotide sequence for the restriction enzyme EcoRI. The second primer contained the nucleotide sequence for the restriction enzyme BsmF I (FIG. 4A).

Also, SNP HC21S00027 was amplified by PCR using the same first primer but a different second primer with the following sequence:

```
Second primer:
5' CTTAAATCAGACGGCTAGGTAAACTTCA 3' (SEQ ID NO: 19)
```

This second primer contained the recognition site for the restriction enzyme BceA I (FIG. 4B).

SNP TSC0095512 was amplified by PCR using the following primers:

```
First primer:
                                    (SEQ ID NO: 11)
5' AAGTTTAGATCAGAATTCGTGAAAGCAGAAGTTGTCTG 3'

Second primer:
                                    (SEQ ID NO: 20)
5' TCTCCAACTAGGGACTCATCGAGTAAAG 3'.
```

The first primer had a biotin tag at the 5' end and contained a restriction enzyme recognition site for EcoRI. The second primer contained a restriction enzyme recognition site for BsmF I (FIG. 4C).

Also, SNP TSC0095512 was amplified using the same first primer and a different second primer with the following sequence:

```
Second primer:
5'TCTCCAACTAACGGCTCATCGAGTAAAG3' (SEQ ID NO: 12)
```

This second primer contained the recognition site for the restriction enzyme BceA I (FIG. 4D).

SNP TSC0264580, which is located on chromosome 13, was amplified with the following primers:

```
First primer:
                                    (SEQ ID NO: 21)
5' AACGCCGGGCGAGAATTCAGTTTTTCAACTTGCAAGG 3'

Second primer:
                                    (SEQ ID NO: 22)
5' CTACACATATCTGGGACGTTGGCCATCC 3'.
```

The first primer contained a biotin tag at the extreme 5' end and had a restriction enzyme recognition site for EcoRI. The second primer contained a restriction enzyme recognition site for BsmF I.

PCR Reaction

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they could also be amplified together in a single PCR reaction. For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest but in this example, 40 ng of template human genomic DNA and 5 μM of each primer were used. Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results. The PCR products for SNP HC21S00027 and SNP TSC095512 are shown in FIGS. 5A-5D.

Purification of Fragment of Interest

The PCR products were separated from the genomic template DNA. Each PCR product was divided into four separate reaction wells of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1× PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme that bound the recognition site incorporated into the PCR products from the second primer. SNP HC21S00027 (FIGS. 6A and 6B) and SNP TSC0095512 (FIGS. 6C and 6D) were amplified in separate reactions using two different second primers. FIG. 6A (SNP HC21S00027) and FIG. 6C (SNP TSC0095512) depict the PCR products after digestion with the restriction enzyme BsmF I (New England Biolabs catalog number R0572S). FIG. 6B (SNP HC21S00027) and FIG. 6D (SNP TSC0095512) depict the PCR products after digestion with the restriction enzyme BceA I (New England Biolabs, catalog number R0623 S). The digests were performed in the Streptawells following the instructions supplied with the restriction enzyme. SNP TSC0264580 was digested with BsmF I. After digestion with the appropriate restriction enzyme, the wells were washed three times with PBS to remove the cleaved fragments.

Incorporation of Labeled Nucleotide

The restriction enzyme digest described above yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

For each SNP, four separate fill in reactions were performed; each of the four reactions contained a different fluorescently labeled dideoxynucleotide (ddATP, ddCTP, ddGTP, or ddTTP). The following components were added to each fill in reaction: 1 μl of a fluorescently labeled dideoxynucleotide, 0.5 μl of unlabeled ddNTPs ( 40 μM), which contained all nucleotides except the nucleotide that was fluorescently labeled, 2 μl of 10× sequenase buffer, 0.25 μl of Sequenase, and water as needed for a 20 μl reaction. All of the fill in reactions were performed at 40° C. for 10 min. Non-fluorescently labeled nucleotides was purchased from Fermentas Inc. (Hanover, Md.). All other labeling reagents were obtained from Amersham (Thermo Sequenase Dye Terminator Cycle Sequencing Core Kit, US 79565). In the presence of fluorescently labeled ddNTPs, the 3' recessed end was extended by one base, which corresponds to the SNP or locus of interest (FIG. 7A-7D).

A mixture of labeled ddNTPs and unlabeled dNTPs also was used for the “fill in” reaction for SNP HC21S00027. The “fill in” conditions were as described above except that a mixture containing 40 μM unlabeled dNTPs, 1 μl fluorescently labeled ddATP, 1 μl fluorescently labeled ddCTP, 1 μl fluorescently labeled ddGTP, and 1 μl ddTTP was used. The fluorescent ddNTPs were obtained from Amersham (Thermo Sequenase Dye Terminator Cycle Sequencing Core Kit, US 79565; Amersham did not publish the concentrations of the fluorescent nucleotides). SNP HC21S00027 was digested with the restriction enzyme BsmF I, which generated a 5' overhang of four bases. As shown in FIG. 7E, if the first nucleotide incorporated is a labeled dideoxynucleotide, the 3' recessed end is filled in by one base, allowing detection of the SNP or locus of interest. However, if the first nucleotide incorporated is a dNTP, the polymerase continues to incorporate nucleotides until a ddNTP is filled in. For example, the first two nucleotides can be filled in with dNTPs, and the third nucleotide with a ddNTP, allowing detection of the third nucleotide in the overhang. Thus, the sequence of the entire 5' overhang can be determined, which increases the information obtained from each SNP or locus of interest.

After labeling, each Streptawell was rinsed with 1× PBS (100 μl) three times. The “filled in” DNA fragments were then released from the Streptawells by digestion with the restriction enzyme EcoRI, according to the manufacturer’s instructions that were supplied with the enzyme (FIGS. 8A-8D). Digestion was performed for 1 hour at 37° C. with shaking at 120 rpm.

Detection of the Locus of Interest

After release from the streptavidin matrix, 2-3 μl of the 10 μl sample was loaded in a 48 well membrane tray (The Gel Company, catalog number TAM48-01). The sample in the tray was absorbed with a 48 Flow Membrane Comb (The Gel Company, catalog number AM48), and inserted into a 36 cm 5% acrylamide (urea) gel (BioWhittaker Molecular Applications, Long Ranger Run Gel Packs, catalog number 50691).

The sample was electrophoresed into the gel at 3000 volts for 3 min. The membrane comb was removed, and the gel was run for 3 hours on an ABI 377 Automated Sequencing Machine. The incorporated labeled nucleotide was detected by fluorescence.

As shown in FIG. 9A, from a sample of thirty six (36) individuals, one of two nucleotides, either adenosine or guanine, was detected at SNP HC21S00027. These are the two nucleotides reported to exist at SNP HC21S00027 (http://snp.cshl.org/snpsearch.shtml).

One of two nucleotides, either guanine or cytosine, was detected at SNP TS00095512 (FIG. 9B). The same results were obtained whether the locus of interest was amplified with a second primer that contained a recognition site for BceA I or the second primer contained a recognition site for BsmF I.

As shown in FIG. 9C, one of two nucleotides was detected at SNP TSC0264580, which was either adenosine or cytosine. These are the two nucleotides reported for this SNP site (http://snp.cshl.org/snpsearch.shtml). In addition, a thymidine was detected one base from the locus of interest. In a sequence dependent manner, BsmF I cuts some DNA molecules at the 10/14 position and other DNA molecules, which have the same sequence, at the 11/15 position. When the restriction enzyme BsmF I cuts 11 nucleotides away on the sense strand and 15 nucleotides away on the antisense strand, the 3' recessed end is one base from the SNP site. The sequence of SNP TSC0264580 indicated that the base immediately preceding the SNP site was a thymidine. The incorporation of a labeled ddNTP into this position generated a fragment one base smaller than the fragment that was cut at the 10/14 position. Thus, the DNA molecules cut at the 11/15 position provided sequence information about the base immediately preceding the SNP site, and the DNA molecules cut at the 10/14 position provided sequence information about the SNP site.

SNP HC21S00027 was amplified using a second primer that contained the recognition site for BsmF I. A mixture of labeled ddNTPs and unlabeled dNTPs was used to fill in the 5' overhang generated by digestion with BsmF I. If a dNTP was incorporated, the polymerase continued to incorporate nucleotides until a ddNTP was incorporated. A population of DNA fragments, each differing by one base, was generated, which allowed the full sequence of the overhang to be determined.

As seen in FIG. 9D, an adenosine was detected, which was complementary to the nucleotide (a thymidine) immediately preceding the SNP or locus of interest. This nucleotide was detected because of the 11/15 cutting property of BsmF I, which is described in detail above. A guanine and an adenosine were detected at the SNP site, which are the two nucleotides reported for this SNP site (FIG. 9A). The two nucleotides were detected at the SNP site because the molecular weights of the dyes differ, which allowed separation of the two nucleotides. The next nucleotide detected was a thymidine, which is complementary to the nucleotide immediately downstream of the SNP site. The next nucleotide detected was a guanine, which was complementary to the nucleotide two bases downstream of the SNP site. Finally, an adenosine was detected, which was complementary to the third nucleotide downstream of the SNP site. Sequence information was obtained not only for the SNP site but for the nucleotide immediately preceding the SNP site and the next three nucleotides.

None of the loci of interest contained a mutation. However, if one of the loci of interest harbored a mutation including but not limited to a point mutation, insertion, deletion, translocation or any combination of said mutations, it could be identified by comparison to the consensus or published sequence. Comparison of the sequences attributed to each of the loci of interest to the native, non-disease related sequence of the gene at each locus of interest determines the presence or absence of a mutation in that sequence. The finding of a mutation in the sequence is then interpreted as the presence of the indicated disease, or a predisposition to develop the same, as appropriate, in that individual. The relative amounts of the mutated vs. normal or non-mutated sequence can be assessed to determine if the subject has one or two alleles of the mutated sequence, and thus whether the subject is a carrier, or whether the indicated mutation results in a dominant or recessive condition.

Example 3

Four loci of interest from chromosome 1 and two loci of interest from chromosome 21 were amplified in separate PCR reactions, pooled together, and analyzed. The primers were designed so that each amplified locus of interest was a different size, which allowed detection of the loci of interest.

Preparation of Template DNA

The template DNA was prepared from a 5 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit. Template DNA was isolated from thirty-six human volunteers, and then pooled into a single sample for further analysis.

Primer Design

SNP TSC 0087315 was amplified using the following primers:

```
First primer:
                                         (SEQ ID NO: 15)
5'TTACAATGCATGAATTCATCTTGGTCTCTCAAAGTGC 3'

Second primer:
                                         (SEQ ID NO: 16)
5'TGGACCATAAACGGCCAAAAACTGTAAG3'.
```

SNP TSC0214366 was amplified using the following primers:

```
First primer:
                                         (SEQ ID NO: 13)
5'ATGACTAGCTATGAATTCGTTCAAGGTAGAAAATGGAA 3'

Second primer:
                                         (SEQ ID NO: 14)
5'GAGAATTAGAACGGCCCAAATCCCACTC 3'
```

SNP TSC 0413944 was amplified with the following primers:

```
First primer:
                                         (SEQ ID NO: 23)
5' TACCTTTTGATCGAATTCAAGGCCAAAAATATTAAGTT 3'

Second primer:
                                         (SEQ ID NO: 24)
5' TCGAACTTTAACGGCCTTAGAGTAGAGA 3'
```

SNP TSC0095512 was amplified using the following primers:

```
First primer:
                                         (SEQ ID NO: 11)
5' AAGTTTAGATCAGAATTCGTGAAAGCAGAAGTTGTCTG 3'

Second primer:
                                         (SEQ ID NO: 12)
5' TCTCCAACTAACGGCTCATCGAGTAAAG 3'
```

SNP HC21S00131 was amplified with the following primers:

```
First primer:
                                         (SEQ ID NO: 25)
5' CGATTTCGATAAGAATTCAAAAGCAGTTCTTAGTTCAG 3'

Second primer:
                                         (SEQ ID NO: 26)
5' TGCGAATCTTACGGCTGCATCACATTCA 3'
```

SNP HC21S00027 was amplified with the following primers:

```
First primer:
                                        (SEQ ID NO: 17)
5' ATAACCGTATGCGAATTCTATAATTTTCCTGATAAAGG 3'

Second primer:
                                        (SEQ ID NO: 19)
5' CTTAAATCAGACGGCTAGGTAAACTTCA 3'
```

For each SNP, the first primer contained a recognition site for the restriction enzyme EcoRI and had a biotin tag at the extreme 5' end. The second primer used to amplify each SNP contained a recognition site for the restriction enzyme BceA I.

PCR Reaction

The PCR reactions were performed as described in Example 2 except that the following annealing temperatures were used: the annealing temperature for the first cycle of PCR was 37° C. for 30 seconds, the annealing temperature for the second cycle of PCR was 57° C. for 30 seconds, and the annealing temperature for the third cycle of PCR was 64° C. for 30 seconds. All subsequent cycles had an annealing temperature of 64° C. for 30 seconds. Thirty seven (37) cycles of PCR were performed. After PCR, ¼ of the volume was removed from each reaction, and combined into a single tube.

Purification of Fragment of Interest

The PCR products (now combined into one sample, and referred to as "the sample") were separated from the genomic template DNA as described in Example 2 except that the sample was bound to a single well of a Streptawell microtiter plate.

Restriction Enzyme Digestion of Isolated Fragments

The sample was digested with the restriction enzyme BceA I, which bound the recognition site in the second primer. The restriction enzyme digestions were performed following the instructions supplied with the enzyme. After the restriction enzyme digest, the wells were washed three times with 1× PBS.

Incorporation of Nucleotides

The restriction enzyme digest described above yielded DNA molecules with a 5' overhang, which contained the SNP site or locus of interest and a 3' recessed end. The 5' overhang functioned as a template allowing incorporation of a nucleotide in the presence of a DNA polymerase.

The following components were used for the fill in reaction: 1 μl of fluorescently labeled ddATP; 1 μl of fluorescently labeled ddTTP; 1 μl of fluorescently labeled ddGTP; 1 μl of fluorescently labeled ddCTP; 2 μl of 10× sequenase buffer, 0.25 μl of Sequenase, and water as needed for a 20 μl reaction. The fill in reaction was performed at 40° C. for 10 min. All labeling reagents were obtained from Amersham (Thermo Sequenase Dye Terminator Cycle Sequencing Core Kit (US 79565); the concentration of the ddNTPS provided in the kit is proprietary and not published by Amersham). In the presence of fluorescently labeled ddNTPs, the 3' recessed end was filled in by one base, which corresponds to the SNP or locus of interest.

After the incorporation of nucleotide, the Streptawell was rinsed with 1× PBS (100 μl) three times. The "filled in" DNA fragments were then released from the Streptawell by digestion with the restriction enzyme EcoRI following the manufacturer's instructions. Digestion was performed for 1 hour at 37° C. with shaking at 120 rpm.

Detection of the Locus of Interest

After release from the streptavidin matrix, 2-3 μl of the 10 μl sample was loaded in a 48 well membrane tray (The Gel Company, catalog number TAM48-01). The sample in the tray was absorbed with a 48 Flow Membrane Comb (The Gel Company, catalog number AM48), and inserted into a 36 cm 5% acrylamide (urea) gel (BioWhittaker Molecular Applications, Long Ranger Run Gel Packs, catalog number 50691).

The sample was electrophoresed into the gel at 3000 volts for 3 min. The membrane comb was removed, and the gel was run for 3 hours on an ABI 377 Automated Sequencing Machine. The incorporated nucleotide was detected by fluorescence.

The primers were designed so that each amplified locus of interest differed in size. As shown in FIG. 10, each amplified loci of interest differed by about 5-10 nucleotides, which allowed the loci of interest to be separated from one another by gel electrophoresis. Two nucleotides were detected for SNP TSC0087315, which were guanine and cytosine. These are the two nucleotides reported to exist at SNP TSC0087315 (http://snp.cshl.org/snpsearch.shtml). The sample comprised template DNA from 36 individuals and because the DNA molecules that incorporated a guanine differed in molecular weight from those that incorporated a cytosine, distinct bands were seen for each nucleotide.

Two nucleotides were detected at SNP HC21S00027, which were guanine and adenosine (FIG. 10). The two nucleotides reported for this SNP site are guanine and adenosine (http://snp.cshl.org/snpsearch.shtml). As discussed above, the sample contained template DNA from thirty-six individuals, and one would expect both nucleotides to be represented in the sample. The molecular weight of the DNA fragments that incorporated a guanine was distinct from the DNA fragments that incorporated an adenosine, which allowed both nucleotides to be detected.

The nucleotide cytosine was detected at SNP TSC0214366 (FIG. 10). The two nucleotides reported to exist at this SNP position are thymidine and cytosine.

The nucleotide guanine was detected at SNP TSC0413944 (FIG. 10). The two nucleotides reported for this SNP are guanine and cytosine (http://spp.cshl.org/snpsearch.shtml).

The nucleotide cytosine was detected at SNP TS00095512 (FIG. 10). The two nucleotides reported for this SNP site are guanine and cytosine (http://snp.cshl.org/snpsearch.shtml).

The nucleotide detected at SNP HC21S 00131 was guanine. The two nucleotides reported for this SNP site are guanine and adenosine (http://snp.cshl.org/snpsearch.shtml).

As discussed above, the sample was comprised of DNA templates from thirty-six individuals and one would expect both nucleotides at the SNP sites to be represented. For SNP TSC0413944, TSC0095512, TSC0214366 and HC21S00131, one of the two nucleotides was detected. It is likely that both nucleotides reported for these SNP sites are present in the sample but that one fluorescent dye overwhelms the other. The molecular weight of the DNA molecules that incorporated one nucleotide did not allow efficient separation of the DNA molecules that incorporated the other nucleotide. However, the SNPs were readily separated from one another, and for each SNP, a proper nucleotide was incorporated. The sequences of multiple loci of interest from multiple chromosomes, which were treated as a single sample after PCR, were determined.

A single reaction containing fluorescently labeled ddNTPs was performed with the sample that contained multiple loci of interest. Alternatively, four separate fill in reactions can be performed where each reaction contains one fluorescently labeled nucleotide (ddATP, ddTTP, ddGTP, or ddCTP) and unlabeled ddNTPs (see Example 2, FIGS. 7A-7D and FIGS. 9A-C). Four separate "fill in" reactions will allow detection of any nucleotide that is present at the loci of interest. For example, if analyzing a sample that contains multiple loci of interest from a single individual, and said individual is heterozygous at one or more than one loci of interest, four separate "fill in" reactions can be used to determine the nucleotides at the heterozygous loci of interest.

Also, when analyzing a sample that contains templates from multiple individuals, four separate "fill in" reactions will allow detection of nucleotides present in the sample, independent of how frequent the nucleotide is found at the locus of interest. For example, if a sample contains DNA templates from 50 individuals, and 49 of the individuals have a thymidine at the locus of interest, and one individual has a guanine, the performance of four separate "fill in" reactions, wherein each "fill in" reaction is run in a separate lane of a gel, such as in FIGS. 9A-9C, will allow detection of the guanine. When analyzing a sample comprised of multiple DNA templates, multiple "fill in" reactions will alleviate the need to distinguish multiple nucleotides at a single site of interest by differences in mass.

In this example, multiple single nucleotide polymorphisms were analyzed. It is also possible to determine the presence or absence of mutations, including but not limited to point mutations, transitions, transversions, translocations, insertions, and deletions from multiple loci of interest. The multiple loci of interest can be from a single chromosome or from multiple chromosomes. The multiple loci of interest can be from a single gene or from multiple genes.

The sequence of multiple loci of interest that cause or predispose to a disease phenotype can be determined. For example, one could amplify one to tens to hundreds to thousands of genes implicated in cancer or any other disease. The primers can be designed so that each amplified loci of interest differs in size. After PCR, the amplified loci of interest can be combined and treated as a single sample. Alternatively, the multiple loci of interest can be amplified in one PCR reaction or the total number of loci of interest, for example 100, can be divided into samples, for example 10 loci of interest per PCR reaction, and then later pooled. As demonstrated herein, the sequence of multiple loci of interest can be determined. Thus, in one reaction, the sequence of one to ten to hundreds to thousands of genes that predispose or cause a disease phenotype can be determined.

Example 4

The ability to determine the sequence or detect chromosomal abnormalities of a fetus using free fetal DNA in a sample from a pregnant female has been hindered by the low percentage of free fetal DNA. Increasing the percentage of free fetal DNA would enhance the detection of mutation, insertion, deletion, translocation, transversion, monosomy, trisomy, trisomy 21, trisomy 18, trisomy 13, XXY, XXX, other aneuoplodies, deletion, addition, amplification, translocation and rearrangement. The percent of fetal DNA in plasma obtained from a pregnant female was determined both in the absence and presence of inhibitors of cell lysis. A genetic marker on the Y chromosome was used to calculate the percent of fetal DNA.

Preparation of Template DNA

The DNA template was prepared from a 5 ml sample of blood obtained by venipuncture from a human volunteer with informed consent. The blood was aliquoted into two tubes (Fischer Scientific, 9 ml EDTA Vacuette tubes, catalog number NC9897284). Formaldehyde (25 μl/ml of blood) was added to one of the tubes. The sample in the other tube remained untreated, except for the presence of the EDTA. The tubes were spun at 1000 rpm for ten minutes. Two milliliters of the supernatant (the plasma) of each sample was transferred to a new tube and spun at 3000 rpm for ten minutes. 800 μl of each sample was used for DNA purification. DNA was isolated using the Qiagen Midi Kit for purification of DNA from blood cells (QIAmp DNA Blood Midi Kit, Catalog number 51183). DNA was eluted in 100 μl of distilled water. Two DNA templates were obtained: one from the blood sample treated with EDTA, and one from the blood sample treated with EDTA and formaldehyde.

Primer Design

Two different sets of primers were used: one primer set was specific for the Y chromosome, and thus specific for fetal DNA, and the other primer set was designed to amplify the cystic fibrosis gene, which is present on both maternal template DNA and fetal template DNA.

In this example, the first and second primers were designed so that the entire 5' and 3' sequence of each primer annealed to the template DNA. In this example, the fetus had an XY genotype, and the Y chromosome was used as a marker for the presence of fetal DNA. The following primers were designed to amplify the SRY gene on the Y chromosome.

```
First primer:
5' TGGCGATTAAGTCAAATTCGC 3'      (SEQ ID NO: 263)

Second primer:
5 CCCCCTAGTACCCTGACAATGTATT 3'   (SEQ ID NO: 264)
```

Primers designed to amplify any gene, or region of a region, or any part of any chromosome could be used to detect maternal and fetal DNA. In this example, the following primers were designed to amplify the cystic fibrosis gene:

```
First primer:
5' CTGTTCTGTGATATTATGTGTGGT 3'   (SEQ ID NO: 268)

Second primer:
5' AATTGTTGGCATTCCAGCATTG 3'     (SEQ ID NO: 266)
```

PCR Reaction

The SRY gene and the cystic fibrosis gene were amplified from the template genomic DNA using PCR (U.S. Pat. Nos. 4,683,195 and 4,683,202). For increased specificity, a "hot-start" PCR was used. PCR reactions were performed using the HotStarTaq Master Mix Kit supplied by Qiagen (Catalog No. 203443). For amplification of the SRY gene, the DNA eluted from the Qiagen purification column was diluted serially 1:2. For amplification of the cystic fibrosis gene, the DNA from the Qiagen purification column was diluted 1:4, and then serially diluted 1:2. The following components were used for each PCR reaction: 8 μl of template DNA (diluted or undiluted), 1 μl of each primer (5 μM), 10 μl of HotStar Taq mix. The following PCR conditions were used:

(1) 950 C for 15'
(2) 94° C. for 1'
(3) 54° C. for 15"
(4) 72° C. for 30"
(5) Repeat steps 2-4 for 45 cycles.
(6) 10' at 72° C.

Quantification of Fetal DNA

The DNA templates that were eluted from the Qiagen columns were serially diluted to the following concentrations: 1:2, 1:4, 1:8, 1:16, 1:32, 1:64, 1:128, 1:256, 1:512, 1:1024, 1:2048, and 1:4096. Amplification of the SRY gene was performed using the templates that were undiluted, 1:2, 1:4, 1:8, 1:16, 1:32, 1:64, 1:128, 1:256, 1:512. Amplification of the cystic fibrosis gene was performed using the DNA templates that were diluted 1:4, 1:8, 1:16, 1:32, 1:64, 1:128, 1:256, 1:512, 1:1024, 1:2048, and 1:4096. The same dilution series was performed with the DNA templates that were purified from the plasma sample treated with EDTA alone and the plasma sample treated with EDTA and formaldehyde.

The results of the PCR reactions using the DNA template that was isolated from the plasma sample treated with EDTA are shown in FIG. 11A. The SRY gene was amplified from the undiluted DNA template, and also in the sample that was diluted 1:2 (FIG. 11A). The SRY gene was not amplified in the next seven serial dilutions. On the other hand, the cystic fibrosis gene was detected in the serial dilutions up to 1:256. A greater presence of the cystic fibrosis gene was expected because of the higher percentage of maternal DNA present in the plasma. The last dilution sample that provided for amplification of the gene product was assumed to have one copy of the cystic fibrosis gene or the SRY gene.

The results of the PCR reactions using the DNA template that was isolated from the plasma sample treated with formaldehyde and EDTA are shown in FIG. 11B. The SRY gene was amplified from the undiluted DNA template, and also in the sample that was diluted 1:2 (FIG. 11B). The SRY gene was not amplified in the next six dilutions. However, in the 1:256 dilution, the SRY gene was detected. It is unlikely that the amplification in the 1:256 sample represents a real signal because the prior six dilution series were all negative for amplification of SRY. Amplification of the SRY gene in this sample was likely an experimental artifact resulting from the high number of PCR cycles used. Thus, the 1:256 sample was not used in calculating the amount of fetal DNA present in the sample.

Amplification of the cystic fibrosis gene was detected in the sample that was diluted 1:16 (FIG. 11B). The presence of the formalin prevents maternal cell lysis, and thus, there is a lower percentage of maternal DNA in the sample. This is in strong contrast to the sample that was treated with only EDTA, which supported amplification up to a dilution of 1:256.

The percent of fetal DNA present in the maternal plasma was calculated using the following formula: % fetal DNA=(amount of SRY gene/amount of cystic fibrosis gene)*2*100.

The amount of SRY gene was represented by the highest dilution value in which the gene was amplified. Likewise, the amount of cystic fibrosis gene was represented by the highest dilution value in which it was amplified. The formula contains a multiplication factor of two (2), which is used to normalize for the fact that there is only one copy of the SRY gene (located on the Y chromosome), while there are two copies of the cystic fibrosis gene.

For the above example, the percentage of fetal DNA present in the sample that was treated with only EDTA was 1.56% (2/256*2*100). The reported percentage of fetal DNA present in the plasma is between 0.39-11.9% (Pertl and Bianchi, *Obstetrics and Gynecology, Vol.* 98, No. 3, 483-490 (2001). The percentage of fetal DNA present in the sample treated with formalin and EDTA was 25% (2/16*2*100). The experiment was repeated numerous times, and each time the presence of formalin increased the overall percentage of fetal DNA.

The percent fetal DNA from eighteen blood samples with and without formalin was calculated as described above with the exception that serial dilutions of 1:5 were performed. As 1:5 dilutions were performed, the last serial dilution that allowed detection of either the SRY gene or the cystic fibrosis gene may have had one copy of the gene or it may have had 4 copies of the gene. The results from the eighteen samples with and without formalin are summarized in Table V. The low range assumes that the last dilution sample had one copy of the genes and the high range assumes that the last dilution had four copies of the genes.

TABLE V

Mean Percentage Fetal DNA with and without formalin.

| Sample | Lower Range | Upper Range |
|---|---|---|
| Formalin | 19.47 | 43.69 |
| Without Formalin | 7.71 | 22.1 |

An overall increase in fetal DNA was achieved by reducing the maternal cell lysis, and thus, reducing the amount of maternal DNA present in the sample. In this example, formaldehyde was used to prevent lysis of the cells, however any agent that prevents the lysis of cells or increases the structural integrity of the cells can be used. Two or more than two cell lysis inhibitors can be used. The increase in fetal DNA in the maternal plasma allows the sequence of the fetal DNA to be determined, and provides for the rapid detection of abnormal DNA sequences or chromosomal abnormalities including but not limited to point mutation, reading frame shift, transition, transversion, addition, insertion, deletion, addition-deletion, frame-shift, missense, reverse mutation, and microsatellite alteration, trisomy, monosomy, other aneuploidies, amplification, rearrangement, translocation, transversion, deletion, addition, amplification, fragment, translocation, and rearrangement.

Example 5

A DNA template from an individual with a genotype of trisomy 21 was analyzed. Three loci of interest were analyzed on chromosome 13 and two loci of interest were analyzed on chromosome 21.

Preparation of Template DNA

The template DNA was prepared from a 5 ml sample of blood obtained by venipuncture from a human volunteer with informed consent. The human volunteer had previously been genotyped to have an additional chromosome 21 (trisomy 21). Template DNA was isolated using QIAamp DNA Blood Midi Kit supplied by QIAGEN (Catalog number 51183).

Primer Design

The following five single nucleotide polymorphisms were analyzed: SNP TSC 0115603 located on chromosome 21; SNP TSC 03209610 located on chromosome 21; SNP TSC 0198557 located on chromosome 13; and SNP TSC 0200347 located on chromosome 13. The DNA template from another individual was used as an internal control. The SNP TSC 0200347, which was previously identified as being homozygous for guanine, was used as the internal control. The SNP Consortium Ltd database can be accessed at http://snp.cshl.org/, website address effective as of Apr. 1, 2002.

SNP TSC 0115603 was amplified using the following primers:

```
First primer:
                                    (SEQ ID NO: 267)
5' GTGCACTTACGTGAATTCAGATGAACGTGATGTAGTAG 3'

Second Primer:
                                    (SEQ ID NO: 268)
5' TCCTCGTACTCAACGGCTTTCTCTGAAT 3'
```

The first primer was biotinylated at the 5' end, and contained the restriction enzyme recognition site for EcoR I. The second primer contained the restriction enzyme recognition site for the restriction enzyme BceA I.

SNP TSC 0309610 was amplified using the following primers:

```
First primer:
                                    (SEQ ID NO: 269)
5' TCCGGAACACTAGAATTCTTATTTACATACACACTTGT 3'

Second primer:
                                    (SEQ ID NO: 270)
5' CGAATAAGGTAGACGGCAACAATGAGAA 3'
```

The first primer contained a biotin group at the 5' end, and a restriction enzyme recognition site for the restriction enzyme EcoR I. The second primer contained the restriction enzyme recognition site for BceA I.

Submitted SNP (ss) 813773 (accession number assigned by the NCBI Submitted SNP (ss) Database) was amplified with the following primers:

```
First primer:
                                    (SEQ ID NO: 271)
5' CGGTAAATCGGAGAATTCAGAGGATTTAGAGGAGCTAA 3'

Second primer:
                                    (SEQ ID NO: 272)
5' CTCACGTTCGTTACGGCCATTGTGATAGC 3'
```

The first primer contains a biotin group at the 5' end, and a recognition site for the restriction enzyme EcoR I. The second primer contained the restriction enzyme recognition site for BceA I.

SNP TSC 0198557 was amplified with the following primers:

```
First primer:
                                    (SEQ ID NO: 273)
5' GGGGAAACAGTAGAATTCCATATGGACAGAGCTGTACT 3'

Second primer:
                                    (SEQ ID NO: 274)
5' TGAAGCTGTCGGACGGCCTTTGCCCTCTC 3'
```

The first primer contains a biotin group at the 5' end, and a recognition site for the restriction enzyme EcoR I. The second primer contained the restriction enzyme recognition site for BceA I.

SNP TSC 0197279 was amplified with the following primers:

```
First primer:
                                    (SEQ ID NO: 275)
5' ATGGGCAGTTATGAATTCACTACTCCCTGTAGCTTGTT 3'

Second primer:
                                    (SEQ ID NO: 276)
5' TGATTGGCGCGAACGGCACTCAGAGAAGA 3'
```

The first primer contained a biotin group at the 5' end, and a recognition site for the restriction enzyme for EcoR I. The second primer contained the recognition site for the restriction enzyme BceA I.

SNP TSC 0200347 was amplified with the following primers:

```
First primer:
                                    (SEQ ID NO: 277)
5' CTCAAGGGGACCGAATTCGCTGGGGTCTTCTGTGGGTC 3'

Second primer:
                                    (SEQ ID NO: 278)
5' TAGGGCGGCGTGACGGCCAGCCAGTGGT 3'
```

The first primer contained a biotin group at the 5' end, and the recognition site for the restriction enzyme EcoR I. The second primer contained the restriction enzyme recognition site for BceA I.

PCR Reaction

All five loci of interest were amplified from the template genomic DNA using PCR (U.S. Pat. Nos. 4,683,195 and 4,683,202). For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest; in this example, 40 ng of template human genomic DNA and 5 μM of each primer were used. Thirty-eight cycles of PCR were performed. The following PCR conditions were used for SNP TSC 0115603, SNP TSC 0309610, and SNP TSC 02003437:

(1) 95° C. for 15 minutes and 15 seconds;
(2) 42° C. for 30 seconds;
(3) 95° C. for 30 seconds;
(4) 60° C. for 30 seconds;
(5) 95° C. for 30 seconds;
(6) 69° C. for 30 seconds;
(7) 95° C. for 30 seconds;
(8) Repeat steps 6 and 7 thirty nine (37) times;
(9) 72° C. for 5 minutes.

The following PCR conditions were used for SNP ss813773, SNP TSC 0198557, and SNP TSC 0197279:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (37) times; and
(9) 72° C. for 5 minutes.

In the first cycle of each PCR, the annealing temperature was about the melting temperature of the 3' annealing region of the second primer. The annealing temperature in the second cycle of PCR was about the melting temperature of the 3' region, which anneals to the template DNA, of the first primer. The annealing temperature in the third cycle of PCR was about the melting temperature of the entire sequence of the second primer. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used. The temperatures and times for denaturing, annealing, and extension, can be optimized by trying various settings and using the parameters that yield the best results.

Purification of Fragment of Interest

PCR products were separated from the components of the PCR reaction using Qiagen's MinElute PCR Purification Kit following manufacturer's instructions (Catalog number 28006). The PCR products were eluted in 20 μl of distilled water. For each amplified SNP, one microliter of PCR product, 1 μl of amplified internal control DNA (SNP TSC 0200347), and 8 μl of distilled water were mixed. Five microliters of each sample was placed into two separate reaction wells of a Pierce StreptaWell Microtiter plate (catalog number 15501). The first primers contained a 5' biotin tag so the PCR products bound to the Streptavidin coated wells while the genomic template DNA did not. The streptavidin binding reaction was performed using a Thermomixer (Eppendorf) at 150 rpm for 1 hour at 45° C. Each well was aspirated to remove unbound material, and washed three times with 1× PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme that bound the recognition site that was incorporated into the PCR products from the second primer. The purified PCR products were digested with the restriction enzyme BceA I (New England Biolabs, catalog number R0623S). The digests were performed in the wells of the microtiter plate following the instructions supplied with the restriction enzyme. After digestion with the appropriate restriction enzyme, the wells were washed three times with PBS to remove the cleaved fragments.

Incorporation of Labeled Nucleotide

The restriction enzyme digest described above yielded a DNA fragment with a 5' overhang, which contained the SNP and a 3' recessed end. The 5' overhang functioned as a template allowing incorporation of a nucleotide or nucleotides in the presence of a DNA polymerase.

For each SNP, two fill in reactions were performed; each reaction contained a different fluorescently labeled dideoxynucleotide (ddATP, ddCTP, ddGTP, or ddTTP, depending on the reported nucleotides to exist at a particular SNP). For example, the nucleotides adenine and thymidine have been reported at SNP TSC 0115603. Therefore, the digested PCR product for SNP TSC 0115603 was mixed with either fluorescently labeled ddATP or fluorescently labeled ddTTP. Each reaction contained fluorescently labeled ddGTP for the internal control. The following components were added to each fill in reaction: 2 μl of a ROX-conjugated dideoxynucleotide (depending on the nucleotides reported for each SNP), 2 μl of ROX-conjugated ddGTP (internal control), 2.5 μl of 10× sequenase buffer, 2 μl of Sequenase, and water as needed for a 25 μl reaction. All of the fill in reactions were performed at 45° C. for 45 min. However, shorter time periods of incorporation can be used. Non-fluorescently labeled ddNTPs were purchased from Fermentas Inc. (Hanover, Md.). The ROX-conjugated ddNTPs were obtained from Perkin Elmer. In the presence of fluorescently labeled ddNTPs, the 3' recessed end was extended by one base, which corresponds to the SNP or locus of interest.

After labeling, each Streptawell was rinsed with 1× PBS (100 μl ) three times. The "filled in" DNA fragments were then released from the Streptawells by digestion with the restriction enzyme EcoR I following manufacturer's recommendations. Digestion was performed for 1 hour at 37° C. with shaking at 120 rpm.

Detection of the Locus of Interest

After release from the streptavidin matrix, 3 μl of the 10 μl sample was loaded in a 48 well membrane tray (The Gel Company, catalog number TAM48-01). The sample in the tray was absorbed with a 48 Flow Membrane Comb (The Gel Company, catalog number AM48), and inserted into a 36 cm 5% acrylamide (urea) gel (BioWhittaker Molecular Applications, Long Ranger Run Gel Packs, catalog number 50691).

The sample was electrophoresed into the gel at 3000 volts for 3 min. The membrane comb was removed, and the gel was run for 3 hours on an ABI 377 Automated Sequencing Machine. The incorporated labeled nucleotide was detected by fluorescence.

As seen in FIG. 12, SNP TSC 0115603 was "filled in" with labeled ddTTP (lane 1) and in a separate reaction with labeled ddATP (lane 3). The calculated ratio between the nucleotides, using the raw data, was 66:34, which is consistent with the theoretical ratio of 66:33 for a SNP on chromosome 21 in an individual with trisomy 21. Both the ddTTP and ddATP were labeled with the same fluorescent dye to minimize variability in incorporation efficiencies of the dyes. However, nucleotides with different fluorescent labels or any detectable label can be used. It is preferable to calculate the coefficients of incorporation when different labels are used.

Each fill in reaction was performed in a separate well so it was possible that there could be variability in DNA binding between the wells of the microtiter plate. To account for the potential variability of DNA binding to the streptavidin-coated plates, an internal control was used. The internal control (SNP TSC 0200347), which is homozygous for guanine, was added to the sample prior to splitting the sample into two separate wells, and thus, an equal amount of the internal control should be present in each well. The amount of incorporated ddGTP can be fixed between the two reactions. If the amount of DNA in each well is equal, the amount of incorporated ddGTP should be equal because the reaction is performed under saturating conditions, with saturating conditions being defined as conditions that support incorporation of a nucleotide at each template molecule. Using the internal control, the ratio of incorporated ddATP to ddTTP was 63.4:36.6. This ratio was very similar to the ratio obtained with the raw data, indicating that there are minor differences in the two fill in reactions for a particular SNP.

TABLE VI

Allele Frequencies at Multiple SNPs on DNA Template from Individual with Trisomy 21

| SNP | Allele | Peak Area | Allele Ratio | Internal Control | Normalized Peak Area | Allele Ratio (%) |
|---|---|---|---|---|---|---|
| TSC | A | 5599 | 66 | 723 | 5599 | 63.4 |
| 0115603 | T | 2951 | 34 | 661 | 3227 ((723/661) * 2951) | 36.6 |
| TSC | T | 4126 | 64 | 1424 | 4126 | 66.8 |
| 0309610 | C | 2342 | 36 | 1631 | 2045 ((1424/1631) * 2342) | 33.2 |
| ss813773 | A | 4199 | 46 | 808 | 4199 | 41 |
| | C | 4870 | 54 | 647 | 6082 ((808/647) * 4870) | 59 |

TABLE VI-continued

| Allele Frequencies at Multiple SNPs on DNA Template from Individual with Trisomy 21 | | | | | | |
|---|---|---|---|---|---|---|
| SNP | Allele | Peak Area | Allele Ratio | Internal Control | Normalized Peak Area | Allele Ratio (%) |
| TSC | T | 3385 | 55 | 719 | 3385 | 49 |
| 0198557 | C | 2741 | 45 | 559 | 3525 719/559 * 2741) | 51 |
| TSC | T | 8085 | 53 | 2752 | 8085 | 50.7 |
| 0197279 | C | 7202 | 47 | 2520 | 7865 (2752/2520 * 7202 | 49.3 |

SNP TSC 0309610 was filled in with ddTTP (lane 3) or ddCTP (lane 4) (FIG. 12). The calculated ratio for the nucleotides, using the raw data, was 64:36. Both ddTTP and ddCTP were labeled with the same fluorescent dye. After normalization to the internal control, as discussed above, the calculated allele ratio of ddTTP to ddCTP was 66.8:33.2 (Table VI). Again, both the calculated ratio from the raw data and the calculated ratio using the internal control are very similar to the theoretical ratio of 66.6:33.4 for a SNP on chromosome 21 in an individual with trisomy.

To demonstrate that the 66:33 ratios for nucleotides at heterozygous SNPS represented loci on chromosomes present in three copies, SNPs on chromosome 13 were analyzed. The individual from whom the blood sample was obtained had previously been genotyped with one maternal chromosome 13, and one paternal chromosome 13.

Submitted SNP (ss) 813773 was filled in with ddATP (lane 5) or ddCTP (lane 6) (FIG. 12). The calculated ratio for the nucleotides at this heterozygous SNP, using the raw data, was 46:54. This ratio is within 10% of the expected ratio of 50:50. Importantly, the ratio does not approach the 66:33 ratio expected when there is an additional copy of a chromosome.

After normalization to the internal control, the calculated ratio was 41:59. Contrary to the expected result, normalization to the internal control increased the discrepancy between the calculated ratio and the theoretical ratio. This result may represent experimental error that occurred in aliquoting the DNA samples.

Also, it is possible that the restriction enzyme used to generate the overhang, which was used as a template for the "fill-in" reaction, preferentially cut one DNA template over the other DNA template. The two templates differ, with respect to the nucleotide at the SNP site, and this may influence the cutting. The primers can be designed such that the nucleotides adjacent to the cut site are the same, independent of the nucleotide at the SNP site (discussed further in the section entitled "Primer Design").

SNP TSC 0198557, which is on chromosome 13, was filled in with ddTTP (lane 7) in one reaction and ddCTP (lane 8) in another (FIG. 12). The calculated ratio for the nucleotides at this SNP, using the raw data, was 55:45. After normalization to the internal control, the calculated allele ratio of T:C was 49:51. The normalized ratio was closer to the theoretical ratio of 50:50 for an individual with two copies of chromosome 13.

SNP TSC 0197279, which is on chromosome 13, was filled in with ddTTP (lane 9) in one reaction and ddCTP (lane 10) in another (FIG. 12). The calculated ratio for the nucleotides at this SNP, using the raw data, was 53:47. After normalization to the internal control, the calculated allele ratio of T:C was 50.7:49.3. This is consistent with the theoretical ratio of 50:50 for an individual with only two copies of chromosome 13.

The ratio for the nucleotides at two of the analyzed SNPs on chromosome 13 was approximately 50:50. One SNP, ss813773, showed a ratio of 46:54, and when normalized to the internal control, the ratio was 41:59. These ratios deviate from the expected 50:50, but at the same time, the ratios are not indicative of an extra chromosome, which is indicated with a ratio of 66:33. While the data from this particular SNP is inconclusive, it does not represent a false positive. No conclusion could be drawn on the data from this SNP. However, the other two SNPs provided data that indicated a normal number of chromosomes. It is preferable to analyze multiple SNPs on a chromosome including but not limited to 1-5, 5-10, 10-50, 50-100, 100-200, 200-300, 300-400, 400-500, 500-600, 600-700, 700-800, 800-900, 900-1000, 1000-2000, 2000-3000, and greater than 3000. Preferably, the average of the ratios for a particular chromosome will be used to determine the presence or absence of a chromosomal abnormality. However, it is still possible to analyze one locus of interest. In the event that inconclusive data is obtained, another locus of interest can be analyzed.

The individual from whom the DNA template was obtained had previously been genotyped with trisomy 21, and the allele frequencies at SNPs on chromosome 21 indicate the presence of an additional chromosome 21. The additional chromosome contributes an additional nucleotide for each SNP, and thus alters the traditional 50:50 ratio at a heterozygous SNP. These results are consistent for multiple SNPs, and are specific for those found on chromosome 21. The allele frequencies for SNPs on chromosome 13 gave the expected ratios of approximately 50:50. These results demonstrate that this method of SNP detection can be used to detect chromosomal abnormalities including but not limited to translocations, transversions, monosomies, trisomy 21, trisomy 18, trisomy 13, other aneuplodies, deletions, additions, amplifications, translocations and rearrangements.

Example 6

Genomic DNA was obtained from four individuals after informed consent was obtained. Six SNPs on chromosome 13 (TSC0837969, TSC0034767, TSC1130902, TSC0597888, TSC0195492, TSC0607185) were analyzed using the template DNA. Information regarding these SNPs can be found at the following website www.snp.chsl.org/snpsearch.shtml; website active as of Feb. 11, 2003).

A single nucleotide labeled with one fluorescent dye was used to genotype the individuals at the six selected SNP sites. The primers were designed to allow the six SNPs to be analyzed in a single reaction.

Preparation of Template DNA

The template DNA was prepared from a 9 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit.

Design of Primers

SNP TSC0837969 was amplified using the following primer set:

```
First primer:
                                    (SEQ ID NO: 30)
5' GGGCTAGTCTCCGAATTCCACCTATCCTACCAAATGTC 3'

Second primer:
                                    (SEQ ID NO: 31)
5' TAGCTGTAGTTAGGGACTGTTCTGAGCAC 3'
```

The first primer had a biotin tag at the 5' end and contained a restriction enzyme recognition site for EcoRI. The first primer was designed to anneal 44 bases from the locus of interest. The second primer contained a restriction enzyme recognition site for BsmF I.

SNP TSC0034767 was amplified using the following primer set:

```
First primer:
                                    (SEQ ID NO: 32)
5' CGAATGCAAGGCGAATTCGTTAGTAATAACACAGTGCA 3'

Second primer:
                                    (SEQ ID NO: 33)
5' AAGACTGGATCCGGGACCATGTAGAATAC 3'
```

The first primer had a biotin tag at the 5' end and contained a restriction enzyme recognition site for EcoRI. The first primer was designed to anneal 50 bases from the locus of interest. The second primer contained a restriction enzyme recognition site for BsmF I.

SNP TSC1130902 was amplified using the following primer set:

```
First primer:
                                    (SEQ ID NO: 34)
5' TCTAACCATTGCGAATTCAGGGCAAGGGGGGTGAGATC 3'

Second primer:
                                    (SEQ ID NO: 35)
5' TGACTTGGATCCGGGACAACGACTCATCC 3'
```

The first primer had a biotin tag at the 5' end and contained a restriction enzyme recognition site for EcoRI. The first primer was designed to anneal 60 bases from the locus of interest. The second primer contained a restriction enzyme recognition site for BsmF I.

SNP TSC0597888 was amplified using the following primer set:

```
First primer:
                                    (SEQ ID NO: 36)
5' ACCCAGGCGCCAGAATTCTTTAGATAAAGCTGAAGGGA 3'

Second primer:
                                    (SEQ ID NO: 37)
5' GTTACGGGATCCGGGACTCCATATTGATC 3'
```

The first primer had a biotin tag at the 5' end and contained a restriction enzyme recognition site for EcoRI. The first primer was designed to anneal 70 bases from the locus of interest. The second primer contained a restriction enzyme recognition site for BsmF I.

SNP TSC0195492 was amplified using the following primer set:

```
First primer:
                                    (SEQ ID NO: 38)
5'CGTTGGCTTGAGGAATTCGACCAAAAGAGCCAAGAGAA

Second primer:
                                    (SEQ ID NO: 39)
5' AAAAAGGGATCCGGGACCTTGACTAGGAC 3'
```

The first primer had a biotin tag at the 5' end and contained a restriction enzyme recognition site for EcoRI. The first primer was designed to anneal 80 bases from the locus of interest. The second primer contained a restriction enzyme recognition site for BsmF I.

SNP TSC0607185 was amplified using the following primer set:

```
First primer:
                                    (SEQ ID NO: 40)
5' ACTTGATTCCGTGAATTCGTTATCAATAAATCTTACAT 3'

Second primer:
                                    (SEQ ID NO: 41)
5' CAAGTTGGATCCGGGACCCAGGGCTAACC 3'
```

The first primer had a biotin tag at the 5' end and contained a restriction enzyme recognition site for EcoRI. The first primer was designed to anneal 90 bases from the locus of interest. The second primer contained a restriction enzyme recognition site for BsmF I.

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they could also be amplified together in a single PCR reaction. For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest but in this example, 40 ng of template human genomic DNA and 5 μM of each primer were used. Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results. In this example, the first primer was designed to anneal at various distances from the locus of interest. The skilled artisan understands that the annealing location of the first primer can be 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-105, 106-110, 111-115, 116-120, 121-125, 126-130, 131-140, 1410-160, 1610-180, 1810-200, 2010-220, 2210-240, 2410-260, 2610-280, 2810-300, 3010-350, 3510-400, 4010-450, 450-500, or greater than 500 bases from the locus of interest.

Purification of Fragment of Interest

The PCR products were separated from the genomic template DNA. After the PCR reaction, ¼ of the volume of each PCR reaction from one individual was mixed together in a well of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1× PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

Below, a schematic of the 5' overhang for SNP TSC0837969 is shown. The entire DNA sequence is not reproduced, only the portion to demonstrate the overhang (where R indicates the variable site).

```
5' TTAA
3' AATT                 R    A    C    A
Overhang position       1    2    3    4
```

The observed nucleotides for TSC0837969 on the 5' sense strand (here depicted as the top strand) are adenine and guanine. The third position in the overhang on the antisense strand corresponds to cytosine, which is complementary to guanine. As this variable site can be adenine or guanine, fluorescently labeled ddGTP in the presence of unlabeled dCTP, dTTP, and dATP was used to determine the sequence of both alleles. The fill-in reactions for an individual homozygous for guanine, homozygous for adenine or heterozygous are diagrammed below.

```
Homozygous for guanine at TSC 0837969:

Allele 1             5' TTAA    G*
                     3' AATT    C    A    C    A
Overhang position               1    2    3    4

Allele 2             5' TTAA    G*
                     3' AATT    C    A    C    A
Overhang position               1    2    3    4
```

Labeled ddGTP is incorporated into the first position of the overhang. Only one signal is seen, which corresponds to the molecules filled in with labeled ddGTP at the first position of the overhang.

```
Homozygous for adenine at TSC 0837969:

Allele 1             5' TTAA    A    T    G*
                     3' AATT    T    A    C    A
Overhang position               1    2    3    4

Allele 2             5' TTAA    A    T    G*
                     3' AATT    T    A    C    A
Overhang position               1    2    3    4
```

Unlabeled dATP is incorporated at position one of the overhang, and unlabeled dTTP is incorporated at position two of the overhang. Labeled ddGTP was incorporated at position three of the overhang. Only one signal will be seen; the molecules filled in with ddGTP at position 3 will have a different molecular weight from molecules filled in at position one, which allows easy identification of individuals homozygous for adenine or guanine.

```
Heterozygous at TSC0837969:

Allele 1             5' TTAA    G*
                     3' AATT    C    A    C    A
Overhang position               1    2    3    4

Allele 2             5' TTAA    A    T    G*
                     3' AATT    T    A    C    A
Overhang position               1    2    3    4
```

Two signals will be seen; one signal corresponds to the DNA molecules filled in with ddGTP at position 1, and a second signal corresponding to molecules filled in at position 3 of the overhang. The two signals can be separated using any technique that separates based on molecular weight including but not limited to gel electrophoresis.

Below, a schematic of the 5' overhang for SNP TSC0034767 is shown. The entire DNA sequence is not reproduced, only the portion to demonstrate the overhang (where R indicates the variable site).

```
A    C    A    R    GTGT 3'
                    CACA 5'
4    3    2    1    Overhang Position
```

The observed nucleotides for TSC0034767 on the 5' sense strand (here depicted as the top strand) are cytosine and guanine. The second position in the overhang corresponds to adenine, which is complementary to thymidine. The third position in the overhang corresponds to cytosine, which is complementary to guanine. Fluorescently labeled ddGTP in the presence of unlabeled dCTP, dTTP, and dATP is used to determine the sequence of both alleles.

In this case, the second primer anneals upstream of the locus of interest, and thus the fill-in reaction occurs on the anti-sense strand (here depicted as the bottom strand). Either the sense strand or the antisense strand can be filled in depending on whether the second primer, which contains the type IIS restriction enzyme recognition site, anneals upstream or downstream of the locus of interest.

Below, a schematic of the 5' overhang for SNP TSC1130902 is shown. The entire DNA sequence is not reproduced, only a portion to demonstrate the overhang (where R indicates the variable site).

```
5' TTCAT
3' AAGTA            R    T    C    C
Overhang position   1    2    3    4
```

The observed nucleotides for TSC1130902 on the 5' sense strand (here depicted as the top strand) are adenine and guanine. The second position in the overhang corresponds to a thymidine, and the third position in the overhang corresponds to cytosine, which is complementary to guanine.

Fluorescently labeled ddGTP in the presence of unlabeled dCTP, dTTP, and dATP is used to determine the sequence of both alleles.

Below, a schematic of the 5' overhang for SNP TSC0597888 is shown. The entire DNA sequence is not reproduced, only the portion to demonstrate the overhang (where R indicates the variable site).

```
T    C    T    R    ATTC 3'
                    TAAG 5'
4    3    2    1    Overhang position
```

The observed nucleotides for TSC0597888 on the 5' sense strand (here depicted as the top strand) are cytosine and guanine. The third position in the overhang corresponds to cytosine, which is complementary to guanine. Fluorescently labeled ddGTP in the presence of unlabeled dCTP, dTTP, and dATP is used to determine the sequence of both alleles.

Below, a schematic of the 5' overhang for SNP TSC0607185 is shown. The entire DNA sequence is not reproduced, only the portion to demonstrate the overhang (where R indicates the variable site).

```
C    C    T    R    TGTC 3'
                    ACAG 5'
4    3    2    1    Overhang position
```

The observed nucleotides for TSC0607185 on the 5' sense strand (here depicted as the top strand) are cytosine and thymidine. In this case, the second primer anneals from the locus of interest, which allows the anti-sense strand to be filled in. The anti-sense strand (here depicted as the bottom strand) will be filled in with guanine or adenine.

The second position in the 5' overhang is thymidine, which is complementary to adenine, and the third position in the overhang corresponds to cytosine, which is complementary to guanine. Fluorescently labeled ddGTP in the presence of unlabeled dCTP, dTTP, and dATP is used to determine the sequence of both alleles.

Below, a schematic of the 5' overhang for SNP TSC0195492 is shown. The entire DNA sequence is not reproduced, only the portion to demonstrate the overhang.

```
5' ATCT
3' TAGA             R    A    C    A
Overhang position   1    2    3    4
```

The observed nucleotides at this site are cytosine and guanine (here depicted as the top strand). The second position in the 5' overhang is adenine, which is complementary to thymidine, and the third position in the overhang corresponds to cytosine, which is complementary to guanine. Fluorescently labeled ddGTP in the presence of unlabeled dCTP, dTTP, and dATP is used to determine the sequence of both alleles.

As demonstrated above, the sequence of both alleles of the six SNPs can be determined by labeling with ddGTP in the presence of unlabeled dATP, dTTP, and dCTP. The following components were added to each fill in reaction: 1 μl of fluorescently labeled ddGTP, 0.5 μl of unlabeled dNTPs (40 μM), which contained all nucleotides except guanine, 2 μl of 10× sequenase buffer, 0.25 μl of Sequenase, and water as needed for a 20 μl reaction. The fill in reaction was performed at 40° C. for 10 min. Non-fluorescently labeled dNTP was purchased from Fermentas Inc. (Hanover, Md.). All other labeling reagents were obtained from Amersham (Thermo Sequenase Dye Terminator Cycle Sequencing Core Kit, US 79565).

After labeling, each Streptawell was rinsed with 1× PBS (100 μl) three times. The "filled in" DNA fragments were then released from the Streptawells by digestion with the restriction enzyme EcoRI, according to the manufacturer's instructions that were supplied with the enzyme. Digestion was performed for 1 hour at 37 ° C. with shaking at 120 rpm.

Detection of the Locus of Interest

After release from the streptavidin matrix, the sample was loaded into a lane of a 36 cm 5% acrylamide (urea) gel (BioWhittaker Molecular Applications, Long Ranger Run Gel Packs, catalog number 50691). The sample was electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence.

As shown in FIG. 11, the template DNA in lanes 1 and 2 for SNP TSC0837969 is homozygous for adenine. The following fill-in reaction was expected to occur if the individual was homozygous for adenine:

```
Homozygous for adenine at TSC 0837969:

5' TTAA             A    T    G*
3' AATT             T    A    C    A
Overhang position   1    2    3    4
```

Unlabeled dATP was incorporated in the first position complementary to the overhang. Unlabeled dTTP was incorporated in the second position complementary to the overhang. Labeled ddGTP was incorporated in the third position complementary to the overhang. Only one band was seen, which migrated at about position 46 of the acrylamide gel. This indicated that adenine was the nucleotide filled in at position one. If the nucleotide guanine had been filled in, a band would be expected at position 44.

However, the template DNA in lanes 3 and 4 for SNP TSC0837969 was heterozygous. The following fill-in reactions were expected if the individual was heterozygous:

```
Heterozygous at TSC0837969:

Allele 1 5' TTAA    G*
         3' AATT    C    A    C    A
Overhang position   1    2    3    4
```

-continued

```
Allele 2 5' TTAA      A      T      G*
       3' AATT      T      A      C      A
Overhang position     1      2      3      4
```

Two distinct bands were seen; one band corresponds to the molecules filled in with ddGTP at position 1 complementary to the overhang (the G allele), and the second band corresponds to molecules filled in with ddGTP at position 3 complementary to the overhang (the A allele). The two bands were separated based on the differences in molecular weight using gel electrophoresis. One fluorescently labeled nucleotide ddGTP was used to determine that an individual was heterozygous at a SNP site. This is the first use of a single nucleotide to effectively detect the presence of two different alleles.

For SNP TSC0034767, the template DNA in lanes 1 and 3 is heterozygous for cytosine and guanine, as evidenced by the two distinct bands. The lower band corresponded to ddGTP filled in at position 1 complementary to the overhang. The second band of slightly higher molecular weight corresponded to ddGTP filled in at position 3, indicating that the first position in the overhang was filled in with unlabeled dCTP, which allowed the polymerase to continue to incorporate nucleotides until it incorporated ddGTP at position 3 complementary to the overhang. The template DNA in lanes 2 and 4 was homozygous for guanine, as evidenced by a single band of higher molecular weight than if ddGTP had been filled in at the first position complementary to the overhang.

For SNP TSC1130902, the template DNA in lanes 1, 2, and 4 is homozygous for adenine at the variable site, as evidenced by a single higher molecular weight band migrating at about position 62 on the gel. The template DNA in lane 3 is heterozygous at the variable site, as indicated by the presence of two distinct bands. The lower band corresponds to molecules filled in with ddGTP at position 1 complementary to the overhang (the guanine allele). The higher molecular weight band corresponds to molecules filled in with ddGTP at position 3 complementary to the overhang (the adenine allele).

For SNP TSC0597888, the template DNA in lanes 1 and 4 was homozygous for cytosine at the variable site; the template DNA in lane 2 was heterozygous at the variable site, and the template DNA in lane 3 was homozygous for guanine. The expected fill-in reactions are diagrammed below:

<u>Homozygous for cytosine:</u>

```
Allele 1  T    C    T    G    ATTC 3'
               G*   A    C    TAAG 5'
          4    3    2    1    Overhang position

Allele 2  T    C    T    G    ATTC 3'
               G*   A    C    TAAG 5'
          4    3    2    1    Overhang position
```

<u>Homozygous for guanine:</u>

```
Allele 1  T    C    T    C    ATTC 3'
                         G*   TAAG 5'
          4    3    2    1    Overhang position

Allele 2  T    C    T    C    ATTC 3'
                         G*   TAAG 5'
          4    3    2    1    Overhang position
```

<u>Heterozygous for guanine/cytosine:</u>

```
Allele 1  T    C    T    G    ATTC 3'
               G*   A    C    TAAG 5'
          4    3    2    1    Overhang position
```

-continued

```
Allele 2  T    C    T    C    ATTC 3'
                         G*   TAAG 5'
          4    3    2    1    Overhang position
```

Template DNA homozygous for guanine at the variable site displayed a single band, which corresponded to the DNA molecules filled in with ddGTP at position 1 complementary to the overhang. These DNA molecules were of lower molecular weight compared to the DNA molecules filled in with ddGTP at position 3 of the overhang (see lane 3 for SNP TSC0597888). The DNA molecules differed by two bases in molecular weight.

Template DNA homozygous for cytosine at the variable site displayed a single band, which corresponds to the DNA molecules filled in with ddGTP at position 3 complementary to the overhang. These DNA molecules migrated at a higher molecular weight than DNA molecules filled in with ddGTP at position 1 (see lanes 1 and 4 for SNP TSC0597888).

Template DNA heterozygous at the variable site displayed two bands; one band corresponded to the DNA molecules filled in with ddGTP at position 1 complementary to the overhang and was of lower molecular weight, and the second band corresponded to DNA molecules filled in with ddGTP at position 3 complementary to the overhang, and was of higher molecular weight (see lane 3 for SNP TSC0597888).

For SNP TSC0195492, the template DNA in lanes 1 and 3 was heterozygous at the variable site, which was demonstrated by the presence of two distinct bands. The template DNA in lane 2 was homozygous for guanine at the variable site. The template DNA in lane 4 was homozygous for cytosine. Only one band was seen in lane 4 for this SNP, and it had a higher molecular weight than the DNA molecules filled in with ddGTP at position 1 complementary to the overhang (compare lanes 2, 3 and 4).

The observed alleles for SNP TSC0607185 are reported as cytosine or thymidine. For consistency, the SNP consortium denotes the observed alleles as they appear in the sense strand www.snp.cshl.org/shpsearch.shtml; website active as of Feb. 11, 2003). For this SNP, the second primer annealed upstream of the locus of interest, which allowed the fill-in reaction to occur on the antisense strand after digestion with BsmF I.

The template DNA in lanes 1 and 3 was heterozygous; the template DNA in lane 2 was homozygous for thymidine, and the template DNA in lane 4 was homozygous for cytosine. The antisense strand was filled in with ddGTP, so the nucleotide on the sense strand corresponded to cytosine.

Molecular weight markers can be used to identify the positions of the expected bands. Alternatively, for each SNP analyzed, a known heterozygous sample can be used, which will identify precisely the position of the two expected bands.

As demonstrated in FIG. 11, one nucleotide labeled with one fluorescent dye can be used to determine the identity of a variable site including but not limited to SNPs and single nucleotide mutations. Typically, to determine if an individual is homozygous or heterozygous at a SNP site, multiple reactions are performed using one nucleotide labeled with one dye and a second nucleotide labeled with a second dye. However, this introduces problems in comparing results because the two dyes have different quantum coefficients. Even if different nucleotides are labeled with the same dye, the quantum coefficients are different. The use of a single nucleotide labeled with one dye eliminates any errors from the quantum coefficients of different dyes.

In this example, fluorescently labeled ddGTP was used. However, the method is applicable for a nucleotide tagged with any signal generating moiety including but not limited to radioactive molecule, fluorescent molecule, antibody, antibody fragment, hapten, carbohydrate, biotin, derivative of biotin, phosphorescent moiety, luminescent moiety, electrochemiluminescent moiety, chromatic moiety, and moiety having a detectable electron spin resonance, electrical capacitance, dielectric constant or electrical conductivity. In addition, labeled ddATP, ddTTP, or ddCTP can be used.

The above example used the third position complementary to the overhang as an indicator of the second allele. However, the second or fourth position of the overhang can be used as well (see Section on Incorporation of Nucleotides). Furthermore, the overhang was generated with the type IIS enzyme BsmF I; however any enzymes that cuts DNA at a distance from its binding site can be used including but not limited to the enzymes listed in Table I.

Also, in the above example, the nucleotide immediately preceding the SNP site was not a guanine on the strand that was filled in. This eliminated any effects of the alternative cutting properties of the type IIS restriction enzyme to be removed. For example, at SNP TSC0837969, the nucleotide from the SNP site on the sense strand was an adenine. If BsmF I displayed alternate cutting properties, the following overhangs would be generated for the adenine allele and the guanine allele:

```
G allele-11/15 Cut       5' TTA
                         3' AAT   T    C    A    C
Overhang position                 0    1    2    3

G allele after fill-in   5' TTA   A    G*
                         3' AAT   T    C    A    C
Overhang position                 0    1    2    3

A allele 11/15 Cut       5' TTA
                         3' AAT   T    T    A    C
Overhang position                 0    1    2    3

A allele after fill-in   5' TTA   A    A    T    G*
                         3' AAT   T    T    A    C
Overhang position                 0    1    2    3
```

For the guanine allele, the first position in the overhang would be filled in with dATP, which would allow the polymerase to incorporate ddGTP at position 2 complementary to the overhang. There would be no detectable difference between molecules cut at the 10/14 position or molecules cut at the 11/15 position.

For the adenine allele, the first position complementary to the overhang would be filled in with dATP, the second position would be filled in with dATP, the third position would be filled in with dTTP, and the fourth position would be filled in with ddGTP. There would be no difference in the molecular weights between molecules cut at 10/14 or molecules cut at 11/15. The only differences would correspond to whether the DNA molecules contained an adenine at the variable site or a guanine at the variable site.

As seen in FIG. 11, positioning the annealing region of the first primer allows multiple SNPs to be analyzed in a single lane of a gel. Also, when using the same nucleotide with the same dye, a single fill-in reaction can be performed. In this example, 6 SNPs were analyzed in one lane. However, any number of SNPs including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30-40, 40-50, 51-60, 61-70, 71-80, 81-100, 101-120, 121-140, 141-160, 161-180, 181-200, and greater than 200 can be analyzed in a single reaction.

Furthermore, one labeled nucleotide used to detect both alleles can be mixed with a second labeled nucleotide used to detect a different set of SNPs provided that neither of the nucleotides that are labeled occur immediately before the variable site (complementary to nucleotide at position 0 of the 11/15 cut). For example, suppose SNP X can be guanine or thymidine at the variable site and has the following 5' overhang generated after digestion with BsmF I:

```
SNP X 10/14          5' TTGAC
G allele             3' AACTG    C    A    C    T
Overhang position                1    2    3    4

SNP X 11/15          5' TTGA
G allele             3' AACT     G    C    A    C
Overhang position                0    1    2    3

SNP X 10/14          5' TTGAC
T allele             3' AACTG    A    A    C    T
Overhang position                1    2    3    4

SNP X 11/15          5' TTGA
T allele             3' AACT     G    A    A    C
Overhang position                0    1    2    3
```

After the fill-in reaction with labeled ddGTP, unlabeled dATP, dCTP, and dTTP, the following molecules would be generated:

```
SNP X 10/14          5' TTGAC   G*
G allele             3' AACTG   C    A    C    T
Overhang position               1    2    3    4

SNP X 11/15          5' TTGA    C    G*
G allele             3' AACT    G    C    A    C
Overhang position               0    1    2    3

SNP X 10/14          5' TTGAC   T    T    G*
T allele             3' AACTG   A    A    C    T
Overhang position               1    2    3    4

SNP X 11/15          5' TTGA    C    T    T    G*
T allele             3' AACT    G    A    A    C
Overhang position               0    1    2    3
```

Now suppose SNP Y can be adenine or thymidine at the variable site, and has the following 5' overhangs generated after digestion with BsmF I.

```
SNP Y 10/14          5' GTTT
A allele             3' CAAA     T    G    T    A
Overhang position                1    2    3    4

SNP Y 11/15          5' GTT
A allele             3' CAA      A    T    G    T
Overhang position                0    1    2    3

SNP Y 10/14          5' GTTT
T allele             3' CAAA     A    G    T    A
Overhang position                1    2    3    4

SNP Y 11/15          5' GTT
T allele             3' CAA      A    A    G    T
Overhang position                0    1    2    3
```

After fill-in with labeled ddATP and unlabeled dCTP, dGTP, and dTTP, the following molecules would be generated:

```
SNP Y 10/14          5' GTTT    A*
A allele             3' CAAA    T    G    T    A
Overhang position               1    2    3    4

SNP Y 11/15          5' GTT     T    A*
A allele             3' CAA     A    T    G    T
Overhang position               0    1    2    3
```

-continued

```
SNP Y 10/14         5' GTTT    T    C    A*
T allele            3' CAAA    A    G    T    A
Overhang position              1    2    3    4

SNP Y 11/15         5' GTT     T    T    C    A*
T allele            3' CAA     A    A    G    T
Overhang position              0    1    2    3
```

In this example, labeled ddGTP and labeled ddATP are used to determine the identity of both alleles of SNP X and SNP Y respectively. The nucleotide immediately preceding (the complementary nucleotide to position 0 of the overhang from the 11/15 cut SNP X is not guanine or adenine on the strand that is filled-in. Likewise, the nucleotide immediately preceding SNPY is not guanine or adenine on the strand that is filled-in. This allows the fill-in reaction for both SNPs to occur in a single reaction with labeled ddGTP, labeled ddATP, and unlabeled dCTP and dTTP. This reduces the number of reactions that need to be performed and increases the number of SNPs that can be analyzed in one reaction.

The first primers for each SNP can be designed to anneal at different distances from the locus of interest, which allows the SNPs to migrate at different positions on the gel. For example, the first primer used to amplify SNP X can anneal at 30 bases from the locus of interest, and the first primer used to amplify SNP Y can anneal at 35 bases from the locus of interest. Also, the nucleotides can be labeled with fluorescent dyes that emit at spectrums that do not overlap. After running the gel, the gel can be scanned at one wavelength specific for one dye. Only those molecules labeled with that dye will emit a signal. The gel then can be scanned at the wavelength for the second dye. Only those molecules labeled with that dye will emit a signal. This method allows maximum compression for the number of SNPs that can be analyzed in a single reaction.

In this example, the nucleotide preceding the variable site on the strand that was filled-in was not adenine or guanine, and the nucleotide following the variable site can not be adenine or guanine on the sense strand. This method can work with any combination of labeled nucleotides, and the skilled artisan would understand which labeling reactions can be mixed and those that can not. For instance, if one SNP is labeled with thymidine and a second SNP is labeled with cytosine, the SNPs can be labeled in a single reaction if the nucleotide immediately preceding each variable site is not thymidine or cytosine on the sense strand and the nucleotide immediately after the variable site is not thymidine or cytosine on the sense strand.

This method allows the signals from one allele to be compared to the signal from a second allele without the added complexity of determining the degree of alternate cutting, or having to correct for the quantum coefficients of the dyes. This method is especially useful when trying to quantitate a ratio for one allele to another. For example, this method is useful for detecting chromosomal abnormalities. The ratio of alleles at a heterozygous site is expected to be about 1:1 (one A allele and one G allele). However, if an extra chromosome is present the ratio is expected to be about 1:2 (one A allele and 2 G alleles or 2 A alleles and 1 G allele). This method is especially useful when trying to detect fetal DNA in the presence of maternal DNA.

In addition, this method is useful for detecting two genetic signals in one sample. For example, this method can detect mutant cells in the presence of wild type cells (see Example 5). If a mutant cell contains a mutation in the DNA sequence of a particular gene, this method can be used to detect both the mutant signal and the wild type signal. This method can be used to detect the mutant DNA sequence in the presence of the wild type DNA sequence. The ratio of mutant DNA to wild type DNA can be quantitated because a single nucleotide labeled with one signal generating moiety is used.

Example 7

Non-invasive methods for the detection of various types of cancer have the potential to reduce morbidity and mortality from the disease. Several techniques for the early detection of colorectal tumors have been developed including colonoscopy, barium enemas, and sigmoidoscopy; however the techniques are limited in use because they are invasive, which causes a low rate of patient compliance. Non-invasive genetic tests may be useful in identifying early stage colorectal tumors.

In 1991, researchers identified the Adenomatous Polyposis Coli gene (APC), which plays a critical role in the formation of colorectal tumors (Kinzler et al., Science 253:661-665, 1991). The APC gene resides on chromosome 5q21-22 and a total of 15 exons code for an RNA molecule of 8529 nucleotides, which produces a 300 Kd APC protein. The protein is expressed in numerous cell types and is essential for cell adhesion.

Mutations in the APC gene generally initiate colorectal neoplasia (Tsao, J. et al., Am, J. Pathol. 145:531-534, 1994). Approximately 95% of the mutations in the APC gene result in nonsense/frameshift mutations. The most common mutations occur at codons 1061 and 1309; mutations at these codons account for ⅓ of all germline mutations. With regard to somatic mutations, 60% occur within codons 1286-1513, which is about 10% of the coding sequence. This region is termed the mutation Cluster Region (MCR). Numerous types of mutations have been identified in the APC gene including nucleotide substitutions (see Table VII), splicing errors (see Table VIII), small deletions (see Table IX), small insertions (see Table X), small insertions/deletions (see Table XI), gross deletions (see Table XII), gross insertions (see Table XIII), and complex rearrangements (see Table XIV).

Researchers have attempted to identify cells harboring mutations in the APC gene in stool samples (Traverso, G. et al., New England Journal of Medicine, Vol 346:311-320, 2002). While APC mutations are found in nearly all tumors, about 1 in 250 cells in the stool sample has a mutation in the APC gene; most of the cells are normal cells that have been shed into the feces. Furthermore, human DNA represents about one-billionth of the total DNA found in stool samples; the majority of DNA is bacterial. The technique employed by Traverso et al. only detects mutations that result in a truncated protein.

As discussed above, numerous mutations in the APC gene have been implicated in the formation of colorectal tumors. Thus, a need still exists for a highly sensitive, non-invasive technique for the detection of colorectal tumors. Below, methods are described for detection of two mutations in the APC gene. However, any number of mutations can be analyzed using the methods described herein.

Preparation of Template DNA

The template DNA is purified from a sample containing colon cells including but not limited to a stool sample. The template DNA is purified using the procedures described by Ahlquist et al. (Gastroenterology, 119:1219-1227, 2000). If stool samples are frozen, the samples are thawed at room temperature, and homogenized with an Exactor stool shaker (Exact Laboratories, Maynard, Mass.) Following homogenization, a 4 gram stool equivalent of each sample is centrifuged at 2536×g for 5 minutes. The samples are centrifuged a second time at 16,500×g for 10 minutes. Supernatants are incubated with 20 μl of RNase (0.5 mg per milliliter) for 1 hour at 37° C. DNA is precipitated with 1/10 volume of 3 mol of sodium acetate per liter and an equal volume of isopropanol. The DNA is dissolved in 5 ml of TRIS-EDTA (0.01 mol of Tris per liter (pH 7.4) and 0.001 mole of EDTA per liter.

Design of Primers

To determine if a mutation resides at codon 1370, the following primers are used:

```
First primer:
                                          (SEQ ID NO: 42)
5' GTGCAAAGGCCTGAATTCCCAGGCACAAAGCTGTTGAA 3'

Second primer:
                                          (SEQ ID NO: 43)
5' TGAAGCGAACTAGGGACTCAGGTGGACTT
```

The first primer contains a biotin tag at the extreme 5' end, and the nucleotide sequence for the restriction enzyme EcoRI. The second primer contains the nucleotide sequence for the restriction enzyme BsmF I.

To determine if a small deletion exists at codon 1302, the following primers are used:

```
First primer:
                                          (SEQ ID NO: 44)
5' GATTCCGTAAACGAATTCAGTTCATTATCATCTTTGTC 3'

Second primer:
                                          (SEQ ID NO: 45)
5' CCATTGTTAAGCGGGACTTCTGCTATTTG 3'
```

The first primer has a biotin tag at the 5' end and contains a restriction enzyme recognition site for EcoRI. The second primer contains a restriction enzyme recognition site for BsmF I.

PCR Reaction

The loci of interest are amplified from the template genomic DNA using the polymerase chain reaction (PCR, U.S. Pat. Nos. 4,683,195 and 4,683,202, incorporated herein by reference). The loci of interest are amplified in separate reaction tubes; they can also be amplified together in a single PCR reaction. For increased specificity, a "hot-start" PCR reaction is used, e.g. by using the HotStarTaq Master Mix Kit supplied by QIAGEN (catalog number 203443). The amount of template DNA and primer per reaction are optimized for each locus of interest but in this example, 40 ng of template human genomic DNA and 5 μM of each primer are used. Forty cycles of PCR are performed. The following PCR conditions are used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature is about the melting temperature of the 3' annealing region of the second primers, which is 37° C. The annealing temperature in the second cycle of PCR is about the melting temperature of the 3' region, which anneals to the template DNA, of the first primer, which is 57° C. The annealing temperature in the third cycle of PCR is about the melting temperature of the entire sequence of the second primer, which is 64° C. The annealing temperature for the remaining cycles is 64° C. Escalating the annealing temperature from TM1 to TM2 to TM3 in the first three cycles of PCR greatly improves specificity. These annealing temperatures are representative, and the skilled artisan understands that the annealing temperatures for each cycle are dependent on the specific primers used.

The temperatures and times for denaturing, annealing, and extension, are optimized by trying various settings and using the parameters that yield the best results.

Purification of Fragment of Interest

The PCR products are separated from the genomic template DNA. Each PCR product is divided into four separate reaction wells of a Streptawell, transparent, High-Bind plate from Roche Diagnostics GmbH (catalog number 1 645 692, as listed in Roche Molecular Biochemicals, 2001 Biochemicals Catalog). The first primers contain a 5' biotin tag so the PCR products bound to the Streptavidin coated wells while the genomic template DNA does not. The streptavidin binding reaction is performed using a Thermomixer (Eppendorf) at 1000 rpm for 20 min. at 37° C. Each well is aspirated to remove unbound material, and washed three times with 1× PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Alternatively, the PCR products are placed into a single well of a streptavidin plate to perform the nucleotide incorporation reaction in a single well.

Restriction Enzyme Digestion of Isolated Fragments

The purified PCR products are digested with the restriction enzyme BsmF I (New England Biolabs catalog number R0572S), which binds to the recognition site incorporated into the PCR products from the second primer. The digests are performed in the Streptawells following the instructions supplied with the restriction enzyme. After digestion with the appropriate restriction enzyme, the wells are washed three times with PBS to remove the cleaved fragments.

Incorporation of Labeled Nucleotide

The restriction enzyme digest described above yields a DNA fragment with a 5' overhang, which contains the locus of interest and a 3' recessed end. The 5' overhang functions as a template allowing incorporation of a nucleotide or nucleotides in the presence of a DNA polymerase.

For each locus of interest, four separate fill in reactions are performed; each of the four reactions contains a different fluorescently labeled ddNTP (ddATP, ddTTP, ddGTP, or ddCTP). The following components are added to each fill in reaction: 1 μl of a fluorescently labeled ddNTP, 0.5 μl of unlabeled ddNTPs (40 μM), which contains all nucleotides except the nucleotide that is fluorescently labeled, 2 μl of 10× sequenase buffer, 0.25 μl of Sequenase, and water as needed for a 20 μl reaction. The fill are performed in reactions at 40° C. for 10 min. Non-fluorescently labeled ddNTP are purchased from Fernentas Inc. (Hanover, Md.). All other labeling reagents are obtained from Amersham (Thermo Sequenase Dye Terminator Cycle Sequencing Core Kit, US 79565). In the presence of fluorescently labeled ddNTPs, the 3' recessed end is extended by one base, which corresponds to the locus of interest.

A mixture of labeled ddNTPs and unlabeled dNTPs also can be used for the fill-in reaction. The "fill in" conditions are as described above except that a mixture containing 40 μM unlabeled dNTPs, 1 μl fluorescently labeled ddATP, 1 μl fluorescently labeled ddTTP, 1 μl fluorescently labeled ddCTP, and 1 μl ddGTP are used. The fluorescent ddNTPs are obtained from Amersham (Thermo Sequenase Dye Terminator Cycle Sequencing Core Kit, US 79565; Amersham does not publish the concentrations of the fluorescent nucleotides). The locus of interest is digested with the restriction enzyme BsmF I, which generates a 5' overhang of four bases. If the first nucleotide incorporated is a labeled ddNTP, the 3' recessed end is filled in by one base, allowing detection of the locus of interest. However, if the first nucleotide incorporated is a dNTP, the polymerase continues to incorporate nucleotides until a ddNTP is filled in. For example, the first two nucleotides may be filled in with dNTPs, and the third nucleotide with a ddNTP, allowing detection of the third nucleotide in the overhang. Thus, the sequence of the entire 5' overhang is determined, which increases the information obtained from each SNP or locus of interest. This type of fill in reaction is especially useful when detecting the presence of insertions, deletions, insertions and deletions, rearrangements, and translocations.

Alternatively, one nucleotide labeled with a single dye is used to determine the sequence of the locus of interest. See Example 6. This method eliminates any potential errors when using different dyes, which have different quantum coefficients.

After labeling, each Streptawell is rinsed with 1× PBS (100 μl) three times. The "filled in" DNA fragments are released from the Streptawells by digesting with the restriction enzyme EcoRI, according to the manufacturer's instructions that are supplied with the enzyme. The digestion is performed for 1 hour at 37 ° C. with shaking at 120 rpm.

Detection of the Locus of Interest

After release from the streptavidin matrix, the sample is loaded into a lane of a 36 cm 5% acrylamide (urea) gel (BioWhittaker Molecular Applications, Long Ranger Run Gel Packs, catalog number 50691). The sample is electrophoresed into the gel at 3000 volts for 3 min. The gel is run for 3 hours using a sequencing apparatus (Hoefer SQ3 Sequencer). The incorporated labeled nucleotide is detected by fluorescence.

To determine if any cells contain mutations at codon 1370 of the APC gene when separate fill-in reactions are performed, the lanes of the gel that correspond to the fill-in reaction for ddATP and ddTTP are analyzed. If only normal cells are present, the lane corresponding to the fill in reaction with ddATP is a bright signal. No signal is detected for the "fill-in" reaction with ddTTP. However, if the patient sample contains cells with mutations at codon 1370 of the APC gene, the lane corresponding to the fill in reaction with ddATP is a bright signal, and a signal is detected from the lane corresponding to the fill in reaction with ddTTP. The intensity of the signal from the lane corresponding to the fill in reaction with ddTTP is indicative of the number of mutant cells in the sample.

Alternatively, one labeled nucleotide is used to determine the sequence of the alleles at codon 1370 of the APC gene. At codon 1370, the normal sequence is AAA, which codes for the amino acid lysine. However, a nucleotide substitution has been identified at codon 1370, which is associated with colorectal tumors. Specifically, a change from A to T (AAA-TAA) typically is found at codon 1370, which results in a stop codon. A single fill-in reaction is performed using labeled ddATP, and unlabeled dTTP, dCTP, and dGTP. A single nucleotide labeled with one fluorescent dye is used to determine the presence of both the normal and mutant DNA sequence that codes for codon 1370. The relevant DNA sequence is depicted below with the sequence corresponding to codon 1370 in bold:

```
5' CCCAAAAGTCCACCTGA 3'     (SEQ ID NO: 46)

3' GGGTTTTCAGGTGGACT 5'     (SEQ ID NO: 47)
```

After digest with BsmF I, the following overhang is produced:

```
5' CCC
3' GGG              T     T     T     T
Overhang position   1     2     3     4
```

If the patient sample has no cells harboring a mutation at codon 1370, one signal is seen corresponding to incorporation of labeled ddATP.

```
5' CCC              A*
3' GGG              T     T     T     T
Overhang position   1     2     3     4
```

However, if the patient sample has cells with mutations at codon 1370 of the APC gene, one signal is seen, which corresponds to the normal sequence at codon 1370, and a second signal is seen, which corresponds to the mutant sequence at codon 1370. The signals clearly are identified as they differ in molecular weight.

```
Overhang of normal DNA sequence:   CCC
                                   GGG  T  T  T  T
Overhang position                       1  2  3  4
Normal DNA sequence after fill-in: CCC  A*
                                   GGG  T  T  T  T
Overhang position                       1  2  3  4
Overhang of mutant DNA sequence:   CCC
                                   GGG  A  T  T  T
Overhang position                       1  2  3  4
Mutant DNA sequence after fill-in: CCC  T  A*
                                   GGG  A  T  T  T
Overhang position                       1  2  3  4
```

Two signals are seen when the mutant allele is present. The mutant DNA molecules are filled in one base after the wild type DNA molecules. The two signals are separated using any method that discriminates based on molecular weight. One labeled nucleotide (ddATP) is used to detect the presence of both the wild type DNA sequence and the mutant DNA sequence. This method of labeling reduces the number of reactions that need to be performed and allows accurate quantitation for the number of mutant cells in the patient sample. The number of mutant cells in the sample is used to determine patient prognosis, the degree and the severity of the disease. This method of labeling eliminates the complications associated with using different dyes, which have distinct quantum coefficients. This method of labeling also eliminates errors associated with pipetting reactions.

To determine if any cells contain mutations at codon 1302 of the APC gene when separate fill-in reactions are performed, the lanes of the gel that correspond to the fill-in reaction for ddTTP and ddCTP are analyzed. The normal DNA sequence is depicted below with sequence coding for codon 1302 in bold type-face.

```
Normal Sequence:
5' ACCCTGCAAATAGCAGAA 3'     (SEQ ID NO: 48)

3' TGGGACGTTTATCGTCTT 5'     (SEQ ID NO: 49)
```

After digest, the following 5' overhang is produced:

```
5' ACCC
3' TGGG                  A      C      G      T
Overhang position        1      2      3      4
```

After the fill-in reaction, labeled ddTTP is incorporated.

```
5' ACCC                 T*
3' TGGG                 A      C      G      T
Overhang position       1      2      3      4
```

A deletion of a single base of the APC sequence, which typically codes for codon 1302, has been associated with colorectal tumors. The mutant DNA sequence is depicted below with the relevant sequence in bold:

```
Mutant Sequence:

5' ACCCGCAAATAGCAGAA 3'      (SEQ ID NO: 50)

3' TGGGCGTTTATCGTCTT 5'      (SEQ ID NO: 51)

After digest:

5' ACC
3' TGG                  G      C      G      T
Overhang position       1      2      3      4

After fill-in:

5' ACC                  C*
3' TGG                  G      C      G      T
Overhang position       1      2      3      4
```

If there are no mutations in the APC gene, signal is not detected for the fill in reaction with ddCTP*, but a bright signal is detected for the fill-in reaction with ddTTP*. However, if there are cells in the patient sample that have mutations in the APC gene, signals are seen for the fill-in reactions with ddCTP*and ddTTP*.

Alternatively, a single fill-in reaction is performed using a mixture containing unlabeled dNTPs, fluorescently labeled ddATP, fluorescently labeled ddTTP, fluorescently labeled ddCTP, and fluorescently labeled ddGTP. If there is no deletion, labeled ddTTP is incorporated.

```
5' ACCC                 T*
3' TGGG                 A      C      G      T
Overhang position       1      2      3      4
```

However, if the T has been deleted, labeled ddCTP* is incorporated.

```
5' ACCC*
3' TGGG                 C      G      T
Overhang position       1      2      3      4
```

The two signals are separated by molecular weight because of the deletion of the thymidine nucleotide. If mutant cells are present, two signals are generated in the same lane but are separated by a single base pair (this principle is demonstrated in FIG. 9D). The deletion causes a change in the molecular weight of the DNA fragments, which allows a single fill in reaction to be used to detect the presence of both normal and mutant cells.

In the above example, methods for the detection of a nucleotide substitution and a small deletion are described. However, the methods can be used for the detection of any type of mutation including but not limited to nucleotide substitutions (see Table VII), splicing errors (see Table VIII), small deletions (see Table IX), small insertions (see Table X), small insertions/deletions (see Table XI), gross deletions (see Table XII), gross insertions (see Table XIII), and complex rearrangements (see Table XIV).

In addition, the above-described methods are used for the detection of any type of disease including but not limited to those listed in Table IV. Furthermore, any type of mutant gene is detected using the inventions described herein including but not limited to the genes associated with the diseases listed in Table IV, BRCA1, BRCA2, MSH6, MSH2, MLH1, RET, PTEN, ATM, H-RAS, p53, ELAC2, CDH1, APC, AR, PMS2, MLH3, CYP1A1, GSTP1, GSTM1, AXIN2, CYP19, MET, NAT1, CDKN2A, NQ01, trc8, RAD51, PMS1, TGFBR2, VHL, MC4R, POMC, NROB2, UCP2, PCSK1, PPARG, ADRB2, UCP3, glur1, cart, SORBS1, LEP, LEPR, SIM1, TNF, IL-6, IL-1, IL-2, IL-3, IL1A, TAP2, THPO, THRB, NBS1, RBM15, LIF, MPL, RUNX1, Her-2, glucocorticoid receptor, estrogen receptor, thyroid receptor, p21, p27, K-RAS, N-RAS, retinoblastoma protein, Wiskott-Aldrich (WAS) gene, Factor V Leiden, Factor II (prothrombin), methylene tetrahydrofolate reductase, cystic fibrosis, LDL receptor, HDL receptor, superoxide dismutase gene, SHOX gene, genes involved in nitric oxide regulation, genes involved in cell cycle regulation, tumor suppressor genes, oncogenes, genes associated with neurodegeneration, genes associated with obesity, Abbreviations correspond to the proteins as listed on the Human Gene Mutation Database, which is incorporated herein by reference www.archive.uwcm.ac.uk./uwcm; website address active as of Feb. 12, 2003).

The above-example demonstrates the detection of mutant cells and mutant alleles from a fecal sample. However, the methods described herein are used for detection of mutant cells from any biological sample including but not limited to blood sample, serum sample, plasma sample, urine sample, spinal fluid, lymphatic fluid, semen, vaginal secretion, ascitic fluid, saliva, mucosa secretion, peritoneal fluid, fecal sample, body exudates, breast fluid, lung aspirates, cells, tissues, individual cells or extracts of the such sources that contain the nucleic acid of the same, and subcellular structures such as mitochondria or chloroplasts. In addition, the methods described herein are used for the detection of mutant cells and mutated DNA from any number of nucleic acid containing sources including but not limited to forensic, food, archeological, agricultural or inorganic samples.

The above example is directed to detection of mutations in the APC gene. However, the inventions described herein are used for the detection of mutations in any gene that is associated with or predisposes to disease (see Table XV).

For example, hypermethylation of the glutathione S-transferase P1 (GSTP1) promoter is the most common DNA alteration in prostrate cancer. The methylation state of the promoter is determined using sodium bisulfite and the methods described herein.

Treatment with sodium bisulfite converts unmethylated cytosine residues into uracil, and leaving the methylated cytosines unchanged. Using the methods described herein, a first and second primer are designed to amplify the regions of the GSTP1 promoter that are often methylated. Below, a region of the GSTP1 promoter is shown prior to sodium bisulfite treatment:

Before Sodium Bisulfite treatment:

```
5' ACCGCTACA

3' TGGCGATCA
```

Below, a region of the GSTP1 promoter is shown after sodium bisulfite treatment, PCR amplification, and digestion with the type IIS restriction enzyme BsmF I:

```
Unmethylated

5' ACC
3' TGG              U    G    A    T
Overhang position   1    2    3    4

Methylated

5' ACC
3' TGG              C    G    A    T
Overhang position   1    2    3    4
```

Labeled ddATP, unlabeled dCTP, dGTP, and dTTP are used to fill-in the 5' overhangs. The following molecules are generated:

```
Unmethylated

5' ACC              A*
3' TGG              U    G    A    T
Overhang position   1    2    3    4

Methylated

5' ACC              G    C    T    A*
3' TGG              C    G    A    T
Overhang position   1    2    3    4
```

Two signals are seen; one corresponds to DNA molecules filled in with ddATP at position one complementary to the overhang (unmethylated), and the other corresponds to the DNA molecules filled in with ddATP at position 4 complementary to the overhang (methylated). The two signals are separated based on molecular weight. Alternatively, the fill-in reactions are performed in separate reactions using labeled ddGTP in one reaction and labeled ddATP in another reaction.

The methods described herein are used to screen for prostate cancer and also to monitor the progression and severity of the disease. The use of a single nucleotide to detect both the methylated and unmethylated sequences allows accurate quantitation and provides a high level of sensitivity for the methylated sequences, which is a useful tool for earlier detection of the disease.

The information contained in Tables VII-XIV was obtained from the Human Gene Mutation Database. With the information provided herein, the skilled artisan will understand how to apply these methods for determining the sequence of the alleles for any gene. A large number of genes and there associated mutations can be found at the following website: www.archive.uwcm.ac.uk./uwcm.

TABLE VII

NUCLEOTIDE SUBSTITUTIONS

| Codon | Nucleotide | Amino acid | Phenotype |
|---|---|---|---|
| 99 | CGG-TGG | Arg-Trp | *Adenomatous polyposis coli* |
| 121 | AGA-TGA | Arg-Term | *Adenomatous polyposis coli* |
| 157 | TGG-TAG | Trp-Term | *Adenomatous polyposis coli* |
| 159 | TAC-TAG | Tyr-Term | *Adenomatous polyposis coli* |
| 163 | CAG-TAG | Gln-Term | *Adenomatous polyposis coli* |
| 168 | AGA-TGA | Arg-Term | *Adenomatous polyposis coli* |
| 171 | AGT-ATT | Ser-Ile | *Adenomatous polyposis coli* |
| 181 | CAA-TAA | Gln-Term | *Adenomatous polyposis coli* |
| 190 | GAA-TAA | Glu-Term | *Adenomatous polyposis coli* |
| 202 | GAA-TAA | Glu-Term | *Adenomatous polyposis coli* |
| 208 | CAG-CGG | Gln-Arg | *Adenomatous polyposis coli* |
| 208 | CAG-TAG | Gln-Term | *Adenomatous polyposis coli* |
| 213 | CGA-TGA | Arg-Term | *Adenomatous polyposis coli* |
| 215 | CAG-TAG | Gln-Term | *Adenomatous polyposis coli* |
| 216 | CGA-TGA | Arg-Term | *Adenomatous polyposis coli* |
| 232 | CGA-TGA | Arg-Term | *Adenomatous polyposis coli* |
| 233 | CAG-TAG | Gln-Term | *Adenomatous polyposis coli* |
| 247 | CAG-TAG | Gln-Term | *Adenomatous polyposis coli* |
| 267 | GGA-TGA | Gly-Term | *Adenomatous polyposis coli* |
| 278 | CAG-TAG | Gln-Term | *Adenomatous polyposis coli* |
| 280 | TCA-TGA | Ser-Term | *Adenomatous polyposis coli* |
| 280 | TCA-TAA | Ser-Term | *Adenomatous polyposis coli* |
| 283 | CGA-TGA | Arg-Term | *Adenomatous polyposis coli* |
| 302 | CGA-TGA | Arg-Term | *Adenomatous polyposis coli* |
| 332 | CGA-TGA | Arg-Term | *Adenomatous polyposis coli* |
| 358 | CAG-TAG | Gln-Term | *Adenomatous polyposis coli* |
| 405 | CGA-TGA | Arg-Term | *Adenomatous polyposis coli* |
| 414 | CGC-TGC | Arg-Cys | *Adenomatous polyposis coli* |
| 422 | GAG-TAG | Glu-Term | *Adenomatous polyposis coli* |
| 423 | TGG-TAG | Trp-Term | *Adenomatous polyposis coli* |
| 424 | CAG-TAG | Gln-Term | *Adenomatous polyposis coli* |
| 433 | CAG-TAG | Gln-Term | *Adenomatous polyposis coli* |
| 443 | GAA-TAA | Glu-Term | *Adenomatous polyposis coli* |
| 457 | TCA-TAA | Ser-Term | *Adenomatous polyposis coli* |
| 473 | CAG-TAG | Gln-Term | *Adenomatous polyposis coli* |
| 486 | TAC-TAG | Tyr-Term | *Adenomatous polyposis coli* |
| 499 | CGA-TGA | Arg-Term | *Adenomatous polyposis coli* |
| 500 | TAT-TAG | Tyr-Term | *Adenomatous polyposis coli* |
| 541 | CAG-TAG | Gln-Term | *Adenomatous polyposis coli* |
| 553 | TGG-TAG | Trp-Term | *Adenomatous polyposis coli* |
| 554 | CGA-TGA | Arg-Term | *Adenomatous polyposis coli* |
| 564 | CGA-TGA | Arg-Term | *Adenomatous polyposis coli* |
| 577 | TTA-TAA | Leu-Term | *Adenomatous polyposis coli* |
| 586 | AAA-TAA | Lys-Term | *Adenomatous polyposis coli* |
| 592 | TTA-TGA | Leu-Term | *Adenomatous polyposis coli* |
| 593 | TGG-TAG | Trp-Term | *Adenomatous polyposis coli* |
| 593 | TGG-TGA | Trp-Term | *Adenomatous polyposis coli* |
| 622 | TAC-TAA | Tyr-Term | *Adenomatous polyposis coli* |
| 625 | CAG-TAG | Gln-Term | *Adenomatous polyposis coli* |
| 629 | TTA-TAA | Leu-Term | *Adenomatous polyposis coli* |
| 650 | GAG-TAG | Glu-Term | *Adenomatous polyposis coli* |
| 684 | TTG-TAG | Leu-Term | *Adenomatous polyposis coli* |
| 685 | TGG-TGA | Trp-Term | *Adenomatous polyposis coli* |
| 695 | CAG-TAG | Gln-Term | *Adenomatous polyposis coli* |
| 699 | TGG-TGA | Trp-Term | *Adenomatous polyposis coli* |
| 699 | TGG-TAG | Trp-Term | *Adenomatous polyposis coli* |
| 713 | TCA-TGA | Ser-Term | *Adenomatous polyposis coli* |
| 722 | AGT-GGT | Ser-Gly | *Adenomatous polyposis coli* |
| 747 | TCA-TGA | Ser-Term | *Adenomatous polyposis coli* |
| 764 | TTA-TAA | Leu-Term | *Adenomatous polyposis coli* |
| 784 | TCT-ACT | Ser-Thr | *Adenomatous polyposis coli* |
| 805 | CGA-TGA | Arg-Term | *Adenomatous polyposis coli* |
| 811 | TCA-TGA | Ser-Term | *Adenomatous polyposis coli* |
| 848 | AAA-TAA | Lys-Term | *Adenomatous polyposis coli* |
| 876 | CGA-TGA | Arg-Term | *Adenomatous polyposis coli* |
| 879 | CAG-TAG | Gln-Term | *Adenomatous polyposis coli* |
| 893 | GAA-TAA | Glu-Term | *Adenomatous polyposis coli* |
| 932 | TCA-TAA | Ser-Term | *Adenomatous polyposis coli* |
| 932 | TCA-TGA | Ser-Term | *Adenomatous polyposis coli* |
| 935 | TAC-TAG | Tyr-Term | *Adenomatous polyposis coli* |
| 935 | TAC-TAA | Tyr-Term | *Adenomatous polyposis coli* |
| 995 | TGC-TGA | Cys-Term | *Adenomatous polyposis coli* |
| 997 | TAT-TAG | Tyr-Term | *Adenomatous polyposis coli* |
| 999 | CAA-TAA | Gln-Term | *Adenomatous polyposis coli* |
| 1000 | TAC-TAA | Tyr-Term | *Adenomatous polyposis coli* |

TABLE VII-continued

NUCLEOTIDE SUBSTITUTIONS

| Codon | Nucleotide | Amino acid | Phenotype |
|---|---|---|---|
| 1020 | GAA-TAA | Glu-Term | *Adenomatous polyposis coli* |
| 1032 | TCA-TAA | Ser-Term | *Adenomatous polyposis coli* |
| 1041 | CAA-TAA | Gln-Term | *Adenomatous polyposis coli* |
| 1044 | TCA-TAA | Ser-Term | *Adenomatous polyposis coli* |
| 1045 | CAG-TAG | Gln-Term | *Adenomatous polyposis coli* |
| 1049 | TGG-TGA | Trp-Term | *Adenomatous polyposis coli* |
| 1067 | CAA-TAA | Gln-Term | *Adenomatous polyposis coli* |
| 1071 | CAA-TAA | Gln-Term | *Adenomatous polyposis coli* |
| 1075 | TAT-TAA | Tyr-Term | *Adenomatous polyposis coli* |
| 1075 | TAT-TAG | Tyr-Term | *Adenomatous polyposis coli* |
| 1102 | TAC-TAG | Tyr-Term | *Adenomatous polyposis coli* |
| 1110 | TCA-TGA | Ser-Term | *Adenomatous polyposis coli* |
| 1114 | CGA-TGA | Arg-Term | *Adenomatous polyposis coli* |
| 1123 | CAA-TAA | Gln-Term | *Adenomatous polyposis coli* |
| 1135 | TAT-TAG | Tyr-Term | *Adenomatous polyposis coli* |
| 1152 | CAG-TAG | Gln-Term | *Adenomatous polyposis coli* |
| 1155 | GAA-TAA | Glu-Term | *Adenomatous polyposis coli* |
| 1168 | GAA-TAA | Glu-Term | *Adenomatous polyposis coli* |
| 1175 | CAG-TAG | Gln-Term | *Adenomatous polyposis coli* |
| 1176 | CCT-CTT | Pro-Leu | *Adenomatous polyposis coli* |
| 1184 | GCC-CCC | Ala-Pro | *Adenomatous polyposis coli* |
| 1193 | CAG-TAG | Gln-Term | *Adenomatous polyposis coli* |
| 1194 | TCA-TGA | Ser-Term | *Adenomatous polyposis coli* |
| 1198 | TCA-TGA | Ser-Term | *Adenomatous polyposis coli* |
| 1201 | TCA-TGA | Ser-Term | *Adenomatous polyposis coli* |
| 1228 | CAG-TAG | Gln-Term | *Adenomatous polyposis coli* |
| 1230 | CAG-TAG | Gln-Term | *Adenomatous polyposis coli* |
| 1244 | CAA-TAA | Gln-Term | *Adenomatous polyposis coli* |
| 1249 | TGC-TGA | Cys-Term | *Adenomatous polyposis coli* |
| 1256 | CAA-TAA | Gln-Term | *Adenomatous polyposis coli* |
| 1262 | TAT-TAA | Tyr-Term | *Adenomatous polyposis coli* |
| 1270 | TGT-TGA | Cys-Term | *Adenomatous polyposis coli* |
| 1276 | TCA-TGA | Ser-Term | *Adenomatous polyposis coli* |
| 1278 | TCA-TAA | Ser-Term | *Adenomatous polyposis coli* |
| 1286 | GAA-TAA | Gln-Term | *Adenomatous polyposis coli* |
| 1289 | TGT-TGA | Cys-Term | *Adenomatous polyposis coli* |
| 1294 | GAG-TAG | Gln-Term | *Adenomatous polyposis coli* |
| 1307 | ATA-AAA | Ile-Lys | Colorectal cancer, predisposition to, association |
| 1309 | GAA-TAA | Glu-Term | *Adenomatous polyposis coli* |
| 1317 | GAA-CAA | Glu-Gln | Colorectal cancer, predisposition to |
| 1328 | CAG-TAG | Gln-Term | *Adenomatous polyposis coli* |
| 1338 | CAG-TAG | Gln-Term | *Adenomatous polyposis coli* |
| 1342 | TTA-TAA | Leu-Term | *Adenomatous polyposis coli* |
| 1342 | TTA-TGA | Leu-Term | *Adenomatous polyposis coli* |
| 1348 | AGG-TGG | Arg-Trp | *Adenomatous polyposis coli* |
| 1357 | GGA-TGA | Gly-Term | *Adenomatous polyposis coli* |
| 1367 | CAG-TAG | Gln-Term | *Adenomatous polyposis coli* |
| 1370 | AAA-TAA | Lys-Term | *Adenomatous polyposis coli* |
| 1392 | TCA-TAA | Ser-Term | *Adenomatous polyposis coli* |
| 1392 | TCA-TGA | Ser-Term | *Adenomatous polyposis coli* |
| 1397 | GAG-TAG | Glu-Term | *Adenomatous polyposis coli* |
| 1449 | AAG-TAG | Lys-Term | *Adenomatous polyposis coli* |
| 1450 | CGA-TGA | Arg-Term | *Adenomatous polyposis coli* |
| 1451 | GAA-TAA | Glu-Term | *Adenomatous polyposis coli* |
| 1503 | TCA-TAA | Ser-Term | *Adenomatous polyposis coli* |
| 1517 | CAG-TAG | Gln-Term | *Adenomatous polyposis coli* |
| 1529 | CAG-TAG | Gln-Term | *Adenomatous polyposis coli* |
| 1539 | TCA-TAA | Ser-Term | *Adenomatous polyposis coli* |
| 1541 | CAG-TAG | Gln-Term | *Adenomatous polyposis coli* |
| 1564 | TTA-TAA | Leu-Term | *Adenomatous polyposis coli* |
| 1567 | TCA-TGA | Ser-Term | *Adenomatous polyposis coli* |
| 1640 | CGG-TGG | Arg-Trp | *Adenomatous polyposis coli* |
| 1693 | GAA-TAA | Glu-Term | *Adenomatous polyposis coli* |
| 1822 | GAC-GTC | Asp-Val | *Adenomatous polyposis coli*, association with ? |
| 2038 | CTG-GTG | Leu-Val | *Adenomatous polyposis coli* |
| 2040 | GAG-TAG | Gln-Term | *Adenomatous polyposis coli* |
| 2566 | AGA-AAA | Arg-Lys | *Adenomatous polyposis coli* |
| 2621 | TCT-TGT | Ser-Cys | *Adenomatous polyposis coli* |
| 2839 | CTT-TTT | Leu-Phe | *Adenomatous polyposis coli* |

TABLE VIII

NUCLEOTIDE SUBSTITUTIONS

| Donor/Acceptor | Relative location | Substitution | Phenotype |
|---|---|---|---|
| ds | −1 | G-C | Adenomatous polyposis coli |
| as | −1 | G-A | Adenomatous polyposis coli |
| as | −1 | G-C | Adenomatous polyposis coli |
| ds | +2 | T-A | Adenomatous polyposis coli |
| as | −1 | G-C | Adenomatous polyposis coli |
| as | −1 | G-T | Adenomatous polyposis coli |
| as | −1 | G-A | Adenomatous polyposis coli |
| as | −2 | A-C | Adenomatous polyposis coli |
| as | −5 | A-G | Adenomatous polyposis coli |
| ds | +3 | A-C | Adenomatous polyposis coli |
| as | −1 | G-A | Adenomatous polyposis coli |
| ds | +1 | G-A | Adenomatous polyposis coli |
| as | −1 | G-T | Adenomatous polyposis coli |
| ds | +1 | G-A | Adenomatous polyposis coli |
| as | −1 | G-A | Adenomatous polyposis coli |
| ds | +1 | G-A | Adenomatous polyposis coli |
| ds | +3 | A-G | Adenomatous polyposis coli |
| ds | +5 | G-T | Adenomatous polyposis coli |
| as | −1 | G-A | Adenomatous polyposis coli |
| as | −6 | A-G | Adenomatous polyposis coli |
| as | −5 | A-G | Adenomatous polyposis coli |
| as | −2 | A-G | Adenomatous polyposis coli |
| ds | +2 | T-C | Adenomatous polyposis coli |
| as | −2 | A-G | Adenomatous polyposis coli |
| ds | +1 | G-A | Adenomatous polyposis coli |
| ds | +1 | G-T | Adenomatous polyposis coli |
| ds | +2 | T-G | Adenomatous polyposis coli |

TABLE IX

APC SMALL DELETIONS
Bold letters indicate the codon. Undercase letters represent the deletion. Where deletions extend beyond the coding region, other positional information is provided. For example, the abbreviation 5' UTR represents 5' untranslated region, and the abbreviation E6I6 denotes exon 6/intron 6 boundary.

| Location/codon | Deletion | Phenotype | SEQ ID NO: |
|---|---|---|---|
| 77 | **TTA**gata**GCAGTAATTT** | *Adenomatous polyposis coli* | 52 |
| 97 | **GGAA**Gccgggaag**GATCTGTATC** | *Adenomatous polyposis coli* | 53 |

TABLE IX-continued

APC SMALL DELETIONS
Bold letters indicate the codon. Undercase letters represent the deletion. Where deletions extend beyond the coding region, other positional information is provided. For example, the abbreviation 5' UTR represents 5' untranslated region, and the abbreviation E6I6 denotes exon 6/intron 6 boundary.

| Location/ codon | Deletion | Phenotype | SEQ ID NO: |
|---|---|---|---|
| 138 | **GAG**AaAGAGAG__E3I3__GTAA | *Adenomatous polyposis coli* | 54 |
| 139 | **AAA**GAgag__E3I3__Gtaacttttct | Thyroid cancer | 55 |
| 139 | **AAA**Gagag__E3I3__GTAACTTTTC | *Adenomatous polyposis coli* | 56 |
| 142 | TTTTAAAAAAaAAAAATAG__I3E4__G**TCA** | *Adenomatous polyposis coli* | 57 |
| 144 | AAAATAG__I3E4__GTCatTG**CTT**CTTGC | *Adenomatous polyposis coli* | 58 |
| 149 | **GAC**AaaGAAGAAAAGG | *Adenomatous polyposis coli* | 59 |
| 149 | **GAC**AAagaaGAAAAGGAAA | *Adenomatous polyposis coli* | 60 |
| 155 | AGGAA ^ **AAA**GActggtATTACGCTCA | *Adenomatous polyposis coli* | 61 |
| 169 | AAAAGA ^ **ATA**GatagTCTTCCTTTA | *Adenomatous polyposis coli* | 62 |
| 172 | AGATAGT ^ **CTT**cCTTTAACTGA | *Adenomatous polyposis coli* | 63 |
| 179 | **TCC**TTacaaACAGATATGA | *Adenomatous polyposis coli* | 64 |
| 185 | **ACC**aGAAGGCAATT | *Adenomatous polyposis coli* | 65 |
| 196 | **ATC**AGagTTGCGATGGA | *Adenomatous polyposis coli* | 66 |
| 213 | **CGA**GCaCAG__E5I5__GTAAGTT | *Adenomatous polyposis coli* | 67 |
| 298 | **CAC**tcTGCACCTCGA | *Adenomatous polyposis coli* | 68 |
| 329 | **GAT**aTGTCGCGAAC | *Adenomatous polyposis coli* | 69 |
| 365 | **AAA**GActCTGTATTGTT | *Adenomatous polyposis coli* | 70 |
| 397 | **GAC**aaGAGAGGCAGG | *Adenomatous polyposis coli* | 71 |
| 427 | **CAT**GAacCAGGCATGGA | *Adenomatous polyposis coli* | 72 |
| 428 | **GAA**CCaGGCATGGACC | *Adenomatous polyposis coli* | 73 |
| 436 | **AAT**CCaa__E9I9__gTATGTTCTCT | *Adenomatous polyposis coli* | 74 |
| 440 | **GCT**CCtGTTGAACATC | *Adenomatous polyposis coli* | 75 |
| 455 | **AAA**CTtTCATTTGATG | *Adenomatous polyposis coli* | 76 |
| 455 | **AAA**CtttcaTTTGATGAAG | *Adenomatous polyposis coli* | 77 |
| 472 | **CTA**cAGGCCATTGC | *Adenomatous polyposis coli* | 78 |
| 472 | TAAATTAG__I10E11__GGgGA**CTA**CAGGC | *Adenomatous polyposis coli* | 79 |
| 478 | **TTA**TtGCAAGTGGAC | *Adenomatous polyposis coli* | 80 |
| 486 | **TAC**GgGCTTACTAAT | *Adenomatous polyposis coli* | 81 |
| 494 | **AGT**ATtACACTAAGAC | *Adenomatous polyposis coli* | 82 |
| 495 | **ATT**ACacTAAGACGATA | *Adenomatous polyposis coli* | 83 |
| 497 | **CTA**aGACGATATGC | *Adenomatous polyposis coli* | 84 |
| 520 | **TGC**TCtaTGAAAGGCTG | *Adenomatous polyposis coli* | 85 |
| 526 | **ATG**AGagcacttgtgGCCCAACTAA | *Adenomatous polyposis coli* | 86 |
| 539 | **GAC**TTaCAGCAG__E12I12__GTAC | *Adenomatous polyposis coli* | 87 |
| 560 | **AAA**AAgaCGTTGCGAGA | *Adenomatous polyposis coli* | 88 |

TABLE IX-continued

APC SMALL DELETIONS
Bold letters indicate the codon. Undercase letters represent the deletion. Where deletions extend beyond the coding region, other positional information is provided. For example, the abbreviation 5' UTR represents 5' untranslated region, and the abbreviation E6I6 denotes exon 6/intron 6 boundary.

| Location/ codon | Deletion | Phenotype | SEQ ID NO: |
|---|---|---|---|
| 566 | **GTT**GgaagtGTGAAAGCAT | *Adenomatous polyposis coli* | 89 |
| 570 | **AAA**GCaTTGATGGAAT | *Adenomatous polyposis coli* | 90 |
| 577 | **TTA**GaagtTAAAAAG__E13I13__GTA | *Adenomatous polyposis coli* | 91 |
| 584 | **ACC**CTcAAAAGCGTAT | *Adenomatous polyposis coli* | 92 |
| 591 | **GCC**TtATGGAATTTG | *Adenomatous polyposis coli* | 93 |
| 608 | **GCT**gTAGATGGTGC | *Adenomatous polyposis coli* | 94 |
| 617 | **GTT**ggcactcttacttaccGGAGCCAGAC | *Adenomatous polyposis coli* | 95 |
| 620 | **CTT**ACttacCGGAGCCAGA | *Adenomatous polyposis coli* | 96 |
| 621 | **ACT**TaCCGGAGCCAG | *Adenomatous polyposis coli* | 97 |
| 624 | **AGC**caGACAAACACT | *Adenomatous polyposis coli* | 98 |
| 624 | **AGC**CagacAAACACTTTA | *Adenomatous polyposis coli* | 99 |
| 626 | **ACA**aacaCTTTAGCCAT | *Adenomatous polyposis coli* | 100 |
| 629 | **TTA**GCcATTATTGAAA | *Adenomatous polyposis coli* | 101 |
| 635 | **GGA**GgTGGGATATTA | *Adenomatous polyposis coli* | 102 |
| 638 | **ATA**TtACGGAATGTG | *Adenomatous polyposis coli* | 103 |
| 639 | **TTA**CGgAATGTGTCCA | *Adenomatous polyposis coli* | 104 |
| 657 | **AGA**gaGAACAACTGT | *Adenomatous polyposis coli* | 105 |
| 659 | TATTTCAG__I14E15__GCaaatcctaag agag**AAC**AACTGTC | *Adenomatous polyposis coli* | 106 |
| 660 | **AAC**TgtCTACAAACTT | *Adenomatous polyposis coli* | 107 |
| 665 | **TTA**ttACAACACTTA | *Adenomatous polyposis coli* | 108 |
| 668 | **CAC**ttAAAATCTCAT | *Adenomatous polyposis coli* | 109 |
| 673 | **AGT**ttgacaatagtCAGTAATGCA | *Adenomatous polyposis coli* | 110 |
| 768 | **CAC**TTaTCAGAAACTT | *Adenomatous polyposis coli* | 111 |
| 769 | **TTA**TcAGAAACTTTT | *Adenomatous polyposis coli* | 112 |
| 770 | **TCA**GAaACTTTTGACA | *Adenomatous polyposis coli* | 113 |
| 780 | **AGT**CcCAAGGCATCT | *Adenomatous polyposis coli* | 114 |
| 792 | **AAG**CaAAGTCTCTAT | *Adenomatous polyposis coli* | 115 |
| 792 | **AAG**CAaaGTCTCTATGG | *Adenomatous polyposis coli* | 116 |
| 793 | **CAA**AgTCTCTATGGT | *Adenomatous polyposis coli* | 117 |
| 798 | **GAT**TatGTTTTTGACA | *Adenomatous polyposis coli* | 118 |
| 802 | **GAC**ACcaatcgacatGATGATAATA | *Adenomatous polyposis coli* | 119 |
| 805 | **CGA**CatGATGATAATA | *Adenomatous polyposis coli* | 120 |
| 811 | **TCA**GacaaTTTTAATACT | *Adenomatous polyposis coli* | 121 |
| 825 | **TAT**tTGAATACTAC | *Adenomatous polyposis coli* | 122 |
| 827 | **AAT**AcTACAGTGTTA | *Adenomatous polyposis coli* | 123 |

TABLE IX-continued

APC SMALL DELETIONS
Bold letters indicate the codon. Undercase letters represent the deletion. Where deletions extend beyond the coding region, other positional information is provided. For example, the abbreviation 5' UTR represents 5' untranslated region, and the abbreviation E6I6 denotes exon 6/intron 6 boundary.

| Location/ codon | Deletion | Phenotype | SEQ ID NO: |
|---|---|---|---|
| 830 | **GTG**TTacccagctcctctTCATCAAGAG | *Adenomatous polyposis coli* | 124 |
| 833 | **AGC**TCcTCTTCATCAA | *Adenomatous polyposis coli* | 125 |
| 836 | **TCA**TcAAGAGGAAGC | *Adenomatous polyposis coli* | 126 |
| 848 | **AAA**GAtaGAAGTTTGGA | *Adenomatous polyposis coli* | 127 |
| 848 | **AAA**GatagaagTTTGGAGAGA | *Adenomatous polyposis coli* | 128 |
| 855 | **GAA**CgCGGAATTGGT | *Adenomatous polyposis coli* | 129 |
| 856 | **CGC**GgaattGGTCTAGGCA | *Adenomatous polyposis coli* | 130 |
| 856 | **CGC**GgAATTGGTCTA | *Adenomatous polyposis coli* | 131 |
| 879 | **CAG**aTCTCCACCAC | *Adenomatous polyposis coli* | 132 |
| 902 | **GAA**GAcagaAGTTCTGGGT | *Adenomatous polyposis coli* | 133 |
| 907 | **GGG**TcTACCACTGAA | *Adenomatous polyposis coli* | 134 |
| 915 | **GTG**ACaGATGAGAGAA | *Adenomatous polyposis coli* | 135 |
| 929 | **CAT**ACacatTCAAACACTT | *Adenomatous polyposis coli* | 136 |
| 930 | **ACA**CAttcaAACACTTACA | *Adenomatous polyposis coli* | 137 |
| 931 | **CAT**tCAAACACTTA | *Adenomatous polyposis coli* | 138 |
| 931 | **CAT**TcAAACACTTAC | *Adenomatous polyposis coli* | 139 |
| 933 | **AAC**acttACAATTTCAC | *Adenomatous polyposis coli* | 140 |
| 935 | **TAC**AatttcactAAGTCGGAAA | *Adenomatous polyposis coli* | 141 |
| 937 | **TTC**ActaaGTCGGAAAAT | *Adenomatous polyposis coli* | 142 |
| 939 | **AAG**tcggAAAATTCAAA | *Adenomatous polyposis coli* | 143 |
| 946 | **ACA**TgTTCTATGCCT | *Adenomatous polyposis coli* | 144 |
| 954 | **TTA**GaaTACAAGAGAT | *Adenomatous polyposis coli* | 145 |
| 961 | **AAT**gATAGTTTAAA | *Adenomatous polyposis coli* | 146 |
| 963 | **AGT**TTaAATAGTGTCA | *Adenomatous polyposis coli* | 147 |
| 964 | **TTA**aataGTGTCAGTAG | *Adenomatous polyposis coli* | 148 |
| 973 | **TAT**GgTAAAAGAGGT | *Adenomatous polyposis coli* | 149 |
| 974 | **GGT**AAaAGAGGTCAAA | *Adenomatous polyposis coli* | 150 |
| 975 | **AAA**AgaGGTCAAATGA | Thyroid cancer | 151 |
| 992 | **AGT**AAgTTTTGCAGTT | Thyroid cancer | 152 |
| 993 | **AAG**ttttgcagttaTGGTCAATAC | *Adenomatous polyposis coli* | 153 |
| 999 | **CAA**tacccagCCGACCTAGC | *Adenomatous polyposis coli* | 154 |
| 1023 | **ACA**CcAATAAATTAT | *Adenomatous polyposis coli* | 155 |
| 1030 | **AAA**tATTCAGATGA | *Adenomatous polyposis coli* | 156 |
| 1032 | **TCA**GatgagCAGTTGAACT | *Adenomatous polyposis coli* | 157 |
| 1033 | **GAT**GaGCAGTTGAAC | *Adenomatous polyposis coli* | 158 |
| 1049 | **TGG**GcAAGACCCAAA | *Adenomatous polyposis coli* | 159 |

TABLE IX-continued

APC SMALL DELETIONS
Bold letters indicate the codon. Undercase letters represent the deletion. Where deletions extend beyond the coding region, other positional information is provided. For example, the abbreviation 5' UTR represents 5' untranslated region, and the abbreviation E6I6 denotes exon 6/intron 6 boundary.

| Location/ codon | Deletion | Phenotype | SEQ ID NO: |
|---|---|---|---|
| 1054 | **CAC**AtaataGAAGATGAAA | *Adenomatous polyposis coli* | 160 |
| 1055 | **ATA**AtagaaGATGAAATAA | *Adenomatous polyposis coli* | 161 |
| 1056 | **ATA**GAaGATGAAATAA | *Adenomatous polyposis coli* | 162 |
| 1060 | **ATA**AAacaaaGTGAGCAAAG | *Adenomatous polyposis coli* | 163 |
| 1061 | **AAA**caaaGTGAGCAAAG | *Adenomatous polyposis coli* | 164 |
| 1061 | **AAA**CaaAGTGAGCAAA | *Adenomatous polyposis coli* | 165 |
| 1062 | **CAA**AgtgaGCAAAGACAA | *Adenomatous polyposis coli* | 166 |
| 1065 | **CAA**AGacAATCAAGGAA | *Adenomatous polyposis coli* | 167 |
| 1067 | **CAA**tcaaGGAATCAAAG | *Adenomatous polyposis coli* | 168 |
| 1071 | **CAA**AgtACAACTTATC | *Adenomatous polyposis coli* | 169 |
| 1079 | **ACT**GagAGCACTGATG | *Adenomatous polyposis coli* | 170 |
| 1082 | **ACT**GAtgATAAACACCT | *Adenomatous polyposis coli* | 171 |
| 1084 | **GAT**aaacACCTCAAGTT | *Adenomatous polyposis coli* | 172 |
| 1086 | **CAC**CtcAAGTTCCAAC | *Adenomatous polyposis coli* | 173 |
| 1093 | **TTT**GgACAGCAGGAA | *Adenomatous polyposis coli* | 174 |
| 1098 | **TGT**gtTTCTCCATAC | *Adenomatous polyposis coli* | 175 |
| 1105 | **CGG**gGAGCCAATGG | Thyroid cancer | 176 |
| 1110 | **TCA**GAaACAAATCGAG | *Adenomatous polyposis coli* | 177 |
| 1121 | **ATT**AAtcaaAATGTAAGCC | *Adenomatous polyposis coli* | 178 |
| 1131 | **CAA**gAAGATGACTA | *Adenomatous polyposis coli* | 179 |
| 1134 | **GAC**TAtGAAGATGATA | *Adenomatous polyposis coli* | 180 |
| 1137 | **GAT**gataaGCCTACCAAT | *Adenomatous polyposis coli* | 181 |
| 1146 | **CGT**TAcTCTGAAGAAG | *Adenomatous polyposis coli* | 182 |
| 1154 | **GAA**GaagaaGAGAGACCAA | *Adenomatous polyposis coli* | 183 |
| 1155 | **GAA**GaagaGAGACCAACA | *Adenomatous polyposis coli* | 184 |
| 1156 | **GAA**gagaGACCAACAAA | *Adenomatous polyposis coli* | 185 |
| 1168 | **GAA**gagaaACGTCATGTG | *Adenomatous polyposis coli* | 186 |
| 1178 | **GAT**TAtagtttaAAATATGCCA | *Adenomatous polyposis coli* | 187 |
| 1181 | **TTA**AaATATGCCACA | *Adenomatous polyposis coli* | 188 |
| 1184 | **GCC**acagaTATTCCTTCA | *Adenomatous polyposis coli* | 189 |
| 1185 | **ACA**gaTATTCCTTCA | *Adenomatous polyposis coli* | 190 |
| 1190 | **TCA**CAgAAACAGTCAT | *Adenomatous polyposis coli* | 191 |
| 1192 | **AAA**caGTCATTTTCA | *Adenomatous polyposis coli* | 192 |
| 1198 | **TCA**aaGAGTTCATCT | *Adenomatous polyposis coli* | 193 |
| 1207 | **AAA**AcCGAACATATG | *Adenomatous polyposis coli* | 194 |

TABLE IX-continued

APC SMALL DELETIONS
Bold letters indicate the codon. Undercase letters represent the deletion. Where deletions extend beyond the coding region, other positional information is provided. For example, the abbreviation 5' UTR represents 5' untranslated region, and the abbreviation E6I6 denotes exon 6/intron 6 boundary.

| Location/ codon | Deletion | Phenotype | SEQ ID NO: |
|---|---|---|---|
| 1208 | **ACC**gaacATATGTCTTC | *Adenomatous polyposis coli* | 195 |
| 1210 | **CAT**atGTCTTCAAGC | *Adenomatous polyposis coli* | 196 |
| 1233 | **CCA**AGtTCTGCACAGA | *Adenomatous polyposis coli* | 197 |
| 1249 | **TGC**AaaGTTTCTTCTA | *Adenomatous polyposis coli* | 198 |
| 1259 | **ATA**caGACTTATTGT | *Adenomatous polyposis coli* | 199 |
| 1260 | **CAG**ACttATTGTGTAGA | *Adenomatous polyposis coli* | 200 |
| 1268 | **CCA**aTATGTTTTTC | *Adenomatous polyposis coli* | 201 |
| 1275 | **AGT**tCATTATCATC | *Adenomatous polyposis coli* | 202 |
| 1294 | **CAG**GAaGCAGATTCTG | *Adenomatous polyposis coli* | 203 |
| 1301 | **ACC**CtGCAAATAGCA | *Adenomatous polyposis coli* | 204 |
| 1306 | **GAA**AtaaaAGAAAAGATT | *Adenomatous polyposis coli* | 205 |
| 1307 | **ATA**aAAGAAAAGAT | *Adenomatous polyposis coli* | 206 |
| 1308 | **AAA**gaaaAGATTGGAAC | *Adenomatous polyposis coli* | 207 |
| 1308 | **AAA**GAaaagaTTGGAACTAG | *Adenomatous polyposis coli* | 208 |
| 1318 | **GAT**CcTGTGAGCGAA | *Adenomatous polyposis coli* | 209 |
| 1320 | **GTG**AGcGAAGTTCCAG | *Adenomatous polyposis coli* | 210 |
| 1323 | **GTT**CcAGCAGTGTCA | *Adenomatous polyposis coli* | 211 |
| 1329 | **CAC**CctagaaccAAATCCAGCA | *Adenomatous polyposis coli* | 212 |
| 1336 | **AGA**CtgCAGGGTTCTA | *Adenomatous polyposis coli* | 213 |
| 1338 | **CAG**gGTTCTAGTTT | *Adenomatous polyposis coli* | 214 |
| 1340 | **TCT**AgTTTATCTTCA | *Adenomatous polyposis coli* | 215 |
| 1342 | **TTA**TcTTCAGAATCA | *Adenomatous polyposis coli* | 216 |
| 1352 | **GTT**gAATTTTCTTC | *Adenomatous polyposis coli* | 217 |
| 1361 | **CCC**TcCAAAAGTGGT | *Adenomatous polyposis coli* | 218 |
| 1364 | **AGT**ggtgCTCAGACACC | *Adenomatous polyposis coli* | 219 |
| 1371 | **AGT**CCacCTGAACACTA | *Adenomatous polyposis coli* | 220 |
| 1372 | **CCA**CCtGAACACTATG | *Adenomatous polyposis coli* | 221 |
| 1376 | **TAT**GttCAGGAGACCC | *Adenomatous polyposis coli* | 222 |
| 1394 | **GAT**AgtTTTGAGAGTC | *Adenomatous polyposis coli* | 223 |
| 1401 | **ATT**GCcAGCTCCGTTC | *Adenomatous polyposis coli* | 224 |
| 1415 | **AGT**GGcATTATAAGCC | *Adenomatous polyposis coli* | 225 |
| 1426 | **AGC**CcTGGACAAACC | *Adenomatous polyposis coli* | 226 |
| 1427 | **CCT**GGaCAAACCATGC | *Adenomatous polyposis coli* | 227 |
| 1431 | **ATG**CcACCAAGCAGA | *Adenomatous polyposis coli* | 228 |
| 1454 | **AAA**AAtAAAGCACCTA | *Adenomatous polyposis coli* | 229 |

TABLE IX-continued

APC SMALL DELETIONS
Bold letters indicate the codon. Undercase letters represent the deletion. Where deletions extend beyond the coding region, other positional information is provided. For example, the abbreviation 5' UTR represents 5' untranslated region, and the abbreviation E6I6 denotes exon 6/intron 6 boundary.

| Location/ codon | Deletion | Phenotype | SEQ ID NO: |
|---|---|---|---|
| 1461 | **GAA**aAGAGAGAGAG | *Adenomatous polyposis coli* | 230 |
| 1463 | **AGA**gagaGTGGACCTAA | *Adenomatous polyposis coli* | 231 |
| 1464 | **GAG**AgTGGACCTAAG | *Adenomatous polyposis coli* | 232 |
| 1464 | **GAG**AgtGGACCTAAGC | *Adenomatous polyposis coli* | 233 |
| 1464 | **GAG**agTGGACCTAAG | *Adenomatous polyposis coli* | 234 |
| 1492 | **GCC**aCGGAAAGTAC | *Adenomatous polyposis coli* | 235 |
| 1493 | **ACG**GAaAGTACTCCAG | *Adenomatous polyposis coli* | 236 |
| 1497 | **CCA**gATGGATTTTC | *Adenomatous polyposis coli* | 237 |
| 1503 | **TCA**tccaGCCTGAGTGC | *Adenomatous polyposis coli* | 238 |
| 1522 | **TTA**agaataaTGCCTCCAGT | *Adenomatous polyposis coli* | 239 |
| 1536 | **GAA**ACagAATCAGAGCA | *Adenomatous polyposis coli* | 240 |
| 1545 | **TCA**AAtgaaaACCAAGAGAA | *Adenomatous polyposis coli* | 241 |
| 1547 | **GAA**aACCAAGAGAA | *Adenomatous polyposis coli* | 242 |
| 1550 | **GAG**AaagaGGCAGAAAAA | *Adenomatous polyposis coli* | 243 |
| 1577 | **GAA**TgtATTATTTCTG | *Adenomatous polyposis coli* | 244 |
| 1594 | **CCA**GCcCAGACTGCTT | *Adenomatous polyposis coli* | 245 |
| 1596 | **CAG**ACtGCTTCAAAAT | *Adenomatous polyposis coli* | 246 |
| 1823 | **TTC**AaTGATAAGCTC | *Adenomatous polyposis coli* | 247 |
| 1859 | **AAT**GAttctTTGAGTTCTC | *Adenomatous polyposis coli* | 248 |
| 1941 | **CCA**GAcagaGGGGCAGCAA | Desmoid tumours | 249 |
| 1957 | **GAA**aATACTCCAGT | *Adenomatous polyposis coli* | 250 |
| 1980 | **AAC**aATAAAGAAAA | *Adenomatous polyposis coli* | 251 |
| 1985 | **GAA**CCtATCAAAGAGA | *Adenomatous polyposis coli* | 252 |
| 1986 | **CCT**aTCAAAGAGAC | *Adenomatous polyposis coli* | 253 |
| 1998 | **GAA**CcAAGTAAACCT | *Adenomatous polyposis coli* | 254 |
| 2044 | **AGC**TCcGCAATGCCAA | *Adenomatous polyposis coli* | 255 |
| 2556 | **TCA**TCccttcctcGAGTAAGCAC | *Adenomatous polyposis coli* | 256 |
| 2643 | **CTA**ATttatCAAATGGCAC | *Adenomatous polyposis coli* | 257 |

TABLE X

SMALL INSERTIONS

| Codon | Insertion | Phenotype |
|---|---|---|
| 157 | T | Adenomatous polyposis coli |
| 170 | AGAT | Adenomatous polyposis coli |
| 172 | T | Adenomatous polyposis coli |
| 199 | G | Adenomatous polyposis coli |

TABLE X-continued

SMALL INSERTIONS

| Codon | Insertion | Phenotype |
|---|---|---|
| 243 | AG | Adenomatous polyposis coli |
| 266 | T | Adenomatous polyposis coli |
| 357 | A | Adenomatous polyposis coli |
| 405 | C | Adenomatous polyposis coli |

TABLE X-continued

| SMALL INSERTIONS | | |
|---|---|---|
| Codon | Insertion | Phenotype |
| 413 | T | Adenomatous polyposis coli |
| 416 | A | Adenomatous polyposis coli |
| 457 | G | Adenomatous polyposis coli |
| 473 | A | Adenomatous polyposis coli |
| 503 | ATTC | Adenomatous polyposis coli |
| 519 | C | Adenomatous polyposis coli |
| 528 | A | Adenomatous polyposis coli |
| 561 | A | Adenomatous polyposis coli |
| 608 | A | Adenomatous polyposis coli |
| 620 | CT | Adenomatous polyposis coli |
| 621 | A | Adenomatous polyposis coli |
| 623 | TTAC | Adenomatous polyposis coli |
| 627 | A | Adenomatous polyposis coli |
| 629 | A | Adenomatous polyposis coli |
| 636 | GT | Adenomatous polyposis coli |
| 639 | A | Adenomatous polyposis coli |
| 704 | T | Adenomatous polyposis coli |
| 740 | ATGC | Adenomatous polyposis coli |
| 764 | T | Adenomatous polyposis coli |
| 779 | TT | Adenomatous polyposis coli |
| 807 | AT | Adenomatous polyposis coli |
| 827 | AT | Adenomatous polyposis coli |
| 831 | A | Adenomatous polyposis coli |
| 841 | CTTA | Adenomatous polyposis coli |
| 865 | CT | Adenomatous polyposis coli |
| 865 | AT | Adenomatous polyposis coli |
| 900 | TG | Adenomatous polyposis coli |
| 921 | G | Adenomatous polyposis coli |
| 927 | A | Adenomatous polyposis coli |
| 935 | A | Adenomatous polyposis coli |
| 936 | C | Adenomatous polyposis coli |
| 975 | A | Adenomatous polyposis coli |
| 985 | T | Adenomatous polyposis coli |
| 997 | A | Adenomatous polyposis coli |
| 1010 | TA | Adenomatous polyposis coli |
| 1085 | C | Adenomatous polyposis coli |
| 1085 | AT | Adenomatous polyposis coli |
| 1095 | A | Adenomatous polyposis coli |
| 1100 | GTTT | Adenomatous polyposis coli |
| 1107 | GGAG | Adenomatous polyposis coli |
| 1120 | G | Adenomatous polyposis coli |
| 1166 | A | Adenomatous polyposis coli |
| 1179 | T | Adenomatous polyposis coli |
| 1187 | A | Adenomatous polyposis coli |
| 1211 | T | Adenomatous polyposis coli |
| 1256 | A | Adenomatous polyposis coli |
| 1265 | T | Adenomatous polyposis coli |
| 1267 | GATA | Adenomatous polyposis coli |
| 1268 | T | Adenomatous polyposis coli |
| 1301 | A | Adenomatous polyposis coli |
| 1301 | C | Adenomatous polyposis coli |
| 1323 | A | Adenomatous polyposis coli |
| 1342 | T | Adenomatous polyposis coli |
| 1382 | T | Adenomatous polyposis coli |
| 1458 | GTAG | Adenomatous polyposis coli |
| 1463 | AG | Adenomatous polyposis coli |
| 1488 | T | Adenomatous polyposis coli |
| 1531 | A | Adenomatous polyposis coli |
| 1533 | T | Adenomatous polyposis coli |
| 1554 | A | Adenomatous polyposis coli |
| 1555 | A | Adenomatous polyposis coli |
| 1556 | T | Adenomatous polyposis coli |
| 1563 | GACCT | Adenomatous polyposis coli |
| 1924 | AA | Desmoid tumours |

TABLE XI

| SMALL INSERTIONS/DELETIONS | | | | |
|---|---|---|---|---|
| Location/codon | Deletion | Insertion | Phenotype | SEQ ID NO: |
| 538 | **GAA**GAcTTACAGCAGG | gaa | *Adenomatous polyposis coli* | 258 |
| 620 | **CTT**ACttaCCGGAGCCAG | ct | *Adenomatous polyposis coli* | 259 |
| 728 | **AAT**ctcatGGCAAATAGG | ttgcagctttaa | *Adenomatous polyposis coli* | 260 and 261 |
| 971 | **GAT**GgtTATGGTAAAA | taa | *Adenomatous polyposis coli* | 262 |

TABLE XII

| GROSS DELETIONS | |
|---|---|
| 2 kb including ex. 11 | Adenomatous polyposis coli |
| 3 kb I10E11 − 1.5 kb to I12E13 − 170 bp | Adenomatous polyposis coli |
| 335 bp nt. 1409-1743 ex. 11-13 | Adenomatous polyposis coli |
| 6 kb incl. ex. 14 | Adenomatous polyposis coli |
| 817 bp I13E14 − 679 to I13E14 + 138 | Adenomatous polyposis coli |
| ex. 11-15M | Adenomatous polyposis coli |
| ex. 11-3'UTR | Adenomatous polyposis coli |
| ex. 15A-ex. 15F | Adenomatous polyposis coli |
| ex. 4 | Adenomatous polyposis coli |
| ex. 7, 8 and 9 | Adenomatous polyposis coli |
| ex. 8 to beyond ex. 15F | Adenomatous polyposis coli |
| ex. 8-ex. 15F | Adenomatous polyposis coli |
| ex. 9 | Adenomatous polyposis coli |
| >10 mb (del 5q22) | Adenomatous polyposis coli |

TABLE XIII

| GROSS INSERTIONS AND DUPLICATIONS | |
|---|---|
| Description | Phenotype |
| Insertion of 14 bp nt. 3816 | Adenomatous polyposis coli |
| Insertion of 22 bp nt. 4022 | Adenomatous polyposis coli |
| Duplication of 43 bp cd. 1295 | Adenomatous polyposis coli |
| Insertion of 337 bp of Alu I sequence cd. 1526 | Desmoid tumours |

TABLE XIV

| COMPLEX REARRANGEMENTS (INCLUDING INVERSIONS) | |
|---|---|
| A-T nt. 4893 Q1625H, Del C nt. 4897 cd. 1627 | Adenomatous polyposis coli |
| Del 1099 bp I13E14 − 728 to E14I14 + 156, ins 126 bp | Adenomatous polyposis coli |
| Del 1601 bp E14I14 + 27 to E14I14 + 1627, ins 180 bp | Adenomatous polyposis coli |
| Del 310 bp, ins. 15 bp nt. 4394, cd 1464 | Adenomatous polyposis coli |
| Del A and T cd. 1395 | Adenomatous polyposis coli |
| Del TC nt. 4145, Del TGT nt. 4148 | Adenomatous polyposis coli |
| Del. T, nt. 983, Del. 70 bp, nt. 985 | Adenomatous polyposis coli |
| Del. nt. 3892-3903, ins ATTT | Adenomatous polyposis coli |

TABLE XV

DIAGNOSTIC APPLICATIONS

| Cancer Type | Marker | Application | Reference |
| --- | --- | --- | --- |
| Breast | Her2/Neu Detection - polymorphism at codon 655 (GTC/valine to ATC/isoleucine [Val(655)Ile]) | Using methods described herein, design second primer such that after PCR, and digestion with restriction enzyme, a 5' overhang containing DNA sequence for codon 655 of Her2/Neu is generated. Her2/Neu can be detected and quantified as a possible marker for breast cancer. Methods described herein can detect both mutant allele and normal allele, even when mutant allele is small fraction of total DNA. Herceptin therapy for breast cancer is based upon screening for Her2. The earlier the mutant allele can be detected, the faster therapy can be provided. | D. Xie et al., J. Natl. Cancer Institute, 92, 412 (2000) K. S. Wilson et al., Am. J. Pathol., 161, 1171 (2002) L. Newman, Cancer Control, 9, 473 (2002) |
| Breast/Ovarian | Hypermethylation of BRCA1 | Methods described herein can be used to differentiate between tumors resulting from inherited BRCA1 mutations and those from non-inherited abnormal methylation of the gene | M. Esteller et al., New England Jnl Med., 344, 539 (2001) |
| Bladder | Microsatellite analysis of free tumor DNA in Urine, Serum and Plasma | Methods described herein can be applied to microsatellite analysis and FGFR3 mutation analysis for detection of bladder cancer. Methods described herein provide a non-invasive method for detection of bladder cancer. | W. G. Bas et al., Clinical Cancer Res., 9, 257 (2003) M. Utting et al., Clincal Cancer Res., 8, 35 (2002) L. Mao, D. Sidransky et al., Science, 271, 669 (1996) |
| Lung | Microsatellite analysis of DNA from sputum | Methods described herein can be used to detect mutations in sputum samples, and can markedly boost the accuracy of preclinical lung cancer screening | T. Liloglou et al., Cancer Research, 61, 1624, (2001) M. Tockman et al., Cancer Control, 7, 19 (2000) Field et al., Cancer Research, 59, 2690 (1999) |
| Cervical | Analysis of HPV genotype | Methods described herein can be used to detect HPV genotype from a cervical smear preparation. | N. Munoz et al., New England Jnl Med., 348, 518 (2003) |
| Head and Neck | Tumor specific alterations in exfoliated oral mucosal cells (microsatellite markers) | Methods described herein can be used to detect any of 23 microsatellite markers, which are associated with Head and Neck Squamous Cell Carcinoma (HNSCC). | M. Spafford et al. Clinical Cancer Research, 17, 607 (2001) A. El-Naggar et al., J. Mol. Diag., 3, 164 (2001) |
| Colorectal | Screening for mutation in K-ras2 and APC genes. | Methods described herein can be used to detect K-ras 2 mutations, which can be used as a prognostic indicator for colorectal cancer. APC (see Example 5). | B. Ryan et al. Gut, 52, 101 (2003) |
| Prostate | GSTP1 Hypermethylation | Methods described herein can be used to detect GSTP1 hypermethylation in urine from patients with prostate cancer; this can be a more accurate indicator than PSA. | P. Cairns et al. Clin. Can. Res., 7, 2727 (2001) |

TABLE XV-continued

| DIAGNOSTIC APPLICATIONS | | | |
|---|---|---|---|
| Cancer Type | Marker | Application | Reference |
| | | HIV | |
| Antiretroviral resistance | Screening individuals for mutations in HIV virus - e.g. 154V mutation or CCR5 Δ 32 allele. | Methods described herein can be used for detection of mutations in the HIV virus. Treatment outcomes are improved in individuals receiving anti-retroviral therapy based upon resistance screening. | J. Durant et al. The Lancet, 353, 2195 (1999) |
| | | Cardiology | |
| Congestive Heart Failure | Synergistic polymorphisms of beta 1 and alpha2c adrenergic receptors | Methods described herein can be used to genotype these loci and may help identify people who are at a higher risk of heart failure. | K. Small et al. New Eng. Jnl. Med., 347, 1135 (2002) |

Example 8

Single nucleotide polymorphisms (SNPS) represent the most common form of sequence variation; three million common SNPs with a population frequency of over 5% have been estimated to be present in the human genome. A genetic map using these polymorphisms as a guide is being developed (http://research.marshfieldclinic.org/genetics/; internet address as of Feb. 13, 2003).

The allele frequency varies from SNP to SNP; the allele frequency for one SNP may be 50:50, while the allele frequency for another SNP may be 90:10. The closer the allele frequency is to 50:50, the more likely any particular individual will be heterozygous at that SNP. The SNP consortium provides allele frequency information for some SNPs but not for others. www.snp.chsl.org. The allele frequency for a particular SNP provides valuable information as to the utility of that SNP for the non-invasive prenatal screening method described in Example 5. While all SNPs can be used, SNPs with allele frequencies closer to 50:50 are preferable.

Briefly, maternal blood contains fetal DNA. Maternal DNA can be distinguished from fetal DNA by examining SNPs wherein the mother is homozygous. For example, at SNP X, the maternal DNA may be homozygous for guanine. If template DNA obtained from the plasma of a pregnant female is heterozygous, as demonstrated by the detection of signals corresponding to an adenine allele and an guanine allele, the adenine allele can be used as a beacon for the fetal DNA (see Example 5). The closer the allele frequency of a SNP is to 50:50, the more likely there will be allele differences at a particular SNP between the maternal DNA and the fetal DNA.

For example, if at SNP X the observed alleles are adenine and guanine, and the SNP has an allele frequency of 90(A):10(G), it is likely that both mother and father will be homozygous for adenine at that particular SNP. Thus, both the maternal DNA and the fetal DNA will be homozygous for adenine, and there is no distinct signal for the fetal DNA. However, if at SNP X the allele frequency is 50:50, and the mother is homozygous for adenine, the probability is higher that the paternal DNA will contain a guanine allele at SNP X.

Below, a method for determining the allele frequency for a SNP is provided. Seven SNPs located on chromosome 13 were analyzed. The method is applicable for any SNP including but not limited to the SNPs on human chromosomes 1, 2, 3, 4, 5, 6, 7, 8, 9, 10, 11, 12, 13, 14, 15, 16, 17, 18, 19, 20, 21, 22, X and Y.

Preparation of Template DNA

To determine the allele frequency of a particular SNP, DNA was obtained from two hundred and fifty individuals after informed consent had been granted. From each individual, a 9 ml blood sample was collected into a sterile tube (Fischer Scientific, 9 ml EDTA Vacuette tubes, catalog number NC9897284). The tubes were spun at 1000 rpm for ten minutes. The supernatant (the plasma) of each sample was removed, and one milliliter of the remaining blood sample, which is commonly referred to as the "buffy-coat" was transferred to a new tube. One milliliter of 1× PBS was added to each sample.

Template DNA was isolated using the QIAmp DNA Blood Midi Kit supplied by QIAGEN (Catalog number 51183). The template DNA was isolated as per instructions included in the kit. From each individual, 0.76 μg of DNA was pooled together, and the pooled DNA was used in all subsequent reactions.

Design of Primers

SNP TSC0903430 was amplified using the following primer set:

```
First primer:
                                       (SEQ ID NO: 279)
5' GTCTTGCATGTAGAATTCTAGGGACGCTGCTTTTCGTC 3'

Second primer:
                                       (SEQ ID NO: 280)
5' CTCCTAGACATCGGGACTAGAATGTCCAC 3'
```

The first primer contained a recognition site for the restriction enzyme EcoRI, and was designed to anneal eighty-two bases from the locus of interest. The second primer contained the recognition site for the restriction enzyme BsmF I.

SNP TSC0337961 was amplified using the following primer set:

```
First primer:
                                          (SEQ ID NO: 281)
5' ACACAAGGCAGAGAATTCCAGTCCTGAGGGTGGGGGCC 3'

Second primer:
                                          (SEQ ID NO: 282)
5' CCGTGTTTTAACGGGACAAGCTGTTCTTC 3'
```

The first primer contained a recognition site for the restriction enzyme EcoRI, and was designed to anneal ninety-two bases from the locus of interest. The second primer contained the recognition site for the restriction enzyme BsmF I.

SNP TSC0786441 was amplified using the following primer set:

```
First primer:
                                          (SEQ ID NO: 283)
5' GTAGCGGAGGTTGAATTCTATATGTTGTCTTGGACATT 3'

Second primer:
                                          (SEQ ID NO: 284)
5' CATCAGTAGAGTGGGACGAAAGTTCTGGC 3'
```

The first primer contained a recognition site for the restriction enzyme EcoRI, and was designed to anneal one hundred and four bases from the locus of interest. The second primer contained the recognition site for the restriction enzyme BsmF I.

SNP TSC1168303 was amplified using the following primer set:

```
First primer:
                                          (SEQ ID NO: 285)
5' ATCCACGCCGCAGAATTCGTATTCATGGGCATGTCAAA 3'

Second primer:
                                          (SEQ ID NO: 286)
5' CTTGGGACTATTGGGACCAGTGTTCAATC 3'
```

The first primer contained a recognition site for the restriction enzyme EcoRI, and was designed to anneal sixty-four bases from the locus of interest. The second primer contained the recognition site for the restriction enzyme BsmF I.

SNP TSC0056188 was amplified using the following primer set:

```
First primer:
                                          (SEQ ID NO: 287)
5' CCAGAAAGCCGTGAATTCGTTAAGCCAACCTGACTCCA 3'

Second primer:
                                          (SEQ ID NO: 288)
5' TCGGGGTTAGTCGGGACATCCAGCAGCCC 3'
```

The first primer contained a recognition site for the restriction enzyme EcoRI, and was designed to anneal eighty-two bases from the locus of interest. The second primer contained the recognition site for the restriction enzyme BsmF I.

SNP TSC0466177 was amplified using the following primer set:

```
First primer:
                                          (SEQ ID NO: 289)
5' CGAAGGTAATGTGAATTCCAAAACTTAGTGCCACAATT 3'

Second primer:
                                          (SEQ ID NO: 290)
5' ATACCGCCCAACGGGACAGATCCATTGAC 3'
```

The first primer contained a recognition site for the restriction enzyme EcoRI, and was designed to anneal ninety-two bases from the locus of interest. The second primer contained the recognition site for the restriction enzyme BsmF I.

SNP TSC0197424 was amplified using the following primer set:

```
First primer:
                                          (SEQ ID NO: 291)
5' AGAAACCTGTAAGAATTCGATTCCAAATTGTTTTTTGG 3'

Second primer:
                                          (SEQ ID NO: 292)
5' CGATCATAGGGGGGGACAGGAGAGAGCAC 3'
```

The first primer contained a recognition site for the restriction enzyme EcoRI, and was designed to anneal one hundred and four bases from the locus of interest. The second primer contained the recognition site for the restriction enzyme BsmF I.

The first primer was designed to anneal at various distances from the locus of interest. The skilled artisan understands that the annealing location of the first primer can be any distance from the locus of interest including but not limited to 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-105, 106-110, 111-115, 116-120, 121-125, 126-130, 131-140, 141-160, 161-180, 181-200, 201-220, 221-240, 241-260, 261-280, 281-300, 301-350, 351-400, 401-450, 451-500, 501-1000, 1001-2000, 2001-3000, or greater than 3000.

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they can also be amplified together in a single PCR reaction. For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest. In this example, 40 ng of template human genomic DNA (a mixture of template DNA from 245 individuals) and 5 μM of each primer were used. Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results.

Purification of Fragment of Interest

The PCR products were separated from the unused PCR reagents. After the PCR reaction, ½ of the reaction volume for SNP TSC0903430, SNP TSC0337961, and SNP TSC0786441 were mixed together in a single reaction tube. One-half the reaction volumes for SNPs TSC1168303, TSC0056188, TSC0466177, and TSC0197424 were pooled together in a single reaction tube. The un-used primers, and nucleotides were removed from the reaction by using Qiagen MinElute PCR purification kits (Qiagen, Catalog Number 28004). The reactions were performed following the manufacturer's instructions supplied with the columns.

Restriction Enzyme Digestion of Isolated Fragments

The purified PCR products were digested with the restriction enzyme BsmF I, which binds to the recognition site incorporated into the PCR products from the second primer. The digests were performed in eppendorf tubes following the instructions supplied with the restriction enzyme.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

As discussed in detail in Example 6, the sequence of both alleles of a SNP can be determined with one labeled nucleotide in the presence of the other unlabeled nucleotides. The following components were added to each fill in reaction: 1 µl of fluorescently labeled ddGTP, 0.5 µl of unlabeled ddNTPs ( 40 µM), which contained all nucleotides except guanine, 2 µl of 10×sequenase buffer, 0.25 µl of Sequenase, and water as needed for a 20 µl reaction. The fill in reaction was performed at 40° C. for 10 min. Sequenase was the DNA polymerase used in this example. However, any DNA polymerase can be used for a fill-in reaction including but not limited to *E. coli* DNA polymerase, Klenow fragment of *E. coli* DNA polymerase I, T7 DNA polymerase, T4 DNA polymerase, Taq polymerase, Pfu DNA polymerase, Vent DNA polymerase, polymerase from bacteriophage 29, and REDTaq™ Genomic DNA polymerase. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565).

Detection of the Locus of Interest

The sample was loaded into a lane of a 36 cm 5% acrylamide (urea) gel (BioWhittaker Molecular Applications, Long Ranger Run Gel Packs, catalog number 50691). The sample was electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence.

Below, a schematic of the 5' overhang for SNP TSC0056188 is reproduced (where R indicates the variable site). The entire sequence is not shown, only a portion of the overhang.

| | | | | |
|---|---|---|---|---|
| 5'CCA | | | | |
| 3'GGT | R | T | C | C |
| Overhang position | 1 | 2 | 3 | 4 |

As discussed in detail in Example 6, one nucleotide labeled with one chemical moiety can be used to determine the sequence of the alleles of a locus of interest. The observed nucleotides for TSC0056188 on the 5' sense strand (here depicted as the top strand) are adenine and guanine. The third position in the overhang on the antisense strand is cytosine, which is complementary to guanine. As the variable site can be adenine or guanine, fluorescently labeled ddGTP in the presence of unlabeled dCTP, dTTP, and dATP was used to determine the sequence of both alleles. The fill-in reactions for an individual homozygous for guanine, homozygous for adenine or heterozygous are diagrammed below.

<u>Homozygous adenine:</u>

| | | | | | |
|---|---|---|---|---|---|
| | 5'CCA | **A** | A | **G*** | |
| | 3'GGT | T | T | C | C |
| Overhang position | | 1 | 2 | 3 | 4 |

<u>Homozygous guanine:</u>

| | | | | | |
|---|---|---|---|---|---|
| | 5'CCA | **G*** | | | |
| | 3'GGT | C | T | C | C |
| Overhang position | | 1 | 2 | 3 | 4 |

<u>Heterozygous:</u>

| | | | | | |
|---|---|---|---|---|---|
| Allele 1 | 5'CCA | **G*** | | | |
| | 3'GGT | C | T | C | C |
| Overhang position | | 1 | 2 | 3 | 4 |
| Allele 2 | 5'CCA | **A** | A | **G*** | |
| | 3'GGT | **T** | T | C | C |
| Overhang position | | 1 | 2 | 3 | 4 |

As seen in FIG. 14, two bands were detected for SNP TSC0056188. The lower band corresponded to DNA molecules filled in with ddGTP at position one complementary to the overhang, which is representative of the guanine allele. The higher band, separated by a single base from the lower band, corresponded to DNA molecules filled in with ddGTP at position 3 complementary to the overhang. This band represented the adenine allele. The intensity of each band was strong, indicating that each allele was well represented in the population. SNP TSC0056188 is representative of a SNP with high allele frequency.

Below, a schematic of the 5' overhang generated after digestion with BsmF I for SNP TSC0337961 is reproduced (where R indicates the variable site). The entire sequence is not shown, only a portion of the overhang.

| | | | | | |
|---|---|---|---|---|---|
| | 5' GCCA | | | | |
| | 3' CGGT | **R** | G | C | T |
| Overhang position | | 1 | 2 | 3 | 4 |

The observed nucleotides for SNP TSC0337961 on the 5' sense strand (here depicted as the top strand) are adenine and guanine. The third position in the overhang on the antisense strand was cytosine, which is complementary to guanine. As the variable site can be adenine or guanine, fluorescently labeled ddGTP in the presence of unlabeled dCTP, dTTP, and dATP was used to determine the sequence of both alleles. The fill-in reactions for an individual homozygous for guanine, homozygous for adenine or heterozygous are diagrammed below.

<u>Homozygous for guanine:</u>

| | | | | | |
|---|---|---|---|---|---|
| | 5' GCCA | **G*** | | | |
| | 3' CGGT | C | G | C | T |
| Overhang position | | 1 | 2 | 3 | 4 |

-continued

Homozygous for adenine:

| | | | | | |
|---|---|---|---|---|---|
| | 5' GCCA | **A** | C | **G*** | |
| | 3' CGGT | T | G | C | T |
| Overhang position | | 1 | 2 | 3 | 4 |

Heterozygous:

| | | | | | |
|---|---|---|---|---|---|
| Allele 1 | 5' GCCA | **G*** | | | |
| | 3' CGGT | C | G | C | T |
| Overhang position | | 1 | 2 | 3 | 4 |
| Allele 2 | 5' GCCA | **A** | C | **G*** | |
| | 3' CGGT | T | G | C | T |
| Overhang position | | 1 | 2 | 3 | 4 |

As seen in FIG. 14, one band migrating at the position of the expected lower molecular weight band was observed. This band represented the DNA molecules filled in with ddGTP at position one complementary to the overhang, which represents the guanine allele. No band corresponding to the DNA molecules filled in with ddGTP at position 3 complementary to the overhang was detected. SNP TSC0337961 is representative of a SNP that is not highly variable within the population.

Of the seven SNPs analyzed, four of the SNPs (TSC1168303, TSC0056188, TSC0466177, and TSC0197424 had high allele frequencies. Two bands of high intensity were seen for each of the four SNPs, indicating that both alleles were well represented in the population.

However, it is not necessary that the SNPs have allele frequencies of 50:50 to be useful. All SNPs provide useful information. The methods described herein provide a rapid technique for determining the allele frequency of a SNP, or any variable site including but not limited to point mutations. Allele frequencies of 50:50, 51:49, 52:48, 53:47, 54:46, 55:45, 56:46, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1 and 100:0 can be useful.

Two bands were seen for SNP TSC0903430. One band, the lower molecular weight band represented the DNA molecules filled in with labeled ddGTP. A band of weaker intensity was seen for the molecules filled in with labeled ddGTP at position 3 complementary to the overhang, which represented the cytosine allele. SNP TSC0903430 represents a SNP with low allele frequency variation. In the population, the majority of individuals carry the guanine allele, but the cytosine allele is still present.

One band of high intensity was seen for SNP TSC0337961 and SNP TSC0786441. The band detected for both SNP TSC0337961 and SNP TSC0786441 corresponded to the DNA molecules filled in with ddGTP at position 1 complementary to the overhang. No signal was detected from DNA molecules that would have been filled in at position 3 complementary to the overhang, which would have represented the second allele. SNP TSC0337961 and SNP TSC0786441 represent SNPs with little variability in the population.

As demonstrated in FIG. 14, the first primer used to amplify each locus of interest can be designed to anneal at various distances from the locus of interest. This allows multiple SNPs to be analyzed in the same reaction. By designing the first primer to anneal at specified distances from the loci of interest, any number of loci of interest can be analyzed in a single reaction including but not limited to 1-10, 11-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-300, 301-400, 401-500, and greater than 500.

As discussed in Example 6, some type IIs restriction enzymes display alternate cutting patterns. For example, the type IIS restriction enzyme BsmF I typically cuts 10/14 from its binding site; however, the enzyme also can cut 11/15 from the binding site. To eliminate the effect of the alternate cut, the labeled nucleotide used for the fill-in reaction should be chosen such that it is not complementary to position 0 of the overhang generated by the 11/15 cut (discussed in detail in Example 6). For instance, if you label with ddGTP, the nucleotide preceding the variable site on the strand that is filled in should not be a guanine.

The 11/15 overhang generated by BsmF I for SNP TSC0056188 is depicted below, with the variable site in boldtypeface:

11/15 Overhang for TSC0056188

| | | | | | |
|---|---|---|---|---|---|
| Allele 1 | 5'CC | | | | |
| | 3'GG | T | **C** | T | C |
| Overhang position | | 0 | 1 | 2 | 3 |
| Allele 2 | 5'CC | | | | |
| | 3'GG | T | **T** | T | C |
| Overhang position | | 0 | 1 | 2 | 3 |

After the fill-in reaction with labeled ddGTP, unlabeled dATP, dTTP, and dCTP, the following molecules were generated:

| | | | | | | |
|---|---|---|---|---|---|---|
| 11/15 Allele 1 | | 5'CC | A | **G*** | | |
| | | 3'GG | T | C | T | C |
| | Overhang position | | 0 | 1 | 2 | 3 |
| 11/15 Allele 2 | | 5'CC | A | **A** | A | **G*** |
| | | 3'GG | T | T | T | C |
| | Overhang position | | 0 | 1 | 2 | 3 |

Two signals were seen; one band corresponded to molecules filled in with ddGTP at position one of the overhang, and the other band corresponded to the molecules filled in with ddGTP at position 3 complementary to the overhang. These are the same DNA molecules generated after the fill-in reaction of the 10/14 overhang. Thus, the two bands can be compared without any ambiguity from the alternate cut. This method of labeling with a single nucleotide eliminates any errors generated from the alternate cutting properties of the enzymes.

The methods described herein is applicable to determining the allele frequency of any SNP including but not limited to SNPs on human chromosomes 1, 2, 3, 4, 5, 6, 7, 8, 9, 10, 11, 12, 13, 14, 15, 16, 17, 18, 19, 20, 21, 22,X and Y.

Example 9

Heterozygous SNPs, by definition, differ by one nucleotide. At a heterozygous SNP, allele 1 and allele 2 may be present at a ratio of 1:1. However, it is possible that DNA polymerases can incorporate one nucleotide at a faster rate than other nucleotides, and thus the observed ratio of a heterozygous SNP may differ from the theoretically expected 1:1 ratio.

Below, methods are described that allow efficient and accurate quantitation for the expected ratio of allele 1 to allele 2 at a heterozygous SNP.

Preparation of Template DNA

Template DNA was obtained from twenty-four individuals after informed consent had been granted. From each individual, a 9 ml blood sample was collected into a sterile tube (Fischer Scientific, 9 ml EDTA Vacuette tubes, catalog number NC9897284). The tubes were spun at 1000 rpm for ten minutes without brake. The supernatant (the plasma) of each sample was removed, and one milliliter of the remaining blood sample, which is commonly referred to as the "buffy-coat" was transferred to a new tube. One milliliter of 1× PBS was added to each sample.

Template DNA was isolated using the QIAmp DNA Blood Midi Kit supplied by QIAGEN (Catalog number 51183). The template DNA was isolated as per instructions included in the kit.

Design of Primers

SNP TSC0607185 was amplified using the following primer set:

```
First primer:
                                        (SEQ ID NO: 40)
5' ACTTGATTCCGTGAATTCGTTATCAATAAATCTTACAT 3'

Second primer:
                                        (SEQ ID NO: 41)
5' CAAGTTGGATCCGGGACCCAGGGCTAACC 3'
```

SNP TSC1130902 was amplified using the following primer set:

```
First primer:
                                        (SEQ ID NO: 34)
5' TCTAACCATTGCGAATTCAGGGCAAGGGGGGTGAGATC 3'

Second primer:
                                        (SEQ ID NO: 35)
5' TGACTTGGATCCGGGACAACGACTCATCC 3'
```

The first primer contained a biotin tag at the 5' end and a recognition site for the restriction enzyme EcoRI. The second primer contained the recognition site for the restriction enzyme BsmF I. The first primer was designed to anneal at various distances from the locus of interest.

The first primer for SNP TSC0607185 was designed to anneal ninety bases from the locus of interest. The first primer for SNP TSC1130902 was designed to anneal sixty bases from the locus of interest.

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they could also be amplified together in a single PCR reaction. For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest but in this example, 40 ng of template human genomic DNA and 5 μM of each primer were used. Forty cycles of PCR were performed. The following PCR conditions were used:

(1) 95° C. for 15 minutes and 15 seconds;

(2) 37° C. for 30 seconds;

(3) 95° C. for 30 seconds;

(4) 57° C. for 30 seconds;

(5) 95° C. for 30 seconds;

(6) 64° C. for 30 seconds;

(7) 95° C. for 30 seconds;

(8) Repeat steps 6 and 7 thirty nine (39) times;

(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results.

Purification of Fragment of Interest

The PCR products were separated from the genomic template DNA. One half of the PCR reaction was transferred to a well of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with IX PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

As discussed in detail in Example 6, the sequence of both alleles of a SNP can be determined by using one labeled nucleotide in the presence of the other unlabeled nucleotides. The following components were added to each fill in reaction: 1 μl of fluorescently labeled ddGTP, 0.5 μl of unlabeled ddNTPs (40 μM), which contained all nucleotides except guanine, 2 μl of 10× sequenase buffer, 0.25 μl of Sequenase, and water as needed for a 20 μl reaction. The fill in reaction was performed at 40° C. for 10 min. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565).

After labeling, each Streptawell was rinsed with 1× PBS (100 μl) three times. The "filled in" DNA fragments were then released from the Streptawells by digestion with the restriction enzyme EcoRI, according to the manufacturer's instructions that were supplied with the enzyme. Digestion was performed for 1 hour at 37° C. with shaking at 120 rpm.

Detection of the Locus of Interest

The samples were loaded into a lane of a 36 cm 5% acrylamide (urea) gel (BioWhittaker Molecular Applications, Long Ranger Run Gel Packs, catalog number 50691). The samples were electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence. A box was drawn around each band and the intensity of the band was calculated using the Typhoon 9400 Variable Mode Imager software.

Below, a schematic of the 5' overhang for SNP TSC0607185 is shown. The entire DNA sequence is not reproduced, only the portion to demonstrate the overhang (where R indicates the variable site).

```
C    C    T    R     TGTC 3'
                     ACAG 5'
4    3    2    1     Overhang position
```

The observed nucleotides at the variable site for TSC0607185 on the 5' sense strand (here depicted as the top strand) are cytosine and thymidine (depicted here as R). In this case, the second primer anneals from the locus of interest, which allows the fill-in reaction to occur on the anti-sense strand (depicted here as the bottom strand). The antisense strand will be filled in with guanine or adenine.

The second position in the 5' overhang is thymidine, which is complementary to adenine, and the third position in the overhang corresponds to cytosine, which is complementary to guanine. Fluorescently labeled ddGTP in the presence of unlabeled dCTP, dTTP, and dATP was used to determine the sequence of both alleles. After the fill-in reaction, the following DNA molecules were generated:

```
C    C    T    C     TGTC 3'             Allele 1
               G*    ACAG 5'
4    3    2    1     Overhang position

C    C    T    T     TGTC 3'             Allele 1
     G*   A    A     ACAG 5'
4    3    2    1     Overhang position
```

The overhang generated by BsmF I cutting at 11/15 from the recognition site at TSC0607185 is depicted below:

```
C    T    R    T     GTC 3' 11/15
                     CAG 5'
3    2    1    0     Overhang position
```

As labeled ddGTP is used for the fill-in reaction, no new signal will be generated from the molecules cut 11/15 from the recognition site. Position 0 complementary to the overhang was filled in with unlabeled dATP. Only signals generated from molecules filled in with labeled ddGTP at position 1 complementary to the overhang or molecules filled in with labeled ddGTP at position 3 complementary to the overhang were seen.

Five of the twenty-four individuals were heterozygous for SNP TSC0607185. As shown in FIG. 15, two bands were detected. The lower molecular weight band corresponded to DNA molecules filled in with ddGTP at position 1 complementary to the overhang. The higher molecular weight band corresponded to DNA molecules filled in with ddGTP at position 3 complementary to the overhang.

The ratio of the two alleles was calculated for each of the five heterozygous samples (see Table XVI). The average ratio of allele 2 to allele 1 was 1.000 with a standard deviation of 0.044. Thus, the allele ratio at SNP TSC0607185 was highly consistent. The experimentally calculated allele ratio for a particular SNP is hereinafter referred to as the "p" value of the SNP. Analysis of SNP TSC0607185 consistently will provide an allele ratio of 1:1, provided that the number of genomes analyzed is of sufficient quantity that no error is generated from statistical sampling.

If the sample contained a low number of genomes, it is statistically possible that the primers will anneal to one chromosome over another chromosome. For example, if the sample contains 40 genomes, which corresponds to a total of 40 chromosomes of allele 1 and 40 chromosomes of allele 2, the primers may anneal to 40 chromosomes of allele 1 but only 35 chromosome of allele 2. This would cause allele 1 to be amplified preferentially to allele 2, which would alter the ratio of allele 1 to allele 2. This problem is eliminated by having a sufficient number of genomes in the sample.

SNP TSC0607185 represents a SNP where the difference in the nucleotide at the variable site does not affect the PCR reaction, or digestion with the restriction enzyme or the fill-in reaction. The use of one nucleotide labeled with one fluorescent dye assures that the bands for one allele can be accurately compared to the bands for the second allele. There is no added complication of having to compare between two different lanes, or having to correct for the quantum coefficients of the dyes. Additionally, any effect from the alternate cutting properties of the type IIS restriction enzymes has been removed.

TABLE XVI

Ratio of allele 2 to allele 1 at SNPs TSC0607185 and TSC1130902.

| | SNP TSC0607185 | | | SNP TSC1130902 | | |
|---|---|---|---|---|---|---|
| Sample | Allele 1 | Allele 2 | Allele2/ Allele 1 | Allele 1 | Allele 2 | Allele2/ Allele 1 |
| 1 | 2382 | 2313 | 0.971033 | 5877 | 4433 | 0.754296 |
| 2 | 1581 | 1533 | 0.969639 | 3652 | 2695 | 0.737952 |
| 3 | 1795 | 1879 | 1.046797 | 5416 | 3964 | 0.730059 |
| 4 | 1921 | 1855 | 0.965643 | 3493 | 2663 | 0.762382 |
| 5 | 1618 | 1701 | 1.051298 | 3894 | 2808 | 0.721109 |
| Average | | | 1.000882 | | | 0.74116 |
| STD | | | 0.044042 | | | 0.017018 |

Below, a schematic of the 5' overhang for SNP TSC1130902 is shown. The entire DNA sequence is not reproduced, only the portion to demonstrate the overhang (where R indicates the variable site).

```
5' TTCAT
3' AAGTA              R      T      C      C
Overhang position     1      2      3      4
```

The observed nucleotides for TSC1130902 on the 5' sense strand (here depicted as the top strand) are adenine and guanine. The second position in the overhang corresponds to a thymidine, and the third position in the overhang corresponds to cytosine, which is complementary to guanine. Fluorescently labeled ddGTP in the presence of unlabeled dCTP, dTTP, and dATP was used to determine the sequence of both alleles. After the fill-in reaction, the following DNA molecules were generated:

```
Allele 1            5' TTCAT   G*
                    3' AAGTA   C     T     C     C
Overhang position              1     2     3     4

Allele 2            5' TTCAT   A     A     G*
                    3' AAGTA   T     T     C     C
Overhang position              1     2     3     4
```

As shown in FIG. 15, two bands were detected. The lower molecular weight band corresponded to DNA molecules filled in with labeled ddGTP at position 1 complementary to the overhang (the G allele). The higher molecular weight band, separated by a single base from the lower band, corresponded to DNA molecules filled in with ddGTP at position 3 complementary to the overhang (the A allele).

Five of the twenty-four individuals were heterozygous for SNP TSC1130902. As seen in FIG. 15, the band corresponding to allele 1 was more intense than the band corresponding to allele 2. This was seen for each of the five individuals. The actual intensity of the band corresponding to allele 1 varied from individual to individual but it was always more intense than the band corresponding to allele 2. For the five individuals, the average ratio of allele 2 to allele 1 was 0.74116, with a standard deviation of 0.017018.

Template DNA was prepared from five different individuals. Separate PCR reactions, separate restriction enzyme digestions, and separate fill-in reactions were performed. However, for each template DNA, the ratio of allele 2 to allele 1 was about 0.75. The "p" value for this SNP was highly consistent.

For example, for SNP TSCI 130902, the "p" value was 0.75. Any deviation from this value, provided the sample contains an adequate number of genomes to remove statistical sampling errors, will indicate that there is an abnormal copy number of chromosome 13. If there is an additional copy of allele 2, the "p" value will be higher than the expected 0.75. However, if there is an addition copy of allele 1, the "p" value will be lower than the expected 0.75. With the "p" value quantitated for a particular SNP, that SNP can be used to determine the presence or absence of a chromosomal abnormality. An accurate "p" value measured for a single SNP will be sufficient to detect the presence of a chromosomal abnormality.

There are several possible explanations for why the ratio of one allele to the other allele at some SNPs varies from the theoretically expected ratio of 1:1. First, it is possible that the DNA polymerase incorporates one nucleotide faster than the other nucleotide. As the alleles are being amplified by PCR, even a slight preference for one nucleotide over the other may cause variation from the expected 1:1 ratio. This potential preference for one nucleotide over the other is not seen during the fill-in reaction because a single nucleotide labeled with one dye is used.

It is also possible that the variable nucleotide at the SNP site influences the rate of denaturation of the two alleles. If allele 1 contains a guanine and allele 2 contains an adenine, the difference between the strength of the bonds for these nucleotides may affect the rate at which the DNA strands separate. Again, it is important to mention that the alleles are being amplified by PCR so very subtle differences can make a large impact on the final result. It is also possible that the variable nucleotide at the SNP site influences the rate at which the two strands anneal after separation.

Alternatively, it is possible that the type IIS restriction enzyme cuts one allele preferentially to the other allele. As discussed in detail above, type IIS restriction enzymes cut at a distance from the recognition site. It is possible that the variable nucleotide at the SNP site influences the efficiency of the restriction enzyme digestion. It is possible that at some SNPs the restriction enzyme cuts one allele with an efficiency of 100%, while it cuts the other allele with an efficiency of 90%.

However, the fact that the ratio of allele 1 to allele 2 deviates from the theoretically expected ratio of 1:1, does not influence or reduce the utility of that SNP. As demonstrated above, the "p" value for each SNP is consistent among different individuals.

The "p" value for any SNP can be calculated by analyzing the template DNA of any number of heterozygous individuals including but not limited to 1-10, 11-20, 21-30, 31-40, 41-50, 51-60, 61-70, 71-80,81-90,91-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, and greater than 300.

The methods described herein allow the "p" value for any SNP to be determined. It is possible that some SNPs will behave more consistently than other SNPs. In the human genome, there are over 3 million SNPs; it is not possible to speculate on how each SNP will behave. The "p" value for each SNP will have to be experimentally determined. The methods described herein allow identification of SNPs that have highly consistent, and reproducible "p" values.

Example 10

As discussed in Example 9, the ratio of one allele to the other allele at a particular SNP may vary from the theoretically expected ratio of 50:50. These SNPs can be used to detect the presence of additional chromosomes provided that the ratio of one allele to the other allele remains linear in individuals with chromosomal disorders. For example, at SNP X if the percentage of allele 1 to allele 2 is 75:25, the expected percentage of allele 1 to allele 2 for an individual with Down's syndrome must be properly adjusted to reflect the variation from the expected percentage at this SNP.

The percentage of allele 1 to allele 2 for SNP TSC0108992 on chromosome 21 was calculated using template DNA from four normal individuals and template DNA from an individual with Down's syndrome. As demonstrated below, the percentage of one allele to the other allele was consistent and remained linear in an individual with Down's syndrome.

Preparation of Template DNA

DNA was obtained from four individuals with a normal genetic karyotype and an individual identified as having an extra copy of chromosome 21 (Down's syndrome). Informed consent was obtained from all individuals. Informed consent also was obtained from the parents of the individual with Down's syndrome.

From each individual, a 9 ml blood sample was collected into a sterile tube (Fischer Scientific, 9 ml EDTA Vacuette tubes, catalog number NC9897284). Template DNA was isolated using the QIAmp DNA Blood Midi Kit supplied by QIAGEN (Catalog number 51183). The template DNA was isolated as per instructions included in the kit.

Design of Primers

SNP TSC0108992 was amplified using the following primer set:

```
First primer:
                                        (SEQ ID NO: 293)
5' CTACTGAGGGCTCGTAGATCCCAATTCCTTCCCAAGCT 3'

Second primer:
                                        (SEQ ID NO: 294)
5' AATCCTGCTTTAGGGACCATGCTGGTGGA 3'
```

The first primer contained a biotin tag at the 5' end and a recognition site for the restriction enzyme EcoRI. The second primer contained the recognition site for the restriction enzyme BsmF I.

SNP TSC0108992 was amplified from the template genomic DNA using the polymerase chain reaction (PCR, U.S. Pat. Nos. 4,683,195 and 4,683,202, incorporated herein by reference). For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest. In this example, 50 ng of template human genomic DNA and 5 μM of each primer were used. Thirty-eight cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty-seven (37) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results.

Purification of Fragment of Interest

The PCR products were separated from the genomic template DNA. Each PCR reaction was split into two samples and transferred to two separate wells of a Streptawell, transparent, High-Bind plate from Roche Diagnostics GmbH (catalog number 1 645 692, as listed in Roche Molecular Biochemicals, 2001 Biochemicals Catalog). For each PCR reaction, there were two replicates; each in a separate well of a microtiter plate. The first primer contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1×PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with 1×PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

As discussed in detail in Example 6, the sequence of both alleles of a SNP can be determined with one labeled nucleotide in the presence of the other unlabeled nucleotides. The following components were added to each fill in reaction: 1 μl of fluorescently labeled ddTTP, 0.5 μl of unlabeled ddNTPs (40 μM), which contained all nucleotides except thymidine, 2 μl of 10× sequenase buffer, 0.25 μl of Sequenase, and water as needed for a 20 μl reaction. The fill in reaction was performed at 40° C. for 10 min. Non-fluorescently labeled ddNTP was purchased from Fermentas Inc. (Hanover, MD). All other labeling reagents were obtained from Amersham (Thermo Sequenase Dye Terminator Cycle Sequencing Core Kit, US 79565).

After labeling, each Streptawell was rinsed with 1×PBS (100 μl) three times. The "filled in" DNA fragments were then released from the Streptawells by digestion with the restriction enzyme EcoRI, according to the manufacturer's instructions that were supplied with the enzyme. Digestion was performed for 1 hour at 37° C. with shaking at 120 rpm.

Detection of the Locus of Interest

The samples were loaded into the lanes of a 36 cm 5% acrylamide (urea) gel (BioWhittaker Molecular Applications, Long Ranger Run Gel Packs, catalog number 50691). The samples were electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence. A box was drawn around each band and the intensity of the band was calculated using the Typhoon 9400 Variable Mode Imager software.

Below, a schematic of the 5' overhang for SNP TSC0108992 is shown. The entire DNA sequence is not reproduced, only the portion to demonstrate the overhang (where R indicates the variable site).

```
                         GTCC 3'
G     A     C     R      CAGG 5'
4     3     2     1      Overhang Position
```

The observed nucleotides for SNP TSC0108992 are adenine and thymidine on the sense strand (here depicted as the top strand). Position 3 of the overhang corresponds to adenine, which is complementary to thymidine. Labeled ddTTP was used in the presence of unlabeled dATP, dCTP, and. dGTP. After the fill-in reaction with labeled ddTTP, the following DNA molecules were generated:

```
    T*   G    A    GTCC 3'              Allele 1
G   A    C    T    CAGG 5'
4   3    2    1    Overhang Position

              T*   GTCC 3'              Allele 2
G   A    C    A    CAGG 5'
4   3    2    1    Overhang Position
```

There was no difficulty in comparing the values obtained from allele 1 to allele 2 because one labeled nucleotide was used for the fill-in reaction, and the fill-in reaction for both alleles occurred in a single tube. The alternate cutting properties of BsmF I would not influence this analysis because the 11/15 overhang would be filled in just as the 10/14 overhang. Schematics of the filled-in 11/15 overhangs are depicted below:

```
T*  G    A    G    TCC 3' 11/15         Allele 1
A   C    T    C    AGG 5'
3   2    1    0    Overhang Position

         T*   G    TCC 3' 11/15         Allele 2
A   C    A    C    AGG 5'
3   2    1    0    Overhang Position
```

As seen in FIG. 16, two bands were seen for each sample of template DNA. The lower molecular weight band corresponded to the DNA molecules filled in with ddTTP at position one complementary to the overhang, and the higher molecular weight band corresponded to DNA molecules filled in with ddTTP at position 3 complementary to the overhang.

The percentage of allele 2 to allele 1 was highly consistent. (see Table XVII). In addition, for any given individual, the replicates of the PCR reaction showed similar results (see Table XVII). The percentage of allele 2 to allele 1 was calculated by dividing the value of allele 2 by the sum of the values for allele 1 and allele 2 (allele 2/(allele 1+allele 2)). From four individuals, the average percentage of allele 2 to allele 1 was 0.4773 with a standard deviation of 0.0097. The percentage of allele 2 to allele 1 on template DNA isolated from an individual with Down's syndrome was 0.3086.

The theoretically expected percentage of allele 2 to allele 1 using template DNA from a normal individual is 0.50. However, the experimentally determined percentage was 0.4773. The theoretically expected percentage of allele 2 to allele 1 for an individual with an extra copy of chromosome 21 is 0.33. The experimentally determined percentage of allele 2 to allele 1 for SNP TSC0108992 was 0.3086.

The deviation from the theoretically expected percentage is highly consistent and remains linear. The following formula demonstrates that the percentage of allele 2 to allele 1 at SNP TSC0108992 remains linear even on template DNA obtained from an individual with an extra copy of chromosome 21:

$$\frac{0.47}{0.50} = \frac{X}{0.33}$$

$$X = 0.3102$$

If the percentage of allele 2 to allele 1 using template DNA obtained from a normal individual is determined to be 0.47, then the percentage of allele 2 to allele 1 using template DNA from an individual with Down's syndrome should be 0.3102. The experimentally determined ratio was 0.3086, with a standard deviation of 0.00186. There is no difference between the predicted percentage and the experimentally determined percentage of allele 2 to allele 1 on template DNA from an individual with Down's syndrome.

The percentage of one allele to the other allele at a particular SNP is highly consistent, reproducible, and linear. This demonstrates that any SNP, regardless of the calculated percentage for one allele to another, can be used to determine the presence or absence of a chromosomal disorder.

TABLE XVII

Percentage of Allele 2 to Allele 1 at SNP TSC0108992.

| Sample | Allele 2 | Allele 1 | 2/(2 + 1) |
|---|---|---|---|
| 1A | 9568886 | 10578972 | 0.474933 |
| 1B | 8330864 | 9221381 | 0.474632 |
| 2A | 9801053 | 10345444 | 0.486489 |
| 2B | 8970942 | 9603102 | 0.482983 |
| 3A | 8676718 | 9211085 | 0.485063 |
| 3B | 10847024 | 11420943 | 0.487113 |
| 4A | 10512420 | 12227107 | 0.462297 |
| 4B | 7883584 | 9055289 | 0.465414 |
| | | MEAN | 0.477366 |
| | | STDEV | 0.009654 |
| DS | 6797400 | 15138959 | 0.309869 |
| DS | 6025753 | 13586890 | 0.307238 |
| | | MEAN | 0.308554 |
| | | STDEV | 0.00186 |

Example 11

The percentage of allele 2 to allele 1 for a particular SNP is highly consistent. Statistically significant deviation from the experimentally determined ratio indicates the presence of a chromosomal abnormality. Below, the percentage of allele 2 to allele 1 at SNP TSC0108992 on chromosome 21 was calculated using template DNA from a normal individual and template DNA from an individual with Down's syndrome. Mixtures containing various amounts of normal DNA and Down's syndrome DNA were prepared and analyzed in a blind fashion.

Preparation of Template DNA

DNA was obtained from an individual with a normal genetic karyotype and an individual identified as having an extra copy of chromosome 21 (Down's syndrome). Informed consent was obtained from both individuals. Informed consent also was obtained from the parents of the individual with Down's syndrome.

From each individual, a 9 ml blood sample was collected into a sterile tube (Fischer Scientific, 9 ml EDTA Vacuette tubes, catalog number NC9897284). Template DNA was isolated using the QIAmp DNA Blood Midi Kit supplied by QIAGEN (Catalog number 51183). The template DNA was isolated as per instructions included in the kit.

Mixtures of Template DNA

The template DNA from the individual with the normal karyotype and the template DNA from the individual with an extra copy of chromosome 21 were diluted to a concentration of 10 ng/μl. Four mixtures of normal template DNA and Down's syndrome template DNA were made in the following fashion:

| | |
|---|---|
| Mixture 1: | 32 μl of Normal DNA + 8 μl of Down's syndrome DNA |
| Mixture 2: | 28 μl of Normal DNA + 12 μl of Down's syndrome DNA |
| Mixture 3: | 20 μl of Normal DNA + 20 μl of Down's syndrome DNA |
| Mixture 4: | 10 μl of Normal DNA + 30 μl of Down's syndrome DNA |

Three separate PCR reactions were set up for the normal template DNA and the template DNA from the individual with Down's syndrome. Likewise, for each mixture, three separate PCR reactions were set up.

Design of Primers

SNP TSC0108992 was amplified using the following primer set:

```
First primer:
                                    (SEQ ID NO: 293)
5' CTACTGAGGGCTCGTAGATCCCAATTCCTTCCCAAGCT 3'

Second primer:
                                    (SEQ ID NO: 294)
5' AATCCTGCTTTAGGGACCATGCTGGTGGA 3'
```

The first primer contained a biotin tag at the 5' end and a recognition site for the restriction enzyme EcoRI. The second primer contained the recognition site for the restriction enzyme BsmF I.

SNP TSC0108992 was amplified from the template genomic DNA using the polymerase chain reaction (PCR, U.S. Pat. Nos. 4,683,195 and 4,683,202, incorporated herein by reference). For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest but in this example, 50 ng of template human genomic DNA and 5 μM of each primer were used. Thirty-eight cycles of PCR were performed. The following PCR conditions were used:

(1) 95° C. for 15 minutes and 15 seconds;

(2) 37° C. for 30 seconds;

(3) 95° C. for 30 seconds;

(4) 57° C. for 30 seconds;

(5) 95° C. for 30 seconds;

(6) 64° C. for 30 seconds;

(7) 95° C. for 30 seconds;

(8) Repeat steps 6 and 7 thirty-seven (37) times;

(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results.

Purification of Fragment of Interest

The PCR products were separated from the genomic template DNA. Each PCR reaction was split into two samples and transferred to two separate wells of a Streptawell, transparent, High-Bind plate from Roche Diagnostics GmbH (catalog number 1 645 692, as listed in Roche Molecular Biochemicals, 2001 Biochemicals Catalog). For each PCR reaction, there were two replicates, each in a separate well of a microtiter plate. The first primer contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1×PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with 1×PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

As discussed in detail in Example 6, the sequence of both alleles of a SNP can be determined with one labeled nucleotide in the presence of the other unlabeled nucleotides. The following components were added to each fill in reaction: 1 μl of fluorescently labeled ddTTP, 0.5 μl of unlabeled ddNTPs (40 μM), which contained all nucleotides except thymidine, 2 μl of 10× sequenase buffer, 0.25 μl of Sequenase, and water as needed for a 20 μl reaction. The fill in reaction was performed at 40° C. for 10 min. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565).

After labeling, each Streptawell was rinsed with 1×PBS (100 Al) three times. The "filled in" DNA fragments were then released from the Streptawells by digestion with the restriction enzyme EcoRI, according to the manufacturer's instructions that were supplied with the enzyme. Digestion was performed for 1 hour at 37° C. with shaking at 120 rpm.

Detection of the Locus of Interest

The samples were loaded into the lanes of a 36 cm 5% acrylamide (urea) gel (BioWhittaker Molecular Applications, Long Ranger Run Gel Packs, catalog number 50691). The samples were electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence. A box was drawn around each band and the intensity of the band was calculated using the Typhoon 9400 Variable Mode Imager software.

Figure 17:
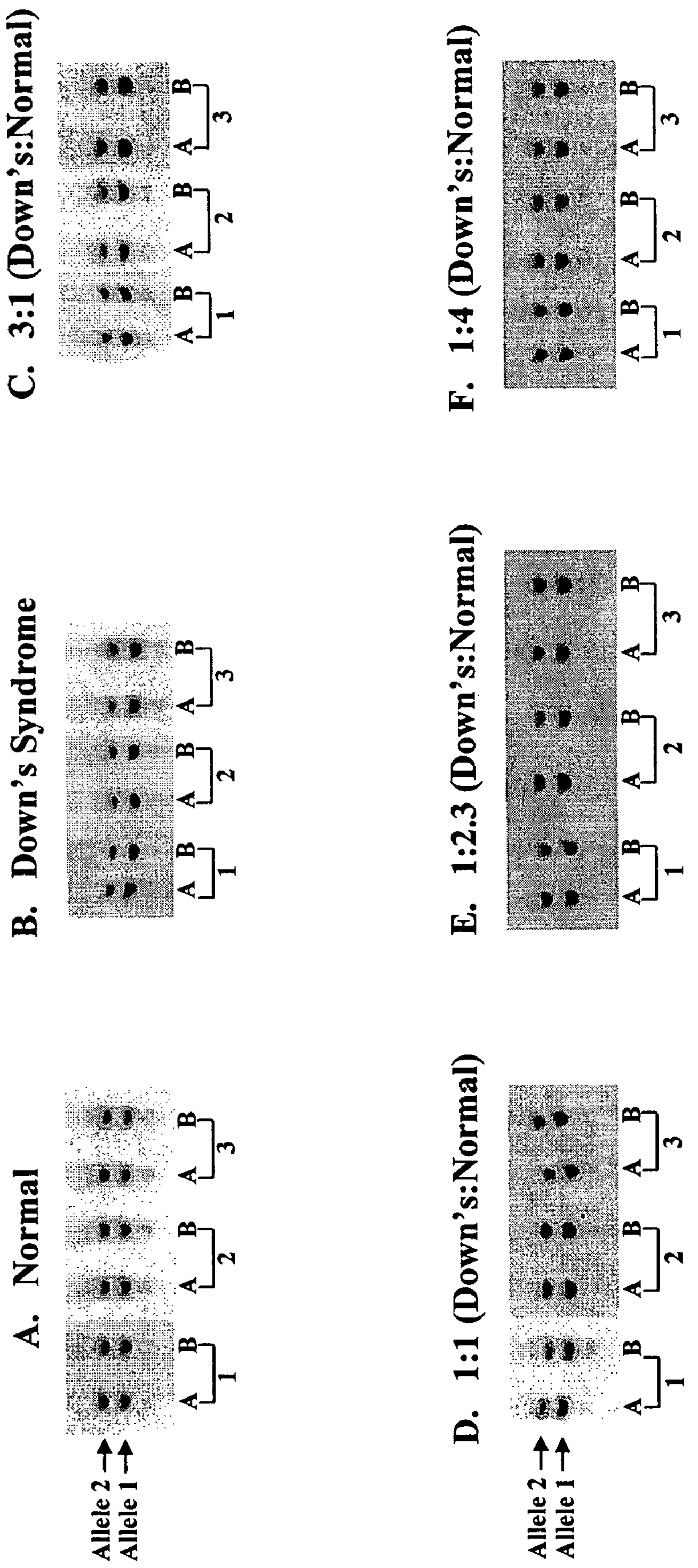

As seen in FIGS. 17 A-F, two bands were seen. The lower molecular weight band corresponded to the DNA molecules filled in with ddTTP at position one complementary to the overhang. The higher molecular weight band corresponded to DNA molecules filled in with ddTTP at position 3 complementary to the overhang.

The experiment was performed in a blind fashion. The tubes were coded so that it was not known what tube corresponded to what template DNA. After the gels were analyzed, each tube was grouped into the following categories: normal template DNA, Down's syndrome template DNA, 3:1 mixture of Down's syndrome template DNA to normal DNA, 1:1 mixture of normal template DNA to Down's syndrome template DNA, 1:2.3 mixture of Down's syndrome template DNA to normal template DNA, and 1:4 mixture of Down's syndrome template DNA to normal template DNA. Each replicate of each PCR reaction successfully was grouped into the appropriate category, which demonstrates that the method can be used to detect abnormal DNA even if it represents only a small percentage of the total DNA.

The percentage of allele 2 to allele 1 for each replicate of the three PCR reactions from normal template DNA are displayed in Table XVIII (also see FIG. 17A). The average percentage of allele 2 to allele 1 was calculated by dividing the value of allele 2 by the sum of the values for allele 1 and allele 2 (allele 2/(allele 1+allele 2)), which resulted in an average of 0.50025 with a standard deviation of 0.002897. Thus, allele 1 and allele 2 were present in a ratio of 50:50. While the intensity of the bands varied from one PCR reaction to another (compare reaction 1 with reaction 3), there was no difference in intensity within a PCR reaction. Furthermore, the values obtained for the two replicates of the PCR reactions were very similar. Most of the variation was between PCR reactions and was likely attributable to pipetting errors.

The percentage of allele 2 to allele 1 for each replicate of the three PCR reactions from Down's syndrome template DNA are displayed in Table XVIII (see FIG. 17B). The percentage of allele 2 to allele 1 was calculated by dividing the value of allele 2 by the sum of the values for allele 1 and allele 2 (allele 2/allele 1+allele 2), which resulted in an average of 0.301314 with a standard deviation of 0.012917. It is clear even upon analysis of the gel by the naked eye that allele 1 is present in a higher copy number than allele 2 (see FIG. 17B). Again, most of the variation occurs between PCR reactions and not within the replicate of a PCR reaction. The majority of the statistical variation likely resulted from pipetting errors.

Analysis of a single SNP was sufficient to detect the presence of the chromosomal abnormality. One SNP is sufficient provided that the "p" value of the SNP is known and that there are an adequate number of genomes so that statistical sampling error is not introduced into the analysis. In this experiment, there were approximately 5,000 genomes in each reaction.

The reactions that consisted of a mixture of Down's syndrome template DNA to normal template DNA at a ratio of 3:1 were clearly distinguishable from the normal template DNA, and the other mixtures of DNA (see FIG. 17C). The calculated percentage of allele 2 to allele 1 was 0.319089 with a standard deviation of 0.004346 (see Table XVIII). Likewise, the reactions that consisted of a mixture of Down's syndrome template DNA to normal template DNA at ratios of 1:1, and 1:2.3 were distinguishable (see FIGS. 17D and 17E) and the values were statistically significant from all other reactions (see Table XVIII).

As the amount of normal template DNA increased, the percentage of allele 2 to allele 1 increased. With a mixture of Down's syndrome template DNA to normal template DNA of 1:4, the percentage of allele 2 to allele 1 was 0.397642, with a standard deviation of 0.001903 (see FIG. 17F). The difference between this value and the value obtained from normal template DNA is statistically significant. Thus, the methods described herein allow the detection of a chromosomal abnormality even when the sample is not a homogeneous sample of abnormal DNA.

As described above, the presence of a small fraction of DNA with an abnormal copy number of chromosomes can be detected even among a large presence of normal DNA. It was clear, even by the naked eye, that as the amount of normal DNA increased and the amount of Down's syndrome DNA decreased, the intensities of the bands that corresponded to alleles 1 and 2 equalized.

The above example analyzed a SNP located on chromosome 21. However, any SNP may be analyzed on any chromosome including but not limited to human chromosomes 1, 2, 3, 4, 5, 6, 7, 8, 9, 10, 11, 12, 13, 14, 15, 16, 17, 18, 19, 20, 21, 22, X, and Y and fetal chromosomes 1, 2, 3, 4, 5, 6, 7, 8, 9, 10, 11, 12, 13, 14, 15, 16, 17, 18, 19, 20, 21, 22, X, and Y. In addition, chromosomes from non-human organisms can be analyzed using the above methods. Any combination of chromosomes can be analyzed. In the above example, an extra copy of a chromosome was detected. However, the same methods can be used to detect monosomies.

TABLE XVIII

Percentage of allele 2 to allele 1 at SNP TSC0108992 using normal template DNA and Down's syndrome template DNA.

| | Allele 1 | Allele 2 | 2/(2 + 1) |
|---|---|---|---|
| | | Normal Template DNA | |
| 1A | 2602115 | 2604525 | 0.500231 |
| 1B | 2855846 | 2923860 | 0.505884 |
| 2A | 1954765 | 1941929 | 0.498353 |
| 2B | 2084476 | 2068106 | 0.498029 |
| 3A | 2044147 | 2035719 | 0.498967 |
| 3B | 1760291 | 1760543 | 0.500036 |
| | | Mean | 0.50025 |
| | | STD | 0.002897 |
| | | Down's Syndrome | |
| 1A | 4046926 | 1595581 | 0.282779 |
| 1B | 4275341 | 1736260 | 0.288818 |
| 2A | 2875698 | 1299509 | 0.311244 |
| 2B | 2453615 | 1069635 | 0.303593 |
| 3A | 3169338 | 1426643 | 0.310411 |
| 3B | 3737440 | 1687286 | 0.311036 |
| | | Mean | 0.301314 |
| | | STD | 0.012917 |
| | | 3:1 (Down's:Normal) | |
| 1A | 4067623 | 1980770 | 0.327487 |
| 1B | 4058506 | 1899853 | 0.318855 |
| 2A | 2315044 | 1085860 | 0.319286 |
| 2B | 2686984 | 1243406 | 0.316357 |
| 3A | 3880385 | 1790764 | 0.315767 |
| 3B | 3718661 | 1724189 | 0.316781 |
| | | Mean | 0.319089 |
| | | STD | 0.004346 |
| | | 1:1 (Down's:Normal) | |
| 1A | 3540255 | 1929840 | 0.352798 |
| 1B | 4004085 | 2161443 | 0.350569 |
| 2A | 2358009 | 1282132 | 0.35222 |
| 2B | 2158132 | 1238377 | 0.364603 |
| 3A | 3052330 | 1648677 | 0.350707 |
| 3B | 3852682 | 2024012 | 0.344413 |
| | | Mean | 0.352552 |
| | | STD | 0.006618 |
| | | 1:2.3 (Down's:Normal) | |
| 1A | 3109326 | 1942597 | 0.384526 |
| 1B | 3392477 | 2118011 | 0.38436 |
| 2A | 2824213 | 1758428 | 0.383715 |
| 2B | 2069889 | 1249545 | 0.376433 |
| 3A | 2335128 | 1433016 | 0.380298 |

TABLE XVIII-continued

| Percentage of allele 2 to allele 1 at SNP TSC0108992 using normal template DNA and Down's syndrome template DNA. | | | |
|---|---|---|---|
| | Allele 1 | Allele 2 | 2/(2 + 1) |
| 3B | 2916772 | 1797965 | 0.38135 |
| | | Mean | 0.38178 |
| | | STD | 0.003128 |
| | | 1:4 (Down's:Normal) | |
| 1A | 3066524 | 2039636 | 0.399446 |
| 1B | 3068284 | 2038770 | 0.399207 |
| 2A | 2325477 | 1542526 | 0.398791 |
| 2B | 2366122 | 1562218 | 0.397679 |
| 3A | 2151205 | 1403120 | 0.394764 |
| 3B | 2397046 | 1571360 | 0.395968 |
| | | Mean | 0.397642 |
| | | STD | 0.001903 |

Example 12

As discussed above in Example 9, the ratio for allele 1 to allele 2 at a heterozygous SNP is constant. However, one factor that can influence the ratio of allele 1 to allele 2 at a heterozygous SNP is a low number of genomes. For example, if there are 40 genomes, which means that there are a total of 40 chromosomes of allele 1 and 40 chromosomes of allele 2, it is statistically possible that the primers may anneal to 40 of the chromosomes with allele 1 but only 30 of the chromosomes with allele 2. This will affect the ratio of allele 1 to allele 2, and can erroneously influence the "p" value for a particular SNP.

Typically, whole genomic amplification, which employs degenerate oligonucleotide PCR, is used to increase low quantities of genomic DNA samples. Oligonucleotides of 8, 10, 12, or 14 bases are used to amplify the genome. It is thought that the primers anneal randomly throughout the genome, and will amplify a small genomic DNA sample into hundreds-fold more DNA for genetic analysis.

The methods described herein exploit the fact that typically the whole genome is not of interest. Particular loci of interest located on one chromosome, or on multiple chromosomes or on chromosomes that represent the entire genome are selected for analysis. Even if the loci of interest are located on chromosomes for the entire genome, it is preferential to amplify the region of those chromosomes that contain the loci of interest.

To overcome the limit of a low number of genomes, which is often seen with fetal DNA obtained from the plasma of a pregnant female, a multiplex method can be used to increase the number of genomes. The method described below preferentially amplifies the chromosome or chromosomes that contain the loci of interest.

Preparation of Template DNA

A 9 ml blood sample was collected into a sterile tube from a human volunteer after informed consent had been granted. (Fischer Scientific, 9 ml EDTA Vacuette tubes, catalog number NC9897284). The tubes were spun at 1000 rpm for ten minutes. The supernatant (the plasma) of each sample was removed, and one milliliter of the remaining blood sample, which is commonly referred to as the "buffy-coat" was transferred to a new tube. One milliliter of 1×PBS was added to each sample. Template DNA was isolated using the QIAmp DNA Blood Midi Kit supplied by QIAGEN (Catalog number 51183).

Design of Multiplex Primers

Primers were designed to anneal at various regions on chromosome 21 to increase the copy number of the loci of interest located on chromosome 21. The primers were 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers were designed to anneal to both the sense strand and the antisense strand.

Nine SNPs located on chromosome 21 were analyzed: TSC0397235, TSC0470003, TSC1649726, TSC1261039, TSC0310507, TSC1650432, TSC1335008, TSC0128307, and TSC0259757. Any number of SNPs can be analyzed including but not limited to 1-10, 11-20, 21-30, 31-40, 41-50, 51-60, 61-70, 71-80, 81-90, 91-100, 101-200, 201-300, 301-400, 401-500, 501-600, 601-700, 701-800, 801-900, 901-1000, 1001-2000, 2001-3000, 3001-4000, 4001-5000, 5001-6000, 6001-7000, 7001-8000, 8001-9000, 9001 -10,000 and greater than 10,000.

For each of the 9 SNPs, a 12 base primer was designed to anneal approximately 130 bases upstream of the loci of interest, and a 12 base primer was designed to anneal approximately 130 bases downstream of the loci of interest (herein referred to as the multiplex primers). The multiplex primers can be designed to anneal at any distance from the loci of interest including but not limited to 10-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 301-310, 311-320, 321-330, 331-340, 341-350, 351-360, 361-370, 371-380, 381-390, 391-400, 401-410, 411-420, 421-430, 431-440, 441-450, 451-460, 461-470, 471-480, 481-490, 491-500, 501-600, 601-700, 701-800, 801-900, 901-1000, 1001-2000, 2001-3000, 3001-4000, 4001-5000, and greater than 5000 bases. In addition, more than one set of multiplex primers can be used for one SNP including but not limited to 1, 2, 3, 4, 5, 6, 7, 8, 9, 10, 10-20, 21-30, 31-40, 41-50, and greaterthan 50.

In addition, 91 sets of forward and reverse primers were used to amplify other regions of chromosome 21, for a total of 100 sets of primers (200 primers in the reaction). These 91 primer sets were used to demonstrate that a large number of primers can be used in a single reaction without producing a large number of non-specific bands. Any number of primers can be used in the reaction including but not limited to 1-10, 11-20, 21-30, 31-40, 41-50, 51-60, 61-70, 71-80, 81-90, 91-100, 101-200, 201-300, 301-400, 401-500, 501-600, 601-700, 701-800, 801-900, 901-1000, 1001-2000, 2001-3000, 3001-4000, 4001-5000, 5001-6000, 6001-7000, 7001-8000, 8001-9000, 9001-10,000, 10,001-20,000, 20,001-30,000 and greater than 30,000.

The multiplex primers were designed to have the same nucleotides at the 3' end of the primer. In this case, the multiplex primers ended in "AA," wherein A indicates adenine. The primers were designed in this manner to minimize primer-dimer formation. However, the primers can terminate in any nucleotides including but not limited to adenine, guanine, cytosine, thymidine, any combination of adenine and guanine, any combination of adenine and cytosine, any combination of adenine and thymidine, any combination of guanine and cytosine, any combination of guanine and thymidine, or any combination of cytosine and thymidine. In addition the multiplex primers can have 1, 2, 3, 4, 5, 6, 7, 8, 9, 10, or more than 10 of the same nucleotides at the 3' end.

The multiplex primers for SNP TSC0397235 were:

```
Forward Primer:
5' CAAGTGTCCTAA 3'      (SEQ ID NO: 295)

Reverse primer:
5' CAGCTGCTAGAA 3'      (SEQ ID NO: 296)
```

The multiplex primers for SNP TSC0470003 were:

```
Forward Primer:
5' GGTTGAGGGCAA 3'      (SEQ ID NO: 297)

Reverse primer:
5' CACAGCGGGTAA 3'      (SEQ ID NO: 298)
```

The multiplex primers for SNP TSC1649726 were:

```
Forward Primer:
5' TTGACTTTTTAA 3'      (SEQ ID NO: 299)

Reverse primer:
5' ACAGAATGGGAA 3'      (SEQ ID NO: 300)
```

The multiplex primers for SNP TSC1261039 were:

```
Forward Primer:
5' TGCAGGTCACAA 3'      (SEQ ID NO: 301)

Reverse primer:
5' TTCTTCTTATAA 3'      (SEQ ID NO: 302)
```

The multiplex primers for SNP TSC0310507 were:

```
Forward Primer:
5' AGGACAACCTAA 3'      (SEQ ID NO: 303)

Reverse primer:
5' TGGTGTTCAGAA 3'      (SEQ ID NO: 304)
```

The multiplex primers for SNP TSC1650432 were:

```
Forward Primer:
5' TCAGCATATGAA 3'      (SEQ ID NO: 305)

Reverse primer:
5' GTTGCCACACAA 3'      (SEQ ID NO: 306)
```

The multiplex primers for SNP TSC1335008 were:

```
Forward Primer:
5' CCCAGCTAGCAA 3'      (SEQ ID NO: 307)

Reverse primer:
5' GGGTCACTGTAA 3'      (SEQ ID NO: 308)
```

The multiplex primers for SNP TSC0128307 were:

```
Forward Primer:
5' TTAAATACCCAA 3'      (SEQ ID NO: 309)

Reverse primer:
5' TTAGGAGGTTAA 3'      (SEQ ID NO: 310)
```

The multiplex primers for SNP TSC0259757 were:

```
Forward Primer:
5' ACACAGAATCAA 3'      (SEQ ID NO: 311)

Reverse primer:
5' CGCTGAGGTCAA 3'      (SEQ ID NO: 312)
```

Ninety-one (91) additional sets of primers, which annealed to various regions along chromosome 2-1, were included in the reaction:

<u>Set 1:</u>

```
Forward Primer:
5' AAGTAGAGTCAA 3'      (SEQ ID NO: 313)

Reverse primer:
5' CTTCCCATGGAA 3'      (SEQ ID NO: 314)
```

<u>Set 2:</u>

```
Forward Primer:
5' TTGGTTATTAAA 3'      (SEQ ID NO: 315)

Reverse primer:
5' CAACTTACTGAA 3'      (SEQ ID NO: 316)
```

<u>Set 3:</u>

```
Forward Primer:
5' CACTAAGTGAAA 3'      (SEQ ID NO: 317)

Reverse primer:
5' CTCACCTGCCAA 3'      (SEQ ID NO: 318)
```

<u>Set 4:</u>

```
Forward Primer:
5' ATGCATATATAA 3'      (SEQ ID NO: 319)

Reverse primer:
5' AGAGATCAGCAA 3'      (SEQ ID NO: 320)
```

<u>Set 5:</u>

```
Forward Primer:
5' TATATTTTTCAA 3'      (SEQ ID NO: 321)

Reverse primer:
5' CAGAAAGCAGAA 3'      (SEQ ID NO: 322)
```

<u>Set 6:</u>

```
Forward Primer:
5' GTATTGGGTTAA 3'      (SEQ ID NO: 323)

Reverse primer:
5' CTGACCCAGGAA 3'      (SEQ ID NO: 324)
```

<u>Set 7:</u>

```
Forward Primer:
5' CAGTTTTCCCAA 3'      (SEQ ID NO: 325)

Reverse primer:
5' AGGGCACAGGAA 3'      (SEQ ID NO: 326)
```

<u>Set 8:</u>

```
Forward Primer:
5' GTATCAGAGGAA 3'      (SEQ ID NO: 327)

Reverse primer:
5' GCATGAAAAGAA 3'      (SEQ ID NO: 328)
```

<u>Set 9:</u>

```
Forward Primer:
5' GATTTGACAGAA 3'      (SEQ ID NO: 329)

Reverse primer:
5' TACAGTTTACAA 3'      (SEQ ID NO: 330)
```

<u>Set 10:</u>

```
Forward Primer:
5' TGTGATTTTTAA 3'      (SEQ ID NO: 331)
```

-continued

Reverse primer:
5' TTATGTTCTCAA 3' (SEQ ID NO: 332)

Set 11:

Forward Primer:
5' CAAGTACTTGAA 3' (SEQ ID NO: 333)

Reverse primer:
5' CTTGTGTGGCAA 3' (SEQ ID NO: 334)

Set 12:

Forward Primer:
5' AGACTTCTGCAA 3' (SEQ ID NO: 335)

Reverse primer:
5' GTTGTCTTTCAA 3' (SEQ ID NO: 336)

Set 13:

Forward Primer:
5' GGGACACTCCAA 3' (SEQ ID NO: 337)

Reverse primer:
5' ATTATTATTCAA 3' (SEQ ID NO: 338)

Set 14:

Forward Primer:
5' ACATGATGACAA 3' (SEQ ID NO: 339)

Reverse primer:
5' TCAATTATAGAA 3' (SEQ ID NO: 340)

Set 15:

Forward Primer:
5' CTATGGGCTGAA 3' (SEQ ID NO: 341)

Reverse primer:
5' TGTGTGCCTGAA 3' (SEQ ID NO: 342)

Set 16:

Forward Primer:
5' CCATTTGTTGAA 3' (SEQ ID NO: 343)

Reverse primer:
5' TCTCCATCAAAA 3' (SEQ ID NO: 344)

Set 17:

Forward Primer:
5' AATGCTGACAAA 3' (SEQ ID NO: 345)

Reverse primer:
5' TTTCATGTCCAA 3' (SEQ ID NO: 346)

Set 18:

Forward Primer:
5' GGCCTCTTGGAA 3' (SEQ ID NO: 347)

Reverse primer:
5' TCATTTTTTGAA 3' (SEQ ID NO: 348)

Set 19:

Forward Primer:
5' GGACTACCATAA 3' (SEQ ID NO: 349)

Reverse primer:
5' AGTCACTCAGAA 3' (SEQ ID NO: 350)

Set 20:

Forward Primer:
5' CCTTGGCAGGAA 3' (SEQ ID NO: 351)

-continued

Reverse primer:
5' TTTCTGGTAGAA 3' (SEQ ID NO: 352)

Set 21:

Forward Primer:
5' CCCCCCCCCGAA 3' (SEQ ID NO: 353)

Reverse primer:
5' GCCCAGGCAGAA 3' (SEQ ID NO: 354)

Set 22:

Forward Primer:
5' GAATGCGAAGAA 3' (SEQ ID NO: 355)

Reverse primer:
5' TTAGGTAGAGAA 3' (SEQ ID NO: 356)

Set 23:

Forward Primer:
5' TGCTTTGGTCAA 3' (SEQ ID NO: 357)

Reverse primer:
5' GCCCATTAATAA 3' (SEQ ID NO: 358)

Set 24:

Forward Primer:
5' TGAGATCTTTAA 3' (SEQ ID NO: 359)

Reverse primer:
5' CAGTTTGTTCAA 3' (SEQ ID NO: 360)

Set 25:

Forward Primer:
5' GCTGGGCAAGAA 3' (SEQ ID NO: 361)

Reverse primer:
5' AGTCAAAGTCAA 3' (SEQ ID NO: 362)

Set 26:

Forward Primer:
5' TCTCTGCAGTAA 3' (SEQ ID NO: 363)

Reverse primer:
5' TGAATAACTTAA 3' (SEQ ID NO: 364)

Set 27:

Forward Primer:
5' CGGTTAGAAAAA 3' (SEQ ID NO: 365)

Reverse primer:
5' CATCCCTTTCAA 3' (SEQ ID NO: 366)

Set 28:

Forward Primer:
5' TCTCTTTCTGAA 3' (SEQ ID NO: 367)

Reverse primer:
5' CTCAGATTGTAA 3' (SEQ ID NO: 368)

Set 29:

Forward Primer:
5' TTTGCACCAGAA 3' (SEQ ID NO: 369)

Reverse primer:
5' GGTTAACATGAA 3' (SEQ ID NO: 370)

Set 30:

Forward Primer:
5' ATTATCAACTAA 3' (SEQ ID NO: 371)

-continued

Reverse primer:
5' GCCATTTTGTAA 3' (SEQ ID NO: 372)

Set 31:

Forward Primer:
5' GATCTAGATGAA 3' (SEQ ID NO: 373)

Reverse primer:
5' TTAATGTATTAA 3' (SEQ ID NO: 374)

Set 32:

Forward Primer:
5' CTAGGGAGACAA 3' (SEQ ID NO: 375)

Reverse primer:
5' TGGAGGAGACAA 3' (SEQ ID NO: 376)

Set 33:

Forward Primer:
5' CATCACATTTAA 3' (SEQ ID NO: 377)

Reverse primer:
5' GGGGTCCTGCAA 3' (SEQ ID NO: 378)

Set 34:

Forward Primer:
5' CAGTTGTGCTAA 3' (SEQ ID NO: 379)

Reverse primer:
5' TCTGCAGCCTAA 3' (SEQ ID NO: 380)

Set 35:

Forward Primer:
5' GAGTCATTTAAA 3' (SEQ ID NO: 381)

Reverse primer:
5' TCTATGGATTAA 3' (SEQ ID NO: 382)

Set 36:

Forward Primer:
5' CAAAAAGTAGAA 3' (SEQ ID NO: 383)

Reverse primer:
5' AATATACTCCAA 3' (SEQ ID NO: 384)

Set 37:

Forward Primer:
5' CGTCCAGCACAA 3' (SEQ ID NO: 385)

Reverse primer:
5' GGATGGTGAGAA 3' (SEQ ID NO: 386)

Set 38:

Forward Primer:
5' TCTCCTTTGTAA 3' (SEQ ID NO: 387)

Reverse primer:
5' TCGTTATTTCAA 3' (SEQ ID NO: 388)

Set 39:

Forward Primer:
5' GATTTTATAGAA 3' (SEQ ID NO: 389)

Reverse primer:
5' AGACATAAGCAA 3' (SEQ ID NO: 390)

Set 40:

Forward Primer:
5' TTCACCTCACAA 3' (SEQ ID NO: 391)

-continued

Reverse primer:
5' GGATTGCTTGAA 3' (SEQ ID NO: 392)

Set 41:

Forward Primer:
5' ACTGCATGTGAA 3' (SEQ ID NO: 393)

Reverse primer:
5' TTTATCACAGAA 3' (SEQ ID NO: 394)

Set 42:

Forward Primer:
5' TCAGTAACACAA 3' (SEQ ID NO: 395)

Reverse primer:
5' TACATCTTTGAA 3' (SEQ ID NO: 396)

Set 43:

Forward Primer:
5' TTGTTTCAGTAA 3' (SEQ ID NO: 397)

Reverse primer:
5' TATGAGCATCAA 3' (SEQ ID NO: 398)

Set 44:

Forward Primer:
5' CTCAGCAGGCAA 3' (SEQ ID NO: 399)

Reverse primer:
5' ACCCCTGTATAA 3' (SEQ ID NO: 400)

Set 45:

Forward Primer:
5' TCTGCTCAGCAA 3' (SEQ ID NO: 401)

Reverse primer:
5' GTTCTTTTTTAA 3' (SEQ ID NO: 402)

Set 46:

Forward Primer:
5' GTGATAATCCAA 3' (SEQ ID NO: 403)

Reverse primer:
5' GAGCCCTCAGAA 3' (SEQ ID NO: 404)

Set 47:

Forward Primer:
5' TTTATTGGTTAA 3' (SEQ ID NO: 405)

Reverse primer:
5' GGTACTGGGCAA 3' (SEQ ID NO: 406)

Set 48:

Forward Primer:
5' AGTGTTTTTCAA 3' (SEQ ID NO: 407)

Reverse primer:
5' TGTTATTGGTAA 3' (SEQ ID NO: 408)

Set 49:

Forward Primer:
5' GCGCATTCACAA 3' (SEQ ID NO: 409)

Reverse primer:
5' AAACAAAAGCAA 3' (SEQ ID NO: 410)

Set 50:

Forward Primer:
5' TATATGATAGAA 3' (SEQ ID NO: 411)

-continued

Reverse primer:
5' TCCCAGTTCCAA 3' (SEQ ID NO: 412)

Set 51:

Forward Primer:
5' AAAGCCCATAAA 3' (SEQ ID NO: 413)

Reverse primer:
5' TGTCATCCACAA 3' (SEQ ID NO: 414)

Set 52:

Forward Primer:
5' TTGTGAATGCAA 3' (SEQ ID NO: 415)

Reverse primer:
5' GTATTCATACAA 3' (SEQ ID NO: 416)

Set 53:

Forward Primer:
5' TGACATAGGGAA 3' (SEQ ID NO: 417)

Reverse primer:
5' AGCAAATTGCAA 3' (SEQ ID NO: 418)

Set 54:

Forward Primer:
5' AGTAGATGTTAA 3' (SEQ ID NO: 419)

Reverse primer:
5' AAAAGATAATAA 3' (SEQ ID NO: 420)

Set 55:

Forward Primer:
5' ACCTCATGGGAA 3' (SEQ ID NO: 421)

Reverse primer:
5' TGGTCGACCTAA 3' (SEQ ID NO: 422)

Set 56:

Forward Primer:
5' TTTGCATGGTAA 3' (SEQ ID NO: 423)

Reverse primer:
5' GCGGCTGCCGAA 3' (SEQ ID NO: 424)

Set 57:

Forward Primer:
5' TCAGGAGTCTAA 3' (SEQ ID NO: 425)

Reverse primer:
5' GCCTACCAGGAA 3' (SEQ ID NO: 426)

Set 58:

Forward Primer:
5' ATCTTCTGTTAA 3' (SEQ ID NO: 427)

Reverse primer:
5' AGGTAAGGACAA 3' (SEQ ID NO: 428)

Set 59:

Forward Primer:
5' TGCTTTGAGGAA 3' (SEQ ID NO: 429)

Reverse primer:
5' AACAGTTTTAAA 3' (SEQ ID NO: 430)

Set 60:

Forward Primer:
5' TTAAATGTTTAA 3' (SEQ ID NO: 431)

-continued

Reverse primer:
5' ATAGAAAATCAA 3' (SEQ ID NO: 432)

Set 61:

Forward Primer:
5' GTGTTGTGTTAA 3' (SEQ ID NO: 433)

Reverse primer:
5' GAGGACCTCGAA 3' (SEQ ID NO: 434)

Set 62:

Forward Primer:
5' AGAGGCTGAGAA 3' (SEQ ID NO: 435)

Reverse primer:
5' GGTATTTATTAA 3' (SEQ ID NO: 436)

Set 63:

Forward Primer:
5' ATTTATCTGGAA 3' (SEQ ID NO: 437)

Reverse primer:
5' AGTGCAAACTAA 3' (SEQ ID NO: 438)

Set 64:

Forward Primer:
5' TGAACACCTTAA 3' (SEQ ID NO: 439)

Reverse primer:
5' AATTTTTTCTAA 3' (SEQ ID NO: 440)

Set 65:

Forward Primer:
5' TTACTATTATAA 3' (SEQ ID NO: 441)

Reverse primer:
5' TGCTATAGTGAA 3' (SEQ ID NO: 442)

Set 66:

Forward Primer:
5' TGGACTATGGAA 3' (SEQ ID NO: 443)

Reverse primer:
5' CTGCAGTCCGAA 3' (SEQ ID NO: 444)

Set 67:

Forward Primer:
5' GCTACTGCCCAA 3' (SEQ ID NO: 445)

Reverse primer:
5' TCACATGGTGAA 3' (SEQ ID NO: 446)

Set 68:

Forward Primer:
5' GTGGCTCTGGAA 3' (SEQ ID NO: 447)

Reverse primer:
5' GAATTCCATTAA 3' (SEQ ID NO: 448)

Set 69:

Forward Primer:
5' TGGGGTGTCCAA 3' (SEQ ID NO: 449)

Reverse primer:
5' GCAAGCTCCGAA 3' (SEQ ID NO: 450)

Set 70:

Forward Primer:
5' ATGTTTTTTCAA 3' (SEQ ID NO: 451)

-continued

Reverse primer:
5' AGATCTGTTGAA 3' (SEQ ID NO: 452)

Set 71:

Forward Primer:
5' AAGTGCTGTGAA 3' (SEQ ID NO: 453)

Reverse primer:
5' ACTTTTTTGGAA 3' (SEQ ID NO: 454)

Set 72:

Forward Primer:
5' AATCGGCAGGAA 3' (SEQ ID NO: 455)

Reverse primer:
5' GGCATGTCACAA 3' (SEQ ID NO: 456)

Set 73:

Forward Primer:
5' AGGAAGAAAGAA 3' (SEQ ID NO: 457)

Reverse primer:
5' CAGTTTCACCAA 3' (SEQ ID NO: 458)

Set 74:

Forward Primer:
5' CACAGAATTTAA 3' (SEQ ID NO: 459)

Reverse primer:
5' AAGAATAAGTAA 3' (SEQ ID NO: 460)

Set 75:

Forward Primer:
5' GGGATAGTACAA 3' (SEQ ID NO: 461)

Reverse primer:
5' TTCCCATGATAA 3' (SEQ ID NO: 462)

Set 76:

Forward Primer:
5' TGATTAGTTGAA 3' (SEQ ID NO: 463)

Reverse primer:
5' GCATTCAGTGAA 3' (SEQ ID NO: 464)

Set 77:

Forward Primer:
5' AGGGAATATTAA 3' (SEQ ID NO: 465)

Reverse primer:
5' GACCTTAGGTAA 3' (SEQ ID NO: 466)

Set 78:

Forward Primer:
5' TTCTTTTCACAA 3' (SEQ ID NO: 467)

Reverse primer:
5' CCAAACTAAGAA 3' (SEQ ID NO: 468)

Set 79:

Forward Primer:
5' GTGCTCTTAGAA 3' (SEQ ID NO: 469)

Reverse primer:
5' ATGAGTTTAGAA 3' (SEQ ID NO: 470)

Set 80:

Forward Primer:
5' ATGAGCATAGAA 3' (SEQ ID NO: 471)

-continued

Reverse primer:
5' GACAAATGAGAA 3' (SEQ ID NO: 472)

Set 81:

Forward Primer:
5' AAACCCAGAGAA 3' (SEQ ID NO: 473)

Reverse primer:
5' CCTCACACAGAA 3' (SEQ ID NO: 474)

Set 82:

Forward Primer:
5' CACACTGTGGAA 3' (SEQ ID NO: 475)

Reverse primer:
5' CACTGTACCCAA 3' (SEQ ID NO: 476)

Set 83:

Forward Primer:
5' GTAGTATTTCAA 3' (SEQ ID NO: 477)

Reverse primer:
5' TGGATACACTAA 3' (SEQ ID NO: 478)

Set 84:

Forward Primer:
5' CCCATGATTCAA 3' (SEQ ID NO: 479)

Reverse primer:
5' TCATAGGAGGAA 3' (SEQ ID NO: 480)

Set 85:

Forward Primer:
5' AGGAAAGAGAAA 3' (SEQ ID NO: 481)

Reverse primer:
5' ATATGGTGATAA 3' (SEQ ID NO: 482)

Set 86:

Forward Primer:
5' GATGCCATCCAA 3' (SEQ ID NO: 483)

Reverse primer:
5' ATACTATTTCAA 3' (SEQ ID NO: 484)

Set 87:

Forward Primer:
5' GTGTGCATGGAA 3' (SEQ ID NO: 485)

Reverse primer:
5' AGGTGTTGAGAA 3' (SEQ ID NO: 486)

Set 88:

Forward Primer:
5' CAGCCTGGGCAA 3' (SEQ ID NO: 487)

Reverse primer:
5' GGAGCTCTACAA 3' (SEQ ID NO: 488)

Set 89:

Forward Primer:
5' AACTAAGGTTAA 3' (SEQ ID NO: 489)

Reverse primer:
5' AACTTATGTTAA 3' (SEQ ID NO: 490)

Set 90:

Forward Primer:
5' ATCTCAACAGAA 3' (SEQ ID NO: 491)

-continued

```
Reverse primer:
5' TAACAATGTGAA 3'     (SEQ ID NO: 492)

Set 91:

Forward Primer:
5' AAGGATCAGGAA 3'     (SEQ ID NO: 493)

Reverse primer:
5' CTCAAGTCTTAA 3'     (SEQ ID NO: 494)
```

Multiplex PCR

Regions on chromosome 21 surrounding SNPs TSC0397235, TSC0470003, TSC1649726, TSC1261039, TSC0310507, TSC1650432, TSC1335008, TSC0128307, and TSC0259757 were amplified from the template genomic DNA using the polymerase chain reaction (PCR, U.S. Pat. Nos. 4,683,195 and 4,683,202, incorporated herein by reference). This PCR reaction used primers that annealed approximately 130 bases upstream and downstream of the loci of interest. It was used to increases the number of copies of the loci of interest to eliminate any errors that may result from a low number of genomes.

For increased specificity, a "hot-start" PCR reaction was used. PCR reactions were performed using the HotStarTaq Master Mix Kit supplied by QIAGEN (catalog number 203443). The amount of template DNA and primer per reaction can be optimized for each locus of interest. In this example, 15 ng of template human genomic DNA and 5 μM of each primer were used.

Two microliters of each forward and reverse primer, at concentrations of 5 mM were pooled into a single microcentrifuge tube and mixed. Eight microliters of the primer mix was used in a total PCR reaction volume of 40 μl (1.5 μl of template DNA, 10.5 μl of sterile water, 8 μl of primer mix, and 20 μl of HotStar Taq). Twenty-five cycles of PCR were performed. The following PCR conditions were used:

(1) 95° C. for 15 minutes;
(2) 95° C. for 30 seconds;
(3) 4° C. for 30 seconds;
(4) 37° C. for 30 seconds;
(5) Repeat steps 2-4 twenty-four (24) times;
(6) 72° C. for 10 minutes.

The temperatures and times for denaturing, annealing, and extension, can be optimized by trying various settings and using the parameters that yield the best results.

In another embodiment, the loci of interest are amplified using 6-base oligonucleotides, 7-base oligonucleotides, 8-base oligonucleotides, 9-base oligonucleotides, 10-base oligonucleotides, 11-base oligonucleotides, 12-base oligonucleotides, 13-base oligonucleotides, 14-base oligonucleotides, or greater than 14-base oligonucleotides. In a preferred embodiment, 6-base oligonucleotides, 7-base oligonucleotides, 8-base oligonucleotides, 9-base oligonucleotides, 10-base oligonucleotides, 11-base oligonucleotides, or 12-base oligonucleotides are used to amplify the loci of interest. In another embodiment, any number of oligonucleotides can be used including but not limited to 1-5, 5-10, 10-15, 15-20, 20-25, 25-30, 30-35, 35-40, 40-45, 45-50, 50-100, 100-500, 500-1000, 1000-2000, 2000-4000, 4000-8000, 8000-10,000 or greater than 10,000. With a small number of random oligos, the concentration of the oligos is large enough to allow efficient amplification, and yet, the number of oligos is small enough that it does not cause interference between the oligos. This allows efficient amplification of the genome.

In another embodiment, the upstream and downstream sequences of the loci of interest are analyzed to identify a 6-base, 7-base, 8-base, 9-base, 10-base, 11-base, or 12-base sequence that is present in the sequence upstream or downstream for each of the loci of interest, which is then used to amplify the loci of interest. In another embodiment, any number of 6-base oligonucleotides can be used to amplify the loci of interest including but not limited to 1-10, 10-50, 50-100, 100-200, 200-500, or greater than 500.

In another embodiment, the number of loci of interest from a small number of genomes can be increased by amplifying a limited number of the loci of interest, followed by removal of the primers, and amplification of the remaining loci of interest. All the loci of interest do not have to be multiplexed in one reaction. Any number of experimentally determined loci of interest can be multiplexed in a single reaction including but not limited to 1-5, 5-10, 10-25, 25-50, 50-100, 100-200, 200-400, or greater than 400. After increasing the number of copies of these loci of interest, the sample can be passed through a column that allows the amplified products to bind and the primers and unused dNTPs to be removed. After eluting the bound products from the column, different loci of interest can be amplified in a single reaction. This reduces the amount of interaction between the primers.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

Purification of Fragment of Interest

The excess primers and nucleotides were removed from the reaction by using Qiagen MinElute PCR purification kits (Qiagen, Catalog Number 28004). The reactions were performed following the manufacturer's instructions supplied with the columns. The DNA was eluted in 100 μl of sterile water.

PCR Reaction Two

SNP TSC0397235 was amplified using the following primer set:

```
First Primer:
                                    (SEQ ID NO: 495)
5' TTAGTCATCGCAGAATTCTACTTCTTTCTGAAGTGGGA 3'

Second primer:
                                    (SEQ ID NO: 496)
5' GGACAGCTCGATGGGACTAATGCATACTC 3'
```

The first primer contained a biotin tag at the 5' end and a recognition site for the restriction enzyme EcoRI, and was designed to anneal 103 bases from the locus of interest. The second primer contained the recognition site for the restriction enzyme BsmF I.

SNP TSC0470003 was amplified using the following primer set:

```
First Primer:
                                    (SEQ ID NO: 497)
5' GTAGCCACTGGTGAATTCGTGCCATCGCAAAAGAATAA 3'
```

-continued

```
Second primer:
                                        (SEQ ID NO: 498)
5' ATTAGAATGATGGGGACCCCTGTCTTCCC 3'
```

The first primer contained a biotin tag at the 5' end and a recognition site for the restriction enzyme EcoRI, and was designed to anneal 80 bases from the locus of interest. The second primer contained the recognition site for the restriction enzyme BsmF I.

SNP TSC 1649726 was amplified using the following primer set:

```
First Primer:
                                        (SEQ ID NO: 499)
5' ACGCATAGGAAGGAATTCATTCTGACACGTGTGAGATA 3'

Second primer:
                                        (SEQ ID NO: 500)
5' GAAATTGACCACGGGACTGCACACTTTTC 3'
```

The first primer contained a biotin tag at the 5' end and a recognition site for the restriction enzyme EcoRI, and was designed to anneal 113 bases from the locus of interest. The second primer contained the recognition site for the restriction enzyme BsmF I.

SNP TSC1261039 was amplified using the following primer set:

```
First Primer:
                                        (SEQ ID NO: 501)
5' CGGTAAATCGGAGAATTCAAGTTGAGGCATGCATCCAT 3'

Second primer:
                                        (SEQ ID NO: 502)
5' TCGGGGCTCAGCGGGACCACAGCCACTCC 3'
```

The first primer contained a biotin tag at the 5' end and a recognition site for the restriction enzyme EcoRI, and was designed to anneal 54 bases from the locus of interest. The second primer contained the recognition site for the restriction enzyme BsmF I.

SNP TSC0310507 was amplified using the following primer set:

```
First Primer:
                                        (SEQ ID NO: 503)
5' TCTATGCACCACGAATTCAATATGTGTTCAAGGACATT 3'

Second primer:
                                        (SEQ ID NO: 504)
5' TGCTTAATCGGTGGGACTTGTAATTGTAC 3'
```

The first primer contained a biotin tag at the 5' end and a recognition site for the restriction enzyme EcoRI, and was designed to anneal 93 bases from the locus of interest. The second primer contained the recognition site for the restriction enzyme BsmF I.

SNP TSC1650432 was amplified using the following primer set:

```
First Primer:
                                        (SEQ ID NO: 505)
5' CGCGTTGTATGCGAATTCCCTGGGGTATAAAGATAAGA 3'

Second primer:
                                        (SEQ ID NO: 506)
5' CTCACGGGAACTGGGACACCTGACCCTGC 3'
```

The first primer contained a biotin tag at the 5' end and a recognition site for the restriction enzyme EcoRI, and was designed to anneal 80 bases from the locus of interest. The second primer contained the recognition site for the restriction enzyme BsmF I.

SNP TSC1335008 was amplified using the following primer set:

```
First Primer:
                                        (SEQ ID NO: 507)
5' GTCTTGCCGCTTGAATTCCCATAGAAGAATGCGCCAAA 3'

Second primer:
                                        (SEQ ID NO: 508)
5' TTGAGTAGTACAGGGACACACTAACAGAC 3'
```

The first primer contained a biotin tag at the 5' end and a recognition site for the restriction enzyme EcoRI, and was designed to anneal 94 bases from the locus of interest. The second primer contained the recognition site for the restriction enzyme BsmF I.

SNP TSC0128307 was amplified using the following primer set:

```
First Primer:
                                        (SEQ ID NO: 509)
5' AATACTGTAGGTGAATTCTTGCCTAAGCATTTTCCCAG 3'

Second primer:
                                        (SEQ ID NO: 510)
5' GTGTTGACATTCGGGACTGTAATCTTGAC 3'
```

The first primer contained a biotin tag at the 5' end and a recognition site for the restriction enzyme EcoRI, and was designed to anneal 54 bases from the locus of interest. The second primer contained the recognition site for the restriction enzyme BsmF I.

SNP TSC0259757 was amplified using the following primer set:

```
First Primer:
                                        (SEQ ID NO: 511)
5' TCTGTAGATTCGGAATTCTTTAGAGCCTGTGCGCTGAG 3'

Second primer:
                                        (SEQ ID NO: 512)
5' CGTACCAGTACAGGGACGCAAACTGAGAC 3'
```

The first primer contained a biotin tag at the 5' end and a recognition site for the restriction enzyme EcoRI, and was designed to anneal 100 bases from the locus of interest. The second primer contained the recognition site for the restriction enzyme BsmF I.

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they can also be amplified together in a single PCR reaction. For increased specificity, a "hot-start" PCR was used. PCR reactions were performed using the HotStarTaq Master Mix Kit supplied by QIAGEN (catalog number 203443).

One microliter of the elutate from the multiplex reaction (PCR product eluted from the MinElute column) was used as template DNA for each PCR reaction. Each SNP was amplified in triplicate when the multiplex sample was used as the template. As a control, each SNP was amplified from 15 ng of the original template DNA (DNA that did not undergo the multiplex reaction). The amount of template DNA and primer per reaction can be optimized for each locus of interest but in this example, 5 μM of each primer was used. Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results.

Agarose Gel Analysis

Four microliters of a twenty microliter PCR reaction for each SNP from the original template DNA was analyzed by agarose gel electrophoresis (see FIG. 18A). Four microliters of a twenty microliter PCR reaction for each SNP that was amplified from the multiplexed template was analyzed on by agarose gel electrophoresis (see FIG. 18B).

As seen in FIG. 18A, for 8/9 of the SNPs amplified from the original template DNA, a single band of high intensity was seen (lanes 1-3, and 5-9). The band migrated at the correct position for each of the 8 SNPs. Amplification of TSC1261039 from the original template DNA produced a band of high intensity, which migrated at the correct position, and a faint band of lower molecular weight (lane 4). Only two bands were seen, and the bands could clearly be distinguished based on molecular weight. The PCR method described herein allows clean amplification of the loci of interest from genomic DNA without any concentration or enrichment of the loci of interest.

As seen in FIG. 18B, the primers used to amplify SNPs TSC0397235, TSC0470003, TSC0310507, and TSC0128307 from the multiplexed template DNA produced a single band of high intensity, which migrated at the correct position (lanes 1, 2, 5, and 8). No additional bands were introduced despite the fact that the multiplex reaction contained two hundred primers. While the multiplex primers were 12 bases in length and likely annealed to additional sequences other than those located on chromosome 21, the products were not seen because the bands were not amplified in the second PCR reaction. The second PCR reaction employed primers specific for the loci of interest and used asymmetric oligonucleotides and escalating annealing temperatures, which allows specific amplification from the genome (see Example 1).

Amplification of TSC1649726 from the multiplex template DNA produced one band of high intensity and two weaker bands, which could clearly be distinguished based on molecular weight (see FIG. 18B, lane 3). Amplification of TSC1261039 from the multiplex template DNA produced a high intensity band of the correct molecular weight and a faint band of lower molecular weight (see FIG. 18B, lane 4). The low molecular weight band was the same size as the band seen from the amplification of TSC1261039 from the original template DNA (compare FIG. 18A, lane 4 with FIG. 18B, lane 4). Thus, amplification of TSC1261039 on the multiplex template DNA did not introduce any additional non-specific bands Amplification of SNPs TSC1650432, TSC1335008, and TSC0259757 from the multiplex template DNA produced one band of high intensity, which migrated at the correct position, and one weaker band (lanes 6, 7, and 9). For SNPs TSC1650432 and TSC0259757, the weaker band was of lower molecular weight, and clearly was distinguishable from the band of interest (see FIG. 18B, lanes 6 and 9). For SNP TSC1335008, the weaker band was of slightly higher molecular weight. However, the correct band can be identified by comparing to the amplification products of TSC1335008 from the original template DNA, (compare FIG. 18A, lane 7 and FIG. 18B, lane 7). The PCR conditions can also be optimized for TSC1335008. All 9 SNPs were amplified under the exact same conditions, which produced clearly distinguishable bands for the amplified SNPs.

Purification of Fragment of Interest

The PCR products were separated from the genomic template DNA. One half of the PCR reaction was transferred to a well of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1×PBS, with gentle mixing (Kandpal etal., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

As discussed in detail in Example 6, the sequence of both alleles of a SNP can be determined by using one labeled nucleotide in the presence of the other unlabeled nucleotides. The following components were added to each fill in reaction: 1 μl of fluorescently labeled ddGTP, 0.5 μl of unlabeled ddNTPs (40 μM), which contained all nucleotides except guanine, 2 μl of 10× sequenase buffer, 0.25 μl of Sequenase, and water as needed for a 20 μl reaction. The fill in reaction was performed at 40° C. for 10 min. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565).

After labeling, each Streptawell was rinsed with 1×PBS (100 μl) three times. The "filled in" DNA fragments then were released from the Streptawells by digestion with the restriction enzyme EcoRI, according to the manufacturer's instructions that were supplied with the enzyme. Digestion was performed for 1 hour at 37° C. with shaking at 120 rpm.

Detection of the Locus of Interest

The samples were loaded into a lane of a 36 cm 5% acrylamide (urea) gel (BioWhittaker Molecular Applications, Long Ranger Run Gel Packs, catalog number 50691). The samples were electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence. A box was drawn around each band and the intensity of the band was calculated using the ImageQuant software.

Below, a schematic of the 5' overhang for TSC0470003 after digestion with BsmF I is depicted:

```
5' CTCT
3' GAGA               R      A      C      C
Overhang position     1      2      3      4
```

The observed nucleotides for TSC0470003 are adenine and guanine on the sense strand (herein depicted as the top strand). The third position of the overhang corresponds to cytosine, which is complementary to guanine. Labeled ddGTP was used in the presence of unlabeled dATP, dCTP, and dTTP. Schematics of the DNA molecules after the fill-in reaction are depicted below:

```
Allele 1              5' CTCT   G*
                      3' GAGA   C     A     C     C
Overhang position               1     2     3     4

Allele 2              5' CTCT   A     T     G*
                      3' GAGA   T     A     C     C
Overhang position               1     2     3     4
```

Figure 19:

Two bands were seen; the lower molecular weight band corresponded to the DNA molecules filled in with ddGTP at position 1 complementary to the overhang and the higher molecular weight band corresponded to the DNA molecules filled in with ddGTP at position 3 complementary to the overhang (see FIG. 19).

The percentage of allele 2 to allele 1 at TSC0470003 after amplification from the original template DNA and the multiplexed template DNA was calculated. The use of one fluorescently labeled nucleotide to detect both alleles in a single reaction reduces the amount of error that is introduced through pipetting reactions, and the error that is introduced through the quantum coefficients of different dyes.

For SNP TSC047003, the percentage of allele 2 to allele 1 was calculated by dividing the value of allele 2 by the sum of the values for allele 2 and allele 1. The percentage of allele 2 to allele 1 for TSC047003 on the original template DNA was calculated to be 0.539 (see Table XIX). Three PCR reactions were performed for each SNP on the multiplexed template DNA. The average percentage of allele 2 to allele 1 for TSC047003 on the multiplexed DNA was 0.49 with a standard deviation of 0.0319 (see Table XIX). There was no statistically significant difference between the percentage obtained on the original template DNA and the multiplexed template DNA.

For SNP TSC1261039, the percentage of allele 2 to allele 1 for TSC1261039 on the original template DNA was calculated to be 0.44 (see Table XIX). Three PCR reactions were performed for each SNP on the multiplexed template DNA (see FIG. 19B). The average percentage of allele 2 to allele 1 for TSC1261039 on the multiplexed DNA was 0.468 with a standard deviation of 0.05683 (see Table XIX). There was no statistically significant difference between the percentages of allele 2 to allele 1 obtained on the original template DNA and the multiplexed template DNA.

The variation seen in the percentage of allele 2 to allele 1 for TSC1261039 on the multiplexed template DNA was likely due to pipetting reactions. The variation can be reduced by increasing the number of replicates. With a large number of replicates, a percentage can be obtained with minimum statistical variation.

Likewise, there was no statistical difference between the percentage of allele 2 to allele 1 on the original template DNA and on the multiplexed template DNA for SNPs TSC0310507 and TSC1335008 (see Table XIX, and FIGS. 19C and 19D). Thus, a multiplex reaction can be used to increase the number of chromosomal regions containing the loci of interest without affecting the percentage of one allele to the other at the variable sites.

TABLE XIX

Percentage of allele 2 to allele 1 at various SNPs with and without multiplexing.

| | Allele 1 | Allele 2 | 2/(2 + 1) |
|---|---|---|---|
| TSC047003 | | | |
| IA | 5535418 | 6487873 | 0.539608748 |
| M1 | 4804358 | 4886716 | 0.504249168 |
| M2 | 5549389 | 5958585 | 0.517778803 |
| M3 | 8356275 | 7030245 | 0.45690936 |
| Mean (M1-M3) | | | 0.49297911 |
| STDEV | | | 0.031961429 |
| TSC1261039 | | | |
| IA | 3488765 | 2768066 | 0.442407027 |
| M1 | 3603388 | 2573244 | 0.41660957 |
| M2 | 4470423 | 5026872 | 0.529295131 |
| M3 | 4306015 | 36694012 | 0.46008898 |
| Mean (M1-M3) | | | 0.46866456 |
| STDEV | | | 0.056830136 |
| TSC0310507 | | | |
| IA | 2966511 | 2688190 | 0.475390299 |
| M1 | 4084472 | 2963451 | 0.420471535 |
| M2 | 4509891 | 4052892 | 0.47331481 |
| M3 | 7173191 | 4642069 | 0.39288759 |
| Mean (M1-M3) | | | 0.428891312 |
| STDEV | | | 0.040869352 |
| TSC1335008 | | | |
| IA | 2311629 | 2553016 | 0.524810341 |
| M1 | 794790 | 900879 | 0.531282343 |
| M2 | 1261568 | 1780689 | 0.5853184 |
| M3 | 1165156 | 1427840 | 0.550653 |
| Mean (M1-M3) | | | 0.555751248 |
| STDEV | | | 0.027376412 |

The methods described herein used two distinct amplification reactions to amplify the loci of interest. In the first PCR reaction, oligonucleotides were designed to anneal upstream and downstream of the loci of interest. Unlike traditional genomic amplification, these primers were not degenerate and annealed at a specified distance from the loci of interest.

However, due to the length of the primers, it is likely that the primers annealed to other regions of the genome. These primers were used to increase the amount of DNA available for genetic analysis.

The second PCR reaction employs the methods described in Examples 1-6. The primers are designed to amplify the loci of interest, and the sequence is determined at the loci of interest. The conditions of the second PCR reaction allowed specific amplification of the loci of interest from the multiplexed template DNA. If there were any non-specific products from the multiplex reaction, they did not impede amplification of the loci of interest. There was no statistical difference in the percentages of allele 2 to allele 1 at the four SNPs analyzed, regardless of whether the amplification was performed on original template DNA or multiplexed template DNA.

The SNPs analyzed in this example were located on human chromosome 21. However, the methods can be applied to non-human and human DNA including but not limited to chromosomes 1, 2, 3, 4, 5, 6, 7, 8, 9, 10, 11, 12, 13, 14, 15, 16, 17, 18, 19, 20, 21, 22, X, and Y. The multiplex methods can also be applied to analysis of genetic mutations including, but not limited to nucleotide substitutions, insertions, deletions, and rearrangements.

The above methods can be used to increase the amount of DNA available for genetic analysis whenever the starting template DNA is limiting in quantity. For example, pre-malignant and pre-invasive lesions with malignant cells usually constitute a small fraction of the cells in the specimen, which reduces the number of genetic analyses that can be performed. The methods described herein can be used to increase the amounts of malignant DNA available for genetic analysis. Also, the number of fetal genomes present in the maternal blood is often low; the methods described herein can be used to increase the amount of fetal DNA.

Example 13

Plasma isolated from blood of a pregnant female contains both maternal template DNA and fetal template DNA. As discussed earlier, the percentage of fetal DNA in the maternal plasma varies for each pregnant female. However, the percentage of fetal DNA can be determined by analyzing SNPs wherein the maternal template DNA is homozygous and the template DNA obtained from the plasma displays a heterozygous pattern.

For example, assume SNP X can either be adenine or guanine, and the maternal DNA for SNP X is homozygous for guanine. The labeling method described in Example 6 can be used to determine the sequence of the template DNA in the plasma sample. If the plasma sample contains fetal DNA, which is heterozygous at SNP X, the following DNA molecules are expected after digestion with the type IIS restriction enzyme BsmF I, and the fill-in reaction with labeled ddGTP, unlabeled dATP, dTTP, and dCTP.

```
Maternal Allele 1   5' GGGT    G*
                    3' CCCA    C    T    C    A

Maternal Allele 2   5' GGGT    G*
                    3' CCCA    C    T    C    A

Fetal Allele 1      5' GGGT    G*
                    3' CCCA    C    T    C    A

Fetal Allele 2      5' GGGT    A    A    G*
                    3' CCCA    T    T    C    A
```

Two signals are seen; one signal corresponds to the DNA molecules filled in with ddGTP at position one complementary to the overhang and the second signal corresponds to the DNA molecules filled in with ddGTP at position three complementary to the overhang. However, the maternal DNA is homozygous for guanine, which corresponds to the DNA molecules filled in at position one complementary to the overhang. The signal from the DNA molecules filled in with ddGTP at position three complementary to the overhang corresponds to the adenine allele, which represents the fetal DNA. This signal becomes a beacon for the fetal DNA, and can used to measure the amount of fetal DNA present in the plasma sample.

There is no difference in the amount of fetal DNA from one chromosome to another. For instance, the percentage of fetal DNA in any given individual from chromosome 1 is the same as the percentage of fetal DNA from chromosome 2, 3, 4, 5, 6, 7, 8, 9, 10, 11, 12, 13, 14, 15, 16, 17, 18, 19, 20, 21, 22, X and Y. Thus, the allele ratio calculated for SNPs on one chromosome can be compared to the allele ratio for the SNPs on another chromosome.

For example, the allele ratio for the SNPs on chromosome 1 should be equal to the allele ratio for the SNPs on chromosomes 2, 3, 4, 5, 6, 7, 8, 9, 10, 11, 12, 13, 14, 15, 16, 17, 18, 19, 20, 21, 22, X, and Y. However, if the fetus has a chromosomal abnormality, including but not limited to a trisomy or monosomy, the ratio for the chromosome that is present in an abnormal copy number will differ from the ratio for the other chromosomes.

Blood from a pregnant female was collected after informed consent had been obtained. The blood sample was used to demonstrate that fetal DNA can be detected in the maternal plasma by analyzing SNPs wherein the maternal DNA was homozygous, and the same SNP displayed a heterozygous pattern from DNA obtained from the plasma of a pregnant woman.

Preparation of Plasma from Whole Blood

Plasma was isolated from 4 tubes each containing 9 ml of blood (Fischer Scientific, 9 ml EDTA Vacuette tubes, catalog number NC9897284). The blood was obtained by venipuncture from a pregnant female who had given informed consent. After collecting the blood, formaldehyde (25 μl/ml of blood) was added to each of the tubes. The tubes were placed at 4° C. until shipment. The tubes were shipped via Federal Express in a foam container containing an ice pack.

The blood was centrifuged at 1000 rpm for 10 minutes. The brake on the centrifuge was not used. This centrifugation step was repeated. The supernatant was transferred to a new tube and spun at 3,000 rpm for ten minutes. The brake on the centrifuge was not used. The supernatant from each of the four tubes was pooled and aliquoted into two tubes. The plasma was stored at −80° C. until the DNA was purified.

Template DNA was isolated using the QIAmp DNA Blood Midi Kit supplied by QIAGEN (Catalog number 51183). The template DNA was isolated as per instructions included in the kit. The template DNA from the plasma was eluted in a final volume of 20 microliters.

Isolation of Maternal DNA

After the plasma was removed from the sample described above, one milliliter of the remaining blood sample, which is commonly referred to as the "buffy-coat," was transferred to a new tube. One milliliter of 1×PBS was added to the sample. Template DNA was isolated using the QIAmp DNA Blood Midi Kit supplied by QIAGEN (Catalog number 51183).

Identification of Homozygous Maternal SNPs

Example 8 describes a method for identifying SNPs that are highly variable within the population or for identifying heterozygous SNPs for a given individual. The methods as described in Example 8 were applied to the maternal template DNA to identify SNPs on chromosome 13 wherein the maternal DNA was homozygous. Any number of SNPs can be screened. The number of SNPs to be screened is proportional to the number of heterozygous SNPs in the fetal DNA that need to be analyzed.

As described in detail in Example 6, one labeled nucleotide can be used to determine the sequence of both alleles at a particular SNP. SNPs for which the sequence can be determined with labeled ddGTP in the presence of unlabeled dATP, dTTP, and dCTP were chosen for this example. However, SNPs for which the sequence can be determined with labeled ddATP, ddCTP or ddTTP can also be used. Additionally, the SNPs to be analyzed can be chosen such that all are labeled with the same nucleotide or any combination of the four nucleotides. For instance, if 400 SNPs are to be screened, 100 can be chosen such that the sequence is determined with labeled ddATP, 100 can be chosen such that the sequence is determined with labeled ddTTP, 100 can be chosen such that the sequence is determined with labeled ddGTP, and 100 can be chosen such that the sequence is determined with labeled ddCTP, or any combination of the four labeled nucleotides.

Twenty-nine SNPs wherein the maternal DNA was homozygous were identified: TSC0052277, TSC1225391, TSC0289078, TSC1349804, TSC0870209, TSC0194938, TSC0820373, TSC0902859, TSC0501510, TSC1228234, TSC0082910, TSC0838335, TSC0818982, TSC0469204, TSC1084457, TSC0466177, TSC1270598, TSC1002017, TSC1104200, TSC0501389, TSC0039960, TSC0418134, TSC0603688, TSC0129188, TSC1103570, TSC0813449, TSC0701940, TSC0087962, and TSC0660274. Heterozygous SNPs will vary from individual to individual.

Design of Multiplex Primers

A low copy number of fetal genomes typically is present in the maternal plasma. To increase the copy number of the loci of interest located on chromosome 13, primers were designed to anneal at approximately 130 bases upstream and 130 bases downstream of each loci of interest. This was done to reduce statistical sampling error that can occur when working with a low number of genomes, which can influence the ratio of one allele to another (see Example 11). The primers were 12 bases in length. However, primers of any length can be used including but not limited to 2, 3, 4, 5, 6, 7, 8, 9, 10, 11, 12, 13, 14, 15, 16, 17, 18, 19, 20, 21,22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers were designed to anneal to both the sense strand and the antisense strand.

The primers were designed to terminate at the 3' end in the dinucleotide "AA" to reduce the formation of primer-dimers. However, the primers can be designed to end in any of the four nucleotides and in any combination of the four nucleotides.

The multiplex primers for SNPTSC0052277 were

```
Forward primer:
5' GACATGTTGGAA 3'      (SEQ ID NO: 513)

Reverse primer:
5' ACTTCCAGTTAA 3'      (SEQ ID NO: 514)
```

The multiplex primers for SNP TSC1225391 were:

```
Forward primer:
5' GTTTCCTGTTAA 3'      (SEQ ID NO: 515)

Reverse primer
5' CGATGATGACAA 3'      (SEQ ID NO: 516)
```

The multiplex primers for SNP TSC0289078 were:

```
Forward primer
5' GAGTAGAGACAA 3'      (SEQ ID NO: 517)

Reverse primer
5' TCCCGGATACAA 3'      (SEQ ID NO: 518)
```

The multiplex primes for SNP TSC1349804 were:

```
Forward primer:
5' CATCCTCTAGAA 3'      (SEQ ID NO: 519)

Reverse primer:
5' TATTCCTGAGAA 3'      (SEQ ID NO: 520)
```

The multiplex primers for SNP TSC0870209 were:

```
Forward primer:
5' AGTTTGTTTTAA 3'      (SEQ ID NO: 521)

Reverse primer:
5' TATAAACGATAA 3'      (SEQ ID NO: 522)
```

The multiplex primers for SNP TSC0194938 were:

```
Forward primer:
5' TTTGACCGATAA 3'      (SEQ ID NO: 523)

Reverse primer:
5' TGACAGGACCAA 3'      (SEQ ID NO: 524)
```

The multiplex primers for SNP TSC0820373 were:

```
Forward primer:
5' TTATTCATTCAA 3'      (SEQ ID NO: 525)

Reverse primer:
5' AGTTTTTCACAA 3'      (SEQ ID NO: 526)
```

The multiplex primers for SNP TSC0902859 were:

```
Forward primer:
5' CACCTCCCTGAA 3'      (SEQ ID NO: 527)

Reverse primer:
5' CCAGATTGAGAA 3'      (SEQ ID NO: 528)
```

The multiplex primers for SNP TSC0501510 were:

```
Forward primer:
5' TGTGTCCACCAA 3'      (SEQ ID NO: 529)

Reverse primer:
5' CTTCTATTCCAA 3'      (SEQ ID NO: 530)
```

The multiplex primers for SNP TSC1228234 were:

```
Forward primer:
5' TCACAATAGGAA 3'      (SEQ ID NO: 531)
```

-continued

Reverse primer:
5' TACAAGTGAGAA 3' (SEQ ID NO: 532)

The multiplex primers for SNP TSC0082910 were:

Forward primer:
5' GAGTTTTCGTAA 3' (SEQ ID NO: 533)

Reverse primer:
5' GTGTGCCCCCAA 3' (SEQ ID NO: 534)

The multiplex primers for SNP TSC0838335 were:

Forward primer:
5' GCACCACTGCAA 3' (SEQ ID NO: 535)

Reverse primer:
5' GAACACAATGAA 3' (SEQ ID NO: 536)

The multiplex primers for SNP TSC0818982 were:

Forward primer:
5' TATCCTATTCAA 3' (SEQ ID NO: 537)

Reverse primer:
5' CAACCATTATAA 3' (SEQ ID NO: 538)

The multiplex primers for SNP TSC0469204 were:

Forward primer:
5' TATGCTTTACAA 3' (SEQ ID NO: 539)

Reverse primer:
5' TTTGTTTACCAA 3' (SEQ ID NO: 540)

The multiplex primers for SNP TSC1084457 were:

Forward primer:
5' AGGAAATTAGAA 3' (SEQ ID NO: 541)

Reverse primer:
5' TGTTAGACTTAA 3' (SEQ ID NO: 542)

The multiplex primers for SNP TSC0466177 were:

Forward primer:
5' TATTTGGAGGAA 3' (SEQ ID NO: 543)

Reverse primer:
5' GGCATTTGTCAA 3' (SEQ ID NO: 444)

The multiplex primers for SNP TSC1270598 were:

Forward primer:
5' ATACTCCAGGAA 3' (SEQ ID NO: 545)

Reverse primer:
5' CAGCCTGGACAA 3' (SEQ ID NO: 546)

The multiplex primers for SNP TSC1002017 were:

Forward primer:
5' CCATTGCAGTAA 3' (SEQ ID NO: 547)

Reverse primer:
5' AGGTTCTCATAA 3' (SEQ ID NO: 548)

The multiplex primers for SNP TSC1104200 were:

Forward primer:
5' TGTCATCATTAA 3' (SEQ ID NO: 549)

Reverse primer:
5' TGGTATTTGCAA 3' (SEQ ID NO: 550)

The multiplex primers for SNP TSC0501389 were:

Forward primer:
5' TAGGGTTTGTAA 3' (SEQ ID NO: 551)

Reverse primer:
5' CCCTAAGTAGAA 3' (SEQ ID NO: 552)

The multiplex primers for SNP TSC0039960 were:

Forward primer:
5' GTATTTCTTTAA 3' (SEQ ID NO: 553)

Reverse primer:
5' GAGTCTTCCCAA 3' (SEQ ID NO: 554)

The multiplex primers for SNP TSC0418134 were:

Forward primer:
5' CAGGTAGAGTAA 3' (SEQ ID NO: 555)

Reverse primer:
5' ATAGGATGTGAA 3' (SEQ ID NO: 556)

The multiplex primers for SNP TSC0603688 were:

Forward primer:
5' CAATGTGTATAA 3' (SEQ ID NO: 557)

Reverse primer:
5' AGAGGGCATCAA 3' (SEQ ID NO: 558)

The multiplex primers for SNP TSC0129188 were:

Forward primer:
5' CCAGTGGTCTAA 3' (SEQ ID NO: 559)

Reverse primer:
5' TAAACAATAGAA 3' (SEQ ID NO: 560)

The multiplex primers for SNP TSC1103570 were:

Forward primer:
5' GCACACTTTTAA 3' (SEQ ID NO: 561)

Reverse primer:
5' ATGGCTCTGCAA 3' (SEQ ID NO: 562)

The multiplex primers for SNP TSC0813449 were:

Forward primer:
5' GTCATCTTGTAA 3' (SEQ ID NO: 563)

Reverse primer:
5' TGCTTCATCTAA 3' (SEQ ID NO: 564)

The multiplex primers for SNP TSC0701940 were:

Forward primer:
5' AGAAAGGGGCAA 3' (SEQ ID NO: 565)

-continued

```
Reverse primer:
5' CTTTTCTTTCAA 3'     (SEQ ID NO: 566)
```

The multiplex primers for SNP TSC0087962 were:

```
Forward primer:
5' CTACTCTCTCAA 3'     (SEQ ID NO: 567)

Reverse primer:
5' ACAGCATTATAA 3'     (SEQ ID NO: 568)
```

The multiplex primers for SNP TSC0660274 were:

```
Forward primer:
5' ACTGCTCTGGAA 3'     (SEQ ID NO: 569)

Reverse primer:
5' GCAGAGGCACAA 3'     (SEQ ID NO: 570)
```

Multiplex PCR

Regions on chromosome 13 surrounding the above-mentioned 29 SNPs were amplified from the template genomic DNA using the polymerase chain reaction (PCR, U.S. Pat. Nos. 4,683,195 and 4,683,202, incorporated herein by reference). This PCR reaction used primers that annealed approximately 150 bases upstream and downstream of each loci of interest. The fifty-eight primers were mixed together and used in a single reaction to amplify the template DNA. This reaction was done to increase the number of copies of the loci of interest, which eliminates error generated from a low number of genomes.

For increased specificity, a "hot-start" PCR reaction was used. PCR reactions were performed using the HotStarTaq Master Mix Kit supplied by QIAGEN (catalog number 203443). The amount of template DNA and primer per reaction can be optimized for each locus of interest. In this example, the 20 μl of plasma template DNA was used.

Two microliters of each forward and reverse primer, at concentrations of 5 mM were pooled into a single microcentrifuge tube and mixed. Four microliters of the primer mix was used in a total PCR reaction volume of 50 μl (20 μl of template plasma DNA, 1 μl of sterile water, 4 μl of primer mix, and 25 μl of HotStar Taq. Twenty-five cycles of PCR were performed. The following PCR conditions were used:

(1) 95° C. for 15 minutes;

(2) 95° C. for 30 second;

(3) 4° C. for 30 seconds;

(4) 37° C. for 30 seconds;

(5) Repeat steps 2-4 twenty-four (24) times;

(6) 72° C. for 10 minutes.

The temperatures and times for denaturing, annealing, and extension, can be optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

Purification of Fragment of Interest

The unused primers, and nucleotides were removed from the reaction by using Qiagen MinElute PCR purification kits (Qiagen, Catalog Number 28004). The reactions were performed following the manufacturer's instructions supplied with the columns. The DNA was eluted in 100 μl of sterile water.

PCR Reaction Two

Design of Primers

SNPTSC0052277 was amplified using the following primer set:

```
First primer:
                                        (SEQ ID NO: 571)
5' CTCCGTGGTATGGAATTCCACTCAAATCTTCATTCAGA 3'

Second primer:
                                        (SEQ ID NO: 572)
5' ACGTCGGGTTACGGGACACCTGATTCCTC 3'
```

SNP TSC1225391 was amplified using the following primer set:

```
First primer:
                                        (SEQ ID NO: 573)
5' TACCATTGGTTTGAATTCTTGTTTCCTGTTAACCATGC 3'

Second primer:
                                        (SEQ ID NO: 574)
5' GCCGAGTTCTACGGGACAGAAAAGGGAGC 3'
```

SNP TSC0289078 was amplified using the following primer set:

```
First primer:
                                        (SEQ ID NO: 575)
5' TGCAGTGATTTCGAATTCGAGACAATGCTGCCCAGTCA 3'

Second primer:
                                        (SEQ ID NO: 576)
5' TCTAAATTCTCTGGGACCATTCCTTCAAC 3'
```

SNP TSC1349804 was amplified using the following primer set:

```
First primer:
                                        (SEQ ID NO: 577)
5' ACTAACAGCACTGAATTCCATGCTCTTGGACTTTCCAT 3'

Second primer:
                                        (SEQ ID NO: 578)
5' TCCCCTAACGTTGGGACACAGAATACTAC 3'
```

SNP TSC0870209 was amplified using the following primer set:

```
First primer:
                                        (SEQ ID NO: 579)
5' GTCGACGATGGCGAATTCCTGCCACTCATTCAGTTAGC 3'

Second primer:
                                        (SEQ ID NO: 580)
5' GAACGGCCCACAGGGACCTGGCATAACTC 3'
```

SNP TSC0194938 was amplified using the following primer set:

```
First primer:
                                        (SEQ ID NO: 581)
5' TCATGGTAGCAGGAATTCTGCTTTGACCGATAAGGAGA 3'
```

-continued

Second primer:
(SEQ ID NO: 582)
5' ACTGTGGGATTCGGGACTGTCTACTACCC 3'

SNP TSC0820373 was amplified using the following primer set:

First primer:
(SEQ ID NO: 583)
5' ACCTCTCGGCCGGAATTCGGAAAAGTGTACAGATCATT 3'

Second primer:
(SEQ ID NO: 584)
5' GCCGGATACGAAGGGACGGCTCGTGACTC 3'

SNP TSC0902859 was amplified using the following primer set:

First primer:
(SEQ ID NO: 585)
5' CCGTAGACTAAAGAATTCCCTGATGTCAGGCTGTCACC 3'

Second primer:
(SEQ ID NO: 586)
5' ATCGGATCAGTCGGGACGGTGTCTTTGCC 3'

SNP TSC0501510 was amplified using the following primer set:

First primer:
(SEQ ID NO: 587)
5' GCATAGGCGGGAGAATTCCCTGTGTCCACCAAAGTCGG 3'

Second primer:
(SEQ ID NO: 588)
5' CCCACATAGGGCGGGACAAAGAGCTGAAC 3'

SNP TSC1228234 was amplified using the following primer set:

First primer:
(SEQ ID NO: 589)
5' GGCTTGCCGAGCGAATTCTAGGAAAGATACGGAATCAA 3'

Second primer:
(SEQ ID NO: 590)
5' TAACCCTCATACGGGACTTTCATGGAAGC 3'

SNP TSC0082910 was amplified using the following primer set:

First primer:
(SEQ ID NO: 591)
5' ATGAGCACCCGGGAATTCTGATTGGAGTCTAGGCCAAA 3'

Second primer:
(SEQ ID NO: 592)
5' TGCTCACCTTCTGGGACGTGGCTGGTCTC 3'

SNP TSC0838335 was amplified using the following primer set:

First primer:
(SEQ ID NO: 593)
5' ACCGTCTGCCACGAATTCTGGAAAACATGCAGTCTGGT 3'

Second primer:
(SEQ ID NO: 594)
5' TACACGGGAGGCGGGACAGGGTGATTAAC 3'

SNP TSC0818982 was amplified using the following primer set:

First primer:
(SEQ ID NO: 595)
5' CTTAAAGCTAACGAATTCAGAGCTGTATGAAGATGCTT 3'

Second primer:
(SEQ ID NO: 596)
5' AACGCTAAAGGGGGGACAACATAATTGGC 3'

SNP TSC0469204 was amplified using the following primer set:

First primer:
(SEQ ID NO: 597)
5' TTGTAAGAACGAGAATTCTGCAACCTGTCTTTATTGAA 3'

Second primer:
(SEQ ID NO: 598)
5' CTTCACCACTTTGGGACACTGAAGCCAAC 3'

SNP TSC1084457 was amplified using the following primer set:

First primer:
(SEQ ID NO: 599)
5' AACCATTGATTTGAATTCGAAATGTCCACCAAAGTTCA 3'

Second primer:
(SEQ ID NO: 600)
5' TGTCTAGTTCCAGGGACGCTGTTACTTAC 3'

SNP TSC0466177 was amplified using the following primer set:

First primer:
(SEQ ID NO: 601)
5' CGAAGGTAATGTGAATTCTGCCACAATTAAGACTTGGA 3'

Second primer:
(SEQ ID NO: 602)
5' ATACCGGTTTTCGGGACAGATCCATTGAC 3'

SNP TSC1270598 was amplified using the following primer set:

First primer:
(SEQ ID NO: 603)
5' CCTGAAATCCACGAATTCCACCCTGGCCTCCCAGTGCA 3'

Second primer:
(SEQ ID NO: 604)
5' TAGATGGTAGGTGGGACAGGACTGGCTTC 3'

SNP TSC1002017 was amplified using the following primer set:

First primer:
(SEQ ID NO: 605)
5' GCATATCTTAGCGAATTCCTGTGACTAATACAGAGTGC 3'

Second primer:
(SEQ ID NO: 606)
5' CCAAATATGGTAGGGACGTGTGAACACTC 3'

SNP TSC1104200 was amplified using the following primer set:

First primer:
(SEQ ID NO: 607)
5' TGCCGCTACAGGGAATTCATATGGCAGATATTCCTGAA 3'

-continued

Second primer:
(SEQ ID NO: 608)
5' ACGTTGCGGACCGGGACTTCCACAGAGCC 3'

SNP TSC0501389 was amplified using the following primer set:

First primer:
(SEQ ID NO: 609)
5' CTTCGCCCAATGGAATTCGGTACAGGGGTATGCCTTAT 3'

Second primer:
(SEQ ID NO: 610)
5' TGCACTTCTGCCGGGACCAGAGGAGAAAC 3'

SNP TSC0039960 was amplified using the following primer set:

First primer:
(SEQ ID NO: 611)
5' TGTGGGTATTCTGAATTCCACAAAATGGACTAACACGC 3'

Second primer:
(SEQ ID NO: 612)
5' ACGTCGTTCAGTGGGACATTAAAAGGCTC 3'

SNP TSC0418134 was amplified using the following primer set:

First primer:
(SEQ ID NO: 613)
5' GGTTATGTGTCAGAATTCTGAAACTAGTTTGGAAGTAC 3'

Second primer:
(SEQ ID NO: 614)
5' GCCTCAGTTTCGGGGACAGTTCTGAGGAC 3'

SNP TSC0603688 was amplified using the following primer set:

First primer:
(SEQ ID NO: 615)
5' TGTAACACGGCCGAATTCCTCATTTGTATGAAATAGGT 3'

Second primer:
(SEQ ID NO: 616)
5' AATCTAACTTGAGGGACCGGCACACACAC 3'

SNP TSC0129188 was amplified using the following primer set:

First primer:
(SEQ ID NO: 617)
5' AGTGTCCCCTTAGAATTCGCAGAGACACCACAGTGTGC 3'

Second primer:
(SEQ ID NO: 618)
5' TTTGCTACAGTCGGGACCCTTGTGTGCTC 3'

SNP TSC1103570 was amplified using the following primer set:

First primer:
(SEQ ID NO: 619)
5' AGCACATCACTAGAATTCAATACCATGTGTGAGCTCAA 3'

Second primer:
(SEQ ID NO: 620)
5' AATCCTGCTTCCGGGACCTAACTTTGAAC 3'

SNP TSC0813449 was amplified using the following primer set:

First primer:
(SEQ ID NO: 621)
5' TTTCATTTTCTGGAATTCCTCTAATGATTTTCTGGAGC 3'

Second primer:
(SEQ ID NO: 622)
5' CGTCGCCGCGTAGGGACTTTTTCTTCCAC 3'

SNP TSC0701940 was amplified using the following primer set:

First primer:
(SEQ ID NO: 623)
5' TTACTTAATCCTGAATTCGAGAAAAGCCATGTTGATAA 3'

Second primer:
(SEQ ID NO: 624)
5' TCATGGGTCGCTGGGACTTTGCCCTCTGC 3'

SNP TSC0087962 was amplified using the following primer set:

First primer:
(SEQ ID NO: 625)
5' ACTAACAGCACTGAATTCATTTTACTATAATCTGCTAC 3'

Second primer:
(SEQ ID NO: 626)
5' GTTAGCCGAGAAGGGACTGTCTGTGAAGC 3'

SNP TSC0660274 was amplified using the following primer set:

First primer:
(SEQ ID NO: 627)
5' AAATATGCAGCGGAATTCGTAAGTGACCTATTAATAAC 3'

Second primer:
(SEQ ID NO: 628)
5' GCGATGGTTACGGGGACAGCCAGGCAACC 3'

Each first primer had a biotin tag at the 5' end and contained a restriction enzyme recognition site for EcoRI, and was designed to anneal at a specified distance from the locus of interest. This allows a single reaction to be performed for the loci of interest, as each loci of interest will migrate at a distinct position (based on annealing position of first primer). The second primer contained a restriction enzyme recognition site for BsmF I.

All loci of interest were amplified from the multiplexed template DNA using the polymerase chain reaction (PCR, U.S. Pat. Nos. 4,683,195 and 4,683,202, incorporated herein by reference). In this example, the loci of interest were amplified in separate reaction tubes but they could also be amplified together in a single PCR reaction. For increased specificity, a "hot-start" PCR was used. PCR reactions were performed using the HotStarTaq Master Mix Kit supplied by QIAGEN (catalog number 203443).

The amount of multiplexed template DNA and primer per reaction can be optimized for each locus of interest. One microliter of the multiplexed template DNA eluted from the MinElute column was used in the PCR reaction for each locus of interest, and 5 μM of each primer was used. The twenty-nine SNPs described above also were amplified from the maternal DNA (15 ng of DNA was used in the PCR reaction;

primer concentrations were as stated above). Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results. In this example, the first primer was designed to anneal at various distances from the locus of interest. The skilled artisan understands that the annealing location of the first primer can be 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-105, 106-110, 111-115, 116-120, 121-125, 126-130, 131-140, 140-160, 160-180, 180-200, 200-220, 220-240, 240-260, 260-280, 280-300, 300-350, 350-400, 400-450, 450-500, or greater than 500 bases from the locus of interest.

Purification of Fragment of Interest

The PCR products were separated from the genomic template DNA. Each PCR product was placed into a well of a Streptawell, transparent, High-Bind plate from Roche Diagnostics GmbH (catalog number 1 645 692, as listed in Roche Molecular Biochemicals, 2001 Biochemicals Catalog). Alternatively, the PCR products can be pooled into a single well because the first primer was designed to allow the loci of interest to separate based on molecular weight. The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1×PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

As demonstrated in Example 6, the sequence of both alleles of a SNP can be determined by filling in the overhang with one labeled nucleotide in the presence of the other unlabeled nucleotides. The following components were added to each fill in reaction: 1 μl of fluorescently labeled ddGTP, 0.5 μl of unlabeled ddNTPs (40 μM), which contained all nucleotides except guanine, 2 μl of 10× sequenase buffer, 0.25 μl of Sequenase, and water as needed for a 20μl reaction. The fill in reaction was performed at 40° C. for 10 min. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565).

After labeling, each Streptawell was rinsed with 1×PBS (100 μl) three times. The "filled in" DNA fragments were then released from the Streptawells by digestion with the restriction enzyme EcoRI, according to the manufacturer's instructions that were supplied with the enzyme. Digestion was performed for 1 hour at 37° C. with shaking at 120 rpm.

Detection of the Locus of Interest

After release from the streptavidin matrix, the sample was loaded into a lane of a 36 cm 5% acrylamide (urea) gel (BioWhittaker Molecular Applications, Long Ranger Run Gel Packs, catalog number 50691). The sample was electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence.

Below a schematic of the 5' overhang for SNP TSC0838335 is depicted. The entire sequence is not reproduced, only a portion to depict the overhang (where R indicates the variable site).

```
10/14                  5' TAA
                       3' ATT   R   A   C   A
Overhang position               1   2   3   4
```

The observed nucleotides for TSC0838335 are adenine and guanine on the 5' sense strand (herein depicted as the top strand). The nucleotide in position three of the overhang corresponded to cytosine, which is complementary to guanine. Labeled ddGTP can be used to determine the sequence of both allele in the presence of unlabeled dATP, dCTP, and dTTP.

The restriction enzyme BsmF I was used to create the 5' overhang, which typically cuts 10/14 from the recognition site. At times, BsmF I will cut 11/15 from the recognition site and generate the following overhang:

```
11/15                  5' TA
                       3' AT    T   R   A   C
Overhang position               0   1   2   3
```

Position 0 in the overhang is thymidine, which is complementary to adenine. Position 0 complementary to the overhang was filled in with unlabeled dATP, and thus after the fill-in reaction, the exact same molecules were generated whether the enzyme cut at 10/14 or 11/15 from the recognition site. The DNA molecules generated after the fill-in reaction are depicted below:

```
G allele 10/14      5' TAA     G*
                    3' ATT     C    A    C    A
Overhang position              1    2    3    4

G allele 11/15      5' TA      A    G*
                    3' AT      T    C    A    C
Overhang position              0    1    2    3

A allele 10/14      5' TAAA    T    G*
                    3' ATTT    A    C    A
Overhang position              1    2    3    4

A allele 11/15      5' TA      A    A    T    G*
                    3' AT      T    T    A    C
Overhang position              0    1    2    3
```

The maternal template DNA amplified for TSC0838335 displayed a single band that migrated at the expected position of the higher molecular weight band, which corresponded to the "A" allele (see FIG. 20, lane 1). The maternal template DNA was homozygous for adenine at SNP TSC0838335.

However, in lane 2, amplification of the multiplexed template DNA for TSC0838335 isolated from the plasma of the same individual displayed two bands; a lower molecular weight band, which corresponded to the "G" allele, and the higher molecular weight band, which corresponded to the "A" allele. The template DNA isolated from the plasma of a pregnant female contains both maternal template DNA and fetal template DNA.

As seen in FIG. 20, lane 1, the maternal template DNA was homozygous for adenine at this SNP (compare lanes 1 and 2). The "G" allele represented the fetal DNA. Signals from the maternal template DNA and the fetal template DNA clearly have been distinguished. The "G" allele becomes a beacon for the fetal DNA and can be used to measure the amount of fetal DNA present in the sample. Additionally, once the percentage of fetal DNA in the matemal plasma for a given sample has been determined, any deviation from this percentage indicates a chromosomal abnormality. This method provides the first non-invasive method for the detection of fetal chromosomal abnormalities.

As seen in FIG. 20, lane 3, analysis of the maternal DNA for SNP TSC0418134 generated a single band that migrated at the expected position of the higher molecular weight band, which corresponded to the adenine allele. Likewise, analysis of the multiplexed template DNA isolated from the maternal plasma gave a single band, which migrated at the expected position of the adenine allele (see FIG. 20, lane 4). Both the maternal DNA and the fetal DNA are homozygous for adenine at TSC0418134.

Below, a schematic of the 5' overhang for TSC0129188 is depicted, wherein R indicates the variable site:

```
10/14          5' TCAT
               3' AGTA    R      A      C      T
Overhang position         1      2      3      4
```

The nucleotide upstream of the variable site (R) does not correspond to guanine on the sense strand. Thus, the 5' overhang generated by the 11/15 cutting properties of BsmF I will be filled-in identically to the 5' overhang generated by the 10/14 cut. Labeled ddGTP in the presence of unlabeled dATP, dTTP, and dCTP was used for the fill-in reaction. The DNA molecules generated after the fill-in reaction are depicted below:

```
A allele 10/14      5' TCAT   A      T  G*
                    3' AGTA   T      A  C     T
Overhang position             1      2  3     4

G allele 10/14      5' TCAT   G*
                    3' AGTA   C      A  C     T
Overhang position             1      2  3     4
```

Analysis of the maternal DNA for SNP TSC0129188 gave a single band that corresponded to the DNA molecules filled in with ddGTP at position 1 complementary to the overhang, which represented the "G" allele (see FIG. 20, lane 5). No band was detected for adenine allele, indicating that the maternal DNA is homozygous for guanine.

In contrast, analysis of the multiplexed template DNA from the maternal plasma, which contains both maternal DNA, and fetal DNA, gave two distinct bands (see FIG. 20, lane 6). The lower molecular weight band corresponded to the "G" allele, while the higher molecular weight corresponded to the "A" allele. The "A" allele represents the fetal DNA. Thus, a method has been developed that allows separation of maternal DNA and fetal DNA signals without the added complexity of having to isolate fetal cells. In addition, a sample of paternal DNA is not required to detect differences between the maternal DNA and the fetal DNA.

Analysis of the maternal DNA for SNP TSC0501389 gave a single band that migrated at the higher molecular weight position, which corresponded to the "A" allele. No band was detected that corresponded to the "G" allele. Similarly, analysis of the multiplexed template DNA from the maternal plasma for SNP TSC0501389 gave a single band that migrated at the higher molecular weight position, which corresponded to the "A" allele. Both the maternal template DNA and the fetal template DNA were homozygous for adenine at SNP TSC0501389.

The maternal DNA and the template DNA from the plasma originated from the same sample. One sample, which was obtained through a non-invasive procedure, provided a genetic fingerprint for both the mother and the fetus.

Of the twenty-nine SNPs for which the maternal template DNA was homozygous, the fetal template DNA was heterozygous at two of the twenty-nine SNPs. The fetal DNA was homozygous for the same allele as the maternal template DNA at the remaining 27 SNPs (data not shown). Comparing the homozygous allele of the maternal template DNA and the plasma template DNA at a given SNP provides an added level of quality control. It is not possible that the maternal template DNA and the plasma template DNA are homozygous for different alleles at the same SNP. If this is seen, it would indicate that an error in processing had occurred.

The methods described herein demonstrate that the maternal genetic signal can be separated and distinguished from the fetal genetic signal in a maternal plasma sample. The above-example analyzed SNPs located on chromosome 13, however any chromosome can be analyzed including human chromosome 1, 2, 3, 4, 5, 6, 7, 8, 9, 10, 11, 12, 13, 14, 15, 16, 17, 18, 19, 20, 21, 22, X and Y and fetal chromosomes 1, 2, 3, 4, 5, 6, 7, 8, 9, 10, 11, 12, 13, 14, 15, 16, 17, 18, 19, 20, 21, 22, X and Y.

In addition, the methods described herein can be used to detect fetal DNA in any biological sample including but not limited to cell, tissue, blood, serum, plasma, saliva, urine, tears, vaginal secretions, umbilical cord blood, chorionic villi, amniotic fluid, embryonic tissues, lymph fluid, cerebrospinal fluid, mucosa secretions, peritoneal fluid, ascitic fluid, fecal matter, or body exudates.

The methods described herein demonstrate that the percentage of fetal DNA in the maternal sample can be determined by analyzing SNPs wherein the maternal DNA is homozygous, and the DNA isolated from the plasma of the pregnant female is heterozygous. The percentage of fetal DNA can be used to determine if the fetal genotype has any chromosomal disorders.

For example, if the percentage of fetal DNA present in the sample is calculated to be 30% by analysis of chromosome 1 (chromosomal abnormalities involving chromosome 1 terminate early in the pregnancy), then any deviation from 30% fetal DNA is indicative of a chromosomal abnormality. For example, if upon analysis of a SNP or multiple SNPs on chromosome 18, the percentage of fetal DNA is higher than 30%, this would indicate that an additional copy of chromosome 18 is present. The calculated percentage of fetal DNA from any chromosome can be compared to any other chromosome. In particular, the percentage of fetal DNA on chromosome 13 can be compared to the percentage of fetal DNA on chromosomes 18 and 21.

This analysis is assisted by knowledge of the expected ratio of one allele to the other allele at each SNP. As discussed in Example 9, not all heterozygous SNPs display ratios of 50:50. Knowledge of the expected ratio of one allele to the other reduces the overall number of variable sites that must be analyzed. However, even without knowledge of the expected ratios for the various SNPs, the percentage of fetal DNA can be calculated by analyzing a large number of SNPs. When the sampling size of SNPs is large enough, the statistical variation arising from the values of the expected ratios will be eliminated.

In addition, heterozygous maternal SNPs also provide valuable information. The analysis is not limited to homozygous maternal SNPs. For example, if at a heterozygous SNP on maternal DNA, the ratio of allele 1 to allele 2 is 1:1, then in the plasma template DNA the ratio should remain 1:1 unless the fetal DNA carries a chromosomal abnormality.

The above methods can also be used to detect mutations in the fetal DNA including but not limited to point mutations, transitions, transversions, translocations, insertions, deletions, and duplications. As seen in FIG. 20, fetal DNA can readily be distinguished from maternal DNA. The above methods can be used to determine the sequence of any locus of interest for any gene.

Example 14

Plasma isolated from blood of a pregnant female contains both maternal template DNA and fetal template DNA. As discussed above, fetal chromosomal abnormalities can be determined by analyzing SNPs wherein the maternal template DNA is homozygous and the template DNA obtained from the plasma displays a heterozygous pattern.

For example, assume SNP X can either be adenine or guanine, and the maternal DNA for SNP X is homozygous for guanine. The labeling method described in Example 6 can be used to determine the sequence of the DNA in the plasma sample. If the plasma sample contains fetal DNA, which is heterozygous at SNP X, the following DNA molecules are expected after digestion with the type IIS restriction enzyme BsmF I, and the fill-in reaction with labeled ddGTP, unlabeled dATP, dTTP, and dCTP.

```
Maternal Allele 1    5' GGGT  G*
                     3' CCCA  C      T  C    A
```

-continued

```
Maternal Allele 2    5' GGGT  G*
                     3' CCCA  C      T  C    A

Fetal Allele 1       5' GGGT  G*
                     3' CCCA  C      T  C    A

Fetal Allele 2       5' GGGT  A      A  G*
                     3' CCCA  T      T  C    A
```

Two signals are seen; one signal corresponds to the DNA molecules filled in with ddGTP at position one complementary to the overhang and the second signal corresponds to the DNA molecules filled in with ddGTP at position three complementary to the overhang. However, the maternal DNA is homozygous for guanine, which corresponds to the DNA molecules filled in at position one complementary to the overhang. The signal from the DNA molecules filled in with ddGTP at position three complementary to the overhang corresponds to the adenine allele, which represents the fetal DNA. This signal becomes a beacon for the fetal DNA, and can used to measure the amount of fetal DNA present in the plasma sample.

There is no difference in the amount of fetal DNA from one chromosome to another. For instance, the percentage of fetal DNA in any given individual from chromosome 1 is the same as the percentage of fetal DNA from chromosome 2, 3, 4, 5, 6, 7, 8, 9, 10, 11, 12, 13, 14, 15, 16, 17, 18, 19, 20, 21, 22, X and Y. Thus, the allele ratio calculated for SNPs on one chromosome can be compared to the allele ratio for the SNPs on another chromosome.

For example, the allele ratio for the SNPs on chromosome 1 should be equal to the allele ratio for the SNPs on chromosomes 2, 3, 4, 5, 6, 7, 8, 9, 10, 11, 12, 13, 14, 15, 16, 17, 18, 19, 20, 21, 22, X, and Y. However, if the fetus has a chromosomal abnormality, including but not limited to a trisomy or monosomy, the ratio for the chromosome that is present in an abnormal copy number will differ from the ratio for the other chromosomes.

To recapitulate the in vivo scenario of blood from a pregnant female, maternal DNA was mixed with DNA isolated from her child, who previously was diagnosed with Trisomy 21, in various ratios to represent varying percentages of fetal DNA. For example, to replicate the in vivo scenario of 50% fetal DNA in maternal blood, equal amounts of maternal DNA were mixed with DNA isolated from her child with Down's syndrome. The maternal DNA was analyzed to identify homozygous SNPs, and these SNPs then were analyzed using the mixture of 50% maternal DNA and 50% Down's syndrome DNA. The ratio of allele 1 to allele 2 at heterozygous SNPs on chromosome 13 was compared to the ratio of allele 1 to allele 2 at heterozygous SNPs on chromosome 21.

Four different samples were analyzed: a sample with 100% of the DNA from a child with Down syndrome; a sample with 75% DNA from the child with Down syndrome and 25% DNA from the child's mother; a sample with 50% DNA from the child with Down syndrome and 50% DNA from the child's mother; and a sample with 40% DNA from the child with Down syndrome and 60% DNA from the child's mother. The maternal DNA was analyzed to identify homozygous SNPs. The DNA isolated from the child with Down syndrome was genotyped to identify heterozygous SNPs. Then, the samples were genotyped at SNPs where the maternal DNA was homozygous and the DNA from the child was heterozygous. For each sample, these SNPs were analyzed ten times.

Collection of Blood Samples

An Internal Review Board approved study was designed to allow collection of blood samples from children afflicted with Down's syndrome and their parents. For this study, blood was collected from the mother, the father, and the child with Down's syndrome. Informed consent to collect blood from the child with Down's syndrome was granted by the parents as well as the child. Blood was collected into 9 ml EDTA Vacuette tubes (catalog number NC9897284). The tubes were stored at 4° C. until ready for processing.

Isolation of Plasma and Maternal Cells

The blood was stored at 4° C. until processing. The tubes were spun at 1000 rpm for ten minutes in a centrifuge with braking power set to zero. The tubes were spun a second time at 1000 rpm for ten minutes. The supernatant (the plasma) of each sample was transferred to a new tube and spun at 3000 rpm for ten minutes with the brake set to zero. The supernatant was transferred to a new tube and stored at −80° C. Approximately two milliliters of the "buffy coat," which contains maternal cells, was placed into a separate tube and stored at −80° C.

Isolation of DNA

DNA was isolated from the plasma sample using the Qiagen Midi Kit for purification of DNA from blood cells, following the manufacturer's instructions (QIAmp DNA Blood Midi Kit, Catalog number 51183). DNA was eluted in 100 μl of distilled water. The Qiagen Midi Kit also was used to isolate DNA from the maternal cells contained in the "buffy coat." Maternal DNA and the plasma DNA were isolated from the same tube of blood.

Identification of Maternal Homozygous SNPs

The maternal DNA was genotyped to identify homozygous SNPs. Seven hundred and sixty-eight SNPs on chromosome 13 and 768 SNPs on chromosome 21 were genotyped using the methods described in Example 6. Any number of SNPs can be analyzed, and the SNPs can be located on human chromosome 1, 2, 3, 4, 5, 6, 7, 8, 9, 10, 11, 12, 13, 14, 15, 16, 17, 18, 19, 20, 21, 22, X and Y. Preferably, the SNPs that are genotyped have allele frequencies of 50:50, 60:40, 70:30, 80:20, or 90:10. As described in Example 8, the allele frequency of any given SNP can be determined.

Details regarding the SNPs located on chromosome 13 and 21 can be found at the SNP consortium database, which can be accessed via the internet at http://www.snp.cshl.org. The primers were designed following the procedures set fourth in the Examples described above, for example, in Examples 1, 2, 3, 5, and 6.

The first primers were designed so that after digestion with a Type Ius enzyme, the products had different molecular weights as described in Example 6. This allowed the amplified products to be pooled, and run in a single lane of a gel.

For example, the first primer can be designed such that after digestion a 30 base pair product is generated. Likewise, the first primer of a different locus of interest can be designed such that after digestion a 40 base pair product is generated. The first primers can be designed so that in a single reaction, numerous loci can be analyzed in one lane of a gel (30, 40, 50, 60, 70, 80, 90, 100, 110, and 120 base pair products can be run in a single lane). The first primer can be designed to anneal any distance from the locus of interest including but not limited to between 5-10, 10-25, 25-50, 50-75, 75-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000 and greater than 1000 bases.

Amplification of the Loci of Interest

For each SNP that was genotyped, a PCR reaction was used to amplify the loci of interest. The PCR reactions were performed in 96-well plates. The first and second primer (3 μl of 1.25 μM stock concentration) for each SNP was distributed into a well of a microtiter plate. Eight 96-well PCR plates were set-up for chromosome 21 and eight 96-well plates were set-up for chromosome 13. After the primers had been distributed into the wells of the microtiter plates, a mixture containing the genomic DNA and HotStar PCR reagents was added to each well. Each PCR reaction contained 3 μl of each primer, 7.5 μl of HotStar Taq Master mix, 0.5 μl of water, and 1 μl of genomic DNA (10 ng/μl).

The PCR cycling conditions were as follows:

(1) 95° C. for 15 minutes and 15 seconds;
(2) 37° C. for 30 seconds;
(3) 95° C. for 30 seconds;
(4) 52° C. for 30 seconds;
(5) 95° C. for 30 seconds;
(6) 58° C. for 30 seconds;
(7) 95° C. for 30 seconds;
(8) Repeat steps 6 and 7 thirty seven (37) times;
(9) 72° C. for 5 minutes.

Purification of Fragment of Interest

After the PCR reaction, 3 μl of a PCR product generated with a first primer designed to produce a 30 base pair product, 3 μl of a PCR product generated with a first primer designed to produce a 40 base pair product, 3 μl of a PCR product generated with a first primer designed to produce a 50 base pair product, 3 μl of a PCR product generated with a first primer designed to produce a 60 base pair product, 3 μl of a PCR product generated with a first primer designed to produce a 70 base pair product, 3 μl of a PCR product generated with a first primer designed to produce a 80 base pair product, 3 μl of a PCR product generated with a first primer designed to produce a 90 base pair product, 3 μl of a PCR product generated with a first primer designed to produce a 100 base pair product were mixed together in a well of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1×PBS, with gentle mixing (Kandpal et al., Nucl. Acids Res. 18:1789-1795 (1990); Kaneoka et al., Biotechniques 10:30-34 (1991); Green et al., Nucl. Acids Res. 18:6163-6164 (1990)).

Restriction Enzyme Digestion of Isolated Fragments

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase. As discussed in detail in Example 6, a single nucleotide labeled with one chemical moiety can be used to determine the sequence at a SNP.

The amplified loci of interest were pooled into the streptavidin-well based on size, and on the nucleotide used in the fill-in reaction. The sequence of SNPs that were determined by using a guanine nucleotide were pooled together. Likewise, the sequence of SNPs that were determined by using an adenine nucleotide were pooled together; the sequence of SNPs that were determined by using a thymidine nucleotide were pooled together; and the sequence of SNPs that were determined by using a cytosine nucleotide were pooled together.

Thus, a typical fill-in reaction contained 8 amplified loci, ranging in size of 30-120 base pair products; the sequence of all eight was determined using a single nucleotide labeled with one chemical moiety. Any number of amplified loci can be pooled together.

The following components were added to each fill in reaction: 1 μl of fluorescently labeled dideoxynucleotide (ddGTP for G fill-in reactions; ddATP for A fill-in reactions; ddTTP for thymidine fill-in reactions; and ddCTP for cytosine fill-in reactions), 0.5 μl of unlabeled dNTPs (40 μM), which contained all nucleotides except the labeled nucleotide, 2 μl of 10× sequenase buffer, 0.25 μl of Sequenase, and water as needed for a 20 μl reaction.

The fill in reaction was performed at 40° C. for 10 min. Non-fluorescently labeled dNTP was purchased from Fermentas Inc. (Hanover, Md.). All other labeling reagents were obtained from Amersham (Thermo Sequenase Dye Terminator Cycle Sequencing Core Kit, US 79565).

After labeling, each Streptawell was rinsed with 1×PBS (100 μl) three times. The "filled in" DNA fragments were then released from the Streptawells by digestion with the restriction enzyme EcoRI, according to the manufacturer's instructions that were supplied with the enzyme. Digestion was performed for 1 hour at 37° C. with shaking at 120 rpm.

Detection of the Locus of Interest

After release from the streptavidin matrix, the sample was loaded into a lane of a 36 cm 5% acrylamide (urea) gel (BioWhittaker Molecular Applications, Long Ranger Run Gel Packs, catalog number 50691). The sample was electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence. The homozygous SNPs were identified.

Identification of Heterozygous SNPs with the Trisomy 21 Template

The DNA isolated from the individual with Down syndrome (the child of the mother who was genotyped above) was analyzed to identify heterozygous SNPs. The same seven hundred and sixty-eight SNPs on chromosome 13 and the same 768 SNPs on chromosome 21 that were analyzed with the maternal DNA were genotyped using the methods described in Example 6. Any number of SNPs can be analyzed, and the SNPs can be located on human chromosome 1, 2, 3, 4, 5, 6, 7, 8, 9, 10, 11, 12, 13, 14, 15, 16, 17, 18, 19, 20, 21, 22, X or Y. Preferably, the SNPs that are genotyped have allele frequencies of 50:50, 60:40, 70:30, 80:20, or 90:10. As described in Example 8, the allele frequency of any given SNP can be determined.

The process for genotyping the SNPS with the DNA isolated from the individual with Down syndrome was as described for the maternal DNA. The heterozygous SNPs were identified.

SNPs that were homozygous for the maternal DNA and heterozygous for the DNA isolated from the individual with Down syndrome were further analyzed using samples that contained mixtures of maternal DNA and Down syndrome DNA.

Generation of Samples Containing Maternal DNA and Down Syndrome DNA

The DNA and the DNA obtained from her child, who has Down's syndrome, were quantitated using a spectrophotometer. The maternal DNA and the child's DNA were mixed together at various percentages to represent the situation of circulating fetal DNA in the maternal blood. The following percentages were analyzed: 100% Down's syndrome DNA, 75% Down's syndrome DNA, 50% Down's syndrome DNA, and 40% Down's syndrome DNA.

The ratio at each heterozygous SNP was calculated by dividing the value obtained for allele 1 by the value obtained for allele 2. For example, if SNP X can either be adenine (A) or guanine (G), the ratio at SNP X was calculated by dividing the value obtained for adenine by the value obtained for guanine.

For the sample containing 100% Down syndrome DNA, sixty-two SNPs on chromosome 13, which were homozygous with the maternal DNA and heterozygous with the DNA isolated from the individual with Down syndrome, were analyzed. For chromosome 21, forty-nine SNPs were analyzed that were homozygous with the maternal DNA and heterozygous with the DNA isolated from the individual with Down syndrome.

The 62 SNPs on chromosome 13 and 49 SNPs on chromosome 21 were analyzed ten separate times. As shown in Table XX, for each of the ten trials, the ratio of allele 1 to allele 2 on chromosome 13 was approximately 1.0 as expected. For chromosome 13, there is one copy of allele 1 and one copy of allele 2. The average of the ten trials was 1.051 with a standard deviation of 0.085.

With a Trisomy 21, there are two copies of one allele, which are usually inherited from the mother, and one copy of the other allele. The expected ratio is approximately 0.5 (one copy of allele 1/two copies of allele 2). As shown in Table XX, the ratio for chromosome 21 varied from a low of 0.462 to a high of 0.634. For every trial, the ratio obtained for chromosome 21 was significantly distinct from the ratio obtained at chromosome 13. The average ratio for the ten trials was 0.531 with a standard deviation of 0.049.

The experiment was repeated ten times so that a true statistical measurement could be obtained. If ten different genetic samples were used, the SNPs that fit the criteria (maternal homozygous, Down syndrome child heterozygous) would be different, making it difficult to compare from sample to sample.

Statistical analysis revealed a confidence value of 99.9% that the ratios obtained on chromosome 13 and on chromosome 21 represented true differences, rather than random numerical fluctuations in value. The Ravgen method identified the presence of the chromosomal abnormality.

For the sample containing 75% Down syndrome DNA and 25% maternal DNA, sixty two SNPS on chromosome 13 and fifty SNPs on chromosome 21 were analyzed, unless stated otherwise. For various trials, not all the SNPS could be quantitated because the bands corresponding to certain SNPs were faint. This may have been caused by poor PCR amplification, poor binding to the streptavidin plate, or a weak fill-in reaction.

For trial 3, 61 SNPs on chromosome 13 were analyzed. For trail 4, 49 SNPs were analyzed on chromosome 21. With regard to trial 5, 47 SNPs on chromosome 21 were analyzed and 61 SNPs on chromosome 13. For trial 7, 49 SNPs were analyzed on chromosome 21 and 61 SNPs on chromosome 13. For trial 8, 49 chromosomes were analyzed on chromosome 21, and 59 SNPs were analyzed on chromosome 13. For trials 9 and 10, 59 SNPs on chromosome 13 were analyzed.

The expected ratio on chromosome 13 for a heterozygous SNP is 0.6. If the maternal chromosomes both contain an adenine nucleotide, and the Down syndrome genome is comprised of one chromosome with an adenine nucleotide and one chromosome with a guanine nucleotide, then the ratio of G:A is 0.75/(0.75 (Down syndrome A allele)+0.25+0.25 (maternal A alleles)), which is 0.6. For the ten trials, the ratios obtained for chromosome 13 varied from 0.567 to 0.645. The average for the ten trials was 0.609 with a standard deviation of 0.032 (see Table XX).

The expected ratio for chromosome 21 in a Trisomy condition is 0.375. If the maternal chromosomes both contain an adenine nucleotide, and the Down syndrome genome is comprised of two chromosomes with an adenine nucleotide and one chromosome with a guanine nucleotide, then the ratio of G:A is 0.75/(0.75+0.75 (Down syndrome A alleles)+0.25+0.25 (maternal A alleles)), which is 0.375.

For the ten trials, the ratios obtained for chromosome 21 varied from 0.350 to 0.4125, with an average of 0.384 and a standard deviation of 0.017 (see Table XX). Statistical analysis revealed a confidence value of 99.9% that the ratios obtained on chromosome 13 and on chromosome 21 represented true differences, rather than random numerical fluctuations in value. The Ravgen method identified the presence of the chromosomal abnormality in the presence of 25% maternal DNA.

With regard to the sample containing 50% Down syndrome DNA, 46 SNPs on chromosome 13 and 35 SNPs on chromosome 21 were analyzed, unless stated otherwise. For trial 1, 45 SNPs on chromosome 13 were analyzed. For trail 2, 44 SNPs on chromosome 13 were analyzed. For trial 3, 42 SNPs on chromosome 13 were analyzed. For trial 4, 44 SNPs on chromosome 13 and 34 SNPs on chromosome 21 were analyzed. For trial 5, 34 SNPs on chromosome 21 were analyzed. For trials 7 and 8, 44 and 41 SNPs on chromosome 13, respectively, were analyzed. For trial 9, 44 SNPs on chromosome 13 and 34 SNPs on chromosome 21 were analyzed. For trial 10, 44 SNPs on chromosome 13 were analyzed.

The expected ratio at a heterozygous SNP on chromosome 13 for the 50% sample is 0.33. If the maternal chromosomes both contain an adenine nucleotide, and the Down syndrome genome is comprised of one chromosome with an adenine nucleotide and one chromosome with a guanine nucleotide, then the ratio of G:A is 0.50/(0.50 (Down syndrome A allele )+0.50+0.50 (maternal A alleles)), which is 0.33. For the ten trials, the ratios obtained for chromosome 13 varied from 0.302 to 0.347. The average for the ten trials was 0.324 with a standard deviation of 0.013 (see Table XX).

The expected ratio for chromosome 21 in a Trisomy condition is 0.25. If the maternal chromosomes both contain an adenine nucleotide, and the Down syndrome genome is comprised of two chromosomes with an adenine nucleotide and one chromosome with a guanine nucleotide, then the ratio of G:A is 0.50/(0.50+0.50 (Down syndrome A alleles)+0.50+0.50 (maternal A alleles)), which is 0.25.

For the ten trials, the ratios obtained for chromosome 21 varied from 0.230 to 0.275, with an average of 0.244 and a standard deviation of 0.015 (see Table XX). Statistical analysis revealed a confidence value of 99.1% that the ratios obtained on chromosome 13 and on chromosome 21 represented true differences, rather than random numerical fluctuations in value. The Ravgen method identified the presence of the chromosomal abnormality in the presence of 50% maternal DNA.

For the sample containing 40% Down syndrome DNA, 60 SNPs on chromosome 13 and 48 SNPs on chromosome 21 were analyzed, unless stated otherwise. For trial 1, 47 SNPs on chromosome 21 were analyzed. For trials 2-4, 59 SNPs on chromosome 13 and 47 SNPs on chromosome 21 were analyzed. For trials 5 and 6, 46 SNPs on chromosome 21 were analyzed. For trail 7, 58 SNPs on chromosome 13 were analyzed. For trial 8, 46 SNPs on chromosome 21 were analyzed and for trials 9 and 10, 47 SNPs on chromosome 21 were analyzed.

The expected ratio at a heterozygous SNP on chromosome 13 for the 40% Down syndrome DNA sample is 0.25. If the maternal chromosomes both contain an adenine nucleotide, and the Down syndrome genome is comprised of one chromosome with an adenine nucleotide and one chromosome with a guanine nucleotide, then the ratio of G:A is 0.40/(0.40 (Down syndrome A allele )+0.60+0.60 (maternal A alleles)), which is 0.25. For the ten trials, the ratios obtained for chromosome 13 varied from 0.254 to 0.285. The average for the ten trials was 0.269 with a standard deviation of 0.009 (See Table XX).

The expected ratio for chromosome 21 in a Trisomy condition is 0.20. If the maternal chromosomes both contain an adenine nucleotide, and the Down syndrome genome is comprised of two chromosomes with an adenine nucleotide and one chromosome with a guanine nucleotide, then the ratio of G:A is 0.40/(0.40+0.40 (Down syndrome A alleles)+0.60+0.60 (maternal A alleles)), which is 0.20.

For the ten trials, the ratios obtained for chromosome 21 varied from 0.216 to 0.249, with an average of 0.23 and a standard deviation of 0.011 (see Table XX). Statistical analysis revealed a confidence value of 94.3% that the ratios obtained on chromosome 13 and on chromosome 21 represented true differences, rather than random numerical fluctuations in value. The Ravgen method identified the presence of the chromosomal abnormality in the presence of 60% maternal DNA.

The presence of the Trisomy 21 condition was identified with the Ravgen method in numerous samples that contained various percentages of abnormal DNA. Each percentage of abnormal DNA was analyzed ten separate times and each time, the presence of the abnormal condition was identified. The ratio of allele 1 to allele 2 at multiple heterozygous SNPs on chromosome 13 was calculated, and the ratios were averaged. The same was done with the SNPs located on chromosome 21. The ratio obtained for the heterozygous SNPs on chromosome 13 was statistically different from the ratio obtained on chromosome 21. The ratios obtained on both chromosome 13 and 21 were near the mathematically predicted values.

In this example, the confidence interval for the samples with 100% Down syndrome DNA and 75% Down syndrome DNA was 99.9%, and the confidence interval for the sample with 50% Down syndrome DNA was 99.1%, which is about the accuracy reported for amniocentesis. The confidence interval for the sample containing 40% Down syndrome DNA was 94.3%, which is more accurate than currently marketed non-invasive tests for prenatal diagnostics.

As discussed above, about 60 SNPs on chromosome 13 and 50 SNPs on chromosome 21 were analyzed. To increase the confidence interval for samples containing 40% fetal DNA or lower, a larger number of SNPs can be analyzed. The Ravgen method provides a highly accurate, cost-effective way to sequence DNA, so sequencing a larger number of SNPs is not difficult. The accuracy of the test is determined by the number of SNPs that are sequenced. For higher accuracy with samples that contain lower percentages of DNA, more SNPs can be analyzed. Alternatively, the methods described in this application can be used to ensure that the samples contain a higher percentage of fetal DNA.

In this example, a sample containing 40% Down syndrome DNA, which represented the fetal DNA in the maternal blood, was analyzed. Maternal blood samples with any percentage of fetal DNA can be analyzed including but not limited to 0.0001-1%, 1-10%, 10-20%, 20-30%, 30-40%, 40% -50%, 50-60%, 60-70%, 70-80%, 80-90%, and 90-100%.

TABLE XX

The Ravgen method identifies chromosomal abnormalities in Samples containing 40% Down syndrome DNA

| Ratio at Chrom. | 13 | 21 | Expected 21 | 13 | 21 | Expected 21 |
|---|---|---|---|---|---|---|
| | 100% DS DNA | | | ~75% DS DNA | | |
| Trial 1 | 0.959 | 0.5708 | 0.49 | 0.637 | .3764 | 0.389 |
| Trial 2 | 0.916 | 0.5024 | 0.48 | 0.567 | .3894 | 0.362 |
| Trial 3 | 1029 | 0.4616 | 0.51 | 0.651 | .3707 | 0.394 |
| Trial 4 | 0.967 | 0.5123 | 0.491 | 0.580 | .3901 | 0.367 |
| Trial 5 | 1.037 | 0.6339 | 0.51 | 0.645 | .4125 | 0.392 |
| Trial 6 | 1.111 | 0.5425 | 0.53 | 0.645 | .3743 | 0.392 |
| Trial 7 | 1.154 | 0.495 | 0.54 | 0.594 | .3974 | 0.373 |
| Trial 8 | 1.135 | 0.5276 | 0.532 | 0.583 | .3901 | 0.368 |
| Trial 9 | 1.148 | 0.5619 | 0.534 | 0.579 | .3899 | 0.367 |
| Trial 10 | 1.057 | 0.4976 | 0.52 | 0.609 | .350 | 0.378 |
| AVG. | 1.051 | .531 | 0.512 | .609 | 0.384 | 0.378 |
| STDEV | .085 | .049 | | .032 | .017 | |
| | ~50% DS DNA | | | ~40% DS DNA | | |
| Trial 1 | 0.347 | 0.275 | 0.258 | 0.277 | 0.239 | 0.217 |
| Trial 2 | 0.316 | 0.237 | 0.24 | 0.265 | 0.249 | 0.21 |
| Trial 3 | 0.338 | 0.247 | 0.253 | 0.266 | 0.227 | 0.21 |
| Trial 4 | 0.331 | 0.264 | 0.249 | 0.254 | 0.216 | 0.202 |
| Trial 5 | 0.330 | 0.241 | 0.248 | 0.274 | 0.246 | 0.215 |
| Trial 6 | 0.324 | 0.240 | 0.244 | 0.268 | 0.22 | 0.211 |
| Trial 7 | 0.318 | 0.233 | 0.241 | 0.275 | 0.227 | 0.216 |
| Trial 8 | 0.302 | 0.230 | 0.231 | 0.258 | 0.228 | 0.21 |
| Trial 9 | 0.315 | 0.238 | 0.240 | 0.285 | 0.231 | 0.222 |
| Trial 10 | 0.318 | 0.235 | 0.241 | 0.266 | 0.218 | 0.21 |
| AVG. | 0.324 | 0.244 | 0.244 | 0.269 | 0.23 | 0.212 |
| STDEV | 0.013 | 0.015 | | 0.009 | 0.011 | |

Example 15

As discussed in Example 4 above, the use of cell lysis inhibitors, cell membrane stabilizers, or cross-linking reagents can be used to increase the percentage of fetal DNA in the maternal blood. In this example, methods for the isolation of free fetal DNA are disclosed, which minimize the amount of maternal cell lysis. The effect of formalin on sixty-nine (69) maternal blood samples from twenty-seven clinical practices located in sixteen different states was analyzed. Formalin was added to all samples collected from the pregnant women, and the percentage of fetal DNA was calculated using serial dilution analysis followed by PCR. A genetic marker on the Y chromosome was used to calculate the percent of fetal DNA.

Collection of Blood Samples

In accordance with an IRB approved study, blood samples were collected from pregnant women after informed consent had been granted. Blood samples were received from 27 different clinical sites operating in 16 different states located throughout the U.S. Blood samples were collected from both women carrying male and female fetuses, however, here, we report results obtained from woman carrying male fetuses, as the Y chromosome is the accepted marker when quantitating percentages of fetal DNA.

Blood is collected by any method or process that results in a substantial increase in the ratio of fetal DNA/maternal DNA in the resulting serum or plasma after appropriate processing. As used herein, a substantial increase in the ratio of fetal DNA/maternal DNA is that which can be detected by the methods as described herein. Such methods or processes typically result in a substantial increase in the ratio of fetal DNA/maternal DNA of about 5%, 10%, 15%, 20%, 30%, 50%, 70%, 80%, 100% or more of the ratio of fetal DNA/maternal DNA found in blood samples collected by standard procedures.

In other embodiments, blood is collected by any method or process that results in a substantial increase in the amount of free fetal DNA compared to the amount of total DNA recovered or detected in the resulting serum or plasma after processing. Such methods or processes typically result in a substantial increase so the fetal DNA recovered or detected is about 10%, 15%, 20%, 25%, 30%, 40%, 50% or more of the total DNA recovered or detected in the processed plasma or serum sample.

All clinical sites were provided with a kit used for the venipuncture procedure, which included 21 gauge needles, 9 ml EDTA Vacuette tubes (catalog number NC9897284) a syringe containing 0.225 ml of 10% neutral buffered solution containing formaldehyde (4% w/v), an icepack, and a shipping container. The clinical sites were instructed to add the formaldehyde immediately after drawing the blood and to gently invert the tubes.

The methods or processes of collecting blood samples may also include other steps that result in lessened or reduced cell lysis. For instance, blood collection devices may be modified to decrease cell lysis due to sheer forces in the collection needle, syringe or tubes used. For instance, needles of large gauge may be employed to reduce cell sheering or vacutainer tubes may be modified to reduce the velocity of blood flow.

Isolation of Plasma

Any method may be used to isolate plasma from the cell components of blood after collection but methods wherein cell lysis is substantially prevented, reduced or inhibited are preferred. The blood was stored at 4° C. until processing. Methods for isolation of the plasma were implemented to reduce the amount of maternal cell lysis. The tubes were spun at 1000 rpm for ten minutes in a centrifuge with braking power and acceleration power set at zero to substantially prevent, reduce or inhibit cell lysis and or mixing of blood cell components into the plasma. The tubes were spun a second time at 1000 rpm for ten minutes with braking power (centrifuge stopped by natural deceleration) and acceleration power set to zero. The supernatant (the plasma) of each sample was transferred carefully to a new tube and spun at 3000 rpm for ten minutes with the brake and acceleration power set at zero. The supernatant (the plasma) of each sample was collected via procedures to substantially prevent mixing of cell components into the plasma. Great care was taken to ensure that the buffy-coat was not disturbed. A percentage of the supernatant can be left in the tube including but not limited to 0.001-1%, 1-10%, 10-20%, 20-30%, 30-40%, 40-50% -60%, 60-70%, 70-80% or greater than 80%. In this example, about 0.5 ml of the supernatant was left in the tube to ensure that the buffy-coat was not disturbed. The supernatant was transferred to a new tube and stored at −80° C.

Isolation of DNA

DNA was isolated from the plasma sample using the Qiagen Midi Kit for purification of DNA from blood cells, following the manufacturer's instructions (QIAmp DNA Blood Midi Kit, Catalog number 51183). DNA was eluted in 100 μl of distilled water. However, any method of DNA isolation can be used including cesium chloride gradients, gradients, sucrose gradients, glucose gradients, centrifugation protocols, boiling, Qiagen purification systems, QIA DNA blood purification kit, HiSpeed Plasmid Maxi Kit, QIAfilter plasmid kit, Promega DNA purification systems, MangeSil Paramagnetic Particle based systems, Wizard SV technology, Wizard Genomic DNA purification kit, Amersham purification systems, GFX Genomic Blood DNA purification kit, Invitrogen Life Technologies Purification Systems, CONCERT purification system, Mo Bio Laboratories purification systems, UltraClean BloodSpin Kits, and UlraClean Blood DNA Kit. The skilled artisan understands that the manufacturer's protocols can modified to increase the yield of DNA. For example, the Qiagen Midi Kit for purification of DNA recommends the use of 1× AL buffer. However, any concentration of AL buffer may be used if the yield of DNA increases including but not limited to 0.1-0.5× AL buffer, 0.5-1× AL buffer, 1×-2× AL buffer, 2-3× AL buffer, 3-4× AL buffer, 4-5× AL buffer, and greater than 5× AL buffer. The skilled artisan understands that the modifications and manipulations of the reagents are not limited to AL buffer.

Quantification of Percentage of Fetal DNA

The percentage of fetal DNA present in the maternal plasma sample was calculated using serial dilution analysis followed by PCR. Two different sets of primers were used: one primer set was specific for the Y chromosome, and thus specific for fetal DNA, and the other primer set was designed to amplify the cystic fibrosis gene, which is present on both maternal template DNA and fetal template DNA.

Primer Design

The following primers were designed to amplify the SRY gene on the Y chromosome:

```
Upstream primer:
5' TGGCGATTAAGTCAAATTCGC 3'       (SEQ ID NO: 263)

Downstream primer:
5' CCCCCTAGTACCCTGACAATGTATT 3'   (SEQ ID NO: 264)
```

The following primers were designed to amplify the cystic fibrosis gene:

```
Upstream primer:
5' CTGTTCTGTGATATTATGTGTGGT 3'    (SEQ ID NO: 265)

Downstream primer:
5' AATTGTTGGCATTCCAGCATTG 3'      (SEQ ID NO: 266)
```

PCR Reaction

The SRY gene and the cystic fibrosis gene were amplified from the template genomic DNA using PCR (U.S. Pat. Nos. 4,683,195 and 4,683,202). For increased specificity, a "hot-start" PCR was used. PCR reactions were performed using the HotStarTaq Master Mix Kit supplied by Qiagen (Catalog No. 203443). For amplification of the SRY gene, the DNA eluted from the Qiagen purification column was diluted serially 1:2. For amplification of the cystic fibrosis gene, the DNA eluted from the Qiagen purification column was diluted 1:4, and then serially diluted 1:2. The following components were used for each PCR reaction: 8 μl of template DNA (diluted or undiluted), 1 μl of each primer (5 μM), 10 μl of HotStar Taq mix. The following PCR conditions were used:

(1) 95° C. for 15'
(2) 94° C. for 1'
(3) 54° C. for 15"
(4) 72° C. for 30"
(5) Repeat steps 2-4 for 45 cycles.
(6) 10' at 72° C.

Amplification of the SRY gene was performed using the following templates: undiluted, diluted 1:2, diluted 1:4, diluted 1:8, diluted 1:16, diluted 1:32, diluted 1:64, diluted 1:128, diluted 1:256, and diluted 1:512. Amplification of the cystic fibrosis gene was performed using the following templates: diluted 1:4, diluted 1:8, diluted 1:16, diluted 1:32, diluted 1:64, diluted 1:128, diluted 1:256, diluted 1:512, diluted 1:1024, diluted 1:2048, and diluted 1:4096.

The percent of fetal DNA present in the maternal plasma was calculated using the following formula:

% fetal DNA=(amount of SRY gene/amount of cystic fibrosis gene)*2*100.

The amount of SRY gene was represented by the highest dilution value in which the gene was amplified. Likewise, the amount of cystic fibrosis gene was represented by the highest dilution value in which it was amplified. The formula contains a multiplication factor of two (2), which is used to normalize for the fact that there is only one copy of the SRY gene (located on the Y chromosome), while there are two copies of the cystic fibrosis gene.

The effect of formalin on sixty-nine (69) maternal blood samples collected from twenty-seven clinical practices located in sixteen different states, spanning from Washington to Massachusetts is shown in Table XXI. In this study, formalin was added to all samples collected from the pregnant women, and the percentage of fetal DNA was calculated using serial dilution analysis followed by PCR. The serial dilutions and PCR amplifications were performed by four different scientists over a period of five months. The samples were collected from women at gestational ages ranging from 11 weeks to 28 weeks, with the majority of women between 16-19 weeks of gestation. A summary is provided in Table XXIII.

The average percentage of free fetal DNA for the 69 samples analyzed in the maternal blood was 33.6%. Lo et al. reported fetal DNA concentrations of 3.4% in woman in late first to mid-second trimester, which was the gestational age of the majority of women in this study. Thus, the addition of formalin led to approximately a ten-fold increase in the average percentage of fetal DNA.

While the calculated percentage of fetal DNA in maternal blood is impressive, it is also informative to examine the range of the percentages of fetal DNA observed in this study. About six percent of the women (4/69 ) had 3.125% of free fetal DNA in the maternal blood, which was the lowest percentage of fetal DNA observed in this study. Another 10.2% of women had 6.25% fetal DNA, which represents a two-fold increase over the reported average in the literature. The total number of women who had less than 10% fetal DNA in the maternal blood was only 16.0%.

Fifty-eight percent of the women in this study had a percentage of fetal DNA of 25% or greater. Importantly, 26.0% of the women had fifty percent or greater fetal DNA in the maternal blood. Fetal DNA percentages of this magnitude have not been reported, and represent a new tool to the field of prenatal genetics.

There were four samples collected from women at the gestational age of eleven weeks. The percentages of fetal DNA in the maternal blood samples were as follows: two samples at 12.5%; one sample at 25%; and one sample at greater than 50%. Thus, the effect of formalin on the percentages of fetal DNA was observed with samples collected from women in early as well as later gestational periods.

The effect of stabilizing cell membranes and reducing the release of free DNA was not limited to formalin. We have tested several different types of agents, and combinations of agents, that prevent cell lysis and/or stabilize cell membranes, such as glutaraldehyde, and have seen that these agents also reduce the amount of free DNA in the blood sample (data not shown).

The above described methods may also include steps of adding an agent to the blood sample at the time or near to the time of collection to substantially inhibit or impede cell lysis or stabilize cell membranes. Any number of agents that impede cell lysis or stabilize cell membranes or cross-link cell membranes can be added to the maternal blood samples including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or the compounds listed in Table XXIII. Additional cross-linkers that can be used are found at the following website: www.piercenet.com/products/.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Any concentration of agent that stabilizes cell membranes, impedes cell lysis or cross-link cell membranes can be added. In a preferred embodiment, the agent that stabilizes cell membranes, impedes cell lysis, or cross-links cell membranes is added at a concentration that does not impede or hinder subsequent reactions.

While impressive percentages of free fetal DNA in maternal blood samples have been reported, it is thought that higher percentages can be achieved by carefully explaining the importance of the formalin to the physicians. Samples randomly were checked for the presence of formalin and found that about ten percent of the samples did not receive formalin. In addition, aggregates were observed in another ten percent of the samples suggesting that the formalin had not been thoroughly mixed with the collected blood. Thus, while the addition of formalin produced an impressive effect, it is likely that under controlled conditions, the percentage of free fetal DNA may be higher.

In addition, we believe that procedures to minimize hemolysis during the venipuncture procedure and temperature controlled shipping containers (specimens were shipped in a Styrofoam container with ice pack, but there was variation in temperature because samples were shipped from varying distances) may cause a further increase in the percentage of free fetal DNA. Needles designed to reduce hemolysis can be used during the venipuncture procedure.

Also, we hypothesized that procedures for carefully isolating the plasma would help to ensure a minimal amount of maternal DNA in the sample. We implemented procedures, as described above, to reduce cell lysis, such as gentle centrifugation parameters, and allowed the rotors to stop without external force (no brake). Also, we carefully removed the supernatant containing the plasma DNA from the buffy-coat, which contains maternal DNA. These procedures coupled with the addition of formalin to prevent cell lysis resulted in a tremendous increase in the percentage of fetal DNA.

TABLE XXI

Formalin increases the percentage of free fetal DNA in blood samples collected at numerous clinical sites from women at various stages of gestation.

| Sample | Wks Gestation | Fetal Genomes/ml | % Fetal DNA |
|---|---|---|---|
| 1 | 16 | 80 | 25 |
| 2 | 19 | 1066 | >50 |
| 3 | 17 | 52 | 50 |
| 4 | 22 | 166 | 25 |
| 5 | 32 | 457 | 50 |
| 6 | 19 | 400 | 100 |
| 7 | 18 | 800 | 100 |
| 8 | 17 | 100 | 50 |
| 9 | 16 | 50 | 25 |
| 10 | 17 | 25 | 12.5 |
| 11 | 16 | 94.74 | 12.5 |
| 12 | 16 | 34.60 | 50 |
| 13 | 16 | 22.5 | 25 |
| 14 | 17 | 50 | 12.5 |
| 15 | 17 | 26.48 | 12.5 |
| 16 | 17 | 45.00 | 25 |
| 17 | 17 | 94.7 | 100 |
| 18 | 17 | 28.13 | 6.25 |
| 19 | 19 | 28.13 | 25 |
| 20 | 20 | 11.25 | 12.5 |
| 21 | 15 | 11.25 | 12.5 |
| 22 | 11 | 16.66 | 12.5 |
| 23 | 18 | 13.23 | 25 |
| 24 | 18 | 12.50 | 6.25 |
| 25 | 16 | 112.50 | 100 |
| 26 | 17 | 124.13 | 25 |
| 27 | 14 | 90.00 | 50 |
| 28 | 11 | 100.00 | 100 |
| 29 | 18 | 232.00 | 100 |
| 30 | 19 | 626.00 | 100 |
| 31 | 19 | 112.50 | 100 |
| 32 | 16 | 423.50 | 100 |
| 33 | 16 | 423.50 | 25 |
| 34 | 11 | 105.88 | 25 |
| 35 | 16 | 49.60 | 3.1 |
| 36 | 11 | 11.84 | 12.5 |
| 37 | 16 | 120.00 | 25 |
| 38 | 18 | 342.90 | 100 |
| 39 | 17 | 51.43 | 25 |
| 40 | 18 | 225.00 | 6.25 |
| 41 | 17 | 400.00 | 12.5 |
| 42 | 28 | 180.00 | 25 |

TABLE XXI-continued

Formalin increases the percentage of free fetal DNA in blood samples collected at numerous clinical sites from women at various stages of gestation.

| Sample | Wks Gestation | Fetal Genomes/ml | % Fetal DNA |
|---|---|---|---|
| 43 | 17 | 20.45 | 12.5 |
| 44 | 18 | 25.73 | 25 |
| 45 | 16 | 68.68 | 3.1 |
| 46 | 17 | 218.18 | 25 |
| 47 | 15 | 75.00 | 6.25 |
| 48 | 16 | 40.58 | 3.1 |
| 49 | 17 | 100.00 | 25 |
| 50 | 17 | 14.06 | 12.5 |
| 51 | 22 | 22.50 | 12.5 |
| 52 | 15 | 28.13 | 12.5 |
| 53 | 17 | 50.00 | 3.125 |
| 54 | 18 | 58.00 | 50 |
| 55 | 14 | 100.00 | 25 |
| 56 | 16 | 58.08 | 25 |
| 57 | 16 | 13.64 | 12.5 |
| 58 | 16 | 25.00 | 6.25 |
| 59 | 20 | 45.00 | 25 |
| 60 | 16 | 23.69 | 12.5 |
| 61 | 18 | 5.92 | 6.25 |
| 62 | 15 | 28.13 | 6.25 |
| 63 | 17 | 50.00 | 25 |
| 64 | 16 | 360.00 | 50 |
| 65 | 16 | 25.00 | 12.5 |
| 66 | 16 | 48.65 | 25 |
| 67 | 16 | 47.38 | 12.5 |
| 68 | 14 | 26.45 | 50 |
| 69 | 17 | 124.15 | 25 |
| Average | 17 | 131.15 | 33.6 |

TABLE XXII

Formalin increases the percentage of free fetal DNA in blood samples collected at numerous clinical sites from women at various stages of gestation.

| | % Fetal DNA | | | | | |
|---|---|---|---|---|---|---|
| | 3.125 | 6.25 | 12.5 | 25 | 50 | Over 50% |
| Number Women (69) | 4 | 7 | 18 | 22 | 7 | 11 |
| % | 5.8 | 10.1 | 26.1 | 31.9 | 10.2 | 15.9 |

TABLE XXIII

A representative list of cross-linkers that can be used to impede maternal cell lysis.

| Cross-Linker | Abbreviation |
|---|---|
| succinimidyl acetylthioacetate | SATA |
| succinimidyl trans-4-(maleimidylmethyl) cyclohexane-1-carboxylate | SMCC |
| succinimidyl 3-(2-pyridyldithio)propionate | SPDP |
| N-((2-pyridyldithio)ethyl)-4-azidosalicylamide | PEAS; AET |
| 4-azido-2,3,5,6-tetrafluorobenzoic acid, succinimidyl ester | ATFB, SE |
| 4-azido-2,3,5,6-tetrafluorobenzoic acid, STP ester, sodium salt | ATFB, STP ester |
| 4-azido-2,3,5,6-tetrafluorobenzyl amine, hydrochloride | |
| benzophenone-4-isothiocyanate | |
| benzophenone-4-maleimide | |
| 4-benzoylbenzoic acid, succinimidyl ester | |
| Disuccinimidylsuberate | DSS |
| Dithiobis(succinimidylpropionate) | DSP |
| 3,3'-Dithiobis(sulfosuccinimidylpropionate) | DTSSP |

TABLE XXIII-continued

A representative list of cross-linkers that can be used to impede maternal cell lysis.

| Cross-Linker | Abbreviation |
|---|---|
| Bis[2-(sulfosuccinimdooxycarbonyloxy)ethyl]sulfone | SULFO BSOCOES |
| Bis[2-(succinimdooxycarbonyloxy)ethyl]sulfone | BSOCOES |
| Disulfosuccinimdyltartrate | SULFO DST |
| Disuccinimdyltartrate | DST |
| Ethylene glycolbis(succinimidylsuccinate) | SULFO EGS |
| Ethylene glycolbis(sulfosuccinimidylsuccinate) | EGS |
| 1,2-Di[3'-(2'-pyridyldithio)propionamido]butane | DPDPB |
| Bis(sulfosuccinimdyl)suberate | BSSS |
| Succinimdyl-4-(p-maleimidophenyl)butyrate | SMPB |
| Sulfosuccinimdyl-4-(p-maleimidophenyl)butyrate | SULFO SMPB |
| 3-Maleimidobenzoyl-N-hydroxysuccinimide ester | MBS |
| 3-Maleimidobenzoyl-N-hydroxysulfosuccinimide ester | SULFO MBS |
| N-Succinimidyl(4-iodoacetyl)aminobenzoate | SIAB |
| N-Sulfosuccinimidyl(4-iodoacetyl)aminobenzoate | SULFO SIAB |
| Succinimidyl-4-(N-maleimidomethyl)cyclohexane-1-carboxylate | SMCC |
| Sulfosuccinimidyl-4-(N-maleimidomethyl)cyclohexane-1-carboxylate | SULFO SMCC |
| Succinimidyl-6-[3-(2-pyridyldithio)propionamido)hexanoate | NHS LC SPDP |
| Sulfosuccinimidyl-6-[3-(2-pyridyldithio)propionamido)hexanoate | SULFO NHS LC SPDP |
| N-Succinimdyl-3-(2-pyridyldithio)propionate | SPDP |
| N-Hydroxysuccinimidylbromoacetate | NHS BROMOACETATE |
| N-Hydroxysuccinimidyliodoacetate | NHS IODOACETATE |
| 4-(N-Maleimidophenyl)butyric acid hydrazide hydrochloride | MPBH |
| 4-(N-Maleimidomethyl)cyclohexane-1-carboxylic acid hydrazide hydrochloride | MCCH |
| m-Maleimidobenzoic acid hydrazidehydrochloride | MBH |
| N-(epsilon-Maleimidocaproyloxy)sulfosuccinimide | SULFO EMCS |
| N-(epsilon-Maleimidocaproyloxy)succinimide | EMCS |
| N-(p-Maleimidophenyl)isocyanate | PMPI |
| N-(kappa-Maleimidoundecanoic acid) hydrazide | KMUH |
| Succinimidyl-4-(N-maleimidomethyl)-cyclohexane-1-carboxy(6-amidocaproate) | LC SMCC |
| N-(gamma-Maleimidobutryloxy)sulfosuccinimide ester | SULFO GMBS |
| Succinimidyl-6-(beta-maleimidopropionamidohexanoate) | SMPH |
| N-(kappa-Maleimidoundecanoyloxy)sulfosuccinimide ester | SULFO KMUS |
| N-(gamma-Maleimidobutyrloxy)succinimide | GMBS |
| Dimethyladipimidate hydrochloride | DMA |
| Dimethylpimelimidate hydrochloride | DMP |
| Dimethylsuberimidate hydrochloride | DMS |
| Methyl-p-hydroxybenzimidate hydrochloride, 98% | MHBH(Wood's Reagent) |
| Amine Reactive | |
| Bis[sulfosuccinimidyl] suberate | BS3 |
| Bis[2-(succinimidooxycarbonyloxy)ethyl]sulfone | BSOCOES |
| Disuccinimidyl glutarate | DSG |
| | DSP (Lomant's Reagent) |
| 1,5-Difluoro-2,4-dinitrobenzene | DFDNB |
| Dithiobis[succinimidylpropionate | DTBP |
| Bis-[b-(4-Azidosalicylamido)ethyl]disulfide | BASED |
| Sulfhydryl Reactive | |
| $BM[PEO]_3$(1,8-bis-Maleimidotriethyleneglycol | $BM[PEO]_3$ |
| $BM[PEO]_4$(1,11-bis-Maleimidotetraethyleneglycol | $BM[PEO]_4$ |
| 1,4-bis-Maleimidobutane | BMB |

TABLE XXIII-continued

A representative list of cross-linkers that can be used to impede maternal cell lysis.

| Cross-Linker | Abbreviation |
|---|---|
| 1,4 bis-Maleimidyl-2,3-dihydroxybutane | BMDB |
| Bis-Maleimidohexane | BMH |
| Bis-Maleimidoethane | BMOE |
| 1,4-Di-[3'-(2'-pyridyldithio)-propionamido]butane | DPDPB |
| Dithio-bis-maleimidoethane | DTME |
| 1,6-Hexane-bis-vinylsulfone | HBVS |
| p-Azidobenzoyl hydrazide | ABH |
| Amine-Sulfhydryl Reactive | |
| N-[a-Maleimidoacetoxy]succinimide ester | AMAS |
| N-[4-(p-Azidosalicylamido) butyl]-3'-(2'-pyridyldithio)propionamide | APDP |
| N-[β-Maleimidopropyloxy]succinimide ester | BMPS |
| N-e-Maleimidocaproic acid | EMCA |
| N-e-Maleimidocaproyloxy]succinimide ester | EMCS |
| N-[g-Maleimidobutyryloxy]succinimide ester | GMBS |
| N-k-Maleimidoundecanoic acid | KMUA |
| Succinimidyl-4-(N-Maleimidomethyl)cyclohexane-1-carboxy-(6-amidocaproate | LC-SMCC |
| Succinimidyl 6-(3-[2-pyridyldithio]-propionamido)hexanoate | LC-SPDP |
| m-Maleimidobenzoyl-N-hydroxysuccinimide ester | MBS |
| Succinimidyl 3-[bromoacetamido]propionate | SBAP |
| N-Succinimidyl iodoacetate | SIA |
| N-Succinimidyl[4-iodoacetyl]aminobenzoate | SIAB |
| Succinimidyl 4-[N-maleimidomethyl]cyclohexane-1-carboxylate | SMCC |
| Succinimidyl 4-[p-maleimidophenyl]butyrate | SMPB |
| Succinimidyl-6-[β-maleimidopropionamido]hexanoate | SMPH |
| 4-Succinimidyloxycarbonyl-methyl-a-[2-pyridyldithio]toluene | SMPT |
| N-Succinimidyl 3-[2-pyridyldithio]-propionamido | SPDP |
| N-e-Maleimidocaproyloxy]sulfosuccinimide ester | Sulfo-EMCS |
| N-[g-Maleimidobutyryloxy]sulfosuccinimide ester | Sulfo-GMBS |
| N-[k-Maleimidoundecanoyloxy]sulfosuccinimide ester | Sulfo-KMUS |
| 4-Sulfosuccinimidyl-6-methyl-a-(2-pyridyldithio)toluamido]hexanoate | Sulfo-LC-SMPT |
| Sulfosuccinimidyl 6-(3'-[2-pyridyldithio]-propionamido)hexanoate | Sulfo-LC-SPDP |
| m-Maleimidobenzoyl-N-hydroxysulfosuccinimide ester | Sulfo-MBS |
| N-Sulfosuccinimidyl[4-iodoacetyl]aminobenzoate | Sulfo-SIAB |
| Sulfosuccinimidyl 4-[N-maleimidomethyl]cyclohexane-1-carboxylate | Sulfo-SMCC |
| Sulfosuccinimidyl-4-(P-Maleimidophenyl) Butyrate | Sulfo-SMPB |
| Amino Groups | |
| N-5-Azido-2-nitrobenzoyloxysuccinimide | ANB-NOS |
| Methyl N-succinimidyl adipate | MSA |
| N-Hydroxysuccinimidyl-4-azidosalicylic acid | NHS-ASA |
| N-Succinimidyl(4-azidophenyl)-1,3'-dithiopropionate | SADP |
| Sulfosuccinimidyl 2-[7-amino-4-methylcoumarin-3-acetamido]ethyl-1,3'dithiopropionate | SAED |
| Sulfosuccinimidyl 2[m-azido-o-nitrobenzamido]-ethyl-1,3'-dithiopropionate | SAND |
| N-Succinimidyl-6-[4'-azido-2'-nitrophenylamino] hexanoate | SANPAH |
| Sulfosuccinimidyl-2-[p-azidosalicylamido]ethyl-1,3'-dithiopropionate | SASD |
| Sulfosuccinimidyl-[perfluoroazidobenzamido]ethyl-1,3'-dithiopropionate | SFAD |
| N-Hydroxysulfosuccinimidyl-4-azidobenzoate | Sulfo-HSAB |
| Sulfosuccinimidyl[4-azidosalicylamido]-hexanoate | Sulfo-NHS-LC-ASA |
| N-Sulfosuccinimidyl(4-azidophenyl)-1,3'-dithiopropionate | Sulfo-SADP |
| N-Sulfosuccinimidyl-6-[4'-azido-2'-nitrophenylamino] hexanoate | Sulfo-SANPAH |
| p-Azidophenyl glyoxal monohydrate | APG |
| N-β-Maleimidopropionic acid | BMPA |
| Carbohydrate Reactive-Photoreactive | |
| N-Succinimidyl-S-acetylthiopropionate | SATP |
| Sulfhydryl-Carbohydrate Reactive | |
| 4-(4-N-Maleimidophenyl)butyric acid hydrazide hydrochloride | MPBH |
| 3-(2-Pyridyldithio)propionyl hydrazide | PDPH |
| Sulfhydryl-carbonyl (aldehyde)/carboxyl reactive | |
| N-[β-Maleimidopropionic acid]hydrazide•TFA | BMPH |
| N-e-Maleimidocaproic acid]hydrazide | EMCH |
| N-[k-Maleimidoundecanoic acid]hydrazide | KMUH |
| N-[p-Maleimidophenyl]isocyanate | PMPI |
| | TFCS |

Example 16

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. Any DNA microarray may be used including but not limited to commercially available and non-commercially available arrays.

A DNA microarray can be designed to contain SNPs located on the chromosome or chromosomes of interest including but not limited to a DNA microarray containing SNPs located on chromosomes 13, 18, and 21, a DNA microarray containing SNPS located on chromosomes 13 and 18, a DNA microarray containing SNPS located on chromosomes 13 and 21, a DNA microarray containing SNPS located on chromosomes 18 and 21, a DNA microarray containing SNPS located on chromosomes 13, 18, 21, 15, 22, X, Y, a DNA microarray containing SNPS located on each of the autosomal chromosomes and each of the sex chromosomes, a DNA microarray containing SNPS located on chromosome 13, a DNA microarray containing SNPS located on chromosome 18, a DNA microarray containing SNPS located on chromosome 21, a DNA microarray containing SNPS located on chromosome 15, a DNA microarray containing SNPS located on chromosome 17, a DNA microarray containing SNPS located on chromosome 22, a DNA microarray containing SNPS located on a single chromosome, and a DNA microarray containing SNPS located on multiple chromosomes.

In this example, SNPs are analyzed by GeneChip HuSNP Arrays from Affymetrix, however any number of DNA arrays, including but not limited to GeneChip arrays, GenFlex Tag arrays, Mapping 10K Array, other Affymetrix arrays, and other DNA arrays can be used.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis or stabilize cell membranes or cross-link cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes, impedes cell lysis or cross-link cell membranes can be added. In a preferred embodiment, the agent that stabilizes cell membranes, impedes cell lysis, or cross-links cell membranes is added at a concentration that does not impede or hinder subsequent reactions.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the “buffy coat,” which contains maternal cells, is placed into a separate tube and stored at −80° C.

Isolation of DNA

DNA is isolated from the plasma sample using the Qiagen Midi Kit for purification of DNA from blood cells, following the manufacturer’s instructions (QIAmp DNA Blood Midi Kit, Catalog number 51183). DNA is eluted in 100 μl of distilled water. The Qiagen Midi Kit also is used to isolate DNA from the maternal cells contained in the “buffy coat.”

Identification of Homozygous Maternal SNPs

HuSNP Assay

The HuSNP assay is done as described by K. Lindblad-Toh et al. (Nature Biotechnology, Vol. 18, 1001-1005). The GeneChip® HuSNP™ Array is thought to enable whole genome surveys by simultaneously tracking nearly 1,500 SNPs dispersed throughout the genome. In this example, HuSNP array is used as a representative Affymetrix array, and is not meant to limit the use of other arrays including but not limited to GeneChip CYP450, and Affymetrix custom arrays that are designed to meet specific user requirements.

PCR Amplification

Maternal DNA is assayed according to the HuSNP protocol supplied by Affymetrix Inc. For each sample, 24 pools of primer pairs (50-100 loci/pool at 50 nM each) are mixed with 5 ng of maternal DNA., 5 mM $MgCl_2$, 0.5 mM dNTPs, 1.25 U Amplitaq Gold (PE Biosystems, Foster City, Calif.), and the supplied buffer in 12.5 μl per pool. Samples are denatured for 5 min at 95° C. followed by 30 cycles of 95° C. for 30 s, 52° C.+0.2° C./cycle for 55s, and 72° C. for 30s; 5 cycles of 95° C. for 30 s, 58° C. for 55s, and 72° C. for 30s and a final extension of 72° C. for 7 min. A 1:1000 dilution of each pool is made by adding 1 μl of the amplification product to 999 μl of ddH20. After, 2.5 μl of the 1:1000 dilution is transferred to a new plate and amplified with 0.8 μM biotinylated T7 and 0.8 μM biotinylated T3 primers, 4 mM MgCl2, 0.4 mM dNTPs, 2.5 U Taq and the supplied buffer in 25 μl for 8 min at 95° C., followed by 40 cycles of 95° C. for 30 s, 55° C. for 90s, and 72° C. for 30 s, and a final extension of 72° C. for 7 min. Then 1.5 μl from each pool is tested for amplification on a 3% agarose gel. For each sample, the remainder of each the 24 pools is mixed and loaded on a Microcon-10 spin column (Amicon Bioseparations, Bedford, Mass.). Samples are concentrated by spinning the column for 20 min at 13,000 g at room temperature and are eluted by inverting the column and centrifuging for 3 min at 3,000 g. Volumes are adjusted to 60 μl.

A custom array can be designed using only the SNPs that are of interest. For example, a custom array may be designed that contains SNPs that are located on chromosomes 1, 13, 21, 18, 15, X, and Y.

Additionally, any number of SNPs can be amplified including SNPs located on any human chromosome including chromosome 1, 2, 3, 4, 5, 6, 7, 8, 9, 10, 11, 12, 13, 14, 15, 16, 17, 18, 19, 20, 21, 22, X or Y. Two representative SNPs on chromosome 13 and two representative SNPs on chromosome 21 are chosen. The genomic location and sequence of SNPs may be found at the SNP consortium (httn://snp.cshl.org). If these SNPs are not present on the array, different SNPs can be chosen.

SNP TSC0466917 (C/G), which is located on chromosome 13, is amplified using the following primers:

```
Upstream Primer:
5' CCAGCTGGTAGAACTT 3'      (SEQ ID NO: 629)

Downstream Primer:
5' CCCAATAGACCTATAG 3'      (SEQ ID NO: 630)
```

SNP TSC1172576 (T/A), which is located on chromosome 13, is amplified using the following primers:

```
Upstream Primer:
5' TAGCAGAATCTCTCAT 3'      (SEQ ID NO: 631)

Downstream Primer:
5' AGAGTATCTCATTTGTT 3'     (SEQ ID NO: 632)
```

SNP TSC0271628 (A/G), which is located on chromosome 21, is amplified using the following primers:

```
Upstream Primer:
5' AGGAAATTGTGAAGTA 3'      (SEQ ID NO: 633)

Downstream Primer:
5' TAACTCACTCACTATC 3'      (SEQ ID NO: 634)
```

SNP TSC0069805 (C/T), which is located on chromosome 21, is amplified using the following primers:

```
Upstream Primer:
5' CTGCTGAGTCATAGTC 3'      (SEQ ID NO: 635)

Downstream Primer:
5' TGTTCTTTGAATCAAC 3'      (SEQ ID NO: 636)
```

Hybridization to GeneChip Probe Arrays, Washing and Staining 5-30 μl of the sample (depending on the intensity of the chip lot) is diluted in 3 M tetramethylammonium chloride (TMACl), 2 mM control oligonucleotide B1 (supplied by Affymetrix), 5× Denhardt's solution, 100 μg/ml herring sperm DNA, 5 mM EDTA pH 8.0, 10 mM Tris pH7.8, and 0.01% Tween 20 in a volume of 135 μl and is denatured for 10 min at 95° C. After two minutes on ice, the samples are loaded into HuSNP chips and hybridized for 16 h at 44° C. and 40 r.p.m.

Each chip is washed and stained on the Affymetrix fluidics. Chips are washed for two cycles of two mixes with 6×SSPET (Bio Whitaker, Walkersville, Md.) (6×SSPE (sodium chloride, sodium phosphate, sodium EDTA)+0.01% Triton-X-100) at 25° C., and for six cycles of five mixes with 4×SSPET (4×SSPE+0.01% Triton X-100) at 35° C. Chips are stained for 30 min at 25° C. with 50 μg/ml streptavidin-phycoerhthrin and 0.25 mg/ml biotinylated anti-streptavidin antibody in 6×SSPE, 1× Denhardt's solution, and 0.01% Tween 20 in a volume of 500 μl. The chip is filled with 6×SSPET following six washes of four mixes with 6×SSPET at 25° C.

After the hybridization, washing, and staining procedures, the HuSNP probe arrays are scanned using the HP GeneArray Scanner (HuSNP Mapping Assay Manual Affymetrix PIN 700308).

Scanning

The HuSNP probe arrays are scanned using the HP GeneArray Scanner according to the HuSNP Mapping Assay Manual (Affymetrix P/N 700308). Other scanners may be used including but not limited to the AlphaArray™ Reader. Genotype calls are made automatically from the collected hybridization signal intensities by the Affymetrix Microarray Suite version 5.0 software. Each allele of a SNP is represented by four or five complementary probes with different locations of the SNP base position within the 20-nucleotide probes. Each of these probes, in turn, is paired with a probe of the same sequence except for a central mismatch at or near a SNP position, intended to correct the fluorescence value for non-specific binding to the probe.

Each SNP is genotyped. SNPs located on chromosomes 13 and 21, wherein the maternal DNA is homozygous, are analyzed with the DNA isolated from the plasma.

Analysis of DNA Isolated from Maternal Plasma

After the maternal DNA is analyzed and homozygous SNPs are identified, these SNPs are analyzed with the DNA isolated from the plasma. A low copy number of fetal genomes typically is present in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 μl of plasma template DNA is used.

Two microliters of each forward and reverse primer, at concentrations of 5 mM are pooled into a single microcentrifuge tube and mixed. Four microliters of the primer mix is used in a total PCR reaction volume of 50 μl (20 μl of template plasma DNA, 1 μl of sterile water, 4 μl of primer mix, and 25 μl of HotStar Taq. Twenty-five cycles of PCR are performed. The following PCR conditions are used:

(1) 95° C. for 15 minutes;

(2) 95° C. for 30 second;

(3) 4° C. for 30 seconds;

(4) 37° C. for 30 seconds;

(5) Repeat steps 2-4 twenty-four (24) times;

(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

It is important to ensure that the region amplified contains annealing sequences for the primers that are used with the HuSNP assay. Upon purchase of the HuSNP array, each SNP and the primers used to amplify each SNP can be identified.

With this knowledge, the multiplex primers are designed to encompass annealing regions for the primers in the HuSNP Array.

Purification of Fragment of Interest

The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 μl of sterile water. 5 μl of each amplified loci is mixed together HuSNP Assay, Washing, Staining and Scanning The pooled DNA is assayed with the HuSNP Array as described above. Washing, staining, and scanning procedures are as described above.

Each SNP is genotyped. SNPs located on chromosomes 13 and 21, wherein the maternal DNA is homozygous, and DNA isolated from the plasma is heterozygous are quantitated.

Quantification

The intensity of the signal for each allele at a heterozygous is SNP is quantitated. As discussed above, the expected ratio of allele 1 to allele 2 can be used to determine the presence or absence of a chromosomal abnormality. If the maternal genome is homozygous at SNP X (A/A), and the plasma DNA is heterozygous at SNP X (A/G), then the G represents the distinct fetal signal. The ratio of G:A depends on the percentage of fetal DNA present in the maternal blood.

For example, if the sample contains 50% fetal DNA, then the expected ratio is 0.33 (1 fetal G allele/(2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

This example explained the use of Affymetrix HuSNP Arrays, but it not intended to limit the use of arrays. Any DNA array may be used including but not limited to the DNA arrays listed in Table XXIV, or DNA arrays available from any of the companies listed in Table XXIV, or XXV. Custom DNA arrays can be made for detecting fetal chromosomal abnormalities in maternal blood using any number of products or services including but not limited to those listed in Tables XXIV, XXV, XXVI and XXVII.

TABLE XXIV

Features of some hybridization microarray formats.

| Company | Product Name | Array Method | Hybridization Step | Readout |
|---|---|---|---|---|
| Affymetrix, Inc, | GeneChip ® | In situ (on-chip) photolithographic synthesis of ~20-25-mer oligos onto silicon wafers, which are cut into 1.25 $cm^2$ or 5.25 $cm^2$ chips | 10,000-260,000 oligo features probed with labeled 30-40 nucleotide fragments of sample cDNA or antisense RNA | Fluorescence |
| Agilent Technologies | DNA Microarray Access Program | Custom Designed Arrays | | |
| Amersham Biosciences | CodeLink Arrays | | | |
| BD PharMimgen | RiboScreen Human-1 Membrane | | | |
| CLONTECH | Atlas Glass Human<br>Atlas Glass Human 1.2<br>Atlas Glass Human 1.2 II<br>Atlas Glass Human 1.2 III<br>Atlas Human Cancer<br>Atlas Human Apoptosis<br>Atlas Human Cancer cDNA<br>Atlas Human Cardiovascular<br>Atlas Human cDNA<br>Atlas Human cell cycle<br>Atlas Human Cell Interaction<br>Atlas Human | Variable | Variable | Variable |

TABLE XXIV-continued

Features of some hybridization microarray formats.

| Company | Product Name | Array Method | Hybridization Step | Readout |
|---|---|---|---|---|
| | Cytokine Receptor | | | |
| | Atlas Human Hematology array | | | |
| | Atlas Human Neurobiology | | | |
| | Atlas Human Oncogene | | | |
| | Atlas Human Stress array | | | |
| | Atlas Human Toxicology | | | |
| | Atlas Human Tumor array | | | |
| | Atlas Human Oncogene | | | |
| | Custom Atlas arrays | | | |
| | Custom Atlas select arrays | | | |
| Brax, | | Short synthetic oligo, synthesized off-chip | 1000 oligos on a "universal chip" probed with tagged nucleic acid | Mass spectrometry |
| Display Systems Biotech | discoveryArray Human Gene Display slide | Uses restriction fragment differential display PCR | | |
| Gene Logic, Inc., | READS ™ | Flow-thru Chip Probe Arrays | Chips with microscopic channels with probes attached to their walls | |
| Genmed | Star Profiler Arrays | | | |
| Genometrix Inc., | Universal Arrays ™ | SNP screening services, 96-well X 250 proprietary array | | |
| Genomic Solutions | GenMAP Cancer Chips | Cancer related sequences spotted in duplicate | | |
| Hyseq Inc., | HyChip ™ | 500-2000 nt DNA samples printed onto 0.6 $cm^2$ (HyGnostics) or ~18 $cm^2$ (Gene Discovery) membranes | 64 sample cDNA spots probed with 8,000 7-mer oligos (HyGnostics) <=55,000 sample cDNA spots probed with 300 7-mer oligo (Gene Discovery) | Radioisotope |
| | | Fabricated 5-mer oligos printed as 1.15 $cm^2$ arrays onto glass (HyChip) | Universal 1024 oligo spots probed 10 kb sample cDNAs, labeled 5-mer oligo, and ligase | Fluorescence |
| Incyte Pharmaceuticals, Inc. | GEM | Piezoelectric printing for spotting PCR fragments and on-chip synthesis of oligos | <=1000 (eventually 10,000) oligo/PCR fragment spots probed with labeled RNA | Fluorescence and radioisotope |
| INTERACTIVIA | | Gold affinity array | | |

TABLE XXIV-continued

Features of some hybridization microarray formats.

| Company | Product Name | Array Method | Hybridization Step | Readout |
|---|---|---|---|---|
| Mergen | | ExpressChip DNA microarray system | | |
| Molecular Dynamics, Inc | Storm ® FluorImager ® | 500-5000 nt cDNAs printed by pen onto ~10 $cm^2$ on glass slide | ~10,000 cDNA spots probed with 200-400 nt labeled sample cDNAs | Fluorescence |
| Motorola | CodeLink Array | | | |
| MWG-Biotech | Biochip service, licensed by Affymatrix | | | |
| NEN Life Science Products | MICROMAX Human cDNA MICROMAX Human Kinases and phosphatases MICROMAX human transcription factors MICROMAX human oncogene and tumor suppressor genes | | | |
| Operon Technologies | OpArray Human Collagen OpArray Human apoptosis OpArray Human stress and aging | | | |
| Origene Technologies | SmartArray Human Smartset 1 SmartArray Human Smartset 2 SmartArray Human Smartset 3 SmartArray Human Smartset 4 | | | |
| Nanogen | Semiconductor Microchip | Prefabricated ~20-mer oligos, captured onto electroactive spots on silicon wafers, which are diced into <=1 $cm^2$ chips | 25, 64, 400 (and eventually 10,000) oligo spots polarized to enhance hybridization to 200-400 nt labeled sample cDNAs | Fluorescence |
| Phase-1 Molecular Toxicology | Human 350 Gene Array | | | |
| ProtoGene Laboratories | DNA FlexChip technology | Surface tension based arraying; On-chip synthesis of 40-50-mer oligos onto 9 $cm^2$ glass chip via printing to a surface-tension array | <=8,000 oligo spots probed with 200-400 nt labeled sample nucleic acids | Fluorescence |

TABLE XXIV-continued

Features of some hybridization microarray formats.

| Company | Product Name | Array Method | Hybridization Step | Readout |
|---|---|---|---|---|
| R&D Systems | Human Cytokine Expression Array | | | |
| | Human Apoptosis Expression Array | | | |
| Research Genetics | Human Genefilters Micorarray Releases I-VII | | | |
| | Human "Named Genes" Genefilters Micorarray Releases I | | | |
| | Human Prostate specific Genefilters Micorarray Releases I | | | |
| | Human Ovary Specific Genefilters Micorarray | | | |
| | Human Breast specific Genefilters Micorarray | | | |
| | Human Colon specific Genefilters Micorarray Releases I | | | |
| | Dermarray Human Skin Genefilters Micorarray | | | |
| Radius Biosciences | Custom Arraying Services | | | |
| Rosetta Impharmatics | FlexJet DNA Microarrays; Resolver ™ | | | |
| Sequenom | MassArray SpectroChip | Off-set printing of array; around 20-25-mer oligos | 250 locations per SpectroChip interrogated by laser desorbtion and mass spectrometry | Mass spectrometry |
| SEQWRIGHT | Arraying Services | | | |
| Sigma-Genosys | Panorama Human Cytokine Gene Arrays | | | |
| | Panorama Human Apoptosis Gene Arrays | | | |
| Stratagene | GeneConnection Discovery Microarray | | | |
| SuperArray | Human Apoptosis-1, 2, 3, GEArray Kit | | | |
| | Human Apoptosis-4, Bcl-2 Family and Regulators | | | |

TABLE XXIV-continued

Features of some hybridization microarray formats.

| Company | Product Name | Array Method | Hybridization Step | Readout |
|---|---|---|---|---|
| | GEArray Kit Human Apoptosis-5/TNF and Ras Network | | | |
| | GEArray Kit Human p53 | | | |
| | GEArray Kit Human Toxicity/Stress | | | |
| | GEArray Kit Human Cell Cycle 1, 2 | | | |
| | GEArray Kit Human Cancer Metastasis | | | |
| | GEArray Kit Human Cancer/Oncogene | | | |
| | GEArray Kit Human Cancer/Tumor Suppressor | | | |
| | GEArray Kit Human Cancer/Angiogenesis | | | |
| | GE Array Kit Human Cancer/Radiation Sensitivity Marker | | | |
| | GEArray Kit Human PathwayFinder | | | |
| | GEArray Kit Human Jak-Stat Pathway | | | |
| | GEArray Kit Human P13 Kinase and AKT Pathway | | | |
| | GEArray Kit Human NFkB Pathway | | | |
| | GEArray Kit Human Common Cytokine | | | |
| | GEArray Kit Human Interleukin Receptor | | | |
| | GEArray Kit Human Inflammatory Response | | | |
| | GEArray Kit Human Choice GEArrays | | | |
| Synteni, Inc., (acquired by Incyte Pharmaceuticals, Inc.) | UniGEM ™ | 500-5,000 nt cDNAs printed by tip onto ~4 $cm^2$ glass chip | <=10,000 cDNA spots probed with 200-400 nt labeled sample cDNAs | Fluorescence |
| TeleChem International, Inc. | Flex-Chips Custom Arrays<br>eChips Custom Arrays<br>Discovery Chip Arrays | | | |

TABLE XXIV-continued

Features of some hybridization microarray formats.

| Company | Product Name | Array Method | Hybridization Step | Readout |
|---|---|---|---|---|
| Vysis Inc. | AmpliOnc Microarray kit | | | |
| The German Cancer Institute | | Prototypic PNA macrochip with on-chip synthesis of probes using f-moc or t-moc chemistry | Around 1,000 spots on a 8 × 12 cm chip | Fluorescence/mass spectrometry |

TABLE XXV

Companies that produce arrays, or devices and instrumentations involved in the production of arrays.

| COMPANY | PRODUCT/RESEARCH | Website Address |
|---|---|---|
| ACLARA BioSciences, Inc. | Plastic chips and microfluidic systems based on "Lab-On-A-Chip" microfluidics U.S. Pat. No. 5,750,015: "Method and device for moving molecules by the application of a plurality of electrical fields"). | |
| Advanced Array Technology S.A. | BIO-CD ™: compact disc platform for DNA detection | http://www.aat-array.com |
| Affymetrix, Inc., | GeneChip ® arrays, including HIV, p450, p53, Rat Toxicology U34 arrays, | http://www.affymetrix.com |
| Agilent Technologies, Inc | A subsidiary of Hewlett-Packard Company, plans to expand its presence in the life science market through the introduction of a new DNA microarray program. It uses inkjet printing technology to manufacture its oligo-based DNA microarrays. Licensed from Ed Southern/OGT. LabChip ™-based DNA and RNA bioanalyzer | http://www.agilent.com |
| Alpha Innotech Corp. | Alpha Innotech provides innovation bioinformatic imaging solutions for genetic discovery designed to acquire, manage, and analyze fluorescence, chemiluminescence, or colorimetric microarray slides, plates, gels, blots, or films. | http://www.alpha-tec.net |
| Amersham Biosciences | Lucidea array spotter, automated slide processor, scanner, spotfinder, scoring system | http://www.apbiotech.com |
| AlphaGene, Inc. | Full length cDNA FLEX ™ and MicroFLEX library construction; High Throughput Gene Expression Profiling; High Throughput DNA Sequencing; Bioinformatics | |
| Applied Precision, Inc. | Array WoRx is a wide field light source based microarray scanner, combines limitless wavelength possibilities with automation and image processing software. | |

TABLE XXV-continued

Companies that produce arrays, or devices and instrumentations involved in the production of arrays.

| COMPANY | PRODUCT/RESEARCH | Website Address |
|---|---|---|
| Asper Ltd. | Arrayed Primer Extension (APEX) and Asper ChipReader 003 | |
| AVIVA Biosciences Corp. | Dedicated to the application of breakthrough multiple-force biochip technology for genomics and proteomics. The company is developing an integrated sample-to-result AVIChip ™ system with an emphasis on biological sample preparation and chip-based molecular manipulation. The AVIChip ™ system will separate and transport a variety of mRNA, or other molecules from crude biological samples and simultaneously perform a wide range of biological and biochemical analyses. AVIVA's technology allows fast, accurate, automated, and high-throughput biological analysis on integrated biochip systems and provides novel approaches to both drug development and clinical diagnostics | |
| Axon Instruments, Inc. | Integrated Microarray Scanner and Analysis Software, simultaneously scans microarray slides at two wavelengths using a dual laser scanning system, displays images from two wavelengths and a ratio image as they are acquired in real time; US$50,000) | |
| BioArray Solutions, LLC | Light-controlled Electrokinetic Assembly of Particles near Surfaces (LEAPS), enables computer controlled assembly of beads and cells into planar arrays within a miniaturized, enclosed fluid compartment on the surface of a semiconductor wafer. | |
| BioCat | Distributor of catalogue and custom arrays | http://biocat.de |
| bioDevice Partners, | Provides consulting services to the microarraying community in the area of optics and instrumentation | |
| BioDiscovery, Inc. | ImaGene ™, special image processing and data extraction software; CloneTracker: Databases clones, plates, and slides, and offers array design tool and interfaces to arrayers; GeneSight: Powerful expression analysis software which features statistical methods as well a visualization tools. | |

TABLE XXV-continued

Companies that produce arrays, or devices and instrumentations involved in the production of arrays.

| COMPANY | PRODUCT/RESEARCH | Website Address |
|---|---|---|
| Biomedical Photometrics, Inc., | MACROscope ™ for reading genetic microarrays, in collaboration with Canadian Genetic Microarray Consortium | |
| BioRobotics Ltd. | MicroGrid, for arraying oligonucleotides or cDNA clones on glass slides and plastic chips) | |
| Caliper Technologies Corp | LabChips ™ based on microfluidics | |
| Capital Biochip Corp | Created to develop and commercialize various biochip technologies. | |
| Cartesian Technologies, Inc. | PixSys PA Series: for Automated liquid handling system for creating high-density arrays for genomics research. Scan Array 3000: A Fluorescent Imaging System for microarray biochips | |
| Cellomics, Inc. | ArrayScan ™, cell-based "High Content Screening" (HCS) for drug discovery | |
| Cepheid | Microfluidics | |
| Clinical Micro Sensors, Inc. | DNA microchip-based medical diagnostics; detection of directly detect DNA via electron transfer. | |
| Clondiag Chip Technologies | Working on generation and application of DNA microarrays | |
| Clontech's Atlas ™ human cDNA array | Sells various human arrays | http://www.clontech.com |
| CombiMatrix Corporation | CombiMatrix' core technology is the Lab-on-a-Chip integrated circuit. These integrated circuits contain arrays of microelectrodes that are individually addressable using logic circuitry on the chip. | |
| Compugen | LEADS ™ drug discovery platform for identifying drug targets based on the analysis of EST (Expressed Sequence Tag) and genomic databases, expression results from chips and proteomics, and polymorphism detection and qualification; DNA chip design and analysis. | |
| Corning Science Products Division | Provides the Corning Microarray Technology CMT-GAPS amino silane coated slides and CMT-Hybridization chamber. | |
| Cruachem Ltd, U.K | Manufactures the phosphoramidite building blocks for the synthesis of DNA. | |
| CuraGen Corp. | GeneCalling ™ and Quantitative Expression Analysis (QEA ™), CuraMode, CuraTox | |
| diaDexus, LLC | Specialized in using microarray technology for molecular diagnostics | |

TABLE XXV-continued

Companies that produce arrays, or devices and instrumentations involved in the production of arrays.

| COMPANY | PRODUCT/RESEARCH | Website Address |
|---|---|---|
| Display Systems Biotech, Inc, | discoveryARRAY slides (over 2400 expressed cDNA fragments); will soon offer over 40,000 arrayed mouse and human genes | |
| DNAmicroarray.com | Offers complete “made to order” high density DNA microarray synthesis and analysis services. | |
| Erie Scientific Company | Manufactures microslides for microarrays. | |
| Exiqon | Microarray slides and chips | http://www.exiqon.com |
| Expression Analysis Inc | Company was formed to provide GeneChip processing and gene expression analysis using Affymetrix GeneChip microarrays | |
| Febit | System for gene expression profiling or genotyping | http://febit.com |
| Gene Logic, Inc. | Flow-thru Chip ™: has hundreds of thousands of discrete microscopic channels that pass completely through it. Probe molecules are attached to the inner surface of these channels, and target molecules flow through the channels, coming into close proximity to the probes. This proximity facilitates hybridization. READS ™, Restriction Enzyme Analysis of Differentially-expressed Sequences, for capturing and analyzing the overall gene expression profile of a given cell or tissue type to identify drug targets | |
| Geneka Biotechnology Inc. | Oligonucleotide-based microarray slide, the P.R.O.M. (Proteomic Regulatory Oligonucleotide Microarray). 35-45-mers | |
| Genemachines Genomic Instrumentation Services, Inc. | OmniGrid, glass slides or nylon membranes | |
| GeneScan | Biochip technology; high throughput production of biochips | http://www.genescan-europe.com |
| General Scanning Inc | Laser scanning and micropositioning, manufactures MicroArray Biochip Scanning System: ScanArray ™). Now called GSI Lumonics | |
| Genisphere | Provides fluorescently-labeled kits for gene expression arrays. Uses highly branched nucleic acids—dendrimer technology. | http://www.genisphere.com |
| Genetic MicroSystems Inc. | Instrumentation for DNA microarray-based analysis. Acquired by Affymetrix | |
| Genicon Sciences Corp | Developed an ultra-sensitive signal generation and detection platform technology based on | |

TABLE XXV-continued

Companies that produce arrays, or devices and instrumentations involved in the production of arrays.

| COMPANY | PRODUCT/RESEARCH | Website Address |
|---|---|---|
| | Resonance Light Scattering (RLS) for the simple and efficient detection, measurement and analysis of biological interactions | |
| Genometrix Inc. | Bioscanner ™, GeneView ®, Universal Arrays ™, Risk-Tox | |
| Genomic Solutions, | Flexys ™ modular robotic system, GeneTAC ™ and Genomic Integrator ™ array analysis products automates the imaging and analysis of gene microarrays | http://www.genomicsolutions.com |
| GENPAK Inc | genpakARRAY 21 robotic microarrayer system and genSTATION 3XL manual microarrayer system. | |
| GeSiM | The Nano-Plotter is based on piezoelectric pipetting principle | |
| Genzyme Molecular Oncology | SAGE ®: Serial Analysis of Gene Expression | |
| Greiner Bio-one | Ready to use biochip kits for genotyping and SNP detection, modified slides for microarraying | http://www.greinerbioone.com |
| HP GeneArray Scanner | Used by Affymetrix and others | |
| Hypromatrix, Inc. | Hypromatrix AntibodyArray TM is designed to detect protein-protein interactions, post-translational modification and protein expression. | |
| Hyseq Inc. | Sequencing By Hybridization. HyX platform and Gene Discovery, HyGnostics, and HyChip ™ modules | |
| Illumina, Inc. | Utilizes fiber optics, microfabrication, and advanced information processing to create arrays where 250,000 discrete sensors fit on a probe the diameter of the head of a pin. Technology: "BeadArray." | http://www.illumina.com |
| Incyte Genomics, Inc. | GEM Microarrays, GeneJet ™ array, LifeSeq ® Database with estimated 100,000 genes, and LifeArray Microarray Software. | |
| IntegriDerm, Inc | Produces DermArray DNA microarrays for dermatologic research | |
| JMAR's Precision Systems, Inc | Designer and manufacturer of UV exposure and mask aligner systems specifically designed for bio-chip manufacturers. Also produces custom micropositioning systems for micro-spotting equipment and high resolution dimensional metrology and defect inspection systems for quality assurance of bio-chips and DNA microarrays | |

TABLE XXV-continued

Companies that produce arrays, or devices and instrumentations involved in the production of arrays.

| COMPANY | PRODUCT/RESEARCH | Website Address |
|---|---|---|
| Lab-on-a-Chip.com | Provides focused information on all Lab-on-a-Chip technologies. It includes published papers, news, events, new products, suppliers, research links, jobs and discussion forums. | |
| Labman Automation Ltd., | HDMS: Labman High-Density Microarray Spotter | |
| Lambda | Ready to use biochip kits for genotyping and SNP detection | http://www.lambda.at |
| Lifecodes Corp. | Lifecodes MicroArray System: LMAS | |
| Lynx | Megasort ™ is a bead-based process providing differential DNA analysis | |
| Medway | MEDWAY designs, develops, manufactures and commercialises medical devices for diagnostics, robotic systems, optical instruments, fluorescent molecular markers, sieving microchips | |
| Mergen Ltd | ExpressChip ™ oligonucleotide microarray | |
| Memorec Stoffel | PIQOR technology for producing custom and generic murine and human cDNA arrays | http://www.memorec.com |
| MetriGenix Inc | The 4D Array utilizes a patented flow through design that optimizes the surface area to volume ratio, has shorter hybridization times, provides larger binding/signal capacity, and is more readily automated than flat biochips | |
| Micralyne Inc. | Fabricates micromachined glass, silicon and thin film components for use in microfluidics. | |
| MicroFab Technologies, Inc. | Manufactures piezoelectric drop-on-demand ink-jet printing technology for microdispensing fluids. | |
| Micronics, Inc | Microfluidics based systems for application to clinical laboratory diagnostics: Microcytometer ™, H-Filter ™, T-Sensor ™, and O.R.C.A. µFluidics | |
| Molecular Dynamics, Inc | Storm ® and FluorImager ® | |
| Molecular Tool, Inc | Genetic Bit Analysis, GBA ®, Genomatic ™. Acquired by Orchid Biocomputer on Sep. 14, 1998. | |
| Mosaic Technologies, Inc., | EZ-RAYS ™ activated slide kits for DNA microarrays | |
| Motorola BioChip Systems | Licensed a 3-D gel pad technology from Argonne National Laboratory; CodeLink Array System. | http://www.motorola.com/lifesciences |
| MWG Biotech | Oligo-based microarrays, custom chips, automated systems | http://mwgatccn.mwgdna.com |

TABLE XXV-continued

Companies that produce arrays, or devices and instrumentations involved in the production of arrays.

| COMPANY | PRODUCT/RESEARCH | Website Address |
|---|---|---|
| Nanolytics | Developing Custom Array Synthesis Technology | |
| Nanogen | Electronic Addressing, Concentration, and Hybridization; NanoChip automated workstations for SNP and STR analysis | http://www.nanogen.com |
| NEN Life Science Products | MICROMAX ™ Human cDNA Microarray System I for differential gene expression analysis | |
| Operon Technologies, Inc. | Low density (320 or 370 genes, 70-mers) OpArrays ™ microarrays. | |
| Orchid BioSciences, Inc. | SNP-IT technology; Microfluidic chips; applying microfabrication processes in glass, silicon, and other materials to create three dimensional structures. Contained within these devices are small capillary channels less than a millimeter wide. | http://www.orchid.com |
| OriGene Technologies Inc. | Offers SmartArray ™ chips (Huamn), including nuclear hormone receptors, homeobox/b-zip/HLH transciption factors, tissue-specific/inducible transcription factors, and phosphotyrosine Kinases | |
| Oxford Gene Technology Ltd | Oligo-based microarray | http://www.ogt.co.uk |
| Packard Bioscience (Division of PerkinElmer) | Hydrogel-coated slides, arrayers, scanner and data analysis software | http://www.packardbioscience.com |
| Packard Instrument Company | BioChip Arrayer | |
| PamGene B.V. | Flow-through technology for microarray | http://www.pamgene.com |
| PanVera | Intelligence Microarrays | http://www.panvera.com |
| PE Applied Biosystems | TaqMan Assay, SYBER Green I dye Assay; Integrated, Micro-Sample Preparation System for Genetic Analysis | http://lifesciences.perkinelmer.com |
| PharmaSeq, Inc | Multiplex DNA Diagnostic Assay Based on Microtransponder | |
| Phase-1 Molecular Toxicology, Inc. | Molecular and high throughput toxicology using gene chips (Licensed from Xenometrix) | |
| PicoRapid Technologie | Picoarrays. PicoSlides and microarray spotting service | http://www.picorapid.de |
| Protogene Laboratories | Surface tension array on glass substrate; "Printing" reagents using drop-on-demand technology. | |
| Qiagen Operon | Custom arrays and Array-Ready oligo sets | http://www.operon.com |
| R&D Systems | Cytokine Expression Array allows one to determine the RNA level for approximately 400 cytokines and related factors in one standard hybridization experiment. (charged nylon membrane) | |
| Radius Biosciences | Custom DNA, RNA, PNA, and Protein MicroArray Chips | |

TABLE XXV-continued

Companies that produce arrays, or devices and instrumentations involved in the production of arrays.

| COMPANY | PRODUCT/RESEARCH | Website Address |
|---|---|---|
| RELAB AG | Developing BioChip arrays for diagnostic applications (oncology). The GeneStick platform with arrays on plastic sticks and a new chemiluminescence imager. | |
| ResGen Invitrogen | GeneFilters microarrays/VastArray tissue arrays/GeneStorm Expression Ready full-length clones | http://www.resgen.com |
| RoboDesign International Inc. | Its RoboArrayer is integrated with a vision system to allow for real-time quantification of spot size and spot volume during the printing process. | |
| Rosetta Inpharmatics | FlexJet ™ DNA oligonucleotides microarrays (in-situ synthesized on a glass support via ink-jet printing process); Resolver ™ Expression Data Analysis System. | |
| Scienion | Generic and customized arrays | http://www.scienion.de |
| SciMatrix, Inc | Offers ArrayWorks ™, a complete line of custom microarray services, for the production, processing, and analysis of microarrays, using PixSys ™ arrayers from Cartesian Technologies. It also provides customized ArrayEngine ™ microarray systems. | |
| Sequenom | DNA MassArray, BiomassPROBE, Biomass SIZE, BiomassSEQUENCE, BiomassSCAN, BiomassINDEX, and SpectroChip | |
| Sigma-Genosys Ltd | Panorama ™ *E. coli* Gene Arrays, 4,290 genes per array | http://www.sigma-genosys.com |
| SmartBead Technologies | 3D UltraPlex ™ microarray technology for applications in SNP genotyping and gene expression | http://www.smartbead.com |
| SuperArray Inc | Their gene expression array (GEArray ™) systems (Human and mouse) are designed for pathway-specific gene expression profiling | http://www.superarray.com |
| SurModics, Inc | Manufactures 3D-Link ™ activated slides for the production of microarrays. Uses amine-modified DNA to hybridize on the surface of the slide | |
| Synteni, Inc. | UniGEM ™ Gene Expression Microarray | |
| TeleChem International | Offers whole system parts: ChipMaker, SmartChips, ArrayIt, Hybridization Cassette, ScanArray 3000, ImaGene Quantification Software, and Super Microarray Substrates | |

TABLE XXV-continued

Companies that produce arrays, or devices and instrumentations involved in the production of arrays.

| COMPANY | PRODUCT/RESEARCH | Website Address |
|---|---|---|
| Third Wave Technologies, Inc | Develops and commercializes simple, low-cost nucleic acid platform technologies to fundamentally alter disease discovery, diagnosis and treatment. Invader ® assay and CFLP ® Technology | |
| Tissue Array | Expression study of protein and in situ screening of mRNA. | |
| VBC Genomics | Custom oligonucleotide microarrays and Affymetrix GeneChip Services | http://www.vbc-genomics.com |
| V&P Scientific, Inc | Supplies replicators that will make macroarrays on membranes, or microarrays on slides. | |
| Virtek Vision International Inc | ChipReader ™ is a high-sensitivity laser confocal system for rapid imaging of the DNA microarrays. | |
| Vysis, Inc. | CGH-Comparative Genomic Hybridization; The GenoSensor Microarray System includes genomic microarrays, reagents, instrumentation and analysis software. | http://www.vysis.com |
| Xanthon | Developed a multiplexed, microplate-based electrochemical detection system for high-throughput screening of compounds for their effects on gene expression. Based on measurement of the oxidation of guanine on an electrode | |
| Xenometrix, Inc. | Gene Profile Assay and bioinformatics for gene induction profile analysis. | |
| XENOPORE Corp | Manufacturer of coated microscope slides, including silanated, silylated, epoxy, streptavidin, nickel chelate, and many other surfaces. | |

TABLE XXVI

Array Databases and On-line Tools

| Database | Overview |
|---|---|
| GeneX | A comprehensive list of is gene expression database and analysis tools is available at NCGR's GeneX site |
| Microarray Gene Expression Database (MGED) Group | Microarray Gene Expression Database (MGED) Group, was formed to facilitate the adoption of standards for DNA-array experiment annotation and data representation, as well as the introduction of standard experimental controls and data normalisation methods. |
| Gene Expression Omnibus (GEO | NCBI's Gene Expression Omnibus (GEO) public gene expression repository in development. |

TABLE XXVI-continued

Array Databases and On-line Tools

| Database | Overview |
| --- | --- |
| ArrayDB (http://genome.nhgri.nih.gov/arraydb/schema.html) at the National Human Genome Research Institute (NHGRI) | |
| µArray Center | National Cancer Institute's array schema. |
| expressDB. | George Church Lab's at Harvard Medical School: a relational database containing yeast RNA expression data. |
| MAT | Microarray Analysis Tool) at Albert Einstein College of Medicine: based on Java, JDBC, and Sybase SQL. |
| GATC consortium's published schema | |
| GeneX: | A Collaborative Internet Database and Toolset for Gene Expression Data at the National Center for Genome Resources |
| GenEx ™ | GenEx ™ of Silicon Genetics is a public web database that allows scientists to freely distribute and visualize gene expression data (text and image) from microarrays, Affymetrix chips, and related technologies. It can also dynamically generate several graphs from the data being viewed, such as: scatter plots, trees, overlays, ordered lists, line graphs, or physical position graphs. It is designed to store annotations and interpretations on finished experiments, and can access data from SQL databases like GATC or even from flat text files. |
| Stanford MicroArray Database (Oracle) | |
| *Arabidopsis* cDNA Microarray Results | The Arabidopsis Functional Genomics Consortium (AFGC)'s *Arabidopsis* cDNA Microarray Results |
| ArrayExpress | ArrayExpress, being developed at the European Bioinformatics Institute, will be a public array-based gene expression data repository. An international meeting on Microarray Gene Expression Databases, Nov. 14-15, 1999. |
| MicroArray Explorer (MAExplorer), | Dr. Peter Lemkin at the NCI developed a Java applet, MicroArray Explorer (MAExplorer), which is currently being used in the Mammary Genome Anatomy Program |
| CLUSFAVOR | Dr. Leif Peterson's CLUSFAVOR: Partitioning Large-sample Microarray-based Gene Expression Profiles Using Principal Components Analysis |
| SAGEmap | SAGEmap: A Public Gene Expression Resource, Alex E. Lash et al., Genome Res. 2000 Jul. 1; 10(7): p. 1051-1060 |
| J-Express | Java program for analyzing microarray data. SOM and PCA implemented, by Bjarte Dysvik. |
| MicroArray Informatics at the EBI | |

TABLE XXVII

Microarray Databases on the World Wide Web

| Project | Name |
| --- | --- |
| Abberdeen university | aeFDM |
| Affymetrix & Molecular dynamics | Consorsium GATC |
| Albert Einstein College of Medicine | MAT |
| Another Microarray Database. (Jan. 1, 2000 - v1.01) | AMAD |
| Ecole Normale Superieure (private database) | LGM database |
| Ecole Normale Superieure (public database) | yMGV |
| European Bioinformatique Institute | Arrayexpress |
| George Church Lab's (Harvard) | ExpressDB |
| Pevsner Lab's (Kennedy Krieger Institute) | Dragon |
| Manchester bioinformatics | maxd |
| National center for Biotechnology Information (NCBI) | Geo |
| NCI-LECB | MAExplorer |

TABLE XXVII-continued

Microarray Databases on the World Wide Web

| Project | Name |
| --- | --- |
| National Human Genome Research Institute (NIH) | ArrayDB |
| National Cancer Institute Array Center server (NIH-CIT) | µArray Database |
| NIEHS-NIH | MAPS |
| San Diego Supercomputer Center (SDSC) | 2HAPI |
| Silicon Genetics | GenEx |
| Stanford | SMD |
| University of Pennsylvania | RAD |
| Young lab (White head institute-MIT) | chipDB |

Example 17

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. In this example, SNPs are analyzed by the CodeLink SNP Bioarray System, which is manufactured in a collaborative effort by Motorola and Amersham Biosciences, however other microarrays may be used. Amersham sells the CodeLink P450 Bioarray, which is designed to genotype various regions of the P450, which is located on chromosome 6.

However, Amersham may produce custom CodeLink arrays, which can be designed to analyze regions of any chromosome including chromosome 1, 2, 3, 4, 5, 6, 7, 8, 9, 10, 11, 12, 13, 14, 15, 16, 17, 18, 19, 20, 21, 22, X or Y.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis, stabilize cell membranes, or cross-link cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes, impedes cell lysis, or cross-links cell membranes can be added. In a preferred embodiment, the agent that stabilizes cell membranes or impedes cell lysis is added at a concentration that does not impede or hinder subsequent reactions.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Isolation of DNA

DNA is isolated from the plasma sample using the Qiagen Midi Kit for purification of DNA from blood cells, following the manufacturer's instructions (QIAmp DNA Blood Midi Kit, Catalog number 51183). DNA is eluted in 100 μl of distilled water. The Qiagen Midi Kit also is used to isolate DNA from the maternal cells contained in the "buffy coat."

Identification of Homozygous Maternal SNPs

CodeLink SNP Bioarray

CodeLink SNP is a bioarray system solution for broad based SNP genotyping. CodeLink SNP involves a multiplexed assay involving PCR amplification and amplicon fragmentation, followed by surface based enzymatic allele discrimination and array based labeling and detection. The reagents for the CodeLink array are supplied in the P450 Reagent Kit, which provides enough reagents for 24 reactions.

The CodeLink™ platform consists of a glass slide that has been silanized to generate coverage with long-chain alkyl groups (Ramakrishnan et al., Nucleic Acids Research, Vol. 30, No. 7, e30, Apr. 1, 2002). A prepolymer, which contains an activated ester, of acrylamide is photo-coupled to the slide. The activated ester provides the attachment site for C6-amino-oligonucleotides. 5'Amine-terminated oligonucleotides are deposited onto the polymer using dispensing robotics. Oligonucleotides are dispensed with a fluorescein-derivative dye, which enables scanning of every slide after dispensing. To enable attachment of the oligonucleotides, the slides are placed into a humidified chamber. Additional sites are blocked and slides are washed, rinsed and dried prior to attachment of an integrated, polypropylene hybridization chamber.

A custom CodeLink Array could be synthesized containing SNPs located on the chromosome of interest; SNPs located on any chromosome may be analyzed. In this example, a representative CodeLink Array with two SNPs located on chromosome 21 (TSC0271628, TSC0069805) and two SNPs located on chromosome 13 (TSC0466917, TSC 1172576) is used. However, a CodeLink Array with any number of probes for SNPs, including but not limited to 1-10, 11-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-300, 301-400, 401-500, 501-600, 601-700, 701-800, 801-900, 901-1000, 1001-2000, 2001-3000, 3001-4000, 4001-5000, 5001-6000, 6001-7000, 7001-8000, 8001-9000, 9001-10,000 and greater than 10,000 probes can be used. The SNPs that are used can be located on a single chromosome, more than one chromosome, or any combination of chromosomes.

The CodeLink Array consists of a single stranded probe attached to a surface (a detailed diagram is available at http://www5.amershambiosciences.com/APTRIX/upp01077.nsf/Content/codelink_snp) The nucleotide farthest from the surface corresponds to the locus of interest.

For example, SNP TSC09466917, which is located on chromosome 13, can either be a cytosine nucleotide or a guanine nucleotide. Two types of probes are made: TAAAAG and TAAAC. The probes are attached with the guanine or cytosine farthest from the surface. The probes can be longer or shorter in sequence.

The nucleotides at SNP TS1172576, which is located on chromosome 13, can either be thymidine or adenine. Two probes are made: TACCGCATAT (SEQ ID NO: 712) and TACCGCATAA (SEQ ID NO: 713). The probes for the SNPs on the CodeLink Array can be of the same length or different lengths.

The nucleotides at SNP TSC0271628, which is located on chromosome 21, can either be adenine or guanine. Two probes are made: TTTCCACTCATCCAG (SEQ ID NO: 714) and TTTCCACTCATCCAA (SEQ ID NO: 715). The probes for the SNPs can either be to the sense or antisense strand of the DNA.

The nucleotides at SNP TSC0069085, which is located on chromosome 21, can either be cytosine or thymidine. Two probes are made: TATCTTAATAC (SEQ ID NO: 716) and TATCTTAATAT (SEQ ID NO: 717).

Representative probes for these four SNPs are provided above. However, the probes can be longer or shorter in sequence and can be made to the sense or antisense strand of the DNA. In addition, more than one probe to each SNP can be used. Multiple probes with different sequences or the same sequences can be used for the same SNP. For example, one probe for SNP TSC0069085 can be of 10 nucleotides in length and another probe for SNP TSC6069085 can be of 20 nucleotides in length. Alternatively, one probe for SNP TSC0069085 can be to the sense strand and a second probe for SNP TSC0069085 can be to the antisense strand.

PCR Amplification

Once a CodeLink Array is designed, the next step is amplification. Any method of amplification can be used, preferably PCR. Primers are designed to amplify two SNPs on chromosome 13 and two SNPs located on chromosome 21 using information provided at the SNP Consortium (http://snp.cshl.org). The skilled artisan will understand how to design primers for any other SNP of interest.

SNP TSC0466917 (C/G), which is located on chromosome 13, is amplified using the following primers:

```
Upstream Primer:
5' CCAGCTGGTAGAACTT 3'      (SEQ ID NO: 718)

Downstream Primer:
5' CCCAATAGACCTATAG 3'      (SEQ ID NO: 719)
```

SNP TSC1172576 (T/A), which is located on chromosome 13, is amplified using the following primers:

```
Upstream Primer:
5' TAGCAGAATCTCTCAT 3'      (SEQ ID NO: 720)

Downstream Primer:
5' AGAGTATCTCATTTGTT 3'     (SEQ ID NO: 721)
```

SNP TSC0271628 (A/G), which is located on chromosome 21, is amplified using the following primers:

```
Upstream Primer:
5' AGGAAATTGTGAAGTA 3'      (SEQ ID NO: 722)

Downstream Primer:
5' TAACTCACTCACTATC 3'      (SEQ ID NO: 723)
```

SNP TSC0069085 (C/T), which is located on chromosome 21, is amplified using the following primers:

```
Upstream Primer:
5' CTGCTGAGTCATAGTC 3'      (SEQ ID NO: 724)

Downstream Primer:
5' TGTTCTTTGAATCAAC 3'      (SEQ ID NO: 725)
```

Oligonucleotide probes may be of any length including but not limited to 5-10, 11-15, 16-20, 21-25, 26-29, 30, 31-35, 36-45, 46-55, 56-65, 66-75, and greater than 75 bases in length.

PCR conditions should be designed according to the manufacturer's suggestion. Representative PCR conditions are provided here. The loci of interest are amplified in separate reaction tubes but they can also be amplified together in a single PCR reaction. For increased specificity, a "hot-start" PCR is used. PCR reactions are performed using the HotStarTaq Master Mix Kit supplied by QIAGEN (catalog number 203443). The amount of template DNA and primer per reaction can be optimized for each locus of interest but in this example, 40 ng of template human genomic DNA and 5 μM of each primer are used. Forty cycles of PCR are performed. The following PCR conditions are used:

(1) 95° C. for 15 minutes and 15 seconds;
(2) 95° C. for 30 seconds;
(4) 57° C. for 30 seconds;
(5) 72° C. for 30 seconds;
(6) Repeat steps 2-5 thirty two (32) times;
(7) 72° C. for 5 minutes.

PCR Purification and Fragmentation

The PCR products are purified following the procedures recommended by the makers of CodeLink. One mode of PCR purifications is provided here. PCR products are separated from the components of the PCR reaction using Qiagen's MinElute PCR Purification Kit following manufacturer's instructions (Catalog number 28006).

The purified PCR products are fragmented following the procedures recommended by the makers of CodeLink. The PCR products can be fragmented using enzymes including but not limited to DNase or using mechanical forces, including but not limited to sonication or shearing through a needle.

Hybridization

The purified, fragmented PCR products are hybridized to the CodeLink Arrays following the procedures recommended by the makers of CodeLink. Typical hybridization procedures involve hybridizing the target probe and the sample DNA in a solution containing mild detergents, such as SDS or Triton-100, salts, such as $MgCl_2$, and a buffer such as Tris or PBS. The hybridization reaction is performed usually with mild shaking at 25-44° C. for 8-16 hours. The hybridization reactions can be performed using the Shaker Kit, available for Amersham Biosciences.

Alternatively, hybridizations are performed using the Motorola 12-slide shaker tray, which contains hybridization chambers. The hybridization chamber ports are sealed with I cm sealing strips (Motorola Life Sciences) and the shaker trays containing the slides are loaded into the New Brunswick Innova™ 4080 shaking incubator, with the hybridization chambers facing up. Slides are incubated for 18 h at 37° C., while shaking at 3000 r.p.m.

There may be specific procedures and solutions for hybridization with CodeLink Arrays. Representatives at CodeLink would not provide the protocols without prior purchase of an array.

Allele Specific Extension

After hybridization, an extension reaction is performed following the procedures recommended by the makers of CodeLink. A typical extension reaction requires the presence of nucleotides (dATP, dCTP, dGTP, dTTP), a polymerase, and a buffered solution containing salts. The concentration of nucleotides and the polymerase that is used should be as recommended by the makers of CodeLink. Any DNA polymerase can be used including but not limited to *E. coli* DNA polymerase, Klenow fragment of *E. coli* DNA polymerase I, T7 DNA polymerase, T4 DNA polymerase, T5 DNA polymerase, Klenow class polymerases, Taq polymerase, Pfu DNA polymerase, Vent polymerase, bacteriophage 29, RED-Taq™ Genomic DNA polymerase, or sequenase. Preferably, the polymerase that is used is the one recommended by the makers of CodeLink.

Wash, Label and Detect

After the extension reaction, the arrays are washed, preferably with the solution recommended by the makers of CodeLink. A typical wash solution contains detergent(s) and salts in a buffered solution. For example, the arrays can be washed with a TNT buffer (0.1 M Tris-HCl, pH 7.6, 0.15 M NaCl, 0.05% Tween-20. The arrays are washed at the temperature recommended by the makers of CodeLink including but not limited to room temperature, 10-16° C., 17-24° C., 25° C., 26-36° C, 37° C., 38-41° C., 42° C., 43-54° C., 55° C., or higher than 55° C.

The signal is developed following the protocol recommended by the makers of CodeLink. A representative protocol is provided here. The signal is developed using a 1:500 dilution of a streptavidin-Alexa 647 (Molecular Probes), for 30 minutes at room termperature. Excess dye is removed by washing four times with TNT buffer, for 5 min each, at room temperature. The signal intensity can be increased by using a 1:200 dilution of tyramide-cy3 in amplification dilutent buffer (PE/NEN).

Slides are rinsed with deionized water and dried using a nitrogen gun. Processed slides are scanned using the Axon GenePix Scanner with the laser set to 635 nm, the photomultiplier tube voltage to 600 and the scan resolution to 10μ. Slides are scanned and analyzed using CodeLink™ SNP Software kit, which is available from Amersham Biosciences.

Each SNP is genotyped. SNPs located on chromosomes 13 and 21, wherein the maternal DNA is homozygous, are analyzed with the DNA isolated from the plasma.

Analysis of DNA Isolated from Maternal Plasma

After the maternal DNA is analyzed and homozygous SNPs are identified, these SNPs are analyzed with the DNA isolated from the plasma. A low copy number of fetal genomes typically is present in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 μl of plasma template DNA is used.

Two microliters of each forward and reverse primer, at concentrations of 5 mM are pooled into a single microcentrifuge tube and mixed. Four microliters of the primer mix is used in a total PCR reaction volume of 50 μl (20 μl of template plasma DNA, 1 μl of sterile water, 4 μl of primer mix, and 25 μl of HotStar Taq. Twenty-five cycles of PCR are performed. The following PCR conditions are used:

(1) 95° C. for 15 minutes;

(2) 95° C. for 30 second;

(3) 4° C. for 30 seconds;

(4) 37° C. for 30 seconds;

(5) Repeat steps 2-4 twenty-four (24) times;

(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

It is important to ensure that the region amplified (done to increase the copy number of the fetal loci of interest) contains annealing sequences for the primers that are used with the CodeLink assay. Upon purchase of the CodeLink array, each SNP and the primers used to amplify each SNP can be identified. With this knowledge, the multiplex primers are designed to encompass annealing regions for the primers in the HuSNP Array.

Purification of Fragment of Interest

The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 μl of sterile water. 5 μl of each amplified loci is mixed together CodeLink Assay, Washing, Staining and Scanning The pooled DNA is assayed with the CodeLink Array as described above. Washing, staining, and scanning procedures are as described above.

Each SNP is genotyped. SNPs located on chromosomes 13 and 21, wherein the maternal DNA is homozygous, and DNA isolated from the plasma is heterozygous are quantitated.

Quantification

The intensity of the signal for each allele at a heterozygous is SNP is quantitated. As discussed above, the expected ratio of allele 1 to allele 2 can be used to determine the presence or absence of a chromosomal abnormality. If the maternal genome is homozygous at SNP X (A/A), and the plasma DNA is heterozygous at SNP X (A/G), then the G represents the distinct fetal signal. The ratio of G:A depends on the percentage of fetal DNA present in the maternal blood.

For example, if the sample contains 50% fetal DNA, then the expected ratio is 0.33 (1 fetal G allele/(2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

This example explained the use of CodeLink Arrays, but it not intended to limit the use of arrays. Any DNA array may be used including but not limited to the DNA arrays listed in Table XXIII, or DNA arrays available from any of the companies listed in Table XXIV.

Example 18

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. In this example, SNPs are analyzed using Illumina's BeadArray™ platform, available form Illumina in San Diego, Calif.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, BM(PEO)$_3$, BM(PEO)$_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Isolation of DNA

DNA is isolated from the plasma sample using the Qiagen Midi Kit for purification of DNA from blood cells, following the manufacturer's instructions (QIAmp DNA Blood Midi Kit, Catalog number 51183). DNA is eluted in 100 μl of distilled water. The Qiagen Midi Kit also is used to isolate DNA from the maternal cells contained in the "buffy coat."

Identification of Homozygous Maternal SNPs

Illumina's BeadArray™ technology consists of a fiber optic based array system that allegedly allows miniaturized, very-high throughput genetic analysis. Illumina's 96-bundle Sentrix Array™ allegedly enable parallel processing of nearly 150,000 SNPs.

Fiber bundles are manufactured to contain nearly 50,000 individual, light transmitting fiber strands. Each fiber bundle is converted into an array by first chemically etching a microscopic well at the end of each fiber strand within a bundle, which creates up to 50, 000 discrete microscopic wells per bundle.

In a separate process, sensors are created by affixing a specific type of molecule to the beads, each bead approximately 3 microns in diameter. For SNP analysis, a particular DNA sequence is attached to each bead in a batch. Illumina states that hundreds of thousands of molecules of the same type coat each bead. Batches of coated beads are combined to form a pool specific to the type of array desired. For SNP analysis, the array pool allegedly uses DNA sequences that do not cross hybridize with themselves or with known genomic DNA.

Next, the self-assembled array is created. By dipping bundles into a pre-mixed bead pool, the coated beads self-assemble individually, one bead per well, on the end of each fiber in the bundle to create the array. In Illumina's SNP genotyping array, the bead pool consists of up to 1500 sequences, which self assemble in each bundle of 50,000 fibers to create an array with an approximately thirty-fold redundancy.

The BeadArray bundles are assembled into a matrixed device, which is called the Array of Arrays™ platform, where each fiber bundle of the larger array matches a well of a standardized microtiter plate.

Following array assembly, a decoding process is used to determine the bead type that resides in each fiber core. The DNA molecules are synthesized using the Oligator™ custom DNA synthesis technology.

Illumina's SNP genotyping service using the BeadArray technology and other technologies that have sprung from the BeadArray technology are provided at Illumina's facilities or at facilities that have received a license to the BeadArray technology.

Maternal DNA samples are analyzed using BeadArrays that contain oligonucleotide probes to SNPs. The oligonucleotide probes can be for SNPs located on any chromosome including human chromosome 1, 2, 3, 4, 5, 6, 7, 8, 9, 10, 11, 12, 13, 14, 15, 16, 17, 18, 19, 20, 21, 22, X, and Y. The BeadArrays are analyzed to identify SNPs, wherein the maternal template DNA is homozygous. The identified homozygous SNPs are then analyzed using the DNA isolated from the maternal plasma.

Analysis of DNA Isolated from Maternal Plasma

After the maternal DNA is analyzed and homozygous SNPs are identified, these SNPs are analyzed with the DNA isolated from the plasma. A low copy number of fetal genomes typically exists in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 μl of plasma template DNA is used.

Two microliters of each forward and reverse primer, at concentrations of 5 mM are pooled into a single microcentrifuge tube and mixed. Four microliters of the primer mix is used in a total PCR reaction volume of 50 μl (20 μl of template plasma DNA, 1 μl of sterile water, 4 μl of primer mix, and 25 μl of HotStar Taq. Twenty-five cycles of PCR are performed. The following PCR conditions are used:

(1) 95° C. for 15 minutes;
(2) 95° C. for 30 second;
(3) 4° C. for 30 seconds;
(4) 37° C. for 30 seconds;
(5) Repeat steps 2-4 twenty-four (24) times;
(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

It is important to ensure that the region amplified contains annealing sequences for the oligonucleotide probes in the BeadArray. Upon purchase of the BeadArray service, each SNP and the primers used to analyze each SNP are identified. With this knowledge, the multiplex primers are designed to encompass annealing regions for the primers in the BeadArray.

Purification of Fragment of Interest

The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 μl of sterile water. 5 μl of each amplified loci is mixed together BeadArray Technology The pooled DNA is assayed with the BeadArray as described above. Each SNP is genotyped. SNPs located on chromosomes 13 and 21, wherein the maternal DNA is homozygous, and DNA isolated from the plasma is heterozygous are quantitated.

Quantification

The intensity of the signal for each allele at a heterozygous is SNP is quantitated. As discussed above, the expected ratio of allele 1 to allele 2 can be used to determine the presence or absence of a chromosomal abnormality. If the maternal genome is homozygous at SNP X (A/A), and the plasma DNA is heterozygous at SNP X (A/G), then the G represents the distinct fetal signal. The ratio of G:A depends on the percentage of fetal DNA present in the maternal blood.

For example, if the sample contains 50% fetal DNA, then the expected ratio is 0.33 (1 fetal G allele/(2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

This example explained the use of Illumina's BeadArray Technology, but it not intended to limit the use of arrays. Any DNA array may be used including but not limited to the DNA arrays listed in Table XXIII, or DNA arrays available from any of the companies listed in Table XXIV.

Example 19

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. In this example, SNPs are analyzed using Sequenom's MassArray™ System, which uses Sequenom's homogenous MassCleave™ (hMC) method.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Isolation of DNA

DNA is isolated from the plasma sample using the Qiagen Midi Kit for purification of DNA from blood cells, following the manufacturer's instructions (QIAmp DNA Blood Midi Kit, Catalog number 51183). DNA is eluted in 100 µl of distilled water. The Qiagen Midi Kit also is used to isolate DNA from the maternal cells contained in the "buffy coat."

Identification of Homozygous Maternal SNPs

Targeted SNP Discovery: hMC Method

Sequenom's hMC method uses nucleotide base-specific cleavage for genotyping. The cleaved fragments are measured using MALDI-TOF to generate a characteristic peak signal, based on the mass of each fragment, for any particular sequence.

Primer Design

Four primers are needed for the two PCR reactions (one forward reaction and one reverse reaction). The recommended size range for PCR amlicons is 300-700 base pairs. The primers contain a T-7 promoter tagged forward or reverse primer to obtain an appropriate product for in vitro transcription. An 8 base insert is included to prevent abortive cycling. The primer that lacks the T-7 promoter contains a 10-mer tag in order to balance the primers.

The primers for one SNP are provided below. SNP TSC1172576 (T/A), which is located on chromosome 13, is amplified using the following primers for the forward reaction:

```
Forward reaction:
Upstream Primer:
5' CAGTAATACGACTCACTATAGGGGTCAGGA   (SEQ ID NO: 637)
TTAGCAGAATCTCTCAT 3'

Downstream Primer:
5' GCATTCTATGAGAGTATCTCATTTGTT 3'   (SEQ ID NO: 638)

Reverse Reaction:
Upstream Primer
5' CAGTAATACGACTCACTATAGGGGTCAGGA   (SEQ ID NO: 639)
AGAGTATCTCATTTGTT 3'

Downstream Primer
5' GCATTCTATGTAGCAGAATCTCTCAT 3'    (SEQ ID NO: 640)
```

The sequence of the T-7 promoter are in italics, the 8 base insert is underlined, the 10-base balancing sequence is double underlined, and the gene specific sequences are unmodified.

PCR Amplification

Five nanograms of DNA is amplified in a 5 µl volume using a 384-microtiter format. The following PCR conditions are used:

1) 94° C. for 15 minutes;
2) 94° C. for 20 seconds;
3) 62° C. for 30 seconds;
4) 72° C. for 1 minute;
5) Repeat steps 2-4 44 times; and
6) 72° C. for 3 minutes.

Dephosphorylation

Shrimp Alkaline Phosphatase (SAP) (2 µl) is added to each 5 µl PCR reaction to dephosphorylate unincorporated dNTPs from the PCR reaction. The plates are incubated at 37° C. for 20 minutes. Then, the plates are incubated at 85° C. for 5 minutes.

In Vitro Transcription

For each transcription reaction, 2 µl of transcription cocktail and 2 µl of PCR/SAP sample are needed. Add 2 µl of transcription cocktail and 2 µl of PCR/SAP sample to a new microtiter plate. The plates are incubated at 37° C. for two hours. For detailed information regarding these protocols see the "Processing homogeneous MassCLEAVE Reactions" chapter in the MassARRAY Liquid Handler SNP Discovery User's Guide for instructions, which is fully incorporated herein by reference.

RNase A Cleavage

RNase A cocktail (2.5 µl) is added to each reaction (T cleavage and C cleavage). The plates are incubated at 37° C. for one hour.

Depending on the nucleotide at the SNP site, various fragments of different weights are generated. For example, the DNA sequence surrounding SNP TSC1172576, which is located on chromosome 13, is as follows:

```
5' CCGCATA T/A CTCAGCACA 3'    (SEQ ID NO: 641)

3' GGCGTAT A/T GAGTCGTGT 5'    (SEQ ID NO: 642)
```

After PCR, in vitro transcription, and base-specific cleavage, the following fragments for each allele are generated:

| | T allele | A allele |
|---|---|---|
| Products of forward Transcription | 1) TA**T**CTCA<br>2) A**T**C | 1) CTCAGC<br>2) A**A**C |
| Products of reverse transcription | 1) AG**T**TA<br>2) G**T**TATGC | 1) AG**A**TA<br>2) **A**TATGCG |

For the ATC and AAC fragments, the weight difference between T and A is used to determine the genotype at SNP TSC1172576. Likewise, the weight difference between T and A in fragments AGTTA and AGATA is used to determine the genotype at SNP TSC1172576.

Sample Conditioning

Double distilled water (20 µl) is added to each sample within the 384-well plate. Clean Resin (6 mg) is added to each well. The plate is rotated for 10 minutes, followed by a centrifugation at 3200×g. It is recommended that water always be added before the Clean Resin.

Sample Transfer

The hMC reaction product (10-15 µl) is dispensed onto a 384 element SpectroCHIP®. For further information, see the "Dispensing MassCLEAVE Reaction Products onto SpectroCHIPs" chapter in the MassARRAY Nanodispenser SNP Discovery User's Guide for instructions.

Sample Analysis

Spectra from the four cleavage reactions is acquired using the MassARRAY™ system. For further instructions, see the "Acquiring Spectra" chapter in the MassARRAY Discovery RT Software User's guide for instructions on acquiring spectra from SpectroCHIPS®.

SNP Analysis

The results are analyzed using the SNP Discovery Analysis software. For further instructions, see the "Analyzing SNPs" chapter in the MassARRAY Discovery RT Software User's Guide for instructions on using the SNP Discovery Analysis software. Components that are useful for the MassARRAY procedure include MassARRAY™ Analyzer (part number 004500), MassARRAY™ Discovery RT Software version 1.2 (part number 11434), MassARRAY™ SNP Discovery Starter Kit (part number 10027), and Liquid Handler SNP Discovery Methods and Macros (part number 11433).

The SpectroCHIP array is used to genotype the maternal DNA following the manufacturer's recommended protocols and procedures, which are made available after purchase of the SpectroCHIP array. SNPs at which the maternal DNA is homozygous are used to analyze the DNA isolated from the maternal plasma.

Analysis of DNA Isolated from Maternal Plasma

After the maternal DNA is analyzed and homozygous SNPs are identified, these SNPs are analyzed with the DNA isolated from the plasma. A low copy number of fetal genomes typically exists in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 µl of plasma template DNA is used.

Two microliters of each forward and reverse primer, at concentrations of 5 mM are pooled into a single microcentrifuge tube and mixed. Four microliters of the primer mix is used in a total PCR reaction volume of 50 µl (20 µl of template plasma DNA, 1 µl of sterile water, 4 µl of primer mix, and 25 µl of HotStar Taq. Twenty-five cycles of PCR are performed. The following PCR conditions are used:

(1) 95° C. for 15 minutes;

(2) 95° C. for 30 second;

(3) 4° C. for 30 seconds;

(4) 37° C. for 30 seconds;

(5) Repeat steps 2-4 twenty-four (24) times;

(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

It is important to ensure that the region amplified contains annealing sequences for the PCR primers in the targeted SNP discovery, hMC method Purification of Fragment of Interest The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 µl of sterile water. 5 µl of each amplified loci is mixed together Targeted SNP Discovery: hMC Method The pooled DNA is assayed with the hMC method as described above. Each SNP is genotyped. SNPs located on chromosomes 13 and 21, wherein the maternal DNA is homozygous, and DNA isolated from the plasma is heterozygous are quantitated. However, SNPs located on other chromosomes can also be quantitated if so desired.

Quantification

The intensity of each peak, wherein each peak corresponds to a DNA fragment with a specific molecular weight, is quantitated. As discussed above, the expected ratio of allele 1 to allele 2 is used to determine the presence or absence of a chromosomal abnormality. If the maternal genome is homozygous at SNP X (A/A), and the plasma DNA is heterozygous at SNP X (A/G), then the G represents the distinct fetal signal.

There will be some fragments that differ in molecular due to the presence of the G nucleotide at SNP X in the fetal genome. The intensity of the peak with the A nucleotide is quantitated and the intensity of the peak that corresponds to fragments with the G nucleotide is quantitated. The ratio of G:A depends on the percentage of fetal DNA present in the maternal blood.

For example, if the sample contains 50% fetal DNA, then the expected ratio is 0.33 (1 fetal G allele/(2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

This example explained the use of Sequenom's hMC method, but it not intended to limit the use of other mass spectrometry techniques.

Example 20

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. In this example, SNPs are analyzed using Sequenom's MassArray™ Homogenous MassEXTEND™ (hME) Assay.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, BM(PEO)$_3$, BM(PEO)$_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Isolation of DNA

DNA is isolated from the plasma sample using the Qiagen Midi Kit for purification of DNA from blood cells, following the manufacturer's instructions (QIAmp DNA Blood Midi Kit, Catalog number 51183). DNA is eluted in 100 μl of distilled water. The Qiagen Midi Kit also is used to isolate DNA from the maternal cells contained in the "buffy coat."

Identification of Homozygous Maternal SNPs

MassARRAY Homogenous MassEXTEND™ (hME) Assay

The Homogenous MassEXTEND™ (hME) Assay uses a beadless, label-free primer extension chemistry for genotyping. Each of the primer products has a unique molecular weight that allows the associated genotype to be precisely identified using mass spectrometry.

Template Amplification

The isolated maternal DNA is amplified (2.5 ng) in a 5 μl volume using a 384-microtiter plate format. Any number of SNPs can be amplified, either in a single reaction or in multiple reactions. Representative primers that are used to amplify SNP TSC0271628 (A/G), which is located on chromosome 21, are provided below:

```
Upstream Primer:
5' AGGAAATTGTGAAGTA 3'      (SEQ ID NO: 643)

Downstream Primer:
5' TAACTCACTCACTATC 3'      (SEQ ID NO: 644)
```

The primers can be longer or shorter in nucleotide sequence. PCR conditions recommended by the makers of MassARRAY Homogenous MassEXTEND Assay are followed. Representative PCR conditions are provided below:

(1) 95° C. for 15 minutes and 15 seconds;
(2) 95° C. for 30 seconds;
(4) 57° C. for 30 seconds;
(5) 72° C. for 30 seconds;
(6) Repeat steps 2-5 thirty two (32) times;
(7) 72° C. for 5 minutes.

Dephosphorylation

Arctic shrimp alkaline phosphatase is added to the samples, which are then incubated at 37° C. for 20 minutes. This step is done to dephosphorylate any remaining nucleotides, which prevents their future incorporation and interference with MassARRAY Homogenous MassEXTEND Assay. Samples are then incubated at 85° C. to inactivate the heat-labile SAP.

hME Reaction

A MassEXTEND primer is designed to anneal close to the polymorphic site, and is designed to identify both alleles of the polymorphic site. For SNP TSC0271628, a representative MassEXTEND primer is:

```
5' CTTTTTATGCCTTTCCACTCATCCA 3' (SEQ ID NO: 645)
```

The length of the MassEXTEND primer is designed according to the instructions provided by the makers of the MassARRAY Homogenous MassEXTEND Assay.

The MassEXTEND primer, DNA polymerase, and a cocktail mixture of deoxynucleotides (dNTPs) and dideoxynucleotides (ddNTPs) are added to the initial primer extension reaction. Allele-specific primer products are generated that are generally one to four bases longer than the original MassEXTEND primer.

A MASSEXTEND primer is hybridized closely adjacent to the polymorphic site following the conditions recommended by the makers of the MassARRAY Homogenous MassEXTEND Assay. Nucleotide mixtures are selected to maximize mass differences for all possible MassEXTEND products. Appropriate dNTPS are incorporated until a single ddNTP is incorporated, and the reaction is terminated. The manufacturer's protocols are followed for all steps of the hME assay.

Representative reaction products for SNP TSC0271628 are provided below:

<u>A allele Before Primer Extension</u>

```
                                          (SEQ ID NO: 646)
MassEXTEND primer:  CT TTTT ATGCCT T TCCACTCATCCA

                                          (SEQ ID NO: 647)
Sample DNA:         GAAAAATACGGAAAGGTGAGTAGGTTTCC
```

The SNP site is identified in bold. After incubation with DNA polymerase, ddATP, dCTP, dGTP, and dTTP, the following product is generated:

<u>A allele After Primer Extension</u>

```
                                          (SEQ ID NO: 648)
MassEXTEND primer:  CT TTTT ATGCCT T TCCACTCATCCAA*

                                          (SEQ ID NO: 649)
Sample DNA:         GAAAAATACGGAAAGGTGAGTAGGTTTCC
```

ddATP is incorporated into the primer. Either labeled or unlabeled ddNTPs can be used. The asterisk indicates ddATP that is unlabeled. After the incorporation reaction, a 24-mer primer is generated.

<u>G allele Before Primer Extension</u>

```
                                          (SEQ ID NO: 650)
MassEXTEND primer:  CT TTTT ATGCCT T TCCACTCATCCA

                                          (SEQ ID NO: 651)
Sample DNA:         GAAAAATACGGAAAGGTGAGTAGGTCTCC
```

The SNP site is identified in bold. After incubation with DNA polymerase, ddATP, dCTP, dGTP, and dTTP, the following product is generated:

G allele After Primer Extension

```
                                  (SEQ ID NO: 652)
MassEXTEND primer: CT TTTT ATGCCT T TCCACTCATCCAGA*
                                  (SEQ ID NO: 653)
Sample DNA:        GAAAAATACGGAAAGGTGAGTAGGTCTCC
```

After the incorporation reaction, a 25-mer primer is generated. The difference in molecular weight between the reaction product for the A allele (24-mer) and the reaction product for the G allele (25-mer) is used to genotype the locus of interest.

Sample Conditioning

SpectroCLEAN™ resin is added to the reaction to remove extraneous salts that interfere with MALDI-TOF analysis.

Sample Transfer 15 nl of sample is transferred from the 384-microtiter plate and spotted onto the pad of the 384 SpectroCHIP™ microarray.

Sample Analysis

The SpectroCHIP™ is placed into the MALDI-TOF, which measures the mass of the extension products. Once determined, the genotype is called in real-time with SpectroTYPER™ RT software. SNPs at which the maternal DNA are homozygous are identified, and analyzed with the DNA that is isolated from the plasma.

Analysis of DNA Isolated from Maternal Plasma

After the maternal DNA is analyzed and homozygous SNPs are identified, these SNPs are analyzed with the DNA isolated from the plasma. A low copy number of fetal genomes typically exists in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 μl of plasma template DNA is used.

Two microliters of each forward and reverse primer, at concentrations of 5 mM are pooled into a single microcentrifuge tube and mixed. Four microliters of the primer mix is used in a total PCR reaction volume of 50 μl (20 μl of template plasma DNA, 1 μl of sterile water, 4 μl of primer mix, and 25 μl of HotStar Taq. Twenty-five cycles of PCR are performed. The following PCR conditions are used:

(1) 95° C. for 15 minutes;
(2) 95° C. for 30 second;
(3) 4° C. for 30 seconds;
(4) 37° C. for 30 seconds;
(5) Repeat steps 2-4 twenty-four (24) times;
(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

Purification of Fragment of Interest

The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 μl of sterile water. 5 μl of each amplified loci is mixed together MassARRAY Homogenous MassEXTEND Assay The pooled DNA is assayed with the hME assay as described above. Each SNP is genotyped. SNPs located on chromosomes 13 and 21, wherein the maternal DNA is homozygous, and DNA isolated from the plasma is heterozygous are quantitated.

Quantification

The intensity of each peak, wherein each peak corresponds to a DNA fragment with a specific molecular weight, is quantitated. As discussed above, the expected ratio of allele 1 to allele 2 is used to determine the presence or absence of a chromosomal abnormality. If the maternal genome is homozygous at SNP X (A/A), and the plasma DNA is heterozygous at SNP X (A/G), then the G represents the distinct fetal signal.

There will be some fragments that differ in molecular due to the presence of the G nucleotide at SNP X in the fetal genome. The intensity of the peak with the A nucleotide is quantitated and the intensity of the peak that corresponds to fragments with the G nucleotide is quantitated. The ratio of G:A depends on the percentage of fetal DNA present in the maternal blood.

For example, if the sample contains 50% fetal DNA, then the expected ratio is 0.33 (1 fetal G allele/(2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

This example explained the use Sequenom's MassARRAY Homogenous MassEXTEND (hME) assay, but it not intended to limit the use of techniques that differentiate molecules based on molecular weight.

Example 21

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. In this example, SNPs are analyzed using Orchid's SNP-IT™ Assay. However, other SNP detection methods based on primer extension may also be used.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, $BM(PEO)_3$, $BM(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Isolation of DNA

DNA is isolated from the plasma sample using the Qiagen Midi Kit for purification of DNA from blood cells, following the manufacturer's instructions (QIAmp DNA Blood Midi Kit, Catalog number 51183). DNA is eluted in 100 μl of distilled water. The Qiagen Midi Kit also is used to isolate DNA from the maternal cells contained in the "buffy coat."

Identification of Homozygous Maternal SNPs

SNP-IT™ Assay

The SNP-IT Assay is based on a single base primer extension. Prior to the SNP-IT Assay, a PCR product that includes the SNP of interest is prepared, using one unmodified and one phosphorothiolate modified primer. The PCR product is then rendered single stranded using exonuclease, and the single stranded DNA is annealed to a SNP-IT oligonucleotide immobilized on the surface of a 96-well microtiter plate. Following hybridization, single base extension occurs by the addition of DNA polymerase and the labeled terminators. The incorporated base is detected using antibodies specific to the label followed by colorimetric detection. Data analysis can be done visually or with the use of the absorbance plate reader.

Primer Design

For each locus of interest, the SNP-IT™ Assay requires three primers. The primers are designed to produce an amplicon of 100-50 base pairs. The sequence of the SNP-IT primer, which is designed to anneal immediately upstream of the SNP site, is the best sequence available from between the upper and the lower strands. The sequence of the SNP-IT primer is designed to minimize hybridization to self and other sites in the amplicon. In addition, the SNP-IT primer may contain modified bases to prevent self-priming. The length of the primers is designed according to the makers of the SNP-IT Assay.

Representative primers for the amplification and genotyping of SNP TSC0069085, which is located on chromosome 21, are provided below:

```
Upstream Primer:
5' ATCACACTGGGGATC 3'          (SEQ ID NO: 654)

Downstream Primer:
5' CTAAACCTATGACTC 3'          (SEQ ID NO: 655)

SNP-IT primer
5' TTCACAGAGGATATCTTAATA 3'    (SEQ ID NO: 656)
```

The upstream primer is unmodified and the downstream primer is phosphorothiolate modified.

SNP-IT Plate Coating

SNP-IT primer is added to coat wells of empty 96-well plates. This reaction typically incubates overnight. The manufacturer's protocols and procedures are followed.

PCR

Template DNA (15 ng) is amplified either in a reaction vessel including but not limited to an eppendorf tube or a well of a microtiter plate. The manufacturer's protocols and procedures are followed for the PCR reaction.

Exonuclease

PCR product is treated with exonuclease to degrade the unmodified strand. The protected phosphorothiolate-labeled strand is used in the SNP-IT Assay. The manufacturer's protocols and procedures are followed for the exonuclease reaction.

Annealing

Single stranded PCR product is transferred to SNP-IT plate and is allowed to form a hybrid with the SNP-IT primer. The annealing reaction typically proceeds for one hour. The manufacturer's protocols and procedures are followed for the annealing reaction.

SNP-IT Reaction

The extension reagent, which contains DNA polymerase, two terminating nucleotides labeled with either fluorescein or biotin and two unlabeled terminators, is added to the SNP-IT well containing the annealed template and primer complex. For SNP TSC0069085, ddCTP is labeled with fluorescein and ddTTP is labeled with biotin, and the unlabeled terminators are ddATP, and ddGTP. The manufacturer's protocols and procedures are followed for the extension reaction.

The SNP specific base is incorporated by single base extension of the SNP-IT primer. Primers are washed manually or in a plate washer to remove unincorporated material. The manufacturer's protocols and procedures are followed for the washing reaction.

Detection

Anti-fluorescein labeled with alkaline phosphatase (AP) is added to the plate and allowed to bind to any incorporated fluorescein labeled terminator. The manufacturer's protocols and procedures for the labeling reaction are followed.

The plates are washed, and then color development is performed using pNPP as the detection substrate. The absorbance is read at 405 nm to detect yellow colored pNPP substrate followed by a washing step to remove pNPP detection reagents. The manufacturer's protocols and procedures are followed for color development and washing steps.

Streptavidin labeled with horse radish peroxidase (HRP) is added to the plate and allowed to bind to any incorporated biotin labeled terminator. The manufacturer's protocols and procedures are followed for the labeling reaction.

Following washing, color development is performed using TMB as the detection substrate. The absorbance is read at 620 nm to detect blue colored TMB substrate.

Analysis

Absorbance is plotted to generate a scather plot from which genotype calls are made. SNPs at which the maternal DNA is homozygous are identified, and analyzed with the DNA isolated from the maternal plasma.

Analysis of DNA Isolated from Maternal Plasma

After the maternal DNA is analyzed and homozygous SNPs are identified, these SNPs are analyzed with the DNA isolated from the plasma. A low copy number of fetal genomes typically exists in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 μl of plasma template DNA is used.

Two microliters of each forward and reverse primer, at concentrations of 5 mM are pooled into a single microcentrifuge tube and mixed. Four microliters of the primer mix is used in a total PCR reaction volume of 50 μl (20 μl of template plasma DNA, 1 μl of sterile water, 4 μl of primer mix, and 25 μl of HotStar Taq. Twenty-five cycles of PCR are performed. The following PCR conditions are used:

(1) 95° C. for 15 minutes;

(2) 95° C. for 30 second;

(3) 4° C. for 30 seconds;

(4) 37° C. for 30 seconds;

(5) Repeat steps 2-4 twenty-four (24) times;

(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

Purification of Fragment of Interest

The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 μl of sterile water. 5 μl of each amplified loci is mixed together SNP-IT Assay The pooled DNA is assayed with the SNP-IT assay as described above. Each SNP is genotyped. SNPs located on chromosomes 13 and 21, wherein the maternal DNA is homozygous, and DNA isolated from the plasma is heterozygous are quantitated.

Quantification

The fluorescence intensity of each allele is quantitated. As discussed above, the expected ratio of allele 1 to allele 2 is used to determine the presence or absence of a chromosomal abnormality. If the maternal genome is homozygous at SNP X (A/A), and the plasma DNA is heterozygous at SNP X (A/G), then the G represents the distinct fetal signal.

The intensity of the allele with the A nucleotide is quantitated and the intensity of the allele with the G nucleotide is quantitated. The ratio of G:A depends on the percentage of fetal DNA present in the maternal blood.

For example, if the sample contains 50% fetal DNA, then the expected ratio is 0.33 (1 fetal G allele/(2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

In this example, the terminator nucleotides are labeled with different chemical moieties. However, using the methods described in this application (see Example 6), the SNP-IT assay could be modified to allow detection of both alleles with a single labeled terminator.

This example explained the use of Orchid's SNP-IT assay, but it not intended to limit the use of other techniques that rely on primer extension. Orchid's SNPstream 25K, as well accompanying software including but not limited to GetGenos™, QCreview™, and ValidGenos™, can also be used to detect the presence of chromosomal abnormalities in the maternal blood. Additional information about these products can be found at:

http://www.orchidbio.com/products/lsg/products/snpstream.asp.

Example 22

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. In this example, SNPs are analyzed using the TaqMan® assay. However, other methods that rely on fluorogenic 5' nuclease assay can be used.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, BM$(PEO)_3$, BM$(PEO)_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

An agent that stabilizes cell membranes may be added to the maternal blood sample to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Isolation of DNA

DNA is isolated from the plasma sample using the Qiagen Midi Kit for purification of DNA from blood cells, following the manufacturer's instructions (QIAmp DNA Blood Midi Kit, Catalog number 51183). DNA is eluted in 100 μl of distilled water. The Qiagen Midi Kit also is used to isolate DNA from the maternal cells contained in the "buffy coat."

Identification of Homozygous Maternal SNPs

TaqMan Assay

PE Biosystems has two instruments in its Sequence Detection Systems product line, the ABI Prism® 7700 Sequence Detection System and the GeneAmp® 5700 Sequence Detection System. These real-time systems allegedly are capable of detecting PCR products as they accumulate during PCR and so enable the quantitation of DNA in the sample.

One chemistry available for use on the ABI PRISM® 7700 and GeneAmp® 5700 detection systems is the fluorogenic 5' nuclease assay, or the TaqMan® assay, which uses a fluorogenic probe to enable the detection of a specific PCR product as it accumulates during PCR. PE Biosystems' patented fluorogenic probe design that incorporates the reporter due on the 5' end and the quencher on the 3' end has assisted with the design of TaqMan probes.

The basis for PCR quantitation in the ABI 7700 instrument is to continuously measure PCR product accumulation using a dual-labeled flourogenic oligonucleotide probe called a TaqMan® probe, which is composed of a short (20-25 bases) oligodeoxynucleotide that is labeled with two different fluorescent dyes. On the 5' terminus is a reporter dye and on the 3' terminus is a quenching dye. This oligonucleotide probe sequence is homologous to an internal sequence present in the PCR amplicon. When the probe is intact, energy transfer occurs between the two fluorophors and emission from the reporter is quenched by the quencher (Livak et al., PCR Methods and Applications, 4:357-362, 1995a; U.S. Pat. Nos. 5,538,848; 5,723,591).

During the extension phase of PCR, the probe is cleaved by 5' nuclease activity of Taq polymerase thereby releasing the reporter from the oligonucleotide-quencher and producing an increase in reporter emission intensity. The ABI Prism 7700 uses fiber optic systems which connect to each well in a 96-well PCR tray format. The laser light source excites each well and a CCD camera measures the fluorescence spectrum and intensity from each well to generate real-time data during PCR amplification. The ABI 7700 Prism software examines the fluorescence intensity of reporter and quencher dyes and calculates the increase in normalized reporter emission intensity over the course of the amplification. The results are then plotted versus time, represented by cycle number, to produce a continuous measure of PCR amplification. To provide precise quantification of initial target in each PCR reaction, the amplification plot is examined at a point during the early log phase of product accumulation. This is accomplished by assigning a fluorescence threshold above background and determining the time point at which each sample's amplification plot reaches the threshold (defined as the threshold cycle number or CT). Differences in threshold cycle number are used to quantify the relative amount of PCR target contained within each tube as described previously.

For SNP analysis, a TaqMan probe can be designed for each allele of the SNP. The reporter emission is used to determine the presence or absence of each allele at the SNP. For example, for a SNP that can either be adenine or guanine, a TaqMan probe will be designed with a complementary nucleotide to the adenine and a separate TaqMan probe will be designed with a complementary nucleotide to the guanine. The two TaqMan probes can be used in separate reaction vessels, which allows the amount of the adenine allele and the amount of the guanine allele to be calculated.

Primer and Probe Design

Primer and probes can be designed using the Primer Express® software. The probe is designed first, and then the primers are designed as close as possible to the probe without overlapping it. Amplicons of 50-150 base pairs are strongly recommended.

The primer and probes should be designed following the manufacturer's recommendations. For both the primer and the probes, the G/C is in the range of 20-80%. The primer, and probes are designed to avoid runs of an identical nucleotide. This is especially true for guanine, where runs of four or more Gs should be avoided.

For the probe, the TM is about 68-70° C., and is designed so that there is no guanine on the 5' end. Also, the probe is designed so that there are more C than G bases.

For the primers, the TM is about 58-60° C., and the primers are designed so that the five nucleotides at the 3' end have no more than 2 G and/or C bases.

For example, representative primers and probes for SNP TSC0271628 (A/G), which is located on chromosome 21, are provided below:

Forward Primer ($T_M$ of 60° C.)
5' AGTCTTGTAATACGACAGTCTT 3' (SEQ ID NO: 657)

Reverse Primer ($T_M$ of 58° C.)
5' CCATATCAATCAGTACTCTTG 3' (SEQ ID NO: 658)

TaqMan Probe A allele ($T_M$ of 68° C.; bold indicates variable nucleotide at SNP)
5' CCTTTCCACTCATCCAAAGGTTG 3' (SEQ ID NO: 659)

TaqMan Probe G allele ($T_M$ of 70° C.; bold indicates variable nucleotide at SNP)
5' CCTTTCCACTCATCCAGAGGTTG 3' (SEQ ID NO: 660)

Information regarding the sequence surrounding SNPs is found at: http://www.snp.cshl.org. By independently varying forward and reverse primer concentrations, the concentrations that provide optimal assay conditions can be identified. Primer concentration ranges of 50 nM –900 nM are tested.

If the maternal DNA is homozygous for one allele, for example, adenine, then in the sample that contains the TaqMan probe specific for the guanine nucleotide, the reporter is not separated from the quencher because the TaqMan probe does not anneal to the template DNA. However, if the maternal DNA is homozygous, then the reporter will be separated from the quencher in both samples containing the TaqMan probe specific for the guanine allele and samples containing the TaqMan probe specific for the adenine allele.

Reagent Solution

The polymerase recommended for the TaqMan Assay is AmpliTaq Gold DNA polymerase. It is thought that the use of AmpliTaq Gold DNA polymerase reduces the amount of non-specific product formation. The incorporation of AmpErase® Uracil n-glycosylase (UNG) and dUTP provide protection against PCR carryover contamination. For PCR reactions, the TaqMan Universal PCR Master mix, which is a reagent designed to provide optimal performance for TaqMan assays, is recommended by the manufacturer.

The TaqMan reaction buffer contains 5.5 mM MgC12, 200 nM each of dATP, dCTP, dGTP, 400 nM dUTP, 0.5 U of uracyl DNA glycosylase, and 1.25 U of AmpliTaq gold.

Thermal Cycling Parameters

PCR amplification and detection for all primer-probe combinations are performed with the ABI 7700 Sequence Detection System. The recommended cycling parameters for the TaqMan assay are provided below:

1) 50° C. for 2 min;

2) 95° C. for 10 min;

3) 95° C. for 15 sec;

4) 60° C. for 1 min;

5) Repeat steps 3-4 for 40 cycles.

TaqMan Quantitation

External standards are generated from know quantities of DNA containing an adenine nucleotide at SNP TSC0271628 and a guanine nucleotide at SNP TSC0271628, spanning 6 orders of magnitude (from $5\times10^0$ to $5\times10^6$ copies). The detection threshold is set at 10 times the standard deviation of the mean baseline emission calculated for PCR cycles 3 to 15 (Stults et al., Applied and Environmental Microbiology, Vol. 67, No. 6, 2781-2789, 2001). Standard curves relating the threshold cycle to DNA concentrations are generated with the ABI Prism 7700 software (available from Perkin Elmer).

SNPs at which the maternal DNA is homozygous are identified, and are analyzed with the DNA isolated from the plasma sample.

Analysis of DNA Isolated from Maternal Plasma

After the maternal DNA is analyzed and homozygous SNPs are identified, these SNPs are analyzed with the DNA isolated from the plasma. A low copy number of fetal genomes typically exists in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 μl of plasma template DNA is used.

Two microliters of each forward and reverse primer, at concentrations of 5 mM are pooled into a single microcentrifuge tube and mixed. Four microliters of the primer mix is used in a total PCR reaction volume of 50 μl (20 μl of template plasma DNA, 1 μl of sterile water, 4 μl of primer mix, and 25 μl of HotStar Taq. Twenty-five cycles of PCR are performed. The following PCR conditions are used:

(1) 95° C. for 15 minutes;
(2) 95° C. for 30 second;
(3) 4° C. for 30 seconds;
(4) 37° C. for 30 seconds;
(5) Repeat steps 2-4 twenty-four (24) times;
(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

It is important to ensure that the region amplified contains annealing sequences for the oligonucleotide probes in the BeadArray. Upon purchase of the BeadArray service, each SNP and the primers used to analyze each SNP are identified. With this knowledge, the multiplex primers are designed to encompass annealing regions for the primers in the BeadArray.

Purification of Fragment of Interest

The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 μl of sterile water.

TaqMan Assay

The amplified DNA is assayed with the TaqMan assay as described above. Each SNP is genotyped. SNPs located on chromosomes 13 and 21, wherein the maternal DNA is homozygous, and DNA isolated from the plasma is heterozygous are quantitated.

Quantification

The fluorescent intensity of the TaqMan allele specific probe is quantitated. As discussed above, the expected ratio of allele 1 to allele 2 is used to determine the presence or absence of a chromosomal abnormality. If the maternal genome is homozygous at SNP X (A/A), and the plasma DNA is heterozygous at SNP X (A/G), then the G represents the distinct fetal signal.

The fluorescent intensity of the allele with the A nucleotide is quantitated and the intensity of the allele with the G nucleotide is quantitated. The ratio of G:A depends on the percentage of fetal DNA present in the maternal blood.

For example, if the sample contains 50% fetal DNA, then the expected ratio is 0.33 (1 fetal G allele/(2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

This example explained the use of the TaqMan assay, but it not intended to limit the use of other techniques that employ 5' nuclease activity. For example, the SYBR® Green I double stranded dye can also be used with the ABI PRISM 7700 Sequence Detection System and the GeneAmp® 5700 Sequence Detection system for determining the sequence of maternal and fetal DNA. The SYBR® Green I double stranded dye assay may be used to detect the presence of fetal chromosomal abnormalities in the maternal blood.

SYBR® Green I double stranded dye is a highly specific double-stranded DNA binding dye that allows the detection of product accumulation during PCR. However, the SYBR® Green I double stranded dye assay detects all double stranded DNA including non-specific reaction products. The advantage of the SYBR® Green I double stranded dye assay is that it does not require a probe.

The same primers design parameters are recommended for both the TaqMan Assay and the SYBR® Green I double stranded dye assay (see Primer Design section in Example 21). The primer optimization parameters recommended for the TaqMan assay should also be followed for the SYBR® Green I double stranded dye assay. In addition, no template controls should also be run with the various concentrations of primers.

Furthermore, Applied Biosystems sell other products that may be used to determine the sequence of maternal and fetal DNA including but not limited to Assays-on-Demand™ SNP genotyping products, and Assasys-by-Designs™ Service SNP genotyping products.

Having now fully described the invention, it will be understood by those of skill in the art that the invention can be performed with a wide and equivalent range of conditions, parameters, and the like, without affecting the spirit or scope of the invention or any embodiment thereof.

All documents, e.g., scientific publications, patents and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

Example 23

Fetal chromosomal abnormalities are determined by analyzing SNPs wherein the maternal template DNA is homozygous and the template DNA obtained from the plasma is heterozygous. Plasma that is isolated from blood of a pregnant female contains both maternal template DNA and fetal template DNA. Any number of SNP detection methods can be used to analyze the maternal and plasma DNA. In this example, SNPs are analyzed by ThirdWave Technologies' Invader™ Assay for Nucleic Acid Detection. However, other techniques that exploit and quantitate biological structures formed in the presence of the correct sequence can be used.

Collection of Blood Samples

In accordance with an IRB approved study, blood samples are collected from pregnant women after informed consent is granted. Blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Any number of agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, AEDP, APG, BASED, BM(PEO)$_3$, BM(PEO)$_4$, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, Sulfo-EGS or compounds listed in Table XXIII. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

An agent that stabilizes cell membranes may be added to the maternal blood samples to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenytoin, zinc citrate, mexitil, dilantin, sodium hyaluronate, or polaxamer 188.

Isolation of Plasma and Maternal Cells

The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Isolation of DNA

DNA is isolated from the plasma sample using the Qiagen Midi Kit for purification of DNA from blood cells, following the manufacturer's instructions (QIAmp DNA Blood Midi Kit, Catalog number 51183). DNA is eluted in 100 μl of distilled water. The Qiagen Midi Kit also is used to isolate DNA from the maternal cells contained in the "buffy coat."

Identification of Homozygous Maternal SNPs

ThirdWave Technologies Invader™ Assay

The Invader™ Assay, which was developed by Third Wave Technologies (Madison, Wis.), is an isothermal, "PCR-free" approach to the detection and quantitative analysis of DNA. The Invader Assay produces and amplifies an unrelated signal only in the presence of the correct target sequence. The Invader™ Assay relies on a thermostable member of the structure-specific archeabacterial flap endonuclease (FEN) family, which cleaves nucleic acid molecules at specific sites based on structure rather than sequence. When uses with structure forming probes for known sequences, the enzymes cleave in a structure and target sequence-specific manner. The nucleases used with Third Wave Technologies' assays are referred to as "Cleavase®" enzymes.

The Invader™ Assay uses two target-specific oligonucleotides to create the substrate complex recognized by Cleavase Enzymes (L. DeFrancesco, The Scientist, 12(21):16, 1998). The substrate complex is formed when an upstream Invader oligo and a downstream signal probe hybridize in tandem to the nucleic acid. The 3' end of the Invader oligo must overlap the hybridization site of the signal probe by at least one base (Harrington et al., Genes and Development, 8:1344-55, 1994). The 5' end of the signal probe has additional unpaired bases to form a 5' flap. Cleavase enzymes cleave the signal probe where it overlaps the Invader oligo, releasing the 5' arm. Reaction mixtures contain excess signal probe and are carried out near the melting temperature of the probe. Many signal probes can be cleaved for each copy of the target without temperature cycling.

The overlap between the Invader oligo and the signal probe is important. A mismatch positioned at the site of the overlap will block the cleavage by disrupting the overlap, which may allow discrimination of SNPs and mutations.

The Invader assay utilizes two sequential cleavage steps. The 5' arm of the signal probe released in the first reaction is not detected directly. Rather, a secondary cleavage product is the actual source of the signal, detected by fluorescence resonance energy transfer (FRET). The primary cleavage product, which is the 5' arm released in the first reaction, is used as an Invader oligo that hybridizes to a supplied FRET probe in the secondary reaction. The FRET probe is labeled with two dyes: a donor fluorophore and a quenching acceptor fluorophore. When the nuclease cleaves the secondary probe, the two fluorophores are separated, quenching is eliminated, and the enhanced fluorescence signal from the donor dye is detected.

Probe Design

The following probes are designed to determine the sequence at SNP TSC1172576 (T/A), which is located on chromosome 13:

```
Invader Oligo for T allele:
5' CATGCAGATATACCGCATAT 3'     (SEQ ID NO: 661)

Invader Oligo for A allele:
5' CATGCAGATATACCGCATAA 3'     (SEQ ID NO: 662)
```

Invader oligonucleotides are designed to be complementary to an 18-22 base region immediately upstream of the signal probe, with an additional one base at the 3' end that "invades" the region hybridized to the signal probe by one base.

```
Signal probe for T allele:
GGTAGCATCTCTCAGCACAAGAG         (SEQ ID NO: 663)

Signal probe for A allele:
GGTAGCATCACTCAGCACAAGAG         (SEQ ID NO: 664)
```

The signal probes are designed to contain a 3' region that is complementary to the target sequence and a non-complementary 5' arm (the underlined sequence above) that is used for detection. The signal probes are labeled on the 5' end with 6-carboxyfluorescein (TET), hexachloro-6-carboxyfluorescein (HEX), 6-carboxyfluorescein (FAM). However, the 5' end can be labeled with any chemical moiety including but not limited to radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, and combinations thereof Both invader and signal probes are complementary to either the sense or the antisense target DNA strand, depending on which results in the formation of the least number of predictable secondary structures.

PCR Amplification

A fragment of DNA that surrounds SNP TSC1172576 is amplified by PCR. The sequence of the upstream and downstream primers is provided below:

```
Upstream Primer:
5' TAGCAGAATCTCTCAT 3'       (SEQ ID NO: 665)

Downstream Primer:
5' AGAGTATCTCATTTGTT 3'      (SEQ ID NO: 666)
```

Amplification reactions are performed in a final volume of 100 μl of containing 2 μl of genomic DNA, 35 pmol of each primer, 50 μm of each deoxynucleotide (Perkin-Elmer Applied Biosystems, Inc., Foster City, Calif.), 1×PCR buffer (20 mM Tris-Hcl, 50 mM KCl, 1.5 mM $MgCl_2$, 0.05% Tween-20, 0.05% NP40), 1 M betaine, 5% dimethylsulfoxide (DMSO), and 2.5 U of Taq polymerase (Roche Boehringer Mannheim, Indianapolis, Ind.). PCR cycling conditions consist of an initial denaturation step at 95° C. for 5 min, 30 cycles of denaturation at 95° C. for 1 min, annealing at 68° C. for 1 min, and extension at 72° C. for 1 min, and a final extension at 72° C. for 5 min.

Invader Reaction

One microliter of each PCR product is added to 0.5 pmol of the appropriate Invader oligonucleotide, 10 ng human genomic DNA (Promega Corp., Madison, Wis.) as the carrier, and mopholinepropanesulfonic acid (MOPS) buffer (pH 8.0) at a final concentration of 10 mM in a volume of 7 μl. The mixtures are denatured for 5 min at 95° C. and then cooled to reaction temperature of 60° C. Invader reactions are inititated by the addition of a mixture containing 30 ng of Cleavase VIII (Third Wave Technologies, Inc., Madison, Wis.) 25 mM $MgCl_2$, and 10 pmol of the appropriate signal probe oligonucleotide in a volume of 3 μl. Reaction mixtures are incubated for 60 min. The reactions are terminated by the addition of 10 μl of 95% formamide −10 mM EDTA (pH 8.0)−0.05% crystal violet. Following termination, the reactions are diluted 1:10 in reagent-grade water. Samples of 2 μl are loaded and electrophoresed in a 24% denaturing polyacrylamide gel (18 cm by 25.5 cm by mm) on an automated fluorescence sequencing apparatus (model 377, PE-ABI). The data are collected using filter set C and processed with GeneScan software.

In addition, 5 μl of each sample is electrophoresed in 20% (acrylamide to bisacrylamide, 19:1) denaturing polyacrylamide gels at 20 W. Gel cassettes (20 cm by 20 cm by 0.5 mM) are scanned with a fluorescent scanner (FMBIO-100; Hitachi Corp, San Bruno, Calif.) by using a 585 nm filter for TET and HEX labeled probes and a 505 nm filter for FAM labeled probes.

With the Invader assay, it is also possible to perform a second cleavage reaction where the released 5' arm of the signal probe is hybridized to another probe, and fluorescence resonance energy transfer (FRET) is used to detect the presence of a specific nucleic acid. The manufacturer's protocols are followed when using the FRET probe.

The genotype at each SNP is determined by analyzing the fluorescence intensity of each allele-specific signal probe. For example, for SNP TSC1172576, the presence of the T allele is determined by analyzing the amount of released 5' signal probe using the signal probe from the T allele signal probe (as described above). Likewise, the presence of the A allele is determined by analyzing the amount of released 5' signal probe from the A allele signal probe. The reactions can be performed in a single reaction vessel using two different chemical moieties, which can be analyzed under distinct conditions, or the A and T allele reactions can be performed in two different reaction vessels.

Analysis of DNA Isolated from Maternal Plasma

After the maternal DNA is analyzed and homozygous SNPs are identified, these SNPs are analyzed with the DNA isolated from the plasma. A low copy number of fetal genomes typically exist in the maternal plasma. To increase the copy number of the loci of interest, which are the SNPs at which the maternal DNA is homozygous, primers are designed to anneal at approximately 130 bases upstream and 130 bases downstream of each loci of interest. This is done to reduce statistical sampling error that can occur when working with a low number of genomes, which can influence the ratio of one allele to another (see Example 11).

Design of Multiplex Primers

The primers are 12 bases in length. However, primers of any length can be used including but not limited to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31,32, 33, 34, 35, 36-45, 46-55, 56-65, 66-75, 76-85, 86-95, 96-105, 106-115, 116-125, and greater than 125 bases. Primers are designed to anneal to both the sense strand and the antisense strand.

The maternal homozygous SNPs vary from sample to sample so defined sequences are not provided here. Primers are designed to anneal about 130 bases upstream and downstream of the maternal homozygous SNPs. The primers are designed to terminate at the 3' end in the dinucleotide "AA" to reduce the formation of primer-dimers. However, the primers can be designed to end in any of the four nucleotides and in any combination of the four nucleotides.

Multiplex PCR

Regions upstream and downstream of the maternal homozygous SNPs are amplified from the template genomic DNA using the polymerase chain reaction (PCR, U.S. Pat. Nos. 4,683,195 and 4,683,202, incorporated herein by reference). This PCR reaction uses primers that anneal approximately 130 bases upstream and downstream of each loci of interest. The primers are mixed together and are used in a single reaction to amplify the template DNA. This reaction is done to increase the number of copies of the loci of interest, which eliminates error generated from a low number of genomes.

For increased specificity, a "hot-start" PCR reaction is used. PCR reactions are performed using the HotStarTaq Master Mix Kit supplied by QIAGEN (catalog number 203443). The amount of template DNA and primer per reaction is optimized for each locus of interest. In this example, the 20 μl of plasma template DNA is used.

Two microliters of each forward and reverse primer, at concentrations of 5 mM are pooled into a single microcentrifuge tube and mixed. Four microliters of the primer mix is used in a total PCR reaction volume of 50 μl (20 μl of template plasma DNA, 1 μl of sterile water, 4 μl of primer mix, and 25 μl of HotStar Taq. Twenty-five cycles of PCR are performed. The following PCR conditions are used:

(1) 95° C. for 15 minutes;

(2) 95° C. for 30 second;

(3) 4° C. for 30 seconds;

(4) 37° C. for 30 seconds;

(5) Repeat steps 2-4 twenty-four (24) times;

(6) 72° C. for 10 minutes.

The temperatures and times for denaturing, annealing, and extension, are optimized by trying various settings and using the parameters that yield the best results.

Other methods of genomic amplification can also be used to increase the copy number of the loci of interest including but not limited to primer extension preamplification (PEP) (Zhang et al., PNAS, 89:5847-51, 1992), degenerate oligonucleotide primed PCR (DOP-PCR) (Telenius, et al., Genomics 13:718-25, 1992), strand displacement amplification using DNA polymerase from bacteriophage 29, which undergoes rolling circle replication (Dean et al., Genomic Research 11:1095-99, 2001), multiple displacement amplification (U.S. Pat. No. 6,124,120), REPLI-g™ Whole Genome Amplification kits, and Tagged PCR.

It is important to ensure that the region amplified contains annealing sequences for the oligonucleotide probes in the BeadArray. Upon purchase of the BeadArray service, each SNP and the primers used to analyze each SNP are identified. With this knowledge, the multiplex primers are designed to encompass annealing regions for the primers in the BeadArray.

Purification of Fragment of Interest

The unused primers, and nucleotides are removed from the reaction by using Qiagen MinElute PCR purification kits (Qiagen, Catalog Number 28004). The reactions are performed following the manufacturer's instructions supplied with the columns. The DNA is eluted in 100 μl of sterile water.

Invader Assay

The amplified DNA is assayed with the Invader assay as described above. Each SNP is genotyped. SNPs located on chromosomes 13 and 21, wherein the maternal DNA is homozygous, and DNA isolated from the plasma is heterozygous are quantitated.

Quantification

The fluorescent intensity of the allele specific signal probe is quantitated. As discussed above, the expected ratio of allele 1 to allele 2 is used to determine the presence or absence of a chromosomal abnormality. If the maternal genome is homozygous at SNP X (A/A), and the plasma DNA is heterozygous at SNP X (A/G), then the G represents the distinct fetal signal.

The fluorescent intensity of the allele with the A nucleotide is quantitated and the intensity of the allele with the G nucleotide is quantitated. The ratio of G:A depends on the percentage of fetal DNA present in the maternal blood.

For example, if the sample contains 50% fetal DNA, then the expected ratio is 0.33 (1 fetal G allele/ (2 maternal A alleles+1 fetal A allele)). This ratio should be constant for all chromosomes that are present in two copies. The ratio that is obtained for SNPs on chromosome 13 should be the same as the ratio that is obtained for chromosome 21.

However, if the fetal genome contains an additional copy of chromosome 21, then the ratio for this chromosome will deviate from the expected ratio. The expected ratio for a Trisomy condition with 50% fetal DNA in the maternal blood is 0.25. Thus, by analyzing SNPs wherein the maternal genome is homozygous, and the DNA that is isolated from the plasma is heterozygous, fetal chromosomal abnormalities can be detected.

What is claimed is:

1. A composition comprising total free genomic DNA that comprises free fetal genomic DNA and free maternal genomic DNA, wherein the percentage of free fetal genomic DNA in the total free genomic DNA of the composition is selected from the group consisting of: about 24-25% free fetal genomic DNA, about 25-35% free fetal genomic DNA, about 35-45% free fetal genomic DNA, about 45-55% free fetal genomic DNA, about 55-65% free fetal genomic DNA, about 65-75% free fetal genomic DNA, about 75-85% free fetal genomic DNA, about 85-90% free fetal genomic DNA, about 90-91% free fetal genomic DNA, about 91-92% free fetal genomic DNA, about 92-93% free fetal genomic DNA, about 93-94% free fetal genomic DNA, about 94-95% free fetal genomic DNA, about 95-96% free fetal genomic DNA, about 96-97% free fetal genomic DNA, about 97-98% free fetal genomic DNA, about 98-99% free fetal genomic DNA, and about 99-99.7% free fetal genomic DNA, and further wherein said composition is obtained from a sample from a pregnant female.

2. A composition comprising total free genomic DNA that comprises free fetal genomic DNA and free maternal genomic DNA, wherein the percentage of free fetal genomic DNA in the total free genomic DNA of the composition is selected from the group consisting of: about 24-25% free fetal genomic DNA, about 25-35% free fetal genomic DNA, about 35-45% free fetal genomic DNA, about 45-55% free fetal genomic DNA, about 55-65% free fetal genomic DNA, about 65-75% free fetal genomic DNA, about 75-85% free fetal genomic DNA, about 85-90% free fetal genomic DNA, about 90-91% free fetal genomic DNA, about 91-92% free fetal genomic DNA, about 92-93% free fetal genomic DNA, about 93-94% free fetal genomic DNA, and about 94-95% free fetal genomic DNA, and further wherein said composition is obtained from a sample from a pregnant female.

3. A prenatal diagnostic method comprising analyzing a composition comprising total free genomic DNA that comprises free fetal genomic DNA and free maternal genomic DNA, wherein the percentage of free fetal genomic DNA in the total free genomic DNA of the composition is selected from the group consisting of: about 24-25% free fetal genomic DNA, about 25-35% free fetal genomic DNA, about 35-45% free fetal genomic DNA, about 45-55% free fetal genomic DNA, about 55-65% free fetal genomic DNA, about 65-75% free fetal genomic DNA, about 75-85% free fetal genomic DNA, about 85-90% free fetal genomic DNA, about 90-91% free fetal genomic DNA, about 91-92% free fetal genomic DNA, about 92-93% free fetal genomic DNA, about 93-94% free fetal genomic DNA, and about 94-95% free fetal genomic DNA, and further wherein said composition is obtained from a sample from a pregnant female.

4. The composition of claim 1, wherein said pregnant female is human.

5. The composition of claim 4, wherein the composition is obtained from blood from said pregnant female.

6. The composition of claim 5, wherein the composition is obtained from serum of said blood.

7. The composition of claim 5, wherein the composition is obtained from plasma of said blood.

8. The composition of claim 1, wherein the percentage of free fetal genomic DNA in the total free genomic DNA of the composition is about 25-35% free fetal genomic DNA.

9. The composition of claim 1, wherein the percentage of free fetal genomic DNA in the total free genomic DNA of the composition is about 35-45% free fetal genomic DNA.

10. The composition of claim 1, wherein the percentage of free fetal genomic DNA in the total free genomic DNA of the composition is about 45-55% free fetal genomic DNA.

11. The composition of claim 1, wherein the percentage of free fetal genomic DNA in the total free genomic DNA of the composition is about 55-65% free fetal genomic DNA.

12. The composition of claim 1, wherein the percentage of free fetal genomic DNA in the total free genomic DNA of the composition is about 65-75% free fetal genomic DNA.

13. The composition of claim 1, wherein the percentage of free fetal genomic DNA in the total free genomic DNA of the composition is about 75-85% free fetal genomic DNA.

14. The composition of claim 1, wherein the percentage of free fetal genomic DNA in the total free genomic DNA of the composition is about 85-90% free fetal genomic DNA.

* * * * *

SEQUENCE LISTING

<160> NUMBER OF SEQ ID NOS: 725

<210> SEQ ID NO 1
<211> LENGTH: 15
<212> TYPE: DNA
<213> ORGANISM: Unknown
<220> FEATURE:
<223> OTHER INFORMATION: Restriction site
<220> FEATURE:
<221> NAME/KEY: misc_feature
<222> LOCATION: (6)...(15)
<223> OTHER INFORMATION: n = A,T,C or G

<400> SEQUENCE: 1
gggacnnnnn nnnnn 15

<210> SEQ ID NO 2
<211> LENGTH: 19
<212> TYPE: DNA
<213> ORGANISM: Unknown
<220> FEATURE:
<223> OTHER INFORMATION: Restriction site
<220> FEATURE:
<221> NAME/KEY: misc_feature
<222> LOCATION: (1)...(14)
<223> OTHER INFORMATION: n = A,T,C or G

<400> SEQUENCE: 2
nnnnnnnnnn nnnngtccc 19

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ggaaattcca tgatgcgtgg g 21

<210> SEQ ID NO 4
<211> LENGTH: 23
<212> TYPE: DNA
<213> ORGANISM: Homo sapiens
<220> FEATURE:
<221> NAME/KEY: misc_feature
<222> LOCATION: (19)...(21)
<223> OTHER INFORMATION: n = A,T,C or G

<400> SEQUENCE: 4
ggaaattcca tgatgcctnn nac 23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ggaaattcca tgatgcgtac c 21

-continued

<210> SEQ ID NO 6
<211> LENGTH: 25
<212> TYPE: DNA
<213> ORGANISM: Homo sapiens
<220> FEATURE:
<221> NAME/KEY: misc_feature
<222> LOCATION: (22)...(23)
<223> OTHER INFORMATION: n = A,T,C or G

<400> SEQUENCE: 6
ggaaattcca tgatgcctac cnngg 25

<210> SEQ ID NO 7
<211> LENGTH: 11
<212> TYPE: DNA
<213> ORGANISM: Unknown
<220> FEATURE:
<223> OTHER INFORMATION: Restriction site
<220> FEATURE:
<221> NAME/KEY: misc_feature
<222> LOCATION: (4)...(8)
<223> OTHER INFORMATION: n = A,T,C or G

<400> SEQUENCE: 7
cctnnnnnag g 11

<210> SEQ ID NO 8
<211> LENGTH: 25
<212> TYPE: DNA
<213> ORGANISM: Homo sapiens
<220> FEATURE:
<221> NAME/KEY: misc_feature
<222> LOCATION: (20)...(23)
<223> OTHER INFORMATION: n = A,T,C or G

<400> SEQUENCE: 8
ggaaattcca tgatgcctan nnngg 25

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
tagaatagca ctgaattcag gaatacaatc attgtcac 38

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
atcacgataa acggccaaac tcaggtta 28

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11

-continued aagtttagat cagaattcgt gaaagcagaa gttgtctg 38

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
tctccaacta acggctcatc gagtaaag 28

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
atgactagct atgaattcgt tcaaggtaga aaatggaa 38

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
gagaattaga acggcccaaa tcccactc 28

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
ttacaatgca tgaattcatc ttggtctctc aaagtgc 37

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
tggaccataa acggccaaaa actgtaag 28

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
ataaccgtat gcgaattcta taattttcct gataaagg 38

<210> SEQ ID NO 18
<211> LENGTH: 28
<212> TYPE: DNA
<213> ORGANISM: Artificial Sequence -continued
<220> FEATURE:
<223> OTHER INFORMATION: Primer

<400> SEQUENCE: 18
cttaaatcag gggactaggt aaacttca 28

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
cttaaatcag acggctaggt aaacttca 28

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
tctccaacta gggactcatc gagtaaag 28

<210> SEQ ID NO 21
<211> LENGTH: 37
<212> TYPE: DNA
<213> ORGANISM: Artificial Sequence
<220> FEATURE:
<223> OTHER INFORMATION: Primer

<400> SEQUENCE: 21
aacgccgggc gagaattcag tttttcaact tgcaagg 37

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
ctacacatat ctgggacgtt ggccatcc 28

<210> SEQ ID NO 23
<211> LENGTH: 38
<212> TYPE: DNA
<213> ORGANISM: Artificial Sequence
<220> FEATURE:
<223> OTHER INFORMATION: Primer

<400> SEQUENCE: 23
taccttttga tcgaattcaa ggccaaaaat attaagtt 38

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
tcgaacttta acggccttag agtagaga 28

-continued

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
cgatttcgat aagaattcaa aagcagttct tagttcag 38

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
tgcgaatctt acggctgcat cacattca 28

<210> SEQ ID NO 27
<211> LENGTH: 23
<212> TYPE: DNA
<213> ORGANISM: Homo sapiens
<220> FEATURE:
<221> NAME/KEY: misc_feature
<222> LOCATION: (3)...(5)
<223> OTHER INFORMATION: n = A,T,C or G

<400> SEQUENCE: 27
gtnnnacgca tcatggaatt tcc 23

<210> SEQ ID NO 28
<211> LENGTH: 25
<212> TYPE: DNA
<213> ORGANISM: Homo sapiens
<220> FEATURE:
<221> NAME/KEY: misc_feature
<222> LOCATION: (3)...(4)
<223> OTHER INFORMATION: n = A,T,C or G

<400> SEQUENCE: 28
ccnnggtacg catcatggaa tttcc 25

<210> SEQ ID NO 29
<211> LENGTH: 25
<212> TYPE: DNA
<213> ORGANISM: Homo sapiens
<220> FEATURE:
<221> NAME/KEY: misc_feature
<222> LOCATION: (3)...(6)
<223> OTHER INFORMATION: n = A,T,C or G

<400> SEQUENCE: 29
ccnnnntacg catcatggaa tttcc 25

<210> SEQ ID NO 30
<211> LENGTH: 38
<212> TYPE: DNA
<213> ORGANISM: Artificial Sequence
<220> FEATURE:
<223> OTHER INFORMATION: Primer

<400> SEQUENCE: 30
gggctagtct ccgaattcca cctatcctac caaatgtc 38

-continued

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
tagctgtagt tagggactgt tctgagcac 29

<210> SEQ ID NO 32
<211> LENGTH: 38
<212> TYPE: DNA
<213> ORGANISM: Artificial Sequence
<220> FEATURE:
<223> OTHER INFORMATION: Primer

<400> SEQUENCE: 32
cgaatgcaag gcgaattcgt tagtaataac acagtgca 38

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
aagactggat ccgggaccat gtagaatac 29

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34
tctaaccatt gcgaattcag ggcaaggggg gtgagatc 38

<210> SEQ ID NO 35
<211> LENGTH: 29
<212> TYPE: DNA
<213> ORGANISM: Artificial Sequence
<220> FEATURE:
<223> OTHER INFORMATION: Primer

<400> SEQUENCE: 35
tgacttggat ccgggacaac gactcatcc 29

<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36
acccaggcgc cagaattctt tagataaagc tgaaggga 38

<210> SEQ ID NO 37
<211> LENGTH: 29
<212> TYPE: DNA
<213> ORGANISM: Artificial Sequence
<220> FEATURE:
<223> OTHER INFORMATION: Primer -continued

<400> SEQUENCE: 37
gttacgggat ccgggactcc atattgatc 29

<210> SEQ ID NO 38
<211> LENGTH: 38
<212> TYPE: DNA
<213> ORGANISM: Artificial Sequence
<220> FEATURE:
<223> OTHER INFORMATION: Primer

<400> SEQUENCE: 38
cgttggcttg aggaattcga ccaaaagagc caagagaa 38

<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39
aaaaagggat ccgggacctt gactaggac 29

<210> SEQ ID NO 40
<211> LENGTH: 38
<212> TYPE: DNA
<213> ORGANISM: Artificial Sequence
<220> FEATURE:
<223> OTHER INFORMATION: Primer

<400> SEQUENCE: 40
acttgattcc gtgaattcgt tatcaataaa tcttacat 38

<210> SEQ ID NO 41
<211> LENGTH: 29
<212> TYPE: DNA
<213> ORGANISM: Artificial Sequence
<220> FEATURE:
<223> OTHER INFORMATION: Primer

<400> SEQUENCE: 41
caagttggat ccgggaccca gggctaacc 29

<210> SEQ ID NO 42
<211> LENGTH: 38
<212> TYPE: DNA
<213> ORGANISM: Artificial Sequence
<220> FEATURE:
<223> OTHER INFORMATION: Primer

<400> SEQUENCE: 42
gtgcaaaggc ctgaattccc aggcacaaag ctgttgaa 38

<210> SEQ ID NO 43
<211> LENGTH: 29
<212> TYPE: DNA
<213> ORGANISM: Artificial Sequence
<220> FEATURE:
<223> OTHER INFORMATION: Primer

<400> SEQUENCE: 43
tgaagcgaac tagggactca ggtggactt 29

<210> SEQ ID NO 44
<211> LENGTH: 38

-continued

<212> TYPE: DNA
<213> ORGANISM: Artificial Sequence
<220> FEATURE:
<223> OTHER INFORMATION: Primer

<400> SEQUENCE: 44
gattccgtaa acgaattcag ttcattatca tctttgtc 38

<210> SEQ ID NO 45
<211> LENGTH: 29
<212> TYPE: DNA
<213> ORGANISM: Artificial Sequence
<220> FEATURE:
<223> OTHER INFORMATION: Primer

<400> SEQUENCE: 45
ccattgttaa gcgggacttc tgctatttg 29

<210> SEQ ID NO 46
<211> LENGTH: 17
<212> TYPE: DNA
<213> ORGANISM: Homo sapiens

<400> SEQUENCE: 46
cccaaaagtc cacctga 17

<210> SEQ ID NO 47
<211> LENGTH: 17
<212> TYPE: DNA
<213> ORGANISM: Homo sapiens

<400> SEQUENCE: 47
tcaggtggac ttttggg 17

<210> SEQ ID NO 48
<211> LENGTH: 18
<212> TYPE: DNA
<213> ORGANISM: Homo sapiens

<400> SEQUENCE: 48
accctgcaaa tagcagaa 18

<210> SEQ ID NO 49
<211> LENGTH: 18
<212> TYPE: DNA
<213> ORGANISM: Homo sapiens

<400> SEQUENCE: 49
ttctgctatt tgcagggt 18

<210> SEQ ID NO 50
<211> LENGTH: 17
<212> TYPE: DNA
<213> ORGANISM: Homo sapiens

<400> SEQUENCE: 50
acccgcaaat agcagaa 17

<210> SEQ ID NO 51
<211> LENGTH: 17
<212> TYPE: DNA
<213> ORGANISM: Homo sapiens

<400> SEQUENCE: 51

-continued ttctgctatt tgcgggt 17

<210> SEQ ID NO 52
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 52
ttagatagca gtaattt 17

<210> SEQ ID NO 53
<211> LENGTH: 23
<212> TYPE: DNA
<213> ORGANISM: Homo sapiens
<220> FEATURE:
<221> NAME/KEY: misc_feature
<222> LOCATION: (6)...(13)
<223> OTHER INFORMATION: These nucleotides may be absent

<400> SEQUENCE: 53
ggaagccggg aaggatctgt atc 23

<210> SEQ ID NO 54
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 54
gagaaagaga ggtaa 15

<210> SEQ ID NO 55
<211> LENGTH: 19
<212> TYPE: DNA
<213> ORGANISM: Homo sapiens
<220> FEATURE:
<221> NAME/KEY: misc_feature
<222> LOCATION: (6)...(8)
<223> OTHER INFORMATION: These nucleotides may be absent
<220> FEATURE:
<221> NAME/KEY: misc_feature
<222> LOCATION: (10)...(19)
<223> OTHER INFORMATION: These nucleotides may be absent

<400> SEQUENCE: 55
aaagagaggt aacttttct 19

<210> SEQ ID NO 56
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 56
aaagagaggt aactttc 18

<210> SEQ ID NO 57
<211> LENGTH: 23

-continued

<212> TYPE: DNA
<213> ORGANISM: Homo sapiens
<220> FEATURE:
<221> NAME/KEY: misc_feature
<222> LOCATION: 11
<223> OTHER INFORMATION: This nucleotide may be absent

<400> SEQUENCE: 57
ttttaaaaaa aaaaaatagg tca 23

<210> SEQ ID NO 58
<211> LENGTH: 22
<212> TYPE: DNA
<213> ORGANISM: Homo sapiens
<220> FEATURE:
<221> NAME/KEY: misc_feature
<222> LOCATION: (11)...(12)
<223> OTHER INFORMATION: These nucleotides may be absent

<400> SEQUENCE: 58
aaaataggtc attgcttctt gc 22

<210> SEQ ID NO 59
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 59
gacaaagaag aaaagg 16

<210> SEQ ID NO 60
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 60
gacaaagaag aaaaggaaa 19

<210> SEQ ID NO 61
<211> LENGTH: 25
<212> TYPE: DNA
<213> ORGANISM: Homo sapiens
<220> FEATURE:
<221> NAME/KEY: misc_feature
<222> LOCATION: (11)...(15)
<223> OTHER INFORMATION: These nucleotides may be absent

<400> SEQUENCE: 61
aggaaaaaga ctggtattac gctca 25

<210> SEQ ID NO 62
<211> LENGTH: 24
<212> TYPE: DNA
<213> ORGANISM: Homo sapiens
<220> FEATURE:
<221> NAME/KEY: misc_feature
<222> LOCATION: (11)...(14)
<223> OTHER INFORMATION: These nucleotides may be absent

<400> SEQUENCE: 62

-continued

```
aaaagaatag atagtcttcc ttta                                              24


<210> SEQ ID NO 63
<211> LENGTH: 21
<212> TYPE: DNA
<213> ORGANISM: Homo sapiens
<220> FEATURE:
<221> NAME/KEY: misc_feature
<222> LOCATION: 11
<223> OTHER INFORMATION: This nucleotide may be absent

<400> SEQUENCE: 63

agatagtctt cctttaactg a                                                 21


<210> SEQ ID NO 64
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 64

tccttacaaa cagatatga                                                    19


<210> SEQ ID NO 65
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 65

accagaaggc aatt                                                         14


<210> SEQ ID NO 66
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 66

atcagagttg cgatgga                                                      17


<210> SEQ ID NO 67
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 67

cgagcacagg taagtt                                                       16


<210> SEQ ID NO 68
<211> LENGTH: 15
<212> TYPE: DNA
<213> ORGANISM: Homo sapiens
<220> FEATURE:
<221> NAME/KEY: misc_feature
```

-continued

<222> LOCATION: (4)...(5)
<223> OTHER INFORMATION: These nucleotides may be absent

<400> SEQUENCE: 68
cactctgcac ctcga 15

<210> SEQ ID NO 69
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 69
gatatgtcgc gaac 14

<210> SEQ ID NO 70
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 70
aaagactctg tattgtt 17

<210> SEQ ID NO 71
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 71
gacaagagag gcagg 15

<210> SEQ ID NO 72
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 72
catgaaccag gcatgga 17

<210> SEQ ID NO 73
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 73
gaaccaggca tggacc 16

<210> SEQ ID NO 74

-continued

<211> LENGTH: 18
<212> TYPE: DNA
<213> ORGANISM: Homo sapiens
<220> FEATURE:
<221> NAME/KEY: misc_feature
<222> LOCATION: (6)...(8)
<223> OTHER INFORMATION: These nucleotides may be absent

<400> SEQUENCE: 74
aatccaagta tgttctct 18

<210> SEQ ID NO 75
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 75
gctcctgttg aacatc 16

<210> SEQ ID NO 76
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 76
aaactttcat ttgatg 16

<210> SEQ ID NO 77
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 77
aaactttcat ttgatgaag 19

<210> SEQ ID NO 78
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 78
ctacaggcca ttgc 14

<210> SEQ ID NO 79
<211> LENGTH: 21
<212> TYPE: DNA
<213> ORGANISM: Homo sapiens
<220> FEATURE:
<221> NAME/KEY: misc_feature
<222> LOCATION: 11
<223> OTHER INFORMATION: This nucleotide may be absent

<400> SEQUENCE: 79

-continued taaattaggg ggactacagg c 21

<210> SEQ ID NO 80
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 80
ttattgcaag tggac 15

<210> SEQ ID NO 81
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 81
tacgggctta ctaat 15

<210> SEQ ID NO 82
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 82
agtattacac taagac 16

<210> SEQ ID NO 83
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 83
attacactaa gacgata 17

<210> SEQ ID NO 84
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 84
ctaagacgat atgc 14

<210> SEQ ID NO 85
<211> LENGTH: 17
<212> TYPE: DNA
<213> ORGANISM: Homo sapiens
<220> FEATURE:

-continued

<221> NAME/KEY: misc_feature
<222> LOCATION: (6)...(7)
<223> OTHER INFORMATION: These nucleotides may be absent

<400> SEQUENCE: 85
tgctctatga aaggctg 17

<210> SEQ ID NO 86
<211> LENGTH: 25
<212> TYPE: DNA
<213> ORGANISM: Homo sapiens
<220> FEATURE:
<221> NAME/KEY: misc_feature
<222> LOCATION: (6)...(15)
<223> OTHER INFORMATION: These nucleotides may be absent

<400> SEQUENCE: 86
atgagagcac ttgtggccca actaa 25

<210> SEQ ID NO 87
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 87
gacttacagc aggtac 16

<210> SEQ ID NO 88
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 88
aaaaagacgt tgcgaga 17

<210> SEQ ID NO 89
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 89
gttggaagtg tgaaagcat 19

<210> SEQ ID NO 90
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 90
aaagcattga tggaat 16

-continued

<210> SEQ ID NO 91
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 91
ttagaagtta aaaaggta 18

<210> SEQ ID NO 92
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 92
accctcaaaa gcgtat 16

<210> SEQ ID NO 93
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 93
gccttatgga atttg 15

<210> SEQ ID NO 94
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 94
gctgtagatg gtgc 14

<210> SEQ ID NO 95
<211> LENGTH: 29
<212> TYPE: DNA
<213> ORGANISM: Homo sapiens
<220> FEATURE:
<221> NAME/KEY: misc_feature
<222> LOCATION: (4)...(19)
<223> OTHER INFORMATION: These nucleotides may be absent

<400> SEQUENCE: 95
gttggcactc ttacttaccg gagccagac 29

<210> SEQ ID NO 96
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent -continued

<400> SEQUENCE: 96
cttacttacc ggagccaga 19

<210> SEQ ID NO 97
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 97
acttaccgga gccag 15

<210> SEQ ID NO 98
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 98
agccagacaa acact 15

<210> SEQ ID NO 99
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 99
agccagacaa acacttta 18

<210> SEQ ID NO 100
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 100
acaaacactt tagccat 17

<210> SEQ ID NO 101
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 101
ttagccatta ttgaaa 16

<210> SEQ ID NO 102
<211> LENGTH: 15
<212> TYPE: DNA
<213> ORGANISM: Homo sapiens -continued
<220> FEATURE:
<221> NAME/KEY: misc_feature
<222> LOCATION: 5
<223> OTHER INFORMATION: This nucleotide may be absent

<400> SEQUENCE: 102
ggaggtggga tatta 15

<210> SEQ ID NO 103
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 103
atattacgga atgtg 15

<210> SEQ ID NO 104
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 104
ttacggaatg tgtcca 16

<210> SEQ ID NO 105
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 105
agagagaaca actgt 15

<210> SEQ ID NO 106
<211> LENGTH: 34
<212> TYPE: DNA
<213> ORGANISM: Homo sapiens
<220> FEATURE:
<221> NAME/KEY: misc_feature
<222> LOCATION: (11)...(24)
<223> OTHER INFORMATION: These nucleotides may be absent

<400> SEQUENCE: 106
tatttcaggc aaatcctaag agagaacaac tgtc 34

<210> SEQ ID NO 107
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 107
aactgtctac aaactt 16

-continued

<210> SEQ ID NO 108
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 108
ttattacaac actta 15

<210> SEQ ID NO 109
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 109
cacttaaaat ctcat 15

<210> SEQ ID NO 110
<211> LENGTH: 24
<212> TYPE: DNA
<213> ORGANISM: Homo sapiens
<220> FEATURE:
<221> NAME/KEY: misc_feature
<222> LOCATION: (4)...(14)
<223> OTHER INFORMATION: These nucleotides may be absent

<400> SEQUENCE: 110
agtttgacaa tagtcagtaa tgca 24

<210> SEQ ID NO 111
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 111
cacttatcag aaactt 16

<210> SEQ ID NO 112
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 112
ttatcagaaa ctttt 15

<210> SEQ ID NO 113
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent -continued

<400> SEQUENCE: 113
tcagaaactt ttgaca 16

<210> SEQ ID NO 114
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 114
agtcccaagg catct 15

<210> SEQ ID NO 115
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 115
aagcaaagtc tctat 15

<210> SEQ ID NO 116
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 116
aagcaaagtc tctatgg 17

<210> SEQ ID NO 117
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: These nucleotides may be absent

<400> SEQUENCE: 117
caaagtctct atggt 15

<210> SEQ ID NO 118
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 118
gattatgttt ttgaca 16

<210> SEQ ID NO 119
<211> LENGTH: 25
<212> TYPE: DNA

-continued

<213> ORGANISM: Homo sapiens
<220> FEATURE:
<221> NAME/KEY: misc_feature
<222> LOCATION: (6)...(15)
<223> OTHER INFORMATION: These nucleotides may be absent

<400> SEQUENCE: 119
gacaccaatc gacatgatga taata 25

<210> SEQ ID NO 120
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 120
cgacatgatg ataata 16

<210> SEQ ID NO 121
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 121
tcagacaatt ttaatact 18

<210> SEQ ID NO 122
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 122
tatttgaata ctac 14

<210> SEQ ID NO 123
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 123
aatactacag tgtta 15

<210> SEQ ID NO 124
<211> LENGTH: 28
<212> TYPE: DNA
<213> ORGANISM: Homo sapiens
<220> FEATURE:
<221> NAME/KEY: misc_feature
<222> LOCATION: (6)...(18)
<223> OTHER INFORMATION: These nucleotides may be absent

<400> SEQUENCE: 124
gtgttaccca gctcctcttc atcaagag 28

-continued

<210> SEQ ID NO 125
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 125
agctcctctt catcaa 16

<210> SEQ ID NO 126
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 126
tcatcaagag gaagc 15

<210> SEQ ID NO 127
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 127
aaagatagaa gtttgga 17

<210> SEQ ID NO 128
<211> LENGTH: 21
<212> TYPE: DNA
<213> ORGANISM: Homo sapiens
<220> FEATURE:
<221> NAME/KEY: misc_feature
<222> LOCATION: (5)...(11)
<223> OTHER INFORMATION: These nucleotides may be absent

<400> SEQUENCE: 128
aaagatagaa gtttggagag a 21

<210> SEQ ID NO 129
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 129
gaacgcggaa ttggt 15

<210> SEQ ID NO 130
<211> LENGTH: 19
<212> TYPE: DNA
<213> ORGANISM: Homo sapiens
<220> FEATURE:
<221> NAME/KEY: misc_feature
<222> LOCATION: (5)...(9)

-continued

<223> OTHER INFORMATION: These nucleotides may be absent

<400> SEQUENCE: 130
cgcggaattg gtctaggca 19

<210> SEQ ID NO 131
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 131
cgcggaattg gtcta 15

<210> SEQ ID NO 132
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 132
cagatctcca ccac 14

<210> SEQ ID NO 133
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 133
gaagacagaa gttctgggt 19

<210> SEQ ID NO 134
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 134
gggtctacca ctgaa 15

<210> SEQ ID NO 135
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 135
gtgacagatg agagaa 16

<210> SEQ ID NO 136
<211> LENGTH: 19

-continued

<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 136
catacacatt caaacactt 19

<210> SEQ ID NO 137
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 137
acacattcaa acacttaca 19

<210> SEQ ID NO 138
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 138
cattcaaaca ctta 14

<210> SEQ ID NO 139
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 139
cattcaaaca cttac 15

<210> SEQ ID NO 140
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 140
aacacttaca atttcac 17

<210> SEQ ID NO 141
<211> LENGTH: 22
<212> TYPE: DNA
<213> ORGANISM: Homo sapiens
<220> FEATURE:
<221> NAME/KEY: misc_feature
<222> LOCATION: (5)...(12)
<223> OTHER INFORMATION: These nucleotides may be absent

<400> SEQUENCE: 141

-continued tacaatttca ctaagtcgga aa 22

<210> SEQ ID NO 142
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 142
ttcactaagt cggaaaat 18

<210> SEQ ID NO 143
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 143
aagtcggaaa attcaaa 17

<210> SEQ ID NO 144
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 144
acatgttcta tgcct 15

<210> SEQ ID NO 145
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 145
ttagaataca agagat 16

<210> SEQ ID NO 146
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 146
aatgatagtt taaa 14

<210> SEQ ID NO 147
<211> LENGTH: 16
<212> TYPE: DNA
<213> ORGANISM: Homo sapiens
<220> FEATURE:
<221> NAME/KEY: misc_feature -continued
<222> LOCATION: 6
<223> OTHER INFORMATION: This nucleotide may be absent

<400> SEQUENCE: 147
agtttaaata gtgtca 16

<210> SEQ ID NO 148
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 148
ttaaatagtg tcagtag 17

<210> SEQ ID NO 149
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 149
tatggtaaaa gaggt 15

<210> SEQ ID NO 150
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 150
ggtaaaagag gtcaaa 16

<210> SEQ ID NO 151
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 151
aaaagaggtc aaatga 16

<210> SEQ ID NO 152
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 152
agtaagtttt gcagtt 16

<210> SEQ ID NO 153

-continued

<211> LENGTH: 24
<212> TYPE: DNA
<213> ORGANISM: Homo sapiens
<220> FEATURE:
<221> NAME/KEY: misc_feature
<222> LOCATION: (4)...(14)
<223> OTHER INFORMATION: These nucleotides may be absent

<400> SEQUENCE: 153
aagttttgca gttatggtca atac 24

<210> SEQ ID NO 154
<211> LENGTH: 20
<212> TYPE: DNA
<213> ORGANISM: Homo sapiens
<220> FEATURE:
<221> NAME/KEY: misc_feature
<222> LOCATION: (4)...(10)
<223> OTHER INFORMATION: These nucleotides may be absent

<400> SEQUENCE: 154
caatacccag ccgacctagc 20

<210> SEQ ID NO 155
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 155
acaccaataa attat 15

<210> SEQ ID NO 156
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 156
aaatattcag atga 14

<210> SEQ ID NO 157
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 157
tcagatgagc agttgaact 19

<210> SEQ ID NO 158
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 158

-continued gatgagcagt tgaac 15

<210> SEQ ID NO 159
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 159
tgggcaagac ccaaa 15

<210> SEQ ID NO 160
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 160
cacataatag aagatgaaa 19

<210> SEQ ID NO 161
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 161
ataatagaag atgaaataa 19

<210> SEQ ID NO 162
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 162
atagaagatg aaataa 16

<210> SEQ ID NO 163
<211> LENGTH: 20
<212> TYPE: DNA
<213> ORGANISM: Homo sapiens
<220> FEATURE:
<221> NAME/KEY: misc_feature
<222> LOCATION: (6)...(10)
<223> OTHER INFORMATION: These nucleotides may be absent

<400> SEQUENCE: 163
ataaaacaaa gtgagcaaag 20

<210> SEQ ID NO 164
<211> LENGTH: 17
<212> TYPE: DNA
<213> ORGANISM: Homo sapiens
<220> FEATURE:

-continued

<221> NAME/KEY: misc_feature
<222> LOCATION: (4)...(7)
<223> OTHER INFORMATION: These nucleotides may be absent

<400> SEQUENCE: 164
aaacaaagtg agcaaag 17

<210> SEQ ID NO 165
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 165
aaacaaagtg agcaaa 16

<210> SEQ ID NO 166
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 166
caaagtgagc aaagacaa 18

<210> SEQ ID NO 167
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 167
caaagacaat caaggaa 17

<210> SEQ ID NO 168
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 168
caatcaagga atcaaag 17

<210> SEQ ID NO 169
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 169
caaagtacaa cttatc 16

-continued

<210> SEQ ID NO 170
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 170
actgagagca ctgatg 16

<210> SEQ ID NO 171
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 171
actgatgata aacacct 17

<210> SEQ ID NO 172
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 172
gataaacacc tcaagtt 17

<210> SEQ ID NO 173
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 173
cacctcaagt tccaac 16

<210> SEQ ID NO 174
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 174
tttggacagc aggaa 15

<210> SEQ ID NO 175
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent -continued

<400> SEQUENCE: 175
tgtgtttctc catac 15

<210> SEQ ID NO 176
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 176
cggggagcca atgg 14

<210> SEQ ID NO 177
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 177
tcagaaacaa atcgag 16

<210> SEQ ID NO 178
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 178
attaatcaaa atgtaagcc 19

<210> SEQ ID NO 179
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 179
caagaagatg acta 14

<210> SEQ ID NO 180
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 180
gactatgaag atgata 16

<210> SEQ ID NO 181
<211> LENGTH: 18
<212> TYPE: DNA
<213> ORGANISM: Homo sapiens -continued
<220> FEATURE:
<221> NAME/KEY: misc_feature
<222> LOCATION: (4)...(8)
<223> OTHER INFORMATION: These nucleotides may be absent

<400> SEQUENCE: 181
gatgataagc ctaccaat 18

<210> SEQ ID NO 182
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 182
cgttactctg aagaag 16

<210> SEQ ID NO 183
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 183
gaagaagaag agagaccaa 19

<210> SEQ ID NO 184
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 184
gaagaagaga gaccaaca 18

<210> SEQ ID NO 185
<211> LENGTH: 17
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 185
gaagagagac caacaaa 17

<210> SEQ ID NO 186
<211> LENGTH: 18
<212> TYPE: DNA
<213> ORGANISM: Homo sapiens
<220> FEATURE:
<221> NAME/KEY: misc_feature
<222> LOCATION: (4)...(8)
<223> OTHER INFORMATION: These nucleotides may be absent

<400> SEQUENCE: 186
gaagagaaac gtcatgtg 18

-continued

<210> SEQ ID NO 187
<211> LENGTH: 22
<212> TYPE: DNA
<213> ORGANISM: Homo sapiens
<220> FEATURE:
<221> NAME/KEY: misc_feature
<222> LOCATION: (6)...(12)
<223> OTHER INFORMATION: These nucleotides may be absent

<400> SEQUENCE: 187
gattatagtt taaaatatgc ca 22

<210> SEQ ID NO 188
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 188
ttaaaatatg ccaca 15

<210> SEQ ID NO 189
<211> LENGTH: 18
<212> TYPE: DNA
<213> ORGANISM: Homo sapiens
<220> FEATURE:
<221> NAME/KEY: misc_feature
<222> LOCATION: (4)...(8)
<223> OTHER INFORMATION: These nucleotides may be absent

<400> SEQUENCE: 189
gccacagata ttccttca 18

<210> SEQ ID NO 190
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 190
acagatattc cttca 15

<210> SEQ ID NO 191
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: These nucleotides may be absent

<400> SEQUENCE: 191
tcacagaaac agtcat 16

<210> SEQ ID NO 192
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent -continued

<400> SEQUENCE: 192
aaacagtcat tttca 15

<210> SEQ ID NO 193
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 193
tcaaagagtt catct 15

<210> SEQ ID NO 194
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 194
aaaaccgaac atatg 15

<210> SEQ ID NO 195
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 195
accgaacata tgtcttc 17

<210> SEQ ID NO 196
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be present

<400> SEQUENCE: 196
catatgtctt caagc 15

<210> SEQ ID NO 197
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be present

<400> SEQUENCE: 197
ccaagttctg cacaga 16

<210> SEQ ID NO 198
<211> LENGTH: 16
<212> TYPE: DNA

-continued

<213> ORGANISM: Homo sapiens
<220> FEATURE:
<221> NAME/KEY: misc_feature
<222> LOCATION: (5)...(6)
<223> OTHER INFORMATION: These nucleotides may be present

<400> SEQUENCE: 198
tgcaaagttt cttcta 16

<210> SEQ ID NO 199
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be present

<400> SEQUENCE: 199
atacagactt attgt 15

<210> SEQ ID NO 200
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be present

<400> SEQUENCE: 200
cagacttatt gtgtaga 17

<210> SEQ ID NO 201
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 201
ccaatatgtt tttc 14

<210> SEQ ID NO 202
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 202
agttcattat catc 14

<210> SEQ ID NO 203
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 203
caggaagcag attctg 16

-continued

<210> SEQ ID NO 204
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be present

<400> SEQUENCE: 204
accctgcaaa tagca 15

<210> SEQ ID NO 205
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 205
gaaataaaag aaaagatt 18

<210> SEQ ID NO 206
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 206
ataaaagaaa agat 14

<210> SEQ ID NO 207
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 207
aaagaaaaga ttggaac 17

<210> SEQ ID NO 208
<211> LENGTH: 20
<212> TYPE: DNA
<213> ORGANISM: Homo sapiens
<220> FEATURE:
<221> NAME/KEY: misc_feature
<222> LOCATION: (6)...(10)
<223> OTHER INFORMATION: These nucleotides may be present

<400> SEQUENCE: 208
aaagaaaaga ttggaactag 20

<210> SEQ ID NO 209
<211> LENGTH: 15
<212> TYPE: DNA
<213> ORGANISM: Homo sapiens
<220> FEATURE:
<221> NAME/KEY: misc_feature
<222> LOCATION: 5

-continued

<223> OTHER INFORMATION: This nucleotide may be absent

<400> SEQUENCE: 209
gatcctgtga gcgaa 15

<210> SEQ ID NO 210
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 210
gtgagcgaag ttccag 16

<210> SEQ ID NO 211
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be present

<400> SEQUENCE: 211
gttccagcag tgtca 15

<210> SEQ ID NO 212
<211> LENGTH: 22
<212> TYPE: DNA
<213> ORGANISM: Homo sapiens
<220> FEATURE:
<221> NAME/KEY: misc_feature
<222> LOCATION: (5)...(13)
<223> OTHER INFORMATION: These nucleotides may be absent

<400> SEQUENCE: 212
caccctagaa ccaaatccag ca 22

<210> SEQ ID NO 213
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 213
agactgcagg gttcta 16

<210> SEQ ID NO 214
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 214
cagggttcta gttt 14

<210> SEQ ID NO 215
<211> LENGTH: 15

-continued

<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 215
tctagtttat cttca 15

<210> SEQ ID NO 216
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 216
ttatcttcag aatca 15

<210> SEQ ID NO 217
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 217
gttgaatttt cttc 14

<210> SEQ ID NO 218
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 218
ccctccaaaa gtggt 15

<210> SEQ ID NO 219
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 219
agtggtgctc agacacc 17

<210> SEQ ID NO 220
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 220

-continued agtccacctg aacacta 17

<210> SEQ ID NO 221
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 221
ccacctgaac actatg 16

<210> SEQ ID NO 222
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 222
tatgttcagg agaccc 16

<210> SEQ ID NO 223
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 223
gatagttttg agagtc 16

<210> SEQ ID NO 224
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 224
attgccagct ccgttc 16

<210> SEQ ID NO 225
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 225
agtggcatta taagcc 16

<210> SEQ ID NO 226
<211> LENGTH: 15
<212> TYPE: DNA
<213> ORGANISM: Homo sapiens
<220> FEATURE:
<221> NAME/KEY: misc_feature -continued
<222> LOCATION: 5
<223> OTHER INFORMATION: This nucleotide may be absent

<400> SEQUENCE: 226
agccctggac aaacc 15

<210> SEQ ID NO 227
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 227
cctggacaaa ccatgc 16

<210> SEQ ID NO 228
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 228
atgccaccaa gcaga 15

<210> SEQ ID NO 229
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 229
aaaaataaag caccta 16

<210> SEQ ID NO 230
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 230
gaaaagagag agag 14

<210> SEQ ID NO 231
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 231
agagagagtg gacctaa 17

<210> SEQ ID NO 232

<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 232
gagagtggac ctaag 15

<210> SEQ ID NO 233
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 233
gagagtggac ctaagc 16

<210> SEQ ID NO 234
<211> LENGTH: 15
<212> TYPE: DNA
<213> ORGANISM: Homo sapiens
<220> FEATURE:
<221> NAME/KEY: misc_feature
<222> LOCATION: (4)...(5)
<223> OTHER INFORMATION: These nucleotides may be absent

<400> SEQUENCE: 234
gagagtggac ctaag 15

<210> SEQ ID NO 235
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 235
gccacggaaa gtac 14

<210> SEQ ID NO 236
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 236
acggaaagta ctccag 16

<210> SEQ ID NO 237
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 237

-continued

```
ccagatggat tttc                                                  14


<210> SEQ ID NO 238
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 238

tcatccagcc tgagtgc                                               17


<210> SEQ ID NO 239
<211> LENGTH: 20
<212> TYPE: DNA
<213> ORGANISM: Homo sapiens
<220> FEATURE:
<221> NAME/KEY: misc_feature
<222> LOCATION: (4)...(10)
<223> OTHER INFORMATION: These nucleotides may be absent

<400> SEQUENCE: 239

ttaagaataa tgcctccagt                                            20


<210> SEQ ID NO 240
<211> LENGTH: 17
<212> TYPE: DNA
<213> ORGANISM: Homo sapiens
<220> FEATURE:
<221> NAME/KEY: misc_feature
<222> LOCATION: (6)...(7)
<223> OTHER INFORMATION: These nucleotides may be absent

<400> SEQUENCE: 240

gaaacagaat cagagca                                               17


<210> SEQ ID NO 241
<211> LENGTH: 20
<212> TYPE: DNA
<213> ORGANISM: Homo sapiens
<220> FEATURE:
<221> NAME/KEY: misc_feature
<222> LOCATION: (6)...(10)
<223> OTHER INFORMATION: These nucleotides may be absent

<400> SEQUENCE: 241

tcaaatgaaa accaagagaa                                            20


<210> SEQ ID NO 242
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 242

gaaaaccaag agaa                                                  14


<210> SEQ ID NO 243
<211> LENGTH: 18
<212> TYPE: DNA
<213> ORGANISM: Homo sapiens
<220> FEATURE:
```

-continued

<221> NAME/KEY: misc_feature
<222> LOCATION: (5)...(8)
<223> OTHER INFORMATION: These nucleotides may be absent

<400> SEQUENCE: 243
gagaaagagg cagaaaaa 18

<210> SEQ ID NO 244
<211> LENGTH: 16
<212> TYPE: DNA
<213> ORGANISM: Homo sapiens
<220> FEATURE:
<221> NAME/KEY: misc_feature
<222> LOCATION: (5)...(6)
<223> OTHER INFORMATION: These nucleotides may be absent

<400> SEQUENCE: 244
gaatgtatta tttctg 16

<210> SEQ ID NO 245
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 245
ccagcccaga ctgctt 16

<210> SEQ ID NO 246
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 246
cagactgctt caaaat 16

<210> SEQ ID NO 247
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 247
ttcaatgata agctc 15

<210> SEQ ID NO 248
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 248
aatgattctt tgagttctc 19

-continued

<210> SEQ ID NO 249
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 249
ccagacagag gggcagcaa 19

<210> SEQ ID NO 250
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 250
gaaaatactc cagt 14

<210> SEQ ID NO 251
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 251
aacaataaag aaaa 14

<210> SEQ ID NO 252
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 252
gaacctatca aagaga 16

<210> SEQ ID NO 253
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 253
cctatcaaag agac 14

<210> SEQ ID NO 254
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent -continued

<400> SEQUENCE: 254
gaaccaagta aacct 15

<210> SEQ ID NO 255
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 255
agctccgcaa tgccaa 16

<210> SEQ ID NO 256
<211> LENGTH: 23
<212> TYPE: DNA
<213> ORGANISM: Homo sapiens
<220> FEATURE:
<221> NAME/KEY: misc_feature
<222> LOCATION: (6)...(13)
<223> OTHER INFORMATION: These nucleotides may be absent

<400> SEQUENCE: 256
tcatcccttc ctcgagtaag cac 23

<210> SEQ ID NO 257
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 257
ctaatttatc aaatggcac 19

<210> SEQ ID NO 258
<211> LENGTH: 18
<212> TYPE: DNA
<213> ORGANISM: Homo sapiens
<220> FEATURE:
<221> NAME/KEY: misc_feature
<222> LOCATION: 6
<223> OTHER INFORMATION: n = C or G
<220> FEATURE:
<221> NAME/KEY: misc_feature
<222> LOCATION: 7
<223> OTHER INFORMATION: n = A or n is absent
<220> FEATURE:
<221> NAME/KEY: misc_feature
<222> LOCATION: 8
<223> OTHER INFORMATION: n = A or n is absent

<400> SEQUENCE: 258
gaagannntt acagcagg 18

<210> SEQ ID NO 259
<211> LENGTH: 18
<212> TYPE: DNA
<213> ORGANISM: Homo sapiens
<220> FEATURE:
<221> NAME/KEY: misc_feature
<222> LOCATION: 6
<223> OTHER INFORMATION: n = T or C
<220> FEATURE:
<221> NAME/KEY: misc_feature -continued
<222> LOCATION: 7
<223> OTHER INFORMATION: n = T
<220> FEATURE:
<221> NAME/KEY: misc_feature
<222> LOCATION: 8
<223> OTHER INFORMATION: n = A or n is absent

<400> SEQUENCE: 259
cttacnnncc ggagccag 18

<210> SEQ ID NO 260
<211> LENGTH: 25
<212> TYPE: DNA
<213> ORGANISM: Homo sapiens
<220> FEATURE:
<221> NAME/KEY: misc_feature
<222> LOCATION: 4
<223> OTHER INFORMATION: n = C or T
<220> FEATURE:
<221> NAME/KEY: misc_feature
<222> LOCATION: 5
<223> OTHER INFORMATION: n = T
<220> FEATURE:
<221> NAME/KEY: misc_feature
<222> LOCATION: 6
<223> OTHER INFORMATION: n = C or G
<220> FEATURE:
<221> NAME/KEY: misc_feature
<222> LOCATION: 7
<223> OTHER INFORMATION: n = A or C
<220> FEATURE:
<221> NAME/KEY: misc_feature
<222> LOCATION: 8
<223> OTHER INFORMATION: n = T or A
<220> FEATURE:
<221> NAME/KEY: misc_feature
<222> LOCATION: 9
<223> OTHER INFORMATION: n = G or n is absent
<220> FEATURE:
<221> NAME/KEY: misc_feature
<222> LOCATION: 10
<223> OTHER INFORMATION: n = C or n is absent
<220> FEATURE:
<221> NAME/KEY: misc_feature
<222> LOCATION: (11)...(13)
<223> OTHER INFORMATION: n = T or n is absent
<220> FEATURE:
<221> NAME/KEY: misc_feature
<222> LOCATION: (14)...(15)
<223> OTHER INFORMATION: n = A or n is absent

<400> SEQUENCE: 260
aatnnnnnnn nnnnnggcaa atagg 25

<210> SEQ ID NO 261
<211> LENGTH: 12
<212> TYPE: DNA
<213> ORGANISM: Homo sapiens

<400> SEQUENCE: 261
ttgcagcttt aa 12

<210> SEQ ID NO 262
<211> LENGTH: 17
<212> TYPE: DNA
<213> ORGANISM: Homo sapiens
<220> FEATURE:
<221> NAME/KEY: misc_feature
<222> LOCATION: 5
<223> OTHER INFORMATION: n = G or T
<220> FEATURE:
<221> NAME/KEY: misc_feature
<222> LOCATION: 6

-continued

<223> OTHER INFORMATION: n = T or A
<220> FEATURE:
<221> NAME/KEY: misc_feature
<222> LOCATION: 7
<223> OTHER INFORMATION: n = A or n is absent

<400> SEQUENCE: 262
gatgnnntat ggtaaaa 17

<210> SEQ ID NO 263
<211> LENGTH: 21
<212> TYPE: DNA
<213> ORGANISM: Artificial Sequence
<220> FEATURE:
<223> OTHER INFORMATION: Primer

<400> SEQUENCE: 263
tggcgattaa gtcaaattcg c 21

<210> SEQ ID NO 264
<211> LENGTH: 25
<212> TYPE: DNA
<213> ORGANISM: Artificial Sequence
<220> FEATURE:
<223> OTHER INFORMATION: Primer

<400> SEQUENCE: 264
ccccctagta ccctgacaat gtatt 25

<210> SEQ ID NO 265
<211> LENGTH: 24
<212> TYPE: DNA
<213> ORGANISM: Artificial Sequence
<220> FEATURE:
<223> OTHER INFORMATION: Primer

<400> SEQUENCE: 265
ctgttctgtg atattatgtg tggt 24

<210> SEQ ID NO 266
<211> LENGTH: 22
<212> TYPE: DNA
<213> ORGANISM: Artificial Sequence
<220> FEATURE:
<223> OTHER INFORMATION: Primer

<400> SEQUENCE: 266
aattgttggc attccagcat tg 22

<210> SEQ ID NO 267
<211> LENGTH: 38
<212> TYPE: DNA
<213> ORGANISM: Artificial Sequence
<220> FEATURE:
<223> OTHER INFORMATION: Primer

<400> SEQUENCE: 267
gtgcacttac gtgaattcag atgaacgtga tgtagtag 38

<210> SEQ ID NO 268
<211> LENGTH: 28
<212> TYPE: DNA
<213> ORGANISM: Artificial Sequence
<220> FEATURE:
<223> OTHER INFORMATION: Primer

<400> SEQUENCE: 268

-continued

```
tcctcgtact caacggcttt ctctgaat                                      28


<210> SEQ ID NO 269
<211> LENGTH: 38
<212> TYPE: DNA
<213> ORGANISM: Artificial Sequence
<220> FEATURE:
<223> OTHER INFORMATION: Primer

<400> SEQUENCE: 269

tccggaacac tagaattctt atttacatac acacttgt                           38


<210> SEQ ID NO 270
<211> LENGTH: 28
<212> TYPE: DNA
<213> ORGANISM: Artificial Sequence
<220> FEATURE:
<223> OTHER INFORMATION: Primer

<400> SEQUENCE: 270

cgaataaggt agacggcaac aatgagaa                                      28


<210> SEQ ID NO 271
<211> LENGTH: 38
<212> TYPE: DNA
<213> ORGANISM: Artificial Sequence
<220> FEATURE:
<223> OTHER INFORMATION: Primer

<400> SEQUENCE: 271

cggtaaatcg gagaattcag aggatttaga ggagctaa                           38


<210> SEQ ID NO 272
<211> LENGTH: 29
<212> TYPE: DNA
<213> ORGANISM: Artificial Sequence
<220> FEATURE:
<223> OTHER INFORMATION: Primer

<400> SEQUENCE: 272

ctcacgttcg ttacggccat tgtgatagc                                     29


<210> SEQ ID NO 273
<211> LENGTH: 38
<212> TYPE: DNA
<213> ORGANISM: Artificial Sequence
<220> FEATURE:
<223> OTHER INFORMATION: Primer

<400> SEQUENCE: 273

ggggaaacag tagaattcca tatggacaga gctgtact                           38


<210> SEQ ID NO 274
<211> LENGTH: 29
<212> TYPE: DNA
<213> ORGANISM: Artificial Sequence
<220> FEATURE:
<223> OTHER INFORMATION: Primer

<400> SEQUENCE: 274

tgaagctgtc ggacggcctt tgccctctc                                     29


<210> SEQ ID NO 275
<211> LENGTH: 38
<212> TYPE: DNA
```

-continued

<213> ORGANISM: Artificial Sequence
<220> FEATURE:
<223> OTHER INFORMATION: Primer

<400> SEQUENCE: 275
atgggcagtt atgaattcac tactccctgt agcttgtt 38

<210> SEQ ID NO 276
<211> LENGTH: 29
<212> TYPE: DNA
<213> ORGANISM: Artificial Sequence
<220> FEATURE:
<223> OTHER INFORMATION: Primer

<400> SEQUENCE: 276
tgattggcgc gaacggcact cagagaaga 29

<210> SEQ ID NO 277
<211> LENGTH: 38
<212> TYPE: DNA
<213> ORGANISM: Artificial Sequence
<220> FEATURE:
<223> OTHER INFORMATION: Primer

<400> SEQUENCE: 277
ctcaagggga ccgaattcgc tggggtcttc tgtgggtc 38

<210> SEQ ID NO 278
<211> LENGTH: 28
<212> TYPE: DNA
<213> ORGANISM: Artificial Sequence
<220> FEATURE:
<223> OTHER INFORMATION: Primer

<400> SEQUENCE: 278
tagggcggcg tgacggccag ccagtggt 28

<210> SEQ ID NO 279
<211> LENGTH: 38
<212> TYPE: DNA
<213> ORGANISM: Artificial Sequence
<220> FEATURE:
<223> OTHER INFORMATION: Primer

<400> SEQUENCE: 279
gtcttgcatg tagaattcta gggacgctgc ttttcgtc 38

<210> SEQ ID NO 280
<211> LENGTH: 29
<212> TYPE: DNA
<213> ORGANISM: Artificial Sequence
<220> FEATURE:
<223> OTHER INFORMATION: Primer

<400> SEQUENCE: 280
ctcctagaca tcgggactag aatgtccac 29

<210> SEQ ID NO 281
<211> LENGTH: 38
<212> TYPE: DNA
<213> ORGANISM: Artificial Sequence
<220> FEATURE:
<223> OTHER INFORMATION: Primer

<400> SEQUENCE: 281
acacaaggca gagaattcca gtcctgaggg tgggggcc 38

-continued

<210> SEQ ID NO 282
<211> LENGTH: 29
<212> TYPE: DNA
<213> ORGANISM: Artificial Sequence
<220> FEATURE:
<223> OTHER INFORMATION: Primer

<400> SEQUENCE: 282
ccgtgtttta acgggacaag ctgttcttc 29

<210> SEQ ID NO 283
<211> LENGTH: 38
<212> TYPE: DNA
<213> ORGANISM: Artificial Sequence
<220> FEATURE:
<223> OTHER INFORMATION: Primer

<400> SEQUENCE: 283
gtagcggagg ttgaattcta tatgttgtct tggacatt 38

<210> SEQ ID NO 284
<211> LENGTH: 29
<212> TYPE: DNA
<213> ORGANISM: Artificial Sequence
<220> FEATURE:
<223> OTHER INFORMATION: Primer

<400> SEQUENCE: 284
catcagtaga gtgggacgaa agttctggc 29

<210> SEQ ID NO 285
<211> LENGTH: 38
<212> TYPE: DNA
<213> ORGANISM: Artificial Sequence
<220> FEATURE:
<223> OTHER INFORMATION: Primer

<400> SEQUENCE: 285
atccacgccg cagaattcgt attcatgggc atgtcaaa 38

<210> SEQ ID NO 286
<211> LENGTH: 29
<212> TYPE: DNA
<213> ORGANISM: Artificial Sequence
<220> FEATURE:
<223> OTHER INFORMATION: Primer

<400> SEQUENCE: 286
cttgggacta ttgggaccag tgttcaatc 29

<210> SEQ ID NO 287
<211> LENGTH: 38
<212> TYPE: DNA
<213> ORGANISM: Artificial Sequence
<220> FEATURE:
<223> OTHER INFORMATION: Primer

<400> SEQUENCE: 287
ccagaaagcc gtgaattcgt taagccaacc tgactcca 38

<210> SEQ ID NO 288
<211> LENGTH: 29
<212> TYPE: DNA
<213> ORGANISM: Artificial Sequence
<220> FEATURE:

-continued

<223> OTHER INFORMATION: Primer

<400> SEQUENCE: 288
tcggggttag tcgggacatc cagcagccc 29

<210> SEQ ID NO 289
<211> LENGTH: 38
<212> TYPE: DNA
<213> ORGANISM: Artificial Sequence
<220> FEATURE:
<223> OTHER INFORMATION: Primer

<400> SEQUENCE: 289
cgaaggtaat gtgaattcca aaacttagtg ccacaatt 38

<210> SEQ ID NO 290
<211> LENGTH: 29
<212> TYPE: DNA
<213> ORGANISM: Artificial Sequence
<220> FEATURE:
<223> OTHER INFORMATION: Primer

<400> SEQUENCE: 290
ataccgccca acgggacaga tccattgac 29

<210> SEQ ID NO 291
<211> LENGTH: 38
<212> TYPE: DNA
<213> ORGANISM: Artificial Sequence
<220> FEATURE:
<223> OTHER INFORMATION: Primer

<400> SEQUENCE: 291
agaaacctgt aagaattcga ttccaaattg ttttttgg 38

<210> SEQ ID NO 292
<211> LENGTH: 29
<212> TYPE: DNA
<213> ORGANISM: Artificial Sequence
<220> FEATURE:
<223> OTHER INFORMATION: Primer

<400> SEQUENCE: 292
cgatcatagg gggggacagg agagagcac 29

<210> SEQ ID NO 293
<211> LENGTH: 38
<212> TYPE: DNA
<213> ORGANISM: Artificial Sequence
<220> FEATURE:
<223> OTHER INFORMATION: Primer

<400> SEQUENCE: 293
ctactgaggg ctcgtagatc ccaattcctt cccaagct 38

<210> SEQ ID NO 294
<211> LENGTH: 29
<212> TYPE: DNA
<213> ORGANISM: Artificial Sequence
<220> FEATURE:
<223> OTHER INFORMATION: Primer

<400> SEQUENCE: 294
aatcctgctt tagggaccat gctggtgga 29

-continued

<210> SEQ ID NO 295
<211> LENGTH: 12
<212> TYPE: DNA
<213> ORGANISM: Artificial Sequence
<220> FEATURE:
<223> OTHER INFORMATION: Primer

<400> SEQUENCE: 295
caagtgtcct aa 12

<210> SEQ ID NO 296
<211> LENGTH: 12
<212> TYPE: DNA
<213> ORGANISM: Artificial Sequence
<220> FEATURE:
<223> OTHER INFORMATION: Primer

<400> SEQUENCE: 296
cagctgctag aa 12

<210> SEQ ID NO 297
<211> LENGTH: 12
<212> TYPE: DNA
<213> ORGANISM: Artificial Sequence
<220> FEATURE:
<223> OTHER INFORMATION: Primer

<400> SEQUENCE: 297
ggttgagggc aa 12

<210> SEQ ID NO 298
<211> LENGTH: 12
<212> TYPE: DNA
<213> ORGANISM: Artificial Sequence
<220> FEATURE:
<223> OTHER INFORMATION: Primer

<400> SEQUENCE: 298
cacagcgggt aa 12

<210> SEQ ID NO 299
<211> LENGTH: 12
<212> TYPE: DNA
<213> ORGANISM: Artificial Sequence
<220> FEATURE:
<223> OTHER INFORMATION: Primer

<400> SEQUENCE: 299
ttgacttttt aa 12

<210> SEQ ID NO 300
<211> LENGTH: 12
<212> TYPE: DNA
<213> ORGANISM: Artificial Sequence
<220> FEATURE:
<223> OTHER INFORMATION: Primer

<400> SEQUENCE: 300
acagaatggg aa 12

<210> SEQ ID NO 301
<211> LENGTH: 12
<212> TYPE: DNA
<213> ORGANISM: Artificial Sequence
<220> FEATURE:
<223> OTHER INFORMATION: Primer -continued

<400> SEQUENCE: 301
tgcaggtcac aa 12

<210> SEQ ID NO 302
<211> LENGTH: 12
<212> TYPE: DNA
<213> ORGANISM: Artificial Sequence
<220> FEATURE:
<223> OTHER INFORMATION: Primer

<400> SEQUENCE: 302
ttcttcttat aa 12

<210> SEQ ID NO 303
<211> LENGTH: 12
<212> TYPE: DNA
<213> ORGANISM: Artificial Sequence
<220> FEATURE:
<223> OTHER INFORMATION: Primer

<400> SEQUENCE: 303
aggacaacct aa 12

<210> SEQ ID NO 304
<211> LENGTH: 12
<212> TYPE: DNA
<213> ORGANISM: Artificial Sequence
<220> FEATURE:
<223> OTHER INFORMATION: Primer

<400> SEQUENCE: 304
tggtgttcag aa 12

<210> SEQ ID NO 305
<211> LENGTH: 12
<212> TYPE: DNA
<213> ORGANISM: Artificial Sequence
<220> FEATURE:
<223> OTHER INFORMATION: Primer

<400> SEQUENCE: 305
tcagcatatg aa 12

<210> SEQ ID NO 306
<211> LENGTH: 12
<212> TYPE: DNA
<213> ORGANISM: Artificial Sequence
<220> FEATURE:
<223> OTHER INFORMATION: Primer

<400> SEQUENCE: 306
gttgccacac aa 12

<210> SEQ ID NO 307
<211> LENGTH: 12
<212> TYPE: DNA
<213> ORGANISM: Artificial Sequence
<220> FEATURE:
<223> OTHER INFORMATION: Primer

<400> SEQUENCE: 307
cccagctagc aa 12

<210> SEQ ID NO 308
<211> LENGTH: 12

-continued

<212> TYPE: DNA
<213> ORGANISM: Artificial Sequence
<220> FEATURE:
<223> OTHER INFORMATION: Primer

<400> SEQUENCE: 308
gggtcactgt aa 12

<210> SEQ ID NO 309
<211> LENGTH: 12
<212> TYPE: DNA
<213> ORGANISM: Artificial Sequence
<220> FEATURE:
<223> OTHER INFORMATION: Primer

<400> SEQUENCE: 309
ttaaataccc aa 12

<210> SEQ ID NO 310
<211> LENGTH: 12
<212> TYPE: DNA
<213> ORGANISM: Artificial Sequence
<220> FEATURE:
<223> OTHER INFORMATION: Primer

<400> SEQUENCE: 310
ttaggaggtt aa 12

<210> SEQ ID NO 311
<211> LENGTH: 12
<212> TYPE: DNA
<213> ORGANISM: Artificial Sequence
<220> FEATURE:
<223> OTHER INFORMATION: Primer

<400> SEQUENCE: 311
acacagaatc aa 12

<210> SEQ ID NO 312
<211> LENGTH: 12
<212> TYPE: DNA
<213> ORGANISM: Artificial Sequence
<220> FEATURE:
<223> OTHER INFORMATION: Primer

<400> SEQUENCE: 312
cgctgaggtc aa 12

<210> SEQ ID NO 313
<211> LENGTH: 12
<212> TYPE: DNA
<213> ORGANISM: Artificial Sequence
<220> FEATURE:
<223> OTHER INFORMATION: Primer

<400> SEQUENCE: 313
aagtagagtc aa 12

<210> SEQ ID NO 314
<211> LENGTH: 12
<212> TYPE: DNA
<213> ORGANISM: Artificial Sequence
<220> FEATURE:
<223> OTHER INFORMATION: Primer

<400> SEQUENCE: 314

-continued cttcccatgg aa 12

<210> SEQ ID NO 315
<211> LENGTH: 12
<212> TYPE: DNA
<213> ORGANISM: Artificial Sequence
<220> FEATURE:
<223> OTHER INFORMATION: Primer

<400> SEQUENCE: 315
ttggttatta aa 12

<210> SEQ ID NO 316
<211> LENGTH: 12
<212> TYPE: DNA
<213> ORGANISM: Artificial Sequence
<220> FEATURE:
<223> OTHER INFORMATION: Primer

<400> SEQUENCE: 316
caacttactg aa 12

<210> SEQ ID NO 317
<211> LENGTH: 12
<212> TYPE: DNA
<213> ORGANISM: Artificial Sequence
<220> FEATURE:
<223> OTHER INFORMATION: Primer

<400> SEQUENCE: 317
cactaagtga aa 12

<210> SEQ ID NO 318
<211> LENGTH: 12
<212> TYPE: DNA
<213> ORGANISM: Artificial Sequence
<220> FEATURE:
<223> OTHER INFORMATION: Primer

<400> SEQUENCE: 318
ctcacctgcc aa 12

<210> SEQ ID NO 319
<211> LENGTH: 12
<212> TYPE: DNA
<213> ORGANISM: Artificial Sequence
<220> FEATURE:
<223> OTHER INFORMATION: Primer

<400> SEQUENCE: 319
atgcatatat aa 12

<210> SEQ ID NO 320
<211> LENGTH: 12
<212> TYPE: DNA
<213> ORGANISM: Artificial Sequence
<220> FEATURE:
<223> OTHER INFORMATION: Primer

<400> SEQUENCE: 320
agagatcagc aa 12

<210> SEQ ID NO 321
<211> LENGTH: 12
<212> TYPE: DNA
<213> ORGANISM: Artificial Sequence -continued
<220> FEATURE:
<223> OTHER INFORMATION: Primer

<400> SEQUENCE: 321
tatatttttc aa 12

<210> SEQ ID NO 322
<211> LENGTH: 12
<212> TYPE: DNA
<213> ORGANISM: Artificial Sequence
<220> FEATURE:
<223> OTHER INFORMATION: Primer

<400> SEQUENCE: 322
cagaaagcag aa 12

<210> SEQ ID NO 323
<211> LENGTH: 12
<212> TYPE: DNA
<213> ORGANISM: Artificial Sequence
<220> FEATURE:
<223> OTHER INFORMATION: Primer

<400> SEQUENCE: 323
gtattgggtt aa 12

<210> SEQ ID NO 324
<211> LENGTH: 12
<212> TYPE: DNA
<213> ORGANISM: Artificial Sequence
<220> FEATURE:
<223> OTHER INFORMATION: Primer

<400> SEQUENCE: 324
ctgacccagg aa 12

<210> SEQ ID NO 325
<211> LENGTH: 12
<212> TYPE: DNA
<213> ORGANISM: Artificial Sequence
<220> FEATURE:
<223> OTHER INFORMATION: Primer

<400> SEQUENCE: 325
cagttttccc aa 12

<210> SEQ ID NO 326
<211> LENGTH: 12
<212> TYPE: DNA
<213> ORGANISM: Artificial Sequence
<220> FEATURE:
<223> OTHER INFORMATION: Primer

<400> SEQUENCE: 326
agggcacagg aa 12

<210> SEQ ID NO 327
<211> LENGTH: 12
<212> TYPE: DNA
<213> ORGANISM: Artificial Sequence
<220> FEATURE:
<223> OTHER INFORMATION: Primer

<400> SEQUENCE: 327
gtatcagagg aa 12

-continued

<210> SEQ ID NO 328
<211> LENGTH: 12
<212> TYPE: DNA
<213> ORGANISM: Artificial Sequence
<220> FEATURE:
<223> OTHER INFORMATION: Primer

<400> SEQUENCE: 328
gcatgaaaag aa 12

<210> SEQ ID NO 329
<211> LENGTH: 12
<212> TYPE: DNA
<213> ORGANISM: Artificial Sequence
<220> FEATURE:
<223> OTHER INFORMATION: Primer

<400> SEQUENCE: 329
gatttgacag aa 12

<210> SEQ ID NO 330
<211> LENGTH: 12
<212> TYPE: DNA
<213> ORGANISM: Artificial Sequence
<220> FEATURE:
<223> OTHER INFORMATION: Primer

<400> SEQUENCE: 330
tacagtttac aa 12

<210> SEQ ID NO 331
<211> LENGTH: 12
<212> TYPE: DNA
<213> ORGANISM: Artificial Sequence
<220> FEATURE:
<223> OTHER INFORMATION: Primer

<400> SEQUENCE: 331
tgtgattttt aa 12

<210> SEQ ID NO 332
<211> LENGTH: 12
<212> TYPE: DNA
<213> ORGANISM: Artificial Sequence
<220> FEATURE:
<223> OTHER INFORMATION: Primer

<400> SEQUENCE: 332
ttatgttctc aa 12

<210> SEQ ID NO 333
<211> LENGTH: 12
<212> TYPE: DNA
<213> ORGANISM: Artificial Sequence
<220> FEATURE:
<223> OTHER INFORMATION: Primer

<400> SEQUENCE: 333
caagtacttg aa 12

<210> SEQ ID NO 334
<211> LENGTH: 12
<212> TYPE: DNA
<213> ORGANISM: Artificial Sequence
<220> FEATURE:
<223> OTHER INFORMATION: Primer

<400> SEQUENCE: 334
cttgtgtggc aa 12

<210> SEQ ID NO 335
<211> LENGTH: 12
<212> TYPE: DNA
<213> ORGANISM: Artificial Sequence
<220> FEATURE:
<223> OTHER INFORMATION: Primer

<400> SEQUENCE: 335
agacttctgc aa 12

<210> SEQ ID NO 336
<211> LENGTH: 12
<212> TYPE: DNA
<213> ORGANISM: Artificial Sequence
<220> FEATURE:
<223> OTHER INFORMATION: Primer

<400> SEQUENCE: 336
gttgtctttc aa 12

<210> SEQ ID NO 337
<211> LENGTH: 12
<212> TYPE: DNA
<213> ORGANISM: Artificial Sequence
<220> FEATURE:
<223> OTHER INFORMATION: Primer

<400> SEQUENCE: 337
gggacactcc aa 12

<210> SEQ ID NO 338
<211> LENGTH: 12
<212> TYPE: DNA
<213> ORGANISM: Artificial Sequence
<220> FEATURE:
<223> OTHER INFORMATION: Primer

<400> SEQUENCE: 338
attattattc aa 12

<210> SEQ ID NO 339
<211> LENGTH: 12
<212> TYPE: DNA
<213> ORGANISM: Artificial Sequence
<220> FEATURE:
<223> OTHER INFORMATION: Primer

<400> SEQUENCE: 339
acatgatgac aa 12

<210> SEQ ID NO 340
<211> LENGTH: 12
<212> TYPE: DNA
<213> ORGANISM: Artificial Sequence
<220> FEATURE:
<223> OTHER INFORMATION: Primer

<400> SEQUENCE: 340
tcaattatag aa 12

<210> SEQ ID NO 341

-continued

<211> LENGTH: 12
<212> TYPE: DNA
<213> ORGANISM: Artificial Sequence
<220> FEATURE:
<223> OTHER INFORMATION: Primer

<400> SEQUENCE: 341
ctatgggctg aa 12

<210> SEQ ID NO 342
<211> LENGTH: 12
<212> TYPE: DNA
<213> ORGANISM: Artificial Sequence
<220> FEATURE:
<223> OTHER INFORMATION: Primer

<400> SEQUENCE: 342
tgtgtgcctg aa 12

<210> SEQ ID NO 343
<211> LENGTH: 12
<212> TYPE: DNA
<213> ORGANISM: Artificial Sequence
<220> FEATURE:
<223> OTHER INFORMATION: Primer

<400> SEQUENCE: 343
ccatttgttg aa 12

<210> SEQ ID NO 344
<211> LENGTH: 12
<212> TYPE: DNA
<213> ORGANISM: Artificial Sequence
<220> FEATURE:
<223> OTHER INFORMATION: Primer

<400> SEQUENCE: 344
tctccatcaa aa 12

<210> SEQ ID NO 345
<211> LENGTH: 12
<212> TYPE: DNA
<213> ORGANISM: Artificial Sequence
<220> FEATURE:
<223> OTHER INFORMATION: Primer

<400> SEQUENCE: 345
aatgctgaca aa 12

<210> SEQ ID NO 346
<211> LENGTH: 12
<212> TYPE: DNA
<213> ORGANISM: Artificial Sequence
<220> FEATURE:
<223> OTHER INFORMATION: Primer

<400> SEQUENCE: 346
tttcatgtcc aa 12

<210> SEQ ID NO 347
<211> LENGTH: 12
<212> TYPE: DNA
<213> ORGANISM: Artificial Sequence
<220> FEATURE:
<223> OTHER INFORMATION: Primer

<400> SEQUENCE: 347

-continued ggcctcttgg aa 12

<210> SEQ ID NO 348
<211> LENGTH: 12
<212> TYPE: DNA
<213> ORGANISM: Artificial Sequence
<220> FEATURE:
<223> OTHER INFORMATION: Primer

<400> SEQUENCE: 348
tcattttttg aa 12

<210> SEQ ID NO 349
<211> LENGTH: 12
<212> TYPE: DNA
<213> ORGANISM: Artificial Sequence
<220> FEATURE:
<223> OTHER INFORMATION: Primer

<400> SEQUENCE: 349
ggactaccat aa 12

<210> SEQ ID NO 350
<211> LENGTH: 12
<212> TYPE: DNA
<213> ORGANISM: Artificial Sequence
<220> FEATURE:
<223> OTHER INFORMATION: Primer

<400> SEQUENCE: 350
agtcactcag aa 12

<210> SEQ ID NO 351
<211> LENGTH: 12
<212> TYPE: DNA
<213> ORGANISM: Artificial Sequence
<220> FEATURE:
<223> OTHER INFORMATION: Primer

<400> SEQUENCE: 351
ccttggcagg aa 12

<210> SEQ ID NO 352
<211> LENGTH: 12
<212> TYPE: DNA
<213> ORGANISM: Artificial Sequence
<220> FEATURE:
<223> OTHER INFORMATION: Primer

<400> SEQUENCE: 352
tttctggtag aa 12

<210> SEQ ID NO 353
<211> LENGTH: 12
<212> TYPE: DNA
<213> ORGANISM: Artificial Sequence
<220> FEATURE:
<223> OTHER INFORMATION: Primer

<400> SEQUENCE: 353
cccccccccg aa 12

<210> SEQ ID NO 354
<211> LENGTH: 12
<212> TYPE: DNA

-continued

<213> ORGANISM: Artificial Sequence
<220> FEATURE:
<223> OTHER INFORMATION: Primer

<400> SEQUENCE: 354
gcccaggcag aa 12

<210> SEQ ID NO 355
<211> LENGTH: 12
<212> TYPE: DNA
<213> ORGANISM: Artificial Sequence
<220> FEATURE:
<223> OTHER INFORMATION: Primer

<400> SEQUENCE: 355
gaatgcgaag aa 12

<210> SEQ ID NO 356
<211> LENGTH: 12
<212> TYPE: DNA
<213> ORGANISM: Artificial Sequence
<220> FEATURE:
<223> OTHER INFORMATION: Primer

<400> SEQUENCE: 356
ttaggtagag aa 12

<210> SEQ ID NO 357
<211> LENGTH: 12
<212> TYPE: DNA
<213> ORGANISM: Artificial Sequence
<220> FEATURE:
<223> OTHER INFORMATION: Primer

<400> SEQUENCE: 357
tgctttggtc aa 12

<210> SEQ ID NO 358
<211> LENGTH: 12
<212> TYPE: DNA
<213> ORGANISM: Artificial Sequence
<220> FEATURE:
<223> OTHER INFORMATION: Primer

<400> SEQUENCE: 358
gcccattaat aa 12

<210> SEQ ID NO 359
<211> LENGTH: 12
<212> TYPE: DNA
<213> ORGANISM: Artificial Sequence
<220> FEATURE:
<223> OTHER INFORMATION: Primer

<400> SEQUENCE: 359
tgagatcttt aa 12

<210> SEQ ID NO 360
<211> LENGTH: 12
<212> TYPE: DNA
<213> ORGANISM: Artificial Sequence
<220> FEATURE:
<223> OTHER INFORMATION: Primer

<400> SEQUENCE: 360
cagtttgttc aa 12

-continued

<210> SEQ ID NO 361
<211> LENGTH: 12
<212> TYPE: DNA
<213> ORGANISM: Artificial Sequence
<220> FEATURE:
<223> OTHER INFORMATION: Primer

<400> SEQUENCE: 361
gctgggcaag aa 12

<210> SEQ ID NO 362
<211> LENGTH: 12
<212> TYPE: DNA
<213> ORGANISM: Artificial Sequence
<220> FEATURE:
<223> OTHER INFORMATION: Primer

<400> SEQUENCE: 362
agtcaaagtc aa 12

<210> SEQ ID NO 363
<211> LENGTH: 12
<212> TYPE: DNA
<213> ORGANISM: Artificial Sequence
<220> FEATURE:
<223> OTHER INFORMATION: Primer

<400> SEQUENCE: 363
tctctgcagt aa 12

<210> SEQ ID NO 364
<211> LENGTH: 12
<212> TYPE: DNA
<213> ORGANISM: Artificial Sequence
<220> FEATURE:
<223> OTHER INFORMATION: Primer

<400> SEQUENCE: 364
tgaataactt aa 12

<210> SEQ ID NO 365
<211> LENGTH: 12
<212> TYPE: DNA
<213> ORGANISM: Artificial Sequence
<220> FEATURE:
<223> OTHER INFORMATION: Primer

<400> SEQUENCE: 365
cggttagaaa aa 12

<210> SEQ ID NO 366
<211> LENGTH: 12
<212> TYPE: DNA
<213> ORGANISM: Artificial Sequence
<220> FEATURE:
<223> OTHER INFORMATION: Primer

<400> SEQUENCE: 366
catccctttc aa 12

<210> SEQ ID NO 367
<211> LENGTH: 12
<212> TYPE: DNA
<213> ORGANISM: Artificial Sequence
<220> FEATURE:

-continued

<223> OTHER INFORMATION: Primer

<400> SEQUENCE: 367
tctctttctg aa 12

<210> SEQ ID NO 368
<211> LENGTH: 12
<212> TYPE: DNA
<213> ORGANISM: Artificial Sequence
<220> FEATURE:
<223> OTHER INFORMATION: Primer

<400> SEQUENCE: 368
ctcagattgt aa 12

<210> SEQ ID NO 369
<211> LENGTH: 12
<212> TYPE: DNA
<213> ORGANISM: Artificial Sequence
<220> FEATURE:
<223> OTHER INFORMATION: Primer

<400> SEQUENCE: 369
tttgcaccag aa 12

<210> SEQ ID NO 370
<211> LENGTH: 12
<212> TYPE: DNA
<213> ORGANISM: Artificial Sequence
<220> FEATURE:
<223> OTHER INFORMATION: Primer

<400> SEQUENCE: 370
ggttaacatg aa 12

<210> SEQ ID NO 371
<211> LENGTH: 12
<212> TYPE: DNA
<213> ORGANISM: Artificial Sequence
<220> FEATURE:
<223> OTHER INFORMATION: Primer

<400> SEQUENCE: 371
attatcaact aa 12

<210> SEQ ID NO 372
<211> LENGTH: 12
<212> TYPE: DNA
<213> ORGANISM: Artificial Sequence
<220> FEATURE:
<223> OTHER INFORMATION: Primer

<400> SEQUENCE: 372
gccattttgt aa 12

<210> SEQ ID NO 373
<211> LENGTH: 12
<212> TYPE: DNA
<213> ORGANISM: Artificial Sequence
<220> FEATURE:
<223> OTHER INFORMATION: Primer

<400> SEQUENCE: 373
gatctagatg aa 12

-continued

<210> SEQ ID NO 374
<211> LENGTH: 12
<212> TYPE: DNA
<213> ORGANISM: Artificial Sequence
<220> FEATURE:
<223> OTHER INFORMATION: Primer

<400> SEQUENCE: 374
ttaatgtatt aa 12

<210> SEQ ID NO 375
<211> LENGTH: 12
<212> TYPE: DNA
<213> ORGANISM: Artificial Sequence
<220> FEATURE:
<223> OTHER INFORMATION: Primer

<400> SEQUENCE: 375
ctagggagac aa 12

<210> SEQ ID NO 376
<211> LENGTH: 12
<212> TYPE: DNA
<213> ORGANISM: Artificial Sequence
<220> FEATURE:
<223> OTHER INFORMATION: Primer

<400> SEQUENCE: 376
tggaggagac aa 12

<210> SEQ ID NO 377
<211> LENGTH: 12
<212> TYPE: DNA
<213> ORGANISM: Artificial Sequence
<220> FEATURE:
<223> OTHER INFORMATION: Primer

<400> SEQUENCE: 377
catcacattt aa 12

<210> SEQ ID NO 378
<211> LENGTH: 12
<212> TYPE: DNA
<213> ORGANISM: Artificial Sequence
<220> FEATURE:
<223> OTHER INFORMATION: Primer

<400> SEQUENCE: 378
ggggtcctgc aa 12

<210> SEQ ID NO 379
<211> LENGTH: 12
<212> TYPE: DNA
<213> ORGANISM: Artificial Sequence
<220> FEATURE:
<223> OTHER INFORMATION: Primer

<400> SEQUENCE: 379
cagttgtgct aa 12

<210> SEQ ID NO 380
<211> LENGTH: 12
<212> TYPE: DNA
<213> ORGANISM: Artificial Sequence
<220> FEATURE:
<223> OTHER INFORMATION: Primer -continued

<400> SEQUENCE: 380
tctgcagcct aa 12

<210> SEQ ID NO 381
<211> LENGTH: 12
<212> TYPE: DNA
<213> ORGANISM: Artificial Sequence
<220> FEATURE:
<223> OTHER INFORMATION: Primer

<400> SEQUENCE: 381
gagtcattta aa 12

<210> SEQ ID NO 382
<211> LENGTH: 12
<212> TYPE: DNA
<213> ORGANISM: Artificial Sequence
<220> FEATURE:
<223> OTHER INFORMATION: Primer

<400> SEQUENCE: 382
tctatggatt aa 12

<210> SEQ ID NO 383
<211> LENGTH: 12
<212> TYPE: DNA
<213> ORGANISM: Artificial Sequence
<220> FEATURE:
<223> OTHER INFORMATION: Primer

<400> SEQUENCE: 383
caaaaagtag aa 12

<210> SEQ ID NO 384
<211> LENGTH: 12
<212> TYPE: DNA
<213> ORGANISM: Artificial Sequence
<220> FEATURE:
<223> OTHER INFORMATION: Primer

<400> SEQUENCE: 384
aatatactcc aa 12

<210> SEQ ID NO 385
<211> LENGTH: 12
<212> TYPE: DNA
<213> ORGANISM: Artificial Sequence
<220> FEATURE:
<223> OTHER INFORMATION: Primer

<400> SEQUENCE: 385
cgtccagcac aa 12

<210> SEQ ID NO 386
<211> LENGTH: 12
<212> TYPE: DNA
<213> ORGANISM: Artificial Sequence
<220> FEATURE:
<223> OTHER INFORMATION: Primer

<400> SEQUENCE: 386
ggatggtgag aa 12

<210> SEQ ID NO 387
<211> LENGTH: 12

<212> TYPE: DNA
<213> ORGANISM: Artificial Sequence
<220> FEATURE:
<223> OTHER INFORMATION: Primer

<400> SEQUENCE: 387
tctcctttgt aa 12

<210> SEQ ID NO 388
<211> LENGTH: 12
<212> TYPE: DNA
<213> ORGANISM: Artificial Sequence
<220> FEATURE:
<223> OTHER INFORMATION: Primer

<400> SEQUENCE: 388
tcgttatttc aa 12

<210> SEQ ID NO 389
<211> LENGTH: 12
<212> TYPE: DNA
<213> ORGANISM: Artificial Sequence
<220> FEATURE:
<223> OTHER INFORMATION: Primer

<400> SEQUENCE: 389
gattttatag aa 12

<210> SEQ ID NO 390
<211> LENGTH: 12
<212> TYPE: DNA
<213> ORGANISM: Artificial Sequence
<220> FEATURE:
<223> OTHER INFORMATION: Primer

<400> SEQUENCE: 390
agacataagc aa 12

<210> SEQ ID NO 391
<211> LENGTH: 12
<212> TYPE: DNA
<213> ORGANISM: Artificial Sequence
<220> FEATURE:
<223> OTHER INFORMATION: Primer

<400> SEQUENCE: 391
ttcacctcac aa 12

<210> SEQ ID NO 392
<211> LENGTH: 12
<212> TYPE: DNA
<213> ORGANISM: Artificial Sequence
<220> FEATURE:
<223> OTHER INFORMATION: Primer

<400> SEQUENCE: 392
ggattgcttg aa 12

<210> SEQ ID NO 393
<211> LENGTH: 12
<212> TYPE: DNA
<213> ORGANISM: Artificial Sequence
<220> FEATURE:
<223> OTHER INFORMATION: Primer

<400> SEQUENCE: 393

-continued actgcatgtg aa 12

<210> SEQ ID NO 394
<211> LENGTH: 12
<212> TYPE: DNA
<213> ORGANISM: Artificial Sequence
<220> FEATURE:
<223> OTHER INFORMATION: Primer

<400> SEQUENCE: 394
tttatcacag aa 12

<210> SEQ ID NO 395
<211> LENGTH: 12
<212> TYPE: DNA
<213> ORGANISM: Artificial Sequence
<220> FEATURE:
<223> OTHER INFORMATION: Primer

<400> SEQUENCE: 395
tcagtaacac aa 12

<210> SEQ ID NO 396
<211> LENGTH: 12
<212> TYPE: DNA
<213> ORGANISM: Artificial Sequence
<220> FEATURE:
<223> OTHER INFORMATION: Primer

<400> SEQUENCE: 396
tacatctttg aa 12

<210> SEQ ID NO 397
<211> LENGTH: 12
<212> TYPE: DNA
<213> ORGANISM: Artificial Sequence
<220> FEATURE:
<223> OTHER INFORMATION: Primer

<400> SEQUENCE: 397
ttgtttcagt aa 12

<210> SEQ ID NO 398
<211> LENGTH: 12
<212> TYPE: DNA
<213> ORGANISM: Artificial Sequence
<220> FEATURE:
<223> OTHER INFORMATION: Primer

<400> SEQUENCE: 398
tatgagcatc aa 12

<210> SEQ ID NO 399
<211> LENGTH: 12
<212> TYPE: DNA
<213> ORGANISM: Artificial Sequence
<220> FEATURE:
<223> OTHER INFORMATION: Primer

<400> SEQUENCE: 399
ctcagcaggc aa 12

<210> SEQ ID NO 400
<211> LENGTH: 12
<212> TYPE: DNA
<213> ORGANISM: Artificial Sequence -continued
<220> FEATURE:
<223> OTHER INFORMATION: Primer

<400> SEQUENCE: 400
acccctgtat aa                                                              12

<210> SEQ ID NO 401
<211> LENGTH: 12
<212> TYPE: DNA
<213> ORGANISM: Artificial Sequence
<220> FEATURE:
<223> OTHER INFORMATION: Primer

<400> SEQUENCE: 401
tctgctcagc aa                                                              12

<210> SEQ ID NO 402
<211> LENGTH: 12
<212> TYPE: DNA
<213> ORGANISM: Artificial Sequence
<220> FEATURE:
<223> OTHER INFORMATION: Primer

<400> SEQUENCE: 402
gttctttttt aa                                                              12

<210> SEQ ID NO 403
<211> LENGTH: 12
<212> TYPE: DNA
<213> ORGANISM: Artificial Sequence
<220> FEATURE:
<223> OTHER INFORMATION: Primer

<400> SEQUENCE: 403
gtgataatcc aa                                                              12

<210> SEQ ID NO 404
<211> LENGTH: 12
<212> TYPE: DNA
<213> ORGANISM: Artificial Sequence
<220> FEATURE:
<223> OTHER INFORMATION: Primer

<400> SEQUENCE: 404
gagccctcag aa                                                              12

<210> SEQ ID NO 405
<211> LENGTH: 12
<212> TYPE: DNA
<213> ORGANISM: Artificial Sequence
<220> FEATURE:
<223> OTHER INFORMATION: Primer

<400> SEQUENCE: 405
tttattggtt aa                                                              12

<210> SEQ ID NO 406
<211> LENGTH: 12
<212> TYPE: DNA
<213> ORGANISM: Artificial Sequence
<220> FEATURE:
<223> OTHER INFORMATION: Primer

<400> SEQUENCE: 406
ggtactgggc aa                                                              12

-continued

<210> SEQ ID NO 407
<211> LENGTH: 12
<212> TYPE: DNA
<213> ORGANISM: Artificial Sequence
<220> FEATURE:
<223> OTHER INFORMATION: Primer

<400> SEQUENCE: 407
agtgtttttc aa 12

<210> SEQ ID NO 408
<211> LENGTH: 12
<212> TYPE: DNA
<213> ORGANISM: Artificial Sequence
<220> FEATURE:
<223> OTHER INFORMATION: Primer

<400> SEQUENCE: 408
tgttattggt aa 12

<210> SEQ ID NO 409
<211> LENGTH: 12
<212> TYPE: DNA
<213> ORGANISM: Artificial Sequence
<220> FEATURE:
<223> OTHER INFORMATION: Primer

<400> SEQUENCE: 409
gcgcattcac aa 12

<210> SEQ ID NO 410
<211> LENGTH: 12
<212> TYPE: DNA
<213> ORGANISM: Artificial Sequence
<220> FEATURE:
<223> OTHER INFORMATION: Primer

<400> SEQUENCE: 410
aaacaaaagc aa 12

<210> SEQ ID NO 411
<211> LENGTH: 12
<212> TYPE: DNA
<213> ORGANISM: Artificial Sequence
<220> FEATURE:
<223> OTHER INFORMATION: Primer

<400> SEQUENCE: 411
tatatgatag aa 12

<210> SEQ ID NO 412
<211> LENGTH: 12
<212> TYPE: DNA
<213> ORGANISM: Artificial Sequence
<220> FEATURE:
<223> OTHER INFORMATION: Primer

<400> SEQUENCE: 412
tcccagttcc aa 12

<210> SEQ ID NO 413
<211> LENGTH: 12
<212> TYPE: DNA
<213> ORGANISM: Artificial Sequence
<220> FEATURE:
<223> OTHER INFORMATION: Primer -continued

<400> SEQUENCE: 413
aaagcccata aa 12

<210> SEQ ID NO 414
<211> LENGTH: 12
<212> TYPE: DNA
<213> ORGANISM: Artificial Sequence
<220> FEATURE:
<223> OTHER INFORMATION: Primer

<400> SEQUENCE: 414
tgtcatccac aa 12

<210> SEQ ID NO 415
<211> LENGTH: 12
<212> TYPE: DNA
<213> ORGANISM: Artificial Sequence
<220> FEATURE:
<223> OTHER INFORMATION: Primer

<400> SEQUENCE: 415
ttgtgaatgc aa 12

<210> SEQ ID NO 416
<211> LENGTH: 12
<212> TYPE: DNA
<213> ORGANISM: Artificial Sequence
<220> FEATURE:
<223> OTHER INFORMATION: Primer

<400> SEQUENCE: 416
gtattcatac aa 12

<210> SEQ ID NO 417
<211> LENGTH: 12
<212> TYPE: DNA
<213> ORGANISM: Artificial Sequence
<220> FEATURE:
<223> OTHER INFORMATION: Primer

<400> SEQUENCE: 417
tgacataggg aa 12

<210> SEQ ID NO 418
<211> LENGTH: 12
<212> TYPE: DNA
<213> ORGANISM: Artificial Sequence
<220> FEATURE:
<223> OTHER INFORMATION: Primer

<400> SEQUENCE: 418
agcaaattgc aa 12

<210> SEQ ID NO 419
<211> LENGTH: 12
<212> TYPE: DNA
<213> ORGANISM: Artificial Sequence
<220> FEATURE:
<223> OTHER INFORMATION: Primer

<400> SEQUENCE: 419
agtagatgtt aa 12

<210> SEQ ID NO 420

-continued

<211> LENGTH: 12
<212> TYPE: DNA
<213> ORGANISM: Artificial Sequence
<220> FEATURE:
<223> OTHER INFORMATION: Primer

<400> SEQUENCE: 420
aaaagataat aa 12

<210> SEQ ID NO 421
<211> LENGTH: 12
<212> TYPE: DNA
<213> ORGANISM: Artificial Sequence
<220> FEATURE:
<223> OTHER INFORMATION: Primer

<400> SEQUENCE: 421
acctcatggg aa 12

<210> SEQ ID NO 422
<211> LENGTH: 12
<212> TYPE: DNA
<213> ORGANISM: Artificial Sequence
<220> FEATURE:
<223> OTHER INFORMATION: Primer

<400> SEQUENCE: 422
tggtcgacct aa 12

<210> SEQ ID NO 423
<211> LENGTH: 12
<212> TYPE: DNA
<213> ORGANISM: Artificial Sequence
<220> FEATURE:
<223> OTHER INFORMATION: Primer

<400> SEQUENCE: 423
tttgcatggt aa 12

<210> SEQ ID NO 424
<211> LENGTH: 12
<212> TYPE: DNA
<213> ORGANISM: Artificial Sequence
<220> FEATURE:
<223> OTHER INFORMATION: Primer

<400> SEQUENCE: 424
gcggctgccg aa 12

<210> SEQ ID NO 425
<211> LENGTH: 12
<212> TYPE: DNA
<213> ORGANISM: Artificial Sequence
<220> FEATURE:
<223> OTHER INFORMATION: Primer

<400> SEQUENCE: 425
tcaggagtct aa 12

<210> SEQ ID NO 426
<211> LENGTH: 12
<212> TYPE: DNA
<213> ORGANISM: Artificial Sequence
<220> FEATURE:
<223> OTHER INFORMATION: Primer

<400> SEQUENCE: 426

-continued gcctaccagg aa 12

<210> SEQ ID NO 427
<211> LENGTH: 12
<212> TYPE: DNA
<213> ORGANISM: Artificial Sequence
<220> FEATURE:
<223> OTHER INFORMATION: Primer

<400> SEQUENCE: 427
atcttctgtt aa 12

<210> SEQ ID NO 428
<211> LENGTH: 12
<212> TYPE: DNA
<213> ORGANISM: Artificial Sequence
<220> FEATURE:
<223> OTHER INFORMATION: Primer

<400> SEQUENCE: 428
aggtaaggac aa 12

<210> SEQ ID NO 429
<211> LENGTH: 12
<212> TYPE: DNA
<213> ORGANISM: Artificial Sequence
<220> FEATURE:
<223> OTHER INFORMATION: Primer

<400> SEQUENCE: 429
tgctttgagg aa 12

<210> SEQ ID NO 430
<211> LENGTH: 12
<212> TYPE: DNA
<213> ORGANISM: Artificial Sequence
<220> FEATURE:
<223> OTHER INFORMATION: Primer

<400> SEQUENCE: 430
aacagtttta aa 12

<210> SEQ ID NO 431
<211> LENGTH: 12
<212> TYPE: DNA
<213> ORGANISM: Artificial Sequence
<220> FEATURE:
<223> OTHER INFORMATION: Primer

<400> SEQUENCE: 431
ttaaatgttt aa 12

<210> SEQ ID NO 432
<211> LENGTH: 12
<212> TYPE: DNA
<213> ORGANISM: Artificial Sequence
<220> FEATURE:
<223> OTHER INFORMATION: Primer

<400> SEQUENCE: 432
atagaaaatc aa 12

<210> SEQ ID NO 433
<211> LENGTH: 12
<212> TYPE: DNA

-continued

<213> ORGANISM: Artificial Sequence
<220> FEATURE:
<223> OTHER INFORMATION: Primer

<400> SEQUENCE: 433
gtgttgtgtt aa 12

<210> SEQ ID NO 434
<211> LENGTH: 12
<212> TYPE: DNA
<213> ORGANISM: Artificial Sequence
<220> FEATURE:
<223> OTHER INFORMATION: Primer

<400> SEQUENCE: 434
gaggacctcg aa 12

<210> SEQ ID NO 435
<211> LENGTH: 12
<212> TYPE: DNA
<213> ORGANISM: Artificial Sequence
<220> FEATURE:
<223> OTHER INFORMATION: Primer

<400> SEQUENCE: 435
agaggctgag aa 12

<210> SEQ ID NO 436
<211> LENGTH: 12
<212> TYPE: DNA
<213> ORGANISM: Artificial Sequence
<220> FEATURE:
<223> OTHER INFORMATION: Primer

<400> SEQUENCE: 436
ggtatttatt aa 12

<210> SEQ ID NO 437
<211> LENGTH: 12
<212> TYPE: DNA
<213> ORGANISM: Artificial Sequence
<220> FEATURE:
<223> OTHER INFORMATION: Primer

<400> SEQUENCE: 437
atttatctgg aa 12

<210> SEQ ID NO 438
<211> LENGTH: 12
<212> TYPE: DNA
<213> ORGANISM: Artificial Sequence
<220> FEATURE:
<223> OTHER INFORMATION: Primer

<400> SEQUENCE: 438
agtgcaaact aa 12

<210> SEQ ID NO 439
<211> LENGTH: 12
<212> TYPE: DNA
<213> ORGANISM: Artificial Sequence
<220> FEATURE:
<223> OTHER INFORMATION: Primer

<400> SEQUENCE: 439
tgaacacctt aa 12

```
<210> SEQ ID NO 440
<211> LENGTH: 12
<212> TYPE: DNA
<213> ORGANISM: Artificial Sequence
<220> FEATURE:
<223> OTHER INFORMATION: Primer

<400> SEQUENCE: 440

aattttttct aa                                                         12

<210> SEQ ID NO 441
<211> LENGTH: 12
<212> TYPE: DNA
<213> ORGANISM: Artificial Sequence
<220> FEATURE:
<223> OTHER INFORMATION: Primer

<400> SEQUENCE: 441

ttactattat aa                                                         12

<210> SEQ ID NO 442
<211> LENGTH: 12
<212> TYPE: DNA
<213> ORGANISM: Artificial Sequence
<220> FEATURE:
<223> OTHER INFORMATION: Primer

<400> SEQUENCE: 442

tgctatagtg aa                                                         12

<210> SEQ ID NO 443
<211> LENGTH: 12
<212> TYPE: DNA
<213> ORGANISM: Artificial Sequence
<220> FEATURE:
<223> OTHER INFORMATION: Primer

<400> SEQUENCE: 443

tggactatgg aa                                                         12

<210> SEQ ID NO 444
<211> LENGTH: 12
<212> TYPE: DNA
<213> ORGANISM: Artificial Sequence
<220> FEATURE:
<223> OTHER INFORMATION: Primer

<400> SEQUENCE: 444

ctgcagtccg aa                                                         12

<210> SEQ ID NO 445
<211> LENGTH: 12
<212> TYPE: DNA
<213> ORGANISM: Artificial Sequence
<220> FEATURE:
<223> OTHER INFORMATION: Primer

<400> SEQUENCE: 445

gctactgccc aa                                                         12

<210> SEQ ID NO 446
<211> LENGTH: 12
<212> TYPE: DNA
<213> ORGANISM: Artificial Sequence
<220> FEATURE:
```

```
<223> OTHER INFORMATION: Primer

<400> SEQUENCE: 446

tcacatggtg aa                                                          12

<210> SEQ ID NO 447
<211> LENGTH: 12
<212> TYPE: DNA
<213> ORGANISM: Artificial Sequence
<220> FEATURE:
<223> OTHER INFORMATION: Primer

<400> SEQUENCE: 447

gtggctctgg aa                                                          12

<210> SEQ ID NO 448
<211> LENGTH: 12
<212> TYPE: DNA
<213> ORGANISM: Artificial Sequence
<220> FEATURE:
<223> OTHER INFORMATION: Primer

<400> SEQUENCE: 448

gaattccatt aa                                                          12

<210> SEQ ID NO 449
<211> LENGTH: 12
<212> TYPE: DNA
<213> ORGANISM: Artificial Sequence
<220> FEATURE:
<223> OTHER INFORMATION: Primer

<400> SEQUENCE: 449

tggggtgtcc aa                                                          12

<210> SEQ ID NO 450
<211> LENGTH: 12
<212> TYPE: DNA
<213> ORGANISM: Artificial Sequence
<220> FEATURE:
<223> OTHER INFORMATION: Primer

<400> SEQUENCE: 450

gcaagctccg aa                                                          12

<210> SEQ ID NO 451
<211> LENGTH: 12
<212> TYPE: DNA
<213> ORGANISM: Artificial Sequence
<220> FEATURE:
<223> OTHER INFORMATION: Primer

<400> SEQUENCE: 451

atgttttttc aa                                                          12

<210> SEQ ID NO 452
<211> LENGTH: 12
<212> TYPE: DNA
<213> ORGANISM: Artificial Sequence
<220> FEATURE:
<223> OTHER INFORMATION: Primer

<400> SEQUENCE: 452

agatctgttg aa                                                          12
```

-continued

<210> SEQ ID NO 453
<211> LENGTH: 12
<212> TYPE: DNA
<213> ORGANISM: Artificial Sequence
<220> FEATURE:
<223> OTHER INFORMATION: Primer

<400> SEQUENCE: 453
aagtgctgtg aa 12

<210> SEQ ID NO 454
<211> LENGTH: 12
<212> TYPE: DNA
<213> ORGANISM: Artificial Sequence
<220> FEATURE:
<223> OTHER INFORMATION: Primer

<400> SEQUENCE: 454
acttttttgg aa 12

<210> SEQ ID NO 455
<211> LENGTH: 12
<212> TYPE: DNA
<213> ORGANISM: Artificial Sequence
<220> FEATURE:
<223> OTHER INFORMATION: Primer

<400> SEQUENCE: 455
aatcggcagg aa 12

<210> SEQ ID NO 456
<211> LENGTH: 12
<212> TYPE: DNA
<213> ORGANISM: Artificial Sequence
<220> FEATURE:
<223> OTHER INFORMATION: Primer

<400> SEQUENCE: 456
ggcatgtcac aa 12

<210> SEQ ID NO 457
<211> LENGTH: 12
<212> TYPE: DNA
<213> ORGANISM: Artificial Sequence
<220> FEATURE:
<223> OTHER INFORMATION: Primer

<400> SEQUENCE: 457
aggaagaaag aa 12

<210> SEQ ID NO 458
<211> LENGTH: 12
<212> TYPE: DNA
<213> ORGANISM: Artificial Sequence
<220> FEATURE:
<223> OTHER INFORMATION: Primer

<400> SEQUENCE: 458
cagtttcacc aa 12

<210> SEQ ID NO 459
<211> LENGTH: 12
<212> TYPE: DNA
<213> ORGANISM: Artificial Sequence
<220> FEATURE:
<223> OTHER INFORMATION: Primer -continued

<400> SEQUENCE: 459
cacagaattt aa 12

<210> SEQ ID NO 460
<211> LENGTH: 12
<212> TYPE: DNA
<213> ORGANISM: Artificial Sequence
<220> FEATURE:
<223> OTHER INFORMATION: Primer

<400> SEQUENCE: 460
aagaataagt aa 12

<210> SEQ ID NO 461
<211> LENGTH: 12
<212> TYPE: DNA
<213> ORGANISM: Artificial Sequence
<220> FEATURE:
<223> OTHER INFORMATION: Primer

<400> SEQUENCE: 461
gggatagtac aa 12

<210> SEQ ID NO 462
<211> LENGTH: 12
<212> TYPE: DNA
<213> ORGANISM: Artificial Sequence
<220> FEATURE:
<223> OTHER INFORMATION: Primer

<400> SEQUENCE: 462
ttcccatgat aa 12

<210> SEQ ID NO 463
<211> LENGTH: 12
<212> TYPE: DNA
<213> ORGANISM: Artificial Sequence
<220> FEATURE:
<223> OTHER INFORMATION: Primer

<400> SEQUENCE: 463
tgattagttg aa 12

<210> SEQ ID NO 464
<211> LENGTH: 12
<212> TYPE: DNA
<213> ORGANISM: Artificial Sequence
<220> FEATURE:
<223> OTHER INFORMATION: Primer

<400> SEQUENCE: 464
gcattcagtg aa 12

<210> SEQ ID NO 465
<211> LENGTH: 12
<212> TYPE: DNA
<213> ORGANISM: Artificial Sequence
<220> FEATURE:
<223> OTHER INFORMATION: Primer

<400> SEQUENCE: 465
agggaatatt aa 12

<210> SEQ ID NO 466
<211> LENGTH: 12

-continued

<212> TYPE: DNA
<213> ORGANISM: Artificial Sequence
<220> FEATURE:
<223> OTHER INFORMATION: Primer

<400> SEQUENCE: 466
gaccttaggt aa 12

<210> SEQ ID NO 467
<211> LENGTH: 12
<212> TYPE: DNA
<213> ORGANISM: Artificial Sequence
<220> FEATURE:
<223> OTHER INFORMATION: Primer

<400> SEQUENCE: 467
ttcttttcac aa 12

<210> SEQ ID NO 468
<211> LENGTH: 12
<212> TYPE: DNA
<213> ORGANISM: Artificial Sequence
<220> FEATURE:
<223> OTHER INFORMATION: Primer

<400> SEQUENCE: 468
ccaaactaag aa 12

<210> SEQ ID NO 469
<211> LENGTH: 12
<212> TYPE: DNA
<213> ORGANISM: Artificial Sequence
<220> FEATURE:
<223> OTHER INFORMATION: Primer

<400> SEQUENCE: 469
gtgctcttag aa 12

<210> SEQ ID NO 470
<211> LENGTH: 12
<212> TYPE: DNA
<213> ORGANISM: Artificial Sequence
<220> FEATURE:
<223> OTHER INFORMATION: Primer

<400> SEQUENCE: 470
atgagtttag aa 12

<210> SEQ ID NO 471
<211> LENGTH: 12
<212> TYPE: DNA
<213> ORGANISM: Artificial Sequence
<220> FEATURE:
<223> OTHER INFORMATION: Primer

<400> SEQUENCE: 471
atgagcatag aa 12

<210> SEQ ID NO 472
<211> LENGTH: 12
<212> TYPE: DNA
<213> ORGANISM: Artificial Sequence
<220> FEATURE:
<223> OTHER INFORMATION: Primer

<400> SEQUENCE: 472

-continued gacaaatgag aa 12

<210> SEQ ID NO 473
<211> LENGTH: 12
<212> TYPE: DNA
<213> ORGANISM: Artificial Sequence
<220> FEATURE:
<223> OTHER INFORMATION: Primer

<400> SEQUENCE: 473
aaacccagag aa 12

<210> SEQ ID NO 474
<211> LENGTH: 12
<212> TYPE: DNA
<213> ORGANISM: Artificial Sequence
<220> FEATURE:
<223> OTHER INFORMATION: Primer

<400> SEQUENCE: 474
cctcacacag aa 12

<210> SEQ ID NO 475
<211> LENGTH: 12
<212> TYPE: DNA
<213> ORGANISM: Artificial Sequence
<220> FEATURE:
<223> OTHER INFORMATION: Primer

<400> SEQUENCE: 475
cacactgtgg aa 12

<210> SEQ ID NO 476
<211> LENGTH: 12
<212> TYPE: DNA
<213> ORGANISM: Artificial Sequence
<220> FEATURE:
<223> OTHER INFORMATION: Primer

<400> SEQUENCE: 476
cactgtaccc aa 12

<210> SEQ ID NO 477
<211> LENGTH: 12
<212> TYPE: DNA
<213> ORGANISM: Artificial Sequence
<220> FEATURE:
<223> OTHER INFORMATION: Primer

<400> SEQUENCE: 477
gtagtatttc aa 12

<210> SEQ ID NO 478
<211> LENGTH: 12
<212> TYPE: DNA
<213> ORGANISM: Artificial Sequence
<220> FEATURE:
<223> OTHER INFORMATION: Primer

<400> SEQUENCE: 478
tggatacact aa 12

<210> SEQ ID NO 479
<211> LENGTH: 12
<212> TYPE: DNA
<213> ORGANISM: Artificial Sequence -continued
<220> FEATURE:
<223> OTHER INFORMATION: Primer

<400> SEQUENCE: 479
cccatgattc aa 12

<210> SEQ ID NO 480
<211> LENGTH: 12
<212> TYPE: DNA
<213> ORGANISM: Artificial Sequence
<220> FEATURE:
<223> OTHER INFORMATION: Primer

<400> SEQUENCE: 480
tcataggagg aa 12

<210> SEQ ID NO 481
<211> LENGTH: 12
<212> TYPE: DNA
<213> ORGANISM: Artificial Sequence
<220> FEATURE:
<223> OTHER INFORMATION: Primer

<400> SEQUENCE: 481
aggaaagaga aa 12

<210> SEQ ID NO 482
<211> LENGTH: 12
<212> TYPE: DNA
<213> ORGANISM: Artificial Sequence
<220> FEATURE:
<223> OTHER INFORMATION: Primer

<400> SEQUENCE: 482
atatggtgat aa 12

<210> SEQ ID NO 483
<211> LENGTH: 12
<212> TYPE: DNA
<213> ORGANISM: Artificial Sequence
<220> FEATURE:
<223> OTHER INFORMATION: Primer

<400> SEQUENCE: 483
gatgccatcc aa 12

<210> SEQ ID NO 484
<211> LENGTH: 12
<212> TYPE: DNA
<213> ORGANISM: Artificial Sequence
<220> FEATURE:
<223> OTHER INFORMATION: Primer

<400> SEQUENCE: 484
atactatttc aa 12

<210> SEQ ID NO 485
<211> LENGTH: 12
<212> TYPE: DNA
<213> ORGANISM: Artificial Sequence
<220> FEATURE:
<223> OTHER INFORMATION: Primer

<400> SEQUENCE: 485
gtgtgcatgg aa 12

-continued

<210> SEQ ID NO 486
<211> LENGTH: 12
<212> TYPE: DNA
<213> ORGANISM: Artificial Sequence
<220> FEATURE:
<223> OTHER INFORMATION: Primer

<400> SEQUENCE: 486
aggtgttgag aa 12

<210> SEQ ID NO 487
<211> LENGTH: 12
<212> TYPE: DNA
<213> ORGANISM: Artificial Sequence
<220> FEATURE:
<223> OTHER INFORMATION: Primer

<400> SEQUENCE: 487
cagcctgggc aa 12

<210> SEQ ID NO 488
<211> LENGTH: 12
<212> TYPE: DNA
<213> ORGANISM: Artificial Sequence
<220> FEATURE:
<223> OTHER INFORMATION: Primer

<400> SEQUENCE: 488
ggagctctac aa 12

<210> SEQ ID NO 489
<211> LENGTH: 12
<212> TYPE: DNA
<213> ORGANISM: Artificial Sequence
<220> FEATURE:
<223> OTHER INFORMATION: Primer

<400> SEQUENCE: 489
aactaaggtt aa 12

<210> SEQ ID NO 490
<211> LENGTH: 12
<212> TYPE: DNA
<213> ORGANISM: Artificial Sequence
<220> FEATURE:
<223> OTHER INFORMATION: Primer

<400> SEQUENCE: 490
aacttatgtt aa 12

<210> SEQ ID NO 491
<211> LENGTH: 12
<212> TYPE: DNA
<213> ORGANISM: Artificial Sequence
<220> FEATURE:
<223> OTHER INFORMATION: Primer

<400> SEQUENCE: 491
atctcaacag aa 12

<210> SEQ ID NO 492
<211> LENGTH: 12
<212> TYPE: DNA
<213> ORGANISM: Artificial Sequence
<220> FEATURE:
<223> OTHER INFORMATION: Primer -continued

<400> SEQUENCE: 492
taacaatgtg aa 12

<210> SEQ ID NO 493
<211> LENGTH: 12
<212> TYPE: DNA
<213> ORGANISM: Artificial Sequence
<220> FEATURE:
<223> OTHER INFORMATION: Primer

<400> SEQUENCE: 493
aaggatcagg aa 12

<210> SEQ ID NO 494
<211> LENGTH: 12
<212> TYPE: DNA
<213> ORGANISM: Artificial Sequence
<220> FEATURE:
<223> OTHER INFORMATION: Primer

<400> SEQUENCE: 494
ctcaagtctt aa 12

<210> SEQ ID NO 495
<211> LENGTH: 38
<212> TYPE: DNA
<213> ORGANISM: Artificial Sequence
<220> FEATURE:
<223> OTHER INFORMATION: Primer

<400> SEQUENCE: 495
ttagtcatcg cagaattcta cttctttctg aagtggga 38

<210> SEQ ID NO 496
<211> LENGTH: 29
<212> TYPE: DNA
<213> ORGANISM: Artificial Sequence
<220> FEATURE:
<223> OTHER INFORMATION: Primer

<400> SEQUENCE: 496
ggacagctcg atgggactaa tgcatactc 29

<210> SEQ ID NO 497
<211> LENGTH: 38
<212> TYPE: DNA
<213> ORGANISM: Artificial Sequence
<220> FEATURE:
<223> OTHER INFORMATION: Primer

<400> SEQUENCE: 497
gtagccactg gtgaattcgt gccatcgcaa aagaataa 38

<210> SEQ ID NO 498
<211> LENGTH: 29
<212> TYPE: DNA
<213> ORGANISM: Artificial Sequence
<220> FEATURE:
<223> OTHER INFORMATION: Primer

<400> SEQUENCE: 498
attagaatga tggggacccc tgtcttccc 29

<210> SEQ ID NO 499

-continued

<211> LENGTH: 38
<212> TYPE: DNA
<213> ORGANISM: Artificial Sequence
<220> FEATURE:
<223> OTHER INFORMATION: Primer

<400> SEQUENCE: 499
acgcatagga aggaattcat tctgacacgt gtgagata 38

<210> SEQ ID NO 500
<211> LENGTH: 29
<212> TYPE: DNA
<213> ORGANISM: Artificial Sequence
<220> FEATURE:
<223> OTHER INFORMATION: Primer

<400> SEQUENCE: 500
gaaattgacc acgggactgc acacttttc 29

<210> SEQ ID NO 501
<211> LENGTH: 38
<212> TYPE: DNA
<213> ORGANISM: Artificial Sequence
<220> FEATURE:
<223> OTHER INFORMATION: Primer

<400> SEQUENCE: 501
cggtaaatcg gagaattcaa gttgaggcat gcatccat 38

<210> SEQ ID NO 502
<211> LENGTH: 29
<212> TYPE: DNA
<213> ORGANISM: Artificial Sequence
<220> FEATURE:
<223> OTHER INFORMATION: Primer

<400> SEQUENCE: 502
tcggggctca gcgggaccac agccactcc 29

<210> SEQ ID NO 503
<211> LENGTH: 38
<212> TYPE: DNA
<213> ORGANISM: Artificial Sequence
<220> FEATURE:
<223> OTHER INFORMATION: Primer

<400> SEQUENCE: 503
tctatgcacc acgaattcaa tatgtgttca aggacatt 38

<210> SEQ ID NO 504
<211> LENGTH: 29
<212> TYPE: DNA
<213> ORGANISM: Artificial Sequence
<220> FEATURE:
<223> OTHER INFORMATION: Primer

<400> SEQUENCE: 504
tgcttaatcg gtgggacttg taattgtac 29

<210> SEQ ID NO 505
<211> LENGTH: 38
<212> TYPE: DNA
<213> ORGANISM: Artificial Sequence
<220> FEATURE:
<223> OTHER INFORMATION: Primer

<400> SEQUENCE: 505

-continued cgcgttgtat gcgaattccc tggggtataa agataaga 38

<210> SEQ ID NO 506
<211> LENGTH: 29
<212> TYPE: DNA
<213> ORGANISM: Artificial Sequence
<220> FEATURE:
<223> OTHER INFORMATION: Primer

<400> SEQUENCE: 506
ctcacgggaa ctgggacacc tgaccctgc 29

<210> SEQ ID NO 507
<211> LENGTH: 38
<212> TYPE: DNA
<213> ORGANISM: Artificial Sequence
<220> FEATURE:
<223> OTHER INFORMATION: Primer

<400> SEQUENCE: 507
gtcttgccgc ttgaattccc atagaagaat gcgccaaa 38

<210> SEQ ID NO 508
<211> LENGTH: 29
<212> TYPE: DNA
<213> ORGANISM: Artificial Sequence
<220> FEATURE:
<223> OTHER INFORMATION: Primer

<400> SEQUENCE: 508
ttgagtagta cagggacaca ctaacagac 29

<210> SEQ ID NO 509
<211> LENGTH: 38
<212> TYPE: DNA
<213> ORGANISM: Artificial Sequence
<220> FEATURE:
<223> OTHER INFORMATION: Primer

<400> SEQUENCE: 509
aatactgtag gtgaattctt gcctaagcat tttcccag 38

<210> SEQ ID NO 510
<211> LENGTH: 29
<212> TYPE: DNA
<213> ORGANISM: Artificial Sequence
<220> FEATURE:
<223> OTHER INFORMATION: Primer

<400> SEQUENCE: 510
gtgttgacat tcgggactgt aatcttgac 29

<210> SEQ ID NO 511
<211> LENGTH: 38
<212> TYPE: DNA
<213> ORGANISM: Artificial Sequence
<220> FEATURE:
<223> OTHER INFORMATION: Primer

<400> SEQUENCE: 511
tctgtagatt cggaattctt tagagcctgt gcgctgag 38

<210> SEQ ID NO 512
<211> LENGTH: 29
<212> TYPE: DNA

-continued

<213> ORGANISM: Artificial Sequence
<220> FEATURE:
<223> OTHER INFORMATION: Primer

<400> SEQUENCE: 512
cgtaccagta cagggacgca aactgagac 29

<210> SEQ ID NO 513
<211> LENGTH: 12
<212> TYPE: DNA
<213> ORGANISM: Artificial Sequence
<220> FEATURE:
<223> OTHER INFORMATION: Primer

<400> SEQUENCE: 513
gacatgttgg aa 12

<210> SEQ ID NO 514
<211> LENGTH: 12
<212> TYPE: DNA
<213> ORGANISM: Artificial Sequence
<220> FEATURE:
<223> OTHER INFORMATION: Primer

<400> SEQUENCE: 514
acttccagtt aa 12

<210> SEQ ID NO 515
<211> LENGTH: 12
<212> TYPE: DNA
<213> ORGANISM: Artificial Sequence
<220> FEATURE:
<223> OTHER INFORMATION: Primer

<400> SEQUENCE: 515
gtttcctgtt aa 12

<210> SEQ ID NO 516
<211> LENGTH: 12
<212> TYPE: DNA
<213> ORGANISM: Artificial Sequence
<220> FEATURE:
<223> OTHER INFORMATION: Primer

<400> SEQUENCE: 516
cgatgatgac aa 12

<210> SEQ ID NO 517
<211> LENGTH: 12
<212> TYPE: DNA
<213> ORGANISM: Artificial Sequence
<220> FEATURE:
<223> OTHER INFORMATION: Primer

<400> SEQUENCE: 517
gagtagagac aa 12

<210> SEQ ID NO 518
<211> LENGTH: 12
<212> TYPE: DNA
<213> ORGANISM: Artificial Sequence
<220> FEATURE:
<223> OTHER INFORMATION: Primer

<400> SEQUENCE: 518
tcccggatac aa 12

-continued

<210> SEQ ID NO 519
<211> LENGTH: 12
<212> TYPE: DNA
<213> ORGANISM: Artificial Sequence
<220> FEATURE:
<223> OTHER INFORMATION: Primer

<400> SEQUENCE: 519
catcctctag aa 12

<210> SEQ ID NO 520
<211> LENGTH: 12
<212> TYPE: DNA
<213> ORGANISM: Artificial Sequence
<220> FEATURE:
<223> OTHER INFORMATION: Primer

<400> SEQUENCE: 520
tattcctgag aa 12

<210> SEQ ID NO 521
<211> LENGTH: 12
<212> TYPE: DNA
<213> ORGANISM: Artificial Sequence
<220> FEATURE:
<223> OTHER INFORMATION: Primer

<400> SEQUENCE: 521
agtttgtttt aa 12

<210> SEQ ID NO 522
<211> LENGTH: 12
<212> TYPE: DNA
<213> ORGANISM: Artificial Sequence
<220> FEATURE:
<223> OTHER INFORMATION: Primer

<400> SEQUENCE: 522
tataaacgat aa 12

<210> SEQ ID NO 523
<211> LENGTH: 12
<212> TYPE: DNA
<213> ORGANISM: Artificial Sequence
<220> FEATURE:
<223> OTHER INFORMATION: Primer

<400> SEQUENCE: 523
tttgaccgat aa 12

<210> SEQ ID NO 524
<211> LENGTH: 12
<212> TYPE: DNA
<213> ORGANISM: Artificial Sequence
<220> FEATURE:
<223> OTHER INFORMATION: Primer

<400> SEQUENCE: 524
tgacaggacc aa 12

<210> SEQ ID NO 525
<211> LENGTH: 12
<212> TYPE: DNA
<213> ORGANISM: Artificial Sequence
<220> FEATURE:

-continued

<223> OTHER INFORMATION: Primer

<400> SEQUENCE: 525
ttattcattc aa 12

<210> SEQ ID NO 526
<211> LENGTH: 12
<212> TYPE: DNA
<213> ORGANISM: Artificial Sequence
<220> FEATURE:
<223> OTHER INFORMATION: Primer

<400> SEQUENCE: 526
agtttttcac aa 12

<210> SEQ ID NO 527
<211> LENGTH: 12
<212> TYPE: DNA
<213> ORGANISM: Artificial Sequence
<220> FEATURE:
<223> OTHER INFORMATION: Primer

<400> SEQUENCE: 527
cacctccctg aa 12

<210> SEQ ID NO 528
<211> LENGTH: 12
<212> TYPE: DNA
<213> ORGANISM: Artificial Sequence
<220> FEATURE:
<223> OTHER INFORMATION: Primer

<400> SEQUENCE: 528
ccagattgag aa 12

<210> SEQ ID NO 529
<211> LENGTH: 12
<212> TYPE: DNA
<213> ORGANISM: Artificial Sequence
<220> FEATURE:
<223> OTHER INFORMATION: Primer

<400> SEQUENCE: 529
tgtgtccacc aa 12

<210> SEQ ID NO 530
<211> LENGTH: 12
<212> TYPE: DNA
<213> ORGANISM: Artificial Sequence
<220> FEATURE:
<223> OTHER INFORMATION: Primer

<400> SEQUENCE: 530
cttctattcc aa 12

<210> SEQ ID NO 531
<211> LENGTH: 12
<212> TYPE: DNA
<213> ORGANISM: Artificial Sequence
<220> FEATURE:
<223> OTHER INFORMATION: Primer

<400> SEQUENCE: 531
tcacaatagg aa 12

-continued

<210> SEQ ID NO 532
<211> LENGTH: 12
<212> TYPE: DNA
<213> ORGANISM: Artificial Sequence
<220> FEATURE:
<223> OTHER INFORMATION: Primer

<400> SEQUENCE: 532
tacaagtgag aa 12

<210> SEQ ID NO 533
<211> LENGTH: 12
<212> TYPE: DNA
<213> ORGANISM: Artificial Sequence
<220> FEATURE:
<223> OTHER INFORMATION: Primer

<400> SEQUENCE: 533
gagttttcgt aa 12

<210> SEQ ID NO 534
<211> LENGTH: 12
<212> TYPE: DNA
<213> ORGANISM: Artificial Sequence
<220> FEATURE:
<223> OTHER INFORMATION: Primer

<400> SEQUENCE: 534
gtgtgccccc aa 12

<210> SEQ ID NO 535
<211> LENGTH: 12
<212> TYPE: DNA
<213> ORGANISM: Artificial Sequence
<220> FEATURE:
<223> OTHER INFORMATION: Primer

<400> SEQUENCE: 535
gcaccactgc aa 12

<210> SEQ ID NO 536
<211> LENGTH: 12
<212> TYPE: DNA
<213> ORGANISM: Artificial Sequence
<220> FEATURE:
<223> OTHER INFORMATION: Primer

<400> SEQUENCE: 536
gaacacaatg aa 12

<210> SEQ ID NO 537
<211> LENGTH: 12
<212> TYPE: DNA
<213> ORGANISM: Artificial Sequence
<220> FEATURE:
<223> OTHER INFORMATION: Primer

<400> SEQUENCE: 537
tatcctattc aa 12

<210> SEQ ID NO 538
<211> LENGTH: 12
<212> TYPE: DNA
<213> ORGANISM: Artificial Sequence
<220> FEATURE:
<223> OTHER INFORMATION: Primer -continued

<400> SEQUENCE: 538
caaccattat aa 12

<210> SEQ ID NO 539
<211> LENGTH: 12
<212> TYPE: DNA
<213> ORGANISM: Artificial Sequence
<220> FEATURE:
<223> OTHER INFORMATION: Primer

<400> SEQUENCE: 539
tatgctttac aa 12

<210> SEQ ID NO 540
<211> LENGTH: 12
<212> TYPE: DNA
<213> ORGANISM: Artificial Sequence
<220> FEATURE:
<223> OTHER INFORMATION: Primer

<400> SEQUENCE: 540
tttgtttacc aa 12

<210> SEQ ID NO 541
<211> LENGTH: 12
<212> TYPE: DNA
<213> ORGANISM: Artificial Sequence
<220> FEATURE:
<223> OTHER INFORMATION: Primer

<400> SEQUENCE: 541
aggaaattag aa 12

<210> SEQ ID NO 542
<211> LENGTH: 12
<212> TYPE: DNA
<213> ORGANISM: Artificial Sequence
<220> FEATURE:
<223> OTHER INFORMATION: Primer

<400> SEQUENCE: 542
tgttagactt aa 12

<210> SEQ ID NO 543
<211> LENGTH: 12
<212> TYPE: DNA
<213> ORGANISM: Artificial Sequence
<220> FEATURE:
<223> OTHER INFORMATION: Primer

<400> SEQUENCE: 543
tatttggagg aa 12

<210> SEQ ID NO 544
<211> LENGTH: 12
<212> TYPE: DNA
<213> ORGANISM: Artificial Sequence
<220> FEATURE:
<223> OTHER INFORMATION: Primer

<400> SEQUENCE: 544
ggcatttgtc aa 12

<210> SEQ ID NO 545
<211> LENGTH: 12

-continued

<212> TYPE: DNA
<213> ORGANISM: Artificial Sequence
<220> FEATURE:
<223> OTHER INFORMATION: Primer

<400> SEQUENCE: 545
atactccagg aa 12

<210> SEQ ID NO 546
<211> LENGTH: 12
<212> TYPE: DNA
<213> ORGANISM: Artificial Sequence
<220> FEATURE:
<223> OTHER INFORMATION: Primer

<400> SEQUENCE: 546
cagcctggac aa 12

<210> SEQ ID NO 547
<211> LENGTH: 12
<212> TYPE: DNA
<213> ORGANISM: Artificial Sequence
<220> FEATURE:
<223> OTHER INFORMATION: Primer

<400> SEQUENCE: 547
ccattgcagt aa 12

<210> SEQ ID NO 548
<211> LENGTH: 12
<212> TYPE: DNA
<213> ORGANISM: Artificial Sequence
<220> FEATURE:
<223> OTHER INFORMATION: Primer

<400> SEQUENCE: 548
aggttctcat aa 12

<210> SEQ ID NO 549
<211> LENGTH: 12
<212> TYPE: DNA
<213> ORGANISM: Artificial Sequence
<220> FEATURE:
<223> OTHER INFORMATION: Primer

<400> SEQUENCE: 549
tgtcatcatt aa 12

<210> SEQ ID NO 550
<211> LENGTH: 12
<212> TYPE: DNA
<213> ORGANISM: Artificial Sequence
<220> FEATURE:
<223> OTHER INFORMATION: Primer

<400> SEQUENCE: 550
tggtatttgc aa 12

<210> SEQ ID NO 551
<211> LENGTH: 12
<212> TYPE: DNA
<213> ORGANISM: Artificial Sequence
<220> FEATURE:
<223> OTHER INFORMATION: Primer

<400> SEQUENCE: 551

-continued tagggtttgt aa 12

<210> SEQ ID NO 552
<211> LENGTH: 12
<212> TYPE: DNA
<213> ORGANISM: Artificial Sequence
<220> FEATURE:
<223> OTHER INFORMATION: Primer

<400> SEQUENCE: 552
ccctaagtag aa 12

<210> SEQ ID NO 553
<211> LENGTH: 12
<212> TYPE: DNA
<213> ORGANISM: Artificial Sequence
<220> FEATURE:
<223> OTHER INFORMATION: Primer

<400> SEQUENCE: 553
gtatttcttt aa 12

<210> SEQ ID NO 554
<211> LENGTH: 12
<212> TYPE: DNA
<213> ORGANISM: Artificial Sequence
<220> FEATURE:
<223> OTHER INFORMATION: Primer

<400> SEQUENCE: 554
gagtcttccc aa 12

<210> SEQ ID NO 555
<211> LENGTH: 12
<212> TYPE: DNA
<213> ORGANISM: Artificial Sequence
<220> FEATURE:
<223> OTHER INFORMATION: Primer

<400> SEQUENCE: 555
caggtagagt aa 12

<210> SEQ ID NO 556
<211> LENGTH: 12
<212> TYPE: DNA
<213> ORGANISM: Artificial Sequence
<220> FEATURE:
<223> OTHER INFORMATION: Primer

<400> SEQUENCE: 556
ataggatgtg aa 12

<210> SEQ ID NO 557
<211> LENGTH: 12
<212> TYPE: DNA
<213> ORGANISM: Artificial Sequence
<220> FEATURE:
<223> OTHER INFORMATION: Primer

<400> SEQUENCE: 557
caatgtgtat aa 12

<210> SEQ ID NO 558
<211> LENGTH: 12
<212> TYPE: DNA
<213> ORGANISM: Artificial Sequence -continued
<220> FEATURE:
<223> OTHER INFORMATION: Primer

<400> SEQUENCE: 558
agagggcatc aa 12

<210> SEQ ID NO 559
<211> LENGTH: 12
<212> TYPE: DNA
<213> ORGANISM: Artificial Sequence
<220> FEATURE:
<223> OTHER INFORMATION: Primer

<400> SEQUENCE: 559
ccagtggtct aa 12

<210> SEQ ID NO 560
<211> LENGTH: 12
<212> TYPE: DNA
<213> ORGANISM: Artificial Sequence
<220> FEATURE:
<223> OTHER INFORMATION: Primer

<400> SEQUENCE: 560
taaacaatag aa 12

<210> SEQ ID NO 561
<211> LENGTH: 12
<212> TYPE: DNA
<213> ORGANISM: Artificial Sequence
<220> FEATURE:
<223> OTHER INFORMATION: Primer

<400> SEQUENCE: 561
gcacactttt aa 12

<210> SEQ ID NO 562
<211> LENGTH: 12
<212> TYPE: DNA
<213> ORGANISM: Artificial Sequence
<220> FEATURE:
<223> OTHER INFORMATION: Primer

<400> SEQUENCE: 562
atggctctgc aa 12

<210> SEQ ID NO 563
<211> LENGTH: 12
<212> TYPE: DNA
<213> ORGANISM: Artificial Sequence
<220> FEATURE:
<223> OTHER INFORMATION: Primer

<400> SEQUENCE: 563
gtcatcttgt aa 12

<210> SEQ ID NO 564
<211> LENGTH: 12
<212> TYPE: DNA
<213> ORGANISM: Artificial Sequence
<220> FEATURE:
<223> OTHER INFORMATION: Primer

<400> SEQUENCE: 564
tgcttcatct aa 12

-continued

<210> SEQ ID NO 565
<211> LENGTH: 12
<212> TYPE: DNA
<213> ORGANISM: Artificial Sequence
<220> FEATURE:
<223> OTHER INFORMATION: Primer

<400> SEQUENCE: 565
agaaaggggc aa 12

<210> SEQ ID NO 566
<211> LENGTH: 12
<212> TYPE: DNA
<213> ORGANISM: Artificial Sequence
<220> FEATURE:
<223> OTHER INFORMATION: Primer

<400> SEQUENCE: 566
cttttctttc aa 12

<210> SEQ ID NO 567
<211> LENGTH: 12
<212> TYPE: DNA
<213> ORGANISM: Artificial Sequence
<220> FEATURE:
<223> OTHER INFORMATION: Primer

<400> SEQUENCE: 567
ctactctctc aa 12

<210> SEQ ID NO 568
<211> LENGTH: 12
<212> TYPE: DNA
<213> ORGANISM: Artificial Sequence
<220> FEATURE:
<223> OTHER INFORMATION: Primer

<400> SEQUENCE: 568
acagcattat aa 12

<210> SEQ ID NO 569
<211> LENGTH: 12
<212> TYPE: DNA
<213> ORGANISM: Artificial Sequence
<220> FEATURE:
<223> OTHER INFORMATION: Primer

<400> SEQUENCE: 569
actgctctgg aa 12

<210> SEQ ID NO 570
<211> LENGTH: 12
<212> TYPE: DNA
<213> ORGANISM: Artificial Sequence
<220> FEATURE:
<223> OTHER INFORMATION: Primer

<400> SEQUENCE: 570
gcagaggcac aa 12

<210> SEQ ID NO 571
<211> LENGTH: 38
<212> TYPE: DNA
<213> ORGANISM: Artificial Sequence
<220> FEATURE:
<223> OTHER INFORMATION: Primer -continued

<400> SEQUENCE: 571
ctccgtggta tggaattcca ctcaaatctt cattcaga 38

<210> SEQ ID NO 572
<211> LENGTH: 29
<212> TYPE: DNA
<213> ORGANISM: Artificial Sequence
<220> FEATURE:
<223> OTHER INFORMATION: Primer

<400> SEQUENCE: 572
acgtcgggtt acgggacacc tgattcctc 29

<210> SEQ ID NO 573
<211> LENGTH: 38
<212> TYPE: DNA
<213> ORGANISM: Artificial Sequence
<220> FEATURE:
<223> OTHER INFORMATION: Primer

<400> SEQUENCE: 573
taccattggt ttgaattctt gtttcctgtt aaccatgc 38

<210> SEQ ID NO 574
<211> LENGTH: 29
<212> TYPE: DNA
<213> ORGANISM: Artificial Sequence
<220> FEATURE:
<223> OTHER INFORMATION: Primer

<400> SEQUENCE: 574
gccgagttct acgggacaga aaagggagc 29

<210> SEQ ID NO 575
<211> LENGTH: 38
<212> TYPE: DNA
<213> ORGANISM: Artificial Sequence
<220> FEATURE:
<223> OTHER INFORMATION: Primer

<400> SEQUENCE: 575
tgcagtgatt tcgaattcga gacaatgctg cccagtca 38

<210> SEQ ID NO 576
<211> LENGTH: 29
<212> TYPE: DNA
<213> ORGANISM: Artificial Sequence
<220> FEATURE:
<223> OTHER INFORMATION: Primer

<400> SEQUENCE: 576
tctaaattct ctgggaccat tccttcaac 29

<210> SEQ ID NO 577
<211> LENGTH: 38
<212> TYPE: DNA
<213> ORGANISM: Artificial Sequence
<220> FEATURE:
<223> OTHER INFORMATION: Primer

<400> SEQUENCE: 577
actaacagca ctgaattcca tgctcttgga ctttccat 38

<210> SEQ ID NO 578

-continued

<211> LENGTH: 29
<212> TYPE: DNA
<213> ORGANISM: Artificial Sequence
<220> FEATURE:
<223> OTHER INFORMATION: Primer

<400> SEQUENCE: 578
tcccctaacg ttgggacaca gaatactac 29

<210> SEQ ID NO 579
<211> LENGTH: 38
<212> TYPE: DNA
<213> ORGANISM: Artificial Sequence
<220> FEATURE:
<223> OTHER INFORMATION: Primer

<400> SEQUENCE: 579
gtcgacgatg gcgaattcct gccactcatt cagttagc 38

<210> SEQ ID NO 580
<211> LENGTH: 29
<212> TYPE: DNA
<213> ORGANISM: Artificial Sequence
<220> FEATURE:
<223> OTHER INFORMATION: Primer

<400> SEQUENCE: 580
gaacggccca cagggacctg gcataactc 29

<210> SEQ ID NO 581
<211> LENGTH: 38
<212> TYPE: DNA
<213> ORGANISM: Artificial Sequence
<220> FEATURE:
<223> OTHER INFORMATION: Primer

<400> SEQUENCE: 581
tcatggtagc aggaattctg ctttgaccga taaggaga 38

<210> SEQ ID NO 582
<211> LENGTH: 29
<212> TYPE: DNA
<213> ORGANISM: Artificial Sequence
<220> FEATURE:
<223> OTHER INFORMATION: Primer

<400> SEQUENCE: 582
actgtgggat tcgggactgt ctactaccc 29

<210> SEQ ID NO 583
<211> LENGTH: 38
<212> TYPE: DNA
<213> ORGANISM: Artificial Sequence
<220> FEATURE:
<223> OTHER INFORMATION: Primer

<400> SEQUENCE: 583
acctctcggc cggaattcgg aaaagtgtac agatcatt 38

<210> SEQ ID NO 584
<211> LENGTH: 29
<212> TYPE: DNA
<213> ORGANISM: Artificial Sequence
<220> FEATURE:
<223> OTHER INFORMATION: Primer

<400> SEQUENCE: 584

-continued gccggatacg aagggacggc tcgtgactc 29

<210> SEQ ID NO 585
<211> LENGTH: 38
<212> TYPE: DNA
<213> ORGANISM: Artificial Sequence
<220> FEATURE:
<223> OTHER INFORMATION: Primer

<400> SEQUENCE: 585
ccgtagacta aagaattccc tgatgtcagg ctgtcacc 38

<210> SEQ ID NO 586
<211> LENGTH: 29
<212> TYPE: DNA
<213> ORGANISM: Artificial Sequence
<220> FEATURE:
<223> OTHER INFORMATION: Primer

<400> SEQUENCE: 586
atcggatcag tcgggacggt gtctttgcc 29

<210> SEQ ID NO 587
<211> LENGTH: 38
<212> TYPE: DNA
<213> ORGANISM: Artificial Sequence
<220> FEATURE:
<223> OTHER INFORMATION: Primer

<400> SEQUENCE: 587
gcataggcgg gagaattccc tgtgtccacc aaagtcgg 38

<210> SEQ ID NO 588
<211> LENGTH: 29
<212> TYPE: DNA
<213> ORGANISM: Artificial Sequence
<220> FEATURE:
<223> OTHER INFORMATION: Primer

<400> SEQUENCE: 588
cccacatagg gcgggacaaa gagctgaac 29

<210> SEQ ID NO 589
<211> LENGTH: 38
<212> TYPE: DNA
<213> ORGANISM: Artificial Sequence
<220> FEATURE:
<223> OTHER INFORMATION: Primer

<400> SEQUENCE: 589
ggcttgccga gcgaattcta ggaaagatac ggaatcaa 38

<210> SEQ ID NO 590
<211> LENGTH: 29
<212> TYPE: DNA
<213> ORGANISM: Artificial Sequence
<220> FEATURE:
<223> OTHER INFORMATION: Primer

<400> SEQUENCE: 590
taaccctcat acgggacttt catggaagc 29

<210> SEQ ID NO 591
<211> LENGTH: 38
<212> TYPE: DNA

-continued

<213> ORGANISM: Artificial Sequence
<220> FEATURE:
<223> OTHER INFORMATION: Primer

<400> SEQUENCE: 591
atgagcaccc gggaattctg attggagtct aggccaaa 38

<210> SEQ ID NO 592
<211> LENGTH: 29
<212> TYPE: DNA
<213> ORGANISM: Artificial Sequence
<220> FEATURE:
<223> OTHER INFORMATION: Primer

<400> SEQUENCE: 592
tgctcacctt ctgggacgtg gctggtctc 29

<210> SEQ ID NO 593
<211> LENGTH: 38
<212> TYPE: DNA
<213> ORGANISM: Artificial Sequence
<220> FEATURE:
<223> OTHER INFORMATION: Primer

<400> SEQUENCE: 593
accgtctgcc acgaattctg gaaaacatgc agtctggt 38

<210> SEQ ID NO 594
<211> LENGTH: 29
<212> TYPE: DNA
<213> ORGANISM: Artificial Sequence
<220> FEATURE:
<223> OTHER INFORMATION: Primer

<400> SEQUENCE: 594
tacacgggag gcgggacagg gtgattaac 29

<210> SEQ ID NO 595
<211> LENGTH: 38
<212> TYPE: DNA
<213> ORGANISM: Artificial Sequence
<220> FEATURE:
<223> OTHER INFORMATION: Primer

<400> SEQUENCE: 595
cttaaagcta acgaattcag agctgtatga agatgctt 38

<210> SEQ ID NO 596
<211> LENGTH: 29
<212> TYPE: DNA
<213> ORGANISM: Artificial Sequence
<220> FEATURE:
<223> OTHER INFORMATION: Primer

<400> SEQUENCE: 596
aacgctaaag gggggacaac ataattggc 29

<210> SEQ ID NO 597
<211> LENGTH: 38
<212> TYPE: DNA
<213> ORGANISM: Artificial Sequence
<220> FEATURE:
<223> OTHER INFORMATION: Primer

<400> SEQUENCE: 597
ttgtaagaac gagaattctg caacctgtct ttattgaa 38

-continued

<210> SEQ ID NO 598
<211> LENGTH: 29
<212> TYPE: DNA
<213> ORGANISM: Artificial Sequence
<220> FEATURE:
<223> OTHER INFORMATION: Primer

<400> SEQUENCE: 598
cttcaccact ttgggacact gaagccaac 29

<210> SEQ ID NO 599
<211> LENGTH: 38
<212> TYPE: DNA
<213> ORGANISM: Artificial Sequence
<220> FEATURE:
<223> OTHER INFORMATION: Primer

<400> SEQUENCE: 599
aaccattgat ttgaattcga aatgtccacc aaagttca 38

<210> SEQ ID NO 600
<211> LENGTH: 29
<212> TYPE: DNA
<213> ORGANISM: Artificial Sequence
<220> FEATURE:
<223> OTHER INFORMATION: Primer

<400> SEQUENCE: 600
tgtctagttc cagggacgct gttacttac 29

<210> SEQ ID NO 601
<211> LENGTH: 38
<212> TYPE: DNA
<213> ORGANISM: Artificial Sequence
<220> FEATURE:
<223> OTHER INFORMATION: Primer

<400> SEQUENCE: 601
cgaaggtaat gtgaattctg ccacaattaa gacttgga 38

<210> SEQ ID NO 602
<211> LENGTH: 29
<212> TYPE: DNA
<213> ORGANISM: Artificial Sequence
<220> FEATURE:
<223> OTHER INFORMATION: Primer

<400> SEQUENCE: 602
ataccggttt tcgggacaga tccattgac 29

<210> SEQ ID NO 603
<211> LENGTH: 38
<212> TYPE: DNA
<213> ORGANISM: Artificial Sequence
<220> FEATURE:
<223> OTHER INFORMATION: Primer

<400> SEQUENCE: 603
cctgaaatcc acgaattcca ccctggcctc ccagtgca 38

<210> SEQ ID NO 604
<211> LENGTH: 29
<212> TYPE: DNA
<213> ORGANISM: Artificial Sequence
<220> FEATURE:

-continued

<223> OTHER INFORMATION: Primer

<400> SEQUENCE: 604
tagatggtag gtgggacagg actggcttc 29

<210> SEQ ID NO 605
<211> LENGTH: 38
<212> TYPE: DNA
<213> ORGANISM: Artificial Sequence
<220> FEATURE:
<223> OTHER INFORMATION: Primer

<400> SEQUENCE: 605
gcatatctta gcgaattcct gtgactaata cagagtgc 38

<210> SEQ ID NO 606
<211> LENGTH: 29
<212> TYPE: DNA
<213> ORGANISM: Artificial Sequence
<220> FEATURE:
<223> OTHER INFORMATION: Primer

<400> SEQUENCE: 606
ccaaatatgg tagggacgtg tgaacactc 29

<210> SEQ ID NO 607
<211> LENGTH: 38
<212> TYPE: DNA
<213> ORGANISM: Artificial Sequence
<220> FEATURE:
<223> OTHER INFORMATION: Primer

<400> SEQUENCE: 607
tgccgctaca gggaattcat atggcagata ttcctgaa 38

<210> SEQ ID NO 608
<211> LENGTH: 29
<212> TYPE: DNA
<213> ORGANISM: Artificial Sequence
<220> FEATURE:
<223> OTHER INFORMATION: Primer

<400> SEQUENCE: 608
acgttgcgga ccgggacttc cacagagcc 29

<210> SEQ ID NO 609
<211> LENGTH: 38
<212> TYPE: DNA
<213> ORGANISM: Artificial Sequence
<220> FEATURE:
<223> OTHER INFORMATION: Primer

<400> SEQUENCE: 609
cttcgcccaa tggaattcgg tacaggggta tgccttat 38

<210> SEQ ID NO 610
<211> LENGTH: 29
<212> TYPE: DNA
<213> ORGANISM: Artificial Sequence
<220> FEATURE:
<223> OTHER INFORMATION: Primer

<400> SEQUENCE: 610
tgcacttctg ccgggaccag aggagaaac 29

-continued

<210> SEQ ID NO 611
<211> LENGTH: 38
<212> TYPE: DNA
<213> ORGANISM: Artificial Sequence
<220> FEATURE:
<223> OTHER INFORMATION: Primer

<400> SEQUENCE: 611
tgtgggtatt ctgaattcca caaaatggac taacacgc 38

<210> SEQ ID NO 612
<211> LENGTH: 29
<212> TYPE: DNA
<213> ORGANISM: Artificial Sequence
<220> FEATURE:
<223> OTHER INFORMATION: Primer

<400> SEQUENCE: 612
acgtcgttca gtgggacatt aaaaggctc 29

<210> SEQ ID NO 613
<211> LENGTH: 38
<212> TYPE: DNA
<213> ORGANISM: Artificial Sequence
<220> FEATURE:
<223> OTHER INFORMATION: Primer

<400> SEQUENCE: 613
ggttatgtgt cagaattctg aaactagttt ggaagtac 38

<210> SEQ ID NO 614
<211> LENGTH: 29
<212> TYPE: DNA
<213> ORGANISM: Artificial Sequence
<220> FEATURE:
<223> OTHER INFORMATION: Primer

<400> SEQUENCE: 614
gcctcagttt cggggacagt tctgaggac 29

<210> SEQ ID NO 615
<211> LENGTH: 38
<212> TYPE: DNA
<213> ORGANISM: Artificial Sequence
<220> FEATURE:
<223> OTHER INFORMATION: Primer

<400> SEQUENCE: 615
tgtaacacgg ccgaattcct catttgtatg aaataggt 38

<210> SEQ ID NO 616
<211> LENGTH: 29
<212> TYPE: DNA
<213> ORGANISM: Artificial Sequence
<220> FEATURE:
<223> OTHER INFORMATION: Primer

<400> SEQUENCE: 616
aatctaactt gagggaccgg cacacacac 29

<210> SEQ ID NO 617
<211> LENGTH: 38
<212> TYPE: DNA
<213> ORGANISM: Artificial Sequence
<220> FEATURE:
<223> OTHER INFORMATION: Primer -continued

<400> SEQUENCE: 617
agtgtcccct tagaattcgc agagacacca cagtgtgc 38

<210> SEQ ID NO 618
<211> LENGTH: 29
<212> TYPE: DNA
<213> ORGANISM: Artificial Sequence
<220> FEATURE:
<223> OTHER INFORMATION: Primer

<400> SEQUENCE: 618
tttgctacag tcgggaccct tgtgtgctc 29

<210> SEQ ID NO 619
<211> LENGTH: 38
<212> TYPE: DNA
<213> ORGANISM: Artificial Sequence
<220> FEATURE:
<223> OTHER INFORMATION: Primer

<400> SEQUENCE: 619
agcacatcac tagaattcaa taccatgtgt gagctcaa 38

<210> SEQ ID NO 620
<211> LENGTH: 29
<212> TYPE: DNA
<213> ORGANISM: Artificial Sequence
<220> FEATURE:
<223> OTHER INFORMATION: Primer

<400> SEQUENCE: 620
aatcctgctt ccgggaccta actttgaac 29

<210> SEQ ID NO 621
<211> LENGTH: 38
<212> TYPE: DNA
<213> ORGANISM: Artificial Sequence
<220> FEATURE:
<223> OTHER INFORMATION: Primer

<400> SEQUENCE: 621
tttcattttc tggaattcct ctaatgattt tctggagc 38

<210> SEQ ID NO 622
<211> LENGTH: 29
<212> TYPE: DNA
<213> ORGANISM: Artificial Sequence
<220> FEATURE:
<223> OTHER INFORMATION: Primer

<400> SEQUENCE: 622
cgtcgccgcg tagggacttt ttcttccac 29

<210> SEQ ID NO 623
<211> LENGTH: 38
<212> TYPE: DNA
<213> ORGANISM: Artificial Sequence
<220> FEATURE:
<223> OTHER INFORMATION: Primer

<400> SEQUENCE: 623
ttacttaatc ctgaattcga gaaaagccat gttgataa 38

<210> SEQ ID NO 624
<211> LENGTH: 29

-continued

<212> TYPE: DNA
<213> ORGANISM: Artificial Sequence
<220> FEATURE:
<223> OTHER INFORMATION: Primer

<400> SEQUENCE: 624
tcatgggtcg ctgggacttt gccctctgc 29

<210> SEQ ID NO 625
<211> LENGTH: 38
<212> TYPE: DNA
<213> ORGANISM: Artificial Sequence
<220> FEATURE:
<223> OTHER INFORMATION: Primer

<400> SEQUENCE: 625
actaacagca ctgaattcat tttactataa tctgctac 38

<210> SEQ ID NO 626
<211> LENGTH: 29
<212> TYPE: DNA
<213> ORGANISM: Artificial Sequence
<220> FEATURE:
<223> OTHER INFORMATION: Primer

<400> SEQUENCE: 626
gttagccgag aagggactgt ctgtgaagc 29

<210> SEQ ID NO 627
<211> LENGTH: 38
<212> TYPE: DNA
<213> ORGANISM: Artificial Sequence
<220> FEATURE:
<223> OTHER INFORMATION: Primer

<400> SEQUENCE: 627
aaatatgcag cggaattcgt aagtgaccta ttaataac 38

<210> SEQ ID NO 628
<211> LENGTH: 29
<212> TYPE: DNA
<213> ORGANISM: Artificial Sequence
<220> FEATURE:
<223> OTHER INFORMATION: Primer

<400> SEQUENCE: 628
gcgatggtta cggggacagc caggcaacc 29

<210> SEQ ID NO 629
<211> LENGTH: 16
<212> TYPE: DNA
<213> ORGANISM: Artificial Sequence
<220> FEATURE:
<223> OTHER INFORMATION: Primer

<400> SEQUENCE: 629
ccagctggta gaactt 16

<210> SEQ ID NO 630
<211> LENGTH: 16
<212> TYPE: DNA
<213> ORGANISM: Artificial Sequence
<220> FEATURE:
<223> OTHER INFORMATION: Primer

<400> SEQUENCE: 630

-continued cccaatagac ctatag 16

<210> SEQ ID NO 631
<211> LENGTH: 16
<212> TYPE: DNA
<213> ORGANISM: Artificial Sequence
<220> FEATURE:
<223> OTHER INFORMATION: Primer

<400> SEQUENCE: 631
tagcagaatc tctcat 16

<210> SEQ ID NO 632
<211> LENGTH: 17
<212> TYPE: DNA
<213> ORGANISM: Artificial Sequence
<220> FEATURE:
<223> OTHER INFORMATION: Primer

<400> SEQUENCE: 632
agagtatctc atttgtt 17

<210> SEQ ID NO 633
<211> LENGTH: 16
<212> TYPE: DNA
<213> ORGANISM: Artificial Sequence
<220> FEATURE:
<223> OTHER INFORMATION: Primer

<400> SEQUENCE: 633
aggaaattgt gaagta 16

<210> SEQ ID NO 634
<211> LENGTH: 16
<212> TYPE: DNA
<213> ORGANISM: Artificial Sequence
<220> FEATURE:
<223> OTHER INFORMATION: Primer

<400> SEQUENCE: 634
taactcactc actatc 16

<210> SEQ ID NO 635
<211> LENGTH: 16
<212> TYPE: DNA
<213> ORGANISM: Artificial Sequence
<220> FEATURE:
<223> OTHER INFORMATION: Primer

<400> SEQUENCE: 635
ctgctgagtc atagtc 16

<210> SEQ ID NO 636
<211> LENGTH: 16
<212> TYPE: DNA
<213> ORGANISM: Artificial Sequence
<220> FEATURE:
<223> OTHER INFORMATION: Primer

<400> SEQUENCE: 636
tgttctttga atcaac 16

<210> SEQ ID NO 637
<211> LENGTH: 47
<212> TYPE: DNA
<213> ORGANISM: Artificial Sequence -continued
<220> FEATURE:
<223> OTHER INFORMATION: Primer

<400> SEQUENCE: 637
cagtaatacg actcactata ggggtcagga ttagcagaat ctctcat 47

<210> SEQ ID NO 638
<211> LENGTH: 27
<212> TYPE: DNA
<213> ORGANISM: Artificial Sequence
<220> FEATURE:
<223> OTHER INFORMATION: Primer

<400> SEQUENCE: 638
gcattctatg agagtatctc atttgtt 27

<210> SEQ ID NO 639
<211> LENGTH: 47
<212> TYPE: DNA
<213> ORGANISM: Artificial Sequence
<220> FEATURE:
<223> OTHER INFORMATION: Primer

<400> SEQUENCE: 639
cagtaatacg actcactata ggggtcagga agagtatctc atttgtt 47

<210> SEQ ID NO 640
<211> LENGTH: 26
<212> TYPE: DNA
<213> ORGANISM: Artificial Sequence
<220> FEATURE:
<223> OTHER INFORMATION: Primer

<400> SEQUENCE: 640
gcattctatg tagcagaatc tctcat 26

<210> SEQ ID NO 641
<211> LENGTH: 17
<212> TYPE: DNA
<213> ORGANISM: Homo sapiens
<220> FEATURE:
<221> NAME/KEY: misc_feature
<222> LOCATION: 8
<223> OTHER INFORMATION: n = T or A

<400> SEQUENCE: 641
ccgcatanct cagcaca 17

<210> SEQ ID NO 642
<211> LENGTH: 17
<212> TYPE: DNA
<213> ORGANISM: Homo sapiens
<220> FEATURE:
<221> NAME/KEY: misc_feature
<222> LOCATION: 10
<223> OTHER INFORMATION: n = A or T

<400> SEQUENCE: 642
tgtgctgagn tatgcgg 17

<210> SEQ ID NO 643
<211> LENGTH: 16
<212> TYPE: DNA
<213> ORGANISM: Artificial Sequence
<220> FEATURE:
<223> OTHER INFORMATION: Primer -continued

<400> SEQUENCE: 643
aggaaattgt gaagta 16

<210> SEQ ID NO 644
<211> LENGTH: 16
<212> TYPE: DNA
<213> ORGANISM: Artificial Sequence
<220> FEATURE:
<223> OTHER INFORMATION: Primer

<400> SEQUENCE: 644
taactcactc actatc 16

<210> SEQ ID NO 645
<211> LENGTH: 25
<212> TYPE: DNA
<213> ORGANISM: Artificial Sequence
<220> FEATURE:
<223> OTHER INFORMATION: Primer

<400> SEQUENCE: 645
ctttttatgc ctttccactc atcca 25

<210> SEQ ID NO 646
<211> LENGTH: 25
<212> TYPE: DNA
<213> ORGANISM: Artificial Sequence
<220> FEATURE:
<223> OTHER INFORMATION: Primer

<400> SEQUENCE: 646
ctttttatgc ctttccactc atcca 25

<210> SEQ ID NO 647
<211> LENGTH: 29
<212> TYPE: DNA
<213> ORGANISM: Homo sapiens

<400> SEQUENCE: 647
gaaaaatacg gaaaggtgag taggtttcc 29

<210> SEQ ID NO 648
<211> LENGTH: 26
<212> TYPE: DNA
<213> ORGANISM: Artificial Sequence
<220> FEATURE:
<223> OTHER INFORMATION: Primer

<400> SEQUENCE: 648
ctttttatgc ctttccactc atccaa 26

<210> SEQ ID NO 649
<211> LENGTH: 29
<212> TYPE: DNA
<213> ORGANISM: Homo sapiens

<400> SEQUENCE: 649
gaaaaatacg gaaaggtgag taggtttcc 29

<210> SEQ ID NO 650
<211> LENGTH: 25
<212> TYPE: DNA
<213> ORGANISM: Artificial Sequence
<220> FEATURE:
<223> OTHER INFORMATION: Primer -continued

<400> SEQUENCE: 650 cttttatgc ctttccactc atcca 25

<210> SEQ ID NO 651
<211> LENGTH: 29
<212> TYPE: DNA
<213> ORGANISM: Homo sapiens

<400> SEQUENCE: 651
gaaaaatacg gaaaggtgag taggtctcc 29

<210> SEQ ID NO 652
<211> LENGTH: 27
<212> TYPE: DNA
<213> ORGANISM: Artificial Sequence
<220> FEATURE:
<223> OTHER INFORMATION: Primer

<400> SEQUENCE: 652
ctttttatgc ctttccactc atccaga 27

<210> SEQ ID NO 653
<211> LENGTH: 29
<212> TYPE: DNA
<213> ORGANISM: Homo sapiens

<400> SEQUENCE: 653
gaaaaatacg gaaaggtgag taggtctcc 29

<210> SEQ ID NO 654
<211> LENGTH: 15
<212> TYPE: DNA
<213> ORGANISM: Artificial Sequence
<220> FEATURE:
<223> OTHER INFORMATION: Primer

<400> SEQUENCE: 654
atcacactgg ggatc 15

<210> SEQ ID NO 655
<211> LENGTH: 15
<212> TYPE: DNA
<213> ORGANISM: Artificial Sequence
<220> FEATURE:
<223> OTHER INFORMATION: Primer

<400> SEQUENCE: 655
ctaaacctat gactc 15

<210> SEQ ID NO 656
<211> LENGTH: 21
<212> TYPE: DNA
<213> ORGANISM: Artificial Sequence
<220> FEATURE:
<223> OTHER INFORMATION: Primer

<400> SEQUENCE: 656
ttcacagagg atatcttaat a 21

<210> SEQ ID NO 657
<211> LENGTH: 22
<212> TYPE: DNA
<213> ORGANISM: Artificial Sequence
<220> FEATURE:

-continued

<223> OTHER INFORMATION: Primer

<400> SEQUENCE: 657
agtcttgtaa tacgacagtc tt 22

<210> SEQ ID NO 658
<211> LENGTH: 21
<212> TYPE: DNA
<213> ORGANISM: Artificial Sequence
<220> FEATURE:
<223> OTHER INFORMATION: Primer

<400> SEQUENCE: 658
ccatatcaat cagtactctt g 21

<210> SEQ ID NO 659
<211> LENGTH: 23
<212> TYPE: DNA
<213> ORGANISM: Artificial Sequence
<220> FEATURE:
<223> OTHER INFORMATION: Oligonucleotide probe

<400> SEQUENCE: 659
cctttccact catccaaagg ttg 23

<210> SEQ ID NO 660
<211> LENGTH: 23
<212> TYPE: DNA
<213> ORGANISM: Artificial Sequence
<220> FEATURE:
<223> OTHER INFORMATION: Oligonucleotide probe

<400> SEQUENCE: 660
cctttccact catccagagg ttg 23

<210> SEQ ID NO 661
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 661
catgcagata taccgcatat 20

<210> SEQ ID NO 662
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 662
catgcagata taccgcataa 20

<210> SEQ ID NO 663
<211> LENGTH: 23
<212> TYPE: DNA
<213> ORGANISM: Artificial Sequence
<220> FEATURE:
<223> OTHER INFORMATION: Oligonucleotide probe

<400> SEQUENCE: 663
ggtagcatct ctcagcacaa gag 23

-continued

<210> SEQ ID NO 664
<211> LENGTH: 23
<212> TYPE: DNA
<213> ORGANISM: Artificial Sequence
<220> FEATURE:
<223> OTHER INFORMATION: Oligonucleotide probe

<400> SEQUENCE: 664
ggtagcatca ctcagcacaa gag 23

<210> SEQ ID NO 665
<211> LENGTH: 16
<212> TYPE: DNA
<213> ORGANISM: Artificial Sequence
<220> FEATURE:
<223> OTHER INFORMATION: Primer

<400> SEQUENCE: 665
tagcagaatc tctcat 16

<210> SEQ ID NO 666
<211> LENGTH: 17
<212> TYPE: DNA
<213> ORGANISM: Artificial Sequence
<220> FEATURE:
<223> OTHER INFORMATION: Primer

<400> SEQUENCE: 666
agagtatctc atttgtt 17

<210> SEQ ID NO 667
<211> LENGTH: 125
<212> TYPE: DNA
<213> ORGANISM: Homo sapiens
<220> FEATURE:
<221> NAME/KEY: misc_feature
<222> LOCATION: (36)...(94)
<223> OTHER INFORMATION: n = A,T,C or G

<400> SEQUENCE: 667
gccaagtata atttcctga taaaggctgg gctgcnnnnn nnnnnnnnnn nnnnnnnnnn 60
nnnnnnnnnn nnnnnnnnnn nnnnnnnnnn nnnncaattt gcactartga agtttaccta 120
acaat 125

<210> SEQ ID NO 668
<211> LENGTH: 125
<212> TYPE: DNA
<213> ORGANISM: Homo sapiens
<220> FEATURE:
<221> NAME/KEY: misc_feature
<222> LOCATION: (32)...(90)
<223> OTHER INFORMATION: n = A,T,C or G

<400> SEQUENCE: 668
attgttaggt aaacttcayt agtgcaaatt gnnnnnnnnn nnnnnnnnnn nnnnnnnnnn 60
nnnnnnnnnn nnnnnnnnnn nnnnnnnnnn gcagcccagc ctttatcagg aaaattatac 120
ttggc 125

<210> SEQ ID NO 669
<211> LENGTH: 140
<212> TYPE: DNA
<213> ORGANISM: Homo sapiens
<220> FEATURE:
<221> NAME/KEY: misc_feature
<222> LOCATION: (33)...(114)

-continued

<223> OTHER INFORMATION: n = A,T,C or G

<400> SEQUENCE: 669
ctatatgtga aagcagaagt tgtctgataa tcnnnnnnnn nnnnnnnnnn nnnnnnnnnn 60
nnnnnnnnnn nnnnnnnnnn nnnnnnnnnn nnnnnnnnnn nnnnnnnnnn nnnnccaagg 120
sctttactcg atgatagctg 140

<210> SEQ ID NO 670
<211> LENGTH: 140
<212> TYPE: DNA
<213> ORGANISM: Homo sapiens
<220> FEATURE:
<221> NAME/KEY: misc_feature
<222> LOCATION: (27)...(108)
<223> OTHER INFORMATION: n = A,T,C or G

<400> SEQUENCE: 670
cagctatcat cgagtaaags ccttggnnnn nnnnnnnnnn nnnnnnnnnn nnnnnnnnnn 60
nnnnnnnnnn nnnnnnnnnn nnnnnnnnnn nnnnnnnnnn nnnnnnnnga ttatcagaca 120
acttctgctt tcacatatag 140

<210> SEQ ID NO 671
<211> LENGTH: 141
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (42)...(100)
<223> OTHER INFORMATION: n = A,T,C or G

<400> SEQUENCE: 671
ataaccgtat gcgaattcta taattttcct gataaaggct gnnnnnnnnn nnnnnnnnnn 60
nnnnnnnnnn nnnnnnnnnn nnnnnnnnnn nnnnnnnnnn caatttgcac tartgaagtt 120
tacctagtcc ccagatttaa g 141

<210> SEQ ID NO 672
<211> LENGTH: 141
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (42)...(100)
<223> OTHER INFORMATION: n = A,T,C or G

<400> SEQUENCE: 672
cttaaatcag gggactaggt aaacttcayt agtgcaaatt gnnnnnnnnn nnnnnnnnnn 60
nnnnnnnnnn nnnnnnnnnn nnnnnnnnnn nnnnnnnnnn cagcctttat caggaaaatt 120
atagaattcg catacggtta t 141

<210> SEQ ID NO 673
<211> LENGTH: 141
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (42)...(100)
<223> OTHER INFORMATION: n = A,T,C or G

<400> SEQUENCE: 673
ataaccgtat gcgaattcta taattttcct gataaaggct gnnnnnnnnn nnnnnnnnnn 60
nnnnnnnnnn nnnnnnnnnn nnnnnnnnnn nnnnnnnnnn caatttgcac tartgaagtt 120
tacctagccg tcagatttaa g 141

<210> SEQ ID NO 674
<211> LENGTH: 141
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (42)...(100)
<223> OTHER INFORMATION: n = A,T,C or G

<400> SEQUENCE: 674
cttaaatcag acggctaggt aaacttcayt agtgcaaatt gnnnnnnnnn nnnnnnnnnn 60
nnnnnnnnnn nnnnnnnnnn nnnnnnnnnn nnnnnnnnnn cagcctttat caggaaaatt 120
atagaattcg catacggtta t 141

<210> SEQ ID NO 675
<211> LENGTH: 161
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (45)...(126)
<223> OTHER INFORMATION: n = A,T,C or G

<400> SEQUENCE: 675
aagtttagat cagaattcgt gaaagcagaa gttgtctgat aatcnnnnnn nnnnnnnnnn 60
nnnnnnnnnn nnnnnnnnnn nnnnnnnnnn nnnnnnnnnn nnnnnnnnnn nnnnnnnnnn 120
nnnnnnccaa ggsctttact cgatgagtcc cttatcgtga t 161

<210> SEQ ID NO 676
<211> LENGTH: 161
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (36)...(117)
<223> OTHER INFORMATION: n = A,T,C or G

<400> SEQUENCE: 676
atcacgataa gggactcatc gagtaaagsc cttggnnnnn nnnnnnnnnn nnnnnnnnnn 60
nnnnnnnnnn nnnnnnnnnn nnnnnnnnnn nnnnnnnnnn nnnnnnnnnn nnnnnnngat 120
tatcagacaa cttctgcttt cacgaattct gatctaaact t 161

<210> SEQ ID NO 677
<211> LENGTH: 161
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (45)...(126)

-continued

<223> OTHER INFORMATION: n = A,T,C or G

<400> SEQUENCE: 677
aagtttagat cagaattcgt gaaagcagaa gttgtctgat aatcnnnnnn nnnnnnnnnn 60
nnnnnnnnnn nnnnnnnnnn nnnnnnnnnn nnnnnnnnnn nnnnnnnnnn nnnnnnnnnn 120
nnnnnnccaa ggsctttact cgatgagccg tttatcgtga t 161

<210> SEQ ID NO 678
<211> LENGTH: 161
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (36)...(117)
<223> OTHER INFORMATION: n = A,T,C or G

<400> SEQUENCE: 678
atcacgataa acggctcatc gagtaaagsc cttggnnnnn nnnnnnnnnn nnnnnnnnnn 60
nnnnnnnnnn nnnnnnnnnn nnnnnnnnnn nnnnnnnnnn nnnnnnnnnn nnnnnnngat 120
tatcagacaa cttctgcttt cacgaattct gatctaaact t 161

<210> SEQ ID NO 679
<211> LENGTH: 112
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (52)...(100)
<223> OTHER INFORMATION: n = A,T,C or G

<400> SEQUENCE: 679
ataaccgtat gcgaattcta taattttcct gataaaggct gnnnnnnnnn nnnnnnnnnn 60
nnnnnnnnnn nnnnnnnnnn nnnnnnnnnn nnnnnnnnnn caatttgcac ta 112

<210> SEQ ID NO 680
<211> LENGTH: 29
<212> TYPE: DNA
<213> ORGANISM: Artificial Sequence
<220> FEATURE:
<223> OTHER INFORMATION: PCR product after restriction enzyme digestion

<400> SEQUENCE: 680
rtgaagttta cctagtcccc agatttaag 29

<210> SEQ ID NO 681
<211> LENGTH: 116
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (17)...(75)
<223> OTHER INFORMATION: n = A,T,C or G

<400> SEQUENCE: 681
tcaytagtgc aaattgnnnn nnnnnnnnnn nnnnnnnnnn nnnnnnnnnn nnnnnnnnnn 60
nnnnnnnnnn nnnnncagcc tttatcagga aaattataga attcgcatac ggttat 116

-continued

<210> SEQ ID NO 682
<211> LENGTH: 25
<212> TYPE: DNA
<213> ORGANISM: Artificial Sequence
<220> FEATURE:
<223> OTHER INFORMATION: PCR product after restriction enzyme digestion

<400> SEQUENCE: 682
cttaaatcag gggactaggt aaact 25

<210> SEQ ID NO 683
<211> LENGTH: 29
<212> TYPE: DNA
<213> ORGANISM: Artificial Sequence
<220> FEATURE:
<223> OTHER INFORMATION: PCR product after restriction enzyme digestion

<400> SEQUENCE: 683
rtgaagttta cctagccgtc agatttaag 29

<210> SEQ ID NO 684
<211> LENGTH: 114
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (15)...(73)
<223> OTHER INFORMATION: n = A,T,C or G

<400> SEQUENCE: 684
aytagtgcaa attgnnnnnn nnnnnnnnnn nnnnnnnnnn nnnnnnnnnn nnnnnnnnnn 60
nnnnnnnnnn nnncagcctt tatcaggaaa attatagaat tcgcatacgg ttat 114

<210> SEQ ID NO 685
<211> LENGTH: 27
<212> TYPE: DNA
<213> ORGANISM: Artificial Sequence
<220> FEATURE:
<223> OTHER INFORMATION: PCR product after restriction enzyme digestion

<400> SEQUENCE: 685
cttaaatcag acggctaggt aaacttc 27

<210> SEQ ID NO 686
<211> LENGTH: 132
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (45)...(126)
<223> OTHER INFORMATION: n = A,T,C or G

<400> SEQUENCE: 686
aagtttagat cagaattcgt gaaagcagaa gttgtctgat aatcnnnnnn nnnnnnnnnn 60
nnnnnnnnnn nnnnnnnnnn nnnnnnnnnn nnnnnnnnnn nnnnnnnnnn nnnnnnnnnn 120
nnnnnnccaa gg 132

<210> SEQ ID NO 687
<211> LENGTH: 29
<212> TYPE: DNA
<213> ORGANISM: Artificial Sequence
<220> FEATURE:

-continued

<223> OTHER INFORMATION: PCR product after restriction enzyme digestion

<400> SEQUENCE: 687
sctttactcg atgagtccct tatcgtgat 29

<210> SEQ ID NO 688
<211> LENGTH: 136
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (11)...(92)
<223> OTHER INFORMATION: n = A,T,C or G

<400> SEQUENCE: 688
aagsccttgg nnnnnnnnnn nnnnnnnnnn nnnnnnnnnn nnnnnnnnnn nnnnnnnnnn 60
nnnnnnnnnn nnnnnnnnnn nnnnnnnnnn nngattatca gacaacttct gctttcacga 120
attctgatct aaactt 136

<210> SEQ ID NO 689
<211> LENGTH: 25
<212> TYPE: DNA
<213> ORGANISM: Artificial Sequence
<220> FEATURE:
<223> OTHER INFORMATION: PCR product after restriction enzyme digestion

<400> SEQUENCE: 689
atcacgataa gggactcatc gagta 25

<210> SEQ ID NO 690
<211> LENGTH: 29
<212> TYPE: DNA
<213> ORGANISM: Artificial Sequence
<220> FEATURE:
<223> OTHER INFORMATION: PCR product after restriction enzyme digestion

<400> SEQUENCE: 690
sctttactcg atgagccgtt tatcgtgat 29

<210> SEQ ID NO 691
<211> LENGTH: 134
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (9)...(90)
<223> OTHER INFORMATION: n = A,T,C or G

<400> SEQUENCE: 691
gsccttggnn nnnnnnnnnn nnnnnnnnnn nnnnnnnnnn nnnnnnnnnn nnnnnnnnnn 60
nnnnnnnnnn nnnnnnnnnn nnnnnnnnnn gattatcaga caacttctgc tttcacgaat 120
tctgatctaa actt 134

<210> SEQ ID NO 692
<211> LENGTH: 27
<212> TYPE: DNA
<213> ORGANISM: Artificial Sequence
<220> FEATURE:
<223> OTHER INFORMATION: PCR product after restriction enzyme digestion

<400> SEQUENCE: 692

-continued atcacgataa acggctcatc gagtaaa 27

<210> SEQ ID NO 693
<211> LENGTH: 113
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (42)...(100)
<223> OTHER INFORMATION: n = A,T,C or G

<400> SEQUENCE: 693
ataaccgtat gcgaattcta taattttcct gataaaggct gnnnnnnnnn nnnnnnnnnn 60
nnnnnnnnnn nnnnnnnnnn nnnnnnnnnn nnnnnnnnnn caatttgcac tar 113

<210> SEQ ID NO 694
<211> LENGTH: 116
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (17)...(75)
<223> OTHER INFORMATION: n = A,T,C or G

<400> SEQUENCE: 694
tcaytagtgc aaattgnnnn nnnnnnnnnn nnnnnnnnnn nnnnnnnnnn nnnnnnnnnn 60
nnnnnnnnnn nnnnncagcc tttatcagga aaattataga attcgcatac ggttat 116

<210> SEQ ID NO 695
<211> LENGTH: 114
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (15)...(73)
<223> OTHER INFORMATION: n = A,T,C or G

<400> SEQUENCE: 695
aytagtgcaa attgnnnnnn nnnnnnnnnn nnnnnnnnnn nnnnnnnnnn nnnnnnnnnn 60
nnnnnnnnnn nnncagcctt tatcaggaaa attatagaat tcgcatacgg ttat 114

<210> SEQ ID NO 696
<211> LENGTH: 133
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (45)...(126)
<223> OTHER INFORMATION: n = A,T,C or G

<400> SEQUENCE: 696
aagtttagat cagaattcgt gaaagcagaa gttgtctgat aatcnnnnnn nnnnnnnnnn 60
nnnnnnnnnn nnnnnnnnnn nnnnnnnnnn nnnnnnnnnn nnnnnnnnnn nnnnnnnnnn 120
nnnnnnccaa ggs 133

<210> SEQ ID NO 697

-continued

<211> LENGTH: 136
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (11)...(92)
<223> OTHER INFORMATION: n = A,T,C or G

<400> SEQUENCE: 697
aagsccttgg nnnnnnnnnn nnnnnnnnnn nnnnnnnnnn nnnnnnnnnn nnnnnnnnnn 60
nnnnnnnnnn nnnnnnnnnn nnnnnnnnnn nngattatca gacaacttct gctttcacga 120
attctgatct aaactt 136

<210> SEQ ID NO 698
<211> LENGTH: 134
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (9)...(90)
<223> OTHER INFORMATION: n = A,T,C or G

<400> SEQUENCE: 698
gsccttggnn nnnnnnnnnn nnnnnnnnnn nnnnnnnnnn nnnnnnnnnn nnnnnnnnnn 60
nnnnnnnnnn nnnnnnnnnn nnnnnnnnnn gattatcaga caacttctgc tttcacgaat 120
tctgatctaa actt 134

<210> SEQ ID NO 699
<211> LENGTH: 114
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (42)...(100)
<223> OTHER INFORMATION: n = A,T,C or G

<400> SEQUENCE: 699
ataaccgtat gcgaattcta taattttcct gataaaggct gnnnnnnnnn nnnnnnnnnn 60
nnnnnnnnnn nnnnnnnnnn nnnnnnnnnn nnnnnnnnnn caatttgcac tart 114

<210> SEQ ID NO 700
<211> LENGTH: 115
<212> TYPE: DNA
<213> ORGANISM: Artificial Sequence
<220> FEATURE:
<223> OTHER INFORMATION: Polymerase extension product
<220> FEATURE:
<221> NAME/KEY: misc_feature
<222> LOCATION: (42)...(100)
<223> OTHER INFORMATION: n = A,T,C or G

<400> SEQUENCE: 700
ataaccgtat gcgaattcta taattttcct gataaaggct gnnnnnnnnn nnnnnnnnnn 60
nnnnnnnnnn nnnnnnnnnn nnnnnnnnnn nnnnnnnnnn caatttgcac tartg 115

<210> SEQ ID NO 701
<211> LENGTH: 116
<212> TYPE: DNA
<213> ORGANISM: Artificial Sequence -continued

```
<220> FEATURE:
<223> OTHER INFORMATION: Polymerase extension product
<220> FEATURE:
<221> NAME/KEY: misc_feature
<222> LOCATION: (42)...(100)
<223> OTHER INFORMATION: n = A,T,C or G

<400> SEQUENCE: 701

ataaccgtat gcgaattcta taattttcct gataaaggct gnnnnnnnnn nnnnnnnnnn     60

nnnnnnnnnn nnnnnnnnnn nnnnnnnnnn nnnnnnnnnn caatttgcac tartga        116


<210> SEQ ID NO 702
<211> LENGTH: 13
<212> TYPE: DNA
<213> ORGANISM: Artificial Sequence
<220> FEATURE:
<223> OTHER INFORMATION: PCR product after restriction enzyme digestion

<400> SEQUENCE: 702

ataaccgtat gcg                                                        13


<210> SEQ ID NO 703
<211> LENGTH: 100
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (29)...(87)
<223> OTHER INFORMATION: n = A,T,C or G

<400> SEQUENCE: 703

aattctataa ttttcctgat aaaggctgnn nnnnnnnnnn nnnnnnnnnn nnnnnnnnnn     60

nnnnnnnnnn nnnnnnnnnn nnnnnnncaa tttgcactar                          100


<210> SEQ ID NO 704
<211> LENGTH: 17
<212> TYPE: DNA
<213> ORGANISM: Artificial Sequence
<220> FEATURE:
<223> OTHER INFORMATION: PCR product after restriction enzyme digestion

<400> SEQUENCE: 704

aattcgcata cggttat                                                    17


<210> SEQ ID NO 705
<211> LENGTH: 99
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (17)...(75)
<223> OTHER INFORMATION: n = A,T,C or G

<400> SEQUENCE: 705

tcaytagtgc aaattgnnnn nnnnnnnnnn nnnnnnnnnn nnnnnnnnnn nnnnnnnnnn     60

nnnnnnnnnn nnnnncagcc tttatcagga aaattatag                            99


<210> SEQ ID NO 706
<211> LENGTH: 97
<212> TYPE: DNA
<213> ORGANISM: Artificial Sequence
<220> FEATURE:
```

-continued

<223> OTHER INFORMATION: PCR product after restriction enzyme digestion
<220> FEATURE:
<221> NAME/KEY: misc_feature
<222> LOCATION: (15)...(73)
<223> OTHER INFORMATION: n = A,T,C or G

<400> SEQUENCE: 706
aytagtgcaa attgnnnnnn nnnnnnnnnn nnnnnnnnnn nnnnnnnnnn nnnnnnnnnn 60
nnnnnnnnnn nnncagcctt tatcaggaaa attatag 97

<210> SEQ ID NO 707
<211> LENGTH: 13
<212> TYPE: DNA
<213> ORGANISM: Artificial Sequence
<220> FEATURE:
<223> OTHER INFORMATION: PCR product after restriction enzyme digestion

<400> SEQUENCE: 707
aagtttagat cag 13

<210> SEQ ID NO 708
<211> LENGTH: 120
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (32)...(113)
<223> OTHER INFORMATION: n = A,T,C or G

<400> SEQUENCE: 708
aattcgtgaa agcagaagtt gtctgataat cnnnnnnnnn nnnnnnnnnn nnnnnnnnnn 60
nnnnnnnnnn nnnnnnnnnn nnnnnnnnnn nnnnnnnnnn nnnnnnnnnn nnnccaaggs 120

<210> SEQ ID NO 709
<211> LENGTH: 17
<212> TYPE: DNA
<213> ORGANISM: Artificial Sequence
<220> FEATURE:
<223> OTHER INFORMATION: PCR product after restriction enzyme digestion

<400> SEQUENCE: 709
aattctgatc taaactt 17

<210> SEQ ID NO 710
<211> LENGTH: 119
<212> TYPE: DNA
<213> ORGANISM: Artificial Sequence
<220> FEATURE:
<223> OTHER INFORMATION: PCR product after restriction enzyme digestion
<220> FEATURE:
<221> NAME/KEY: misc_feature
<222> LOCATION: (11)...(92)
<223> OTHER INFORMATION: n = A,T,C or G

<400> SEQUENCE: 710
aagsccttgg nnnnnnnnnn nnnnnnnnnn nnnnnnnnnn nnnnnnnnnn nnnnnnnnnn 60
nnnnnnnnnn nnnnnnnnnn nnnnnnnnnn nngattatca gacaacttct gctttcacg 119

<210> SEQ ID NO 711
<211> LENGTH: 117
<212> TYPE: DNA
<213> ORGANISM: Artificial Sequence
<220> FEATURE:
<223> OTHER INFORMATION: PCR product after restriction enzyme digestion -continued
<220> FEATURE:
<221> NAME/KEY: misc_feature
<222> LOCATION: (9)...(90)
<223> OTHER INFORMATION: n = A,T,C or G

<400> SEQUENCE: 711
gsccttggnn nnnnnnnnnn nnnnnnnnnn nnnnnnnnnn nnnnnnnnnn nnnnnnnnnn 60
nnnnnnnnnn nnnnnnnnnn nnnnnnnnnn gattatcaga caacttctgc tttcacg 117

<210> SEQ ID NO 712
<211> LENGTH: 10
<212> TYPE: DNA
<213> ORGANISM: Homo Sapiens

<400> SEQUENCE: 712
taccgcatat 10

<210> SEQ ID NO 713
<211> LENGTH: 10
<212> TYPE: DNA
<213> ORGANISM: Homo Sapiens

<400> SEQUENCE: 713
taccgcataa 10

<210> SEQ ID NO 714
<211> LENGTH: 15
<212> TYPE: DNA
<213> ORGANISM: Homo Sapiens

<400> SEQUENCE: 714
tttccactca tccag 15

<210> SEQ ID NO 715
<211> LENGTH: 15
<212> TYPE: DNA
<213> ORGANISM: Homo Sapiens

<400> SEQUENCE: 715
tttccactca tccaa 15

<210> SEQ ID NO 716
<211> LENGTH: 11
<212> TYPE: DNA
<213> ORGANISM: Homo Sapiens

<400> SEQUENCE: 716
tatcttaata c 11

<210> SEQ ID NO 717
<211> LENGTH: 11
<212> TYPE: DNA
<213> ORGANISM: Homo Sapiens

<400> SEQUENCE: 717
tatcttaata t 11

<210> SEQ ID NO 718
<211> LENGTH: 16
<212> TYPE: DNA
<213> ORGANISM: Artificial Sequence
<220> FEATURE:
<223> OTHER INFORMATION: Primer -continued

<400> SEQUENCE: 718
ccagctggta gaactt 16

<210> SEQ ID NO 719
<211> LENGTH: 16
<212> TYPE: DNA
<213> ORGANISM: Artificial Sequence
<220> FEATURE:
<223> OTHER INFORMATION: Primer

<400> SEQUENCE: 719
cccaatagac ctatag 16

<210> SEQ ID NO 720
<211> LENGTH: 16
<212> TYPE: DNA
<213> ORGANISM: Artificial Sequence
<220> FEATURE:
<223> OTHER INFORMATION: Primer

<400> SEQUENCE: 720
tagcagaatc tctcat 16

<210> SEQ ID NO 721
<211> LENGTH: 17
<212> TYPE: DNA
<213> ORGANISM: Artificial Sequence
<220> FEATURE:
<223> OTHER INFORMATION: Primer

<400> SEQUENCE: 721
agagtatctc atttgtt 17

<210> SEQ ID NO 722
<211> LENGTH: 16
<212> TYPE: DNA
<213> ORGANISM: Artificial Sequence
<220> FEATURE:
<223> OTHER INFORMATION: Primer

<400> SEQUENCE: 722
aggaaattgt gaagta 16

<210> SEQ ID NO 723
<211> LENGTH: 16
<212> TYPE: DNA
<213> ORGANISM: Artificial Sequence
<220> FEATURE:
<223> OTHER INFORMATION: Primer

<400> SEQUENCE: 723
taactcactc actatc 16

<210> SEQ ID NO 724
<211> LENGTH: 16
<212> TYPE: DNA
<213> ORGANISM: Artificial Sequence
<220> FEATURE:
<223> OTHER INFORMATION: Primer

<400> SEQUENCE: 724
ctgctgagtc atagtc 16

<210> SEQ ID NO 725
<211> LENGTH: 16

-continued

```
<212> TYPE: DNA
<213> ORGANISM: Artificial Sequence
<220> FEATURE:
<223> OTHER INFORMATION: Primer

<400> SEQUENCE: 725

tgttctttga atcaac                                                   16
```